US011410748B2

(12) United States Patent
Modlin et al.

(10) Patent No.: US 11,410,748 B2
(45) Date of Patent: Aug. 9, 2022

(54) METHODS FOR PROSTATE CANCER DETECTION AND TREATMENT

(71) Applicant: Liquid Biopsy Research LLC, Charlestown (KN)

(72) Inventors: Irvin Mark Modlin, Woodbridge, CT (US); Mark Kidd, New Haven, CT (US); Ignat Drozdov, Warwick (GB)

(73) Assignee: Liquid Biopsy Research LLC, Charlestown (KN)

(*) Notice: Subject to any disclaimer, the term of this patent is extended or adjusted under 35 U.S.C. 154(b) by 337 days.

(21) Appl. No.: 16/281,315

(22) Filed: Feb. 21, 2019

(65) Prior Publication Data

US 2019/0259471 A1 Aug. 22, 2019

Related U.S. Application Data

(60) Provisional application No. 62/633,675, filed on Feb. 22, 2018.

(51) Int. Cl.
*C12Q 1/68* (2018.01)
*G16B 25/10* (2019.01)
*C12Q 1/6886* (2018.01)

(52) U.S. Cl.
CPC .......... *G16B 25/10* (2019.02); *C12Q 1/6886* (2013.01); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

2014/0249041 A1 9/2014 Sorensen et al.

FOREIGN PATENT DOCUMENTS

| | | | |
|---|---|---|---|
| EP | 3 147 373 | A1 | 3/2017 |
| EP | 3 179 393 | A2 | 6/2017 |
| WO | WO 2015/021158 | A1 | 2/2015 |

OTHER PUBLICATIONS

Kalinin et al; Future Medicine, vol. 19, pp. 629-650, 2018.*
Liu et al; PLOS One, vol. 10, pp. 1-11, 2015.*
Antonarakis, E. S. et al. (2015) "Androgen Receptor Splice Variant 7 and Efficacy of Taxane Chemotherapy in Patients With Metastatic Castration-Resistant Prostate Cancer" *JAMA Oncol*, 1(5):582-591.
ArrayExpress Database Accession No. E-GEOD-46602 (Aug. 19, 2015) "Expression data from prostate cancer and benign prostate glands" EMBL-EBI [online]. Retrieved from: https://www.ebi.ac.uk/arrayexpress/experiments/E-GEOD-46602/; retrieved on May 23, 2019, 3 pages.
ArrayExpress Database Accession No. E-GEOD-46691 (Jul. 9, 2013) "Discovery and validation of a prostate cancer genomic classifier that predicts early metastasis following radical prostatectomy" EMBL-EBI [online]. Retrieved from: https://www.ebi.ac.uk/arrayexpress/experiments/E-GEOD-46691/; retrieved on May 23, 2019, 3 pages.
ArrayExpress Database Accession No. E-GEOD-62116 (May 25, 2016) "Validation of a genomic classifier that predicts metastasis following radical prostatectomy in at risk patient population" EMBL-EBI [online]. Retrieved from: https://www.ebi.ac.uk/arrayexpress/experiments/E-GEOD-62116/; retrieved on May 23, 2019, 4 pages.
ArrayExpress Database Accession No. E-GEOD-62667 (Nov. 30, 2014) "A genomic classifier improves prediction of metastatic disease within 5 years after surgery in node-negative high-risk prostate cancer patients managed by radical prostatectomy without adjuvant therapy" EMBL-EBI [online]. Retrieved from: https://www.ebi.ac.uk/arrayexpress/experiments/E-GEOD-62667/; retrieved on May 24, 2019, 2 pages.
ArrayExpress Database Accession No. E-GEOD-72220 (Mar. 11, 2016) "Application of a clinical assay for staging and prognosis of prostate cancer diagnosed in needle core biopsy specimens" EMBL-EBI [online]. Retrieved from: https://www.ebi.ac.uk/arrayexpress/experiments/E-GEOD-72220/; retrieved on May 24, 2019, 3 pages.
Barbieri, C.E. et al. (2012) "Exome sequencing identifies recurrent SPOP, FOXA1 and MED12 mutations in prostate cancer" *Nat Genet*, 44(6):685-689, plus 2 pages of supplementary information.
Cooperberg, M.R. et al. (Jun. 2005) "The University of California, San Francisco Cancer of the Prostate Risk Assessment Score: A Straightforward and Reliable Preoperative Predictor of Disease Recurrence After Radical Prostatectomy" *J Urol*, 173:1938-1942.
Cuzick, J. et al. (Mar. 2011) "Prognostic value of an RNA expression signature derived from cell cycle proliferation genes in patients with prostate cancer: a retrospective study" *Lancet Oncol*, 12:245-255.
Danila, D.C. et al. (2014) "Analytic and clinical validation of a prostate cancer-enhanced messenger RNA detection assay in whole blood as a prognostic biomarker for survival" *Eur Urol*, 65:1191-1197.
Day, J.R. et al. (2011) "PCA3: From basic molecular science to the clinical lab" *Cancer Lett*, 301:1-6.
Diaz-Uriarte, R. et al. (2006) "Gene selection and classification of microarray data using random forest" *BMC Bioinformatics*, 7:3; doi: 10.1186/1471-2105-7-3, 13 pages.
Erho, N. et al. (Jun. 2013) "Discovery and validation of a prostate cancer genomic classifier that predicts early metastasis following radical prostatectomy" *PLoS One*, 8(6):e66855; DOI: 10.1371/journal.pone.0066855, 12 pages.

(Continued)

*Primary Examiner* — Jehanne S Sitton
(74) *Attorney, Agent, or Firm* — Cooley LLP; Ivor R. Elrifi; Matthew Pavao

(57) ABSTRACT

The present invention is directed to methods for detecting a prostate cancer, methods for determining whether a prostate cancer is stable or progressive, low or high Gleason score, methods for differentiating benign prostate hyperplasia (BPH) from prostate cancer, methods for determining the completeness of surgery, and methods for evaluating the response to a prostate cancer therapy.

9 Claims, 12 Drawing Sheets
(9 of 12 Drawing Sheet(s) Filed in Color)
Specification includes a Sequence Listing.

(56) References Cited

OTHER PUBLICATIONS

Ferlay, J. et al. (2013) "Cancer incidence and mortality patterns in Europe: Estimates for 40 countries in 2012" *Eur J Cancer*, 49:1374-1403.
GenBank Accession No. DQ204772 (Nov. 2, 2005) "*Homo sapiens* TMPRSS2/ERGa fusion transcript", www.ncbi.nlm.nih.gov/nuccore/DQDQ204772.1; 1 printed page.
GenBank Accession No. NC_012920.1 (Oct. 31, 2014) "*Homo sapiens* mitochondrion, complete genome", www.ncbi.nlm.nih.gov/nuccore/NC_012920; 17 printed pages.
GenBank Accession No. NM_000044.3 (Jul. 9, 2016) "*Homo sapiens* androgen receptor (AR), transcript variant 1, mRNA", www.ncbi.nlm.nih.gov/nuccore/NM_000044.3; 10 printed pages.
GenBank Accession No. NM_000088.3 (Jun. 16, 2019) "*Homo sapiens* collagen type I alpha 1 chain (COL1A1), mRNA", www.ncbi.nlm.nih.gov/nuccore/NM_000088.3; 22 printed pages.
GenBank Accession No. NM_000141.4 (Jun. 4, 2019) "*Homo sapiens* fibroblast growth factor receptor 2 (FGFR2), transcript variant 1, mRNA" www.ncbi.nlm.nih.gov/nuccore/NM_000141.4; 11 printed pages.
GenBank Accession No. NM_000181.3 (Jul. 8, 2018) "*Homo sapiens* glucuronidase beta (GUSB), transcript variant 1, mRNA"; www.ncbi.nlm.nih.gov/nuccore/NM_000181.3; 5 printed pages.
GenBank Accession No. NM_000194.2 (Sep. 16, 2018) "*Homo sapiens* hypoxanthine phosphoribosyltransferase 1 (HPRT1), mRNA", www.ncbi.nlm.nih.gov/nuccore/NM_000194.2; 5 printed pages.
GenBank Accession No. NM_000291.3 (Oct. 20, 2018) "*Homo sapiens* phosphoglycerate kinase 1 (PGK1), mRNA", www.ncbi.nlm.nih.gov/nuccore/NM_000291.3; 8 pages.
GenBank Accession No. NM_001001891.3 (May 24, 2019) "*Homo sapiens* anoctamin 7 (ANO7), transcript variant NGEP-L, mRNA", www.ncbi.nlm.nih.gov/nuccore/NM_001001891.3; 7 printed pages.
GenBank Accession No. NM_001002.3 (Oct. 20, 2018) "*Homo sapiens* ribosomal protein lateral stalk subunit P0 (RPLP0), transcript variant 1, mRNA", www.ncbi.nlm.nih.gov/nuccore/NM_001002.3; 5 printed pages.
GenBank Accession No. NM_001002800.2 (Oct. 21, 2018) "*Homo sapiens* structural maintenance of chromosomes 4 (SMC4), transcript variant 2, mRNA", www.ncbi.nlm.nih.gov/nuccore/NM_001002800.2; 8 printed pages.
GenBank Accession No. NM_001020658.1 (Apr. 13, 2019) "*Homo sapiens* pumilio RNA binding family member 1 (PUM1), transcript variant 1, mRNA", www.ncbi.nlm.nih.gov/nuccore/NM_001020658.1; 11 printed pages.
GenBank Accession No. NM_001039675.1 (Jul. 6, 2019) "*Homo sapiens* unc-45 myosin chaperone A (UNC45A), transcript variant 3, mRNA", www.ncbi.nlm.nih.gov/nuccore/NM_001039675.1; 6 printed pages.
GenBank Accession No. NM_001077690.1 (Feb. 17, 2019) "*Homo sapiens* ALG9 alpha-1,2-mannosyltransferase (ALG9), transcript variant 2, mRNA", www.ncbi.nlm.nih.gov/nuccore/NM_001077690.1; 7 printed pages.
GenBank Accession No. NM_001087.4 (May 4, 2019) "*Homo sapiens* angio associated migratory cell protein (AAMP), transcript variant 2, mRNA", www.ncbi.nlm.nih.gov/nuccore/NM_001087.4; 5 printed pages.
GenBank Accession No. NM_001098514.2 (May 1, 2019) "*Homo sapiens* chromosome 16 open reading frame 89 (C16orf89), transcript variant 2, mRNA", www.ncbi.nlm.nih.gov/nuccore/NM_001098514.2; 3 printed pages.
GenBank Accession No. NM_001101.4 (Oct. 21, 2018) "*Homo sapiens* actin beta (ACTB), mRNA" www.ncbi.nlm.nih.gov/nuccore/NM_001101.4; 5 printed pages.
GenBank Accession No. NM_001128588.3 (Jan. 6, 2019) "*Homo sapiens* solute carrier family 14 member 1 (Kidd blood group) (SLC14A1), transcript variant 1, mRNA", www.ncbi.nlm.nih.gov/nuccore/NM_001128588.3; 6 printed pages.
GenBank Accession No. NM_001130110.1 (Feb. 24, 2019) "*Homo sapiens* SET binding protein 1 (SETBP1), transcript variant 2, mRNA", www.ncbi.nlm.nih.gov/nuccore/NM_001130110.1; 4 printed pages.
GenBank Accession No. NM_001145152.1 (Feb. 21, 2019) "*Homo sapiens* VPS37A subunit of ESCRT-I (VPS37A), transcript variant 2, mRNA" www.ncbi.nlm.nih.gov/nuccore/NM_001145152.1; 6 printed pages.
GenBank Accession No. NM_001166159.1 (Jul. 5, 2019) "*Homo sapiens* NADH:ubiquinone oxidoreductase core subunit S2 (NDUFS2), transcript variant 2, mRNA", www.ncbi.nlm.nih.gov/nuccore/NM_001166159.1; 5 printed pages.
GenBank Accession No. NM_001206612.1 (Jul. 6, 2019) "*Homo sapiens* chromatin target of PRMT1 (CHTOP), transcript variant 2, mRNA" www.ncbi.nlm.nih.gov/nuccore/NM_001206612.1; 6 printed pages.
GenBank Accession No. NM_001265603.1 (Jun. 8, 2019) "*Homo sapiens* mortality factor 4 like 1 (MORF4L1), transcript variant 3, mRNA" www.ncbi.nlm.nih.gov/nuccore/NM_001265603.1; 5 printed pages.
GenBank Accession No. NM_001270362.1 (Jul. 6, 2019) "*Homo sapiens* RAD23 homolog A, nucleotide excision repair protein (RAD23A), transcript variant 2, mRNA", www.ncbi.nlm.nih.gov/nuccore/NM_001270362.1; 6 printed pages.
GenBank Accession No. NM_001270768.1 (Jun. 4, 2019) "*Homo sapiens* striatin interacting protein 1 (STRIP1), transcript variant 2, mRNA", www.ncbi.nlm.nih.gov/nuccore/NM_001270768.1; 6 printed pages.
GenBank Accession No. NM_001282433.1 (Jun. 30, 2018) "*Homo sapiens* keratin 23 (KRT23), transcript variant 2, mRNA", www.ncbi.nlm.nih.gov/nuccore/NM_001282433.1; 5 printed pages.
GenBank Accession No. NM_001286272.1 (May 21, 2019) "*Homo sapiens* tumor protein, translationally-controlled 1 (TPT1), transcript variant 1, mRNA", www.ncbi.nlm.nih.gov/nuccore/NM_001286272.1; 6 printed pages.
GenBank Accession No. NM_001288727.1 (Jul. 6, 2019) "*Homo sapiens* PPARG related coactivator 1 (PPRC1), transcript variant 2, mRNA", www.ncbi.nlm.nih.gov/nuccore/NM_001288727.1; 5 printed pages.
GenBank Accession No. NM_001292038.1 (Oct. 9, 2018) "*Homo sapiens* mannosidase alpha class 2B member 2 (MAN2B2), transcript variant 2, mRNA", www.ncbi.nlm.nih.gov/nuccore/NM_001292038.1; 5 printed pages.
GenBank Accession No. NM_001303523.1 (Jun. 30, 2018) "*Homo sapiens* TOX high mobility group box family member 4 (TOX4), transcript variant 2, mRNA" www.ncbi.nlm.nih.gov/nuccore/NM_001303523.1; 5 printed pages.
GenBank Accession No. NM_001309443.1 (May 7, 2019) "*Homo sapiens* secreted protein acidic and cysteine rich (SPARC), transcript variant 2, mRNA", www.ncbi.nlm.nih.gov/nuccore/NM_001309443.1; 6 printed pages.
GenBank Accession No. NM_001320415.1 (Mar. 12, 2019) "*Homo sapiens* MYC associated factor X (MAX), transcript variant 11, mRNA", www.ncbi.nlm.nih.gov/nuccore/NM_001320415.1; 4 printed pages.
GenBank Accession No. NM_002046.6 (Oct. 21, 2018) "*Homo sapiens* glyceraldehyde-3-phosphate dehydrogenase (GAPDH), transcript variant 1, mRNA", www.ncbi.nlm.nih.gov/nuccore/NM_002046.6; 9 printed pages.
GenBank Accession No. NM_002151.2 (May 1, 2019) "*Homo sapiens* hepsin (HPN), transcript variant 2, mRNA", www.ncbi.nlm.nih.gov/nuccore/NM_002151.2; 5 printed pages.
GenBank Accession No. NM_002275.3 (Nov. 12, 2018) "*Homo sapiens* keratin 15 (KRT15), mRNA", www.ncbi.nlm.nih.gov/nuccore/NM_002275.3; 6 printed pages.
GenBank Accession No. NM_003054.4 (Apr. 15, 2018) "*Homo sapiens* solute carrier family 18 member A2 (SLC18A2), mRNA", www.ncbi.nlm.nih.gov/nuccore/NM_003054.4; 7 printed pages.
GenBank Accession No. NM_003129.3 (Nov. 11, 2018) "*Homo sapiens* squalene epoxidase (SQLE), mRNA", www.ncbi.nlm.nih.gov/nuccore/NM_003129.3; 5 printed pages.
GenBank Accession No. NM_003234.3 (May 7, 2019) "*Homo sapiens* transferrin receptor (TFRC), transcript variant 1, mRNA", www.ncbi.nlm.nih.gov/nuccore/NM_003234.3; 8 printed pages.

(56) References Cited

OTHER PUBLICATIONS

GenBank Accession No. NM_003406.3 (May 27, 2019) "*Homo sapiens* tyrosine 3-monooxygenase/tryptophan 5-monooxygenase activation protein zeta (YWHAZ), transcript variant 1, mRNA", www.ncbi.nlm.nih.gov/nuccore/NM_003406.3; 6 printed pages.
GenBank Accession No. NM_004048.2 (Mar. 29, 2018) "*Homo sapiens* beta-2-microglobulin (B2M), mRNA", www.ncbi.nlm.nih.gov/nuccore/NM_004048.2; 5 printed pages.
GenBank Accession No. NM_004168.3 (Oct. 21, 2018) "*Homo sapiens* succinate dehydrogenase complex flavoprotein subunit A (SDHA), transcript variant 1, mRNA" www.ncbi.nlm.nih.gov/nuccore/NM_004168.3; 9 printed pages.
GenBank Accession No. NM_004501.3 (Jul. 6, 2019) "*Homo sapiens* heterogeneous nuclear ribonucleoprotein U (HNRNPU), transcript variant 2, mRNA", www.ncbi.nlm.nih.gov/nuccore/NM_004501.3; 9 printed pages.
GenBank Accession No. NM_004628.4 (Jul. 2, 2019) "*Homo sapiens* XPC complex subunit, DNA damage recognition and repair factor (XPC), transcript variant 1, mRNA", www.ncbi.nlm.nih.gov/nuccore/NM_004628.4; 9 printed pages.
GenBank Accession No. NM_005128.3 (Feb. 24, 2019) "*Homo sapiens* DOP1 leucine zipper like protein B (DOP1B), transcript variant 2, mRNA", www.ncbi.nlm.nih.gov/nuccore/NM_005128.3; 8 printed pages.
GenBank Accession No. NM_005877.5 (Jun. 3, 2018) "*Homo sapiens* splicing factor 3a subunit 1 (SF3A1), mRNA", www.ncbi.nlm.nih.gov/nuccore/NM_005877.5; 8 printed pages.
GenBank Accession No. NM_006826.3 (Nov. 18, 2018) "*Homo sapiens* tyrosine 3-monooxygenase/tryptophan 5-monooxygenase activation protein theta (YWHAQ), mRNA", www.ncbi.nlm.nih.gov/nuccore/NM_006826.3; 6 printed pages.
GenBank Accession No. NM_012101.3 (Oct. 20, 2018) "*Homo sapiens* tripartite motif containing 29 (TRIM29), transcript variant 1, mRNA", www.ncbi.nlm.nih.gov/nuccore/NM_012101.3; 6 printed pages.
GenBank Accession No. NM_012423.3 (Oct. 20, 2018) "*Homo sapiens* ribosomal protein L13a (RPL13A), transcript variant 1, mRNA", www.ncbi.nlm.nih.gov/nuccore/NM_012423.3; 5 printed pages.
GenBank Accession No. NM_013261.3 (Jan. 29, 2016) "*Homo sapiens* PPARG coactivator 1 alpha (PPARGC1A), mRNA", www.ncbi.nlm.nih.gov/nuccore/NM_013261.3; 8 printed pages.
GenBank Accession No. NM_013318.3 (May 4, 2019) "*Homo sapiens* proline rich coiled-coil 2B (PRRC2B), mRNA", www.ncbi.nlm.nih.gov/nuccore/NM_013318.3; 11 printed pages.
GenBank Accession No. NM_013400.3 (May 4, 2019) "*Homo sapiens* replication initiator 1 (REPIN1), transcript variant 1, mRNA", www.ncbi.nlm.nih.gov/nuccore/NM_013400.3; 5 printed pages.
GenBank Accession No. NM_014329.4 (Oct. 21, 2018) "*Homo sapiens* enhancer of mRNA decapping 4 (EDC4), mRNA", www.ncbi.nlm.nih.gov/nuccore/NM_014329.4; 11 printed pages.
GenBank Accession No. NM_014763.3 (Nov. 11, 2018) "*Homo sapiens* mitochondrial ribosomal protein L19 (MRPL19), mRNA", www.ncbi.nlm.nih.gov/nuccore/NM_014763.3; 6 printed pages.
GenBank Accession No. NM_019056.6 (Apr. 1, 2019) "*Homo sapiens* NADH:ubiquinone oxidoreductase subunit B11 (NDUFB11), transcript variant 1, mRNA", www.ncbi.nlm.nih.gov/nuccore/NM_019056.6; 4 printed pages.
GenBank Accession No. NM_020195.2 (May 4, 2019) "*Homo sapiens* short chain dehydrogenase/reductase family 39U member 1 (SDR39U1), transcript variant 1, mRNA", www.ncbi.nlm.nih.gov/nuccore/NM_020195.2; 3 printed pages.
GenBank Accession No. NM_021130.4 (Nov. 18, 2018) "*Homo sapiens* peptidylprolyl isomerase A (PPIA), transcript variant 1, mRNA", www.ncbi.nlm.nih.gov/nuccore/NM_021130.4; 6 printed pages.
GenBank Accession No. NM_022006.1 (May 4, 2019) "*Homo sapiens* FXYD domain containing ion transport regulator 7 (FXYD7), mRNA", www.ncbi.nlm.nih.gov/nuccore/NM_022006.1; 3 printed pages.
GenBank Accession No. NM_022497.4 (Jul. 1, 2018) "*Homo sapiens* mitochondrial ribosomal protein S25 (MRPS25), transcript variant 1, mRNA", www.ncbi.nlm.nih.gov/nuccore/NM_022497.4; 4 printed pages.
GenBank Accession No. NM_024513.3 (Nov. 11, 2018) "*Homo sapiens* FYVE and coiled-coil domain containing 1 (FYCO1), mRNA", www.ncbi.nlm.nih.gov/nuccore/NM_024513.3; 8 printed pages.
GenBank Accession No. NM_031475.2 (Jul. 8, 2019) "*Homo sapiens* espin (ESPN), mRNA", www.ncbi.nlm.nih.gov/nuccore/NM_031475.2; 7 printed pages.
GenBank Accession No. NM_153001.2 (Jul. 5, 2019) "*Homo sapiens* proteasome 26S subunit, ATPase 4 (PSMC4), transcript variant 2, mRNA", www.ncbi.nlm.nih.gov/nuccore/NM_153001.2; 5 printed pages.
GenBank Accession No. NM_177424.2 (Nov. 12, 2018) "*Homo sapiens* syntaxin 12 (STX12), mRNA", www.ncbi.nlm.nih.gov/nuccore/NM_177424.2; 5 printed pages.
GenBank Accession No. X03205.1 (Dec. 16, 1994) "Human 18S ribosomal RNA", www.ncbi.nlm.nih.gov/nuccore/X03205.1; 4 printed pages.
Jemal, A. et al. (2015) "Prostate Cancer Incidence and PSA Testing Patterns in Relation to USPSTF Screening Recommendations" *JAMA*, 314:2054-2061.
Karnes, R.J. et al. (Dec. 2013) "Validation of a genomic classifier that predicts metastasis following radical prostatectomy in an at risk patient population" *J Urol*, 190:2047-2053.
Klein, E.A. et al. (Sep. 1, 2014) "A 17-gene Assay to Predict Prostate Cancer Aggressiveness in the Context of Gleason Grade Heterogeneity, Tumor Multifocality, and Biopsy Undersampling" *European Urology*, 66(3):550-560.
Knezevic, D. et al. (2013) "Analytical validation of the Oncotype DX prostate cancer assay—a clinical RT-PCR assay optimized for prostate needle biopsies" *BMC Genomics*, 14:690; DOI: 10.1186/471-2164-14-690, 12 pages.
Kohli, M. et al. (2015) "Whole blood defensin mRNA expression is a predictive biomarker of docetaxel response in casutation-resistant prostate cancer" *OncoTargets Ther*, 8:1915-1922.
Lalonde, E. et al. (2014) "Tumour genomic and microenvironmental heterogeneity for integrated prediction of 5-year biochemical recurrence of prostate cancer: a retrospective cohort study" *Lancet Oncol*, 15:1521-1532.
Nam, R.K. et al. (2018) "Next-generation prostate cancer risk calculator for primary care physicians" *Can Urol Assoc J*, 12(2):E64-E70.
Olmos, D. et al. (2012) "Prognostic value of blood mRNA expression signatures in castration-resistant prostate cancer: a prospective, two-stage study" *Lancet Oncol*, 13:1114-1124.
Pettersson, A. et al. (Jun. 26, 2012) "The TMPRSS2:ERG Rearrangement, ERG Expression, and Prostate Cancer Outcomes: A Cohort Study and Meta-analysis" *Cancer Epidemiol Biomarkers Prev*, 21(9):1497-1509.
Ross, R.W. et al. (Nov. 2012) "A whole-blood RNA transcript-based prognostic model in men with castration-resistant prostate cancer: a prospective study" *Lancet Oncol*, 13:1105-1113.
Schröder, F.H. et al. (2008) "Early detection of prostate cancer in 2007. Part 1: PSA and PSA kinetics" *Eur Urol*, 53:468-477.
Schröder, F.H. et al. (Dec. 6, 2014) "Screening and prostate cancer mortality: results of the European Randomised Study of Screening for Prostate Cancer (ERSPC) at 13 years of follow-up" *Lancet*, 384:2027-2035.
Stewart, G.D. et al. (Mar. 2013) "Clinical utility of an epigenetic assay to detect occult prostate cancer in histopathologically negative biopsies: results of the MATLOC study" *J Urol*, 189:1110-1116.
The Cancer Genome Atlas Research Network (2015) "The Molecular Taxonomy of Primary Prostate Cancer" *Cell*, 163:1011-1025.
Tomlins, S.A. et al. (2005) "Recurrent fusion of TMPRSS2 and ETS transcription factor genes in prostate cancer" *Science*, 310:644-648.
Troyer, D.A. et al. (2009) "Prostate cancer detected by methylated gene markers in histopathologically cancer-negative tissues from men with subsequent positive biopsies" *Cancer Epidemiol Biomarkers Prev*, 18:2717-2722.

(56) References Cited

OTHER PUBLICATIONS

Van Neste, L. et al. (2016) "Risk score predicts high-grade prostate cancer in DNA-methylation positive, histopathologically negative biopsies" *Prostate*, 76:1078-1087.
Velonas, V.M. et al. (2013) "Current status of biomarkers for prostate cancer" *Int J Mol Sci*, 14:11034-11060.
Wang, L. et al. (2015) "A robust blood gene expression-based prognostic model for castration-resistant prostate cancer" *BMC Med*, 13:201, DOI: 10.1186/s12916-015-0442-0, 15 pages.
Zhao, S.G. et al. (2015) "The Landscape of Prognostic Outlier Genes in High-Risk Prostate Cancer" *Clin Cancer Res*, 22:1777-1786.
Zhao, S.G. et al. (Nov. 2016) "Development and validation of a 24-gene predictor of response to postoperative radiotherapy in prostate cancer: a matched, retrospective analysis" *Lancet Oncol*, 17:1612-1620.

* cited by examiner

SEQUENCE LISTING

<160> NUMBER OF SEQ ID NOS: 65

<210> SEQ ID NO 1
<211> LENGTH: 1842
<212> TYPE: DNA
<213> ORGANISM: Homo sapiens

<400> SEQUENCE: 1
ctgctgggga gtcgcctacg cctacttcct gccgggagga ggggctcgag ttccgcgtcg 60
tcgcgcagag ctgactctgg gaggcgtttg ggcccagaga agtggatccg ccgcttgcgc 120
cgcatggagt ccgaatcgga aagcggggct gctgctgaca cccccccact ggagacccta 180
agcttccatg gtgatgaaga gattatcgag gtggtagaac ttgatcccgg tccgccggac 240
ccagatgacc tggcccagga gatggaagat gtggactttg aggaagaaga ggaggaagag 300
ggcaacgaag agggctgggt tctagaaccc caggaagggg tggtcggcag catggagggc 360
cccgacgata gcgaggtcac ctttgcattg cactcagcat ctgtgttttg tgtgagcctg 420
gaccccaaga ccaatacctt ggcagtgacc gggggtgaag atgacaaagc cttcgtatgg 480
cggctcagcg atggggagct gctctttgag tgtgcaggcc ataaagactc tgtgacttgt 540
gctggtttca gccatgactc cactctagtg gccacagggg acatgagtgg cctcttgaaa 600
gtgtggcagg tggacactaa ggaggaggtc tggtcctttg aagcgggaga cctggagtgg 660
atggagtggc atcctcgggc acctgtcctg ttggcgggca cagctgacgg caacacctgg 720
atgtggaaag tcccgaatgg tgactgcaag accttccagg gtcccaactg cccagccacc 780
tgtggccgag tcctccctga tgggaagaga gctgtggtag gctatgaaga tgggaccatc 840
aggatttggg acctgaagca gggaagccct atccatgtac tgaaagggac tgagggtcac 900
cagggcccac tcacctgtgt tgctgccaac caggatggca gcttgatcct aactggctct 960
gtggactgcc aggccaagct ggtcagtgcc accaccggca aggtggtggg tgtttttaga 1020
cctgagactg tggcctccca gcccagcctg ggagaagggg aggagagtga gtccaactcg 1080
gtggagtcct tgggcttctg cagtgtgatg cccctggcag ctgttggcta cctggatggg 1140
accttggcca tctatgacct ggctacgcag actcttaggc atcagtgtca gcaccagtcg 1200
ggcatcgtgc agctgctgtg ggaggcaggc actgccgtgg tatatacctg cagcctggat 1260
ggcatcgtgc gcctctggga cgcccggacc ggccgcctgc ttactgacta ccggggccac 1320
acggctgaga tcctggactt tgccctcagc aaagatgcct ccctggtggt gaccacgtca 1380
ggagaccaca aagcgaaagt attttgtgtc caaaggcctg accgttaatg gctgcagccc 1440
ctgcctgtgt gtctggtgtt gaggggacga agggacccct gcccctgtct gccagcagag 1500
gcagtagggc acagagggaa gaggagggtg gggccctgga tgactttcca gcctcttcaa 1560
ctgacttgct cccctctcct tttcttctct ttagagaccc agcccagggc cctcccaccc 1620
ttgtccagac ctggtgggcc cttcagaggg aggggtggac ctgtttctct ttcactttca 1680
tttgctggtg tgagccatgg ggtgtgtatt tgtatgtggg gagtaggtgt ttgaggttcc 1740
cgttctttcc cttcccaagt ctctgggggt ggaaaggagg aagagatact agttaaagat 1800
tttaaaaatg taaataaaat atacttccca gaaaaaaaaa aa 1842

<210> SEQ ID NO 2
<211> LENGTH: 4128
<212> TYPE: DNA

<213> ORGANISM: Homo sapiens

<400> SEQUENCE: 2

```
aaagatagat cctgctccag gagccgggaa gccttgccct ggccagctgt gctgggcacc     60
tcccctgcct gcttcctggc ccacttgcag gcaaggtgag ggcatgcgaa tggctgccac    120
tgcctgggcg gggctccaag ggccacccct ccccaccctc tgtcccgcag tgaggacggg    180
actctactgc cgagaccagg ctcacgctga gaggtgggcc atgacctccg agacctcttc    240
cggaagccac tgtgccagga gcaggatgct gcggcgacgg gcccaggaag aggacagcac    300
cgtcctgatc gatgtgagcc cccctgaggc agagaagagg ggctcttacg ggagcacagc    360
ccacgcctcg gagccaggtg gacagcaagc ggccgcctgc agagctggga gtcctgccaa    420
gccccggatc gcagacttcg tcctcgtttg ggaggaggac ctgaagctag acaggcagca    480
ggacagtgcc gcccgggaca gaacagacat gcacaggacc tggcgggaga cttttctgga    540
taatcttcgt gcggctgggc tgtgtgtaga ccagcaggac gtccaggacg ggaacaccac    600
agtgcactac gccctcctca gcgcctcctg ggctgtgctc tgctactacg ccgaagacct    660
gcgcctgaag ctgcccttgc aggagttacc caaccaggcc tccaactggt cggccggcct    720
gctggcatgg ctgggcatcc ccaacgtcct gctggaggtt gtgccagacg taccccccga    780
gtactactcc tgccggttca gagtgaacaa gctgccacgc ttcctcggga gtgacaacca    840
ggacaccttc ttcacaagca ccaagaggca ccaaattctg tttgagatcc tggccaagac    900
cccgtatggc cacgagaaga aaaacctgct tgggatccac cagctgctgg cagagggtgt    960
cctcagtgcc gccttccccc tgcatgacgg cccctacaag acgcccccag agggcccgca   1020
ggctccacgc ctcaaccagc gccaagtcct tttccagcac tggggcgcgct ggggcaagtg   1080
gaacaagtac cagcccctgg accacgtgcg caggtacttc ggggagaagg tggccctcta   1140
cttcgcctgg ctcgggtttt acacaggctg gctcctgcca gcggcagtgg tgggcacact   1200
ggtgttcctg gtgggctgct tcctggtgtt ctcagacata cccacgcagg aactgtgtgg   1260
cagcaaggac agcttcgaga tgtgcccact ttgcctcgac tgccctttct ggctgctctc   1320
cagcgcctgt gccctggccc aggccggccg gctgttcgac cacggcggca ccgtgttctt   1380
cagcttgttc atggcactgt gggccgtgct gctgctggag tactggaagc ggaagagcgc   1440
cacgctggcc taccgctggg actgctctga ctacgaggac actgaggaga ggcctcggcc   1500
ccagtttgcc gcctcagccc ccatgacagc cccgaacccc atcacgggtg aggacgagcc   1560
ctacttccct gagaggagcc gcgcgcgccg catgctggcc ggctctgtgg tgatcgtggt   1620
gatggtggcc gtggtggtca tgtgcctcgt gtctatcatc ctgtaccgtg ccatcatggc   1680
catcgtggtg tccaggtcgg gcaacaccct tctcgcagcc tggggcctctc gcatcgccag   1740
cctcacgggg tctgtagtga acctcgtctt catcctcatc ctctccaaga tctatgtatc   1800
cctggcccac gtcctgacac gatgggaaat gcaccgcacc cagaccaagt tcgaggacgc   1860
cttcaccctc aaggtgttca tcttccagtt cgtcaacttc tactcctcac ccgtctacat   1920
tgccttcttc aagggcaggt ttgtgggata cccaggcaac taccacacct tgtttggagt   1980
ccgcaatgag gagtgcgcgg ctggaggctg cctgatcgag ctggcacagg agctcctggt   2040
catcatggtg ggcaagcagg tcatcaacaa catgcaggag gtcctcatcc cgaagctaaa   2100
gggctggtgg cagaagttcc ggcttcgctc caagaagagg aaggcgggag cttctgcagg   2160
ggctagccag gggccctggg aggacgacta tgagcttgtg ccctgtgagg gtctgtttga   2220
cgagtacctg gaaatggtgc tgcagttcgg cttcgtcacc atcttcgtgg ccgcctgtcc   2280
```

```
gctcgcgccg ctcttcgccc tgctcaacaa ctgggtggag atccgcttgg acgcgcgcaa   2340

gttcgtctgc gagtaccggc gcccggtggc cgagcgcgcc caggacatcg gcatctggtt   2400

ccacatcctg gcgggcctca cgcacctggc ggtcatcagc aacgccttcc tcctggcctt   2460

ctcgtccgac ttcctgccgc gcgcctacta ccggtggacc cgcgcccacg acctgcgcgg   2520

cttcctcaac ttcacgctgg cgcgagcccc gtcctccttc gccgccgcgc acaaccgcac   2580

gtgcaggtat cgggctttcc gggatgacga tggacattat tcccagacct actggaatct   2640

tcttgccatc cgcctggcct tcgtcattgt gtttgagcat gtggttttct ccgttggccg   2700

cctcctggac ctcctggtgc ctgacatccc agagtctgtg gagatcaaag tgaagcggga   2760

gtactacctg gctaagcagg cactggctga gaatgaggtt ctttttggaa cgaacggaac   2820

aaaggatgag cagcccgagg gctcagagct cagctcccac tggacaccct tcacggttcc   2880

caaggccagc cagctgcagc agtgacgcct ggaaggacat ctggtggtcc ttaggggagt   2940

ggcccctcct gagccctgcg agcagcgtcc ttttcctctt ccctcaggca gcggctgtgt   3000

gaaccgctgg ctgctgttgt gcctcatctc tgggcacatt gcctgcttcc ccccagcgcc   3060

ggcttctctc ctcagagcgc ctgtcactcc atccccggca gggagggacc gtcagctcac   3120

aaggccctct ttgtttcctg ctcccagaca taagcccaag ggcccctgc acccaaggga    3180

ccctgtccct cggtggcctc cccaggcccc tggacacgac agttctcctc aggcaggtgg   3240

gctttgtggt cctcgccgcc cctggccaca tcgccctctc ctcttacacc tggtgacctt   3300

cgaatgtttc agagcgcagg gccgttctcc ctcgtgtcct ctggacccac ccgccccttc   3360

ctgccctgtt tgcgcaggga catcacccac atgccccagc tctcggaccc tgcagctctg   3420

tgtcccaggc cacagcaaag gtctgttgaa cccctccctc cattcccagt tatctgggtc   3480

ctctggattc ttctgtttct tgaatcaggc tctgctttcc ccctagccac tacaggcagc   3540

ctctgacagt gccgctttac ttgcattctg cagcaattac atgtgtcctt ttgatccttg   3600

cccaacttcc ctccctctcc cagctcctgg cccctggccc agggcccctc ttgctgtttt   3660

tacctctgtt ccttggggcc tagtacccag caagcaccca aatgggggag gttttgggat   3720

gagaggagga aacgtgtata cctgtaacat ctggtggctc ttcccccaga agtttgtgtt   3780

catacataat tgttttccac gctggatcat aatgtgacgt gcagttctgc cctgtgctgg   3840

ggagccacat gaagcttccc ctggctaact tgctaccccg cagcaatccc agtgtggccg   3900

tctgcttgct aaaaaatgga tctgtgctca tctgtattga tgtccttgga gttctacaag   3960

tggaacttaa gtgtcaaaaa gaatatgtgg tttttagctg agcgtggtgg ctcacacctg   4020

taatcccagg actttgggag gctgaggcag gaggattaca aggtcaggag ttcgggacta   4080

gcctgtccaa catggtgaaa ccctgtcttt actaaaaatg caaaaatt               4128
```

<210> SEQ ID NO 3
<211> LENGTH: 10661
<212> TYPE: DNA
<213> ORGANISM: Homo sapiens

<400> SEQUENCE: 3

```
cgagatcccg gggagccagc ttgctgggag agcgggacgg tccggagcaa gcccagaggc     60

agaggaggcg acagagggaa aaagggccga gctagccgct ccagtgctgt acaggagccg    120

aagggacgca ccacgccagc cccagcccgg ctccagcgac agccaacgcc tcttgcagcg    180

cggcggcttc gaagccgccg cccggagctg ccctttcctc ttcggtgaag tttttaaaag    240
```

```
ctgctaaaga ctcggaggaa gcaaggaaag tgcctggtag gactgacggc tgcctttgtc    300
ctcctcctct ccaccccgcc tccccccacc ctgccttccc cccctccccc gtcttctctc    360
ccgcagctgc ctcagtcggc tactctcagc caacccccct caccaccctt ctccccaccc    420
gccccccgc ccccgtcggc ccagcgctgc cagcccgagt ttgcagagag gtaactccct    480
ttggctgcga gcgggcgagc tagctgcaca ttgcaaagaa ggctcttagg agccaggcga    540
ctggggagcg gcttcagcac tgcagccacg acccgcctgg ttaggctgca cgcggagaga    600
accctctgtt ttcccccact ctctctccac ctcctcctgc cttccccacc ccgagtgcgg    660
agccagagat caaaagatga aaaggcagtc aggtcttcag tagccaaaaa acaaaacaaa    720
caaaaacaaa aaagccgaaa taaaagaaaa agataataac tcagttctta tttgcaccta    780
cttcagtgga cactgaattt ggaaggtgga ggattttgtt tttttctttt aagatctggg    840
catcttttga atctaccctt caagtattaa gagacagact gtgagcctag cagggcagat    900
cttgtccacc gtgtgtcttc ttctgcacga gactttgagg ctgtcagagc gctttttgcg    960
tggttgctcc cgcaagtttc cttctctgga gcttcccgca ggtgggcagc tagctgcagc   1020
gactaccgca tcatcacagc ctgttgaact cttctgagca agagaagggg aggcggggta   1080
agggaagtag gtggaagatt cagccaagct caaggatgga agtgcagtta gggctgggaa   1140
gggtctaccc tcggccgccg tccaagacct accgaggagc tttccagaat ctgttccaga   1200
gcgtgcgcga agtgatccag aacccgggcc ccaggcaccc agaggccgcg agcgcagcac   1260
ctcccggcgc cagtttgctg ctgctgcagc agcagcagca gcagcagcag cagcagcagc   1320
agcagcagca gcagcagcag cagcagcagc agcaagagac tagccccagg cagcagcagc   1380
agcagcaggg tgaggatggt tctccccaag cccatcgtag aggccccaca ggctacctgg   1440
tcctggatga ggaacagcaa ccttcacagc cgcagtcggc cctggagtgc caccccgaga   1500
gaggttgcgt cccagagcct ggagccgccg tggccgccag caaggggctg ccgcagcagc   1560
tgccagcacc tccggacgag gatgactcag ctgccccatc cacgttgtcc ctgctgggcc   1620
ccactttccc cggcttaagc agctgctccg ctgaccttaa agacatcctg agcgaggcca   1680
gcaccatgca actccttcag caacagcagc aggaagcagt atccgaaggc agcagcagcg   1740
ggagagcgag ggaggcctcg gggctcccca cttcctccaa ggacaattac ttagggggca   1800
cttcgaccat ttctgacaac gccaaggagt tgtgtaaggc agtgtcggtg tccatgggcc   1860
tgggtgtgga ggcgttggag catctgagtc caggggaaca gcttcggggg gattgcatgt   1920
acgccccact tttgggagtt ccacccgctg tgcgtcccac tccttgtgcc ccattggccg   1980
aatgcaaagg ttctctgcta gacgacagcg caggcaagag cactgaagat actgctgagt   2040
attccccttt caagggaggt tacaccaaag ggctagaagg cgagagccta ggctgctctg   2100
gcagcgctgc agcagggagc tccgggacac ttgaactgcc gtctaccctg tctctctaca   2160
agtccggagc actggacgag gcagctgcgt accagagtcg cgactactac aactttccac   2220
tggctctggc cggaccgccg ccccctccgc cgcctcccca tccccacgct cgcatcaagc   2280
tggagaaccc gctggactac ggcagcgcct gggcggctgc ggcggcgcag tgccgctatg   2340
gggacctggc gagcctgcat ggcgcgggtg cagcgggacc cggttctggg tcaccctcag   2400
ccgccgcttc ctcatcctgg cacactctct tcacagccga agaaggccag ttgtatggac   2460
cgtgtggtgg tggtgggggt ggtggcggcg gcggcggcgg cggcggcggc ggcggcggcg   2520
gcggcggcgg cggcgaggcg ggagctgtag ccccctacgg ctacactcgg ccccctcagg   2580
ggctggcggg ccaggaaagc gacttcaccg cacctgatgt gtggtaccct ggcggcatgg   2640
```

```
tgagcagagt gccctatccc agtcccactt gtgtcaaaag cgaaatgggc ccctggatgg   2700
atagctactc cggaccttac ggggacatgc gtttggagac tgccagggac catgttttgc   2760
ccattgacta ttactttcca ccccagaaga cctgcctgat ctgtggagat gaagcttctg   2820
ggtgtcacta tggagctctc acatgtggaa gctgcaaggt cttcttcaaa agagccgctg   2880
aagggaaaca gaagtacctg tgcgccagca gaaatgattg cactattgat aaattccgaa   2940
ggaaaaattg tccatcttgt cgtcttcgga aatgttatga agcagggatg actctgggag   3000
cccggaagct gaagaaactt ggtaatctga aactacagga ggaaggagag gcttccagca   3060
ccaccagccc cactgaggag acaacccaga agctgacagt gtcacacatt gaaggctatg   3120
aatgtcagcc catctttctg aatgtcctgg aagccattga gccaggtgta gtgtgtgctg   3180
gacacgacaa caaccagccc gactcctttg cagccttgct ctctagcctc aatgaactgg   3240
gagagagaca gcttgtacac gtggtcaagt gggccaaggc cttgcctggc ttccgcaact   3300
tacacgtgga cgaccagatg gctgtcattc agtactcctg gatggggctc atggtgtttg   3360
ccatgggctg gcgatccttc accaatgtca actccaggat gctctacttc gcccctgatc   3420
tggttttcaa tgagtaccgc atgcacaagt cccggatgta cagccagtgt gtccgaatga   3480
ggcacctctc tcaagagttt ggatggctcc aaatcacccc ccaggaattc ctgtgcatga   3540
aagcactgct actcttcagc attattccag tggatgggct gaaaaatcaa aaattctttg   3600
atgaacttcg aatgaactac atcaaggaac tcgatcgtat cattgcatgc aaaagaaaaa   3660
atcccacatc ctgctcaaga cgcttctacc agctcaccaa gctcctggac tccgtgcagc   3720
ctattgcgag agagctgcat cagttcactt ttgacctgct aatcaagtca cacatggtga   3780
gcgtggactt tccggaaatg atggcagaga tcatctctgt gcaagtgccc aagatccttt   3840
ctgggaaagt caagcccatc tatttccaca cccagtgaag cattggaaac cctatttccc   3900
caccccagct catgcccccct ttcagatgtc ttctgcctgt tataactctg cactactcct   3960
ctgcagtgcc ttggggaatt tcctctattg atgtacagtc tgtcatgaac atgttcctga   4020
attctatttg ctgggctttt tttttctctt tctctccttt ctttttcttc ttccctccct   4080
atctaaccct cccatggcac cttcagactt tgcttcccat tgtggctcct atctgtgttt   4140
tgaatggtgt tgtatgcctt taaatctgtg atgatcctca tatggcccag tgtcaagttg   4200
tgcttgttta cagcactact ctgtgccagc cacacaaacg tttacttatc ttatgccacg   4260
ggaagtttag agagctaaga ttatctgggg aaatcaaaac aaaaacaagc aaacaaaaaa   4320
aaaaagcaaa aacaaaacaa aaaataagcc aaaaaacctt gctagtgttt tttcctcaaa   4380
aataaataaa taaataaata aatacgtaca tacatacaca catacataca aacatataga   4440
aatccccaaa gaggccaata gtgacgagaa ggtgaaaatt gcaggcccat ggggagttac   4500
tgattttttc atctcctccc tccacgggag actttatttt ctgccaatgg ctattgccat   4560
tagagggcag agtgacccca gagctgagtt gggcaggggg gtggacagag aggagaggac   4620
aaggagggca atggagcatc agtacctgcc cacagccttg gtccctgggg gctagactgc   4680
tcaactgtgg agcaattcat tatactgaaa atgtgcttgt tgttgaaaat ttgtctgcat   4740
gttaatgcct cacccccaaa cccttttctc tctcactctc tgcctccaac ttcagattga   4800
ctttcaatag tttttctaag acctttgaac tgaatgttct cttcagccaa aacttggcga   4860
cttccacaga aaagtctgac cactgagaag aaggagagca gagatttaac cctttgtaag   4920
gccccatttg gatccaggtc tgctttctca tgtgtgagtc agggaggagc tggagccaga   4980
```

```
ggagaagaaa atgatagctt ggctgttctc ctgcttagga cactgactga atagttaaac   5040
tctcactgcc actacctttt ccccaccttt aaaagacctg aatgaagttt tctgccaaac   5100
tccgtgaagc cacaagcacc ttatgtcctc ccttcagtgt tttgtgggcc tgaatttcat   5160
cacactgcat ttcagccatg gtcatcaagc ctgtttgctt cttttgggca tgttcacaga   5220
ttctctgtta agagccccca ccaccaagaa ggttagcagg ccaacagctc tgacatctat   5280
ctgtagatgc cagtagtcac aaagatttct taccaactct cagatcgctg gagcccttag   5340
acaaactgga aagaaggcat caaagggatc aggcaagctg ggcgtcttgc ccttgtcccc   5400
cagagatgat accctcccag caagtggaga agttctcact tccttcttta gagcagctaa   5460
aggggctacc cagatcaggg ttgaagagaa aactcaatta ccagggtggg aagaatgaag   5520
gcactagaac cagaaaccct gcaaatgctc ttcttgtcac ccagcatatc cacctgcaga   5580
agtcatgaga agagagaagg aacaaagagg agactctgac tactgaatta aaatcttcag   5640
cggcaaagcc taaagccaga tggacaccat ctggtgagtt tactcatcat cctcctctgc   5700
tgctgattct gggctctgac attgcccata ctcactcaga ttccccacct ttgttgctgc   5760
ctcttagtca gagggaggcc aaaccattga gactttctac agaaccatgg cttctttcgg   5820
aaaggtctgg ttggtgtggc tccaatactt tgccacccat gaactcaggg tgtgccctgg   5880
gacactggtt ttatatagtc ttttggcaca cctgtgttct gttgacttcg ttcttcaagc   5940
ccaagtgcaa gggaaaatgt ccacctactt tctcatcttg gcctctgcct ccttacttag   6000
ctcttaatct catctgttga actcaagaaa tcaagggcca gtcatcaagc tgcccatttt   6060
aattgattca ctctgtttgt tgagaggata gtttctgagt gacatgatat gatccacaag   6120
ggtttccttc cctgatttct gcattgatat taatagccaa acgaacttca aaacagcttt   6180
aaataacaag ggagagggga acctaagatg agtaatatgc caatccaaga ctgctggaga   6240
aaactaaagc tgacaggttc ccttttttggg gtgggataga catgttctgg ttttctttat   6300
tattacacaa tctggctcat gtacaggatc acttttagct gttttaaaca gaaaaaaata   6360
tccaccactc ttttcagtta cactaggtta cattttaata ggtcctttac atctgttttg   6420
gaatgatttt catcttttgt gatacacaga ttgaattata tcattttcat atctctcctt   6480
gtaaatacta gaagctctcc tttacatttc tctatcaaat ttttcatctt tatgggtttc   6540
ccaattgtga ctcttgtctt catgaatata tgtttttcat ttgcaaaagc caaaaaatcag   6600
tgaaacagca gtgtaattaa aagcaacaac tggattactc caaatttcca aatgacaaaa   6660
ctagggaaaa atagcctaca caagccttta ggcctactct ttctgtgctt gggtttgagt   6720
gaacaaagga gattttagct tggctctgtt ctcccatgga tgaaaggagg aggatttttt   6780
ttttcttttg gccattgatg ttctagccaa tgtaattgac agaagtctca ttttgcatgc   6840
gctctgctct acaaacagag ttggtatggt tggtatactg tactcacctg tgagggactg   6900
gccactcaga cccacttagc tggtgagcta gaagatgagg atcactcact ggaaaagtca   6960
caaggaccat ctccaaacaa gttggcagtg ctcgatgtgg acgaagagtg aggaagagaa   7020
aaagaaggag caccagggag aaggctccgt ctgtgctggg cagcagacag ctgccaggat   7080
cacgaactct gtagtcaaag aaaagagtcg tgtggcagtt tcagctctcg ttcattgggc   7140
agctcgccta ggcccagcct ctgagctgac atgggagttg ttggattctt tgtttcatag   7200
ctttttctat gccataggca atattgttgt tcttggaaag tttattattt ttttaactcc   7260
cttactctga gaaagggata ttttgaagga ctgtcatata tctttgaaaa aagaaaatct   7320
gtaatacata tatttttatg tatgttcact ggcactaaaa aatatagaga gcttcattct   7380
```

```
gtcctttggg tagttgctga ggtaattgtc caggttgaaa aataatgtgc tgatgctaga   7440
gtccctctct gtccatactc tacttctaaa tacatatagg catacatagc aagttttatt   7500
tgacttgtac tttaagagaa aatatgtcca ccatccacat gatgcacaaa tgagctaaca   7560
ttgagcttca agtagcttct aagtgtttgt ttcattaggc acagcacaga tgtggccttt   7620
ccccccttct ctcccttgat atctggcagg gcataaaggc ccaggccact tcctctgccc   7680
cttcccagcc ctgcaccaaa gctgcatttc aggagactct ctccagacag cccagtaact   7740
acccgagcat ggcccctgca tagccctgga aaaataagag gctgactgtc tacgaattat   7800
cttgtgccag ttgcccaggt gagagggcac tgggccaagg gagtggtttt catgtttgac   7860
ccactacaag gggtcatggg aatcaggaat gccaaagcac cagatcaaat ccaaaactta   7920
aagtcaaaat aagccattca gcatgttcag tttcttggaa aaggaagttt ctacccctga   7980
tgcctttgta ggcagatctg ttctcaccat taatcttttt gaaaatcttt taaagcagtt   8040
tttaaaaaga gagatgaaag catcacatta tataaccaaa gattacattg tacctgctaa   8100
gataccaaaa ttcataaggg caggggggga gcaagcatta gtgcctcttt gataagctgt   8160
ccaaagacag actaaaggac tctgctggtg actgacttat aagagctttg tgggtttttt   8220
tttccctaat aatatacatg tttagaagaa ttgaaaataa tttcgggaaa atgggattat   8280
gggtccttca ctaagtgatt ttataagcag aactggcttt ccttttctct agtagttgct   8340
gagcaaattg ttgaagctcc atcattgcat ggttggaaat ggagctgttc ttagccactg   8400
tgtttgctag tgcccatgtt agcttatctg aagatgtgaa acccttgctg ataagggagc   8460
atttaaagta ctagattttg cactagaggg acagcaggca gaaatcctta tttctgccca   8520
ctttggatgg cacaaaaagt tatctgcagt tgaaggcaga aagttgaaat acattgtaaa   8580
tgaatatttg tatccatgtt tcaaaattga aatatatata tatatatata tatatatata   8640
tatatatata tagtgtgtgt gtgtgttctg atagctttaa ctttctctgc atctttatat   8700
ttggttccag atcacacctg atgccatgta cttgtgagag aggatgcagt tttgttttgg   8760
aagctctctc agaacaaaca agacacctgg attgatcagt taactaaaag ttttctcccc   8820
tattgggttt gacccacagg tcctgtgaag gagcagaggg ataaaaagag tagaggacat   8880
gatacattgt actttactag ttcaagacag atgaatgtgg aaagcataaa aactcaatgg   8940
aactgactga gatttaccac agggaaggcc caaacttggg gccaaaagcc tacccaagtg   9000
attgaccagt ggccccctaa tggacctgaa gctgttggaa gaagagaact gttccttggt   9060
cttcaccatc cttgtgagag aagggcagtt tcctgcattg gaacctggag caagcgctct   9120
atctttcaca caaattccct cacctgagat tgaggtgctc ttgttactgg gtgtctgtgt   9180
gctgtaattc tggttttgga tatgttctgt aaagattttg acaaatgaaa atgtgttttt   9240
ctctgttaaa acttgtcaga gtactagaag ttgtatctct gtaggtgcag gtccatttct   9300
gcccacaggt agggtgtttt tctttgatta agagattgac acttctgttg cctaggacct   9360
cccaactcaa ccatttctag gtgaaggcag aaaaatccac attagttact cctcttcaga   9420
catttcagct gagataacaa atcttttgga attttttcac ccatagaaag agtggtagat   9480
atttgaattt agcaggtgga gtttcatagt aaaaacagct tttgactcag ctttgattta   9540
tcctcatttg atttggccag aaagtaggta atatgcattg attggcttct gattccaatt   9600
cagtatagca aggtgctagg ttttttcctt tccccacctg tctcttagcc tggggaatta   9660
aatgagaagc cttagaatgg gtggcccttg tgacctgaaa cacttcccac ataagctact   9720
```

```
taacaagatt gtcatggagc tgcagattcc attgcccacc aaagactaga acacacacat   9780
atccatacac caaaggaaag acaattctga aatgctgttt ctctggtggt tccctctctg   9840
gctgctgcct cacagtatgg gaacctgtac tctgcagagg tgacaggcca gatttgcatt   9900
atctcacaac cttagccctt ggtgctaact gtcctacagt gaagtgcctg gggggttgtc   9960
ctatcccata agccacttgg atgctgacag cagccaccat cagaatgacc cacgcaaaaa  10020
aaagaaaaaa aaaattaaaa agtcccctca caacccagtg acacctttct gctttcctct  10080
agactggaac attgattagg gagtgcctca gacatgacat tcttgtgctg tccttggaat  10140
taatctggca gcaggaggga gcagactatg taaacagaga taaaaattaa ttttcaatat  10200
tgaaggaaaa aagaaataag aagagagaga gaaagaaagc atcacacaaa gattttctta  10260
aaagaaacaa ttttgcttga aatctcttta gatggggctc atttctcacg gtggcacttg  10320
gcctccactg ggcagcagga ccagctccaa gcgctagtgt tctgttctct ttttgtaatc  10380
ttggaatctt ttgttgctct aaatacaatt aaaaatggca gaaacttgtt tgttggacta  10440
catgtgtgac tttgggtctg tctctgcctc tgctttcaga aatgtcatcc attgtgtaaa  10500
atattggctt actggtctgc cagctaaaac ttggccacat cccctgttat ggctgcagga  10560
tcgagttatt gttaacaaag agacccaaga aaagctgcta atgtcctctt atcattgttg  10620
ttaatttgtt aaaacataaa gaaatctaaa atttcaaaaa a                      10661
```

<210> SEQ ID NO 4
<211> LENGTH: 3641
<212> TYPE: DNA
<213> ORGANISM: Homo sapiens

<400> SEQUENCE: 4

```
gacactgaat ttggaaggtg gaggattttg ttttttttctt ttaagatctg ggcatctttt     60
gaatctaccc ttcaagtatt aagagacaga ctgtgagcct agcagggcag atcttgtcca    120
ccgtgtgtct tcttctgcac gagactttga ggctgtcaga gcgctttttg cgtggttgct    180
cccgcaagtt tccttctctg gagcttcccg caggtgggca gctagctgca gcgactaccg    240
catcatcaca gcctgttgaa ctcttctgag caagagaagg ggaggcgggg taagggaagt    300
aggtggaaga ttcagccaag ctcaaggatg gaagtgcagt tagggctggg aagggtctac    360
cctcggccgc cgtccaagac ctaccgagga gctttccaga atctgttcca gagcgtgcgc    420
gaagtgatcc agaacccggg ccccaggcac ccagaggccg cgagcgcagc acctcccggc    480
gccagtttgc tgctgcagca gcagcagcag cagcagcagc agcagcagca gcagcagcag    540
cagcagcagc agcagcagca gcagcagcag cagcagcagc aagagactag ccccaggcag    600
cagcagcagc agcagggtga ggatggttct ccccaagccc atcgtagagg ccccacaggc    660
tacctggtcc tggatgagga acagcaacct tcacagccgc agtcggccct ggagtgccac    720
cccgagagag gttgcgtccc agagcctgga gccgccgtgg ccgccagcaa ggggctgccg    780
cagcagctgc cagcacctcc ggacgaggat gactcagctg ccccatccac gttgtccctg    840
ctgggcccca ctttccccgg cttaagcagc tgctccgctg accttaaaga catcctgagc    900
gaggccagca ccatgcaact ccttcagcaa cagcagcagg aagcagtatc cgaaggcagc    960
agcagcggga gagcgaggga ggcctcgggg gctcccactt cctccaagga caattactta   1020
gggggcactt cgaccatttc tgacaacgcc aaggagttgt gtaaggcagt gtcggtgtcc   1080
atgggcctgg gtgtggaggc gttggagcat ctgagtccag gggaacagct tcggggggat   1140
tgcatgtacg ccccactttt gggagttcca cccgctgtgc gtcccactcc ttgtgcccca   1200
```

```
ttggccgaat gcaaaggttc tctgctagac gacagcgcag gcaagagcac tgaagatact   1260
gctgagtatt cccctttcaa gggaggttac accaaagggc tagaaggcga gagcctaggc   1320
tgctctggca gcgctgcagc agggagctcc gggacacttg aactgccgtc taccctgtct   1380
ctctacaagt ccggagcact ggacgaggca gctgcgtacc agagtcgcga ctactacaac   1440
tttccactgg ctctggccgg accgccgccc cctccgccgc ctccccatcc ccacgctcgc   1500
atcaagctgg agaacccgct ggactacggc agcgcctggg cggctgcggc ggcgcagtgc   1560
cgctatgggg acctggcgag cctgcatggc gcgggtgcag cgggacccgg ttctgggtca   1620
ccctcagccg ccgcttcctc atcctggcac actctcttca cagccgaaga aggccagttg   1680
tatggaccgt gtggtggtgg tgggggtggt ggcggcggcg gcggcggcgg cggcggcggc   1740
ggcggcggcg aggcgggagc tgtagccccc tacggctaca ctcggccccc tcaggggctg   1800
gcgggccagg aaagcgactt caccgcacct gatgtgtggt accctggcgg catggtgagc   1860
agagtgccct atcccagtcc cacttgtgtc aaaagcgaaa tgggcccctg gatggatagc   1920
tactccggac cttacgggga catgcgtttg gagactgcca gggaccatgt tttgcccatt   1980
gactattact ttccacccca gaagacctgc ctgatctgtg gagatgaagc ttctgggtgt   2040
cactatggag ctctcacatg tggaagctgc aaggtcttct tcaaaagagc cgctgaaggg   2100
aaacagaagt acctgtgcgc cagcagaaat gattgcacta ttgataaatt ccgaaggaaa   2160
aattgtccat cttgtcgtct tcggaaatgt tatgaagcag ggatgactct gggagaaaaa   2220
ttccgggttg gcaattgcaa gcatctcaaa atgaccagac cctgaagaaa ggctgacttg   2280
cctcattcaa aatgagggct ctagagggct ctagtggata gtctggagaa acctggcgtc   2340
tgaggcttag gagcttaggt ttttgctcct caacacagac tttgacgttg gggttggggg   2400
ctactctctt gattgctgac tccctccagc gggaccaata gtgttttcct acctcacagg   2460
gatgttgtga ggacgggctg tagaagtaat agtggttacc actcatgtag ttgtgagtat   2520
catgattatt gtttcctgta atgtggcttg gcattggcaa agtgcttttt gattgttctt   2580
gatcacatat gatgggggcc aggcactgac tcaggcggat gcagtgaagc tctggctcag   2640
tcgcttgctt ttcgtggtgt gctgccagga agaaactttg ctgatgggac tcaaggtgtc   2700
accttggaca agaagcaact gtgtctgtct gaggttcctg tggccatctt tatttgtgta   2760
ttaggcaatt cgtatttccc ccttaggttc tagccttctg gatcccagcc agtgacctag   2820
atcttagcct caggccctgt cactgagctg aaggtagtag ctgatccaca gaagttcagt   2880
aaacaaggac cagatttctg cttctccagg agaagaagcc agccaacccc tctcttcaaa   2940
cacactgaga gactacagtc cgactttccc tcttacatct agccttactg tagccacact   3000
ccttgattgc tctctcacat cacatgcttc tcttcatcag ttgtaagcct ctcattcttc   3060
tcccaagcca gactcaaata ttgtattgat gtcaaagaag aatcacttag agtttggaat   3120
atcttgttct ctctctgctc catagcttcc atattgacac cagtttcttt ctagtggaga   3180
agtggagtct gtgaagccag ggaaacacac atgtgagagt cagaaggact ctccctgact   3240
tgcctggggc ctgtctttcc caccttctcc agtctgtcta aacacacaca cacacacaca   3300
cacacacaca cacacacaca cacacgctct ctctctctct cccccccaa cacacacaca   3360
ctctctctct cacacacaca cacatacaca cacacttctt tctctttccc ctgactcagc   3420
aacattctgg agaaaagcca aggaaggact tcaggagggg agtttccccc ttctcagggc   3480
agaattttaa tctccagacc aacaagaagt tccctaatgt ggattgaaag gctaatgagg   3540
```

```
tttattttta actactttct atttgtttga atgttgcata tttctactag tgaaattttc   3600

ccttaataaa gccattaata cacccaaaaa aaaaaaaaaa a                        3641


<210> SEQ ID NO 5
<211> LENGTH: 1575
<212> TYPE: DNA
<213> ORGANISM: Homo sapiens

<400> SEQUENCE: 5

ctacgcccag gactggccta acctccgctg cctaaccgtc atccccctgc agccaccctt     60

cccagagtcc tttgcccagg ccaccccagg cttcttggca gccctgccgg gccacttgtc    120

ttcatgtctg ccagggggag gtgggaagga ggtgggagga gggcgtgcag aggcagtctg    180

ggcttggcca gagctcaggg tgctgagcgt gtgaccagca gtgagcagag gccggccatg    240

gccagcctgg ggctgctgct cctgctctta ctgacagcac tgccaccgct gtggtcctcc    300

tcactgcctg ggctggacac tgctgaaagt aaagccacca ttgcagacct gatcctgtct    360

gcgctggaga gagccaccgt cttcctagaa cagaggctgc ctgaaatcaa cctggatggc    420

atggtggggg tccgagtgct ggaagagcag ctaaaaagtg tccgggagaa gtgggcccag    480

gagcccctgc tgcagccgct gagcctgcgc gtggggatgc tgggggagaa gctggaggct    540

gccatccaga gatccctcca ctacctcaag ctgagtgatc ccaagtacct aagagagttc    600

cagctgaccc tccagcccgg gttttggaag ctcccacatg cctggatcca cactgatgcc    660

tccttggtgt accccacgtt cggggcccag gactcattct cagaggagag aagtgacgtg    720

tgcctggtgc agctgctggg aaccgggacg gacagcagcg agccctgcgg cctctcagac    780

ctctgcagga gcctcatgac caagcccggc tgctcaggct actgcctgtc ccaccaactg    840

ctcttcttcc tctgggccag aatgaggggg tgcacacagg gaccactcca acagagccag    900

gactatatca acctcttctg cgccaacatg atggacttga accgcagagc tgaggccatc    960

ggatacgcct accctacccg ggacatcttc atggaaaaca tcatgttctg tggaatgggc   1020

ggcttctccg acttctacaa gctccggtgg ctggaggcca ttctcagctg gcagaaacag   1080

caggaaggat gcttcgggga gcctgatgct gaagatgaag aattatctaa agctattcaa   1140

tatcagcagc atttttcgag gagagtgaag aggcgagaaa aacaatttcc agatggctgc   1200

tcctcccaca acacagccac agcagtggca gccctgggtg gcttcctata catcctggca   1260

gaatacccc cagcaaacag agagccacac ccatccacac cgccaccacc aagcagccgc   1320

tgagacggac ggttccatgc cagctgcctg gaggaggaac agacccctt agtcctcatc   1380

ccttagatcc tggagggcac ggatcacatc ctgggaagaa ggcatctgga ggataagcaa   1440

agccaccccg acacccaatc ttggaagccc tgagtaggca gggccagggt aggtgggggc   1500

cgggagggac ccaggtgtga acggatgaat aaagttcaac tgcaactgaa aaaaaaaaaa   1560

aaaaaaaaaa aaaaa                                                    1575


<210> SEQ ID NO 6
<211> LENGTH: 2175
<212> TYPE: DNA
<213> ORGANISM: Homo sapiens

<400> SEQUENCE: 6

tttcccgccc tctagtcgtg cgcggatctg acgcctgacg taattgcgta gacgccattt     60

tagccggtca gacaagcact ggacgtggcg gccattttgt tttggacacc gagcaggagc    120

tggcggccgc tgcagacgaa aggcaggaaa gggcaggccg ggtgagcaga cggatcggcc    180
```

```
gactagacag ccaaccagca acaacgaact gagctcgcat actaccgctt acgcatctaa    240
ccaaccgccc atctagctaa cccgagcccc tccaccgtca actcaggttc ggccggtccc    300
cggcccgcct gccggagccg tggtggcagc cccgggagga gcactggcgt ctgtttcctt    360
cgattctcgg gattcgaaga tggctgcaca gtcagcgccg aaagttgtgc taaaaagcac    420
caccaagatg tctctaaatg agcgctttac taatatgctg aagaacaaac agccgacgcc    480
agtgaatatt cgggcttcga tgcagcaaca acagcagcta gccagtgcca gaaacagaag    540
actggcccag cagatggaga atagaccctc tgtccaggca gcattaaaac ttaagcagaa    600
gagcttaaag cagcgcctgg gtaagagtaa catccaggca cggttaggcc gacccatagg    660
ggccctggcc aggggagcaa tcggaggacg aggcctaccc ataatccaga gaggcttgcc    720
cagaggagga ctacgtgggg gacgtgccac cagaacccta cttaggggcg ggatgtcact    780
ccgaggtcaa aacctgctcc gaggtggacg agccgtagct ccccgaatgg gcttaagaag    840
aggtggtgtt cgaggtcgtg gaggtcctgg gagagggggc ctagggcgtg gagctatggg    900
tcgtggcgga atcggtggta gaggtcgggg tatgataggt cggggaagag gggctttgg     960
aggccgaggc cgaggccgtg gacgagggag aggtgccctt gctcgccctg tattgaccaa   1020
ggagcagctg gacaaccaat tggatgcata tatgtcgaaa acaaaaggac acctggatgc   1080
tgagttggat gcctacatgg cgcagacaga tcccgaaacc aatgattgaa gcctgcccat   1140
cctcccatga gagactcttg ttagtcaaca catctgtaaa taaccttgag ataacagatg   1200
agaagaaatc tgattgatgc tggatggacc tatcacaata ggctgtggac ttacttgcca   1260
ccagcttgtg catttagtgt gttcctttta ctttttgata ctgtgttgta tgaaaccctt   1320
ttgtcctttg atttggtttt ttgtttttgt ttttttaggg gggagggggg gtttcccctc   1380
ctttgcccag acttctcttt gaacacaaat gcattagcct tgtggctaga acaccctctt   1440
cctacctctg tctcccctca cttgtcatat gctctgacat gctaacattt cttttgttca   1500
tccctgttgc ccccacagaa acatcccaga aaaaccggtc agtgttcctt cctccctgat   1560
ccttaggttt ctgaaatagg gttctgttac atcctcttcg atagcctgtt taaaatgttt   1620
agaaggtctg gagctcaaaa atgcgttctt ccacattgat aatttagtaa actgagaaca   1680
ttgacatcac tacagggcag cataagaggt tgcttacatg tggtagcagc tctggtttga   1740
ttcaagttgc taccatgtac attgacagca catataccat aaccagcgtg ttgggttgaa   1800
ttgcactttc tacctttgta tgagatttac agactttcct tctgggtttg tatcatgacc   1860
agaggggtac tatagggttg gtttatactg caatatagag gatcagaagc catttgattt   1920
ggtaggtgtg tcagaaggga gaatgatggc agacgaactg ctggaagagg tcagaagata   1980
gccatgctaa aatgcaatta tatcctcatg tttatcccaa actaatcttg gacttttcca   2040
ctcattagct ttgttttgcc cttgtttccc ttgaaggttt aagttcaacc atattctgtc   2100
aactgttcag tttcagtgga atcttgtatt tctggttcat tataacaaac tgttcgctta   2160
aatccaaaaa aaaaa                                                    2175
```

<210> SEQ ID NO 7
<211> LENGTH: 5927
<212> TYPE: DNA
<213> ORGANISM: Homo sapiens

<400> SEQUENCE: 7

```
tcgtcggagc agacgggagt ttctcctcgg ggtcggagca ggaggcacgc ggagtgtgag     60
```

-continued

```
gccacgcatg agcggacgct aaccccctcc ccagccacaa agagtctaca tgtctagggt    120
ctagacatgt tcagctttgt ggacctccgg ctcctgctcc tcttagcggc caccgccctc    180
ctgacgcacg gccaagagga aggccaagtc gagggccaag acgaagacat cccaccaatc    240
acctgcgtac agaacggcct caggtaccat gaccgagacg tgtggaaacc cgagccctgc    300
cggatctgcg tctgcgacaa cggcaaggtg ttgtgcgatg acgtgatctg tgacgagacc    360
aagaactgcc ccggcgccga agtccccgag ggcgagtgct gtcccgtctg ccccgacggc    420
tcagagtcac ccaccgacca agaaaccacc ggcgtcgagg gacccaaggg agacactggc    480
ccccgaggcc caaggggacc cgcaggcccc cctggccgag atggcatccc tggacagcct    540
ggacttcccg gacccccgg acccccgga cctcccggac cccctggcct cggaggaaac    600
tttgctcccc agctgtctta tggctatgat gagaaatcaa ccggaggaat ttccgtgcct    660
ggccccatgg gtccctctgg tcctcgtggt ctccctggcc cccctggtgc acctggtccc    720
caaggcttcc aaggtccccc tggtgagcct ggcgagcctg gagcttcagg tcccatgggt    780
ccccgaggtc ccccaggtcc ccctggaaag aatggagatg atggggaagc tggaaaacct    840
ggtcgtcctg gtgagcgtgg gcctcctggg cctcagggtg ctcgaggatt gcccggaaca    900
gctggcctcc ctggaatgaa gggacacaga ggtttcagtg gtttggatgg tgccaaggga    960
gatgctggtc ctgctggtcc taagggtgag cctggcagcc ctggtgaaaa tggagctcct   1020
ggtcagatgg gcccccgtgg cctgcctggt gagagaggtc gccctggagc ccctggccct   1080
gctggtgctc gtggaaatga tggtgctact ggtgctgccg ggccccctgg tcccaccggc   1140
cccgctggtc ctcctggctt ccctggtgct gttggtgcta agggtgaagc tggtccccaa   1200
gggccccgag gctctgaagg tccccagggt gtgcgtggtg agcctggccc ccctggccct   1260
gctggtgctg ctggccctgc tggaaaccct ggtgctgatg gacagcctgg tgctaaaggt   1320
gccaatggtg ctcctggtat tgctggtgct cctggcttcc ctggtgcccg aggcccctct   1380
ggaccccagg gccccggcgg ccctcctggt cccaagggta acagcggtga acctggtgct   1440
cctggcagca aaggagacac tggtgctaag ggagagcctg gccctgttgg tgttcaagga   1500
ccccctggcc ctgctggaga ggaaggaaag cgaggagctc gaggtgaacc cggacccact   1560
ggcctgcccg gaccccctgg cgagcgtggt ggacctggta gccgtggttt ccctggcgca   1620
gatggtgttg ctggtcccaa gggtcccgct ggtgaacgtg gttctcctgg ccctgctggc   1680
cccaaaggat ctcctggtga agctggtcgt cccggtgaag ctggtctgcc tggtgccaag   1740
ggtctgactg gaagccctgg cagccctggt cctgatggca aaactggccc ccctggtccc   1800
gccggtcaag atggtcgccc cggaccccca ggcccacctg gtgcccgtgg tcaggctggt   1860
gtgatgggat tccctggacc taaaggtgct gctggagagc ccggcaaggc tggagagcga   1920
ggtgttcccg gaccccctgg cgctgtcggt cctgctggca aagatggaga ggctggagct   1980
cagggacccc ctggccctgc tggtcccgct ggcgagagag gtgaacaagg ccctgctggc   2040
tcccccggat tccagggtct ccctggtcct gctggtcctc caggtgaagc aggcaaacct   2100
ggtgaacagg gtgttcctgg agaccttggc gcccctggcc cctctggagc aagaggcgag   2160
agaggtttcc ctggcgagcg tggtgtgcaa ggtccccctg gtcctgctgg tccccgaggg   2220
gccaacggtg ctcccggcaa cgatggtgct aagggtgatg ctggtgcccc tggagctccc   2280
ggtagccagg gcgcccctgg ccttcaggga atgcctggtg aacgtggtgc agctggtctt   2340
ccagggccta agggtgacag aggtgatgct ggtcccaaag gtgctgatgg ctctcctggc   2400
aaagatggcg tccgtggtct gactggcccc attggtcctc ctggccctgc tggtgcccct   2460
```

```
ggtgacaagg gtgaaagtgg tcccagcggc cctgctggtc ccactggagc tcgtggtgcc   2520
cccggagacc gtggtgagcc tggtcccccc ggccctgctg gctttgctgg ccccccctggt   2580
gctgacggcc aacctggtgc taaaggcgaa cctggtgatg ctggtgctaa aggcgatgct   2640
ggtcccccctg gccctgccgg acccgctgga cccccctggcc ccattggtaa tgttggtgct   2700
cctggagcca aaggtgctcg cggcagcgct ggtcccccctg gtgctactgg tttccctggt   2760
gctgctggcc gagtcggtcc tcctggcccc tctggaaatg ctggaccccc tggccctcct   2820
ggtcctgctg gcaaagaagg cggcaaaggt ccccgtggtg agactggccc tgctggacgt   2880
cctggtgaag ttggtccccc tggtcccccct ggccctgctg gcgagaaagg atcccctggt   2940
gctgatggtc ctgctggtgc tcctggtact cccgggcctc aaggtattgc tggacagcgt   3000
ggtgtggtcg gcctgcctgg tcagagagga gagagaggct tccctggtct tcctggcccc   3060
tctggtgaac ctggcaaaca aggtccctct ggagcaagtg gtgaacgtgg tccccccctggt   3120
cccatgggcc cccctggatt ggctggaccc cctggtgaat ctggacgtga gggggctcct   3180
ggtgccgaag gttcccctgg acgagacggt tctcctggcg ccaagggtga ccgtggtgag   3240
accggccccg ctggaccccc tggtgctcct ggtgctcctg gtgcccctgg ccccgttggc   3300
cctgctggca agagtggtga tcgtggtgag actggtcctg ctggtcccgc cggtcctgtc   3360
ggccctgttg gcgcccgtgg ccccgccgga ccccaaggcc cccgtggtga caagggtgag   3420
acaggcgaac agggcgacag aggcataaag ggtcaccgtg gcttctctgg cctccagggt   3480
ccccctggcc ctcctggctc tcctggtgaa caaggtccct ctggagcctc tggtcctgct   3540
ggtccccgag gtccccctgg ctctgctggt gctcctggca aagatggact caacggtctc   3600
cctggcccca ttgggccccc tggtcctcgc ggtcgcactg gtgatgctgg tcctgttggt   3660
ccccccggcc ctcctggacc tcctggtccc cctggtcctc ccagcgctgg tttcgacttc   3720
agcttcctgc cccagccacc tcaagagaag gctcacgatg gtggccgcta ctaccgggct   3780
gatgatgcca atgtggttcg tgaccgtgac ctcgaggtgg acaccaccct caagagcctg   3840
agccagcaga tcgagaacat ccggagccca gagggcagcc gcaagaaccc cgcccgcacc   3900
tgccgtgacc tcaagatgtg ccactctgac tggaagagtg gagagtactg gattgacccc   3960
aaccaaggct gcaacctgga tgccatcaaa gtcttctgca acatggagac tggtgagacc   4020
tgcgtgtacc ccactcagcc cagtgtggcc cagaagaact ggtacatcag caagaacccc   4080
aaggacaaga ggcatgtctg gttcggcgag agcatgaccg atggattcca gttcgagtat   4140
ggcggccagg gctccgaccc tgccgatgtg gccatccagc tgaccttcct gcgcctgatg   4200
tccaccgagg cctcccagaa catcacctac cactgcaaga acagcgtggc ctacatggac   4260
cagcagactg gcaacctcaa gaaggccctg ctcctccagg gctccaacga gatcgagatc   4320
cgcgccgagg gcaacagccg cttcacctac agcgtcactg tcgatggctg cacgagtcac   4380
accggagcct ggggcaagac agtgattgaa tacaaaacca ccaagacctc ccgcctgccc   4440
atcatcgatg tggccccctt ggacgttggt gccccagacc aggaattcgg cttcgacgtt   4500
ggccctgtct gcttcctgta aactccctcc atcccaacct ggctccctcc cacccaacca   4560
actttccccc caacccggaa acagacaagc aacccaaact gaaccccctc aaaagccaaa   4620
aaatgggaga caatttcaca tggactttgg aaaatatttt tttcctttgc attcatctct   4680
caaacttagt ttttatcttt gaccaaccga acatgaccaa aaaccaaaag tgcattcaac   4740
cttaccaaaa aaaaaaaaaa aaaaagaata aataaataac tttttaaaaa aggaagcttg   4800
```

```
gtccacttgc ttgaagaccc atgcgggggt aagtcccttt ctgcccgttg ggcttatgaa   4860
accccaatgc tgccctttct gctcctttct ccacaccccc cttggggcct cccctccact   4920
ccttcccaaa tctgtctccc cagaagacac aggaaacaat gtattgtctg cccagcaatc   4980
aaaggcaatg ctcaaacacc caagtggccc ccaccctcag cccgctcctg cccgcccagc   5040
acccccaggc cctgggggac ctggggttct cagactgcca aagaagcctt gccatctggc   5100
gctcccatgg ctcttgcaac atctcccctt cgtttttgag gggtcatgc cgggggagcc    5160
accagcccct cactgggttc ggaggagagt caggaagggc cacgacaaag cagaaacatc   5220
ggatttgggg aacgcgtgtc aatcccttgt gccgcagggc tgggcgggag agactgttct   5280
gttccttgtg taactgtgtt gctgaaagac tacctcgttc ttgtcttgat gtgtcaccgg   5340
ggcaactgcc tgggggcggg gatgggggca gggtggaagc ggctccccat tttataccaa   5400
aggtgctaca tctatgtgat gggtggggtg gggagggaat cactggtgct atagaaattg   5460
agatgccccc ccaggccagc aaatgttcct ttttgttcaa agtctatttt tattccttga   5520
tatttttctt tttttttttt tttttttgtg gatggggact tgtgaatttt tctaaaggtg   5580
ctatttaaca tgggaggaga gcgtgtgcgg ctccagccca gcccgctgct cactttccac   5640
cctctctcca cctgcctctg cttctcagg cctctgctct ccgacctctc tcctctgaaa    5700
ccctcctcca cagctgcagc ccatcctccc ggctccctcc tagtctgtcc tgcgtcctct   5760
gtccccgggt ttcagagaca acttcccaaa gcacaaagca gtttttcccc ctaggggtgg   5820
gaggaagcaa aagactctgt acctattttg tatgtgtata ataatttgag atgtttttaa   5880
ttattttgat tgctggaata aagcatgtgg aaatgaccca aacataa                 5927
```

<210> SEQ ID NO 8
<211> LENGTH: 4811
<212> TYPE: DNA
<213> ORGANISM: Homo sapiens

<400> SEQUENCE: 8

```
tttcttctcc ggccctggca ggttccggga gcctcggctc gtgggtgccg gaagtggagg     60
cggttggtgg ggttggcggg gctcagcgac gctgcgcggg tggcggtttg cgaactgcgg    120
gtggactgtg tagtgaccgg cgtcccgctg tctcgccccg tggcgggtga gcgagggtgc    180
gtggtgcgcg gcggcggcgg aacgaacgcg gtgcgggcgg ggcgcccgcc gcagggccca    240
tggcctcctg cgcgagcatc gacatcgagg acgccacgca gcacctgcgg gacatcctca    300
agctggaccg gcccgcgggc ggccccagtg cagagagccc acggccatcc agtgcctaca    360
atggggacct caatggactt ctggtcccag acccgctctg ctcaggtgat agtacctcag    420
caaacaagac tggtcttcgg accatgccac ccattaacct gcaagagaag caggtcatct    480
gtctctcagg agatgatagc tccacctgca ttgggatttt ggccaaggag gtggagattg    540
tggctagcag tgactctagc atttcaagca aggcccgggg aagcaacaag gtgaaaattc    600
agcctgtcgc caagtatgac tgggaacaga agtactacta tggcaacctg attgctgtgt    660
ctaactcctt cttggcctat gccattcggg ctgccaacaa tggctctgcc atggtgcggg    720
tgatcagcgt cagcacttcg gagcggacct tgctcaaggg cttcacaggc agtgtggctg    780
atctggcttt cgcgcacctc aactctccac agctggcctg cctggatgag gcaggcaacc    840
tgttcgtgtg gcgcttggct ctggttaatg gcaaaattca agaagagatc ttggtccata    900
ttcggcagcc agagggcacg ccactgaacc actttcgcag gatcatctgg tgccccttca    960
tccctgagga gagcgaagac tgctgtgagg agagcagccc aacagtggcc ctgctgcatg   1020
```

```
aagaccgggc tgaggtgtgg gacctggaca tgctccgctc cagccacagt acctggcctg   1080
tggatgttag ccagatcaag cagggcttca ttgtggtaaa aggtcatagc acgtgcctca   1140
gtgaaggagc cctctctcct gatgggactg tgctggctac tgcgagccac gatggctatg   1200
tcaagttctg gcagatctac attgaggggc aagatgagcc aaggtgtctg cacgagtgga   1260
aacctcatga tgggcggccc ctctcctgcc tcctgttctg tgacaaccat aagaaacaag   1320
accctgatgt ccctttctgg aggttcctta ttactggtgc tgaccagaac cgagagttaa   1380
agatgtggtg tacagtatcc tggacctgcc tgcagactat tcgcttctcc ccagatatct   1440
tcagctcagt gagtgtgccc cctagcctca aggtttgctt ggacctctca gcagaatacc   1500
tgattctcag cgatgtgcaa cggaaggtcc tctatgtgat ggagctgctg caaaaccagg   1560
aggagggcca cgcctgcttc agctccatct cggagttcct gctcacccac cctgtgctga   1620
gctttggtat ccaggttgtg agtcgctgcc ggctacggca cactgaggtg ctgcctgccg   1680
aagaggaaaa tgacagcctg ggtgctgatg gtacccatgg agccggtgcc atggagtctg   1740
cggccggtgt gctcatcaag ctcttttgtg tgcatactaa ggcactgcaa gatgtgcaga   1800
tccgcttcca gccacagctg aaccctgatg tggtggcccc actgcccacc cacactgccc   1860
acgaggactt cacatttgga gagtctcggc ccgaactggg ctctgagggc ctggggtcag   1920
ccgctcacgg ctcccagcct gacctccgac gaatcgtgga gctgcctgca cctgccgact   1980
tcctcagtct gagcagtgag accaagccca agttgatgac acctgacgcc ttcatgacac   2040
ctagcgcctc cttgcagcag atcactgcct ctcccagcag cagcagcagc ggtagcagca   2100
gcagcagcag cagtagcagc agctccctta cagctgtgtc tgccatgagc agcacctcag   2160
ctgtggaccc ctccttgacc aggccacctg aggagctgac cttgagcccc aagctgcagc   2220
tggatggcag cctgacaatg agcagcagtg gcagccttca ggcaagcccg cgtggcctcc   2280
tgcctggcct gctcccagcc ccagctgaca aactgactcc caaggggccg ggccaggtgc   2340
ctactgccac ctctgcactg tccctggagc tgcaggaagt ggagcccctg gggctacccc   2400
aagcctcccc tagccgcact cgttcccctg atgtcatctc ctcagcttcc actgccctgt   2460
cccaggacat ccctgagatt gcatctgagg ccctgtcccg tggttttggc tcctctgcac   2520
cagagggcct tgagccagac agtatggctt cagccgcctc ggcactgcac ctgctgtccc   2580
cacggccccg gccagggccc gagctcggcc cccagctcgg gcttgatgga ggccctgggg   2640
atggagatcg gcataatacc ccctccctcc tggaggcagc cttgacccag gaggcctcga   2700
ctcctgacag tcaggtttgg cccacagcac ctgacattac tcgtgagacc tgcagcaccc   2760
tggcagaaag ccccaggaat ggccttcagg aaaagcacaa gagcctggcc ttccaccgac   2820
caccatatca cctgctgcag caacgtgaca gccaggatgc cagtgctgag caaagtgacc   2880
atgatgatga ggtggccagc cttgcctctg cttcaggagg ctttggcacc aaagttcctg   2940
ctccacggct gcctgccaag gactggaaga ccaagggatc ccctcgaacc tcacccaagc   3000
tcaagaggaa aagcaagaag gatgatgggg atgcagccat gggatcccgg ctcacagagc   3060
accaggtggc agagcccccct gaggactggc cagcactaat ttggcaacag cagagagagc   3120
tggcagagct gcggcacagc caggaagagc tgctgcagcg tctgtgtacc caactcgaag   3180
gcctgcagag cacagtcaca ggccacgtag aacgtgccct tgagactcgg cacgagcagg   3240
aacagcggcg gctggagcga gcactggctg aggggcagca gcggggaggg cagctgcagg   3300
agcagctgac acaacagttg tcccaagcac tgtcgtcagc tgtagctggg cggctagagc   3360
```

```
gcagcatacg ggatgagatc aagaagacag tccctccatg tgtctcaagg agtctggagc   3420
ctatggcagg ccaactgagc aactcagtgg ctaccaagct cacagctgtg gagggcagca   3480
tgaaagagaa catctccaag ctgctcaagt ccaagaactt gactgatgcc atcgcccgag   3540
cagctgcaga cacattacaa gggccgatgc aggctgccta ccgggaagcc ttccagagtg   3600
tggtgctgcc ggcctttgag aagagctgcc aggccatgtt ccagcaaatc aatgatagct   3660
tccggctggg gacacaggaa tacttgcagc agctagaaag ccacatgaag agccggaagg   3720
cacgggaaca ggaggccagg gagcctgtgc tagcccagct gcggggcctg gtcagcacac   3780
tgcagagtgc cactgagcag atggcagcca ccgtggccgg cagtgttcgt gctgaggtgc   3840
agcaccagct gcatgtggct gtgggcagcc tgcaggagtc cattttagca caggtacagc   3900
gcatcgttaa gggtgaggtg agtgtggcgc tcaaggagca gcaggccgcc gtcacctcca   3960
gcatcatgca ggccatgcgc tcagctgctg gcacacctgt cccctctgcc caccttgact   4020
gccaggccca gcaagcccat atcctgcagc tgctgcagca gggccacctc aatcaggcct   4080
tccagcaggc gctgacagct gctgacctga acctggtgct gtatgtgtgt gaaactgtgg   4140
acccagccca ggtttttggg cagccaccct gcccgctctc ccagcctgtg ctcctttccc   4200
tcatccagca gctggcatct gaccttggca ctcgaactga cctcaagctc agctacctgg   4260
aagaggccgt gatgcacctg gaccacagtg accccatcac tcgggaccac atgggctccg   4320
ttatggccca ggtgcgccaa aagctttttc agttcctgca ggctgagcca cacaactcac   4380
ttggcaaagc agctcggcgt ctcagcctca tgctgcatgg cctcgtgacc cccagcctcc   4440
cttagctgct aagcctgcct tgcccagggg tgggatggca ctgaaggcca gcagacaggc   4500
ctaggctggg gcagggtcac ggctggcctt tacctgctca ggcccccatc tctggggtgt   4560
ttgggggtca gggagcaggg agcactggcc gtggtctaca gcgtgtggta gtcagaaggt   4620
ttagctgggc ccagggcagg tattgcgcct gcttgggttc tgccatgcct ggagcatgac   4680
cctgagatcg tgacaccact tgagtggaat tttccatgtt ccttttttacc tctaatttgg   4740
atctttttgt ttttgaaaaa cattgagaaa ttcaattaaa tgcttttgga ataaaatgga   4800
gtatgtgtgt g                                                        4811
```

<210> SEQ ID NO 9
<211> LENGTH: 4654
<212> TYPE: DNA
<213> ORGANISM: Homo sapiens

<400> SEQUENCE: 9

```
ggcggcggct ggaggagagc gcggtggaga gccgagcggg cgggcggcgg gtgcggagcg     60
ggcgagggag cgcgcgcggc cgccacaaag ctcgggcgcc gcggggctgc atgcggcgta    120
cctggcccgg cgcggcgact gctctccggg ctggcggggg ccggccgcga gccccggggg    180
ccccgaggcc gcagcttgcc tgcgcgctct gagccttcgc aactcgcgag caaagtttgg    240
tggaggcaac gccaagcctg agtcctttct tcctctcgtt ccccaaatcc gagggcagcc    300
cgcgggcgtc atgcccgcgc tcctccgcag cctggggtac gcgtgaagcc cgggaggctt    360
ggcgccggcg aagacccaag gaccactctt ctgcgtttgg agttgctccc cgcaaccccg    420
ggctcgtcgc tttctccatc ccgacccacg cggggcgcgg ggacaacaca ggtcgcggag    480
gagcgttgcc attcaagtga ctgcagcagc agcggcagcg cctcggttcc tgagcccacc    540
gcaggctgaa ggcattgcgc gtagtccatg cccgtagagg aagtgtgcag atgggattaa    600
cgtccacatg gagatatgga agaggaccgg ggattggtac cgtaaccatg gtcagctggg    660
```

```
gtcgtttcat ctgcctggtc gtggtcacca tggcaacctt gtccctggcc cggccctcct    720
tcagtttagt tgaggatacc acattagagc cagaagagcc accaaccaaa taccaaatct    780
ctcaaccaga agtgtacgtg gctgcgccag gggagtcgct agaggtgcgc tgcctgttga    840
aagatgccgc cgtgatcagt tggactaagg atggggtgca cttggggccc aacaatagga    900
cagtgcttat tggggagtac ttgcagataa agggcgccac gcctagagac tccggcctct    960
atgcttgtac tgccagtagg actgtagaca gtgaaacttg gtacttcatg gtgaatgtca   1020
cagatgccat ctcatccgga gatgatgagg atgacaccga tggtgcggaa gattttgtca   1080
gtgagaacag taacaacaag agagcaccat actggaccaa cacagaaaag atggaaaagc   1140
ggctccatgc tgtgcctgcg gccaacactg tcaagtttcg ctgcccagcc ggggggaacc   1200
caatgccaac catgcggtgg ctgaaaaacg ggaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaaggccg ccggtgttaa caccacggac aaagagattg   1620
aggttctcta tattcggaat gtaacttttg aggacgctgg ggaatatacg tgcttggcgg   1680
gtaattctat tgggatatcc tttcactctg catggttgac agttctgcca gcgcctggaa   1740
gagaaaagga gattacagct tccccagact acctggagat agccatttac tgcatagggg   1800
tcttcttaat cgcctgtatg gtggtaacag tcatcctgtg ccgaatgaag aacacgacca   1860
agaagccaga cttcagcagc cagccggctg tgcacaagct gaccaaacgt atccccctgc   1920
ggagacaggt aacagtttcg gctgagtcca gctcctccat gaactccaac accccgctgg   1980
tgaggataac aacacgcctc tcttcaacgg cagacacccc catgctggca ggggtctccg   2040
agtatgaact tccagaggac ccaaaatggg agtttccaag agataagctg acactgggca   2100
agcccctggg agaaggttgc tttgggcaag tggtcatggc ggaagcagtg ggaattgaca   2160
aagacaagcc caaggaggcg gtcaccgtgg ccgtgaagat gttgaaagat gatgccacag   2220
agaaagacct ttctgatctg gtgtcagaga tggagatgat gaagatgatt gggaaacaca   2280
agaatatcat aaatcttctt ggagcctgca cacaggatgg gcctctctat gtcatagttg   2340
agtatgcctc taaaggcaac ctccgagaat acctccgagc ccggaggcca cccgggatgg   2400
agtactccta tgacattaac cgtgttcctg aggagcagat gaccttcaag gacttggtgt   2460
catgcaccta ccagctggcc agaggcatgg agtacttggc ttcccaaaaa tgtattcatc   2520
gagatttagc agccagaaat gttttggtaa cagaaaacaa tgtgatgaaa atagcagact   2580
ttggactcgc cagagatatc aacaatatag actattacaa aaagaccacc aatgggcggc   2640
ttccagtcaa gtggatggct ccagaagccc tgtttgatag agtatacact catcagagtg   2700
atgtctggtc cttcggggtg ttaatgtggg agatcttcac tttagggggc tcgccctacc   2760
cagggattcc cgtggaggaa ctttttaagc tgctgaagga aggacacaga atggataagc   2820
cagccaactg caccaacgaa ctgtacatga tgatgaggga ctgttggcat gcagtgccct   2880
cccagagacc aacgttcaag cagttggtag aagacttgga tcgaattctc actctcacaa   2940
ccaatgagga atacttggac ctcagccaac ctctcgaaca gtattcacct agttaccctg   3000
```

```
acacaagaag ttcttgttct tcaggagatg attctgtttt ttctccagac cccatgcctt   3060
acgaaccatg ccttcctcag tatccacaca taaacggcag tgttaaaaca tgaatgactg   3120
tgtctgcctg tccccaaaca ggacagcact gggaacctag ctacactgag cagggagacc   3180
atgcctccca gagcttgttg tctccacttg tatatatgga tcagaggagt aaataattgg   3240
aaaagtaatc agcatatgtg taaagattta tacagttgaa aacttgtaat cttccccagg   3300
aggagaagaa ggtttctgga gcagtggact gccacaagcc accatgtaac ccctctcacc   3360
tgccgtgcgt actggctgtg gaccagtagg actcaaggtg gacgtgcgtt ctgccttcct   3420
tgttaatttt gtaataattg gagaagattt atgtcagcac acacttacag agcacaaatg   3480
cagtatatag gtgctggatg tatgtaaata tattcaaatt atgtataaat atatattata   3540
tatttacaag gagttatttt ttgtattgat tttaaatgga tgtcccaatg cacctagaaa   3600
attggtctct cttttttaa tagctatttg ctaaatgctg ttcttacaca taatttctta   3660
attttcaccg agcagaggtg gaaaaatact tttgctttca gggaaaatgg tataacgtta   3720
atttattaat aaattggtaa tatacaaaac aattaatcat ttatagtttt ttttgtaatt   3780
taagtggcat ttctatgcag gcagcacagc agactagtta atctattgct tggacttaac   3840
tagttatcag atcctttgaa aagagaatat ttacaatata tgactaattt ggggaaaatg   3900
aagttttgat ttatttgtgt ttaaatgctg ctgtcagacg attgttctta gacctcctaa   3960
atgccccata ttaaaagaac tcattcatag gaaggtgttt cattttggtg tgcaaccctg   4020
tcattacgtc aacgcaacgt ctaactggac ttcccaagat aaatggtacc agcgtcctct   4080
taaaagatgc cttaatccat tccttgagga cagaccttag ttgaaatgat agcagaatgt   4140
gcttctctct ggcagctggc cttctgcttc tgagttgcac attaatcaga ttagcctgta   4200
ttctcttcag tgaattttga taatggcttc cagactcttt ggcgttggag acgcctgtta   4260
ggatcttcaa gtcccatcat agaaaattga aacacagagt tgttctgctg atagttttgg   4320
ggatacgtcc atctttttaa gggattgctt tcatctaatt ctggcaggac ctcaccaaaa   4380
gatccagcct catacctaca tcagacaaaa tatcgccgtt gttccttctg tactaaagta   4440
ttgtgttttg ctttggaaac acccactcac tttgcaatag ccgtgcaaga tgaatgcaga   4500
ttacactgat cttatgtgtt acaaaattgg agaaagtatt taataaaacc tgttaatttt   4560
tatactgaca ataaaaatgt ttctacagat attaatgtta acaagacaaa ataaatgtca   4620
cgcaacttat ttttttaata aaaaaaaaaa aaaa                              4654
```

<210> SEQ ID NO 10
<211> LENGTH: 713
<212> TYPE: DNA
<213> ORGANISM: Homo sapiens

<400> SEQUENCE: 10

```
ccccacatcg gtccgtcctg cttccagctg ctgcagcgcg ccttcgccgc caaagcatcc     60
agcagccccc tgctccggcc cagcatggcg accccgaccc agacccccac aaaggctcct    120
gaggaacctg acccatttta ctatgactac aacacggtgc agactgtggg catgactctg    180
gcaaccatct tgttcctgct gggtatcctc atcgtcatca gcaagaaggt gaagtgcagg    240
aaggcggact ccaggtctga gagcccaacc tgcaaatcct gtaagtctga gcttccctct    300
tcagcccctg gtggcggcgg cgtgtaacac cttcccgagg aaactccgct gccgaccctg    360
cctgagcgcg ggagcctgag gaccgggtgg aggcggtggg gacccagccg cgcgccggga    420
gcgctccccg gaatgagccg ccccacccac cccaaggctg gagccgctgc accctgctgt    480
```

```
ccctctccag gccttggcaa tgacgatccc ccaaagagcc cgtctgcacc ccagacccag    540

ggcctcaggc ctccagctcc tgggatccgg gagtccatcc cggcccagca cccccagcat    600

ccccgtgtat ggccccccctg cacctccttg tctcatcccc gaagatccgt ccccctggcc    660

cctcagtgtc catgtcttga gcttaataaa tgtgcatttg gttttttcct ctg          713
```

<210> SEQ ID NO 11
<211> LENGTH: 8518
<212> TYPE: DNA
<213> ORGANISM: Homo sapiens

<400> SEQUENCE: 11

```
accctcttgg tgtgcgcgtc atggccgtca gcaccgcgtt cccgtcctct tccgcttggc     60

cccagaaagt ttcggttctg cccggcggtg gacccacgag cgcgtgccac catggagtct    120

gaccactgct gagcagacag ccaccgaggg ccgaaattct gagccttcct ctggacccag    180

gcaggagaca tacagacaag aaaggcaaac tcaccatggc ctccaccaat gcagagagcc    240

agctccagag aatcatccga gacttgcaag atgctgtgac agaactaagc aaagaatttc    300

aggaagcagg ggaacccatc acggatgaca gcaccagctt gcataaattt tcttataaac    360

ttgagtatct cctgcaattt gatcagaaag agaaggccac cctcctgggc aacaagaagg    420

actactggga ttacttctgt gcctgcctgg ccaaggtgaa aggagccaat gatgggatcc    480

gctttgtcaa gtctatctca gagctccgaa catccttggg gaaaggaaga gcatttattc    540

gctactcctt ggtgcaccag aggttggcag acaccttaca gcagtgcttc atgaacacca    600

aagtgaccag tgactggtac tatgcaagaa gcccctttct gcagccaaag ctgagctcgg    660

acattgtggg ccaactctat gagctgactg aggttcagtt tgacctggcg tcgaggggct    720

ttgacttgga tgctgcctgg ccaacatttg ccaggaggac gctgaccact ggctcttctg    780

cttacctgtg gaaacccccct agccgcagct ccagcatgag cagcttggtg agcagctacc    840

tgcagactca agagatggtg tccaactttg acctgaacag ccccctaaac aacgaggcat    900

tggagggctt tgatgagatg cgactagagc tggaccagtt ggaggtgcgg gagaagcagc    960

tacgggagcg catgcagcag ctggacagag agaaccagga gctgagggca gctgtcagcc   1020

agcaagggga gcaactgcag acagagaggg agagggggcg cactgcagcg gaggacaacg   1080

ttcgcctcac ttgcttggta gctgagctcc agaagcagtg ggaggtcacc caggccaccc   1140

agaacactgt gaaggagctg cagacatgcc tgcagggcct ggagctagga gcagcagaga   1200

aggaggagga ctaccacaca gccctgcggc ggctggagtc catgctgcag cccttggcac   1260

aggagcttga ggccacacgg gactcactgg acaagaaaaa ccagcattta gccagcttcc   1320

caggctggct agccatggct cagcagaagg cagatacggc atcagacaca aagggccggc   1380

aagaacctat tcccagtgat gcggcccagg agatgcagga gctaggggag aagcttcaag   1440

ccctagaaag ggagagaacc aaggtcgagg aggtcaacag acagcagagt gcccaactgg   1500

aacagctggt caaggagctt cagctgaaag aggatgcccg ggccagcctg gagcgcctgg   1560

tgaaggagat ggcccccactc caggaggagt tgtctgggaa gggacaggag gcagaccagc   1620

tctggcgacg gctgcaggag ttgctggccc acacgagctc ctgggaggag gagctagcag   1680

agttgaggcg ggagaaaaaa cagcaacagg aggagaagga gctgctggag caggaggtca   1740

ggtctctgac ccggcagctg cagttcctgg agacccagct ggcacaggtg agccaacatg   1800

tgagtgacct ggaggagcag aagaagcagc tcattcagga caaagaccac ctcagccagc   1860
```

```
aggtgggtat gctcgagcgg cttgctgggc cgcctggccc agaactgcca gtggcaggtg   1920
agaagaatga ggccctggtc cctgtgaact ccagtctgca agaggcctgg gggaagccag   1980
aggaggagca gaggggcctg caggaggcac agttagacga taccaaggtg caagagggca   2040
gccaggagga agagctccgg caggccaaca gggagctgga gaaggagcta cagaatgtgg   2100
tcgggcgtaa ccagctcctg gagggcaagc tgcaagccct gcaggccgat taccaggctt   2160
tgcagcagcg ggaatcagcc atccagggct ccttggcctc cctggaggcc gagcaggcca   2220
gcatccggca cttgggtgac cagatggagg cgagcttgct ggctgtaagg aaggccaagg   2280
aggccatgaa agcccagatg gcagagaagg aggccattct acagagcaag gagggcgagt   2340
gtcagcagct gcgggaggag gtggagcagt gccagcaact ggcagaagcc cggcacagag   2400
agcttagggc tctcgagagc cagtgccagc agcagaccca gctgattgag gtcctcacag   2460
cagagaaagg ccaacaggga gttggcccac ccactgacaa tgaagcccgt gagctggctg   2520
cccagctagc cctgtctcag gcgcagctgg aagtccatca gggggaggtc caacggctgc   2580
aggctcaggt ggtggacctc caggccaaga tgcgggcagc cctggatgac caggacaagg   2640
tgcagagcca gctaagcatg gctgaggccg tcctgaggga gcacaaaacc cttgtgcagc   2700
agctgaagga gcagaatgaa gcccttaaca gagcccatgt ccaggagctg ctgcaatgct   2760
cggagcgtga aggggcactg caggaggaga gggccgatga ggcccagcag agggaggagg   2820
agctgcgggc cctgcaggag gagctgtccc aggccaaatg cagctccgag gaagcacagc   2880
tggagcacgc tgagctgcaa gagcagctgc accgggccaa cacagacaca gctgagctgg   2940
gcatccaggt ttgcgcactg accgtggaaa aggagcgagt ggaggaggca ctggcctgtg   3000
ctgtccagga gctccaggac gccaaagagg cagcctcaag ggagcgagag ggcctggagc   3060
gccaagtagc tgggctgcag caagagaagg agagcttgca ggagaagctg aaggcggcca   3120
aggcagcagc cggctcactg cctggcctgc aggcccagct cgcccaggca gagcagcggg   3180
cccagagcct ccaagaggct gcacaccagg agctcaacac cctcaagttc cagctgagtg   3240
ctgaaatcat ggactaccag agcagactta agaatgctgg tgaagagtgc aagagcctca   3300
ggggccagct tgaggagcaa ggccggcagc tgcaggctgc tgaggaagct gtggagaagc   3360
tgaaggccac ccaagcagac atgggagaga agctgagctg cactagcaac catcttgcag   3420
agtgccaggc ggccatgctg aggaaggaca aggagggggc tgccctgcgt gaagacctag   3480
aaaggaccca gaaggaactc gaaaaagcca caacaaaaat ccaagagtat tacaacaaac   3540
tctgccagga ggtgacaaat cgtgagagga atgaccagaa gatgcttgct gacctggatg   3600
acctcaacag aaccaagaag tatctcgagg agcggctgat agagctgctc agggacaagg   3660
atgctctctg gcagaagtca gatgccctgg aattccagca gaagctcagt gctgaggaga   3720
gatggctcgg agacacagag gcaaaccact gcctcgactg taagcgggag ttcagctgga   3780
tggtgcggcg gcaccactgc aggatatgtg gccgcatctt ctgttactac tgctgcaaca   3840
actacgtcct gagcaagcac ggtggcaaaa aggagcgctg ctgccgagcc tgtttccaga   3900
agctcagtga aggccctggc tcccctgata gcagtggctc aggcactagc cagggagagc   3960
ccagccctgc actgtcacca gcctcacctg ggccccaggc cacaggaggc caaggagcaa   4020
atacagacta caggccaccg gacgacgctg tgtttgatat catcacagat gaggaattgt   4080
gccagataca ggagtccggc tcctctttgc ctgaaacacc cactgaaact gattctctcg   4140
acccaaatgc ggctgaacag gatactacat caacctcgct aacgcctgag gacactgaag   4200
acatgcccgt ggggcaggat tcggaaatct gcctgctgaa gtctggagaa ctgatgatca   4260
```

```
aagtacccct cacagtggat gagatcgcca gcttcgggga gggtagcagg gagctgtttg   4320
tgaggtccag cacctacagc ctgatcccca tcactgtggc cgaggcaggc ctcaccatca   4380
gctgggtctt ctcctctgac cccaagagca tctccttcag tgtggtcttc caggaggccg   4440
aggacacacc gctggatcag tgtaaggtcc tcattcccac gacccgatgc aactcccaca   4500
aggagaacat ccagggccag ctcaaggttc gcacacccgg catctacatg ctcatcttcg   4560
acaatacctt ctcaaggttt gtctctaaaa aggtatttta tcacttgacg gttgatcggc   4620
ctgtgatcta cgatggaagt gatttcctgt agcttcagca cctcagtaac ttcacttcat   4680
ccacaggaaa cactgctctt cctcacctgt cacataaagc atttttttaa aaagtcagct   4740
gctccaaaat catcaactca gcccctgggc tgcccctcag aggcggtgtc tggggaggac   4800
tttgtgctca gcactctgca ccggccactc ttagcccccg aggcgttgaa gggctcaggc   4860
aatgtttcca ttaagtagag actcagctgt tgtcacaccc aaagggatgc tctgccaaag   4920
gtttaaacac ccaggagacc atcagcctct cctgggagca cagttggcta caggcctctt   4980
gtggagagtt tcacgggcag ggtgattcc aacttctgcc tgtggagaga ttttctgccc   5040
tgccccacca gggccctgca tgttggagac tgagctgggt gcactggcca tgccctgtga   5100
atcctcaggc tgtgacgccc tcaggtactc ctgggaaaag gaggtacaca gccatcatgc   5160
gagtcggtgc caggggaccc cccggagatc ctgaccagct cctccagtca tgctcttgtc   5220
cctcactgcc ccagtaagct ggaggctgct ccagaactca gcagtgttgg aggggcctct   5280
aagctgcact ctctttctgg cccttttgtc tgggtgattc tgtcctcaaa taaagccctt   5340
cactcagcca gacctctcca cagctcaaag cattgcccta agaatcagaa gtaaagataa   5400
tccaagagca aaacccactg tacttggggc ctgcaatggc tgtgtgtaca ctacatctaa   5460
tgcccaaatg ccagccagtg tggatgttgt gaccacagag caggattgtg cattggcttt   5520
agagctactc ctcagctgat ggcccacttt tgtttatata aataagagct tctgccccac   5580
ctgcagacat gtttactaat gatcatagcc aggattagaa ccactttcaa acattggggc   5640
cttcttaaca aaagtctttg ataacttaag aaccaaagta acagagtaaa cagaggcatg   5700
atggatccct gggccccact cccctcctga caggttcccc aacagcccat ttgcccactt   5760
cccactgctc agcccacacc agacctccag gagacatccc cccttgaggc agagagatcc   5820
tgttccctat tcccagacaa gaattattta atcttccctg ttctctgtgg tccttttctt   5880
ccccaacaac agatagctca ccttggacag ctcttcgtcc cttgttcatg gaaccagctg   5940
cctgcagtca ggccccaggt tcttccatgg gtgaacagag catctgacaa aaggtcccag   6000
tttggccagg ggtgagggag agagcaccag acaggctatc cgagaatctg agagctgggc   6060
ccggcagttc ctccagctac ccttgtgacc taagtccagt cacacatttc ccaaagtttc   6120
tctttgtcat aaccctggtc tggctggttt tgagggcttg agaatgggtc agggactcca   6180
ggccaagtcc aacagagacc ccaaacccac cacacaccag cagccacaac ctcaccacca   6240
acaaagagga cttttgtggg gccacaagta agaggtcatt tctggaatgg actcagacct   6300
ttaaacagga gagttgagca cttccagtca gtttttaagc aaggcatggg gaacagggaa   6360
tagaaccttt caaagaggtt gcccagagaa aagctgggcc tcttgcattc ggcttccttg   6420
gagcagcctc ttctggcaga aagccatcag gtgctcaatc atcttctcct ggccaaggct   6480
ctgaccatgc ttagtactgg aatagaggtg gccaggcccc cagcgactct tcttggcctg   6540
atgtttgtcc tcacaggcat gccacgtggc ctgagatgat tcagaacaaa tcatgctaac   6600
```

```
tttgaatcca tccagccact tgcaaatgat aatcagaagt cagcttgttc actgttagaa   6660

agaaactaac aaaagagaac ccagagcaat ctagaatctt tgagtgcttg gctttccaag   6720

gatactgcgg agactctggc caagctgatg accttctgaa gtgtcactgg caccatatgc   6780

aacaagaacc accattcact gagtagctaa tgggtttggg gcctgggaca ttccatctga   6840

ggtccttcct gaacatgtca ctccacagca gaggaccggt tgcagcttac ccagaaccac   6900

tcctccagga gagctggatg ttttgcgtgc aacaccttga gcactgactg ctattgttca   6960

aaaaaagcct ttgctgcatt cggaggactg ccccgtgccc tgaggtgact tcctaactat   7020

gtggtttcat tagcgaattt attttttgtg ctgggtggac atttgtattt tgttaggttg   7080

ctgtttaagc tcaagtttgc tgtgctctct gcagctacaa aacatcttgg catatttaag   7140

agtggctttt ataaatagct ttattctgat attaatcaga ttcccaactt tactgagaat   7200

taaggactgg ggtactttaa agaaatgcaa atagcaattg aagaaccact gctgcaggtg   7260

gtagccctgg ctagactgaa ttacactaga aatcagccag aaggaagcgt ccttgggatc   7320

ccagatcact cttttttttt ttttttaaaa ggggcagccc cttgatggct catctctctg   7380

aataacagtt acgtcttcat atcgatacca gatgccttct tcatcatgcc actgaagcca   7440

ctcaccacct tcaagaacat gccaacctct gtcagattca cttacccaca aacaaggagg   7500

cacgtttggc acaaagtgtt gtcctccagg tccaagtgga ctctacagag tgcttgacct   7560

caacacactg gattccaggt ggactggacc aagagcaggc aaagacacgg gaactgaaaa   7620

actccacagg gtttggagaa tagaaatgaa aagccacgtc atataactca agaataaatg   7680

gtgttttgga aattttaaaa ttatcatcga aggtggtgaa actatttcag gcccaaatga   7740

aaggaaatcg ccagttgggg atgaaatcac agagcctgtg ttttatgata tggttggatg   7800

tccactgatg aaattttaaa ggagtttcag ttttaaaagt gcgcatgatt ctacatatga   7860

gaattcttta ggccaagaaa ctgtccttgg ctcagaggtg ttgggaatta aagcagagag   7920

aagccattcg tgatgcttag aaccaaggat ggtcatgtac acaaagacca tcgagacggc   7980

cattcttgtt tacaaaacac ttaccaagaa agcactttgt aggggaactt tagtaagttc   8040

ttctcatttc attatgtttc ttccaaggaa acaggagaga ctgaattaat aattctctct   8100

ttcctcttaa gcacttttaa aataataaag tacatcttga aatttgggga ggcatctctg   8160

atttaaaaaa agaaaaaggc tgcttgatgt atgttatgca gagacactct gcctctggtg   8220

gctgcagagc aatacccaag cctcatttgg aaggctcaac atttggaatt gcactttaat   8280

tgattaatcc tcaattcatg tggccttacg ggatggtggg tctgggaccc caattcattc   8340

ttatctgcca aagaattatc tagaagcaca tcaaatacca gcaccccacc tgctcaatgg   8400

gggtggaaaa cttttgtatc cctaagcata ttattttata gtgtctgcca tgccatgtgg   8460

aaatacttta tttttaacct caggatttaa ataaagtaaa cactatgaca tttagaca     8518
```

<210> SEQ ID NO 12
<211> LENGTH: 6789
<212> TYPE: DNA
<213> ORGANISM: Homo sapiens

<400> SEQUENCE: 12

```
ctcgcgccag gcgagtctcc gcgtctccct cgcgaactcg gtgaaaggaa ttggcgccgt     60

tcgacaccag gcggatccgc tctgcagcac gaacccatct ccagccgcag ccgcagccgc    120

cgcccgggcc gaggagcagc cgcagcagcc gccaccagtg gccgagtgag cggagccgag    180

tttgaggcag cgcctagcgg tgaatcgggg ccctcaccat gagttcctcg cctgttaatg    240
```

```
taaaaaagct gaaggtgtcg gagctgaaag aggagctcaa gaagcgacgc ctttctgaca    300
agggtctcaa ggccgagctc atggagcgac tccaggctgc gctggacgac gaggaggccg    360
ggggccgccc cgccatggag cccgggaacg gcagcctaga cctgggcggg gattccgctg    420
ggcgctcggg agcaggcctc gagcaggagg ccgcggccgg cggcgatgaa gaggaggagg    480
aagaggaaga ggaggaggaa ggaatctccg ctctggacgg cgaccagatg gagctaggag    540
aggagaacgg ggccgcgggg gcggccgact cgggcccgat ggaggaggag gaggccgcct    600
cggaagacga gaacggcgac gatcagggtt tccaggaagg ggaagatgag ctcggggacg    660
aagaggaagg cgcgggcgac gagaacgggc acggggagca gcagcctcaa ccgccggcga    720
cgcagcagca acagccccaa cagcagcgcg gggccgccaa ggaggccgcg gggaagagca    780
gcggccccac ctcgctgttc gcggtgacgg tggcgccgcc cggggcgagg cagggccagc    840
agcaggcggg aggggacggc aaaacagaac agaaaggcgg agataaaaag aggggtgtta    900
aaagaccacg agaagatcat ggccgtggat attttgagta cattgaagag aacaagtata    960
gcagagccaa atctcctcag ccacctgttg aagaagaaga tgaacacttc gatgacacag   1020
tggtttgtct tgatacttat aattgtgatc tacattttaa aatatcaaga gatcgtctca   1080
gtgcttcttc ccttacaatg gagagttttg cttttctttg ggctggagga agagcatcct   1140
atggtgtgtc aaaaggcaaa gtgtgttttg agatgaaggt tacagagaag atcccagtaa   1200
ggcatttata tacaaaagat attgacatac atgaagttcg tattggctgg tcactaacta   1260
caagtggaat gttacttggt gaagaagaat tttcttatgg gtattctcta aaaggaataa   1320
aaacatgcaa ctgtgagact gaagattatg gagaaaagtt tgatgaaaat gatgtgatta   1380
catgttttgc taactttgaa agtgatgaag tagaactctc gtatgctaag aatggacaag   1440
atcttggcgt tgccttcaaa atcagtaagg aagttcttgc tggacggcca ctgttcccgc   1500
atgttctctg ccacaactgt gcagttgaat ttaattttgg tcagaaggaa aagccatatt   1560
ttccaatacc tgaagagtat actttcatcc agaacgtccc cttagaggat cgagttagag   1620
gaccaaaggg gcctgaagag aagaaagatt gtgaagttgt gatgatgatt ggcttgccag   1680
gagctggaaa aactacctgg gttactaaac atgcagcaga aaatccaggg aaatataaca   1740
ttcttggcac aaatactatt atggataaga tgatggtggc aggttttaag aagcaaatgg   1800
cagatactgg aaaactgaac acactgttgc agagagcccc ccagtgtctt gggaaattta   1860
ttgagattgc tgcccgaaag aagcgaaatt ttattctgga tcagacaaat gtgtctgctg   1920
ctgcccagag gagaaaaatg tgcctgtttg caggcttcca gcgaaaagct gttgtagttt   1980
gcccaaaaga tgaagactat aagcaaagaa cacagaagaa agcagaagta gaggggaaag   2040
acctaccaga acatgcggtc ctcaaaatga aaggaaactt taccctccca gaggtagctg   2100
agtgctttga tgaaataacc tatgttgaac ttcagaagga agaagcccaa aaactcttgg   2160
agcaatataa ggaagaaagc aaaaaggctc ttccaccaga aaagaaacag aacactggct   2220
caaagaaaag caataaaaat aagagtggca agaaccagtt taacagaggt ggtggccata   2280
gaggacgtgg aggattcaat atgcgtggtg gaaatttcag aggaggagcc cctgggaatc   2340
gtggcggata taataggagg ggcaacatgc cacagagagg tggtggcggt ggaggaagtg   2400
gtggaatcgg ctatccatac cctcgtgccc ctgtttttcc tggccgtggt agttactcaa   2460
acagagggaa ctacaacaga ggtggaatgc ccaacagagg gaactacaac cagaacttca   2520
gaggacgagg aaacaatcgt ggctacaaaa atcaatctca gggctacaac cagtggcagc   2580
```

```
agggtcaatt ctggggtcag aagccatgga gtcagcatta tcaccaagga tattattgaa   2640
tacccaaata aaacgaactg atacatattt ctccaaaacc ttcacaagaa gtcgactgtt   2700
ttctttagta ggctaacttt ttaaacattc cacaagagga agtgcctgcg ggttcctttt   2760
ttagaagctt tgtgggttga ttttttttct tttcttttt gtacattttt aattgcagtt   2820
taaaagtgaa tcgtaagaga acctcagcat tgtgcacgat aagagaatgt gtcagtattt   2880
cagggttcta cattttatct gtaaaatgtg acttttttt ttttttatca caacagaagt   2940
aaaatgttgc tttgtacctg gtgtctttta ttaagaattt actcccccca tttctcacag   3000
agaataacag tcgggagtca ttgtcacaat ataatagaaa tgttagcaac cagattcatg   3060
taaggactaa gtggtcctca tgaattgcat taagactctg tactgctcat attacactcc   3120
atcctctctg tagtttgctg ggtagtggag gggtaagct aaatcatagt ttctgacaat   3180
aactgggaag gtttttcttt aaaataacaa tggaattggt ataattggga ttgaaaacta   3240
aaacttggaa ctaagataga gaagatggag tgtatgtaga agggctgtta aaaatgtaaa   3300
acttggttgc attatttgtg gaggctcaaa cttgtgaagg ttaataccat aatttttcca   3360
tttgttctgc attttgattc tgaaaagaaa gctggctttg cccatttctt attaaaaaaa   3420
cttgttgtaa atccagttgt ctaatgggat ctatatgaag ttagccatgt ctgtatgccc   3480
ttctcccaca aaatactgta taactagtgt gcttgtagta gttaactcca ccatctttgt   3540
aagctaatga aattgtgagt cacccattta tatcttaatt tttaatcatg tcagttcttg   3600
aatgggtatc tccttagcct gctgatttct ttttctttct aaagaaagtg ggtggagaaa   3660
ttaatttaga cgtttgtttg caataaaaag aattcatttt actcttgttt tgggattctc   3720
gccatcaagg ttcaaaatcc ctttatataa ctcccaagag gagaaattta ttaagtgtgt   3780
gctttctgga cagcttattc tttactctgc atagaacatt taggttttaa aaacttaaat   3840
gtatactgac aattgataca taattatgaa gtaaagttga attcttccct tcccctcccc   3900
cccagacaac ttttaacata tttaatgagg ggaaaaggta ctggctggga gaagttaaca   3960
ctgagtttat catctttaca gaatgctaat gctgtcctca actgattatt ttatatacat   4020
atatatgata catgaaactc tgggatcaga tgcttttaga agccatcatg caagccagtc   4080
attgatgtca ctgctacaca acactgctaa cttgactgta gctatgtaat aacattagat   4140
cccctaattg taattatatt gggtttgcac agaacacttt aatcttcccc tcaccaatgt   4200
gaagtgagga atcaggagtc aaactgtaga actaaaattt gacttcagtc tagcgtttcc   4260
ttggtgtttt taggttgctt tggtaagttt aggtttgcta tatttctgat tgcttagaat   4320
tttgttttag ccctttaaaa tcagatcata aatatgaatt catacttcta aggaattttc   4380
ttgctataag ctggagttta ggtgatgtat aggttcagtt gagacatttt tggaacaggc   4440
aaatccttag ttaacataag atatttaaca gttgaagata gtgtcatgga tttttatctt   4500
ttttagcaag taatgctaag aaccactggc ctgagctact actcttcagt atacattatt   4560
aggattgcat agacttacta gaggaacagt ttcaggtttt gatgctaatc agtgttgtgt   4620
cctaaagttg tcctttgtgc ctttaaaaag ttttggatat atcttctagt ttaaaattgc   4680
ttattaagga attcatttta taattgcagt gggaaagtaa tggtcaagta acactaggta   4740
gactatcatg cctgtttagc ccagagaatt tggggggaga gagaatagat aaaaatggca   4800
cccagaaaaa tgttaaaatc tttagtcaag actagaatta atacaattgt ctacacttgt   4860
atggcagaaa taaccttata aagtgtttaa ggaattcaga gaagggaatg taccaaataa   4920
gcaacaggga gaaaattagg taagaagtaa gatacgaacg agaaacctga tttattgctc   4980
```

```
atccttccct tgcctcccta atggcaagca aaactctgaa catctgaaaa ggatgtagtt   5040

ctggacaaat cctgactacc cagaggaaac tcactgtgag attgctgttg atttgaaggg   5100

tgctttcact aaggttatat tttaaagtag aataacacat gctgagtgta aactggcttt   5160

ggattggtca gctgcagtag tacaaaaaca gcatagaatt tgagaaaact aaaactgcta   5220

tgagatagct atgagaaaac taaaactgct atgagataga aatgatgtaa aattatgtgg   5280

aaagttttcc ctcatatact cacatacagc ctttgaaggg ctctggctct gaccggttga   5340

tggccttgag cgagatgaaa tcatgaaatt gagtcaaatc aatttgacat tgaaatgaca   5400

agaggaaact cttaaataca taaaaacaag ctctcatttg cctaggatag atactgtctt   5460

aaaaataaag actgaaccta gatgttctga gcactagcaa caaggtattt taacaagttt   5520

aaaggaattc tctgaaaaag ttataaaatt attctaggaa acataaccat aatagtgttt   5580

taagggactt tcacctgggg attttatatt catgaacaga gtgtattctg tatttaaaat   5640

gtctcatttg tgggaattgg atgacatgtt ttttgataaa tttattcaca atataaattg   5700

actttttatt ctaggaccat gtgaataatg ggttccattg cacaaataca aatattttaa   5760

tagcttctta ggcagtggtg tagacatctt ggatataaat aattgtagat cttgtatatt   5820

tgatttttaa aaaactagaa taaacagaga ggcataaaca tatcttagag tccaagtggt   5880

agtgtttagc attggatata ataaatggat gttttacaaa gtgtttccat aattctcttc   5940

ctatacataa atgtcttgtt ttcaaaagtg gatggaactt ggctgggtgt ggtggctcac   6000

gcctgtaatc ctagcacttt gggaggccaa ggcgggagga tcacttgagc tcaggagttt   6060

gagaccatcc tgggcaacat agtgagacct ggtctcttga aaaaaaaaaa gtggatggaa   6120

cttgtagcag agaattttat ctacttctca acctgcttca gaatacccat ttgagatgtt   6180

cccctggaaa gatgaacaca atactgcatc tgaagccatt tcttcccacc taacattctt   6240

aaaatgatta gagtctaaac tttgtcattc attcctaatt ctggagctct gaggttgagg   6300

tgttcagagt ttggtgaata attgggttta agttttaaca ttttagtaat aataaaagca   6360

aacacataca tgttaaggcc tgacaatagg ttgcaatacc catgcattgg gactcatacc   6420

cagcataaat ggtgagggac tgaacattag tgctttgagc aagaattggt taactacctg   6480

agatctctaa aacagtaatt tgaattacta atacataaac cacaagtctc ttcgaattgt   6540

taattgccta aatttaccct aaaacttagt taacgctgca gtgcctttat taaagctttt   6600

ttttgggggg gggtgtgggc acagctactc cataacttta aattttaaag catgaaggtg   6660

atctagctag tgttagtgct tgagttggta gttacatagg ctgctcttga atcgtcctgt   6720

tttctttgcc tagtattagc accacaggta catatttgta aaataagcat taaaagtact   6780

ttgtccagc                                                           6789
```

<210> SEQ ID NO 13
<211> LENGTH: 1809
<212> TYPE: DNA
<213> ORGANISM: Homo sapiens

<400> SEQUENCE: 13

```
tcgagcccgc tttccaggga ccctacctga gggcccacag gtgaggcagc ctggcctagc     60

aggccccacg ccaccgcctc tgcctccagg ccgcccgctg ctgcggggcc accatgctcc    120

tgcccaggcc tggagactga cccgaccccg gcactacctc gaggctccgc ccccacctgc    180

tggaccccag ggtcccaccc tggcccagga ggtcagccag ggaatcatta acaagaggca    240
```

```
gtgacatggc gcagaaggag ggtggccgga ctgtgccatg ctgctccaga cccaaggtgg    300

cagctctcac tgcggggacc ctgctacttc tgacagccat cggggcggca tcctgggcca    360

ttgtggctgt tctcctcagg agtgaccagg agccgctgta cccagtgcag gtcagctctg    420

cggacgctcg gctcatggtc tttgacaaga cggaagggac gtggcggctg ctgtgctcct    480

cgcgctccaa cgccagggta gccggactca gctgcgagga gatgggcttc ctcagggcac    540

tgacccactc cgagctggac gtgcgaacgg cgggcgccaa tggcacgtcg ggcttcttct    600

gtgtggacga ggggaggctg ccccacaccc agaggctgct ggaggtcatc tccgtgtgtg    660

attgccccag aggccgtttc ttggccgcca tctgccaaga ctgtggccgc aggaagctgc    720

ccgtggaccg catcgtggga ggccgggaca ccagcttggg ccggtggccg tggcaagtca    780

gccttcgcta tgatggagca cacctctgtg gggatccct gctctccggg gactgggtgc    840

tgacagccgc ccactgcttc ccggagcgga accgggtcct gtcccgatgg cgagtgtttg    900

ccggtgccgt ggcccaggcc tctccccacg gtctgcagct gggggtgcag gctgtggtct    960

accacggggg ctatcttccc tttcgggacc ccaacagcga ggagaacagc aacgatattg   1020

ccctggtcca cctctccagt cccctgcccc tcacagaata catccagcct gtgtgcctcc   1080

cagctgccgg ccaggccctg gtggatggca agatctgtac cgtgacgggc tggggcaaca   1140

cgcagtacta tggccaacag gccggggtac tccaggaggc tcgagtcccc ataatcagca   1200

atgatgtctg caatggcgct gacttctatg gaaaccagat caagcccaag atgttctgtg   1260

ctggctaccc cgagggtggc attgatgcct gccagggcga cagcggtggt ccctttgtgt   1320

gtgaggacag catctctcgg acgccacgtt ggcggctgtg tggcattgtg agttggggca   1380

ctggctgtgc cctggcccag aagccaggcg tctacaccaa agtcagtgac ttccgggagt   1440

ggatcttcca ggccataaag actcactccg aagccagcgg catggtgacc cagctctgac   1500

cggtggcttc tcgctgcgca gcctccaggg cccgaggtga tcccggtggt gggatccacg   1560

ctgggcctag gatgggacgt tttcttctt gggcccggtc cacaggtcca aggacaccct   1620

ccctccaggg tcctctcttc cacagtggcg ggcccactca gccccgagac cacccaacct   1680

caccctcctg acccccatgt aaatattgtt ctgctgtctg ggactcctgt ctaggtgccc   1740

ctgatgacgg gatgctcttt aaataataaa gatggttttg attaaaaaaa aaaaaaaaaa   1800

aaaaaaaaa                                                           1809
```

<210> SEQ ID NO 14
<211> LENGTH: 1861
<212> TYPE: DNA
<213> ORGANISM: Homo sapiens

<400> SEQUENCE: 14

```
cactcaaggt gtgcaggcag ctgtgtttgt caggaaggca gaaggagttg gctttgcttt     60

aggggaggag acgaggtccc acaacaccct ctgaagggta tataaggagc cccagcgtgc    120

agcctggcct ggtacctcct gccagcatct cttgggtttg ctgagaactc acgggctcca    180

gctacctggc catgaccacc acatttctgc aaacttcttc ctccaccttt gggggtggct    240

caacccgagg gggttccctc ctggctgggg gaggtggctt tggtgggggg agtctctctg    300

ggggaggtgg aagccgaagt atctcagctt cttctgctag gtttgtctct tcagggtcag    360

gaggaggata tgggggtggc atgagggtct gtggctttgg tggaggggct ggtagtgttt    420

tcggtggagg ctttggaggg ggcgttggtg ggggttttgg tggtggcttt ggtggtggcg    480

atggtggtct cctctctggc aatgagaaaa ttaccatgca gaacctcaat gaccgcctgg    540
```

```
cctcctacct ggacaaggta cgtgccctgg aggaggccaa tgctgacctg gaggtgaaga    600

tccatgactg gtaccagaag cagaccccaa ccagcccaga atgcgactac agccaatact    660

tcaagaccat tgaagagctc cgggacaaga tcatggccac caccatcgac aactcccggg    720

tcatcctgga gatcgacaat gccaggctgg ctgcggacga cttcaggctc aagtatgaga    780

atgagctggc cctgcgccag ggcgttgagg ctgacatcaa cggcttgcgc cgagtcctgg    840

atgagctgac cctggccagg actgacctgg agatgcagat cgagggcctg aatgaggagc    900

tagcctacct gaagaagaac cacgaagagg agatgaagga gttcagcagc cagctggccg    960

gccaggtcaa tgtggagatg gacgcagcac cgggtgtgga cctgacccgt gtgctggcag   1020

agatgaggga gcagtacgag gccatggcgg agaagaaccg ccgggatgtc gaggcctggt   1080

tcttcagcaa gactgaggag ctgaacaaag aggtggcctc caacacagaa atgatccaga   1140

ccagcaagac ggagatcaca gacctgagac gcacgatgca ggagctggag atcgagctgc   1200

agtcccagct cagcatgaaa gctgggctgg agaactcact ggccgagaca gagtgccgct   1260

atgccacgca gctgcagcag atccaggggc tcattggtgg cctggaggcc cagctgagtg   1320

agctccgatg cgagatggag gctcagaacc aggagtacaa gatgctgctt gacataaaga   1380

cacggctgga gcaggagatc gctacttacc gcagcctgct cgagggccag gatgccaaga   1440

tggctggcat tggcatcagg gaagcctctt caggaggtgg tggtagcagc agcaatttcc   1500

acatcaatgt agaagagtca gtggatggac aggtggtttc ttcccacaag agagaaatct   1560

aagtgtctat tgcaggagaa acgtcccttg ccactcccca ctctcatcag gccaagtgga   1620

ggactggcca gagggcctgc acatgcaaac tccagtccct gccttcagag agctgaaaag   1680

ggtccctcgg tcttttattt cagggctttg catgcgctct attccccctc tgcctctccc   1740

caccttcttt ggagcaagga gatgcagctg tattgtgtaa caagctcatt tgtacagtgt   1800

ctgttcatgt aataaagaat tacttttcct tttgcaaata aaaaaaaaaa aaaaaaaaaa   1860

a                                                                   1861
```

<210> SEQ ID NO 15
<211> LENGTH: 1700
<212> TYPE: DNA
<213> ORGANISM: Homo sapiens

<400> SEQUENCE: 15

```
aactagcacg tggctcccgc ccccagactg cttctttatt cattcctaac ctttaccttg     60

gcagatgaaa tataagattc atcaaccaca tttgacagcc catggcaggt ttcctgtttt    120

ccatcgtccc tctgcaggtc acagacacac agagcccagc cgtggcaggc tcagccgggg    180

tccggggctg ctaacaacgg ctacattcct cccccagggc caagggaaat cctgagcgca    240

ggccagggtt gtttggtttt gaggtgtgct gggatgaaag gcaccctgga agtggaaggt    300

tcggtcattc attaattaat tacatctata attgagggtt tgttcttaag agcgagtcct    360

ttgaaagtac tttccttcaa acagtgactg ccacaaaggc atcagatatt caccaccttc    420

tcggctgcct cagcacagca agctttattc tgggacctga gatcctgttc tgagctggct    480

ttcccttctc caggctcgct caccctccct ttagagatag tggatggtaa gatgaccaat    540

gctcagatta ttcttctcat tgacaatgcc aggatggcag tggatgactt caacctcaag    600

tatgaaaatg aacactcctt taagaaagac ttggaaattg aagtcgaggg cctccgaagg    660

accttagaca acctgaccat tgtcacaaca gacctagaac aggaggtgga aggaatgagg    720
```

```
aaagagctca ttctcatgaa gaagcaccat gagcaggaaa tggagaagca tcatgtgcca    780
agtgacttca atgtcaatgt gaaggtggat acaggtccca gggaagatct gattaaggtc    840
ctggaggata tgagacaaga atatgagctt ataataaaga agaagcatcg agacttggac    900
acttggtata aagaacagtc tgcagccatg tcccaggagg cagccagtcc agccactgtg    960
cagagcagac aaggtgacat ccacgaactg aagcgcacat tccaggccct ggagattgac   1020
ctgcagacac agtacagcac gaaatctgct ttggaaaaca tgttatccga gacccagtct   1080
cggtactcct gcaagctcca ggacatgcaa gagatcatct cccactatga ggaggaactg   1140
acgcagctac gccatgaact ggagcggcag aacaatgaat accaagtgct gctgggcatc   1200
aaaacccacc tggagaagga aatcaccacg taccgacggc tcctggaggg agagagtgaa   1260
gggacacggg aagaatcaaa gtcgagcatg aaagtgtctg caactccaaa gatcaaggcc   1320
ataacccagg agaccatcaa cggaagatta gttctttgtc aagtgaatga aatccaaaag   1380
cacgcatgag accaatgaaa gtttccgcct gttgtaaaat ctattttccc ccaaggaaag   1440
tccttgcaca gacaccagtg agtgagttct aaaagatacc cttggaatta tcagactcag   1500
aaacttttat tttttttttc tgtaacagtc tcaccagact tctcataatg ctcttaatat   1560
attgcacttt tctaatcaaa gtgcgagttt atgagggtaa agctctactt tcctactgca   1620
gccttcagat tctcatcatt ttgcatctat tttgtagcca ataaaactcc gcactagctg   1680
caaaaaaaaa aaaaaaaaaa                                               1700
```

<210> SEQ ID NO 16
<211> LENGTH: 4048
<212> TYPE: DNA
<213> ORGANISM: Homo sapiens

<400> SEQUENCE: 16

```
ggaagtgggc ctggcacctt cccggcctgc cgcagggatg ggcagctgt gctggctgcc      60
gctgctggca ccgctcctgt tgctgcgacc gccaggggtc cagtccgccg gccccatccg    120
ggccttcgtg gtgccccaca gccacatgga cgtgggctgg gtctacactg tgcaggaaag    180
catgcgggcg tacgccgcca atgtctacac ctcagtggtg gaagagctgg cccgcggcca    240
gcagcgccgg ttcatcgctg tggagcagga gtttttccgg ctgtggtggg atggcgtcgc    300
ctcggaccag cagaaatacc aggtccgcca gctcctggag gaaggacgcc tggaatttgt    360
catcggaggc caggtcatgc atgacgaggc tgtgacgcac cttgatgacc agatcctgca    420
gctcacagaa ggacacgggt ttctctatga aacatttggg atccggccac agttctcctg    480
gcacgttgac ccgtttggcg cctctgccac gacgcccacc ctatttgcgc tggcgggctt    540
caatgcccac ctcggctccc ggatcgacta cgacctgaag gcagccatgc aggaggcccg    600
ggggctgcag ttcgtgtggc gagggtcccc atccctctca gagcggcagg aaatcttcac    660
gcacatcatg gaccagtaca gctactgcac cccgtcccac atccctttct ccaacaggtc    720
aggattttac tggaatggcg tggctgtctt ccccaagcct ccccaagatg gggtgtaccc    780
caacatgagt gagcctgtca ccccagccaa catcaacctc tatgccgagc tcggtgtctc    840
ggtgcagtat gccacgctgg gcgactactt ccgtgccctg cacgctctca atgtcacctg    900
gcgtgtccgc gaccaccacg acttcctgcc ctattccaca gaaccattcc aggcctggac    960
gggcttctac acgtcccgca gctcactgaa ggggctggcc cggcgagcca gcgccttgtt   1020
gtatgccggg gagtccatgt tcacacgcta cctgtggccg gcccccgtg ggcatctgga   1080
ccccacctgg gccctgcagc agctccagca gcttcgctgg gccgtctccg aggtccagca   1140
```

```
ccatgatgcc atcactggga ctgagtcccc caaggtgaga gacatgtacg caacgcacct   1200
ggcctcgggg atgctgggca tgcgcaagct gatggcctcc atcgtcctag atgagctcca   1260
gccccaggca cccatggcgg ccagctccga tgcaggacct gcaggacatt ttgcctcggt   1320
ctacaacccg ctggcctgga cggtcaccac catcgtcacc ctgactgttg gtttccctgg   1380
agtccgcgtc acagatgagg cgggccaccc agtgccctcg cagatccaga actcaacaga   1440
gaccccatct gcgtatgacc tgcttattct gaccacaatc ccaggcctca gttaccggca   1500
ctacaacatc agacccactg caggggccca agagggcacc caggagccgg ctgccactgt   1560
ggcgagcacc cttcaatttg gccgcaggct gaggagacgc accagccatg cgggcaggta   1620
cttggtgcct gtggcaaacg actgctacat tgtgctgctc gaccaggata ccaacctgat   1680
gcacagcatc tgggagagac agagtaaccg aacggtgcgc gtgacccagg aattcctgga   1740
gtaccacgtc aacggggatg tgaaacaggg ccccatttcc gataactacc tgttcacacc   1800
gggcaaggcc gcggtgcctg cgtgggaagc tgtggaaatg gagattgtgg cgggacagct   1860
tgtgactgag atccggcagt acttctacag gaacatgaca gcacagaatt acacgtatgc   1920
aatccgctcc cggctcaccc atgtgccgca gggccatgac ggggagctgc tctgccaccg   1980
gatagagcag gagtaccaag ccggccccct ggagctgaac cgtgaggctg tcctgaggac   2040
cagcaccaac ctaaacagcc agcaggtcat ctactcagac aacaacggct accagatgca   2100
gcggaggccc tacgtttcct atgtgaacaa cagcatcgcc cggaattact accccatggt   2160
tcagtcggcc ttcatggagg atggcaaaag caggcttgtg ttgctgtcgg agcgggcaca   2220
tggcatctcc agccaaggga atgggcaggt ggaggtcatg ctccaccggc ggctgtggaa   2280
caacttcgac tgggacctgg gctacaacct cacgctgaac gacacctcag tcgtccaccc   2340
agtgctctgg cttctgctgg gatcctggtc cctcaccact gccctgcgcc agaggagcgc   2400
actggcgctg cagcacaggc ccgtggtgct gttcggagac ctcgctggga ctgcgccgaa   2460
gctcccagga ccccagcagc aagaggccgt gacgctgccc ccgaatcttc acctgcagat   2520
cctgagcatc cctggctggc gctacagctc caaccacacg gagcactctc agaatctccg   2580
gaaaggccat cgaggggaag cccaggctga cctccgccgt gtcctgctgc ggctctacca   2640
cctgtatgaa gtgggcgagg acccagtcct gtctcagcca gtgacagtga atctggaggc   2700
tgtgctgcag gcgctggggt ccgtggtggc agtggaggag cgctcgctca cagggacctg   2760
ggatttgagc atgctgcacc gctggagctg gaggacgggg cctggccgcc acagaggtga   2820
caccacctct ccctcgaggc caccaggagg ccccatcatc accgtccacc caaaggaaat   2880
ccggacgttc tttattcact ttcaacagca gtgagccctg ggcagatgcc ccggccccag   2940
ggcttccccc aggaactcca tgtaacagaa cagacccagg acagggaaaa gcagtgcgga   3000
gggatgggac tggggagtca gctgctcatc tgcaggctaa tggcaggaaa tggtcatatt   3060
tggggttttt ccctaatttt tttaaacaaa aattacatta caagatccag gttcttcccc   3120
cccacactca atcaagccag ccctctcctc ttctgtcacg taaaggatat ttggcacact   3180
catgcgtcat tcattcacaa aacacaaacc caggactttc tgcctaaggc agagcacaag   3240
actcacagca gcaccgaagc gcatctgccg tccgggccct gccaggcttg ccaggctgcc   3300
agtggtaact gtggacctac tgcgtgccac gtgttttcat agactcatcc catgctggca   3360
acagccctgc aaggggcttg gctctgccac agggcaggag aggaagttgt agcgcctagc   3420
gagagttcca gccccagacg cccacctgtg cctcagggca ccgcctgccg agcagagaag   3480
```

gcacagcagc cgtcagagtc catgagaggt gaaaccacac agcagggatg tccaatatca 3540
gaactattaa tatcaataaa agtataacct tcccaggtct atgcccaaga gaattgaaaa 3600
catccatcca cacaatacct gtgctcccgc gttcatagca gcattactca aaagtcaaac 3660
ggtagcaaca acccaaatgt ccatccacag atgaattaag acatgaagtg tgttctgtcc 3720
atacaatgga atattatttg gccataaaaa ggaaggaaat tctgacgcat gccacagcct 3780
gagtgaatcc tacaaatatt acgctaagtg aaagaagcca atcacgagtt tatgtgaaat 3840
gtccagaata ggcaaatctg tgtatcagag acaaagcaca ttggtggttg ccaggtactg 3900
gaggaagaga gaagaggcat gacagctaac agggacgggc tttctttgga agatgatgaa 3960
attgtggaat gatggttgca caactttgtg aatatactag aaaccaatga attaaaaact 4020
ttggaagatg aaaaaaaaaa aaaaaaaa 4048

<210> SEQ ID NO 17
<211> LENGTH: 2141
<212> TYPE: DNA
<213> ORGANISM: Homo sapiens

<400> SEQUENCE: 17
tgcgtgccgc cgttgatccg gtgctgcagt gaggaggtgg ttcttgcccg tgttgtgtgt 60
gtgtgtgagt gagagagcga gtgagtgagt gagtgagtgt gtgtgtgggg gggactcggc 120
ttgttgttgt cggtgacttc cccctcccct tcaccccttc ccctccccgc cgccgctgca 180
gtggccgctc cctgggccgt aggaaatgag cgataacgat gacatcgagg tggagagcga 240
cgaagagcaa ccgaggtttc aatctgcggc tgacaaacgg gctcatcata atgcactgga 300
acgaaaacgt agggaccaca tcaaagacag ctttcacagt ttgcgggact cagtcccatc 360
actccaagga gagaaggcat cccgggccca aatcctagac aaagccacag aatatatcca 420
gtatatgcga aggaaaaacc acacacacca gcaagatatt gacgacctca agcggcagaa 480
tgctcttctg gagcagcaag ggaaagcga gagctgatca agttctttgt tcctggggaa 540
ttcacttctc ttcctccctc atggaagatg caagtaaaag gaaattccgt gcactggaga 600
aggcgaggtc aagtgcccaa ctgcagacca actacccctc ctcagacaac agcctctaca 660
ccaacgccaa gggcagcacc atctctgcct tcgatggggg ctcggactcc agctcggagt 720
ctgagcctga agagccccaa agcaggaaga agctccggat ggaggccagc taagccactc 780
ggggcaggcc agcaataaaa actgtctgtc tccatcgtct catcctcctt tcagttcgtt 840
ggtagagccc tcagaaccat ttaagagact ctttattttt ctctttctcc cttttttttt 900
taaattttta tttttacgta gaagctcttg gacaacagct ctcgttctcc ttccccattt 960
ccactgtata ttttttaatg tattcccttc agggattccc tgtccccaac aggaattttt 1020
aaaccaaaac accccaactt ggcagctttt tctgtggagg acagacggcc ggccggacct 1080
ctgagcacat agtgtcctgc ccaccctacc agctcctcca gccctgccgg gcacatgccc 1140
gggggacgcc tgccctgccc aggtggcctc ctggcccgcc ctcacctctg atagactttg 1200
tgaatctgaa ctgctctact ttgagaagat gaccggtttg gagtaatcag aatgaaccct 1260
cctccttttt aagggttttt tttttttcct ttttctaaaa agctatgtat cgctcctatt 1320
gaaagaccag atccttagag aagtttgtgg tataaaaagg aagtggggac agattcgcag 1380
cacagagtcg ctggcatgtt tcactcctgc ttctctcagc cagctgttta agcctgcggc 1440
gccagcctca cggagggccg tgtgacactc tcgtggtatg tatgggagat ggcagcagtg 1500
aagcagcagc caccagggag tggccatttg ggttgggac agggagggtg ttttgggtgg 1560
catagaggtt ttgtattgag ggccagtgat gatgttttga tatttatttc ctgctactta 1620
aatttgaatc tgagtgaatt gtacctattt ctgatgatgt cggtcttgca aagcgacaga 1680
ttcataaagt aatgatgaaa tctttctttc ttcccgtgtg tatttctaag aaatagagcc 1740
aactgatttt gtatgtaaat accaagagca atttacctgg tactaaaccc gcaccccagt 1800
gcggaccctt cccagccctc atcccacttc ctttcctact gtcctggaac ctgtctccat 1860
tgtgtgatcc agccctggtt ctggctgtgg tcagcagatg ccagtgaagg gttttgtgtg 1920
tttaggcctc atttctttgt ctttttccta ctccgttcct ggcatttgct gatttctagt 1980
gtatactctg tagtctcagt tcgtgtttga ttccattcca tggaaataaa aagtatgttg 2040
tacatactgc cgaagaattg tcttgcaagt taaggcttcc ccctttacta taagactata 2100
aataaaaact tattttatcc ttcttaaaaa aaaaaaaaaa a 2141

<210> SEQ ID NO 18
<211> LENGTH: 4602
<212> TYPE: DNA
<213> ORGANISM: Homo sapiens

<400> SEQUENCE: 18
gaagcgtctc ctgtgcgtct gcgcgggaag tggaacctgg ctctggggag aagccgcgtg 60
agatccgcgc gggtgctagc tagtcctttc tcgtcgctgc tcggctcgcg gcccgtgggg 120
tcggccccgc caccgttgcc gccatgccca tgaagggccg cttccccatc cgccgcaccc 180
tgcaatatct gagccagggg aacgtggtgt tcaaggactc cgtgaaggtc atgacagtga 240
attacaacac gcatggggag ctgggcgagg gcgccaggaa gtttgtgttt ttcaacatac 300
ctcagattca atacaaaaac ccttgggtgc agatcatgat gtttaagaac atgacgccgt 360 caccettcct gcgattctac ttagattctg gggagcaggt cctggtggat gtggagacca 420
agagcaataa ggagatcatg gagcacatca gaaaaatctt ggggaagaat gaggaaaccc 480
tcagggaaga ggaggaggag aaaaagcagc tttctcaccc agccaacttc ggccctcgaa 540
agtactgcct gcgggagtgc atctgtgaag tggaagggca ggtgccctgc cccagcctgg 600
tgccattacc caaggagatg aggggaagt acaaagccgc tctgaaagcc gatgcccagg 660
actaaggccc acggtcactg tgggctgggg tgatggtgtc tgaccagtgg ggagattgga 720
atgggattac tttggcccag ggaagcccct ggttctgtcc ctggagactc tggaaatcct 780
tttgcattaa aaggacttta cacacctgtg taaaaggatg tgggagagga gggtctgaag 840
ctgagctgct aaatgaatat ccctgctctg ctggtcaata aaacgcttcc taatagcagc 900
ttggcgtgta tctggtccta gtgaagagga aggcctgtgt agcagaaagg ctttgggcct 960
gagaggttaa ggccacagcc tgttgacacc tgttttggtc ctgcgaccct ttactggtct 1020
ccgctggctt tgaatcttcc tctgggctct actctggaga acataagggc tgctgtggtt 1080
gagtctggct agcactgtct gtggttggca gtgtgtacac ccctccgttc agttccttgg 1140
gggtattttt cagaaatcca aaggcaaccc ttcgtgcagt gctcactttt ttaagtacag 1200
ttgattaccc ttgcctgctg gggggcctag ccatgggcca gagatggagg agccccagtg 1260
gctgacaggc cagcctcact caggcacgta cctgctgacc agtcagccac tgccaaccca 1320
tggcccagcc actgtgtgca ttagcaggga ggtttgtagg ccatggagga aatgaggaga 1380
caccacctag tggagacatt ggggccctgc tgggggggatg gtgtctatag ctggctctgc 1440
tggctccctc aggccctgct taccaagctc tggaggaggg agtgctgcat tactgagcac 1500

```
cttccttgtt ctttcctcat aggacactga tgttactgtc actttagtta tgctaaagtg   1560
gaggtttcag cctccagaag acagcagagc cttctagggt caccttaaga ataggtttag   1620
ctaggctggg tgtggtggct catgcctgta atcccagcac tttgggaggc tgatgtgggc   1680
ggatagttga gcccaggagt tcgagaccag cctgggcaac atggcaagac cttgtctcta   1740
caaaaagtac aaaaattaga tgggtgtggt gtttcgcgtc tgtagtccca gctatttggg   1800
aagctgaggt gggaggatct cgagcctgcg agatcaaggc tgcagtgaat catgatcgtg   1860
cgctactgca ctccagcctg ggccacagag caagactgtc tcaagaaaaa aaattttta    1920
aataagttta attataaagt gaaggaccag ttggaccacg gacccctaga aactcagcca   1980
aggagacctg actttatctg agacaggaag gcagtggtta aaagaattaa aaaaggacag   2040
tggtgcttga cagagcagga ctgaagtttt cattcctcta cctgctgggg ccttggtcaa   2100
gtcctaaaag ctttccaggt ctgtaactgg ttttgtctgt aaaatgggga aaaggttacc   2160
ttttctgcca catgaagtag ctggctggtg aaatgatgtc atactacgat gtgtttcatt   2220
aactgttgga gattatcaca ttaaattgag cagatttgga tcttttacat ttgatgctca   2280
agtttgattc tgtaccagat ctgggtttgg ggtgatggct tgtcgggggt gggaggggaa   2340
ggtgggcaga gactgatgta taatggacag gtgttccttg agtgacagac ttacaaaggg   2400
agtgtttaat tgaaatctag catcttgtct ctctgctatc agcattttgg ctgggtggaa   2460
aaagctctcc tccacagaga gccctcccat gtctgctggt ttcagttccc cacccaactg   2520
actgaagtct tgaccttgat accacctgcc tgggcgttct acttggctgc aagggctctt   2580
cagaaagcac ctagttcctt ttggctttca tctgcagtgt aggtctccat agctagtgac   2640
acacaaagcc ttatgagagt attccttccc tctagggccc aaagaggctg ctaaccagca   2700
ggaatgtcct gaaccaaaag gagtggtgac cattctctag acagaataaa tgtctggtcc   2760
ctaatgggac agataactag ggtttgagtt caggcttgac acaggagcaa tgggcagtga   2820
ggtggacagc ccagaccctg aaaggacgtg tggagacagc agcagtcctg tggtgcagtt   2880
actgcctgtg tggccagctt cacaggcagc agataatttg tggaaataaa cattattttc   2940
tttttttgtt ccctgtaggc tacttgatcc tggatagttt ctctttaaac ctttgtcttt   3000
ccctattttg tttagtagtg atgaaagatg ggtttaaaat atacagaaat gggagaaaat   3060
taattagaga aaatgtgagg attttataat tgataacatg ttcttaattt tacttgcaca   3120
agcagtgttc acagccttat tctgaagtga ccacttttct tctctttgag gcactacctg   3180
gcagcaccat ctaaacctgt atcatctgct gtggtcccag ttactcagga ggctgaggca   3240
ggaggatcac ttgagcccag gaggttgagg ctggagtgag ccatgactgt accactgcat   3300
tccagcctgg gtgacggagt gaggccctat ctgcctgcca gtgagttctg tcatgcatca   3360
gactttggac ctcagaattt tcacctggaa catgagaggt cagatgacat aatgaatatg   3420
ttctaacttc tgaaactttt ggagcttgtt tttgcccttg atagcacgta tccttagaga   3480
ataagcttgc caatttaagg cctgtctgta atggcatctg aatgttccag cagcctaact   3540
gtgctctgct ccagaaacat gtgtgtggct tccctacctc cacaccaagg agctgccttg   3600
ctgggtggat gtaaagactg tcctgccagg gtttcccact aaaggtatta ataagtccag   3660
tggaccacag agggcccaat ccctcttggc cgctaaggct aaggtaggag ccagagagct   3720
gtagagacag gaccaccagg atgcttcatg tccataacac aagagagcgc tgcattgttt   3780
gggggccagg cattactact atcatgaaga aaaatgaaga gcaggatgca tgttagtctt   3840
taattcactt ttaatagtat aaacctcatt taggtagtag tattaagcca caacaataat   3900
```

gccacattga aacagcattt aataaaatgc ataaagctaa ttcatgcact gcaatactct 3960
atatacaaac acaacaatgc aaattcttct tcaagactga agacattgat tagatataaa 4020
attcagttta aaaagaacat gctatttttt aaatgccatc acataaacaa agtgatttca 4080
cagggagaag aaagctgtat aaagctgcag ctttcaacag gttttaaacc tggcattaaa 4140
atgtaatggc aaaaccaata ttttctatat tgtgaagggc aaaggttaca gaaacggtcc 4200
caagaaaatc taacacccaa attttccttt gatagataga tgcctttaaa agggctggta 4260
atgcagttac attctaacag agaagtccaa actacaggta aaaactacgg cttgtactgt 4320
gaaaaatgtg cagcttttca gttataaaac tagttgaaca ctggtttaca agataatccg 4380
tagaacagag agactgtaga aaaatattcc agcacttgag ttgtgtgtgg cagcagcatt 4440
tgagtccatg aatgctatgg tcattaaaat aattgattat actttcctaa agaaaagcca 4500
ttttttaatg caaagtctac tacttccaaa tgttattcca aacattaaat tttaacagtc 4560
tatcaatcaa taaatgttga acattttttt tctaaaaaaa aa 4602

<210> SEQ ID NO 19
<211> LENGTH: 2082
<212> TYPE: DNA
<213> ORGANISM: Homo sapiens

<400> SEQUENCE: 19
aaaagccagc caggagctgt gggaggaaac gccctcagta aagatgaccg cggtcactgt 60
tatctaaacg caagtgaagc cgagtcacag gacccggatg ttgtcagttc gacggtaaac 120
gaccctgcca gcttccaaga gggcggcttc actgtgcgaa taggtgagaa gccaagaagg 180
aggcgcgctg gagttacttc cgcccggttc tccttcccgc agtctgcagc cggagtaaga 240
tggcggcgct gagggctttg tgcggcttcc ggggcgtcgc ggcccaggtg ctgcggcctg 300
gggctggagt ccgattgccg attcagccca gcagaggtgt tcggcagtgg cagccagatg 360
tggaatgggc acagcagttt gggggagctg ttatgtaccc aagcaaagaa acagccccact 420 ggaagcctcc accttggaat gatgtggacc ctccaaagga cacaattgtg aagaacatta 480
ccctgaactt tgggccccaa cacccagcag cgcatggtgt cctgcgacta gtgatggaat 540
tgagtgggga gatggtgcgg aagtgtgatc ctcacatcgg gctcctgcac cgaggcactg 600
agaagctcat tgaatacaag acctatcttc aggcccttcc atactttgac cggctagact 660
atgtgtccat gatgtgtaac gaacaggcct attctctagc tgtggagaag ttgctaaaca 720
tccggcctcc tcctcgggca cagtggatcc gagtgctgtt tggagaaatc acacgtttgt 780
tgaaccacat catggctgtg accacacatg ccctggacct tggggccatg accccttttct 840 tctggctgtt tgaagaaagg gagaagatgt ttgagttcta cgagcgagtg tctggagccc 900
gaatgcatgc tgcttatatc cggccaggag gagtgcacca ggacctaccc cttgggctta 960
tggatgacat ttatcagttt tctaagaact tctctcttcg gcttgatgag ttggaggagt 1020
tgctgaccaa caataggatc tggcgaaatc ggacaattga cattggggtt gtaacagcag 1080
aagaagcact taactatggt tttagtggag tgatgcttcg gggctcaggc atccagtggg 1140
acctgcggaa gacccagccc tatgatgttt acgaccaggt tgagtttgat gttcctgttg 1200
gttctcgagg ggactgctat gataggtacc tgtgccgggt ggaggagatg cgccagtccc 1260
tgagaattat cgcacagtgt ctaaacaaga tgcctcctgg ggagatcaag gttgatgatg 1320
ccaaagtgtc tccacctaag cgagcagaga tgaagacttc catggagtca ctgattcatc 1380

```
actttaagtt gtatactgag ggctaccaag ttcctccagg agccacatat actgccattg   1440
aggctcccaa gggagagttt ggggtgtacc tggtgtctga tggcagcagc cgcccttatc   1500
gatgcaagat caaggctcct ggttttgccc atctggctgg tttggacaag atgtctaagg   1560
gacacatgtt ggcagatgtc gttgccatca taggtacgag gcctattgtg tagtagaggt   1620
atcctagaca aaggagttcg ggacgcccac tggggacaga aggagaacac ttcctgttca   1680
ccataggcca tggcatggac tcgggtcctc aatcttttga gcacagtaat gggttctgga   1740
tcttgggtaa caccactttt tttgtttgtt ttgcctcaca acaggaagat aagtaacatc   1800
actttttcc tccatcctct cacctaggta cccaagatat tgtatttgga gaagtagatc   1860
ggtgagcagg ggagcagcgt ttgatccccc ctgcctatca gcttcttctg tggagcctgt   1920
tcctcactgg aaattggcct ctgtgtgtgt gtgtgtgtgt gtgtgtgtgt gtatgttcat   1980
gtacacttgg ctgtcaggct ttctgtgcat gtactaaaaa aggagaaatt ataataaatt   2040
agccgtcttg cggcccctag gcctaaaaaa aaaaaaaaaa aa                     2082
```

<210> SEQ ID NO 20
<211> LENGTH: 6318
<212> TYPE: DNA
<213> ORGANISM: Homo sapiens

<400> SEQUENCE: 20

```
tagtaagaca ggtgccttca gttcactctc agtaaggggc tggttgcctg catgagtgtg     60
tgctctgtgt cactgtggat tggagttgaa aaagcttgac tggcgtcatt caggagctgg    120
atggcgtggg acatgtgcaa ccaggactct gagtctgtat ggagtgacat cgagtgtgct    180
gctctggttg gtgaagacca gcctctttgc ccagatcttc ctgaacttga tctttctgaa    240
ctagatgtga acgacttgga tacagacagc tttctgggtg gactcaagtg gtgcagtgac    300
caatcagaaa taatatccaa tcagtacaac aatgagcctt caaacatatt tgagaagata    360
gatgaagaga atgaggcaaa cttgctagca gtcctcacag agacactaga cagtctccct    420
gtggatgaag acggattgcc ctcatttgat gcgctgacag atggagacgt gaccactgac    480
aatgaggcta gtccttcctc catgcctgac ggcacccctc caccccagga ggcagaagag    540
ccgtctctac ttaagaagct cttactggca ccagccaaca ctcagctaag ttataatgaa    600
tgcagtggtc tcagtaccca gaaccatgca aatcacaatc acaggatcag aacaaaccct    660
gcaattgtta agactgagaa ttcatggagc aataaagcga agagtatttg tcaacagcaa    720
aagccacaaa gacgtccctg ctcggagctt ctcaaatatc tgaccacaaa cgatgaccct    780
cctcacacca aacccacaga gaacagaaac agcagcagag acaaatgcac ctccaaaaag    840
aagtcccaca cacagtcgca gtcacaacac ttacaagcca aaccaacaac tttatctctt    900
cctctgaccc cagagtcacc aaatgacccc aagggttccc catttgagaa caagactatt    960
gaacgcacct taagtgtgga actctctgga actgcaggcc taactccacc caccactcct   1020
cctcataaag ccaaccaaga taaccctttt agggcttctc caaagctgaa gtcctcttgc   1080
aagactgtgg tgccaccacc atcaaagaag cccaggtaca gtgagtcttc tggtacacaa   1140
ggcaataact ccaccaagaa agggccggag caatccgagt tgtatgcaca actcagcaag   1200
tcctcagtcc tcactggtgg acacgaggaa aggaagacca agcggcccag tctgcggctg   1260
tttggtgacc atgactattg ccagtcaatt aattccaaaa cagaaatact cattaatata   1320
tcacaggagc tccaagactc tagacaacta gaaaataaag atgtctcctc tgattggcag   1380
gggcagattt gttcttccac agattcagac cagtgctacc tgagagagac tttggaggca   1440
```

```
agcaagcagg tctctccttg cagcacaaga aaacagctcc aagaccagga aatccgagcc   1500
gagctgaaca agcacttcgg tcatcccagt caagctgttt ttgacgacga agcagacaag   1560
accggtgaac tgagggacag tgatttcagt aatgaacaat tctccaaact acctatgttt   1620
ataaattcag gactagccat ggatggcctg tttgatgaca gcgaagatga aagtgataaa   1680
ctgagctacc cttgggatgg cacgcaatcc tattcattgt tcaatgtgtc tccttcttgt   1740
tcttctttta actctccatg tagagattct gtgtcaccac ccaaatcctt attttctcaa   1800
agaccccaaa ggatgcgctc tcgttcaagg tccttttctc gacacaggtc gtgttcccga   1860
tcaccatatt ccaggtcaag atcaaggtct ccaggcagta gatcctcttc aagatcctgc   1920
tattactatg agtcaagcca ctacagacac cgcacgcacc gaaattctcc cttgtatgtg   1980
agatcacgtt caagatcgcc ctacagccgt cggcccaggt atgacagcta cgaggaatat   2040
cagcacgaga ggctgaagag ggaagaatat cgcagagagt atgagaagcg agagtctgag   2100
agggccaagc aaagggagag gcagaggcag aaggcaattg aagagcgccg tgtgatttat   2160
gtcggtaaaa tcagacctga cacaacacgg acagaactga gggaccgttt tgaagttttt   2220
ggtgaaattg aggagtgcac agtaaatctg cgggatgatg gagacagcta tggtttcatt   2280
acctaccgtt atacctgtga tgcttttgct gctcttgaaa atggatacac tttgcgcagg   2340
tcaaacgaaa ctgactttga gctgtacttt tgtggacgca agcaattttt caagtctaac   2400
tatgcagacc tagattcaaa ctcagatgac tttgaccctg cttccaccaa gagcaagtat   2460
gactctctgg attttgatag tttactgaaa gaagctcaga gaagcttgcg caggtaacat   2520
gttccctagc tgaggatgac agagggatgg cgaatacctc atgggacagc gcgtccttcc   2580
ctaaagacta ttgcaagtca tacttaggaa tttctcctac tttacactct ctgtacaaaa   2640
acaaaacaaa acaacaacaa tacaacaaga acaacaacaa caataacaac aatggtttac   2700
atgaacacag ctgctgaaga ggcaagagac agaatgatat ccagtaagca catgtttatt   2760
catgggtgtc agctttgctt ttcctggagt ctcttggtga tggagtgtgc gtgtgtgcat   2820
gtatgtgtgt gtgtatgtat gtgtgtggtg tgtgtgcttg gtttagggga agtatgtgtg   2880
ggtacatgtg aggactgggg gcacctgacc agaatgcgca agggcaaacc atttcaaatg   2940
gcagcagttc catgaagaca cgcttaaaac ctagaacttc aaaatgttcg tattctattc   3000
aaaaggaaat atatatatat atatatatat atatatatat atatataaat taaaaaggaa   3060
agaaaactaa caaccaacca accaaccaac caaccacaaa ccaccctaaa atgacagccg   3120
ctgatgtctg ggcatcagcc tttgtactct gtttttttaa gaaagtgcag aatcaacttg   3180
aagcaagctt tctctcataa cgtaatgatt atatgacaat cctgaagaaa ccacaggttc   3240
catagaacta atatcctgtc tctctctctc tctctctctc tctctttttt ttttcttttt   3300
ccttttgcca tggaatctgg gtgggagagg atactgcggg caccagaatg ctaaagtttc   3360
ctaacatttt gaagtttctg tagttcatcc ttaatcctga cacccatgta aatgtccaaa   3420
atgttgatct tccactgcaa atttcaaaag ccttgtcaat ggtcaagcgt gcagcttgtt   3480
cagcggttct ttctgaggag cggacaccgg gttacattac taatgagagt tgggtagaac   3540
tctctgagat gtgttcagat agtgtaattg ctacattctc tgatgtagtt aagtatttac   3600
agatgttaaa tggagtattt ttattttatg tatatactat acaacaatgt tctttttttgt  3660
tacagctatg cactgtaaat gcagccttct tttcaaaact gctaaatttt tcttaatcaa   3720
gaatattcaa atgtaattat gaggtgaaac aattattgta cactaacata tttagaagct   3780
```

-continued

```
gaacttactg cttatatata tttgattgta aaaacaaaaa gacagtgtgt gtgtctgttg   3840
agtgcaacaa gagcaaaatg atgctttccg cacatccatc ccttaggtga gcttcaatct   3900
aagcatcttg tcaagaaata tcctagtccc ctaaaggtat taaccacttc tgcgatattt   3960
ttccacattt tcttgtcgct tgtttttctt tgaagtttta tacactggat ttgttagggg   4020
aatgaaattt tctcatctaa aatttttcta gaagatatca tgattttatg taaagtctct   4080
caatgggtaa ccattaagaa atgtttttat tttctctatc aacagtagtt ttgaaactag   4140
aagtcaaaaa tctttttaaa atgctgtttt gttttaattt ttgtgatttt aatttgatac   4200
aaaatgctga ggtaataatt atagtatgat ttttacaata attaatgtgt gtctgaagac   4260
tatctttgaa gccagtattt ctttcccttg gcagagtatg acgatggtat ttatctgtat   4320
tttttacagt tatgcatcct gtataaatac tgatatttca ttcctttgtt tactaaagag   4380
acatatttat cagttgcaga tagcctattt attataaatt atgagatgat gaaaataata   4440
aagccagtgg aaattttcta cctaggatgc atgacaattg tcaggttgga gtgtaagtgc   4500
ttcatttggg aaattcagct tttgcagaag cagtgtttct acttgcacta gcatggcctc   4560
tgacgtgacc atggtgttgt tcttgatgac attgcttctg ctaaatttaa taaaaacttc   4620
agaaaaacct ccattttgat catcaggatt tcatctgagt gtggagtccc tggaatggaa   4680
ttcagtaaca tttggagtgt gtattcaagt ttctaaattg agattcgatt actgtttggc   4740
tgacatgact tttctggaag acatgataca cctactactc aattgttctt ttcctttctc   4800
tcgcccaaca cgatcttgta agatggattt cacccccagg ccaatgcagc taattttgat   4860
agctgcattc atttatcacc agcatattgt gttctgagtg aatccactgt ttgtcctgtc   4920
ggatgcttgc ttgatttttt ggcttcttat ttctaagtag atagaaagca ataaaaatac   4980
tatgaaatga aagaacttgt tcacaggttc tgcgttacaa cagtaacaca tctttaatcc   5040
gcctaattct tgttgttctg taggttaaat gcaggtattt taactgtgtg aacgccaaac   5100
taaagtttac agtctttctt tctgaatttt gagtatcttc tgttgtagaa taataataaa   5160
aagactatta agagcaataa attattttta agaaatcgag atttagtaaa tcctattatg   5220
tgttcaagga ccacatgtgt tctctatttt gcctttaaat ttttgtgaac caattttaaa   5280
tacattctcc tttttgccct ggattgttga catgagtgga atacttggtt tcttttctta   5340
cttatcaaaa gacagcacta cagatatcat attgaggatt aatttatccc ccctaccccc   5400
agcctgacaa atattgttac catgaagata gttttcctca atggacttca aattgcatct   5460
agaattagtg gagcttttgt atcttctgca gacactgtgg gtagcccatc aaaatgtaag   5520
ctgtgctcct ctcattttta tttttatttt tttgggagag aatatttcaa atgaacacgt   5580
gcaccccatc atcactggag gcaaatttca gcatagatct gtaggatttt tagaagaccg   5640
tgggccattg ccttcatgcc gtggtaagta ccacatctac aattttggta accgaactgg   5700
tgctttagta atgtggattt ttttcttttt taaaagagat gtagcagaat aattcttcca   5760
gtgcaacaaa atcaattttt tgctaaacga ctccgagaac aacagttggg ctgtcaacat   5820
tcaaagcagc agagagggaa ctttgcacta ttggggtatg atgtttgggt cagttgataa   5880
aaggaaacct tttcatgcct ttagatgtga gcttccagta ggtaatgatt atgtgtcctt   5940
tcttgatggc tgtaatgaga acttcaatca ctgtagtcta agacctgatc tatagatgac   6000
ctagaatagc catgtactat aatgtgatga ttctaaattt gtacctatgt gacagacatt   6060
ttcaataatg tgaactgctg atttgatgga gctactttaa gatttgtagg tgaaagtgta   6120
atactgttgg ttgaactatg ctgaagaggg aaagtgagcg attagttgag cccttgccgg   6180
```

```
gcctttttc cacctgccaa ttctacatgt attgttgtgg ttttattcat tgtatgaaaa   6240

ttcctgtgat ttttttaaa tgtgcagtac acatcagcct cactgagcta ataaagggaa   6300

acgaatgttt caaatcta                                                6318
```

<210> SEQ ID NO 21
<211> LENGTH: 4598
<212> TYPE: DNA
<213> ORGANISM: Homo sapiens

<400> SEQUENCE: 21

```
gtagttcctt tcccacaatc ggctgggcga ggcggcgcca gcgatcagag cagcgctggg     60

tgttcagggg ccaagatggc ggcgcgccgg ggacggagag acggagtcgc gccgcccccg    120

agtgggggcc ccggtccgga ccctggcggg ggagcccgcg gcagtggttg gggaagtcga    180

agccaagcgc cgtatgggac tttgggcgct gtgagcggcg gcgagcaggt gctgctgcat    240

gaggaggcgg gtgattctgg ctttgtcagt ctctctcggc tgggcccatc tctgagggac    300

aaggacctgg aaatggagga gctaatgctg caggatgaga cactgctggg gaccatgcag    360

agctacatgg atgcctccct tatctccctc attgaggatt ttgggagcct tggagagagc    420

aggttatctc tggaggacca gaatgaagtg tcgctgctca cggctctgac ggagatcttg    480

gacaatgcag attctgagaa cctttctcca tttgacagca ttcctgattc ggagctgctt    540

gtgtcacccc gggagggctc ctctctgcac aagctgctta ctctctctcg gacaccccca    600

gaacgtgacc tcatcacccc agttgaccca ctggggccca gtacaggcag cagtagaggg    660

agtggggttg aaatgtctct tccagatccc tcttgggact tctccccacc ctctttctta    720

gagacctctt cccccaagct tcctagctgg agacccccaa gatcaagacc acgctggggc    780

caatccccac ctccccagca gcgcagtgat ggagaagaag aggaggaggt ggccagcttc    840

agtggccaga ttcttgccgg ggagcttgac aactgtgtga gcagtatccc ggacttcccc    900

atgcatttgg cctgccctga ggaggaagat aaagcaacag cagcagagat ggcagtgcca    960

gcagctggtg atgagagcat ctcctccctg agtgagctgg tgcgggccat gcacccatac   1020

tgcctgccca acctcaccca cctggcatca cttgaggatg agcttcagga gcagccagat   1080

gatttgacac tgcctgaggg ctgcgtagtg ctggagattg tggggcaggc agccacagct   1140

ggcgatgacc tggagatccc agttgtggtg cgacaggtct ctcctggacc ccggcctgtg   1200

ctcctggatg actcgctaga gactagttct gccttgcagc tgcttatgcc tacactggag   1260

tcagagacag aggctgctgt gcccaaggta accctctgct ctgagaaaga ggggttgtca   1320

ttgaactcag aggagaagct ggactcagcc tgcttattga agcccaggga ggtcgtggag   1380

ccggtggtgc ccaaggagcc tcagaaccca cctgccaatg cagcaccagg ttcccagaga   1440

gctcgaaagg gcaggaagaa gaagagcaag gagcagccag cagcctgtgt ggaaggctat   1500

gccaggaggc tgaggtcatc ttctcgcggg cagtctactg taggtacaga agtgacctct   1560

caggtagaca acttgcagaa acagcctcag gaagaacttc aaaaagagtc tgggcctctc   1620

cagggtaagg ggaagccccg ggcttgggct cgggcctggg cagctgcctt ggagaattct   1680

agccctaaga acttggagag aagtgctgga caaagtagtc ctgctaaaga aggccctcta   1740

gacctctacc caaagctggc tgacactatc caaaccaatc ctataccaac ccatctctca   1800

ttggtcgact ctgcccaagc cagccccatg ccagttgact ctgttgaagc tgatcccact   1860

gcagttggcc ctgttctagc tggccctgta cctgttgacc ctgggttggt tgaccttgct   1920
```

```
tcaaccagct cagaactggt tgagcctctc ccggctgagc cagtgctgat caacccagtc   1980
ctggctgact cagcagcagt tgaccctgca gtggttccca tctcagataa cttgccacca   2040
gttgatgctg tcccgtctgg cccagcacca gttgatctag cactggttga ccctgttcct   2100
aatgacctga ctccagttga cccagtgcta gttaagtcca gaccaactga tcccagacgt   2160
ggtgcagtgt catcagccct gggggggttca gcaccccagc tcctcgtgga gtcagagtcc   2220
ttggacccac caaagaccat catccctgaa gtcaaagagg ttgtggattc tctgaaaatt   2280
gaaagtggta ccagtgctac aacccatgaa gccagacctc ggcctctcag cttatctgag   2340
taccggcgac gaaggcagca acgccaagca gaaacagaag agagaagtcc acagccccca   2400
actgggaagt ggcctagcct tccagagact cccacagggc tggcagacat cccttgtctt   2460
gtcatcccac cagccccagc caagaagaca gctctgcaga gaagccctga aacacccctt   2520
gagatttgcc ttgtgcctgt aggtcccagc cctgcttctc ctagtcctga gccacctgta   2580
agcaaacctg tggcctcatc tcccactgag caggtgccat cccaggagat gccactgttg   2640
gcgagacctt cccctcctgt gcagtctgtg tcccctgctg tgcccacacc tccctcgatg   2700
tctgctgccc tgcctttccc tgcaggtggg cttggcatgc cccccagtct gcccccacct   2760
cccttgcagc ctcctagtct tccattgtct atggggccag tactacctga tccgtttact   2820
cactatgccc ccttgccatc ctggccttgt tatcctcatg tgtccccttc tggctatcct   2880
tgcctgcccc ccccaccaac ggtgccccta gtgtctggta ctcctggtgc ctatgccgtg   2940
cctcccactt gcagtgtgcc ttgggcaccc cctcctgccc cagtctcacc ttacagttcc   3000
acatgtacct atgggccctt gggatggggc ccagggcctc aacatgctcc attctggtct   3060
actgttcccc cacctccttt gcctccagcc tccattggga gagctgttcc ccaacctaaa   3120
atggagtcta ggggcactcc agctggccct cctgaaaatg tacttccctt gtcgatggct   3180
cctcccctca gtcttgggct acctggccat ggagctcctc agacagagcc taccaaggtg   3240
gaggtcaagc cagtgcctgc atctccccat ccgaaacaca aggtgtctgc cctggtgcaa   3300
agtccccaga tgaaggctct agcatgtgtg tctgctgaag gtgtgactgt tgaggagcct   3360
gcatcagaga ggctaaagcc tgagacccaa gagaccaggc ccagggagaa gccccccttg   3420
cctgctacca aggctgttcc cacaccaagg cagagcactg tccccaagct gcctgctgtc   3480
cacccagccc gtctaaggaa gctgtccttc ctgcctaccc cacgtactca gggttctgaa   3540
gatgtggtac aggctttcat cagtgagatt ggaattgagg catcggacct gtccagtctg   3600
ctggagcagt ttgagaaatc agaagccaaa aaggagtgtc ctcctccggc tcctgctgac   3660
agcttggctg taggaaactc agggtccagc tgtagttcct ctggacgttc tcgaagatgc   3720
tcttcctctt cttcgtcatc atcttcctct tcgtcttcct catcctcatc atccagttct   3780
cgaagccgct cacgatcccc atccccccgc cggagaagtg acaggaggcg gcggtacagc   3840
tcttatcgtt cacatgacca ttaccaaagg caaagagtgc tacaaaagga gcgtgcaata   3900
gaagaaagaa gggtggtctt cattggaaag atacctggcc gcatgactcg atcagagctg   3960
aaacagaggt tctccgtttt tggagagatt gaggagtgca ccatccactt ccgtgtccaa   4020
ggggacaact acggcttcgt cacttatcgc tatgctgagg aggcatttgc agccattgag   4080
agtggccaca agctgcggca ggcagatgag cagccctttg atctctgctt tgggggccga   4140
aggcagttct gcaagaggag ctattctgat cttgactcca accgggaaga ctttgaccca   4200
gcacctgtaa agagcaaatt tgattctctt gactttgaca cattgttgaa acaggcccag   4260
aagaacctca ggaggtaacc ttgggccctt ccctgctatc ctttttctcc tttggaggtg   4320
```

```
cccaacctcc tccacccccct tcccctactc taggggagag agctgctagt gagatgactg   4380
ttttataaag aaatggaaaa aagtgaaata aaaaatatgt tgaatcagat tttttaaaag   4440
gggtatttgt ttttttataa caggtattga aacaagttaa cttgcattcc tatgtaagat   4500
aggaggggct gaggggatcc ccagtgtttg gaacataagt cactatgcag actaataaac   4560
atcaactaga gagaactccc aaaaaaaaaa aaaaaaaa                             4598
```

<210> SEQ ID NO 22
<211> LENGTH: 1818
<212> TYPE: DNA
<213> ORGANISM: Homo sapiens

<400> SEQUENCE: 22

```
ggtggtcagc gcgcgcattg cctgccccgg aagtggtcgg cgcgcggcgc ggcgcgcctg     60
ggcgctaaga tggcggcggc gtgagttgca tgttgtgtga ggatcccggg gccgccgcgt    120
cgctcgggcc ccgccatggc cgtcaccatc acgctcaaaa cgctgcagca gcagaccttc    180
aagatccgca tggagcctga cgagacggtg aaggtgctaa aggagaagat agaagctgag    240
aagggtcgtg atgccttccc cgtggctgga cagaaactca tctatgccgg caagatcttg    300
agtgacgatg tccctatcag ggactatcgc atcgatgaga agaactttgt ggtcgtcatg    360
gtgaccaaga ccaaagccgg ccagggtacc tcagcacccc cagaggcctc acccacagct    420
gccccagagt cctctacatc cttcccgcct gcccccacct caggcatgtc ccatccccca    480
cctgccgcca gagaggacaa gagcccatca gaggaatccg cccccacgac gtccccagag    540
tctgtgtcag gctctgttcc ctcttcaggt agcagcgggc gagaggaaga cgcggcctcc    600
acgctagtga cgggctctga gtatgagacg atgctgacgg agatcatgtc catgggctat    660
gagcgagagc gggtcgtggc cgccctgaga gccagctaca acaaccccca ccgagccgtg    720
gagtatctgc tcacgggaat tcctgggagc ccgagccgg aacacggttc tgtccaggag    780
agccaggtat cggagcagcc ggccacggaa gcaggagaga accccctgga gttcctgcgg    840
gaccagcccc agttccagaa catgcggcag gtgattcagc agaaccctgc gctgctgccc    900
gccctgctcc agcagctggg ccaggagaac cctcagcttt tacagcaaat cagccggcac    960
caggagcagt tcatccagat gctgaacgag cccccctgggg agctggcgga catctcagat   1020
gtggaggggg aggtgggcgc cataggagag gaggccccgc agatgaacta catccaggtg   1080
acgccgcagg agaaagaagc tatagagagg ttgaaggccc tgggcttccc agagagcctg   1140
gtcatccagg cctatttcgc gtgtgaaaaa aatgagaact tggctgccaa cttcctcctg   1200
agtcagaact ttgatgacga gtgatgccag gaagccaggc caccgaagcc cccaccctac   1260
ccttattcca tgaaagtttt ataaaagaaa aaatatatat atattcatgt ttatttaaga   1320
aatggaaaaa aaaatcaaaa atcttaaaaa aacaagcaaa cagtccagct tcctgtcctc   1380
ctaaagtggc ccctgttccc atctcccggg ccagacagct gtcccccgt cctcctcccc     1440
agcccagcct gctcagagaa gctggcagga ctgggaggcg acagatgggc ccctcttggc   1500
ctctgtccca gctctctgca gccagacgga aaggcggctg cttgcctctc catcctccga   1560
aaaacccctg aggacccccc cccatcctct tctaggatga ggggaagctg gagccccaac   1620
tttgatcctc cattggagtg gcccaaatct ttccatctag ggcaagtcct gaaaggccca   1680
aggccccctc cccagtctgg ccttggcctc cagcctggag aagggctaac atcagctcat   1740
tgtcaaggcc acccccaccc cagaacagaa ccgtgtctct gataaaggtt ttgaagtgaa   1800
```

taaagtttta aaaactag 1818

<210> SEQ ID NO 23
<211> LENGTH: 3310
<212> TYPE: DNA
<213> ORGANISM: Homo sapiens

<400> SEQUENCE: 23
cccggcgggg ggaggttggg gacgggcctg gcagttgtga actcgaacct gccgctgtcg 60
ccgcggcggg gcggggagcg agagtgggcc gcggaggccg gccttcgggc tccatggacg 120
ggcgccgcgt ccctgcacag cccgccgcag aggtaaggct ggcctctctg cagtcagagg 180
tctgagctct gccatgggga taggggtgtc tttattactg cagttttctc taacacctgg 240
gggctaccgg agtgtgggcc gaagcaggcg ctgcagccgc ggaagtatcc ccaggaacat 300
ccccaagagg agctggaaaa agcctcatcc ccagctctgc agtctccagg ggagctcagt 360
gtctgtttgt ccagcttctc agagttgctg tgcagctcgg atgtggcata ggaaacagca 420
gacacaggga gagggcagca taaggcactg tagggagcag tggccacatt ttctgcagag 480
gaagaaccga tgctggaacg tcgttgcagg ggcccccctgg ccatgggcct ggcccagccc 540
cgactccttt ctgggccctc ccaggagtca ccccagaccc tggggaagga gtcccgcggg 600
ctgaggcaac aaggcacgtc agtggcccag tctggtgccc aagccccagg cagggcccat 660
cgctgtgccc actgtcgaag gcacttccct ggctgggtgg ctctgtggct tcacacccgc 720
cggtgccagg cccggctgcc cttgccctgc cctgagtgtg gccgtcgctt tcgccatgcc 780
cccttcttag cactgcaccg ccaggtccat gctgctgcca ccccagacct gggctttgcc 840
tgccacctct gtgggcagag cttccgaggc tgggtggccc tggttctgca tctgcgggcc 900
cattcagctg caaagcggcc catcgcttgt cccaaatgcg agagacgctt ctggcgacga 960
aagcagcttc gagctcatct gcggcggtgc caccctcccg ccccggaggc ccggcccttc 1020
atatgcggca actgtggccg gagctttgcc cagtgggacc agctagttgc ccacaagcgg 1080
gtgcacgtag ctgaggccct ggaggaggcc gcagccaagg ctctggggcc ccggcccagg 1140
ggccgccccg cggtgaccgc cccccggccc ggtggagatg ccgtcgaccg ccccttccag 1200
tgtgcctgtt gtggcaagcg cttccggcac aagcccaact tgatcgctca ccgccgcgtg 1260
cacacgggcg agcggcccca ccagtgcccc gagtgcggga agcgctttac caataagccc 1320
tatctgactt cgcaccggcg catccacacc ggcgagaagc cctacccgtg caaagagtgc 1380
ggccgccgct tccggcacaa acccaacctg ctgtctcaca gcaagattca caagcgatcc 1440
gaggggtcgg cccaggccgc ccccggcccg gggagccccc agctgccagc cggcccccag 1500
gagtccgcgg ccgagcccac cccggcggta cctctgaaac cggcccagga gccgccgcca 1560
ggggccccgc cagagcaccc gcaggacccg atcgaagccc cccctccct ctacagctgc 1620 gacgactgcg gcaggagctt ccggctggag cgcttcctgc gggcccacca gcggcagcac 1680
accggggagc ggcccttcac ctgcgccgag tgcgggaaga acttcggcaa gaagacgcac 1740
ctggtggcgc actcgcgcgt gcactccggc gagcggccct tcgcctgcga ggagtgcggc 1800
cgccgcttct cccagggcag ccatctggcg gcgcatcggc gcgaccacgc ccccgatcgg 1860
cccttcgtgt gtcccgactg cggcaaggcc ttccgccaca aaccctacct ggcggcgcac 1920
cggcgcatcc acaccggcga gaagccctac gtctgccccg actgcggcaa agccttcagc 1980
cagaagtcca acctggtgtc gcaccggcgc atccacacgg gcgagcggcc ctacgcctgt 2040
cccgactgcg accgcagctt cagccagaag tccaacctca tcacccaccg caagagccac 2100
atccgggacg gcgccttctg ctgtgccatc tgtggccaga ccttcgacga cgaggagaga 2160
ctcctggccc accagaagaa gcacgatgtc tgagacggtg ggcggggccg tgttggctga 2220
gagagggctg gggtccttcg tggtgggagt cgcagtgggc tgggggtgcc tgcctagtgc 2280
tggagtaggg gacaatggga atcctagagg ggatggaaga cgcggggagt gagctgggtg 2340
ggccctgcta gcgagagagg tcaaccccgg tggccaggga acccacttcc aagcgcaggg 2400
acgccggcct ccagctggtg tgtgctaagg ctccgtcctg actgccctgt gccctggaaa 2460
agcagcaata gcatccgccc cttagagccc tctggctaga ggagccacca gtggaaagga 2520
agaccctcca tcctctggta ttaacgcctt aatgcccctg tcttttactg taagttactt 2580
aagatcattt ttggaagcag gcgtggtaga gtcctgtaaa tgaatgctct gggctagata 2640
cagcttggag aacctgctgg ccttgttaga cagcacttgg gcctttgcca gcagcaagag 2700
gtgaagcgaa gccactctta cctctccctt cccctcccac ctgccccctg cgtaggcacc 2760
cagacttgga gagacccgtc tgctgttaat acttccatcc tcttccttcc caaagagcag 2820
atcccaaggc atttactcct tggtctgtct cgctttatct gtcgcccctc ccagcgctga 2880
gagcctcccc tggctgtcag cagcactgtg tccaggctct tgtctgaaca ccgcagcccc 2940
tccttcgctc cttccagagc tcagcatgtc acggcaagga ctgccgcatt ggtgatggag 3000
ggccagctga ggggaagttg ctggtgagtt tccttttctc catttctagc atatggacac 3060
ctggcctctg cttgagcact taggtgacag gaacttccgc acctcctgag gccctggatg 3120
attctaattg ttagaaattc taattgttag aaatccttcc ttataatgaa tgaattctgc 3180
tttcctataa tttctaccta ttgggccttg ttctgttctc tggaactaaa cagaacaacc 3240
atttacccct ccttttcaaa ctagagaata aagatttggt tttagaactg gtaaaaaaaa 3300
aaaaaaaaaa 3310

<210> SEQ ID NO 24
<211> LENGTH: 1247
<212> TYPE: DNA
<213> ORGANISM: Homo sapiens

<400> SEQUENCE: 24
actttacgca ggcgcgttag gtcctagtcg ctatgcgtgt gcttgtgggt ggcgggacag 60
gcttcattgg gacagcccta acccagctgc tgaatgccag aggccacgaa gtgacgttgg 120
tctcccgaaa gcccgggccc ggccggatca cgtgggatga gctcgctgca tcggggctgc 180
cgagctgcga tgccgccgtc aacctggccg gagagaacat cctcaaccct ctccgaagat 240
ggaatgaaac cttccaaaaa gaggtaatcg gcagccgcct agagaccacc caattgctgg 300
ctaaagccat caccaaagcc ccacaacccc ccaaggcctg ggtcttagtc acaggtgtag 360
cttactacca gcccagtctg actgcggagt atgatgaaga cagcccagga ggggactttg 420
actttttctc caacctcgta accaaatggg aagctgcagc caggcttcct ggagattcta 480
cacgccaggt ggtggtgcgc tcaggggttg tgctgggccg tgggggtggt gccatgggcc 540
acatgctgct gccctttcgc ctgggcctgg ggggccccat cggctcaggc caccaattct 600
tcccctggat acacatcggg gacctggcag gaatcctgac ccatgccctt gaagcaaacc 660
acgtgcacgg ggtcctgaat ggagtggctc catcctccgc cactaatgct gagtttgccc 720
agaccttggg tgctgccctg ggccgccgag ccttcatccc tctccccagc gctgtggtgc 780
aagctgtctt tgggcgacag cgtgccatca tgctgctgga gggccagaag gtgatcccac 840
agcgaacact ggccactggc taccagtatt ccttcccaga gctaggggct gccttaaagg 900
aaattgtagc ctaagtaggt cgtggcaagg gcctgaggcc tgttcctcac aggcttccag 960
gttaggcact gtgaataggc tcagctcctc tagagagctg aagccatctg gttcttagat 1020
tcctctccca gtcctctttc ccattgttct gttgctccac cttattgtct caaggccgta 1080
atctcatcag gttgggacat taatcttttc aactccttgt aagatttccc agtttggttt 1140
ctctacatgt cctgcagctg ccccacttct cctttacgct gtgtagagaa tgctctgcag 1200
tttaggcaat aaaaataaat tgtctcacta aaaaaaaaaa aaaaaaa 1247

<210> SEQ ID NO 25
<211> LENGTH: 1804
<212> TYPE: DNA
<213> ORGANISM: Homo sapiens

<400> SEQUENCE: 25
aagcgcgggg ccggccgggg cgcccgccgc tcgccgccgc ctccgcgcgc ccgggggccc 60
cggcgccccc cgagctaggg cggccagctc gcggctcgcc gtttgacaga tgctcatcgc 120
catggagttg ccgcagcagc acctttgggg gctcgggcga gcgacgggag ccgggatctg 180
agcgagcgcc ggggccagcg gagccggagc cgccgggaca tggttgcaga tctgatctct 240
tctgaacacc tcatcgtgtc tccatccctg ggaatctgac cctagcaact ggaccacttt 300
gttcttggaa ttttgggtgt cctcttttct cacctttccc ttttcccttt tccccttccc 360
cctcctgaga actccggaag actgtagaga ttgtcatgga gtccagggaa accttaagca 420
gctcccggca aagaggggc gagtcagact tcctgccggt ctcctcagcc aagcccccag 480
ctgctcctgg ctgtgcagga gaacctttgc tctccactcc aggacctggg aaggggatcc 540
cggtgggcgg agagcgcatg gagccagagg aggaggatga actaggctca gggcgggatg 600
tggattccaa ctccaacgcg gacagtgaga aatgggtggc aggagatggt ttggaagagc 660
aggaattttc tatcaaggag gcaaacttca cagagggaag tctgaagcta aagattcaga 720
ccacaaagcg ggctaagaaa cccccaaaga atttggagaa ctatatatgt ccacctgaga 780
tcaagatcac catcaagcag tctggggacc agaaggtgtc ccgtgctgga aaaaatagca 840
aagccacgaa ggaggaagaa agaagccact ccaaaaagaa gctcctcaca gccagtgacc 900
ttgcagccag tgacctcaaa ggatttcagc cacagattaa agactccagt aaggaggaag 960
tctggaagag aagaggaggc caaggcatcc cattcaaaaa gcaattcctg tcccaggaac 1020
gtgccatgtg cttctcatgc cccggaacc cattccccgc aaaacccggt tctctcactc 1080
ttccttttca cagtgaacct gcagtctggg cacaagaagt ataacttcgc atggattctg 1140
caaagcccac acctgtggtc attccctgtt ctttccattc aacaatggag acttgcccaa 1200
gattgtaaac tagtgagtga cagcatttgg gcttatgatc ttctctgcct gctagctaga 1260
cattctctct gggtctaaaa gataatccaa aaagatccag cttcacaatg ctgccctgaa 1320
gagataatgc attaggcggc cctgatgcag cattcactgt cttccagggc aggcttgatc 1380
ccatgagttt gcttgctcag acgatcactt aggaaacaca tgcctttact ctctaggcct 1440
tttttctagc ttgccttgta tcagctatgc catggatctt tgctctctta ccccatgcta 1500
tacagagtat gggctccaag ccacagctgg cctgtcaagt gtgtgtcgct ggtccaccat 1560
gggatacatt tagaaacttt tatagcaatt tgacattttt gtgatatcca agcatgtgat 1620
tgttttccta cggatttgtc ttatagtatt ttaccaaagt ttccacacaa aaagtatgga 1680
ttaaggacaa agtatctggt ccttcatcaa agatcgtttg ataagctctg ttctagttaa 1740

```
ccaacactga gctttcctag ttttaataaa agagtaggat ttggaaaaaa aaaaaaaaaa   1800

aaaa                                                                1804


<210> SEQ ID NO 26
<211> LENGTH: 4129
<212> TYPE: DNA
<213> ORGANISM: Homo sapiens

<400> SEQUENCE: 26

acacagagca gagtggggct ctgagtatat aactgttagg tgcctccctc cagcaccatc     60

tcctgagaag cactctccct tgtcgtggag gtgggcaaat ctttatcagc cactgccttc    120

tgctgccagg aagccagcta gagtggtctt taaagaaaac tgggcatctc ctgctactta    180

aaatcaaaaa ctacctaaaa taaagattat aaaaaagtaa ggatgaatgg acggtctttg    240

attggcggcg ctggtgacgc ccgtcatggt cctgtttgga aggacccttt tggaactaaa    300

gctggtgacg cagcgcgcag aggcatcgcc cggctaagct tggccctggc agatgggtcg    360

caggaacagg agccagagga agagatagcc atggaggaca gccccactat ggttagagtg    420

gacagcccca ctatggttag ggtgaaaaac caggtttcgc catgtcaagg gagaaggtgc    480

ttccccaaag ctcttggcta tgtcaccggt gacatgaaag aacttgccaa ccagcttaaa    540

gacaaacccg tggtgctcca gttcattgac tggattctcc ggggcatatc ccaagtggtg    600

ttcgtcaaca accccgtcag tggaatcctg attctggtag gacttcttgt tcagaacccc    660

tggtgggctc tcactggctg gctgggaaca gtggtctcca ctctgatggc cctcttgctc    720

agccaggaca ggtcattaat agcatctggg ctctatggct acaatgccac cctggtggga    780

gtactcatgg ctgtcttttc ggacaaggga gactatttct ggtggctgtt actccctgta    840

tgtgctatgt ccatgacttg cccaattttc tcaagtgcat tgaattccat gctcagcaaa    900

tgggacctcc ccgtcttcac cctccctttc aacatggcgt tgtcaatgta cctttcagcc    960

acaggacatt acaatccatt ctttccagcc aaactggtca tacctataac tacagctcca   1020

aatatctcct ggtctgacct cagtgccctg gagttgttga aatctatacc agtgggagtt   1080

ggtcagatct atggctgtga taatccatgg acagggggca ttttcctggg agccatccta   1140

ctctcctccc cactcatgtg cctgcatgct gccataggat cattgctggg catagcagcg   1200

ggactcagtc tttcagcccc atttgaggac atctactttg gactctgggg tttcaacagc   1260

tctctggcct gcattgcaat gggaggaatg ttcatggcgc tcacctggca aacccacctc   1320

ctggctcttg gctgtgccct gttcacggcc tatcttggag tcggcatggc aaactttatg   1380

gctgaggttg gattgccagc ttgtacctgg cccttctgtt tggccacgct attgttcctc   1440

atcatgacca caaaaaattc caacatctac aagatgcccc tcagtaaagt tacttatcct   1500

gaagaaaacc gcatcttcta cctgcaagcc aagaaaagaa tggtggaaag cccctttgtga  1560

gaacaagccc catttgcagc catggtcacg agtcatttct gcctgactgc tccagctaac   1620

ttccagggtc tcagcaaact gctgtttttc acgagtatca actttcatac tgacgcgtct   1680

gtaatctgtt cttatgctca ttttgtattt tcctttcaac tccaggaata tccttgagca   1740

tatgagagtc acatccaggt gatgtgctct ggtatggaat ttgaaacccc aatggggcct   1800

tggcactaag actggaatgt atataaagtc aaagtgctcc aacagaagga ggaagtgaaa   1860

acaaactatt agtatttatt gatattcttg gtgtttagct ggctcgatga tgttaacagt   1920

attaaaaatt aaaccccata aaccaactaa gccttatgga attcacagtc acaaaatcga   1980
```

```
agttaatcca gaattctgtg ataagcagct tggctttttt tttaaatcaa tgcaagttac   2040
acattatagc cagaatctgt atcacagagg tgcaagctga cagcagagct cagtccccac   2100
ttcctgcaaa caatggcctg caccctatcc cttgtgtgtg tgacattctc tcatgggaca   2160
atgttggggt ttttcagact gacaggactg caagagggag aaaggaattt tgtcaatcaa   2220
aattattctg tattgcaact tttctcagag attgcaaagg attttttagg tagagattat   2280
ttttccttat gaaaaatgat ctgttttaaa tgagataaaa taggagaagt tcctggctta   2340
acctgttctt acatattaaa gaaaagttac ttactgtatt tatgaaatac tcagcttagg   2400
catttttact ttaacccta aattgatttt gtaaatgcca caaatgcata gaattgttac    2460
caacctccaa agggctcttt aaaatcatat tttttattca tttgaggatg tcttataaag   2520
actgaaggca aaggtcagat tgcttacggg tgttattttt ataagttgtt gaattcctta   2580
atttaaaaaa gctcattatt ttttgcacac tcacaatatt ctctctcaga aatcaatggc   2640
atttgaacca ccaaaaagaa ataaagggct gagtgcggtg gctcacgcct gtaatcccag   2700
cactttgggg agcccaggcg ggcagattgc ttgaacccag gagttcaaga ccagcctggg   2760
cagcatggtg aaaccctgta tctacaaaaa atacaaaaat tagccaggca tggtggtggg   2820
tgcctgtagt tccagctact tgggaggctg aggtgggaaa atgacttgag cccaggagga   2880
ggaggctgca gtgagctaag attgcaccac tgcactccaa cctgggcgac aagagtgaaa   2940
ctgtgtctct caaaaaaaaa aaaaaacaaa caaaaacaaa aacaaaacaa aacaaaacaa   3000
aacaaaacag gtaaggattc ccctgttttc ctctctttaa ttttaaagtt atcagttccg   3060
taaagtctct gtaaccaaac atactgaaga cagcaacaga agtcacgttc agggactggc   3120
tcacacctgt aatcccagca ctttgggaga tggaggtaaa aggatctctt gagcccagga   3180
gttcaagacc agcttgggca acatagcaag actccatctc ttaaaaaata aaaatagtaa   3240
cattagccag gtgtagcagc acacatctgc agcagctact caggaggctg aggtggaaag   3300
atcgcttgtg cacagaagtt cgaggctgca gtgagctata tgatcatgtc actgcactcc   3360
agcctgtgtg accgagcaag accctatctc aaaaaaatta attaattaat taattaatta   3420
atttaaaaag gaagtcatgt tcatttactt tccacttcag tgtgtatcgt gtagtatttt   3480
ggaggttgga aagtgaaacg taggaatcct gaagattttt tccacttcta gtttgcagtg   3540
ctcagtgcac aatatacatt ttgctgaatg aataaacaga aatagggaag taaacctaca   3600
aatattttag ggagaagctc acttcttcct tttctcagga aaccaagcaa gcaaacatat   3660
cgttccaatt ttaaaaccca gtgaccaaag cctttggaac tatgaatttg caactgtcat   3720
aggtttatgg atattgctgt ggagaagctc aattttcagt gtttgaactg aaccctttct   3780
tgttagggaa cgtgtgaaag aagaattgtg gggaaaaaaa agcaagcata accaaagatc   3840
atcagcagtg aagaatctag gctgtggctg agagaaccag aggcctctaa aatggacccg   3900
agtcgatctt cagaacaggg atctaccatg caggagcttc ttgtgctcac acaaatctgt   3960
aaatgggaac attgtacatt gtcgaattta aatgatatta attttctcaa gctatttttg   4020
ttactatttt cctaaaattg aatatttgca gggagcactt atactttttc ctaatgtctg   4080
tataacaaat ttctatgcaa gtacatgaat aaattatgct cacagctca               4129
```

<210> SEQ ID NO 27
<211> LENGTH: 3885
<212> TYPE: DNA
<213> ORGANISM: Homo sapiens

<400> SEQUENCE: 27

```
agagccggac ggggtaaact gagcggcggc ggcggggcgc tggggcggag actgcgaccc     60
ggagccgccc ggactgacgg agcccactgc ggtgcgggcg ttggcgcggg cacggaggac    120
ccgggcaggc atcgcaagcg accccgagcg gagccccgga gccatggccc tgagcgagct    180
ggcgctggtc cgctggctgc aggagagccg ccgctcgcgg aagctcatcc tgttcatcgt    240
gttcctggcg ctgctgctgg acaacatgct gctcactgtc gtggtcccca tcatcccaag    300
ttatctgtac agcattaagc atgagaagaa tgctacagaa atccagacgg ccaggccagt    360
gcacactgcc tccatctcag acagcttcca gagcatcttc tcctattatg ataactcgac    420
tatggtcacc gggaatgcta ccagagacct gacacttcat cagaccgcca cacagcacat    480
ggtgaccaac gcgtccgctg ttccttccga ctgtcccagt gaagacaaag acctcctgaa    540
tgaaaacgtg caagttggtc tgttgtttgc ctcgaaagcc accgtccagc tcatcaccaa    600
cccctttcata ggactactga ccaacagaat tggctatcca attcccatat ttgcgggatt    660
ctgcatcatg tttgtctcaa caattatgtt tgccttctcc agcagctatg ccttcctgct    720
gattgccagg tcgctgcagg gcatcggctc gtcctgctcc tctgtggctg ggatgggcat    780
gcttgccagt gtctacacag atgatgaaga gagaggcaac gtcatgggaa tcgccttggg    840
aggcctggcc atgggggtct tagtgggccc cccccttcggg agtgtgctct atgagtttgt    900
ggggaagacg gctccgttcc tggtgctggc cgccctggta ctcttggatg gagctattca    960
gctctttgtg ctccagccgt cccgggtgca gccagagagt cagaagggga cacccctaac   1020
cacgctgctg aaggacccgt acatcctcat tgctgcaggc tccatctgct ttgcaaacat   1080
gggcatcgcc atgctggagc cagccctgcc catctggatg atggagacca tgtgttcccg   1140
aaagtggcag ctgggcgttg ccttcttgcc agctagtatc tcttatctca ttggaaccaa   1200
tatttttggg atacttgcac acaaaatggg gaggtggctt tgtgctcttc tgggaatgat   1260
aattgttgga gtcagcattt tatgtattcc atttgcaaaa aacatttatg gactcatagc   1320
tccgaacttt ggagttggtt ttgcaattgg aatggtggat tcgtcaatga tgcctatcat   1380
gggctacctc gtagacctgc ggcacgtgtc cgtctatggg agtgtgtacg ccattgcgga   1440
tgtggcattt tgtatggggt atgctatagg tccttctgct ggtggtgcta ttgcaaaggc   1500
aattggattt ccatggctca tgacaattat tgggataatt gatattcttt ttgcccctct   1560
ctgctttttt cttcgaagtc cacctgccaa agaagaaaaa atggctattc tcatggatca   1620
caactgccct attaaaacaa aaatgtacac tcagaataat atccagtcat atccgatagg   1680
tgaagatgaa gaatctgaaa gtgactgaga tgagatcctc aaaaatcatc aaagtgttta   1740
attgtataaa acagtgtttc cagtgacaca actcatccag aactgtctta gtcataccat   1800
ccatccctgg tgaaagagta aaaccaaagg ttattatttc ctttccatgg ttatggtcga   1860
ttgccaacag ccttataaag aaaaagaagc ttttctaggg gtttgtataa atagtgttga   1920
aactttattt tatgtattta attttattaa atatcataca atatattttg atgaaatagg   1980
tattgtgtaa atctataaat atttgaatcc aaaccaaata taattttttta acttacatta   2040
acaaacattt gggcaaaaat catattggta atgagtgttt aaaattaaag cacacattat   2100
ctctgagact cttccaacaa agagaaacta gaatgaagtc tgaaaaacag aatcaagtaa   2160
gacagcatgt tatatagtga cactgaatgt tatttaactt gtagttacta tcaatatatt   2220
tatgcgttaa acagctagtt ctctcaagtg tagaggacaa gaacttgtgt cagttatctt   2280
ttgaatccat aaatcttagc tggcattagt tttctatgta atcacctacc tagagagagt   2340
```

```
tgtaaattat atgttaacat gttatctggt tggcagcaaa cactaaagcc aataaaggaa   2400

aaacagtaaa tgttccgaaa gcagagaaaa gcaaccaaac atattgttat gaactaaaag   2460

ctttcccttt aagatgcata cttgtcttac tggatgaaga aaattgaggg tacatgtacc   2520

ttatactgtc aaggttgttt aaacatgata aggttaatcg ccatctactt caagttttag   2580

aaaaggaaac aagaagctga aaacagctgc tctgacttta atatctgact atatctttga   2640

tctgtttgca ggtcatccaa gtgttttcta ggaatatatt tattttaggt tgtctgaaac   2700

tactattttt tagactcctg aaagttgttc acatcaatgt gaagacaaat tttaaatgaa   2760

aatgaagaat gaaattatgt cttgaatcat atattaagaa gtaaaaataa tagtgatcag   2820

gcagaaaaga aaaatggaac atctaaaaat gtatgtgcta actatatcat ccagtgtgca   2880

gtgttgtgta tttttctaag catgacaaca ttgatgtgcc ttttcagtgt aacagcaaat   2940

actgttagtg aacattgtca atttatgtca ttttgttaag agatatgact ggagtgtgca   3000

gtgtggaatg tctctaatac tacttgtgaa tcctgcagtt ctataatcat aaacaaaaat   3060

tacttagttt cgttaagcta agattgtgtt tgtgttaact tcgacatcaa ggagcaaaga   3120

actttagaac agactcctca atcttgtgac tttcttattc tctaggaaag taacacttcg   3180

tttcatgaag cttttctgtg gggcttcgat tatttcaagt ctggtttcta agtgcagtgt   3240

gtttgaagca aacgaacttc caactcactt atttggcatt gggcaacttg gccaagtctg   3300

ccactttgga agatggctct ggaggaaact ctcatatggc taaaaaggca ggctagtttc   3360

ttacttctac aggggtagag ccttaaaaaa gaacgtgcta caaattggtt ctctttgagg   3420

gtttctggtt ctccctgccc ccaataccat atactttatt gcaattttat ttttgccttt   3480

acggctctgt gtctttctgc aagaaggcct ggcaaaggta tgcctgctgt tggtccctcg   3540

ggataagata aaatataaat aaaaccttca gaactgtttt ggagcaaaag atagcttgta   3600

cttggggaaa aaaattctaa gttcttttat atgactaata ttcttggtta gcaagactgg   3660

aaagaggtgt ttttttaaaa tgtacatacc agaacaaaga acatacagct ctctgaacat   3720

ttattttttg aacagaggtg gtttttatgt ttggacctgg taatacagat acaaaaactt   3780

taatgaggta gcaatgaata ttcaactgtt tgactgctaa gtgtatctgt ccatatttta   3840

gcaagtttac ttaataaatc ttctgaacca tgaaaaaaaa aaaaa                   3885
```

<210> SEQ ID NO 28
<211> LENGTH: 5486
<212> TYPE: DNA
<213> ORGANISM: Homo sapiens

<400> SEQUENCE: 28

```
gccctcttct gaagaggcgt ttctggacca ctgagccccg cctcccactg tgagcggaac     60

cctaccgttt ttaaaaaaat ctttttcaaa acttgccagg ttgtctttcc aaatattttt    120

aataatagtg ctgctgctgt agaccacaga gaaaagaatc cctcgctctt ccttttcact    180

tagtagaaac ttctaccgcg taggtcccgc caggagttcg cgcatgcgca ggagcgacaa    240

taagatggcg gtgataatcg ccgcactttt tttcaaatta gtggatccca gaaatcattg    300

cgcgcatttg taacgaattt ccgttcgagt ttgtatttta ggcgccattt tcgagtgaag    360

gacccggagc cgaaacaccg gtaggagcgg ggaggtgggt actacacaac cgtctccagc    420

cttggtctga gtggactgtc ctgcagcgac catgccccgt aaaggcaccc agccctccac    480

tgcccggcgc agagaggaag ggccgccgcc gccgtcccct gacggcgcca gcagcgacgc    540

ggagcctgag ccgccgtccg gccgcacgga gagcccagcc accgccgcag agactgcaag    600
```

```
tgaggaactt gataatagaa gtttagaaga gattttgaac agcattcctc ctcccccgcc    660
tccagcaatg accaatgaag ctggagctcc tcggcttatg ataactcata ttgtaaacca    720
gaacttcaaa tcctatgctg ggagaaaat tctgggacct ttccataagc gcttttcctg    780
tattatcggg ccaaatggca gtggcaaatc caatgttatt gattctatgc tttttgtgtt    840
tggctatcga gcacaaaaaa taagatctaa aaaactctca gtattaatac ataattctga    900
tgaacacaag gacattcaga gttgtacagt agaagttcat tttcaaaaga taattgataa    960
ggaaggggat gattatgaag tcattcctaa cagtaatttc tatgtatcca gaacggcctg   1020
cagagataat acttctgtct atcacataag tggaaagaaa aagacattta aggatgttgg   1080
aaatcttctt cgaagccatg gaattgactt ggaccataat agatttttaa ttttacaggg   1140
tgaagttgaa caaattgcta tgatgaaacc aaaaggccag actgaacacg atgagggtat   1200
gcttgaatat ttagaagata taattggttg tggacggcta aatgaaccta ttaaagtctt   1260
gtgtcggaga gttgaaatat taaatgaaca cagaggagag aagttaaaca gggtaaagat   1320
ggtggaaaag gaaaaggatg ccttagaagg agagaaaaac atagctatcg aatttcttac   1380
cttggaaaat gaaatattta gaaaaaagaa tcatgtttgt caatattata tttatgagtt   1440
gcagaaacga attgctgaaa tggaaactca aaaggaaaaa attcatgaag ataccaaaga   1500
aattaatgag aagagcaata tactatcaaa tgaaatgaaa gctaagaata aagatgtaaa   1560
agatacagaa aagaaactga ataaaattac aaaatttatt gaggagaata aagaaaaatt   1620
tacacagcta gatttggaag atgttcaagt tagagaaaag ttaaaacatg ccacgagtaa   1680
agccaaaaaa ctggagaaac aacttcaaaa agataaagaa aaggttgaag aatttaaaag   1740
tatacctgcc aagagtaaca atatcattaa tgaaacaaca accagaaaca atgccctcga   1800
gaaggaaaaa gagaaagaag aaaaaaaatt aaaggaagtt atggatagcc ttaaacagga   1860
aacacaaggg cttcagaaag aaaaagaaag tcgagagaaa gaacttatgg gtttcagcaa   1920
atcggtaaat gaagcacgtt caaagatgga tgtagcccag tcagaacttg atatctatct   1980
cagtcgtcat aatactgcag tgtctcaatt aactaaggct aaggaagctc taattgcagc   2040
ttctgagact ctcaaagaaa ggaaagctgc aatcagagat atagaaggaa aactccctca   2100
aactgaacaa gaattaaagg agaaagaaaa agaacttcaa aaacttacac aagaagaaac   2160
aaactttaaa agtttggttc atgatctctt tcaaaaagtt gaagaagcaa agagctcatt   2220
agcaatgaat cgaagtaggg ggaaagtcct tgatgcaata attcaagaaa aaaaatctgg   2280
caggattcca ggaatatatg gaagattggg ggacttagga gccattgatg aaaaatacga   2340
cgtggctata tcatcctgtt gtcatgcact ggactacatt gttgttgatt ctattgatat   2400
agcccaagaa tgtgtaaact tccttaaaag acaaaatatt ggagttgcaa cctttatagg   2460
tttagataag atggctgtat gggcgaaaaa gatgaccgaa attcaaactc ctgaaaatac   2520
tcctcgttta tttgatttag taaaagtaaa agatgagaaa attcgccaag ctttttattt   2580
tgctttacga gataccttag tagctgacaa cttggatcaa gccacaagag tagcatatca   2640
aaaagataga agatggagag tggtaacttt acagggacaa atcatagaac agtcaggtac   2700
aatgactggt ggtggaagca aagtaatgaa aggaagaatg ggttcctcac ttgttattga   2760
aatctctgaa gaagaggtaa acaaaatgga atcacagttg caaaacgact ctaaaaaagc   2820
aatgcaaatc caagaacaga aagtacaact tgaagaaaga gtagttaagt tacggcatag   2880
tgaacgagaa atgaggaaca cactagaaaa atttactgca agcatccagc gtttaataga   2940
```

```
gcaagaagaa tatttgaatg tccaagttaa ggaacttgaa gctaatgtac ttgctacagc   3000
ccctgacaaa aaaaagcaga aattgctaga agaaaacgtt agtgctttca aaacagaata   3060
tgatgctgtg gctgagaaag ctggtaaagt agaagctgag gttaaacgct tacacaatac   3120
catcgtagaa atcaataatc ataaactcaa ggcccaacaa gacaaacttg ataaaataaa   3180
taagcaatta gatgaatgtg cttctgctat tactaaagcc caagtagcaa tcaagactgc   3240
tgacagaaac cttcaaaagg cacaagactc tgtcttgcgt acagagaaag aaataaaaga   3300
tactgagaaa gaggtggatg acctaacagc agagctgaaa agtcttgagg acaaagcagc   3360
agaggtcgta aagaatacaa atgctgcaga ggaatcctta ccagagatcc agaaagaaca   3420
tcgcaatctg cttcaagaat taaaagttat tcaagaaaat gaacatgctc ttcaaaaaga   3480
tgcacttagt attaagttga aacttgaaca aatagatggt cacattgctg aacataattc   3540
taaaataaaa tattggcaca aagagatttc aaaaatatca ctgcatccta tagaagataa   3600
tcctattgaa gagatttcgg ttctaagccc agaggatctt gaagcgatca agaatccaga   3660
ttctataaca aatcaaattg cacttttgga agcccggtgt catgaaatga aaccaaacct   3720
cggtgccatc gcagagtata aaaagaagga agaattgtat ttgcaacggg tagcagaatt   3780
ggacaaaatt acttatgaaa gagacagttt tagacaggca tatgaagatc ttcggaaaca   3840
aaggcttaat gaatttatgg caggttttta tataataaca aataaattaa aggaaaatta   3900
ccaaatgctt actttgggag gggacgccga actcgagctt gtagacagct tggatccttt   3960
ctctgaagga atcatgttca gtgttcgacc acctaagaaa agttggaaaa agatcttcaa   4020
cctttcggga ggagagaaaa cacttagttc attggcttta gtatttgctc ttcaccacta   4080
caagcccact cccctttact tcatggatga gattgatgca gcccttgatt ttaaaaatgt   4140
gtccattgtt gcattttata tatatgaaca aacaaaaaat gcacagttca taataatttc   4200
tcttcgaaat aatatgtttg agatttcgga tagacttatt ggaatttaca agacatacaa   4260
cataacaaaa agtgttgctg taaatccaaa agaaattgca tctaagggac tttgttgaac   4320
tttatgctga agattcttca agttgattca gtgtattact gatttttttc tatttgtaaa   4380
ggattatgag ttgtataaaa tacatactcc ctaaactaga tcatgaaact ggtttctgtt   4440
ttatgcagtt gtcatttgta aagtctaata aaatattctc tataattgct tctagattac   4500
aaaaatatga caatcttgta agtagcagac tatggagaaa aatgagttac ctggagggtc   4560
aggtaacttg ccaaactaaa aagtatgtta gttgaggcaa agtcctaagc aaggttgtgc   4620
tatcaaggct cagcatacct tcgtgggcct ttgatttacc aacactggaa atgcctgcca   4680
actaatcttg gatagattct ttaaggcatt ccacttagct tgccagttga gacaatcacc   4740
acagttatta cccaaatact atgaacatat ttttgtaaac cagtcattct gaattatagt   4800
gatgagaatt taaatatatg cttttctaga atttgatgtt tgaccattta tgacttaatt   4860
accagagagc cagtaaatta ggacagtgtt tcaacaagcc taggctatct cgtaagttga   4920
aaaatatccc actatagttg cttcatgagt atgaagtaag atggcctctg atttacactg   4980
gttcaattta caaattttca actttatgat aggtttatcc gggtactaaa tgcatttcaa   5040
cttgatagtt tcaacttatg ataggtttac caggatgtag tcccactgtt gaggagcatc   5100
tatttagggg ttaattactt tagtaataag tggaaagtaa gataccttga gtaatgtttg   5160
cctataaaat tgtcagcgta tttttacact attggctcaa gaatgttata atgctaaggg   5220
acataagttg gcaaccactt ggtttttgga aggactttcg gtattgtatt agaagtctgc   5280
cctagctgtt aaatttctgg gtatttatcc taaggaatta attaaagagt taattgttcc   5340
```

```
tttcttcagt gggccattgt tttagatatt taaaaaatcc aacagtttct atcataatgt   5400

aactgtaaaa atgtaaacac attattagca tggactttta aataaagatt taaagaaagc   5460

aagatcggaa aaaaaaaaaa aaaaaa                                         5486
```

<210> SEQ ID NO 29
<211> LENGTH: 3601
<212> TYPE: DNA
<213> ORGANISM: Homo sapiens

<400> SEQUENCE: 29

```
gggagaagga ggaggccggg ggaaggagga gacaggagga ggagggacca cggggtggag     60

gggagataga cccagcccag agctctgagt ggtttcctgt tgcctgtctc taaacccctc    120

cacattcccg cggtccttca gactgcccgg agagcgcgct ctgcctgccg cctgcctgcc    180

tgccactgag ggttcccagc accatgaggg cctggatctt ctttctcctt tgcctggccg    240

ggagggcctt ggcagcccct caagaagccc tgcctgatga gacagaggtg gtggaagaaa    300

ctgtggcaga ggtgactgag gtatctgtgg gagctaatcc tgtccaggtg gaagtaggag    360

aatttgatga tggtgcagag gaaaccgaag aggaggtggt ggcggaaaat ccctgccaga    420

accaccactg caaacacggc aaggtgtgcg agctggatga gaacaacacc cccatgtgcg    480

tgtgccagga ccccaccagc tgcccagccc ccattggcga gtttgagaag gtgtgcagca    540

atgacaacaa gaccttcgac tcttcctgcc acttctttgc cacaaagtgc accctggagg    600

gcaccaagaa gggccacaag ctccacctgg actacatcgg gccttgcaaa tacatccccc    660

cttgcctgga ctctgagctg accgaattcc ccctgcgcat gcgggactgg ctcaagaacg    720

tcctggtcac cctgtatgag agggatgagg acaacaacct tctgactgag aagcagaagc    780

tgcgggtgaa gaagatccat gagaatgaga agcgcctgga ggcaggagac caccccgtgg    840

agctgctggc ccgggacttc gagaagaact ataacatgta catcttccct gtacactggc    900

agttcggcca gctggaccag caccccattg acgggtacct ctcccacacc gagctggctc    960

cactgcgtgc tcccctcatc cccatggagc attgcaccac ccgctttttc gagacctgtg   1020

acctggacaa tgacaagtac atcgccctgg atgagtgggc cggctgcttc ggcatcaagc   1080

agaaggatat cgacaaggat cttgtgatct aaatccactc cttccacagt accggattct   1140

ctctttaacc ctccccttcg tgtttccccc aatgtttaaa atgtttggat ggtttgttgt   1200

tctgcctgga gacaaggtgc taacatagat ttaagtgaat acattaacgg tgctaaaaat   1260

gaaaattcta acccaagaca tgacattctt agctgtaact taactattaa ggccttttcc   1320

acacgcatta atagtcccat ttttctcttg ccatttgtag ctttgcccat tgtcttattg   1380

gcacatgggt ggacacggat ctgctgggct ctgccttaaa cacacattgc agcttcaact   1440

tttctcttta gtgttctgtt tgaaactaat acttaccgag tcagactttg tgttcatttc   1500

atttcagggt cttggctgcc tgtgggcttc cccaggtggc ctggaggtgg gcaaagggaa   1560

gtaacagaca cacgatgttg tcaaggatgg ttttgggact agaggctcag tggtgggaga   1620

gatccctgca gaacccacca accagaacgt ggtttgcctg aggctgtaac tgagagaaag   1680

attctggggc tgtgttatga aaatatagac attctcacat aagcccagtt catcaccatt   1740

tcctccttta cctttcagtg cagtttcttt tcacattagg ctgttggttc aaacttttgg   1800

gagcacggac tgtcagttct ctgggaagtg gtcagcgcat cctgcagggc ttctcctcct   1860

ctgtcttttg gagaaccagg gctcttctca ggggctctag ggactgccag gctgtttcag   1920
```

```
ccaggaaggc caaaatcaag agtgagatgt agaaagttgt aaaatagaaa aagtggagtt   1980

ggtgaatcgg ttgttctttc ctcacatttg gatgattgtc ataaggtttt tagcatgttc   2040

ctccttttct tcaccctccc ctttttttctt ctattaatca agagaaactt caaagttaat   2100

gggatggtcg gatctcacag gctgagaact cgttcacctc caagcatttc atgaaaaagc   2160

tgcttcttat taatcataca aactctcacc atgatgtgaa gagtttcaca aatccttcaa   2220

aataaaaagt aatgacttag aaactgcctt cctgggtgat ttgcatgtgt cttagtctta   2280

gtcaccttat tatcctgaca caaaaacaca tgagcataca tgtctacaca tgactacaca   2340

aatgcaaacc tttgcaaaca cattatgctt ttgcacacac acacctgtac acacacaccg   2400

gcatgtttat acacagggag tgtatggttc ctgtaagcac taagttagct gttttcattt   2460

aatgacctgt ggtttaaccc ttttgatcac taccaccatt atcagcacca gactgagcag   2520

ctatatcctt ttattaatca tggtcattca ttcattcatt cattcacaaa atatttatga   2580

tgtatttact ctgcaccagg tcccatgcca agcactgggg acacagttat ggcaaagtag   2640

acaaagcatt tgttcatttg gagcttagag tccaggagga atacattaga taatgacaca   2700

atcaaatata aattgcaaga tgtcacaggt gtgatgaagg gagagtagga gagaccatga   2760

gtatgtgtaa caggaggaca cagcattatt ctagtgctgt actgttccgt acggcagcca   2820

ctacccacat gtaacttttt aagatttaaa tttaaattag ttaacattca aaacgcagct   2880

ccccaatcac actagcaaca tttcaagtgc ttgagagcca tgcatgatta gtggttaccc   2940

tattgaatag gtcagaagta gaatcttttc atcatcacag aaagttctat tggacagtgc   3000

tcttctagat catcataaga ctacagagca cttttcaaag ctcatgcatg ttcatcatgt   3060

tagtgtcgta ttttgagctg gggttttgag actcccctta gagatagaga aacagaccca   3120

agaaatgtgc tcaattgcaa tgggccacat acctagatct ccagatgtca tttcccctct   3180

cttattttaa gttatgttaa gattactaaa acaataaaag ctcctaaaaa atcaaactgt   3240

attctggtgt tctcttctac acagtgggag ggcgagcagt aggagagatt ggcccatttg   3300

gtgctggcca tttgaggaat gcaagcccag cactagtctc ataatctcta ggaatctgta   3360

gagagaggaa ttgaagtaaa tttcagcatt ggctcattca gtcattcggc gacattcatc   3420

aggtacctgc aatgtgttag gggatcttat gagtaggcag cgtgcgtgat ccttgctccc   3480

ctggagcttt ctaacattct agcaggcaga ccacacataa atttgcaata ctgtttctga   3540

taaaaacgtg ctgtaaagga aataaagcag agaactatca tggaaaaaaa aaaaaaaaaa   3600

a                                                                   3601
```

<210> SEQ ID NO 30
<211> LENGTH: 2989
<212> TYPE: DNA
<213> ORGANISM: Homo sapiens

<400> SEQUENCE: 30

```
gtctgggccg agcccgccca gctggctgag acgcgtggag cctggcggcg agtgggggcg     60

tgcgacggtt actctggtta ctggggccgc gccgcgctgg cgagagccgc cgcccgcgag    120

ggatgctggt gaggaagccg tcgggagccg ccgccgccat ctgagggagg taccctggaa    180

accacctttt atcggtgggg aagtgcagtc gcggtgggcg gctctggggg ccagcgaaac    240

gggaggcctc taaatcttta ggttggggct gcattgccct ggagccgcac tcttgagtcc    300

gaggccatct tttgttggag aaggcgtcgg cgttggcgtt ttcccgaggt tgggctgtac    360

agtgtctccg tccgcggaaa aagaagcctc tgaacccgcg ccggcccgca gcccccgtgc    420
```

```
cttccggccg ctgctcgccg tcgccagagg ctaggccacg tttcccccag tgccgaggtg    480
tttctgtgac cctccctcca ctcccattcc cttctgaaag ggcacctgct cttggtgaga    540
aaagaaatta tagcacgaag agccagtatc agaagagtat ccatcacccg cagcaaccgc    600
tcagggaaca ccatcaaaaa agaaaaaaag ggaatatctg gatttcctgg gcgaggagga    660
gcgagtctgc tcgggagctg ttccagcagg cgatttttaa atactgcttt ctacgcccta    720
tacaacttgg cttcacatac ttttacacta actttatatg atttttaaaa actggtctga    780
tcggacttct cgtcctggga cactgtttac tggagtctgg ccggctctcc gtgctcctct    840
tggtacctca ttttggggag aaccttaaac ccactcgagc agataatctc cgccttgacc    900
ggtgccacca aagaagcctt ggaaccatgt ggacttttct gggcattgcc actttcacct    960
atttttataa gaagttcggg gacttcatca ctttggccaa cagggaggtc ctgttgtgcg   1020
tgctggtgtt cctctcgctg ggcctggtgc tctcctaccg ctgtcgccac cgaaacgggg   1080
gtctcctcgg gcgccagcag agcggctccc agttcgccct cttctcggat attctctcag   1140
gcctgccttt cattggcttc ttctgggcca aatccccccc tgaatcagaa aataaggagc   1200
agctcgaggc caggaggcgc agaaaaggaa ccaatatttc agaaacaagc ttaataggaa   1260
cagctgcctg tacatcaaca tcttctcaga atgacccaga agttatcatc gtgggagctg   1320
gcgtgcttgg ctctgctttg gcagctgtgc tttccagaga tggaagaaag gtgacagtca   1380
ttgagagaga cttaaaagag cctgacagaa tagttggaga attcctgcag ccgggtggtt   1440
atcatgttct caaagacctt ggtcttggag atacagtgga aggtcttgat gcccaggttg   1500
taaatggtta catgattcat gatcaggaaa gcaaatcaga ggttcagatt ccttaccctc   1560
tgtcagaaaa caatcaagtg cagagtggaa gagctttcca tcacggaaga ttcatcatga   1620
gtctccggaa agcagctatg gcagagccca atgcaaagtt tattgaaggt gttgtgttac   1680
agttattaga ggaagatgat gttgtgatgg gagttcagta caaggataaa gagactggag   1740
atatcaagga actccatgct ccactgactg ttgttgcaga tgggcttttc tccaagttca   1800
ggaaaagcct ggtctccaat aaagtttctg tatcatctca ttttgttggc tttcttatga   1860
agaatgcacc acagtttaaa gcaaatcatg ctgaacttat tttagctaac ccgagtccag   1920
ttctcatcta ccagatttca tccagtgaaa ctcgagtact tgttgacatt agaggagaaa   1980
tgccaaggaa tttaagagaa tacatggttg aaaaaattta cccacaaata cctgatcacc   2040
tgaaagaacc attcttagaa gccactgaca attctcatct gaggtccatg ccagcaagct   2100
tccttcctcc ttcatcagtg aagaaacgag gtgttcttct tttgggagac gcatataata   2160
tgaggcatcc acttactggt ggaggaatga ctgttgcttt taaagatata aaactatgga   2220
gaaaactgct aaagggtatc cctgaccttt atgatgatgc agctattttc gaggccaaaa   2280
aatcatttta ctgggcaaga aaaacatctc attcctttgt cgtgaatatc cttgctcagg   2340
ctctttatga attattttct gccacagatg attccctgca tcaactaaga aaagcctgtt   2400
ttctttattt caaacttggt ggcgaatgtg ttgcgggtcc tgttgggctg ctttctgtat   2460
tgtctcctaa ccctctagtt ttaattggac acttctttgc tgttgcaatc tatgccgtgt   2520
atttttgctt taagtcagaa ccttggatta caaaacctcg agcccttctc agtagtggtg   2580
ctgtattgta caaagcgtgt tctgtaatat ttcctctaat ttactcagaa atgaagtata   2640
tggttcatta agcttaaagg ggaaccattt gtgaatgaat atttggaact taccaagtcc   2700
taagagactt ttggaagagg atatatatag catagtacca taccacttat aaagtggaaa   2760
```

```
ctcttggacc aagatttgga ttaatttgtt tttgaagttt tttgtatata aatatgtaaa   2820

tacatgcttt aatttgcaat ttaaaatgaa ggggttaaat aagttagaca tttaaaagaa   2880

atgattgtta ccataaatta gtgctaatgc tgaggagaac tacagttttt cttttgaatt   2940

tagtatttga gatgagttgt tgggacatgc aaataaaatg aagaatgaa              2989
```

<210> SEQ ID NO 31
<211> LENGTH: 3138
<212> TYPE: DNA
<213> ORGANISM: Homo sapiens

<400> SEQUENCE: 31

```
attttaccca gcccctgttc aagatggagt tgctgtggtt cacacatctc tgacaaaaat     60

acagggctat tcggagtcac cagacctgga gtttgagtat gctgacacag acaagtgggc    120

tgcagagctc tcggagcttt acagctacac ggaagggcca gaattcctga tgaatcgaaa    180

atgctttgag gaggacttcc ggatccatgt gacagacaag aagtggactg agctggatac    240

caaccagcac cggacccatg ccatgaggct cctggatggc ttggaagtca ctgccaggga    300

gaagagactc aaggtggctc gagcaattct ctatgttgct caaggcacgt ttggggagtg    360

cagctcggag gcagaggtgc agtcctggat gcgctacaac atctttctcc tcctggaggt    420

gggcacgttc aatgctttgg tggagcttct gaacatggaa atagacaaca gtgccgcctg    480

cagcagtgct gtgaggaagc ctgccatctc cctggctgac agcacagacc tcagggtcct    540

gctcaacatc atgtacctga tagtggagac cgttcatcag gagtgtgagg gtgacaaggc    600

tgagtggagg accatgcggc agaccttcag agccgagctg ggctccccgc tgtacaacaa    660

tgagccattt gccatcatgc tgtttgggat ggtgaccaaa ttttgcagtg gtcacgcccc    720

tcactttccc atgaagaaag ttctcttgct gctctggaag acagtattgt gcacgctagg    780

cggctttgag gagctgcaga gcatgaaggc tgagaagcgc agcatcctgg gcctcccccc    840

gcttcctgag gacagcatca aagtgattcg caacatgaga gcagcctctc caccagcatc    900

tgcttcagac ttgattgagc agcagcagaa acggggccgc cgagagcaca aggctctgat    960

aaagcaggac aacctagatg ccttcaacga gcgggatccc tacaaggctg atgactctcg   1020

agaagaggaa gaggagaatg atgatgacaa cagtctggag ggggagacgt ttcccctgga   1080

acgggatgaa gtgatgcctc ccccgctaca gcacccacag actgacaggc tgacttgccc   1140

caaagggctc ccgtgggctc ccaaggtcag agagaaagac attgagatgt tccttgagtc   1200

cagccgcagc aaatttatag gttacactct aggcagtgac acgaacacag tggtggggct   1260

gcccaggcca atccacgaaa gcatcaagac tctgaaacag cacaagtaca cgtcgattgc   1320

agaggtccag gcacagatgg aggaggaata cctccgctcc cctctctcag gggagaaga    1380

agaagttgag caagtccctg cagaaaccct ctaccaaggc ttgctcccca gcctgcctca   1440

gtatatgatt gccctcctga agatcctgtt ggctgcagca cccacctcaa aagccaaaac   1500

agactcaatc aacatcctag cggacgtctt gcctgaggag atgcccacca cagtgttgca   1560

gagcatgaag ctgggggtgg atgtaaaccg ccacaaagag gtcattgtta aggccatttc   1620

tgctgtcctg ctgctgctgc tcaagcactt taagttgaac catgtctacc agtttgaata   1680

catggcccag cacctggtgt ttgccaactg cattcctttg atcctaaagt tcttcaatca   1740

aaacatcatg tcctacatca ctgccaagaa cagcatttct gtcctggatt accctcactg   1800

cgtggtgcat gagctgccag agctgacggc ggagagtttg gaagcaggtg acagtaacca   1860

attttgctgg aggaacctct tttcttgtat caatctgctt cggatcttga acaagctgac   1920
```

```
aaagtggaag cattcaagga caatgatgct ggtggtgttc aagtcagccc ccatcttgaa   1980

gcgggcccta aaggtgaaac aagccatgat gcagctctat gtgctgaagc tgctcaaggt   2040

acagaccaaa tacttggggc ggcagtggcg aaagagcaac atgaagacca tgtctgccat   2100

ctaccagaag gtgcggcatc ggctgaacga cgactgggca tacggcaatg atcttgatgc   2160

ccggccttgg gacttccagg cagaggagtg tgcccttcgt gccaacattg aacgcttcaa   2220

cgcccggcgc tatgaccggg cccacagcaa ccctgacttc ctgccagtgg acaactgcct   2280

gcagagtgtc ctgggccaac gggtggacct ccctgaggac tttcagatga actatgacct   2340

ctggttagaa agggaggtct tctccaagcc catttcctgg gaagagctgc tgcagtgagg   2400

ctgttggtta ggggactgaa atggagagaa aagatgatct gaaggtacct gtgggactgt   2460

cctagttcat tgctgcagtg ctcccatccc ccaccaggtg gcagcacagc cccactgtgt   2520

cttccgcagt ctgtcctggg cttgggtgag cccagcttga cctccccttg gttcccaggg   2580

tcctgctccg aagcagtcat ctctgcctga gatccattct tcctttactt cccccaccct   2640

cctctcttgg atatggttgg ttttggctca tttcacaatc agcccaaggc tgggaaagct   2700

ggaatgggat gggaacccct ccgccgtgca tctgaatttc aggggtcatg ctgatgcctc   2760

tcgagacata caaatccttg ctttgtcagc ttgcaaagga ggagagttta ggattagggc   2820

cagggccaga aagtcggtat cttggttgtg ctctggggtg ggggtggggt gtttctgatg   2880

ttattccagc ctcctgctac attatatcca gaagtaattg cggaggctcc ttcagctgcc   2940

tcagcacttt gattttggac agggacaagg taggaagaga agcttccctt aaccagaggg   3000

gccatttttc cttttggctt tcgagggcct gtaaatatct atatataatt ctgtgtgtat   3060

tctgtgtcat gttggggttt ttaatgtgat tgtgtattct gtttacatta aaaagaagca   3120

aaaataaaaa aaaaaaaa                                                 3138
```

<210> SEQ ID NO 32
<211> LENGTH: 3098
<212> TYPE: DNA
<213> ORGANISM: Homo sapiens

<400> SEQUENCE: 32

```
gcacgcagcc ttagctcctt ccccgccctt gctcttccca gtttctccgt cagcctgcgg     60

gtcccggctg gcggctgctt ccggtaggag agcggtgtag agcgagcagg tctcagctcc    120

tcgtcatgtc atacggtccc ttagacatgt accggaaccc ggggccctcg ggcccccagc    180

tccgggactt cagcagcatc atccagacgt gcagcggcaa catccagcgg atcagccaag    240

ccactgctca gataaagaat ttgatgagcc agctaggaac taagcaggac tcaagcaagc    300

tacaggaaaa tctgcaacag ttacaacact ccacaaatca gctcgccaag gaaacaaatg    360

aattgctgaa agaattaggg tccttgcccc ttcccttatc tacttcagaa cagcgccagc    420

agagacttca gaaggaacgc ctcatgaatg acttctctgc agccttaaac aatttccagg    480

ctgtgcagag aagggtatct gaaaaggaaa aggagagtat tgccagagca agagctggat    540

ctcgtctttc tgcagaagag aggcaaagag aggagcagct ggtctcattt gacagccatg    600

aggagtggaa ccagatgcag agccaggagg atgaggtggc catcactgag caggatttgg    660

aacttattaa agaaagagaa acggcaattc ggcagctgga ggctgacatt ttggatgtca    720

atcagatatt taaagatttg gccatgatga tccatgacca gggtgatctg attgatagca    780

tagaagccaa tgtggaaagc tcagaggtgc acgtcgaaag agccactgaa cagttacagc    840
```

```
gagctgctta ctatcagaaa aaatctcgca agaagatgtg tatcctggtg cttgtcctgt    900
cagtgattat tctaatcttg ggacttatta tctggctagt ttataaaacg aagtgattgc    960
ctccgatcgt tctcccgctg agctgttttc aagggcaagt gcttgttgaa gtcttgccag   1020
aacaaactga tcacaagaag acagcatata tcagaacgtc ctgtaatcat ttagttagaa   1080
actaactact aactagtctt tggaattcgt gacctatgga gacagtaatt atcaatttat   1140
tgattctatt gatttctcaa attaggaatt aacttatgtg gattttgctt cctcttgtat   1200
tctgattgcc cttcatccca agtgtttact gaaaattcca ttctagatat tcttgttttg   1260
acaaatgaca ctacagtctc gtaatattgt cttttatgta tatacaaaat ttaccttttt   1320
actagcatct gagatagagt tactttctgg tacccagtat attggagtct gtcagaaact   1380
ctataatagg ccaccagttt ttattattta acatttttat ttgaatttct aagaagccta   1440
ttctctatct attttgaaag attttggcac tatatttaat tggaaggtaa aatattgtac   1500
atgtgatcca gagtaaatga gaagtctcta tctgagctgg tcagttactg gagtacatgt   1560
tactaatctg ggtttaaagt ttacttcatt atctgctagt gtcatccaca gcagttcatc   1620
ctcatccaca ctaagccatc ctgttagctt ttaaaggaag ttaatttaat taacattaat   1680
atactctatg ggctccctct cccacctgtc tgcatagaaa ggcagaatta gacatagcat   1740
gctttggaaa agcaaatagg aattgttggg aatgatttaa tcttgttgtt gttgttgttg   1800
ttgttcactt gtggttctac attcctggtg aatgatgaat gttgctgtca aagggctgcc   1860
ccctacctta taagggttgc tgggcatttg aaggcaggaa gatttttaaa gatagattga   1920
ggttggttta aaattattcc tgtaaaccaa caataaagca aagaagaggt tcatttttgt   1980
aaataacact ggtttcaaat agtgatgtta gacttaacct aatttataaa caagagatta   2040
atatctccat gcatagtttt agacaaaaaa agatgtttca ataaaattac tgtcttgtaa   2100
tataaatgtt gtccacttcc cttttccaca ggcctagaac agttaaaggg aacataattt   2160
gtttaggctc ccacataaat gtgaatctgg ccaacaactt tggttcatcc tttagtgaat   2220
tagaggattt ggctaccctg agtatattta tattcatttc ttctgttctc cttctgttat   2280
tatacttaat cttctaaact aaactaatgt gaacagtagg gaagcaaggg cccaaatgca   2340
taagtttctt tgcactgttg cacttactta atacaaataa atgtttttta aagcttttgt   2400
agtatgtttt tatgagttaa catcctaatg tggtaggtat taggtaatgt gctgtcatga   2460
gaaaaattga gacttccaag aaaactggac accaggtgag ggttggtttg gagacggaat   2520
aggtgtagct gcctttcctt gaaaaacagt gtgtagagat ggctgagtgc aatggctcac   2580
acttgtaatc ccaacacttt ggaaggctga ggcgggagga tcagtatatc ggtacgtctg   2640
agcccaagag ttcaagatca gcctgggcag tatagcaaga ccccatctcc attttttttt   2700
taatgatttt ttaattaaaa aaaagaacaa caggatagag ctgttggggt ggcacagtgg   2760
cccaaagagc agcttcagag ataattcctt ggttctatga tccctgttta actccaaatt   2820
acagtcggac ttggatacat catttgtaac attgtaggaa agaaaaaagt cttggttgtg   2880
aaaaacgatt tgcatttggg taaaataaag tgaccatgct tttgttctgt aatactgtgt   2940
gacctgtggt tgttgtaatg gtgatcatgg agagcaaata tgaacttggc ctggatttta   3000
aatggcctag aatttgtggt agttgccaaa gaggttctcc taggtggtct taataaacct   3060
attcacagaa ttctccttaa aaaaaaaaaa aaaaaaaa                           3098
```

<210> SEQ ID NO 33
<211> LENGTH: 293

<212> TYPE: DNA
<213> ORGANISM: Homo sapiens

<400> SEQUENCE: 33

```
taggcgcgag ctaagcagga ggcggaggcg gaggcggagg gcgaggggcg gggagcgccg     60

cctggagcgc ggcaggaagc cttatcagtt gtgagtgagg accagtcgtt gtttgagtgt    120

gcctacggaa cgccacacct ggctaagaca gagatgaccg cgtcctcctc cagcgactat    180

ggacagactt ccaagatgag cccacgcgtc cctcagcagg attggctgtc tcaaccccca    240

gccagggtca ccatcaaaat ggaatgtaac cctagccagg tgaatggctc aag           293
```

<210> SEQ ID NO 34
<211> LENGTH: 3112
<212> TYPE: DNA
<213> ORGANISM: Homo sapiens

<400> SEQUENCE: 34

```
gggaacaaaa gctggagctc caccgcggtg gcggccgctc tagccctcaa ggaactctcc     60

tgatgaatgc agtgtggcca aaggcgggaa gatggtgggc agcccagaca ccgttgggat    120

gaactacggc agctacatgg aggagaagca catgccaccc ccaaacatga ccacgaacga    180

gcgcagagtt atcgtgccag cagatcctac gctatggagt acagaccatg tgcggcagtg    240

gctggagtgg gcggtgaaag aatatggcct tccagacgtc aacatcttgt tattccagaa    300

catcgatggg aaggaactgt gcaagatgac caaggacgac ttccagaggc tcacccccag    360

ctacaacgcc gacatccttc tctcacatct ccactacctc agagagactc ctcttccaca    420

tttgacttca gatgatgttg ataaagcctt acaaaactct ccacggttaa tgcatgctag    480

aaacacaggg ggtgcagctt ttattttccc aaatacttca gtatatcctg aagctacgca    540

aagaattaca actaggccag atttaccata tgagcccccc aggagatcag cctggaccgg    600

tcacggccac cccacgcccc agtcgaaagc tgctcaacca tctccttcca cagtgcccaa    660

aactgaagac cagcgtcctc agttagaacc ttatcagatt cttggaccaa caagtagccg    720

ccttgcaaat ccaggcagtg gccagatcca gctttggcag ttcctcctgg agctcctgtc    780

ggacagctcc aactccagct gcatcacctg ggaaggcacc aacggggagt tcaagatgac    840

ggatcccgac gaggtggccc ggcgctgggg agagcggaag agcaaaccca acatgaacta    900

cgataagctc agccgcgccc tccgttacta ctatgacaag aacatcatga ccaaggtcca    960

tgggaagcgc tacgcctaca agttcgactt ccacgggatc gcccaggccc tccagcccca   1020

ccccccggag tcatctctgt acaagtaccc ctcagacctc ccgtacatgg gctcctatca   1080

cgcccaccca cagaagatga actttgtggc gccccaccct ccagccctcc ccgtgacatc   1140

ttccagtttt tttgctgccc caaacccata ctggaattca ccaactgggg gtatataccc   1200

caacactagg ctccccacca gccatatgcc ttctcatctg ggcacttact actaaagacc   1260

tggcggaggc ttttcccatc agcgtgcatt caccagccca tcgccacaaa ctctatcgga   1320

gaacatgaat caaaagtgcc tcaagaggaa tgaaaaaagc tttactgggg ctggggaagg   1380

aagccgggga agagatccaa agactcttgg gagggagtta ctgaagtctt actgaagtct   1440

tactacagaa atgaggagga tgctaaaaat gtcacgaata tggacatatc atctgtggac   1500

tgaccttgta aaagacagtg tatgtagaag catgaagtct taaggacaaa gtgccaaaga   1560

aagtggtctt aagaaatgta taaactttag agtagagttt gaatcccact aatgcaaact   1620

gggatgaaac taaagcaata gaaacaacac agttttgacc taacataccg tttataatgc   1680
```

```
cattttaagg aaaactacct gtatttaaaa atagaaacat atcaaaaaca agagaaaaga   1740
cacgagagag actgtggccc atcaacagac gttgatatgc aactgcatgg catgtgctgt   1800
tttggttgaa atcaaataca ttccgtttga tggacagctg tcagctttct caaactgtga   1860
agatgaccca aagtttccaa ctcctttaca gtattaccgg gactatgaac taaaaggtgg   1920
gactgaggat gtgtatagag tgagcgtgtg attgtagaca gaggggtgaa gaaggaggag   1980
gaagaggcag agaaggagga gaccagggct gggaaagaaa cttctcaagc aatgaagact   2040
ggactcagga catttgggga ctgtgtacaa tgagttatgg agactcgagg gttcatgcag   2100
tcagtgttat accaaaccca gtgttaggag aaaggacaca gcgtaatgga gaaaggggaa   2160
gtagtagaat tcagaaacaa aaatgcgcat ctctttcttt gtttgtcaaa tgaaaatttt   2220
aactggaatt gtctgatatt taagagaaac attcaggacc tcatcattat gtgggggctt   2280
tgttctccac agggtcaggt aagagatggc cttcttggct gccacaatca gaaatcacgc   2340
aggcattttg ggtaggcggc ctccagtttt cctttgagtc gcgaacgctg tgcgtttgtc   2400
agaatgaagt atacaagtca atgtttttcc ccctttttat ataataatta tataacttat   2460
gcatttatac actacgagtt gatctcggcc agccaaagac acacgacaaa agagacaatc   2520
gatataatgt ggccttgaat tttaactctg tatgcttaat gtttacaata tgaagttatt   2580
agttcttaga atgcagaatg tatgtaataa aataagcttg gcctagcatg gcaaatcaga   2640
tttatacagg agtctgcatt tgcacttttt ttagtgacta aagttgctta atgaaaacat   2700
gtgctgaatg ttgtggattt tgtgttataa tttactttgt ccaggaactt gtgcaaggga   2760
gagccaagga aataggatgt ttggcaccca aatggcgtca gcctctccag gtccttcttg   2820
cctcccctcc tgtcttttat ttctagcccc ttttggaaca gaaggacccc gggtttcaca   2880
ttggagcctc catatttatg cctggaatgg aaagaggcct atgaagctgg ggttgtcatt   2940
gagaaattct agttcagcac ctggtcacaa atcaccctta attcctgcta tgattaaaat   3000
acatttgttg aacagtgaac aagctaccac tcgtaaggca aactgtatta ttactggcgg   3060
gcggatcccc cgggctgcag gaattcgata tcaagcttat cgataccgtc ga           3112
```

<210> SEQ ID NO 35
<211> LENGTH: 3037
<212> TYPE: DNA
<213> ORGANISM: Homo sapiens

<400> SEQUENCE: 35

```
ctcctcacag gtgtgtctct agtcctcgtg gttgcctgcc ccactccctg ccgagacgcc     60
tgccagaaag gtcacctatc ctgaacccca gcaagcctga aacagctcag ccaagcaccc    120
tgcgatggaa gctgcagatg cctccaggag caacgggtcg agcccagaag ccagggatgc    180
ccggagcccg tcgggcccca gtggcagcct ggagaatggc accaaggctg acggcaagga    240
tgccaagacc accaacgggc acggcgggga ggcagctgag ggcaagagcc tgggcagcgc    300
cctgaagcca ggggaaggta ggagcgccct gttcgcgggc aatgagtggc ggcgacccat    360
catccagttt gtcgagtccg gggacgacaa gaactccaac tacttcagca tggactctat    420
ggaaggcaag aggtcgccgt acgcagggct ccagctgggg gctgccaaga agccacccgt    480
tacctttgcc gaaaagggcg agctgcgcaa gtccattttc tcggagtccc ggaagcccac    540
ggtgtccatc atggagcccg gggagacccg gcggaacagc tacccccggg ccgacacggg    600
cctttttca cggtccaagt ccggctccga ggaggtgctg tgcgactcct gcatcggcaa    660
caagcagaag gcggtcaagt cctgcctggt gtgccaggcc tccttctgcg agctgcatct    720
```

```
caagccccac ctggagggcg ccgccttccg agaccaccag ctgctcgagc ccatccggga    780
ctttgaggcc cgcaagtgtc ccgtgcatgg caagacgatg gagctcttct gccagaccga    840
ccagacctgc atctgctacc tttgcatgtt ccaggagcac aagaatcata gcaccgtgac    900
agtggaggag gccaaggccg agaaggagac ggagctgtca ttgcaaaagg agcagctgca    960
gctcaagatc attgagattg aggatgaagc tgagaagtgg cagaaggaga aggaccgcat   1020
caagagcttc accaccaatg agaaggccat cctggagcag aacttccggg acctggtgcg   1080
ggacctggag aagcaaaagg aggaagtgag ggctgcgctg gagcagcggg agcaggatgc   1140
tgtggaccaa gtgaaggtga tcatggatgc tctggatgag agagccaagg tgctgcatga   1200
ggacaagcag acccgggagc agctgcatag catcagcgac tctgtgttgt ttctgcagga   1260
atttggtgca ttgatgagca attactctct ccccccaccc ctgcccacct atcatgtcct   1320
gctggagggg gagggcctgg gacagtcact aggcaacttc aaggacgacc tgctcaatgt   1380
atgcatgcgc cacgttgaga agatgtgcaa ggcggacctg agccgtaact tcattgagag   1440
gaaccacatg gagaacggtg gtgaccatcg ctatgtgaac aactacacga acagcttcgg   1500
gggtgagtgg agtgcaccgg acaccatgaa gagatactcc atgtacctga cacccaaagg   1560
tggggtccgg acatcatacc agccctcgtc tcctggccgc ttcaccaagg agaccaccca   1620
gaagaatttc aacaatctct atggcaccaa aggtaactac acctcccggg tctgggagta   1680
ctcctccagc attcagaact ctgacaatga cctgcccgtc gtccaaggca gctcctcctt   1740
ctccctgaaa ggctatccct ccctcatgcg gagccaaagc ccccaaggccc agccccagac   1800
ttggaaatct ggcaagcaga ctatgctgtc tcactaccgg ccattctacg tcaacaaagg   1860
caacgggatt gggtccaacg aagccccatg agctcctggc ggaaggaacg aggcgccaca   1920
cccctgctct tcctcctgac cctgctgctc ttgccttcta agctactgtg cttgtctggg   1980
tgggagggag cctggtcctg cacctgccct ctgcagccct ctgccagcct cttgggggca   2040
gttccggcct ctccgacttc cccactggcc acactccatt cagactcctt tcctgccttg   2100
tgacctcaga tggtcaccat cattcctgtg ctcagaggcc aacccatcac aggggtgaga   2160
taggttgggg cctgccctaa cccgccagcc tcctcctctc gggctggatc tgggggctag   2220
cagtgagtac ccgcatggta tcagcctgcc tctcccgccc acgccctgct gtctccaggc   2280
ctatagacgt ttctctccaa ggccctatcc cccaatgttg tcagcagatg cctggacagc   2340
acagccaccc atctcccatt cacatggccc acctcctgct tcccagagga ctggccctac   2400
gtgctctctc tcgtcctacc tatcaatgcc cagcatggca gaacctgcag cccttggcca   2460
ctgcagatgg aaacctctca gtgtcttgac atcaccctac ccaggcggtg ggtctccacc   2520
acagccactt tgagtctgtg gtccctggag ggtggcttct cctgactggc aggatgacct   2580
tagccaagat attcctctgt tccctctgct gagataaaga attcccttaa catgatataa   2640
tccacccatg caaatagcta ctggcccagc taccatttac catttgccta cagaatttca   2700
ttcagtctac actttggcat tctctctggc gatggagtgt ggctgggctg accgcaaaag   2760
gtgccttaca cactgccccc accctcagcc gttgccccat cagaggctgc ctcctccttc   2820
tgattacccc ccatgttgca tatcagggtg ctcaaggatt ggagaggaga caaaaccagg   2880
agcagcacag tggggacatc tcccgtctca acagccccag gcctatgggg gctctggaag   2940
gatgggccag cttgcagggg ttggggaggg agacatccag cttgggcttt cccctttgga   3000
ataaaccatt ggtctgtcaa aaaaaaaaaa aaaaaaa                            3037
```

<210> SEQ ID NO 36
<211> LENGTH: 4035
<212> TYPE: DNA
<213> ORGANISM: Homo sapiens

<400> SEQUENCE: 36

```
acttaacaac cgaagtaacc cgcaatgcgg aagggcgagg ggattgcgag tcaccgagtt      60
tcccgcgcgg cttgagtcac ggcctagaaa gagagatgtt ggggttccca ggaccaggac     120
agaggtggta gtgaactctc atgggcatcc agagaaggtc aggccccttg ctgacaggcc     180
tatctgtggg gctactgctg ctcttcagct gggtgaccct tgtccagcca acctctctct     240
cagctctggt ccaccaccct cacttgtgcc agaccacccg ggatgtccat ggccgtcact     300
accctggttt cttttgccct cgtctgtctg attctccaga ggaagcctac tgctgccacc     360
tgcaggctgc agggggctcc tgctgcaccc gggctgaatt tgaggccctg taccaagtca     420
atctgtccgc tcttccgccc ccgcccatcc tcaggggccc aggcccgctc ctagtgctgg     480
gcctctacaa cctactggtt gtgaccctga tgaccgtaga cctcgtgcac ttctgctgcg     540
gtcggggccg gagtctgggc tggagccacc gcaggcctcc ctctgggtcc tccgccgcga     600
gctccctgca ggtctctgcg gggacagctt aggtgcgccc ggagcttgcc tgcacctgcg     660
atccagagcc aagcgccccg cccctgcccg ggcgcgctcc ctccttagcc ctgcccctct     720
ctgaccccac ctccgacgca agagtggggc ggggcagctg ccggtggcgt cccgaaccca     780
gactcgcccc gccccagaga ctgcgcctgc gcgggcacga gacaacctct ccgcgatgac     840
tgccagctca gtggagcagc tgcggaagga gggcaatgag ctgttcaaat gtggagacta     900
cgggggcgcc ctggcggcct acactcaggc cctgggtctg gacgcgacgc cccaggacca     960
ggccgttctg caccggaacc gggccgcctg ccacctcaag ctggaagatt acgacaaagc    1020
agaaacagag gcatccaaag ccattgaaaa ggatggtggg gatgtcaaag cactctaccg    1080
gcggagccaa gccctagaga agctgggccg cctggaccag gctgtccttg acctgcagag    1140
atgtgtgagc ttggagccca agaacaaagt tttccaggag gccttgcgga acatcggggg    1200
ccagattcag gagaaggtgc gatacatgtc ctcgacggat gccaaagtgg aacagatgtt    1260
tcagatactg ttggacccag aagagaaggg cactgagaaa aagcaaaagg cttctcagaa    1320
cctggtggtg ctggccaggg aggatgctgg agcggagaag atcttccgga gtaatggggt    1380
tcagctcttg caacgtttac tggacatggg agagactgac ctcatgctgg cggctctgcg    1440
tacgctggtt ggcatttgct ctgagcatca gtcacggaca gtggcaaccc tgagcatact    1500
gggaactcgg cgagtagtct ccatcctggg cgtggaaagc caggctgtgt ccctggctgc    1560
ctgccacctg ctgcaggtta tgtttgatgc cctcaaggaa ggtgtcaaaa aaggcttccg    1620
aggcaaagaa ggtgccatca ttgtggatcc tgcccgggag ctgaaggtcc tcatcagtaa    1680
cctcttagat ctgctgacag aggtgggggt ctctggccaa ggccgagaca atgccctgac    1740
cctcctgatt aaagcggtgc cccggaagtc tctcaaggac cccaacaaca gcctcaccct    1800
ctgggtcatc gaccaaggtc tgaaaaagat tttggaagtg gggggctctc tacaggaccc    1860
tcctggggag ctcgcagtga ccgcaaacag ccgcatgagc gcctctattc tcctcagcaa    1920
gctctttgat gacctcaagt gtgatgcgga gagggagaat ttccacagac tttgtgaaaa    1980
ctacatcaag agctggtttg agggccaagg gctggccggg aagctacggg ccatccagac    2040
ggtgtcctgc ctcctgcagg gcccatgtga cgctggcaac cgggccttgg agctgagcgg    2100
tgtcatggag agtgtgattg ctctgtgtgc ctctgagcag gaggaggagc agctggtggc    2160
```

```
cgtggaggct ctgatccatg cagccggcaa ggctaagcgg gcctcattca tcactgccaa   2220

tggtgtctcg ctgctgaagg acctatataa gtgcagcgag aaggacagca tccgcatccg   2280

ggcgctagtg ggactctgta agctcggttc ggctggaggg actgacttca gcatgaagca   2340

gtttgctgaa ggctccactc tcaaactggc taagcagtgt cgaaagtggc tgtgcaatga   2400

ccagatcgac gcaggcactc ggcgctgggc agtggagggc ctggcttacc tgacctttga   2460

tgccgacgtg aaggaagagt ttgtggagga tgcggctgct ctgaaagctc tgttccagct   2520

cagcaggttg gaggagaggt cagtgctctt tgcggtggcc tcagcgctgg tgaactgcac   2580

caacagctat gactacgagg agcccgaccc caagatggtg gagctggcca agtatgccaa   2640

gcagcatgtg cccgagcagc accccaagga caagccaagc ttcgtgcggg ctcgggtgaa   2700

gaagctgctg gcagcgggtg tggtgtcggc catggtgtgc atggtgaaga cggagagccc   2760

tgtgctgacc agttcctgca gagagctgct ctccagggtc ttcttggctt tagtggaaga   2820

ggtagaggac cgaggcactg tggttgccca gggaggcggc agggcgctga tcccgctggc   2880

cctggaaggc acggacgtgg ggcagacaaa ggcagcccag gcccttgcca agctcaccat   2940

cacctccaac ccggagatga ccttccctgg cgagcggatc tatgaggtgg tccggcccct   3000

cgtctccctg ttgcacctca actgctcagg cctgcagaac ttcgaggcgc tcatggccct   3060

aacaaacctg gctgggatca gcgagaggct ccggcagaag atcctgaagg agaaggctgt   3120

gcccatgata gaaggctaca tgtttgagga gcatgagatg atccgccggg cagccacgga   3180

gtgcatgtgt aacttggcca tgagcaagga ggtgcaggac ctcttcgaag cccagggcaa   3240

tgaccgactg aagctgctgg tgctgtacag tggagaggat gatgagctgc tacagcgggc   3300

agctgccggg ggcttggcca tgcttacctc catgcggccc acgctctgca gccgcattcc   3360

ccaagtgacc acacactggc tggagatcct gcaggccctg cttctgagct ccaaccagga   3420

gctgcagcac cggggtgctg tggtggtgct gaacatggtg gaggcctcga gggagattgc   3480

cagcaccctg atggagagtg agatgatgga gatcttgtca gtgctagcta agggtgacca   3540

cagccctgtc acaagggctg ctgcagcctg cctggacaaa gcagtggaat atgggcttat   3600

ccaacccaac caagatggag agtgaggggg ttgtccctgg gcccaaggct catgcacacg   3660

ctacctattg tggcacggag agtaaggacg gaagcagctt tggctggtgg tggctggcat   3720

gcccaatact cttgcccatc ctcgcttgct gccctaggat gtcctctgtt ctgagtcagc   3780

ggccacgttc agtcacacag ccctgcttgg ccagcactgc ctgcagcctc actcagaggg   3840

gcccttttc tgtactactg tagtcagctg ggaatgggga aggtgcatcc caacacagcc   3900

tgtggatcct ggggcatctg gaagggcgca cacatcagca gcctcaccag ctgtgagcct   3960

gctatcaggc ctgcccctcc aataaaagtg tgtagaactc caaaaaaaaa aaaaaaaaaa   4020

aaaaaaaaaa aaaaa                                                    4035
```

```
<210> SEQ ID NO 37
<211> LENGTH: 3729
<212> TYPE: DNA
<213> ORGANISM: Homo sapiens

<400> SEQUENCE: 37

cgaaggggcg tggccaagcg caccgcctcg gggcggggcc ggcgttctag cgcatcgcgg     60

ccgggtgcgt cactcgcgaa gtggaatttg cccagacaag caacatggct cggaaacgcg    120

cggccggcgg ggagccgcgg ggacgcgaac tgcgcagcca gaaatccaag gccaagagca    180
```

-continued

```
aggcccggcg tgaggaggag gaggaggatg cctttgaaga tgagaaaccc ccaaagaaga    240
gccttctctc caaagtttca caaggaaaga ggaaaagagg ctgcagtcat cctgggggtt    300
cagcagatgg tccagcaaaa aagaaagtgg ccaaggtgac tgttaaatct gaaaacctca    360
aggttataaa ggatgaagcc ctcagcgatg ggggatgacct cagggacttt ccaagtgacc    420
tcaagaaggc acaccatctg aagagagggg ctaccatgaa tgaagacagc aatgaagaag    480
aggaagaaag tgaaaatgat tgggaagagg ttgaagaact tagtgagcct gtgctgggtg    540
acgtgagaga aagtacagcc ttctctcgat ctcttctgcc tgtgaagcca gtggagatag    600
agattgaaac gccagagcag gcgaagacaa gagaaagaag tgaaaagata aaactggagt    660
ttgagacata tcttcggagg gcgatgaaac gtttcaataa aggggtccat gaggacacac    720
acaaggttca ccttctctgc ctgctagcaa atggcttcta tcgaaataac atctgcagcc    780
agccagatct gcatgctatt ggcctgtcca tcatcccagc ccgctttacc agagtgctgc    840
ctcgagatgt ggacacctac tacctctcaa acctggtgaa gtggttcatt ggaacattta    900
cagttaatgc agaactttca gccagtgaac aagataacct gcagactaca ttggaaagga    960
gatttgctat ttactctgct cgagatgatg aggaattggt ccatatattc ttactgattc   1020
tccgggctct gcagctcttg acccggctgg tattgtctct acagccaatt cctctgaagt   1080
cagcaacagc aaagggaaag aaaccttcca aggaaagatt gactgcggat ccaggaggct   1140
cctcagaaac ttccagccaa gttctagaaa accacaccaa accaaagacc agcaaaggaa   1200
ccaaacaaga ggaaaccttt gctaagggca cctgcaggcc aagtgccaaa gggaagagga   1260
acaagggagg cagaaagaaa cggagcaagc cctcctccag cgaggaagat gagggcccag   1320
gagacaagca ggagaaggca acccagcgac gtccgcatgg ccgggagcgg cgggtggcct   1380
ccagggtgtc ttataaagag gagagtggga gtgatgaggc tggcagcggc tctgattttg   1440
agctctccag tggagaagcc tctgatccct ctgatgagga ttccgaacct ggccctccaa   1500
agcagaggaa agcccccgct cctcagagga caaaggctgg gtccaagagt gcctccagga   1560
cccatcgtgg gagccatcgt aaggacccaa gcttgccagc ggcatcctca agctcttcaa   1620
gcagtaaaag aggcaagaaa atgtgcagcg atggtgagaa ggcagaaaaa agaagcatag   1680
ctggtataga ccagtggcta gaggtgttct gtgagcagga ggaaaagtgg gtatgtgtag   1740
actgtgtgca cggtgtggtg ggccagcctc tgacctgtta caagtacgcc accaagccca   1800
tgacctatgt ggtgggcatt gacagtgacg gctgggtccg agatgtcaca cagaggtacg   1860
acccagtctg gatgacagtg acccgcaagt gccgggttga tgctgagtgg tgggccgaga   1920
ccttgagacc ataccagagc ccatttatgg acagggagaa gaaagaagac ttggagtttc   1980
aggcaaaaca catggaccag cctttgccca ctgccattgg cttatataag aaccaccctc   2040
tgtatgccct gaagcggcat ctcctgaaat atgaggccat ctatcccgag acagctgcca   2100
tccttgggta ttgtcgtgga gaagcggtct actccaggga ttgtgtgcac actctgcatt   2160
ccagggacac gtggctgaag aaagcaagag tggtgaggct tggagaagta ccctacaaga   2220
tggtgaaagg cttttctaac cgtgctcgga aagcccgact tgctgagccc cagctgcggg   2280
aagaaaatga cctgggcctg tttggctact ggcagacaga ggagtatcag cccccagtgg   2340
ccgtggacgg gaaggtgccc cggaacgagt ttgggaatgt gtacctcttc ctgcccagca   2400
tgatgcctat tggctgtgtc cagctgaacc tgcccaatct acaccgcgtg gcccgcaagc   2460
tggacatcga ctgtgtccag gccatcactg gctttgattt ccatggcggc tactcccatc   2520
ccgtgactga tggatacatc gtctgcgagg aattcaaaga cgtgctcctg actgcctggg   2580
```

```
aaaatgagca ggcagtcatt gaaaggaagg agaaggagaa aaaggagaag cgggctctag   2640

ggaactggaa gttgctggcc aaaggtctgc tcatcaggga gaggctgaag cgtcgctacg   2700

ggcccaagag tgaggcagca gctccccaca cagatgcagg aggtggactc tcttctgatg   2760

aagaggaggg gaccagctct caagcagaag cggccaggat actggctgcc tcctggcctc   2820

aaaaccgaga agatgaagaa aagcagaagc tgaagggtgg gcccaagaag accaaaaggg   2880

aaaagaaagc agcagcttcc cacctgttcc catttgagca gctgtgagct gagcgcccac   2940

tagaggggca cccaccagtt gctgctgccc cactacaggc cccacacctg ccctgggcat   3000

gcccagcccc tggtggtggg ggcttctctg ctgagaaggc aaactgaggc agcatgcacg   3060

gaggcggggt caggggagac gaggccaagc tgaggaggtg ctgcaggtcc cgtctggctc   3120

cagcccttgt cagattcacc cagggtgaag ccttcaaagc tttttgctac caaagcccac   3180

tcaccctttg agctacagaa cactttgcta ggagatactc ttctgcctcc tagacctgtt   3240

ctttccatct ttagaaacat cagtttttgt atggaagcca ccgggagatt tctggatggt   3300

ggtgcatccg tgaatgcgct gatcgtttct tccagttaga gtcttcatct gtccgacaag   3360

ttcactcgcc tcggttgcgg acctaggacc atttctctgc aggccactta ccttcccctg   3420

agtcaggctt actaatgctg ccctcactgc ctctttgcag taggggagag agcagagaag   3480

tacaggtcat ctgctgggat ctagttttcc aagtaacatt ttgtggtgac agaagcctaa   3540

aaaaagctaa aatcaggaaa gaaaaggaaa aatacgaatt gaaaattaag gaaatgttag   3600

taaaatagat gagtgttaaa ctagattgta ttcattacta gataaaatgt ataaagctct   3660

ctgtactaag gagaaatgac ttttataaca ttttgagaaa ataataaagc atttatctaa   3720

aaaaaaaaa                                                           3729
```

<210> SEQ ID NO 38
<211> LENGTH: 6137
<212> TYPE: DNA
<213> ORGANISM: Homo sapiens

<400> SEQUENCE: 38

```
gtcttttgtc cctcggcgga caccgtttgc cagccaaagc tatgtctgcg cgctcaccga     60

cttcataggg tgccgaattc ttttttcccc aggcttgcca tggctagtcg aggggctcgg    120

cagcgcctga agggcagcgg ggccagcagt ggggatacgg ccccggctgc ggacaagctg    180

cgggagctgc tgggcagccg agaggcgggc ggcgcggagc accggaccga gttatctggg    240

aacaaagcag gacaagtctg ggcacctgaa ggatctactg ctttcaagtg tctgctttca    300

gcaaggttat gtgctgctct cctgagcaac atctctgact gtgatgaaac attcaactac    360

tgggagccaa cacactacct catctatggg gaagggtttc agacttggga atattcccca    420

gcatatgcca ttcgctccta tgcttacctg ttgcttcatg cctggccagc tgcatttcat    480

gcaagaattc tacaaactaa taagattctt gtgttttact tttgcgatg tcttctggct    540

tttgtgagct gtatttgtga actttacttt tacaaggctg tgtgcaagaa gtttgggttg    600

cacgtgagtc gaatgatgct agccttcttg gttctcagca ctggcatgtt ttgctcatca    660

tcagcattcc ttcctagtag cttctgtatg tacactacgt tgatagccat gactggatgg    720

tatatggaca agacttccat tgctgtgctg ggagtagcag ctggggctat cttaggctgg    780

ccattcagtg cagctcttgg tttacccatt gcctttgatt tgctggtcat gaaacacagg    840

tggaagagtt tctttcattg gtcgctgatg gccctcatac tatttctggt gcctgtggtg    900
```

```
gtcattgaca gctactatta tgggaagttg gtgattgcac cactcaacat tgttttgtat    960
aatgtcttta ctcctcatgg acctgatctt tatggtacag aaccctggta tttctattta   1020
attaatggat ttctgaattt caatgtagcc tttgctttgg ctctcctagt cctaccactg   1080
acttctctta tggaatacct gctgcagaga tttcatgttc agaatttagg ccacccgtat   1140
tggcttacct tggctccaat gtatatttgg tttataattt tcttcatcca gcctcacaaa   1200
gaggagagat ttcttttccc tgtgtatcca cttatatgtc tctgtggcgc tgtggctctc   1260
tctgcacttc agaaatgtta ccactttgtg tttcaacgat atcgcctgga gcactatact   1320
gtgacatcga attggctggc attaggaact gtcttcctgt ttgggctctt gtcattttct   1380
cgctctgtgg cactgttcag aggatatcac gggccccttg atttgtatcc agaattttac   1440
cgaattgcta cagacccaac catccacact gtcccagaag gcagacctgt gaatgtctgt   1500
gtgggaaaag agtggtatcg atttcccagc agcttccttc ttcctgacaa ttggcagctt   1560
cagttcattc catcagagtt cagaggtcag ttaccaaaac cttttgcaga aggacctctg   1620
gccacccgga ttgttcctac tgacatgaat gaccagaatc tagaagagcc atccagatat   1680
attgatatca gtaaatgcca ttatttagtg gatttggaca ccatgagaga aacaccccgg   1740
gagccaaaat attcatccaa taaagaagaa tggatcagct tggcctatag accattcctt   1800
gatgcttcta gatcttcaaa gctgctgcgg gcattctatg tccccttcct gtcagatcag   1860
tatacagtgt acgtaaacta caccatcctc aaaccccgga aagcaaagca aatcaggaag   1920
aaaagtggag gttagcaaca cacctgtggc cccaaaggac aaccatcttg ttaactattg   1980
attccagtga cctgactccc tgcaagtcat cgcctgtaac atttgtaata aaggtcttct   2040
gacatgaata ctggaatctg ggtgctctgg gctagtcaaa gtctatttca aagtctaatc   2100
aaagtcacat ttgctccctg tgtgtgtctc tgttctgcat gtaaactttt tgcagctagg   2160
cagagaaagg ccctaaagca cagatagata tattgctcca catctcattg tttttcctct   2220
gttcaattat ttactagacc ggagaagagc agaaccaact tacaggaaga attgaaaatc   2280
ctggtactgg atggctgtga taagctgttc tccacactct ggcctggcat ctgagaacta   2340
gcaagcctct cttaggccat atgggcttct ccaccaaagc tgtttggcag ctcctagcag   2400
accttcttat tgaaatcctc atgctgaaaa tgaacacagc ctagttgcca acccacatgt   2460
ccttttcacc tccagcaaga ctaagcttct ttaaagcact tcacaggact aggaccctgt   2520
cctggagcta tctcaggaaa aaggtgacca tttgaggaac tgtgacctaa ttttattata   2580
atgatgcctc taattttcat ttcctttaca accaactgta actataaggt tgtattgctt   2640
ttttgttcag ttttagcatg ctattttttg aattctagac tcctccatgt gaagatatca   2700
acagacaaaa ctacaactgt ataggacata tttggagaaa attctatcaa ttgatacatt   2760
tggatgacat cacattttta agtaatgtaa tctgaggcca ttgctgagga aattaagaat   2820
tttccttttt ttttaaccac ccccagtgaa aaggatcagt gtatatttat agcacctatt   2880
ttttagttct gtctgttgtg aggcacatcc tgcatggggc acttctagtc aaataggcaa   2940
tgataaggac ctaattaaaa tgtgataagt gtatactatt actttaaaag cctttacagt   3000
cagtacttca gtttacaagg cactttcaca gcatctcgtt tgatcctcac agtcacaaca   3060
tgtggtagac aaggcaggtg atttttatcc ccattttaca gataaggaaa caggctgcgg   3120
gtggggagtg aggggaggta aagatagtta gttgcctaag gtcacacagc cagtaagtaa   3180
tagagctggg actggaaccc aggtttcctt actctcatct attgctcctc catattcctc   3240
actcaaccat gaaaacatta cttgaaagga ctgatgaggt taaccagaga cctaactgat   3300
```

```
attgtaactt tctattttaa ggaagaattg tgtctgtatt tgagttcttt ggagcctcca   3360
gtctgcctgt gtgttagacc agcacagcag tgctgtgtga tgcagcctga cctgtggcag   3420
gaaagtagtg cttctgtttg gaagtcatgt tcttttgcag ccacacagga tccaaatatc   3480
agtactattc ctgtagtcaa tctggggtca cattataggt gccttatttc cctaagggta   3540
actgatctga atatctgcaa ataggatgaa tctatttttc agaagttcca tctttcattt   3600
ttcttttttt ttttgagaca gagtctcatt ctgtcgccca tgctggagtg cagtggcgcg   3660
atctcggctc gctgcaacct ctgcctccca ggttgaagca attctcatgc ctcagccacc   3720
cgagtagctg ggattacagg catgcgccat catgcccagc taatttatgt atttttagta   3780
gagttggagt ttcaccatgt tggccaggct ggtcttggac tcctgacctc aggtcatcca   3840
cccgcctcag cctcccaaag tgctggtatt acaggcgtga gccaccgcac ccagccccat   3900
ctttcatttt caaagagaag ggcattctaa taggaactgg tgccaagaga gaagaaaaga   3960
agtgataaca gaagaaatgg ctagttacaa tattaaaaag ctcctctttg agatctcctc   4020
tgcaggaata tcagagacgg agttgaagcg ctggagaggt aataggtcta gacagtacag   4080
aacaataact ggggagtgtg tgaggataga ctgggctccc ccttgcttga aagatctctg   4140
gcatttaatt ctcaattctt gattactatt ttccagtgta aaactagcac atatgatctg   4200
actacaggac agagaatttt aagtgaaaca tttgccttac ttgcagtaat aatgtgctgt   4260
tcttcacagt agctaaggcc ctctatgttt cccagaggta aataagaatc caggaatgga   4320
ggtccatctg tgatgaatgg ctttttttcta atcaaagtag tataatgctg ttttatctgt   4380
tttgtcatct tgtttttttt tttttttaaa aaaacaaaac cttaattata atatagcgca   4440
aagaaaggcc aggactgatg cagggattcc ttggaaatat cagttcctat cacttttaaa   4500
acctgatttt ggatctctct gttctatgta tgtctttagt gagagcacaa tacatggcag   4560
aacgctgtgc caaatgttat aggtaaggaa tatagaaatg aatgtttttt gttgtgaagg   4620
tgttttcatg tgatatttta taaacacatt ttaaaaaatc tccatcactt tttagtatag   4680
gaaggatagc tttgcctggg aaaaacagtt tcaacacacc tgctcagagt agcagttctc   4740
cctcaaaaaa gcagtgttca gcctgcactg actgttctgc ttgccaaaag gaggaagcat   4800
gcaagatact tatttctcca tagattgtgg agtatagagg gatgtgggac tacagattat   4860
tatttttttt ccccgagaca gagtcttgct ctgtcgccca ggttggaaca caatggcacg   4920
acctcagctc actgcaacct ctgtctcccg ggttcaagca attctcctgc ttcagcctcc   4980
tgagtagctg ggattacagg cacacaccac caccgcactc agctaatttt tgtattttta   5040
gtagaggtgg ggttttacca tgttggccag gctggtctta aactcctgac cttgtaatca   5100
tcccgcctcg gcctcctaaa gtgctaggat tacaggcatg agccaccgca cccggcccag   5160
ataattttta atagcctttg atcatggggt gagtgaggga gtaggtatac ttggcaaatg   5220
catggttctc tgatttctag ctctaaagca gccttatctg aatccccaaa tcttgtgatg   5280
ctgagtacca ttactgaacc agtctgcacg gtaggcatct gctaccaaaa tttacctcct   5340
acctggtagg tgtcatctga taagaaagaa gacaggttat tttaattttt tgagataatc   5400
acagaaaatt gcagcccata ctctttatta ccgaattcaa gtttggaaat agaccctttg   5460
ttttaaatca tgatgggtct ttatcccaat catttatctg ggtcattttt ccaactttgg   5520
agttctagga aagaaccttg aaaacctgat atgattctgc agcatgaggt ctacggtgac   5580
catttgggca aagctccagt ggcaatcatt tattgtgttt tgcatttcct gggatttatt   5640
```

```
gaaataagaa ttcactgtga ttatgtagtc ttctggctag tatcaggcag ctctgctttt   5700

aatttggtta attttatttt ctctgaagag ggagaagagg tacaatttaa tcttggcctc   5760

cacaagcata ttaaagctca cgtgttaatc agtgcattct tatgctccta cattaaatgc   5820

cttgggtaaa tggataaatg gacatgtgcc cagctttaat ttttttgca acagaaagat   5880

cagacttccg tatggcatcg ttggatttca gaggctttct ggtgtatctg taaatctgaa   5940

tgttgccttc tgccagtctg tataaccagg tgattcatgc tgcaaatgaa atcaggaagc   6000

agtaaagtgt taaagcaaga gtattgtcca attcacttgt cttcctgatc cttgtacttt   6060

atttcacgtg tcggtgttta cattacatac ttatatttcc tgtgaaagaa agagttaaat   6120

aaattgtagc agtttga                                                  6137
```

<210> SEQ ID NO 39
<211> LENGTH: 3531
<212> TYPE: DNA
<213> ORGANISM: Homo sapiens

<400> SEQUENCE: 39

```
agcggagcgc caggcagcgc ggagcggagg ccaggcccac agccgctccg cctcccggcc     60

cgcagatccc cgacggccgc accgcgggct cctctggccc gcaagaacac gtgcatggcg    120

tcctggggaa ggcgctgagt gcggagtcgc ggcgccgcac gcggcaccat ggccctggag    180

caggcgctgc aggcggcgcg gcagggcgag ctggacgtgc tgaggtcgct gcacgccgca    240

ggcctcctgg ggccctcgct gcgcgacccg ctggacgcgc tgcccgtgca ccacgcggcc    300

cgcgctggga agctgcactg tctgcgcttc ctggtggagg aagccgccct ccccgccgcg    360

gcccgcgccc gcaacggcgc cacaccggcc cacgacgcct ccgccaccgg ccacctcgcc    420

tgcctgcagt ggctgctgtc gcagggcggc tgcagagtgc aggacaaaga caattctggt    480

gccacagtct tgcatctggc tgcccgcttc ggccaccccg aggtggtgaa ctggctcttg    540

catcatggcg gtggggaccc caccgcggcc acagacatgg gcgccctgcc tatccactac    600

gctgccgcca aggagacttt cccctccctg aggcttctcg tcgagcacta ccctgaggga    660

gtgaatgccc aaaccaagaa cggtgccacg cccctgtacc tggcgtgcca ggagggccac    720

ctggaggtga cccagtacct ggtgcaggaa tgcggcgcag acccgcacgc gcgcgcccac    780

gacggcatga ccccgctgca cgccgcggcg cagatgggcc acagcccagt catcgtgtgg    840

ttggtgagct gcaccgacgt gagcctgtcc gagcaggaca aagacggcgc caccgccatg    900

cacttcgcgg cgagccgcgg ccacaccaag gtgctcagct ggctgctgct gcacggcggg    960

gagatctcgg ctgacctgtg gggcgggacc ccgctgcacg acgccgccga gaacggggag   1020

ctagagtgct gccagatcct ggtagtgaac ggcgcggagc tggacgtccg cgaccgcgac   1080

gggtacacgg ccgccgacct gtcggacttc aacggccaca gccactgcac ccgctacctg   1140

cgcacggtgg agaacctgag cgtggagcac cgcgtgcttt cccgggatcc atccgcagag   1200

ctggaggcta agcagccgga ttcaggcatg tcctcaccca ataccacggt gtcggtccag   1260

ccgctgaact ttgacctcag ctcgcctacc agcaccctct ccaactacga ctcctgctcc   1320

tccagccact ccagcatcaa gggccagcac cctccatgtg ggctttccag cgctagagct   1380

gcagacatac agagctacat ggacatgctg aacccggagc tgggcctgcc tcggggcacg   1440

attgggaagc ccacaccccc accaccccca cccagcttcc ccccgccacc cccgccccca   1500

ggcacccaac tgcccccacc cccacctggc tacccagctc ccaagcctcc tgtaggacca   1560

caggcagctg acatctacat gcagaccaag aacaaactcc gccacgtgga gacagaggcc   1620
```

```
ctcaagaagg agctgagctc ctgtgacggc cacgacgggc tgcggaggca ggactccagc   1680

cgcaagcccc gcgccttcag caagcagccc agcacggggg actactaccg gcagctgggc   1740

cgctgccccg gcgagacgct ggccgcacgc ccgggcatgg cgcacagcga ggaggtgcgt   1800

gcccgccagc ccgcgcgcgc cggctgcccg cgcctcggcc ctgccgcccg cggctcactc   1860

gaaggcccct ccgctccccc gcaggcggcg ctgcttcctg ggaaccatgt tcctaacggc   1920

tgcgccgcgg accccaaggc gtccagggag ctgccaccgc cgcccccacc gccgccgccg   1980

cccctgccgg aggccgcgag ttcgccaccg ccggccccgc ctctgcccct cgagagcgct   2040

ggccctggct gcgggcagcg ccgctcctcc tcgtccaccg gcagcaccaa gtctttcaac   2100

atgatgtccc cgacgggcga caactcggag ctactggctg agattaaggc aggcaagagc   2160

ctgaagccga cgccccagag caaggggctg accacagtgt tctcaggcat cgggcagccg   2220

gccttccagc ccgattcgcc gctgccttct gtgtcacctg cactgtcacc agtccggagc   2280

cccacaccgc cagctgcggg gtttcagccg ctgctcaatg gaagcttggt tcccgtgccg   2340

cccactactc ctgcgccggg agtgcagctg gacgtggagg ctctcatccc cacgcacgat   2400

gagcagggcc ggcccatccc cgagtggaag cgccaggtga tggtgcgcaa gatgcagctg   2460

aagatgcagg aggaggagga gcagaggcgg aaggaggagg aggaggaggc ccggctggcc   2520

agcatgcccg cctggaggcg ggacctcctg cggaagaagc tggaagaaga gagggagcag   2580

aagcggaaag aggaggagcg acagaagcag gaggagctgc ggcgggagaa ggaacagtca   2640

gagaagctgc ggacgctggg ctacgatgag agcaagctgg cgccctggca gcgacaggtc   2700

atcctgaaga agggggacat cgctaagtac tagaggccgc agactcctgt ccgcagcctc   2760

gcagctccgt ggggccctcc gccccagccc cagccagcca ggccctggtg gaaaggctgg   2820

gagccgcaca gccctcccct cctgcgctgg aaaccctccc tgacccccac cctggccccc   2880

cgtatcccca gcccttggca acactggagt gcacacgccg ccacggttgc ccagaaaaag   2940

tgcccaagct gctgacgcaa acaacaacaa atgctgctta tttgcatgcc gacttacata   3000

tatttgcatg ttcgttgact atcaaagagt gcagagctct ccccagcccc gtgggtggtg   3060

actttgtttt cctgcggggc tcagcccccct ccaggatgca gccccctccc ccgcaccccg   3120

gaaccggcgt cgctggcgca tcctgggtgg aggcaggccc cgagctcggg gaaggggttt   3180

tcccttcctc tctgacccag atctgcgcgc ggcctagccc gggcctcatt tcttatcccc   3240

gccaagggtt tcctctcagt catttgttta ccagaaacat gaaaactgcc tgtctggccg   3300

ggccgcactt gtggcccccg ggacccacc tctggcccca cctccctcaa gtctgcgccc   3360

cgtccccagc cagacccact cgctgccggg accctttcac tgccccggtg gagtgaatag   3420

aggatgaggg gccctgaccc tgtgtctcca actgctgcac cccatcccga ccctgtctcc   3480

gccacctcgc agccccatta aagcgctctc atctgggctc cggttcactc a            3531
```

<210> SEQ ID NO 40
<211> LENGTH: 2272
<212> TYPE: DNA
<213> ORGANISM: Homo sapiens

<400> SEQUENCE: 40

```
ttgggcggtg gaccgcccct cggccccggg gtaggctgac acgggagggt cctcagctaa     60

agccaaaagc agatcaaagt ggtgggactc gcgtcgcggc cgcggagacg tgaagctctc    120

gaggctcctc ccgctgcggg tcggcgctcg ccctcgctct cctcgccctc cgccccggcc    180
```

```
ccggccccgc gcccgccatg gagaagactg agctgatcca gaaggccaag ctggccgagc    240
aggccgagcg ctacgacgac atggccacct gcatgaaggc agtgaccgag cagggcgccg    300
agctgtccaa cgaggagcgc aacctgctct ccgtggccta caagaacgtg gtcgggggcc    360
gcaggtccgc ctggagggtc atctctagca tcgagcagaa gaccgacacc tccgacaaga    420
agttgcagct gattaaggac tatcgggaga aagtggagtc cgagctgaga tccatctgca    480
ccacggtgct ggaattgttg gataaatatt taatagccaa tgcaactaat ccagagagta    540
aggtcttcta tctgaaaatg aagggtgatt acttccggta ccttgctgaa gttgcgtgtg    600
gtgatgatcg aaaacaaacg atagataatt cccaaggagc ttaccaagag gcatttgata    660
taagcaagaa agagatgcaa cccacacacc caatccgcct ggggcttgct cttaactttt    720
ctgtatttta ctatgagatt cttaataacc cagagcttgc ctgcacgctg gctaaaacgg    780
cttttgatga ggccattgct gaacttgata cactgaatga agactcatac aaagacagca    840
ccctcatcat gcagttgctt agagacaacc taacactttg gacatcagac agtgcaggag    900
aagaatgtga tgcggcagaa ggggctgaaa actaaatcca tacagggtgt catccttctt    960
tccttcaaga aaccttttta cacatctcca ttccttattc cacttggatt tcctatagca   1020
aagaaaccca ttcatgtgta tggaatcaac tgtttatagt cttttcacac tgcagctttg   1080
ggaaaacttc attccttgat ttgtgtttgt cttggccttc ctggtgtgca gtactgctgt   1140
agaaaagtat taatagcttc atttcatata aacataagta actcccaaac acttatgtag   1200
aggactaaaa atgtatctgg tatttaagta atctgaacca gttctgcaag tgactgtgtt   1260
ttgtattact gtgaaaataa gaaaatgtag ttaattacaa tttaaagagt attccacata   1320
acttcttaat ttctacattc cctcccttac tcttcggggg tttcctttca gtaagcaact   1380
tttccatgct cttaatgtat tcctttttag taggaatccg gaagtattag attgaatgga   1440
aaagcacttg ccatctctgt ctaggggtca caaattgaaa tggctcctgt atcacatacg   1500
gaggtcttgt gtatctgtgg caacagggag tttccttatt cactctttat ttgctgctgt   1560
ttaagttgcc aacctcccct cccaataaaa attcacttac acctcctgcc tttgtagttc   1620
tggtattcac tttactatgt gatagaagta gcatgttgct gccagaatac aagcattgct   1680
tttggcaaat taaagtgcat gtcatttctt aatacactag aaaggggaaa taaattaaag   1740
tacacaagtc caagtctaaa actttagtac ttttccatgc agatttgtgc acatgtgaga   1800
gggtgtccag tttgtctagt gattgttatt tagagagttg gaccactatt gtgtgttgct   1860
aatcattgac tgtagtccca aaaaagcctt gtgaaaatgt tatgccctat gtaacagcag   1920
agtaacataa aataaaagta cattttataa accatttact atggctttgt aacaattgca   1980
tacccatatt ttaagggaca ggtgaattta ctactttcta aagtttattg atacttccct   2040
tttatgtaaa atgtagtagt gatacctata tttccacatt gtgcattgtg acacacttgt   2100
ctagggatgc ctggaagtgt ataaaattgg actgcatttc ttagagtgtt ttactataga   2160
tcagtctcat gggccatctc ttcctcagat gtaaatgata tctggttaag tgttatatgg   2220
aataaagtgg acattttaaa actagcaaag ttaaaaaaaa aaaaaaaaaa aa           2272
```

<210> SEQ ID NO 41
<211> LENGTH: 4510
<212> TYPE: DNA
<213> ORGANISM: Homo sapiens

<400> SEQUENCE: 41

```
gcagaggggg cggagagcgc ccccgggggc ggggcacgca agtgacggcg gcgcgggtgg     60
```

```
tggagcgctg ggcggccagg ctccctggct ggccggtttg ggcgtctggg ccgtgaaggt    120
gggacctcct gttccgggcc gcaagtttcc ctctccagcc gcccgccgtt cgtagcatgt    180
cccccagaac tcggggagcg caggcaggac aggcttagag aagacgcggt ccccagcgct    240
tgggccacgg acgtcccacc ccgctcctct gtcgctggag aaccgccggg ccgagccact    300
gggagaagca ggccagagcc ttccagggcc tccggcccgt ggacccgagg aggatgagct    360
ggctttttcc cctgaccaag agcgcctcct cctccgcggc tgggtccccc ggtggcctca    420
ccagcctcca gcagcagaag cagcgcctga tcgagtccct ccggaactca cactccagat    480
tgcttcctcc acagtttcct caggaaaaac cagtgatcag tgtttatcca ccaatacgac    540
atcacttaat ggataaacaa ggagtgtatg ttacctctcc attagtaaac aattttacaa    600
tgcactcaga tcttggaaaa attattcaga gtctgttgga tgagttttgg aagaatcctc    660
cagttttagc tcctacttca acagcatttc cttatctata cagtaaccca agtgggatgt    720
ctccttatgc ttctcagggt tttccatttc ttcctccata tcctccacaa gaagcaaaca    780
ggagtatcac ttctttatct gttgctgaca ctgtttcttc ttcaacaaca agtcatacca    840
cagccaagcc tgccgctcct tcatttggtg tcctttcaaa tctgccatta cccattccca    900
cagtggatgc ttcaataccg acaagccaaa atggttttgg gtacaagatg ccagatgtcc    960
ctgatgcatt tccagaactc tcagaactaa gtgtgtcaca actcacagat atgaatgaac   1020
aagaggaggt attactagaa cagtttctga ctttgcctca actaaaacaa attattaccg   1080
acaaagatga cttagtaaaa agtattgagg aactagcaag aaaaaatctc cttttggagc   1140
ccagcttgga agccaaaaga caaactgttt tagataagta tgaattactt acacagatga   1200
agtccacttt cgaaaagaag atgcaaaggc agcatgaact tagtgagagc tgtagtgcaa   1260
gtgcccttca ggcaagattg aaagtagctg cacatgaagc tgaggaagaa tctgataata   1320
ttgcagaaga cttcttggag ggaaagatgg aaatagatga ttttctcagt agcttcatgg   1380
aaaagagaac aatttgccac tgtagaagag ccaaggaaga gaaacttcag caggcgatag   1440
caatgcacag ccaatttcat gctccactat agattttcct ggaaacatga actgccaaga   1500
gaggaatggg acacaaaacc aaacactgtt ttatatttat ggtttgcaaa ctggcatttc   1560
atcagtggct aaattcacag atatcctata tagattgtat acagaactga gactgatttt   1620
gtaccgatta gaatgattgc tatgatcttt gagaaatttt tctgcactat ttgcactgaa   1680
atgtttattt attgttgata aattgtatca tatttaagtt ccactgctgt tcctcttacc   1740
ttgattaaat gcctatgcat gtacttttag ctagttttta atattttata aaacttcatt   1800
taaatttgta tttttaactt gaagttccat ttctttatca aggatggtat ttagattttt   1860
ttcctcttaa ccttttttca aaaactattt tcaactgtga ggaaaccctt atttttcttt   1920
ctttgtggat aaaactttca aaagcaattt aagatattca tagtgttagg aaacaccaaa   1980
cctgcctatg tgccatctca caaaagaaac ttttaatacc tacaataaat caaaagaata   2040
aaccagctgt tcttatatat tgtttcattt ttaaaactaa agatgcattt aagaagcaat   2100
acaagtaaat attttaccta ataggaaaaa aaaaagttgc ctttcattta aaccattcca   2160
acagaaattc ttatgctaat ttaaaacata tatatatctg gtaggtttgt ggttggatag   2220
gttttctaaa ttcctaatgt taaaaacaat ctttatgtta atatacacta aatctataca   2280
caaaaaaagt cagtgaactt ttctgacctt tactgtgagt taccttttcc taagaggaaa   2340
gctatagtaa taagtaaaat ttaattttta ggcaatcctg atttttaatg aatttaattg   2400
```

```
agtgttcttg tatactacat tgagcagttt gcttctatac cgtgtcacaa aattcatgta   2460

tttcttgaga agccctaaaa gctcataaag gaaaatgccg tgaactatgt agctcaggct   2520

tggtaaggtg ccatctaaat tacaaaacaa actaatgcat aattttgctt aaatttcatc   2580

ccagtatgat tgtcttccca acaccagcat atagtataga ttgtctgtct tttttatatt   2640

ttttagttct tcctgtacat gtttttggca ataaagttat aggaagaaca aaattatttt   2700

gttagaatta aaacatgctt aatatttagt ctgtttgtgg agggcaggta ttcacgtgga   2760

ctgagataca atgttggata cagaaaataa ctttcattgt cttcctgaca ctgtgctaag   2820

gacatgctgt taaagcttca aagtgaccag atgaggaagg aataattaat tattactcct   2880

gatttgtaga taactgaggt aagagtgttt caaatttatg atagtctttt gggtattcag   2940

aaacctttcc ttatactgca ctggccacca gagcttaatt ttcccagcag ttacagcaat   3000

gggagataga acagtctcaa tcttttgcca accatcaggt tcctagaaac caggtaggtg   3060

tatcccataa caagggagga gcataccaca gcccctcatt tgattaattc atttgatcta   3120

tctatgttat taagtaccta ctaggaataa ggcattgtgg aaatactata caaagataaa   3180

cattgtttag atgcttatct actttccttt tcaccagaaa aacagaaaaa aaagaaacat   3240

tttcttacag agtaaaaatg ttctacataa tcacatgagt agttcatctc agtgtttttt   3300

attctttaaa gttgaactat cccagtttca ttctatacca ttcattggat aaccttgtta   3360

caacccagtc atgaaacaga gcagtgtgat cagttatctg catttaacaa atagacaaat   3420

cagtttacat aaaggttatg tatgtcaccc acgatgaaaa gaatctgcat ttgaatatgc   3480

ccgtatgaat gtgggttctg tttttgcaac agagattaag tgaccatttt ttctaatttt   3540

atggctatat attttcttca taaaaattgg tcacatcgga gaagcagtgc cacaggaaaa   3600

atgaaatgca tgtgaaagtt tgtattctga ttttacaaga tgagatagaa atcagaatta   3660

aagaggaata cttaggagtt actaggctaa tcagtgtacg aatttgtcat aggtagagat   3720

ttaaaggtta atatcttaaa atagaagaaa attctaaatc aatcaatcag tgagatataa   3780

actaaacaga cccacttcaa agttgaaaga aatttctagg cataaattga gactaggaaa   3840

tttatatcag aatagagggt gcttgacaca tatatatgct taaattgaag gacagctcag   3900

attcattttt aggagaagaa agtaaactaa tgtgctctta aagaataaaa atttattcta   3960

tggtttctgt ctctgatcat caccttccat tctataaaaa gctcagttac tgatttgctg   4020

ggtcatggtc aaaattctta cctatttatt tcatatcaac tttaaaaaat aaattacttg   4080

cattctatat attactaatt gggaagtaat atgcctcaaa tcagttttat actggattat   4140

tccctatgct ttaaaccact gctctcaata aaacacttcc tgattaatgt ttgattatta   4200

gatattttag tcttgttggg gatattttag tcttgttggg ttagccatgc tctgaagaat   4260

ctgtgaaagt acagtaaagt tttaataagc aataaatgta accttttata taaatctcag   4320

tgctaggtta acttctaata agcagacgaa catgttacat aaattataat gtctgtcttg   4380

taaaaaagtt gaggggacta aaagtttatg actctgatat ggaagttgtc atattaaaaa   4440

actacatttt aaaacatcaa atatttatac tatttgcttt tcaaataaaa gcatagtgct   4500

gtttggcata                                                          4510
```

<210> SEQ ID NO 42
<211> LENGTH: 11062
<212> TYPE: DNA
<213> ORGANISM: Homo sapiens

<400> SEQUENCE: 42

```
gcagatcggg agcggtgccg agaaaaattt ccttactaga tgacatttca tcgcaatgtc     60
cgatcgtttg ggcaaatta ccaagggcaa ggatgggaaa agcaagtact cgactctcag    120
cctgtttgat aagtataaag gaaaatcagt agacgcgatt agatcctcag ttattcctag    180
acatggctta cagagtcttg ggaaagttgc tgcagcccgg cgcatgccac cgcctgcaaa    240
cctgccaagc ttgaagtctg aaaacaaagg aaacgacccc aacatcgtga tagtacccaa    300
ggacgggacg ggatgggcaa acaagcagga tcagcaagac ccaaagagtt ccagtgcgac    360
ggcctctcag ccgccggagt cgctgccgca gccgggtttg cagaaatctg tctccaattt    420
gcagaaaccg acacagtcaa tcagtcagga gaatacaaat tcagtgccag gtggaccaaa    480
gtcatgggca cagctgaatg gaaagccagt aggacacgaa ggtggtttaa ggggctcaag    540
ccgactgtta tccttctctc ccgaggaatt tccgacgctg aaagcagctg gagggcagga    600
caaggctggc aaagaaaagg gcgtcttaga tctgtcgtat gggccaggac caagcctccg    660
ccctcagaat gtgacaagct ggagggaggg cggtgggcga cacataattt ctgccacgtc    720
tctgagcacc tccccaactg agctgggcag caggaactcg agtacgggag atggagcccc    780
ctcctcggca tgtaccagcg attctaagga cccctctctc cgcccggctc agcctgtccg    840
aaaaggggct tcacagttca tgggaaatgt ataccaccca cctacatacc atgacatgct    900
tcctgctttt atgtgttcgc cgaagtcatc agaaaaccag ggtacagtgg aacgaggctc    960
ttttcccctt cctcagctcc gccttgaacc tcgagttcct tttagacagt tccagatgaa   1020
tgaccaagac ggaaaagaaa acaggctggg attgtctcgc ccactccgcc cactaaggca   1080
gctggtggag cgggcaccac ggcccaccat tatcaatgcg gaaaacctga agggccttga   1140
cgatctggac gccgatgccg atgatggctg ggcaggcctc catgaagaag tggactattc   1200
tgagaaactg aagttcagtg atgatgaaga ggaggaagaa gttgtgaagg acggcaggcc   1260
aaagtggaac agttgggacc ctaggaggca gcggcagttg tcaatgagct ctgcagacag   1320
tgcggacgct aagcggactc gagaggaagg gaaggactgg gctgaagcag tgggtgcgtc   1380
ccgtgtggtc cgaaaggcgc cagaccctca gccaccgccc aggaagcttc atggctgggc   1440
accaggccct gactaccaga agtcatcaat gggcagcatg ttccggcaac agtccatcga   1500
ggacaaggag gacaagcccc caccaaggca gaagttcatt cagtcagaga tgtccgaggc   1560
ggtggagcga gcccgaaagc gccgggaaga agaggagcgc cgagcccggg aggagaggct   1620
ggccgcctgt gctgccaaac tcaagcagct ggaccagaag tgtaagcagg cacgaaaggc   1680
aggtgaggcc cggaagcagg cagagaagga agtgccctgg tctccaagtg ctgagaaggc   1740
atctccccag gaaaacggcc ctgctgtcca caaaggctcc ccagaattcc ctgcccaaga   1800
gacccccacc acattcccag aagaggcacc cacagtgtcc ccagcagtgg cacagagcaa   1860
cagcagtgag gaagaggcca gagaggctgg gtcccctgca caggagttca agtatcagaa   1920
gtcccttcct ccccgattcc agcgccagca gcagcaacaa cagcaggagc agctgtacaa   1980
gatgcagcac tggcagccgg tgtacccccc gccgtcccac ccccagcgca cctttaccc    2040
acaccacccc cagatgttgg gcttcgatcc caggtggatg atgatgcctt cctacatgga   2100
cccacgtatc acgcccactc ggaccccggt ggacttctac ccctccgccc tgcatccctc   2160
aggactgatg aagcccatga tgccccagga gtccctcaat gggacaggct gtcgctctga   2220
ggatcagaac tgtgtgcccc cactccaaga aagaaaagtg acccccatcg actcaccccc   2280
tgtgtggagc ccagagggct acatggcact gcagagcaag ggctacccgc tcccgcaccc   2340
```

```
gaagtcgagt gacaccttgg ctatggacat gcgtgtcagg aatgaaagct ctttctctgc   2400
ctcactcgga agggcagggg gcgtaagtgc tcagcgcgat ctctttgagg agagagggga   2460
ggagtacttg agtgcttttg acaagaaggc ccaagcagac tttgacagct gtatctcttc   2520
tcaaagaata ggccaggagc ttttgtttcc accccaagaa aatgttcagg atgcaggtgc   2580
tcctgggggt cacacccaaa acctcaggtg ttccccattg gagcctgact ttgtcccaga   2640
tgagaaaaag ccagagtgtg gcagttggga tgttagccac cagccagaga ccgctgacac   2700
agcccatggt gttgagcggg agacaccccg ggaggggacg gcctttaaca tctcctcctg   2760
ggacaagaac gggagcccca acaaacagcc atcctcggag cctgaatgga ctcccgagcc   2820
ccggagctcc agcagccagc acccggagca gacgggcagg acccggaggt cgggacccat   2880
caagaaacca gtcctgaaag ccctcaaggt ggaagacaag gagaaggagc ttgagaagat   2940
taagcaggag ctaggggagg agagtacccg gctggccaag gagaaggagc agagccccac   3000
ggcagaaaag gatgaggacg aagagaacga tgcctctctg gccaactcct ccaccaccac   3060
tttggaggac aaaggccctg gccatgccac ttttggccgc gaggccacca aatttgaaga   3120
ggaggagaaa cctgacaagg cctgggaagc cagaccccca cgagagtcca gcgatgttcc   3180
ccccatgaag agaaataact ggatctttat tgatgaggag caagcctttg ggggtcagagg   3240
acaggcccgg ggccggggcc gtggtttcag agagttcact tttcgtggtc ggcctgctgg   3300
cggaaatggg agcggcctct gtggtggggg ggtcctgggg gcccgcagca tctactgcag   3360
cagtcagcgc agcggccgtg gccggggcct gcgagagttt gcgcggccag aggactgccc   3420
cagagccaag ccccgacgga gagttgccag tgagacccat agcgagggct cagagtatga   3480
agaacttccc aagcgccgcc ggcagagggg ctccgagaac gggaatgaag gctcgctcct   3540
ggagagggag gagagcacct tgaagaaggg cgactgcaga gattcttggc ggtccaacaa   3600
ggggtgctct gaggaccaca gcggtctaga tgccaagagc cgaggccctc gggcctttgg   3660
gcgagccctc cctccccggc tgagcaattg cgggtatgga cggagaacct tcgtctccaa   3720
agagtcaccc cactggcaga gcaaaagtcc aggcagctct tggcaggaat atggcccttc   3780
cgacacatgc ggatcccggc gacctacaga cagagactat gtcccagatt cctacagaca   3840
ccctgacgca tttggtggcc ggggctttga ggacagccgc gcggaggaca agagatcctt   3900
cttccaagat gaacacgtgg cagattctga aaatgcagag aaccggccct tcaggagaag   3960
gcgcccccca cgccaagata agccccctcg attccggcgc ctccggcaag agcgggagtc   4020
cctgggcctg tggggacccg aggaggagcc ccacctgctg gcaggtcagt ggccaggcag   4080
gcccaaactg tgttctgggg acaagagtgg cactgtgggc cgcaggtccc ctgagctctc   4140
ctaccagaac tcctccgatc acgccaatga ggagtgggag acggcctccg aaagcagcga   4200
cttcagcgag cggcgggagc ggcgggaagg ccctgggtcc gagcccgact cccaggtgga   4260
tggtggcctg tcgggggcta gtttgggtga gaagaaggag ctggccaaga ggagcttctc   4320
cagtcagaga cccgtggttg acagacagag ccgaaagctg gagccgggag ggtttgggga   4380
gaagcccgtt aggccaggtg gtggtgacac ctcccctcgc tatgagagcc aacagaatgg   4440
gacgcctttg aaagtgaaaa gatccccaga cgaggccttg cctggaggtc ttagtggctg   4500
cagcagtggg agtggccact ccccctatgc cctggagcgg gcagcccatg ccagtgctga   4560
ccttcccgaa gcctccagta aaaaggcaga gaaggaggcc aagttggctg ctccgagggc   4620
aggtgaacag ggagaggcca tgaaacagtt tgacctgaac tatggaagtg ccatcattga   4680
aaattgcggg tccagccccg gggaggagag tgaggtgggt tctatggtgg gcgaaggctt   4740
```

```
catcgaagtc ctgaccaaga agcagcgccg cctgctggag gaagagagaa gaaagaagga   4800
gcaggccgtg caggtgcctg tcaaaggtcg aggcctttcc tcccgtattc ctcctcgatt   4860
tgcaaaaaag cagaacaact tatgtctgga gcaaggtgac gtgaccgtgc ctggcagcag   4920
cctgggcact gagatctggg agagcagcag ccaggctctc cctgtgcagg ccccagccaa   4980
cgactcctgg aggaaagctg tcactgcctt cagcagcacc gagactggct ctgcggagca   5040
gggttttaag agcagccagg gagatagtgg cgttgacttg agtgccgagt ctcgggagtc   5100
gtctgcgacc tcctcgcagc gcagctcccc atatgggact ctgaagccag aggagatgag   5160
cgggcccggc ctggcggaac ccaaggccga cagccacaag gagcaggctc caaagccatc   5220
tgagcagaag gattcagaac aaggctctgg acagagcaag gagcacagac caggacccat   5280
cggcaacgag cgttctctga aaaacagaaa gggctcggag ggggccgagc ggctgcaagg   5340
ggctgtcgtc ccgcctgtta acggggtgga gattcacgtg gactccgtgc tgcctgtgcc   5400
acccattgaa tttggagtca gtccaaaaga ctccgatttc agcttgccac ctggttctgc   5460
ctctggtcct actgggagtc cagttgttaa acttcaggat gccttggcca gtaatgcagg   5520
gttaacacag agtatcccca tcctgcggcg ggaccatcac atccagaggg ccatcggtct   5580
ctccccaatg tccttcccca ccgccgacct tactctgaag atggagtctg cgcgcaaggc   5640
ttgggaaaac tcccccagtt tgccggagca gagctctcca ggcggcgctg gctcaggcat   5700
ccagcctcca tcctctgtgg gtgcctccag cggggtcaac tacagctcct tcggtggagt   5760
gtccatgcca cccatgcctg tggcctctgt agcaccttct gcttctatgc caggcagcca   5820
cctcccgccc ctgtacctgg atggccatgt gtttgcaagt cagccccggc tggttcctca   5880
aacgatacct cagcagcaga gttaccaaca ggccgccgct gcccagcaga tcccgatctc   5940
ccttcacaca tctctgcagg cacaagctca gcttggactg aggggtgggc ttcctgtgtc   6000
ccagtcccag gagatcttca gctccttgca gcccttcaga tctcaggtgt acatgcaccc   6060
cagcctgtca ccgcccagca ccatgatcct ctctgggggc acagccttga agcctccata   6120
ctcggcgttc ccaggcatgc agcccttgga gatggtgaag ccgcagtctg gctcacccta   6180
ccagcccatg agcgggaacc aagccctggt ctacgagggc cagctcagcc aggctgctgg   6240
cctgggtgcc tcccagatgt tggactccca gctcccacag ctgaccatgc cactgcctcg   6300
gtacggctcc gggcagcagc cactgatcct gccccagtct attcagctgc cacctgggca   6360
gagcctctcc gttggggccc cccgaaggat tcctccgccc gggtcccagc cgccagtcct   6420
gaacaccagc agagagccct ctcagatgga gatgaaaggc ttccactttg ccgacagtaa   6480
acagaatgtc ccttcaggag gccccgtgcc atcgccacag acctacaggc ctagctctgc   6540
tagccccagt gggaagccct ctggatcagc agttaacatg ggctctgtgc agggacacta   6600
cgtgcaacag gcaaaacaac gagtggatga gaaacccagc ctgggagccg tgaagctgca   6660
ggaggccccc tcggctgcct cccagatgaa gcgaaccgga gcgatcaagc ctcgggctgt   6720
caaagtggag gagagtaagg cctgacagtg cctggctgcc acctcgcctc tccctactga   6780
ggacggtgcc gccatgcggc ctcgacacag ccgacactcg ggagcctcac cagatccacc   6840
gtccaaatgc gtggcccaga ctgagagacc tccctcctct ccactcccga aagctccgtt   6900
gtcaaccagc ttgcacccgt ggatatatgg cattgacccg cttgctttga tacgaaacaa   6960
aaaagcagac gactccttca tcccatctgc tcctaccgtg actgtggagt gacgcctcct   7020
gtgcagtgca gatttgccct ccctgcctcc tccctgtcct gccgcgcagc cagggcgcct   7080
```

```
tctcagcagt gcttccggcc cagccgccca tccctaggca cagtgatttg gcagcagggt   7140
cattttactt tgaggctttt tgttttaaaa tgtagccaag gtttttacaa aggggaaagg   7200
aaaagaaaac aaaaacgcaa gctccatgtg tatagctgaa cttttatatg tttcttgcca   7260
gcccctccgc tcccttccat ctctagcctc tgtcctgttt agtttgatac gtcactgcag   7320
taccttaaga ggtgactctt aagaatgcat cccctcctga ttcctcagct ggttcaccct   7380
tgaggttatt tgcaaaaaga aaaggaggtt cttgagggca ccgattgcga gcattctggt   7440
gcctggctcc ccgcctggga agcgatgggg tgctcagagc agcaggcagg ttgggggagg   7500
gggggggtca tagttgggtt ccagctcctg gcttgatgag cccagggcgc ttacaggcag   7560
cccatgaagt tgatgacagt tttagcatga gaatcacaca gggtccctgt cctgggctcc   7620
tctaaagcca gtggatgtgc tggcaccag agacaaatca tggagatggc tgctggtggc   7680
tcccaggttg gcccagatgg ggtgagctga cataccacag gcccatccca ggccccgtgg   7740
gctctgcttc tggggctcca taccctgccc tgcaggggtg ctgtgttttt cacacatttc   7800
tttccctgaa gccttctgta acctgtcatt ttccttcctt cctcttccgg agcctgctgc   7860
tttctctgga cctgtctcca cctcccacac agctcatcgt gaacaccact tggtgatgga   7920
gggagtggac ccgtgtgtgg tccccaagtg aggccactgg gagtttgtcc ttttcctcct   7980
ttgcttcact cccagcagca gacccaggtt gtcaggacag gagggcctga gctaagcagt   8040
aggcatcagt ctcgtttgtc ttcagacggc gggggcaggt ccagggtgag gctgggtgga   8100
gggctgacca aggtccaaag ggcctgcgca gcctccggga gggcagcttc tccagccaga   8160
ggcttgtgtg agccatcgtg tgctgggctt gtttttaagt aagaaacaag gaaatcactc   8220
cagattctgt cattccaagg aaagggaagg ggacagttca ggtttctcag ctgttcttag   8280
gggtcactga gcgtctacct cctcctccag aggaggctgg ctcagaacac ctagaggagg   8340
gggccgggga tgcacccccc accagaggct gccttcagcg tctcacgggt gcaggacagc   8400
gctcaggctt gggctctaag ctctgtgtct agtgtagaac atggggaagg agcatcttag   8460
gaactgctga agtaacttct tactgctctc acaattctaa ggaagcggga gaacggcctc   8520
ctaccaacag cgcccacccc agagctgcct gggaaagggc agttttactg aaaggtgctt   8580
tactgttcac ctgcatcttt cagcagctcc cctcctgccc tcacctggtc ttttccctct   8640
ttatcccaag cctttatgct tgagtccctt ccccaggggc tgcccacccg acagttccag   8700
gcattcccta cctgagcttc ttgtctgctt ttccttctcc cactgcaagc ggctgcttgt   8760
ggggcctggg atgagccctc tctgtcccca ccggccctcc ttgccaagcc attcctgggt   8820
gagttcaggc ctgcgggagc cacacattca tctccacctg gacacttgag ccgcatggcc   8880
agacccctcc cacctgatgc ggtggtgcgt gtgatttgtc aaaagaaagc cttctggatg   8940
ctgttaagat gtacccttca ggtgaacctg gtatcagacc cacagtactt gctgtttgag   9000
aaaaaataaa aacaaaaagg tcacctgttc tccagccctt ttctcttacc tggtatttcc   9060
ttcctttctc ctcccccacc ccaaataaaa aaacaaaaaa cactagaatt tatttatatg   9120
tattgatgtt gtaggtctag gtgaaaaaaa aagaagtaaa tgtttcactg ctctatttat   9180
atataatgtc tgaattaatt ctgtgcagga aaggccagga aattgcatgt gaagttcggt   9240
gcagtcacca cctgtgtgtg acctgagctg cagtctcttc gctgagatgc aggttttaaa   9300
tgagacttgg ggggctgagg gcaggcctca ggcctcccag cgccccaacc cctccttggt   9360
ctaatgaaat gcagttctta gtgcagagat gttttaaggt gcaatatatc tcttcctttc   9420
ccgtggtttt agagccaagc tcaaggtagt aggacgtagg gtcttatttt gttttcaaac   9480
```

```
ccccatcctc agagcgcaga tacatgcaga ggcttctgcc aggataccac ggggccttag   9540
tgggaacagg tggagaccag cacttccctt tcctgctgct gaggtaggga ttggggggtc   9600
agaacccact cacttttgcc tgttaaagtt gccctcctga cgctggcagc tctgccttgg   9660
tcactgggga tgcggctcgt tgctcagcca ccagtggcct tgcggtattg tccaccatcc   9720
actagagtgg gatgaagtcc agagtgtggg tatacatctc agatgcccat ctacccactg   9780
gggacttcaa tgccagctgc atttggtttg gttttcttaa ctgttggctt ctccccacag   9840
cgttttttgt tttttttaa acattcatat tgttttcaaa cttggaattc atagacactc   9900
tggctctagg ttccttaagg gggaaaacaa aagatgactt tatttcacat tcaagaaaat   9960
cagttcagtt ccaaagctgt ggtccttcca gccacttcta gggacactgg ggaaccttgt  10020
taaacgttga catcagtgct ctccagccgt gctgtcaccc tcctatcttc tggatctgcc  10080
ttcgcgatgg tcagtgacag cttctggaag ctgagcacac acaggtgcac agccatgctg  10140
tggtctggcc tgctacggca gcatggcagc tctggtggag ccttctccct tgccatttgg  10200
ttcccctgtg ccaagtagct gcaggctgcc cctcaaatct tcatttgtcc cttttcactt  10260
cctgcagaac aagcctgggt tagagggtct gctggaaatg gcctttgaag accaaggata  10320
ccaggatgtg tgcactctgt cgtgttctgt gatgaatggg aaacgtaggc ttccagaaag  10380
ccagctctct tctgaaatgt gacggaccta agcaggaagt catccaggac aggagtggct  10440
cagtgttggg gatggacgct gtcgcccagc catgctccac cagggccacc aatgtgtagt  10500
tggctggtgg tcttcgggca tgtgagacct gctcttcact gtttccaccc cacttggtgg  10560
cctccaggat ggtagtggca ccctcagagc cccatcttca gcatgttctg aagcctcaga  10620
gtggaaattc ctgctaaggc tctgtgtgga cgcctttctc ccgtgatcta aaggggacac  10680
tgtactcaag cttttgacct catgccttgt gtagtaaaaa aggatttggg ggttttgttt  10740
ggttcctgag agggttgtgt tttgtttttg tttcctttg tttatgtttt ggcctttcct  10800
ctttgtcttt ccatgtagac cagatatttg aaagggcaga cgatggctag aggtgtaatg  10860
tgcagcttgt ttatacggta ttttgggaaa cttaccttgg atgggaaatc gaatcgtgga  10920
ttcaccaggc cggtgctggc acactcaccc tcgccctttc cctccggttc agtacctatt  10980
gtttctcctt tcaaatatgt gattgtacta gctctttcca tatgaaagaa ttctccttat  11040
ttaaataaaa aaagtttaaa aa                                            11062
```

<210> SEQ ID NO 43
<211> LENGTH: 7689
<212> TYPE: DNA
<213> ORGANISM: Homo sapiens

<400> SEQUENCE: 43

```
tcccacagtg cctggcccag aagccttgct aaatatttga acaggattgc ccaatacttt     60
tctgctgtga gaatgtaaga tggatccaga agagcaggag ctcttaaatg attacagata    120
cagaagctac tcttcagtga ttgaaaaggc tttgagaaat tttgagtcct cgagtgaatg    180
ggcggatctc atatcttcac ttggcaaact caacaaggct cttcagagta acctgaggta    240
ctccttgttg ccaagacggc tcctcatcag caaaagatta gctcagtgtt tgcaccctgc    300
cctgcccagt ggtgtccact taaaagctct ggaaacctac gagattatct ttaaaatcgt    360
ggggaccaaa tggctggcca aggacttgtt tctgtacagc tgcgggttat ttcctctcct    420
ggcacacgcg gcggtgtcgg tgaggccggt gctgctcacc ctgtacgaga agtacttcct    480
```

```
cccactgcag aagctgctcc tgcccagtct gcaggccttc atcgtgggcc tgctgcccgg    540
ccttgaagag ggctccgaga tctccgacag aacggatgct ctgctcctga gactgtcgct    600
ggtggttggc aaagaggtgt tttacaccgc cctctggggg agcgtcctgg ccagcccgtc    660
catccgcctc cctgcctcag tcttcgtggt gggccacatc aacagggatg cccccggccg    720
ggagcagaag tacatgctgg ggaccaatca ccaactcacg gtgaagtctt tgcgtgcctc    780
cctgttggac tcaaatgttc ttgtgcaaag aaataatctg gaaatcgttc tgtttttctt    840
cccattttat acctgtctgg attccaatga gagagccatc cccctcctca gatctgacat    900
cgtgcgcatt ctctcagccg ccacccagac cctactgaga agggacatgt ccctgaacag    960
aagactgtat gcatggttac taggctcaga cataaaagga aataccgttg tgccagaatc   1020
tgaaatctca aattcttatg aagaccagtc gtcttatttt tttgaaaaat actccaagga   1080
tcttttagtt gagggtttgg ctgagatatt gcatcagaag ttcatagatg ctgacgtgga   1140
ggaacgccat catgcatacc tgaagccttt tcgcgtcctc atcagtctgc ttgacaagcc   1200
agaaataggg cctcaagtgg ttgggaattt gtttctcgaa gtcatcaggg cctttttattc   1260
ttactgcaga gatgcccttg gctctgatct taaacttagc tacacccaga gtggaaattc   1320
gctgataagt gcaatcaagg aaaacagaaa tgcctctgag attgtcaaaa cggtaaattt   1380
gctgataact tctctaagca cagactttct ctgggattat atgacaaggt gttttgagga   1440
atgctttaga ccagtgaagc agcgttacag cgtgaggaac agcgtcagcc ctccccccac   1500
ggtctcggag ctctgcgccc tcctggtctt cctgctggat gtcattcctt tggaacttta   1560
ctctgaggtg caaacccagt atctccctca ggtgctcggc tgcctggtgc agcctcttgc   1620
tgaggacatg gaggccttaa gtttacctga actcacgcat gccttgaaga cgtgtttcaa   1680
ggtgctcagc aaagtccaga tgcctccttc ctacctcgac acggagtcca ccagcggaac   1740
ctcgagtcca gtaaaaggtg aaaacggcaa aataattttg gaaacaaagg cagtgattcc   1800
cggtgacgaa gatgcttcgt ttccccctct gaagtctgag gacagtggga tcgggctcag   1860
tgcctcgtca ccggagctct ctgagcactt gagggttcct cgagtttctc tggaaaggga   1920
cgacgtttgg aagaagggcg ggagcatgca gaggacgttt ctttgcatcc aagagctaat   1980
cgccaacttt gccagcaaga acatttttgg agtacagctg acagcgtcag gagaagaaag   2040
caagtccgag gagcctgcag ggaagaggga cagggatggg acgcagagcc tggcagccaa   2100
tgattccagc aggaagaact cttgggagcc caagcccatc actgtgcctc agttcaagca   2160
gatgctgtca gacttgttca cagcacgagg gtctccattc aagacaaaaa gttcagagtc   2220
accatcgtct tcgcccagca gccctgccag gaaaaacggg ggagaatggg atgttgagaa   2280
ggtggtcatt gacctggggg gttccaggga ggaacgcagg gaggcctttg ccgccgcctg   2340
ccacctgctg ctggattgtg ccactttccc tgtctacctg tccgaggaag agaccgagca   2400
gctctgtgca acgctcttcc agctgccagg agccggtgat tccagttttc catcttggct   2460
gaagtccctc atgactattt gctgctgtgt gactgactgc tacctccaga acgtggccat   2520
ttccactctg ctggaagtga taaaccattc ccagtccctg gcgcttgtca ttgaagacaa   2580
gatgaaacgc tataagagct ctggacacaa cccttttttt ggcaagctgc agatggtgac   2640
ggttcctccc attgctccag ggatattgaa agtcattgca gagaaaacag atttctatca   2700
gagggtggct cgtgtgcttt ggaatcagct gaacaaagag acccgggagc atcacgtcac   2760
ctgcgtagaa ttgttctacc ggctgcactg cctggcccct acggccaaca tctgcgagga   2820
catcatctgc catgccctcc tggaccctga caagggaaca aggctggaag ctctgtttag   2880
```

```
attttccgtg atctggcatc tgacaagaga gatccaaggc agtcgagtaa catctcacaa   2940
tcgctccttt gataggtcct tgtttgtcgt gctggacagc ctggcctgca cggatggtgc   3000
catcggtgcg gcagcccagg gctggctggt gcgtgcgctc tccctcgggg acgtggctcg   3060
catcctcgaa cccgtgctcc tgctgctgct gcagccaaaa acccagagaa cctccatcca   3120
ctgcctcaag caggagaact cggccgatga cttgcaccgt tggtttaaca ggaagaaaac   3180
ctctttcaga gaggcatgcg cagtgcccga gcctcaggag agcggctctg aagagcacct   3240
gcctctgagc cagttcacca cagtggaccg tgaagccatt tgggccgaag tggagaagga   3300
gcccgagaag tacccgctgc gaggcgagct gagcgaggaa gagctgccct actacgtgga   3360
gcttccagac aggacggccc acggcgcccc ggacagcagc gagcacaccg agtctgcaga   3420
tacaagctcc tgccacacgg acagcgagaa cacgtcctcc ttctcctccc cttcccacga   3480
cctgcaggag ctgagcaacg aagagaactg ctgtgcaccc atccccatgg ggggcagggc   3540
gtaccccaag cgctcggccc tgctggcggc cttccagtca gaaagcttca aggctggggc   3600
caagttaagc ctggtgcggg tggactcgga caagacgcag gcttctgagt cgttctccag   3660
cgacgaggag gcggacttgg agctccaggc cctcaccaca tccaggctgc taaagcagca   3720
gcgggaaagg caggaggccg tcgaggcctt gttcaagcac atcctgctct acctgcagcc   3780
ctacgactct cggcgggtcc tctatgcctt ctcggtgctg gaggctgtgc tcaaaaccaa   3840
ccctaaggaa ttcatcgagg ctgtgtccag gactagcatg gataccagct ccaccgcgca   3900
cctcaacctc atctccaacc tcctcgctcg ccaccaggag gccctcattg gccagagttt   3960
ctacggaaag ctccagaccc aggtccccaa cgtgtgcccc cactctctgc tcctggagct   4020
gctcacctac ctctgcctga gcttcctgcg ctcctactac ccttgctatt tgaaggtctc   4080
gcaccgagac attctcggca accgggacgt gcaggtcaaa agtgtcgagg ttttgatcag   4140
gataatgatg cagctggtct cagtggccaa gtcttcggaa gggaagaacg tggagttcat   4200
ccacagcttg ctgcagaggt gcaaagttca ggagtttgtc ctgctctccc tgtcggcgtc   4260
catgtacacg agccagaagc gctacgggct ggccaccgcc caccacggca gggccctgcc   4320
agaggacagc ctctttgagg agagtctcat taacttgggt caggaccaga tctggagtga   4380
gcacccgctg cagattgagc tgctgaagct gctgcaggtg ctgattgtct tggaacacca   4440
cctgggtcgg gcccatgagg aggcggaaaa ccagcccgac ctgtcccggg agtggcagag   4500
agccctgaac ttccagcagg ccatcagcgc cctgcagtac gtgcagcccc acccccctcac  4560
ctcccagggt cttctggtct ctgcggtggt gaggggtctg cagcccgcct acggttacgg   4620
catgcatccg gcctgggtga gcttggtcac gcattccttg ccctacttcg gaaagtccct   4680
gggctggacg gtgacaccct ttgttgtcca gatttgcaaa aacttggatg acttggtcaa   4740
gcagtatgaa agcgaatctg tgaagctctc tgtcagcaca acctccaaga gggaaaacat   4800
ttctccagat tatccactca cccttctaga aggtctaacg accattagtc atttttgtct   4860
tttggaacaa gccaaccaaa acaaaaagac catggctgca ggtgatcctg ccaacttgag   4920
gaatgccaga aatgccattt tggaagagct gcctcgaact gttaacacca tggccccttct  4980
ctggaatgtt ctcagaaagg aggagactca aaagagacct gtcgatctcc taggggccac   5040
gaagggatcc tcttccgttt actttaaaac caccaaaacc ataagacaaa aaattttaga   5100
cttcttaaac cccttgacgg cccatcttgg ggttcagttg acagcggctg ttgcggcagt   5160
gtggagcaga aagaaagccc agcgtcacag taagatgaag attatcccaa cggcaagtgc   5220
```

```
atcccagcta acccttgtcg acttggtgtg tgcactcagc accctgcaga ctgacacgct   5280
gctgcacctg gtgaaggagg tggtgaagag gccaccccaa gtcaaagggg gtgatgagaa   5340
atcgccccta gtggacattc ctgtgttgca gttttgctat gcttttctcc aaaggctccc   5400
agtaccagcc ttgcaagaga acttttcttc actgttggga gtattgaaag agtctgtaca   5460
gttgaatcta gccccacctg ggtattttct gcttctcagc atgctgaatg actttgtaac   5520
aagaactccc aacctggaaa acaagaagga ccaaaaagac ctgcaggaaa tcactcagaa   5580
aatcctagaa gctgtgggga acattgccgg ctcttccttg gagcaaacca gctggctaag   5640
cagaaacctg gaagtgaagg cccaacctca ggcctctcta gaagaatctg atgctgagga   5700
ggacctgtat gatgctgctg cagcttcagc aatggtgtct tcatccgccc cgtcggtgta   5760
cagcgtgcaa gccctctctc tcctggcaga ggtactggct tccctcctgg acatggttta   5820
tcgaagtgat gagaaggaga aagctgtgcc gttaatctcc cgtctgcttt actatgtttt   5880
tccatactta cgcaaccaca gtgcctacaa tgctcccagc ttccgggctg gcgctcagct   5940
gctgagctcc ctgagtggct atgcctacac aaagcgagcc tggaggaagg aggtcctgga   6000
gctgtttctc gaccccgctt tctttcagat ggatacttcc tgtgttcatt ggaagtccat   6060
tattgaccat cttttgactc atgagaaaac aatgtttaag gatttaatga acatgcagag   6120
cagttctttg aaactattct caagttttga acagaaagcc atgctgttaa agcgccaggc   6180
ttttgctgtc ttcagtggag aacttgatca ataccacctt taccttccac tgatacaaga   6240
acgcctgaca gacaatctca gagttggaca gacatccata gttgctgctc agatgtttct   6300
tttttcaga gttttgctgc taagaatatc tcctcaacat ttgacttcat tgtggccaat   6360
aatggtctct gaattgattc agacattcac acagcttgaa gaagatctaa aagatgaaga   6420
tgagtcattg agaagcacca acaaagtaaa cagaacgaaa gtttcagtcc cggatgcaaa   6480
tggaccctca gtgggggaga taccccagag tgaactcatc ttgtatttat cagcttgcaa   6540
attcttggac acagcgcttt cttttccacc tgacaagatg ccattatttc aaatttatag   6600
gtgggcattt attccagaag tggacacaga gggccctgcc ttcctgtcgg atgtagagga   6660
gaatcaccaa gaatgcaaac cccacactgt caggattcta gaacttctaa aattaaagtt   6720
tggggaaatc agtagctctg atgagatcac catgaagagt gaattcccgc ttctgcgcca   6780
acattctgtt tccagcatca ggcagttgat gccattcttc atgactctaa atggtgcatt   6840
taagacccag agacagctgc ctgctgatag cccaggaact ccattcttgg actttcctgt   6900
cacagatagc ccaaggatct taaaacaact ggaagaatgc atcgaatatg attttctgga   6960
acatccagaa tgttaaccat gtgagagaga atatgtttaa tccatgtatt ggtactttac   7020
tgaaaaccag gttatattct aaagaagaaa gaaggcagga tagtgctttt gaacaagcct   7080
atttccattt tgaaagtaga tttcaggcta ggtgcggtgg ctcacacctg taatctcagc   7140
actttgggag gccaaggcag gcagatcact tgaggtcagg agttcgagac cagcctgacc   7200
aacatggtga gaccctgtct ctactaaaaa tacaaaaatt agctgggtgt ggtggcggcg   7260
cctgtaatcc cagctacttg ggaggctaag gcatgagaat tgcttgaacc caggaggtgg   7320
aggctgcagt gagccgagat cacgacactg cactccagct gtgtgacaga atgagaccat   7380
ctccaaaaaa aaaaaaaagt agatttcaga taatttactg ttcagcaaca ggacacacct   7440
ccctaaatgc cttgtaatat atttgaatct gattctgcat ttcttcctca atttatgtaa   7500
tgaaaataaa attaatatat catctaacag tagcacaaaa tttgtaatat gaagtaaagt   7560
atgaagataa tgaagaagtt gttttctttg ttgaagcagt tatatgggtc tttctcagta   7620
```

tatttctctt ttctctaaaa gtttaaactt attaaaagaa tgttattttt aacctttcaa 7680
aaaaaaaaa 7689

<210> SEQ ID NO 44
<211> LENGTH: 1138
<212> TYPE: DNA
<213> ORGANISM: Homo sapiens

<400> SEQUENCE: 44
gctctggccg gccccggcga ttggtcaccg cccgctaggg gacagccctg gcctcctctg 60
attggcaagc gctggccacc tccccacacc ccttgcgaac gctcccctag tggagaaaag 120
gagtagctat tagccaattc ggcagggccc gctttttaga agcttgattt cctttgaaga 180
tgaaagacta gcggaagctc tgcctctttc cccagtgggc gagggaactc ggggcgattg 240
gctgggaact gtatccaccc aaatgtcacc gatttcttcc tatgcaggaa atgagcagac 300
ccatcaataa gaaatttctc agcctggccg aaaatggttg gccccacgaa gccacgacaa 360
ctggaggcaa agagggttgc tcaacgcccc gcctcattgg aaaaccaaat cagatctggg 420
acctatatag cgtggcggag gcggggcgat gattgtcgcg ctcgcaccca ctgcagctgc 480
gcacagtcgc atttctttcc ccgcccctga gaccctgcag caccatctgt catggcggct 540
gggctgtttg gtttgagcgc tcgccgtctt ttggcggcag cggcgacgcg agggctcccg 600
gccgcccgcg tccgctggga atctagcttc tccaggactg tggtcgcccc gtccgctgtg 660
gcgggaaagc ggcccccaga accgaccaca ccgtggcaag aggacccaga acccgaggac 720
gaaaacttgt atgagaagaa cccagactcc catggttatg acaaggaccc cgttttggac 780
gtctggaaca tgcgacttgt cttcttcttt ggcgtctcca tcatcctggt ccttggcagc 840
acctttgtgg cctatctgcc tgactacagg tgcacagggt gtccaagagc gtgggatggg 900
atgaaagagt ggtcccgccg cgaagctgag aggcttgtga aataccgaga ggccaatggc 960
cttcccatca tggaatccaa ctgcttcgac cccagcaaga tccagctgcc agaggatgag 1020
tgaccagttg ctaagtgggg ctcaagaagc accgccttcc ccacccccctg cctgccattc 1080 tgacctcttc tcagagcacc taattaaagg ggctgaaagt ctgaaaaaaa aaaaaaaa 1138

<210> SEQ ID NO 45
<211> LENGTH: 1377
<212> TYPE: DNA
<213> ORGANISM: Homo sapiens

<400> SEQUENCE: 45
atgctaaaac taatcgtccc aacaattata ttactaccac tgacatgact ttccaaaaaa 60
cacataattt gaatcaacac aaccacccac agcctaatta ttagcatcat ccctctacta 120
ttttttaacc aaatcaacaa caacctattt agctgttccc caaccttttc ctccgacccc 180
ctaacaaccc ccctcctaat actaactacc tgactcctac ccctcacaat catggcaagc 240
caacgccact tatccagtga accactatca cgaaaaaaac tctacctctc tatactaatc 300
tccctacaaa tctccttaat tataacattc acagccacag aactaatcat attttatatc 360
ttcttcgaaa ccacacttat ccccaccttg gctatcatca cccgatgagg caaccagcca 420
gaacgcctga acgcaggcac atacttccta ttctacaccc tagtaggctc ccttccccta 480
ctcatcgcac taatttacac tcacaacacc ctaggctcac taaacattct actactcact 540
ctcactgccc aagaactatc aaactcctga gccaacaact taatatgact agcttacaca 600
atagctttta tagtaaagat acctctttac ggactccact tatgactccc taaagcccat 660
gtcgaagccc ccatcgctgg gtcaatagta cttgccgcag tactcttaaa actaggcggc 720
tatggtataa tacgcctcac actcattctc aaccccctga caaaacacat agcctacccc 780
ttccttgtac tatccctatg aggcataatt ataacaagct ccatctgcct acgacaaaca 840
gacctaaaat cgctcattgc atactcttca atcagccaca tagccctcgt agtaacagcc 900
attctcatcc aaaccccctg aagcttcacc ggcgcagtca ttctcataat cgcccacggg 960
cttacatcct cattactatt ctgcctagca aactcaaact acgaacgcac tcacagtcgc 1020
atcataatcc tctctcaagg acttcaaact tactcccact aatagctttt tgatgacttc 1080
tagcaagcct cgctaacctc gccttacccc ccactattaa cctactggga gaactctctg 1140
tgctagtaac cacgttctcc tgatcaaata tcactctcct acttacagga ctcaacatac 1200
tagtcacagc cctatactcc ctctacatat ttaccacaac acaatggggc tcactcaccc 1260
accacattaa caacataaaa ccctcattca cacgagaaaa caccctcatg ttcatacacc 1320
tatcccccat tctcctccta tccctcaacc ccgacatcat taccgggttt tcctctt 1377

<210> SEQ ID NO 46
<211> LENGTH: 1779
<212> TYPE: DNA
<213> ORGANISM: Homo sapiens

<400> SEQUENCE: 46
cggcgtgccc tggggcggcg cgggcgcagg ggcgcgtgcg cggcgggctg tcgttggctg 60
gagcagcggc tgcgcgggtc gcggtgctgt gaggtctgcg ggcgctggca aatccggccc 120
aggatgtaga gctggcagtg cctgacggcg cgtctgacgc ggagttgggt ggggtagaga 180
gtagggggcg gtagtcgggg gtggtgggag aaggaggagg cggcgaatca cttataaatg 240
gcgccgaagc aggacccgaa gcctaaattc caggaggttg ggatgaatgg gttccggaga 300
gcagagtact caaatacgtg gacaccaatt tgcagaaaca gcgagaactt caaaaagcca 360
atcaggagca gtatgcagag gggaagatga gaggggctgc cccaggaaag aagacatctg 420
gtctgcaaca gaaaaatgtt gaagtgaaaa cgaaaaagaa caaacagaaa acacctggaa 480
atggagatgg tggcagtacc agtgagaccc ctcagcctcc tcggaagaaa agggcccggg 540
tagatcctac tgttgaaaat gaggaaacat tcatgaacag agttgaagtt aaagtaaaga 600
ttcctgaaga gctaaaaccg tggcttgttg atgactggga cttaattacc aggcaaaaac 660
agctctttta tcttcctgcc aagaagaatg tggattccat tcttgaggat tatgcaaatt 720
acaagaaatc tcgtggaaac acagataata aggagtatgc ggttaatgaa gttgtggcag 780
ggataaaaga atacttcaac gtaatgttgg gtacccagct actctataaa tttgagagac 840
cacagtatgc tgaaattctt gcagatcatc ccgatgcacc catgtcccag gtgtatggag 900
cgccacatct cctgagatta tttgtacgaa ttggagcaat gttggcttat acacctctgg 960
atgagaagag ccttgcttta ttactcaatt atcttcacga tttcctaaag tacctggcaa 1020
agaattctgc aactttgttc agtgccagcg attatgaagt ggctcctcct gagtaccatc 1080
ggaaagctgt gtgagaggca ctctcactca cttatgtttg gatctccgta aacacatttt 1140
tgttcttagt ctatctcttg tacaaacgat gtgctttgaa gatgttagtg tataacaatt 1200
gatgtttgtt ttctgtttga ttttaaacag agaaaaaata aaagggggta atagctcctt 1260
ttttcttctt tctttttttt tttcatttca aaattgctgc cagtgttttc aatgatggac 1320
aacagaggga tatgctgtag agtgttttat tgcctagttg acaaagctgc ttttgaatgc 1380
tggtggttct attcctttga cactacgcac ttttataata catgttaatg ctatatgaca 1440
aaatgctctg attcctagtg ccaaaggttc aattcagtgt atataactga acacactcat 1500
ccatttgtgc ttttgttttt ttttatggtg cttaaagtaa agagcccatc ctttgcaagt 1560
catccatgtt gttacttagg cattttatct tggctcaaat tgttgaagaa tggtggcttg 1620
tttcatggtt tttgtatttg tgtctaatgc acgttttaac atgatagacg caatgcattg 1680
tgtagctagt tttctggaaa agtcaatctt ttaggaattg tttttcagat cttcaataaa 1740
ttttttcttt aaatttcaaa gaacaaaaaa aaaaaaaaa 1779

<210> SEQ ID NO 47
<211> LENGTH: 7827
<212> TYPE: DNA
<213> ORGANISM: Homo sapiens

<400> SEQUENCE: 47
gtagtcttga cgtgagctag ctggcatggc ggcctgcatt gcagcggggc actgggctgc 60
aatgggccta ggccggagtt tccaagccgc caggactctg ctccccccgc cggcctctat 120
cgcctgcagg gtccacgcgg ggcctgtccg gcagcagagc actgggcctt ccgagcccgg 180
tgcgttccaa ccgccgccga aaccggtcat cgtggacaag caccgccccg tggaaccgga 240
acgcaggttc ttgagtcctg aattcattcc tcgaagggga agaacagatc ctctgaaatt 300
tcaaatagaa agaaaagata tgttagaaag gagaaaagta ctccacattc cagagttcta 360
tgttggaagt attcttcgtg ttactacagc tgacccatat gccagtggaa aaatcagcca 420
gtttctgggg atttgcattc agagatcagg aagaggactt ggagctactt tcatccttag 480
gaatgttatc gaaggacaag gtgtcgagat ttgctttgaa ctttataatc ctcgggtcca 540
ggagattcag gtggtcaaat tagagaaacg gctggatgat agcttgctat acttacgaga 600
tgcccttcct gaatatagca cttttgatgt gaatatgaag ccagtagtac aagagcctaa 660
ccaaaaagtt cctgttaatg agctgaaagt aaaaatgaag cctaagccct ggtctaaacg 720
ctgggaacgt ccaaatttta atattaaagg aatcagattt gatctttgtt taactgaaca 780
gcaaatgaaa gaagctcaga agtggaatca gccatggctt gaatttgata tgatgaggga 840
atatgatact tcaaaaattg aagctgcaat atggaaggaa attgaagcgt cgaaaaggtc 900
ttgattctga gaatgaattt ggttagttgc agaagataca ttggctctaa gaggatatat 960
tttgagacca atttaatttc atttataaga acatagtaat taagtgaact aagcattcat 1020
tgttttatta atactttttt tctaaaataa aacttgtaca ccagtttatt actctaaaaa 1080
gagaattaca catgccaaat ggaccaatgt ccatttgctt attggaggca aagctacaat 1140
agaagtcaga gcatcaccag aatggtcttt aatgagcatg gaacctgagc aaagggaata 1200
ggtgggatga atttttttttt taattgtgaa acaattcata agcacaatat gatttacaga 1260
ataataaaca ttcatgtacc cactatcagg ttaagaaata gaacatttat taatatgtag 1320
gaatgttaag aaataaaaca tttaataaga tctcagaaga ctccagtaaa tctgcaattg 1380
tatctctctc ctttttaaat gtaaatatca tcttgacttg ttaattattc ccttgcattt 1440
cttttagttt actgccaaca catatattct tcaacaatat atttaatttt gaaaaacctg 1500
aaaaaaaaaa cctgttagca agtataaagg ggcagtatta ctattattgc atgaaggctt 1560
caagggaaac gttacagtct ttgggtcata gtctggcttc agcttcctct gagagtttac 1620
agaggccaat tttgagcaaa ttcatggcta aggttatgag tgagttctgc taaacagaag 1680

```
gctcaccaca aggtatctgg caggattata ctgggtagct ggatgttgca gaaatgtggt   1740
tagaggaagt aaactgtttt ttgatgctca cagcatgatg aatcaaactc tgtatcttag   1800
gattaggtta aaacaatacc tttggtatga tatgagtgtt gttgctgatc catgcagcat   1860
ggattggaaa gctggggtat aagcacacat gctaaagaaa aacatgtaat ttggtccata   1920
ctcacctgga tatactgttc ctcaggttaa aaaatacagt actatcctaa atcttgaagg   1980
caactctcag cctatccatt gagttacctt cagatctgcc ctctggttcc tagctgtctt   2040
gggactaact tctttcctgc gctcagctgt tttctggatt ccatgttttc cattttattg   2100
agtactaact tgttttgctg cagcacatcc tttggtagct tctagaggaa gtttgtgtgg   2160
aggtaaaatt tttgagacct tgcatgtctc atgtttgatt gatactttat acgtttaggt   2220
aggaggtaat tttccttcag gactttaaaa atattgttgc tccattttct ttgtttctat   2280
tgttgtattg agaaatccaa tgccattttg atttccccat cataaatttc atgatgatgt   2340
gtcttggtgt gggtctatat ttatccattg tattgggttt taggtgaacc cttccagata   2400
gtaactcatt tctgtcagtt ctgggaaaca cttagcattg gttgatgatt tattctctgc   2460
tgctttgttc tcccaactat tatttggatg ttggatatcc agcactgggt atctattttc   2520
ttacctccct cccttgaccc cagtctctgt tttttagctc tttagctcaa tcttccaact   2580
ctttgctatt gtattttaaa atcttaagac cccttcttga tttgtagaag ttccttttct   2640
tacaaccaaa aagcctttat ctatggattt gttcacagat aaggggtatt caatatagtg   2700
tatttttttt tcatttaaaa ttgtttgcgc atctatttcc tccaaatttc tttctgtatt   2760
tattttttgt tgtctatatt tcagactttt ccaggatatc tgataatctt tggctgtctt   2820
cttatggttg aaagagggac taaaaagctt ggaaagcctt tgggttgtgg gaaggggctg   2880
tctttaggat tatctgaatg ggcttttttg ggagtcccct cctccacatg aatattttgg   2940
ttttgtcaga ttccctagaa tagaggcttc caatctcctt cctggagggg tctgtccagg   3000
aaggagattg tctaggggtc tgtcagacag cagctttcag ctacttcctt gatctttttc   3060
actaatgatt atatagtcat ctaactactg tcaacaagta atagatatcc tatccttcac   3120
ttgtttagat tatttgctga gataacctct caaaagaacc tctcaaaata aaaggttaac   3180
aagagcctat atcttatatt tttcttctct ttatcttgtt agaagatagc tattaaaacc   3240
tgttcttttt ctgtcttgat aaacacactt caatcttggt agaatggtag atgggacagt   3300
atattttagg acctaaagct ctgcaaatgt atgatcagct tgtaagtaca ggtgctcaaa   3360
aacatgtaaa caatcatgct ttttactctg taggaatatc tttaaaattc ttgtgaattt   3420
ttccccagaa gtaaagcaaa tcttccccca gaaataaaat taaatgtgca taatctaaag   3480
cttttttttt ttattgtggt aggatatata tataaaacat aatttgccat tgtaaacatt   3540
ttaaatttac aagtcagagg cattaattac atcacaatgt tgtgaaatta ttactactat   3600
ttccaaaatt ttctcatcac cccaaactga aactctgtaa ctgttgagca ataacctcat   3660
tcctgtatct ctcccaaccc caggtaacct caaatctttc tttttatctt tgagacaagg   3720
tctcattcta tcactcaggt aggagtgcag tggtgtgatc atagctcatt gcagcctcaa   3780
aatcctgggc tcaagcaatc ctccttgagt agctaagact ataggcacac attaactgcg   3840
cctggctgat tttgtttttt gtagagatgt ggtcttgcta tgtttcccat gctggtcttg   3900
agttcctggc ctcaagcagt ccttaagatt catccatgtt gtggcatgtg tcagaatttc   3960
atttgttttt atgactaaat aatattccat tgtatgtata tacattttgt tcatccatct   4020
tctgatgaac actgggatat gtctaccttt tggctattgt gaataatgct gcagtaaaca   4080
```

```
ttgacataac aagtatgtat ttgattgcct gtttctaagt tcttttgggt atacatcttg   4140
agtagaattg ctagataatg tcatgtttta tttctcttgt gatttcttct tcgatcccct   4200
ggttgagtgt gttaatttct acatgtttat gaatttccca ctgttttttt gttattgatt   4260
tccaagttca ttccattgtg attagagaag atacttagta tgattttaat gtttttgaga   4320
attggtgtgt ggcctgatag atggtctgtc ctggagaatg ttcctcatac acttgagcaa   4380
aatatttatc atgctattgt tgactgtagt tttctatatg tctcttaggt caaggtggtt   4440
tacaatgtgt taaggttctc tttttttaaa aaaatttttg cacagagtat ctttttctat   4500
gtgttccatg tatttgtgtc tttggagcta tagtctcttg tagacagcat atcactatct   4560
tgttttgttt tgtttttct gtccattctg ccaatttctg ccttttgatt ggaaaattta   4620
atccatttgc atttaaagta attaaggaag gactttcttc taccatttaa cacttcttct   4680
atatgtcata tactttttg gcccctcatt tcctctttat ggccttcttt tctgtttttt   4740
tgtagtgaac tagtctgatt ctctttccac tccccttgt gtatatttgt tagatgtttt   4800
atttgtggtt gctatgggga ttatagttaa catcctacac ttaaaacaat ctaatttaaa   4860
ctgataccaa tttaccttca atagcataca aaatctctac tcctgtaaag ctctgcccct   4920
gcccccctta tgttattgat ggcacaaatt gcctaataaa taatttatag ttatttgtat   4980
gagtttgtct tttaaatcat ttaggaaata aaaagtggag ttagaaaaca gtatgatagt   5040
aatactgact tttatatttg tcaatatatt tatcttattt tggatcctta tttcattata   5100
tagatttgag ttactgtcta gtgcccttcc atttcggccc aaaggattcc cttatgcatt   5160
tcttgcaggg caagtctaat tgtaataaac tccctcagct tttgttttat ctgagaatgt   5220
cttgatttct ccttatttt tgatggataa ttttgccaga tacatgaatt tttggtaaca   5280
gtatttttct ttcagcactt taaatatgtc atcccactac cttctgactt catggtttct   5340
catgagatat tagatgttat aaaatttgag gattcctcat tcttgatgag tcagttctgt   5400
cttattgctt ttcggatttg ctcagctttt gtcttttgac agtttgatta taacgcggct   5460
cagtgtgggt ctctgagttt atcccactta gagtttgttg agtttcttgg agtcatagat   5520
ttatgtcttt tatcaaattt tggacatatt tggctattat ttcttcaatt tttttcactg   5580
cttctttctt ttccttctga aatattctta atgtatatgt tggtctgttt gatgctgtct   5640
caccagtttc ttaggctgtg ttctcttttg ttcctcagac ttgattattg cagttgccct   5700
tctttttatt tttttcaagt ttgttgattc ttctccctgt tcagatcaac tgttgaactc   5760
ctctagtgaa tttatttcag ttactgtact tttcagctcc aagatttatc tttggttcct   5820
ttttataacg tctgtgtctt tattgatatt ctcattttgt tcatatgtct ctttcttcct   5880
ttagttcttt gtccatgttt tcctttagct ctttgggctt atttaagaca attgtttaaa   5940
gtctttgcat agtaagtcca atgtctgtgt ttcttcaggg atggttttca ttattttgtt   6000
ttcaatgagc catactttcc tgtgtctttg tatgctgtct ttttgttgtt gaaaactgta   6060
tgtttgaaca tcataacgtg gtggccctga aaatcagata ttccccctt cctgagagtt   6120
agttttattt ttattattga agattgtagc agtctattgc tacatgtgca gtcatttcca   6180
aactattttt gcaaagactg tattccttct gtgtgtcatc actgaagtct ctgttcctta   6240
gtttgtgttt aatagtttga catagatttc cttgaaagga gttaaaacta gcagaaaaat   6300
ctctctccca gtctttccag tctttgtaga ttggttctgt gctgggcttt tccattaata   6360
cttagccagg cttgtactga gcctaacaat caggcccaaa agcgtagggt ctttgcagat   6420
```

```
cttgtctgag catgcttctt gctgtgtatg cacgtagttt tctaaatctc cctgtatgtg   6480
ctgttgaata ttctaatttc ccaaagaaac tcctttgcag ctttttctca cagaacatag   6540
atggtttttt ggatatcttg accatagtct ttcgacccag gtgtttgcgg ttgttagttc   6600
accttacact tttttcaagc attgcctact gcttacgatg agtgctctgt caatccttta   6660
agtagcccca gacaggctac cagagactta aacaagaatt tgtaagttct gctcagcttc   6720
ctctagaaat ggggatcagg gtccaagaca gaatgcagtt gctgatttca agactgctgc   6780
aacaccaggg agcttgtggg ggaagggcaa gcagaaatgt cacaaagctt tcttgccatt   6840
ttaaagttgc ctgttcttga ctcagcattt gcttcattgc tataaacttt ttactgtttt   6900
tcagagttct gataaaattg gctatgcctg ttcctgcttt aaaaaatata tatatatttt   6960
ttagggattg gggtctcact atactgacca ggctggtctt gaacttctgg cctcaagcca   7020
tcctctcatt tcagcttccc aaagtgctgc aattacacgc gtgaaccacc acacccagcc   7080
cctgcttgtt tttcaatgtg cctactccac catgttgctc aagtatgtat attttctaaa   7140
ctaccttgta gtgttgtgat gggaaataaa tccctgagcc ttttgaataa ctcagagaga   7200
tcaaaaactt agtttatcct attcgaagga ttagaaaaat gatatatctt tcactttttc   7260
agggataggc tcctcattag aaggctccta tgtgccgatg ctgtacaaga catttcattt   7320
ctcttaatgt ttacaacaag cttgttgcca aggctgatct tgaactcctg gcctcaaacg   7380
atcctcccag ctcagtctca caaagtgttg ggatgtctgg ccaactaatg actatcttaa   7440
ctcttgtgtt tcaatgttta tgccttcttt tatcttgact gattgtatga ctatgtcttc   7500
tagaacaatg ttgaacagaa atggtgagag cagacatcct tgctttaata tttcaccatt   7560
atatatgatg ttaggtatag atttttctca cagatgcctt ttatcagatt gaggaattta   7620
tattcctact ttgccgaaag gtttttgtag tatgaggggg tgctgaattt tgtcaaacac   7680
tttttcggta ataattgaga tgattggttc tgcagtcatc gagatgtgga ttttctcctt   7740
tattctgttc gtgagtgatt acactggttg actaatgtta aaacaacctt actttccagg   7800
aataaaccct attatctttt ttataca                                      7827
```

<210> SEQ ID NO 48
<211> LENGTH: 1821
<212> TYPE: DNA
<213> ORGANISM: Homo sapiens

<400> SEQUENCE: 48

```
tgcgggtacg gacagcgcat gagcttatgt tgagggcgga gcccagacca gcccttcgtc     60
ctatcctgcc cttccagcac ctctcagccg taacttaaac tacacttccc agaagcctcc    120
tcagccaggg acttccgttg tcgtcagcgg aagcggtgac agatcatccc aggccacaca    180
gaggccggct tggtcactat ggaggagata ggcatcttgg tggagaaggc tcaggatgag    240
atcccagcac tgtccgtgtc ccggccccag accggcctgt ccttcctggg ccctgagcct    300
gaggacctgg aggacctgta cagccgctac aaggaggagg tgaagcgaat ccaaagcatc    360
ccgctggtca tcggacaatt tctggaggct gtggatcaga atacagccat cgtgggctct    420
accacaggct ccaactatta tgtgcgcatc ctgagcacca tcgatcggga gctgctcaag    480
cccaacgcct cagtggccct ccacaagcac agcaatgcac tggtggacgt gctgcccccc    540
gaagccgaca gcagcatcat gatgctcacc tcagaccaga agccagatgt gatgtacgcg    600
gacatcggag gcatggacat ccagaagcag gaggtgcggg aggccgtgga gctcccgctc    660
acgcatttcg agctctacaa gcagatcggc atcgatcccc cccgaggcgt cctcatgtat    720
```

```
ggcccacctg gctgtgggaa gaccatgttg gcaaaggcgg tggcacatca cacaacagct    780

gcattcatcc gggtcgtggg ctcggagttt gtacagaagt atctgggtga gggcccccgc    840

atggtccggg atgtgttccg cctggccaag gagaatgcac ctgccatcat cttcatagac    900

gagattgatg ccatcgccac caagagattc gatgctcaga caggggccga cagggaggtt    960

cagaggatcc tgctggagct gctgaatcag atggatggat ttgatcagaa tgtcaatgtc   1020

aaggtaatca tggccacaaa cagagcagac accctggatc cggccctgct acggccagga   1080

cggctggacc gtaaaattga atttccactt cctgaccgcc gccagaagag attgattttc   1140

tccactatca ctagcaagat gaacctctct gaggaggttg acttggaaga ctatgtggcc   1200

cggccagata agatttcagg agctgatatt aactccatct gtcaggagag tggaatgttg   1260

gctgtccgtg aaaaccgcta cattgtcctg gccaaggact tcgagaaagc atacaagact   1320

gtcatcaaga aggacgagca ggagcatgag ttttacaagt gacccttccc ttccctccac   1380

cacaccactc aggggctggg gcttctctcg cacccccagc acctctgtcc caaaacctca   1440

ttcccttttt tctttaccca ggattggttt cttcaataaa tagataagat cgaatccatt   1500

taatttcttc ttagaagttt aactcctttg gagaatgtgg gccttgaata ggatcctctg   1560

ggtccctctt aatctgacag atgagcagac gaggtgcatg gcctgggttg cagcttgaga   1620

gaaccaaaat attcaaacca gatgacttcc aaaatgtggg gaaagggatg gaaaatgaac   1680

ctgagatgga gtccttaatc acgggataaa gccctgtgca tctccctcat ttcctacagg   1740

taaaagacag taaagaaatt caggtcacag gccttgggag ttcataggaa ggagatgtcc   1800

agtgctgtcc agtagaactt t                                             1821
```

<210> SEQ ID NO 49
<211> LENGTH: 5159
<212> TYPE: DNA
<213> ORGANISM: Homo sapiens

<400> SEQUENCE: 49

```
ggtcccggaa gtgcgccagt cgtaccttcg cggccgcaac tcgctcggcc gccgccatct     60

tgcgagctcg tcgtactgac cgagcgggga ggctgtcttg aggcggcacc gctcaccgac    120

accgaggcgg actggcagcc ctgagcgtcg cagtcatgcc ggccggaccc gtgcaggcgg    180

tgcccccgcc gccgcccgtg cccacggagc ccaaacagcc cacagaagaa gaagcatctt    240

caaaggagga ttctgcacct tctaagccag ttgtggggat tatttaccct cctccagagg    300

tcagaaatat tgttgacaag actgccagct ttgtggccag aaacgggcct gaatttgaag    360

ctaggatccg acagaacgag atcaacaacc ccaagttcaa ctttctgaac cccaatgacc    420

cttaccatgc ctactaccgc cacaaggtca gcgagttcaa ggaagggaag gctcaggagc    480

cgtccgccgc catccccaag gtcatgcagc agcagcagca gaccacccag cagcagctgc    540

cccagaaggt ccaagcccaa gtaatccaag agaccatcgt gcccaaagag cctcctcctg    600

agtttgagtt cattgctgat cctccctcta tctcagcctt cgacttggat gtggtgaagc    660

tgacggctca gtttgtggcc aggaatgggc gccagtttct gacccagctg atgcagaaag    720

agcagcgcaa ctaccagttt gactttctcc gcccacagca cagcctcttc aactacttca    780

cgaagctagt ggaacagtac accaagatct tgattccacc caaaggttta ttttcaaagc    840

tcaagaaaga ggctgaaaac ccccgagaag ttttggatca ggtgtgttac cgagtggaat    900

gggccaaatt ccaggaacgt gagaggaaga aggaagaaga ggagaaggag aaggagcggg    960
```

-continued

```
tggcctatgc tcagatcgac tggcatgatt ttgtggtggt ggaaacagtg gacttccaac   1020
ccaatgagca agggaacttc cctcccccca ccacgccaga ggagctgggg gcccgaatcc   1080
tcattcagga gcgctatgaa aagtttgggg agagtgagga agttgagatg gaggtcgagt   1140
ctgatgagga ggatgacaaa caggagaagg cggaggagcc tccttcccag ctggaccagg   1200
acacccaagt acaagatatg gatgagggtt cagatgatga agaagaaggg cagaaagtgc   1260
ccccaccccc agagacaccc atgcctccac ctctgccccc aactccagac caagtcattg   1320
tccgcaagga ttatgatccc aaagcctcca agcccttgcc tccagcccct gctccagatg   1380
agtatcttgt gtcccccatt actggggaga agatccccgc cagcaaaatg caggaacaca   1440
tgcgcattgg acttcttgac cctcgctggc tggagcagcg ggatcgctcc atccgtgaga   1500
agcagagcga tgatgaggtg tacgcaccag gtctggatat tgagagcagc ttgaagcagt   1560
tggctgagcg gcgtactgac atcttcggtg tagaggaaac agccattggt aagaagatcg   1620
gtgaggagga gatccagaag ccagaggaaa aggtgacctg ggatggccac tcaggcagca   1680
tggcccggac ccagcaggct gcccaggcca acatcaccct ccaggagcag attgaggcca   1740
ttcacaaggc caaaggcctg gtgccagagg atgacactaa agagaagatt ggccccagca   1800
agcccaatga aatccctcaa cagccaccgc caccatcttc agccaccaac atccccagct   1860
cggctccacc catcacttca gtgccccgac cacccacaat gccacctcca gttcgtacta   1920
cagttgtctc cgcagtaccc gtcatgcccc ggcccccaat ggcatctgtg gtccggctgc   1980
ccccaggctc agtgatcgcc cccatgccgc ccatcatcca cgcgcccaga atcaacgtgg   2040
tgcccatgcc tccctcggcc cctcctatta tggccccccg cccacccccc atgattgtgc   2100
caacagcctt tgtgcctgct ccacctgtgg cacctgtccc agctccagcc ccaatgcccc   2160
ctgtgcatcc cccacctccc atggaagatg agcccacctc caaaaaactg aagacagagg   2220
acagcctcat gccagaggag gagttcctgc gcagaaacaa gggtccagtg tccatcaaag   2280
tccaggtgcc caacatgcag gataagacgg aatggaaact gaatgggcag gtgctggtct   2340
tcaccctccc actcacggac caggtctctg tcattaaggt gaagattcat gaagccacag   2400
gcatgcctgc agggaaacag aagctacagt atgagggtat cttcatcaaa gattccaact   2460
cactggctta ctacaacatg gccaatggcg cagtcatcca cctggccctc aaggagagag   2520
gcgggaggaa gaagtagaca agaggaacct gctgtcaagt ccctgccatt ttgcctctcc   2580
tgtctcccac cccctgcccc agacccagga gcccccctga ggctttgcct tgcctgcata   2640
tttgtttcgc tcttactcag tttgggaatt caaattgtcc tgcagaggtt cattcccctg   2700
accctttccc cacattggta agagtagctg ggttttctaa gccactctct ggaatctctt   2760
tgtgttaggg tctcgatttg aggacattca tttcttcagc agcccattag caactgagag   2820
cccagggatg tcctacagga tagtttcata gtgacaggtg gcacttggct aatagaatat   2880
ggctgatatt gtcattaatc attttgtacc ttgacatggg ttgtctaata aaactcggac   2940
ccttcttgtg aaatcagtta aataagactt gtctcggtca cctgtgccct gtccagactc   3000
gaggcagtgg taacactgca cagtgctatg tggcttctct ttgaggattt ttgggttttg   3060
taactaaatt cttgctgccc tcatactttt tatgtattag aatcatattc gtattgccct   3120
tttaaaacat tgggatcctc caaaggcctg ccccatgtat ttaacagtaa tacaggaagc   3180
atggcaggca ccatgcaaac caaggatgga tggtgcagtc cctgtgtcag tgggcggtgg   3240
tttcctgctg gcctggaatc actcatcacc tgattgattg gctctgtggt cctgggcagg   3300
tgcctcatag gtgtgtggat atgatgacgt ttctttaaaa tgtatgtatt taacaaatac   3360
```

```
ttaattgtat taaggtcatg taccaaggat ttgataaagt ttaaataatt tactctctac   3420

ttttatccat tttatccatt ttaactcatg taatcctcat gtgagtattc ctgtttaaca   3480

cttgagtaaa ctgaggcaca gagaacataa gttgcatgcc atagtcacac actgtgaaag   3540

tgaaaagaga atgtgtgcaa aacacgtcac agtcctggtt tctgagtaaa ggcaggctgt   3600

tatctttaga atcaagctat cacagggaga taggcaatgc tgtgggtgtt ggaggaaggt   3660

gagagcctgt tgctaacaat ttcctggttt taaagctaag gctgatttta ttgggaagat   3720

ctcacatgtg tgtggcccct gagagttccc agtgcctttt atttgcagtc cttccatttg   3780

gacctcctag ctgccccatc aggtcatctc cagggctcag aggggtgaga ccatttccca   3840

aggtcacaga accagctctc tagtcaccac cctgcctctc cctctcaccc agagtcagta   3900

ccagttttat ggctttatta caaactgctg ggtccctccc attttcaact tgattgatgg   3960

gatgtcatcc cttatcctgt ctgacatttg cctctggcct ggttgctaga agtttgcccc   4020

aggggcaaga gttgaaattt ggcttcctga ggtgggcttt gtggtttgcg tccctaaagt   4080

gagcccacta ctggttgctt gtccatggcc aacaccagaa atcccctgag cactacctgg   4140

gtctcattcc aagaaggaag agggtcagga gacctgggga gtctcatatt ccaagttctt   4200

ctttctttct gggagcagtg ggcagttcat ggtgttaggg cactcacccc cacagactgg   4260

caaaccctgc aggacttccg tggctgaggc tgtgaccgga ggccaggaat gccgttgggt   4320

ggattgtgag tgaatgggcc ctttgagctg ccctctagag agcaaatcca gtttcctgga   4380

gctcctgaat gaatatctgt actggctcgc tcagatgcag aagctccatt gaccatgagg   4440

ccttgtgaac atcagtggcc acaggcccag tgtgctgctt ggcactgcac tagtttagga   4500

cctgcagcat gtaggtagcg tcctagtgtt tataatacaa agctgctctg cacagctttt   4560

ctgattcttc ttgcaatctc ctgaggatta tctgccccat ttttaaaacg aggtggaata   4620

cccaaggtca tgtagccagt gagtgctctg gaaagccaaa gcagctcatc ccttcctggg   4680

gaccacactg ctctgctcca ccagaccaca ctatgaaata ggaataagtg ctcctgttgc   4740

aggactgctg ggaaaacagg tggtgtggga cttaagtcac cataattttg aagacttgca   4800

tgcagagggc tccaggaatt gtagacatta aggaatttca ctttcagttc tacccactac   4860

ttaagtactt gtcatgtact cttagaggag gccagtaatg atcagaacca ttttacttta   4920

aaattaataa tattgtatta gagaatatat taaatggtta tattgggtta tgttaggata   4980

tatacttgaa tggaaataca tgtactatta gcaatcatat ttcatttatc cctgtaatta   5040

gacaagaaag cataatatag ctctactcat gggtacacat accagtgtat aagattttta   5100

gaagtttact ttttaaaaat aaaagcaaaa tgtaagatct taaaaaaaaa aaaaaaaaa    5159
```

<210> SEQ ID NO 50
<211> LENGTH: 5416
<212> TYPE: DNA
<213> ORGANISM: Homo sapiens

<400> SEQUENCE: 50

```
agtgggccgc catgttgtcg gagtgaaagg taagggggag cgagagcgcc agagagagaa     60

gatcgggggg ctgaaatcca tcttcatcct accgctccgc ccgtgttggt ggaatgagcg    120

ttgcatgtgt cttgaagaga aaagcagtgc tttggcagga ctctttcagc ccccacctga    180

aacatcaccc tcaagaacca gctaatccca acatgcctgt tgttttgaca tctggaacag    240

ggtcgcaagc gcagccacaa ccagctgcaa atcaggctct tgcagctggg actcactcca    300
```

```
gccctgtccc aggatctata ggagttgcag gccgttccca ggacgacgct atggtggact    360
acttctttca gaggcagcat ggtgagcagc ttgggggagg aggaagtgga ggaggcggct    420
ataataatag caaacatcga tggcctactg ggataacat tcatgcagaa catcaggtgc     480
gttccatgga tgaactgaat catgattttc aagcacttgc tctggaggga agagcgatgg    540
gagagcagct cttgccaggt aaaaagtttt gggaaacaga tgaatccagc aaagatggac    600
caaaaggaat attcctgggt gatcaatggc gagacagtgc ctggggaaca tcagatcatt    660
cagtttccca gccaatcatg gtgcagagaa gacctggtca gagtttccat gtgaacagtg    720
aggtcaattc tgtactgtcc ccacgatcgg agagtggggg actaggcgtt agcatggtgg    780
agtatgtgtt gagctcatcc ccgggcgatt cctgtctaag aaaaggagga tttggcccaa    840
gggatgcaga cagtgatgaa aacgacaaag gtgaaaagaa gaacaagggt acgtttgatg    900
gagataagct aggagatttg aaggaggagg gtgatgtgat ggacaagacc aatggtttac    960
cagtgcagaa tgggattgat gcagacgtca aagattttag ccgtacccct ggtaattgcc   1020
agaactctgc taatgaagtg gatcttctgg gtccaaacca gaatggttct gagggcttag   1080
cccagctgac cagcaccaat ggtgccaagc ctgtggagga tttctccaac atggagtccc   1140
agagtgtccc cttggacccc atggaacatg tgggcatgga gcctcttcag tttgattatt   1200
caggcacgca ggtacctgtg gactcagcag cagcaactgt gggacttttt gactacaatt   1260
ctcaacaaca gctgttccaa agacctaatg cgcttgctgt ccagcagttg acagctgctc   1320
agcagcagca gtatgcactg gcagctgctc atcagccgca catcggttta gctcccgctg   1380
cgtttgtccc caatccatac atcatcagcg ctgctccccc agggacggac ccctacacag   1440
ctggattggc tgcagcagcg acactaggcc cagctgtggt ccctcaccag tattatggag   1500
ttactccctg gggagtctac cctgccagtc ttttccagca gcaagctgcc gctgccgctg   1560
cagcaactaa ttcagctaat caacagacca ccccacaggc tcagcaagga cagcagcagg   1620
ttctccgtgg aggagccagc caacgtcctt tgaccccaaa ccagaaccag cagggacagc   1680
aaacggatcc ccttgtggca gctgcagcag tgaattctgc ccttgcattt ggacaaggtc   1740
tggcagcagg catgccaggt tatccggtgt tggctcctgc tgcttactat gaccaaactg   1800
gtgcccttgt agtgaatgca ggcgcgagaa atggtcttgg agctcctgtt cgacttgtag   1860
ctcctgcccc agtcatcatt agttcctcag ctgcacaagc agctgttgca gcagccgcag   1920
cttcagcaaa tggagcagct ggtggtcttg ctggaacaac aaatggacca tttcgccctt   1980
taggaacaca gcagcctcag ccccagcccc agcagcagcc caataacaac ctggcatcca   2040
gttctttcta cggcaacaac tctctgaaca gcaattcaca gagcagctcc ctcttctccc   2100
agggctctgc ccagcctgcc aacacatcct tgggattcgg aagtagcagt tctctcggcg   2160
ccaccctggg atccgccctt ggagggtttg gaacagcagt tgcaaactcc aacactggca   2220
gtggctcccg ccgtgactcc ctgactggca gcagtgacct ttataagagg acatcgagca   2280
gcttgacccc cattggacac agtttttata acggccttag cttttcctcc tctcctggac   2340
ccgtgggcat gcctctccct agtcagggac caggacattc acagacacca cctccttccc   2400
tctcttcaca tggatcctct tcaagcttaa acctgggagg actcacgaat ggcagtggaa   2460
gatacatctc tgctgctcca ggcgctgaag ccaagtaccg cagtgcaagc agcgcctcca   2520
gcctcttcag cccgagcagc actcttttct cttcctctcg tttgcgatat ggaatgtctg   2580
atgtcatgcc ttctggcagg agcaggcttt tggaagattt tcgaaacaac cggtacccca   2640
atttacaact gcgggagatt gctggacata taatggaatt ttcccaagac cagcatgggt   2700
```

```
ccagattcat tcagctgaaa ctggagcgtg ccacaccagc tgagcgccag cttgtcttca   2760
atgaaatcct ccaggctgcc taccaactca tggtggatgt gtttggtaat tacgtcattc   2820
agaagttctt tgaatttggc agtcttgaac agaagctggc tttggcagaa cggattcgag   2880
gccacgtcct gtcattggca ctacagatgt atggctgccg tgttatccag aaagctcttg   2940
agtttattcc ttcagaccag caggtaatta atgagatggt tcgggaacta gatggccatg   3000
tcttgaagtg tgtgaaagat cagaatggca atcacgtggt tcagaaatgc attgaatgtg   3060
tacagcccca gtctttgcaa tttatcatcg atgcgtttaa gggacaggta tttgccttat   3120
ccacacatcc ttatggctgc cgagtgattc agagaatcct ggagcactgt ctccctgacc   3180
agacactccc tattttagag gagcttcacc agcacacaga gcagcttgta caggatcaat   3240
atggaaatta tgtaatccaa catgtactgg agcacggtcg tcctgaggat aaaagcaaaa   3300
ttgtagcaga aatccgaggc aatgtacttg tattgagtca gcacaaattt gcaagcaatg   3360
ttgtggagaa gtgtgttact cacgcctcac gtacggagcg cgctgtgctc atcgatgagg   3420
tgtgcaccat gaacgacggt ccccacagtg ccttatacac catgatgaag gaccagtatg   3480
ccaactacgt ggtccagaag atgattgacg tggcggagcc aggccagcgg aagatcgtca   3540
tgcataagat ccggccccac atcgcaactc ttcgtaagta cacctatggc aagcacattc   3600
tggccaagct ggagaagtac tacatgaaga acggtgttga cttagggccc atctgtggcc   3660
cccctaatgg tatcatctga ggcagtgtca cccgctgttc cctcattccc gctgacctca   3720
ctggcccact ggcaaatcca accagcaacc agaaatgttc tagtgtagag tctgagacgg   3780
gcaagtggtt gctccaggat tactccctcc tccaaaaaag gaatcaaatc cacgagtgga   3840
aaagcctttg taaatttaat tttattacac ataacatgta ctattttttt taattgacta   3900
attgccctgc tgttttactg gtgtatagga tacttgtaca taggtaacca atgtacatgg   3960
gaggccacat attttgttca ctgttgtatc tatatttcac atgtggaaac tttcagggtg   4020
gttggtttaa caaaaaaaaa aagctttaaa aaaaaaagaa aaaaaggaaa aggtttttag   4080
ctcatttgcc tggccggcaa gttttgcaaa tagctcttcc ccacctcctc attttagtaa   4140
aaaacaaaca aaaacaaaaa aacctgagaa gtttgaattg tagttaaatg accccaaact   4200
ggcatttaac actgtttata aaaaatatat atatatatat atatatatat aatgaaaaag   4260
gtttcagagt tgctaaagct tcagtttgtg acattaagtt tatgaaattc taaaaaaatgc   4320
ctttttttgga gactatatta tgctgaagaa ggctgttcgt gaggaggaga tgcgagcacc   4380
cagaacgtct tttgaggctg ggcgggtgtg attgtttact gcctactgga tttttttcta   4440
ttaacattga aaggtaaaat ctgattattt agcatgagaa aaaaaaatcc aactctgctt   4500
ttggtcttgc ttctataaat atatagtgta tacttggtgt agactttgca tatatacaaa   4560
tttgtagtat tttcttgttt tgatgtctaa tctgtatcta taatgtaccc tagtagtcga   4620
acatactttt gattgtacaa ttgtacattt gtatacctgt aatgtaaatg tggagaagtt   4680
tgaatcaaca taaacacgtt ttttggtaag aaaagagaat tagccagccc tgtgcattca   4740
gtgtatattc tcacctttta tggtcgtagc atatagtgtt gtatattgta aattgtaatt   4800
tcaaccagaa gtaaattttt ttcttttgaa ggaataaatg ttctttatac agcctagtta   4860
atgtttaaaa agaaaaaaat agcttggttt tatttgtcat ctagtctcaa gtatagcgag   4920
attctttcta aatgttattc aagattgagt tctcactagt gttttttttaa tcctaaaaaa   4980
gtaatgtttt gattttgtga cagtcaaaag gacgtgcaaa agtctagcct tgcccgagct   5040
```

ttccttacaa tcagagcccc tctcaccttg taaagtgtga atcgcccttc ccttttgtac 5100
agaagatgaa ctgtattttg cattttgtct acttgtaagt gaatgtaaca tactgtcaat 5160
tttccttgtt tgaatataga attgtaacac tacacggtgt acatttccag agccttgtgt 5220
atatttccaa tgaacttttt tgcaagcaca cttgtaacca tatgtgtata attaacaaac 5280
ctgtgtatgc ttatgcctgg gcaactattt tttgtaactc ttgtgtagat tgtctctaaa 5340
caatgtgtga tctttatttt gaaaaataca gaactttgga atctgaaaaa aaaaaaaaaa 5400
aaaaaaaaaa aaaaaa 5416

<210> SEQ ID NO 51
<211> LENGTH: 1940
<212> TYPE: DNA
<213> ORGANISM: Homo sapiens

<400> SEQUENCE: 51
gagtgagcgg cgcggggcca atcagcgtgc gccgttccga aagttgcctt ttatggctcg 60
agcggccgcg gcggcgccct ataaaaccca gcggcgcgac gcgccaccac cgccgagacc 120
gcgtccgccc cgcgagcaca gagcctcgcc tttgccgatc cgccgcccgt ccacacccgc 180
cgccagctca ccatggatga tgatatcgcc gcgctcgtcg tcgacaacgg ctccggcatg 240
tgcaaggccg gcttcgcggg cgacgatgcc ccccgggccg tcttcccctc catcgtgggg 300
cgccccaggc accagggcgt gatggtgggc atgggtcaga aggattccta tgtgggcgac 360
gaggcccaga gcaagagagg catcctcacc ctgaagtacc ccatcgagca cggcatcgtc 420
accaactggg acgacatgga gaaaatctgg caccacacct tctacaatga gctgcgtgtg 480
gctcccgagg agcaccccgt gctgctgacc gaggcccccc tgaaccccaa ggccaaccgc 540
gagaagatga cccagatcat gtttgagacc ttcaacaccc cagccatgta cgttgctatc 600
caggctgtgc tatccctgta cgcctctggc cgtaccactg gcatcgtgat ggactccggt 660
gacggggtca cccacactgt gcccatctac gaggggtatg ccctccccca tgccatcctg 720
cgtctggacc tggctggccg ggacctgact gactacctca tgaagatcct caccgagcgc 780
ggctacagct tcaccaccac ggccgagcgg gaaatcgtgc gtgacattaa ggagaagctg 840
tgctacgtcg ccctggactt cgagcaagag atggccacgg ctgcttccag ctcctccctg 900
gagaagagct acgagctgcc tgacggccag gtcatcacca ttggcaatga gcggttccgc 960
tgccctgagg cactcttcca gccttccttc ctgggcatgg agtcctgtgg catccacgaa 1020
actaccttca actccatcat gaagtgtgac gtggacatcc gcaaagacct gtacgccaac 1080
acagtgctgt ctggcggcac caccatgtac cctggcattg ccgacaggat gcagaaggag 1140
atcactgccc tggcacccag cacaatgaag atcaagatca ttgctcctcc tgagcgcaag 1200
tactccgtgt ggatcggcgg ctccatcctg gcctcgctgt ccaccttcca gcagatgtgg 1260
atcagcaagc aggagtatga cgagtccggc ccctccatcg tccaccgcaa atgcttctag 1320
gcggactatg acttagttgc gttacaccct ttcttgacaa aacctaactt gcgcagaaaa 1380
caagatgaga ttggcatggc tttatttgtt ttttttgttt tgttttggtt tttttttttt 1440
ttttggcttg actcaggatt taaaaactgg aacggtgaag gtgacagcag tcggttggag 1500
cgagcatccc ccaaagttca caatgtggcc gaggactttg attgcacatt gttgtttttt 1560
taatagtcat tccaaatatg agatgcgttg ttacaggaag tcccttgcca tcctaaaagc 1620
caccccactt ctctctaagg agaatggccc agtcctctcc caagtccaca caggggaggt 1680
gatagcattg ctttcgtgta aattatgtaa tgcaaaattt ttttaatctt cgccttaata 1740 ctttttatt ttgttttatt ttgaatgatg agccttcgtg ccccccttc cccctttttt 1800 gtcccccaac ttgagatgta tgaaggcttt tggtctccct gggagtgggt ggaggcagcc 1860
agggcttacc tgtacactga cttgagacca gttgaataaa agtgcacacc ttaaaaatga 1920
ggaaaaaaaa aaaaaaaaaa 1940

<210> SEQ ID NO 52
<211> LENGTH: 1309
<212> TYPE: DNA
<213> ORGANISM: Homo sapiens

<400> SEQUENCE: 52
gctctctgct cctcctgttc gacagtcagc cgcatcttct tttgcgtcgc cagccgagcc 60
acatcgctca gacaccatgg ggaaggtgaa ggtcggagtc aacggatttg gtcgtattgg 120
gcgcctggtc accagggctg cttttaactc tggtaaagtg gatattgttg ccatcaatga 180
ccccttcatt gacctcaact acatggttta catgttccaa tatgattcca cccatggcaa 240
attccatggc accgtcaagg ctgagaacgg gaagcttgtc atcaatggaa atcccatcac 300
catcttccag gagcgagatc cctccaaaat caagtggggc gatgctggcg ctgagtacgt 360
cgtggagtcc actggcgtct tcaccaccat ggagaaggct ggggctcatt tgcagggggg 420
agccaaaagg gtcatcatct ctgccccctc tgctgatgcc cccatgttcg tcatgggtgt 480
gaaccatgag aagtatgaca acagcctcaa gatcatcagc aatgcctcct gcaccaccaa 540
ctgcttagca cccctggcca aggtcatcca tgacaacttt ggtatcgtgg aaggactcat 600
gaccacagtc catgccatca ctgccaccca gaagactgtg gatggcccct ccgggaaact 660
gtggcgtgat ggccgcgggg ctctccagaa catcatccct gcctctactg gcgctgccaa 720
ggctgtgggc aaggtcatcc ctgagctgaa cgggaagctc actggcatgg ccttccgtgt 780
ccccactgcc aacgtgtcag tggtggacct gacctgccgt ctagaaaaac ctgccaaata 840
tgatgacatc aagaaggtgg tgaagcaggc gtcggagggc cccctcaagg gcatcctggg 900
ctacactgag caccaggtgg tctcctctga cttcaacagc gacacccact cctccacctt 960
tgacgctggg gctggcattg ccctcaacga ccactttgtc aagctcattt cctggtatga 1020
caacgaattt ggctacagca acagggtggt ggacctcatg gcccacatgg cctccaagga 1080
gtaagacccc tggaccacca gccccagcaa gagcacaaga ggaagagaga gaccctcact 1140
gctggggagt ccctgccaca ctcagtcccc caccacactg aatctcccct cctcacagtt 1200
gccatgtaga ccccttgaag aggggagggg cctagggagc cgcaccttgt catgtaccat 1260
caataaagta ccctgtgctc aaccagttaa aaaaaaaaaa aaaaaaaaa 1309

<210> SEQ ID NO 53
<211> LENGTH: 2321
<212> TYPE: DNA
<213> ORGANISM: Homo sapiens

<400> SEQUENCE: 53
gtcctcaacc aagatggcgc ggatggcttc aggcgcatca cgacaccggc gcgtcacgcg 60
acccgcccta cgggcacctc ccgcgctttt cttagcgccg cagacggtgg ccgagcgggg 120
gaccgggaag catggcccgg gggtcggcgg ttgcctgggc ggcgctcggg ccgttgttgt 180
ggggctgcgc gctggggctg cagggcggga tgctgtaccc ccaggagagc ccgtcgcggg 240
agtgcaagga gctggacggc ctctggagct tccgcgccga cttctctgac aaccgacgcc 300

```
ggggcttcga ggagcagtgg taccggcggc cgctgtggga gtcaggcccc accgtggaca    360

tgccagttcc ctccagcttc aatgacatca gccaggactg gcgtctgcgg cattttgtcg    420

gctgggtgtg gtacgaacgg gaggtgatcc tgccggagcg atggacccag gacctgcgca    480

caagagtggt gctgaggatt ggcagtgccc attcctatgc catcgtgtgg gtgaatgggg    540

tcgacacgct agagcatgag gggggctacc tccccttcga ggccgacatc agcaacctgg    600

tccaggtggg gcccctgccc tcccggctcc gaatcactat cgccatcaac aacacactca    660

cccccaccac cctgccacca gggaccatcc aatacctgac tgacacctcc aagtatccca    720

agggttactt tgtccagaac acatattttg actttttcaa ctacgctgga ctgcagcggt    780

ctgtacttct gtacacgaca cccaccacct acatcgatga catcaccgtc accaccagcg    840

tggagcaaga cagtgggctg gtgaattacc agatctctgt caagggcagt aacctgttca    900

agttggaagt gcgtcttttg gatgcagaaa acaaagtcgt ggcgaatggg actgggaccc    960

agggccaact taaggtgcca ggtgtcagcc tctggtggcc gtacctgatg cacgaacgcc   1020

ctgcctatct gtattcattg gaggtgcagc tgactgcaca gacgtcactg ggcctgtgt   1080

ctgacttcta cacactccct gtggggatcc gcactgtggc tgtcaccaag agccagttcc   1140

tcatcaatgg gaaacctttc tatttccacg gtgtcaacaa gcatgaggat gcggacatcc   1200

gagggaaggg cttcgactgg ccgctgctgg tgaaggactt caacctgctt cgctggcttg   1260

gtgccaacgc tttccgtacc agccactacc cctatgcaga ggaagtgatg cagatgtgtg   1320

accgctatgg gattgtggtc atcgatgagt gtcccggcgt gggcctggcg ctgccgcagt   1380

tcttcaacaa cgtttctctg catcaccaca tgcaggtgat ggaagaagtg gtgcgtaggg   1440

acaagaacca ccccgcggtc gtgatgtggt ctgtggccaa cgagcctgcg tcccacctag   1500

aatctgctgg ctactacttg aagatggtga tcgctcacac caaatccttg gacccctccc   1560

ggcctgtgac ctttgtgagc aactctaact atgcagcaga caaggggggct ccgtatgtgg   1620

atgtgatctg tttgaacagc tactactctt ggtatcacga ctacgggcac ctggagttga   1680

ttcagctgca gctggccacc cagtttgaga actggtataa gaagtatcag aagcccatta   1740

ttcagagcga gtatggagca gaaacgattg cagggtttca ccaggatcca cctctgatgt   1800

tcactgaaga gtaccagaaa agtctgctag agcagtacca tctgggtctg gatcaaaaac   1860

gcagaaaata cgtggttgga gagctcattt ggaattttgc cgatttcatg actgaacagt   1920

caccgacgag agtgctgggg aataaaaagg ggatcttcac tcggcagaga caaccaaaaa   1980

gtgcagcgtt ccttttgcga gagagatact ggaagattgc caatgaaacc aggtatcccc   2040

actcagtagc caagtcacaa tgtttggaaa acagcctgtt tacttgagca agactgatac   2100

cacctgcgtg tcccttcctc cccgagtcag ggcgacttcc acagcagcag aacaagtgcc   2160

tcctggactg ttcacggcag accagaacgt ttctggcctg ggttttgtgg tcatctattc   2220

tagcagggaa cactaaaggt ggaaataaaa gattttctat tatggaaata aagagttggc   2280

atgaaagtgg ctactgaaaa aaaaaaaaaa aaaaaaaaaa a                       2321
```

<210> SEQ ID NO 54
<211> LENGTH: 1229
<212> TYPE: DNA
<213> ORGANISM: Homo sapiens

<400> SEQUENCE: 54

```
gtctgacggg cgatggcgca gccaatagac aggagcgcta tccgcggttt ctgattggct     60

actttgttcg cattataaaa ggcacgcgcg ggcgcgaggc ccttctctcg ccaggcgtcc    120
```

```
tcgtggaagt gacatcgtct ttaaaccctg cgtggcaatc cctgacgcac cgccgtgatg    180

cccagggaag acagggcgac ctggaagtcc aactacttcc ttaagatcat ccaactattg    240

gatgattatc cgaaatgttt cattgtggga gcagacaatg tgggctccaa gcagatgcag    300

cagatccgca tgtcccttcg cgggaaggct gtggtgctga tgggcaagaa caccatgatg    360

cgcaaggcca tccgagggca cctggaaaac aacccagctc tggagaaact gctgcctcat    420

atccggggga atgtgggctt tgtgttcacc aaggaggacc tcactgagat cagggacatg    480

ttgctggcca ataaggtgcc agctgctgcc cgtgctggtg ccattgcccc atgtgaagtc    540

actgtgccag cccagaacac tggtctcggg cccgagaaga cctccttttt ccaggcttta    600

ggtatcacca ctaaaatctc caggggcacc attgaaatcc tgagtgatgt gcagctgatc    660

aagactggag acaaagtggg agccagcgaa gccacgctgc tgaacatgct caacatctcc    720

cccttctcct ttgggctggt catccagcag gtgttcgaca atggcagcat ctacaaccct    780

gaagtgcttg atatcacaga ggaaactctg cattctcgct tcctggaggg tgtccgcaat    840

gttgccagtg tctgtctgca gattggctac ccaactgttg catcagtacc ccattctatc    900

atcaacgggt acaaacgagt cctggccttg tctgtggaga cggattacac cttcccactt    960

gctgaaaagg tcaaggcctt cttggctgat ccatctgcct ttgtggctgc tgcccctgtg   1020

gctgctgcca ccacagctgc tcctgctgct gctgcagccc cagctaaggt tgaagccaag   1080

gaagagtcgg aggagtcgga cgaggatatg ggatttggtc tctttgacta atcaccaaaa   1140

agcaaccaac ttagccagtt ttatttgcaa aacaaggaaa taaaggctta cttctttaaa   1200

aagtaaaaaa aaaaaaaaaa aaaaaaaaa                                     1229
```

<210> SEQ ID NO 55
<211> LENGTH: 5234
<212> TYPE: DNA
<213> ORGANISM: Homo sapiens

<400> SEQUENCE: 55

```
agagcgtcgg gatatcgggt ggcggctcgg gacggaggac gcgctagtgt gagtgcgggc     60

ttctagaact acaccgaccc tcgtgtcctc ccttcatcct gcggggctgg ctggagcggc    120

cgctccggtg ctgtccagca gccataggga gccgcacggg gagcgggaaa gcggtcgcgg    180

ccccaggcgg ggcggccggg atggagcggg gccgcgagcc tgtggggaag ggctgtggc     240

ggcgcctcga gcggctgcag gttcttctgt gtggcagttc agaatgatgg atcaagctag    300

atcagcattc tctaacttgt ttggtggaga accattgtca tatacccggt tcagcctggc    360

tcggcaagta gatggcgata acagtcatgt ggagatgaaa cttgctgtag atgaagaaga    420

aaatgctgac aataacacaa aggccaatgt cacaaaacca aaaaggtgta gtggaagtat    480

ctgctatggg actattgctg tgatcgtctt tttcttgatt ggatttatga ttggctactt    540

gggctattgt aaaggggtag aaccaaaaac tgagtgtgag agactggcag gaaccgagtc    600

tccagtgagg gaggagccag gagaggactt ccctgcagca cgtcgcttat attgggatga    660

cctgaagaga aagttgtcgg agaaactgga cagcacagac ttcaccggca ccatcaagct    720

gctgaatgaa aattcatatg tccctcgtga ggctggatct caaaaagatg aaaatcttgc    780

gttgtatgtt gaaaatcaat ttcgtgaatt taaactcagc aaagtctggc gtgatcaaca    840

ttttgttaag attcaggtca aagacagcgc tcaaaactcg gtgatcatag ttgataagaa    900

cggtagactt gtttacctgg tggagaatcc tgggggttat gtggcgtata gtaaggctgc    960
```

-continued

```
aacagttact ggtaaactgg tccatgctaa ttttggtact aaaaaagatt ttgaggattt   1020
atacactcct gtgaatggat ctatagtgat tgtcagagca gggaaaatca cctttgcaga   1080
aaaggttgca aatgctgaaa gcttaaatgc aattggtgtg ttgatataca tggaccagac   1140
taaatttccc attgttaacg cagaactttc attctttgga catgctcatc tggggacagg   1200
tgacccttac acacctggat tcccttcctt caatcacact cagtttccac catctcggtc   1260
atcaggattg cctaatatac ctgtccagac aatctccaga gctgctgcag aaaagctgtt   1320
tgggaatatg gaaggagact gtccctctga ctggaaaaca gactctacat gtaggatggt   1380
aacctcagaa agcaagaatg tgaagctcac tgtgagcaat gtgctgaaag agataaaaat   1440
tcttaacatc tttggagtta ttaaaggctt tgtagaacca gatcactatg ttgtagttgg   1500
ggcccagaga gatgcatggg gccctggagc tgcaaaatcc ggtgtaggca cagctctcct   1560
attgaaactt gcccagatgt tctcagatat ggtcttaaaa gatgggtttc agcccagcag   1620
aagcattatc tttgccagtt ggagtgctgg agactttgga tcggttggtg ccactgaatg   1680
gctagaggga tacctttcgt ccctgcattt aaaggctttc acttatatta atctggataa   1740
agcggttctt ggtaccagca acttcaaggt ttctgccagc ccactgttgt atacgcttat   1800
tgagaaaaca atgcaaaatg tgaagcatcc ggttactggg caatttctat atcaggacag   1860
caactgggcc agcaaagttg agaaactcac tttagacaat gctgctttcc ctttccttgc   1920
atattctgga atcccagcag tttctttctg tttttgcgag gacacagatt atccttattt   1980
gggtaccacc atggacacct ataaggaact gattgagagg attcctgagt tgaacaaagt   2040
ggcacgagca gctgcagagg tcgctggtca gttcgtgatt aaactaaccc atgatgttga   2100
attgaacctg gactatgaga ggtacaacag ccaactgctt tcatttgtga gggatctgaa   2160
ccaatacaga gcagacataa aggaaatggg cctgagttta cagtggctgt attctgctcg   2220
tggagacttc ttccgtgcta cttccagact aacaacagat ttcgggaatg ctgagaaaac   2280
agacagattt gtcatgaaga aactcaatga tcgtgtcatg agagtggagt atcacttcct   2340
ctctccctac gtatctccaa aagagtctcc tttccgacat gtcttctggg gctccggctc   2400
tcacacgctg ccagctttac tggagaactt gaaactgcgt aaacaaaata acggtgcttt   2460
taatgaaacg ctgttcagaa accagttggc tctagctact tggactattc agggagctgc   2520
aaatgccctc tctggtgacg tttgggacat tgacaatgag ttttaaatgt gatacccata   2580
gcttccatga gaacagcagg gtagtctggt ttctagactt gtgctgatcg tgctaaattt   2640
tcagtagggc tacaaaacct gatgttaaaa ttccatccca tcatcttggt actactagat   2700
gtctttaggc agcagctttt aatacagggt agataacctg tacttcaagt taaagtgaat   2760
aaccacttaa aaaatgtcca tgatggaata ttcccctatc tctagaattt taagtgcttt   2820
gtaatgggaa ctgcctcttt cctgttgttg ttaatgaaaa tgtcagaaac cagttatgtg   2880
aatgatctct ctgaatccta agggctggtc tctgctgaag gttgtaagtg gtcgcttact   2940
ttgagtgatc ctccaacttc atttgatgct aaataggaga taccaggttg aaagaccttc   3000
tccaaatgag atctaagcct ttccataagg aatgtagctg gtttcctcat tcctgaaaga   3060
aacagttaac tttcagaaga gatgggcttg ttttcttgcc aatgaggtct gaaatggagg   3120
tccttctgct ggataaaatg aggttcaact gttgattgca ggaataaggc cttaatatgt   3180
taacctcagt gtcatttatg aaaagagggg accagaagcc aaagacttag tatattttct   3240
tttcctctgt cccttccccc ataagcctcc atttagttct ttgttatttt tgtttcttcc   3300
aaagcacatt gaaagagaac cagtttcagg tgtttagttg cagactcagt ttgtcagact   3360
```

```
ttaaagaata atatgctgcc aaattttggc caaagtgtta atcttagggg agagctttct   3420
gtccttttgg cactgagata tttattgttt atttatcagt gacagagttc actataaatg   3480
gtgttttttt aatagaatat aattatcgga agcagtgcct tccataatta tgacagttat   3540
actgtcggtt tttttaaat aaaagcagca tctgctaata aaacccaaca gatactggaa    3600
gttttgcatt tatggtcaac acttaagggt tttagaaaac agccgtcagc caaatgtaat   3660
tgaataaagt tgaagctaag atttagagat gaattaaatt taattagggg ttgctaagaa   3720
gcgagcactg accagataag aatgctggtt ttcctaaatg cagtgaattg tgaccaagtt   3780
ataaatcaat gtcacttaaa ggctgtggta gtactcctgc aaaattttat agctcagttt   3840
atccaaggtg taactctaat tcccattttg caaaatttcc agtacctttg tcacaatcct   3900
aacacattat cgggagcagt gtcttccata atgtataaag aacaaggtag tttttaccta   3960
ccacagtgtc tgtatcggag acagtgatct ccatatgtta cactaagggt gtaagtaatt   4020
atcgggaaca gtgtttccca taattttctt catgcaatga catcttcaaa gcttgaagat   4080
cgttagtatc taacatgtat cccaactcct ataattccct atcttttagt tttagttgca   4140
gaaacatttt gtggtcatta agcattgggt gggtaaattc aaccactgta aaatgaaatt   4200
actacaaaat ttgaaattta gcttgggttt ttgttacctt tatggtttct ccaggtcctc   4260
tacttaatga gatagtagca tacatttata atgtttgcta ttgacaagtc attttaactt   4320
tatcacatta tttgcatgtt acctcctata aacttagtgc ggacaagttt taatccagaa   4380
ttgacctttt gacttaaagc agagggactt tgtatagaag gtttgggggc tgtggggaag   4440
gagagtcccc tgaaggtctg acacgtctgc ctacccattc gtggtgatca attaaatgta   4500
ggtatgaata agttcgaagc tccgtgagtg aaccatcatt ataaacgtga tgatcagctg   4560
tttgtcatag ggcagttgga aacggcctcc tagggaaaag ttcatagggt ctcttcaggt   4620
tcttagtgtc acttacctag atttacagcc tcacttgaat gtgtcactac tcacagtctc   4680
tttaatcttc agttttatct ttaatctcct cttttatctt ggactgacat ttagcgtagc   4740
taagtgaaaa ggtcatagct gagattcctg gttcgggtgt tacgcacacg tacttaaatg   4800
aaagcatgtg gcatgttcat cgtataacac aatatgaata cagggcatgc attttgcagc   4860
agtgagtctc ttcagaaaac ccttttctac agttagggtt gagttacttc ctatcaagcc   4920
agtacgtgct aacaggctca atattcctga atgaaatatc agactagtga caagctcctg   4980
gtcttgagat gtcttctcgt taaggagatg ggccttttgg aggtaaagga taaaatgaat   5040
gagttctgtc atgattcact attctagaac ttgcatgacc tttactgtgt tagctctttg   5100
aatgttcttg aaattttaga ctttctttgt aaacaaatga tatgtcctta tcattgtata   5160
aaagctgtta tgtgcaacag tgtggagatt ccttgtctga tttaataaaa tacttaaaca   5220
ctgaaaaaaa aaaa                                                     5234
```

<210> SEQ ID NO 56
<211> LENGTH: 1869
<212> TYPE: DNA
<213> ORGANISM: Homo sapiens

<400> SEQUENCE: 56

```
tacctggttg atcctgccag tagcatatgc ttgtctcaaa gattaagcca tgcatgtcta     60
agtacgcacg gccggtacag tgaaactgcg aatggctcat taaatcagtt atggttcctt    120
tggtcgctcg ctcctctccc acttggataa ctgtggtaat tctagagcta atacatgccg    180
```

```
acgggcgctg acccccttcg cggggggggat gcgtgcattt atcagatcaa aaccaacccg    240
gtcagcccct ctccggcccc ggccgggggg cgggcgccgg cggctttggt gactctagat    300
aacctcgggc cgatcgcacg ccccccgtgg cggcgacgac ccattcgaac gtctgcccta    360
tcaactttcg atggtagtcg ccgtgcctac catggtgacc acgggtgacg gggaatcagg    420
gttcgattcc ggagagggag cctgagaaac ggctaccaca tccaaggaag gcagcaggcg    480
cgcaaattac ccactcccga cccggggagg tagtgacgaa aaataacaat acaggactct    540
ttcgaggccc tgtaattgga atgagtccac tttaaatcct ttaacgagga tccattggag    600
ggcaagtctg gtgccagcag ccgcggtaat tccagctcca atagcgtata ttaaagttgc    660
tgcagttaaa aagctcgtag ttggatcttg ggagcgggcg ggcggtccgc cgcgaggcga    720
gccaccgccc gtccccgccc cttgcctctc ggcgcccccct cgatgctctt agctgagtgt    780
cccgcggggc ccgaagcgtt tactttgaaa aaattagagt gttcaaagca ggcccgagcc    840
gcctggatac cgcagctagg aataatggaa taggaccgcg gttctatttt gttggttttc    900
ggaactgagg ccatgattaa gagggacggc cgggggcatt cgtattgcgc cgctagaggt    960
gaaattcttg gaccggcgca agacggacca gagcgaaagc atttgccaag aatgttttca   1020
ttaatcaaga acgaaagtcg gaggttcgaa gacgatcaga taccgtcgta gttccgacca   1080
taaacgatgc cgaccggcga tgcggcggcg ttattcccat gacccgccgg gcagcttccg   1140
ggaaaccaaa gtctttgggt tccgggggga gtatggttgc aaagctgaaa cttaaaggaa   1200
ttgacggaag ggcaccacca ggagtggagc ctgcggctta atttgactca acacgggaaa   1260
cctcacccgg cccggacacg gacaggattg acagattgat agctctttct cgattccgtg   1320
ggtggtggtg catggccgtt cttagttggt ggagcgattt gtctggttaa ttccgataac   1380
gaacgagact ctggcatgct aactagttac gcgacccccg agcggtcggc gtcccccaac   1440
ttcttagagg gacaagtggc gttcagccac ccgagattga gcaataacag gtctgtgatg   1500
cccttagatg tccggggctg cacgcgcgct acactgactg gctcagcgtg tgcctaccct   1560
acgccggcag gcgcgggtaa cccgttgaac cccattcgtg atggggatcg ggattgcaa    1620
ttattcccca tgaacgagga attcccagta agtgcgggtc ataagcttgc gttgattaag   1680
tccctgccct ttgtacacac cgcccgtcgc tactaccgat tggatggttt agtgaggccc   1740
tcggatcggc cccgccgggg tcggcccacg gccctggcgg agcgctgaga agacggtcga   1800
acttgactat ctagaggaag taaaagtcgt aacaaggttt ccgtaggtga acctgcggaa   1860
ggatcatta                                                            1869
```

<210> SEQ ID NO 57
<211> LENGTH: 2288
<212> TYPE: DNA
<213> ORGANISM: Homo sapiens

<400> SEQUENCE: 57

```
ggggccgaac gtggtataaa aggggcggga ggccaggctc gtgccgtttt gcagacgcca     60
ccgccgagga aaaccgtgta ctattagcca tggtcaaccc caccgtgttc ttcgacattg    120
ccgtcgacgg cgagcccttg ggccgcgtct cctttgagct gtttgcagac aaggtcccaa    180
agacagcaga aaattttcgt gctctgagca ctggagagaa aggatttggt tataagggtt    240
cctgctttca cagaattatt ccagggttta tgtgtcaggg tggtgacttc acacgccata    300
atggcactgg tggcaagtcc atctatgggg agaaatttga agatgagaac ttcatcctaa    360
agcatacggg tcctggcatc ttgtccatgg caaatgctgg acccaacaca aatggttccc    420
```

```
agtttttcat ctgcactgcc aagactgagt ggttggatgg caagcatgtg gtgtttggca    480

aagtgaaaga aggcatgaat attgtggagg ccatggagcg ctttgggtcc aggaatggca    540

agaccagcaa gaagatcacc attgctgact gtggacaact cgaataagtt tgacttgtgt    600

tttatcttaa ccaccagatc attccttctg tagctcagga gagcacccct ccacccccatt   660

tgctcgcagt atcctagaat ctttgtgctc tcgctgcagt tccctttggg ttccatgttt    720

tccttgttcc ctcccatgcc tagctggatt gcagagttaa gtttatgatt atgaaataaa    780

aactaaataa caattgtcct cgtttgagtt aagagtgttg atgtaggctt tattttaagc    840

agtaatgggt tacttctgaa acatcacttg tttgcttaat tctacacagt acttagattt    900

tttttacttt ccagtcccag gaagtgtcaa tgtttgttga gtggaatatt gaaaatgtag    960

gcagcaactg ggcatggtgg ctcactgtct gtaatgtatt acctgaggca gaagaccacc   1020

tgagggtagg agtcaagatc agcctgggca acatagtgag acgctgtctc tacaaaaaat   1080

aattagcctg gcctggtggt gcatgcctag tcctagctga tctggaggct gacgtgggag   1140

gattgcttga gcctagagtg agctattatc atgccactgt acagcctggg tgttcacaga   1200

tcttgtgtct caaaggtagg cagaggcagg aaaagcaagg agccagaatt aagaggttgg   1260

gtcagtctgc agtgagttca tgcatttaga ggtgttcttc aagatgacta atgtcaaaaa   1320

ttgagacatc tgttgcggtt tttttttttt tttttcccc tggaatgcag tggcgtgatc    1380

tcagctcact gcagcctccg cctcctgggt tcaagtgatt ctagtgcctc agcctcctga   1440

gtagctggga taatgggcgt gtgccaccat gcccagctaa tttttgtatt tttagtatag   1500

atggggtttc atcattttga ccaggctggt ctcaaactct tgacctcagc tgatgcgcct   1560

gccttggcct cccaaactgc tgagattaca gatgtgagcc accgcaccct acctcatttt   1620

ctgtaacaaa gctaagcttg aacactgttg atgttcttga gggaagcata ttgggcttta   1680

ggctgtaggt caagtttata catcttaatt atggtggaat tcctatgtag agtctaaaaa   1740

gccaggtact tggtgctaca gtcagtctcc ctgcagaggg ttaaggcgca gactacctgc   1800

agtgaggagg tactgcttgt agcatataga gcctctccct agctttggtt atggaggctt   1860

tgaggttttg caaacctgac caatttaagc cataagatct ggtcaaaggg ataccccttcc  1920

cactaaggac ttggtttctc aggaaattat atgtacagtg cttgctggca gttagatgtc   1980

aggacaatct aagctgagaa aacccccttct ctgcccacct taacagacct ctagggttct  2040

taacccagca atcaagtttg cctatcctag aggtggcgga tttgatcatt tggtgtgttg   2100

ggcaattttt gttttactgt ctggttcctt ctgcgtgaat taccaccacc accacttgtg   2160

catctcagtc ttgtgtgttg tctggttacg tattccctgg gtgataccat tcaatgtctt   2220

aatgtacttg tggctcagac ctgagtgcaa ggtggaaata aacatcaaac atcttttcat   2280

tatcccta                                                            2288
```

<210> SEQ ID NO 58
<211> LENGTH: 2439
<212> TYPE: DNA
<213> ORGANISM: Homo sapiens

<400> SEQUENCE: 58

```
gagagcagcg gccgggaagg ggcggtgcgg gaggcggggt gtggggcggt agtgtgggcc     60

ctgttcctgc ccgcgcggtg ttccgcattc tgcaagcctc cggagcgcac gtcggcagtc    120

ggctccctcg ttgaccgaat caccgacctc tctccccagc tgtatttcca aaatgtcgct    180
```

```
ttctaacaag ctgacgctgg acaagctgga cgttaaaggg aagcgggtcg ttatgagagt    240

cgacttcaat gttcctatga agaacaacca gataacaaac aaccagagga ttaaggctgc    300

tgtcccaagc atcaaattct gcttggacaa tggagccaag tcggtagtcc ttatgagcca    360

cctaggccgg cctgatggtg tgcccatgcc tgacaagtac tccttagagc cagttgctgt    420

agaactcaaa tctctgctgg gcaaggatgt tctgttcttg aaggactgtg taggcccaga    480

agtggagaaa gcctgtgcca acccagctgc tgggtctgtc atcctgctgg agaacctccg    540

ctttcatgtg gaggaagaag ggaagggaaa agatgcttct gggaacaagg ttaaagccga    600

gccagccaaa atagaagctt tccgagcttc actttccaag ctaggggatg tctatgtcaa    660

tgatgctttt ggcactgctc acagagccca cagctccatg gtaggagtca atctgccaca    720

gaaggctggt gggtttttga tgaagaagga gctgaactac tttgcaaagg ccttggagag    780

cccagagcga cccttcctgg ccatcctggg cggagctaaa gttgcagaca agatccagct    840

catcaataat atgctggaca aagtcaatga gatgattatt ggtggtggaa tggcttttac    900

cttccttaag gtgctcaaca acatggagat tggcacttct ctgtttgatg aagagggagc    960

caagattgtc aaagacctaa tgtccaaagc tgagaagaat ggtgtgaaga ttaccttgcc   1020

tgttgacttt gtcactgctg acaagtttga tgagaatgcc aagactggcc aagccactgt   1080

ggcttctggc atacctgctg gctggatggg cttggactgt ggtcctgaaa gcagcaagaa   1140

gtatgctgag gctgtcactc gggctaagca gattgtgtgg aatggtcctg tgggggtatt   1200

tgaatgggaa gcttttgccc ggggaaccaa agctctcatg gatgaggtgg tgaaagccac   1260

ttctaggggc tgcatcacca tcataggtgg tggagacact gccacttgct gtgccaaatg   1320

gaacacggag gataaagtca gccatgtgag cactgggggt ggtgccagtt tggagctcct   1380

ggaaggtaaa gtccttcctg ggtggatgc tctcagcaat atttagtact ttcctgcctt   1440

ttagttcctg tgcacagccc ctaagtcaac ttagcatttt ctgcatctcc acttggcatt   1500

agctaaaacc ttccatgtca agattcagct agtggccaag agatgcagtg ccaggaaccc   1560

ttaaacagtt gcacagcatc tcagctcatc ttcactgcac cctggatttg catacattct   1620

tcaagatccc atttgaattt tttagtgact aaaccattgt gcattctaga gtgcatatat   1680

ttatattttg cctgttaaaa agaaagtgag cagtgttagc ttagttctct tttgatgtag   1740

gttattatga ttagctttgt cactgtttca ctactcagca tggaaacaag atgaaattcc   1800

atttgtaggt agtgagacaa aattgatgat ccattaagta aacaataaaa gtgtccattg   1860

aaaccgtgat tttttttttt ttcctgtcat actttgttag gaagggtgag aatagaatct   1920

tgaggaacgg atcagatgtc tatattgctg aatgcaagaa gtggggcagc agcagtggag   1980

agatgggaca attagataaa tgtccattct ttatcaaggg cctactttat ggcagacatt   2040

gtgctagtgc ttttattcta acttttattt ttatcagtta cacatgatca taatttaaaa   2100

agtcaaggct tataacaaaa aagccccagc ccattcctcc cattcaagat tcccactccc   2160

cagaggtgac cactttcaac tcttgagttt ttcaggtata tacctccatg tttctaagta   2220

atatgcttat attgttcact tctttttttt ttattttta aagaaatcta tttcatacca   2280

tggaggaagg ctctgttcca catatatttc cacttcttca ttctctcggt atagttttgt   2340

cacaattata gattagatca aaagtctaca taactaatac agctgagcta tgtagtatgc   2400

tatgattaaa tttacttatg taaaaaaaaa aaaaaaaaa                         2439
```

<210> SEQ ID NO 59
<211> LENGTH: 1196

<212> TYPE: DNA
<213> ORGANISM: Homo sapiens

<400> SEQUENCE: 59
cacttctgcc gcccctgttt caagggataa gaaaccctgc gacaaaacct cctccttttc 60
caagcggctg ccgaagatgg cggaggtgca ggtcctggtg cttgatggtc gaggccatct 120
cctgggccgc ctggcggcca tcgtggctaa acaggtactg ctgggccgga aggtggtggt 180
cgtacgctgt gaaggcatca acatttctgg caatttctac agaaacaagt tgaagtacct 240
ggctttcctc cgcaagcgga tgaacaccaa cccttcccga ggcccctacc acttccgggc 300
ccccagccgc atcttctggc ggaccgtgcg aggtatgctg ccccacaaaa ccaagcgagg 360
ccaggccgct ctggaccgtc tcaaggtgtt tgacggcatc ccaccgccct acgacaagaa 420
aaagcggatg gtggttcctg ctgccctcaa ggtcgtgcgt ctgaagccta caagaaagtt 480
tgcctatctg gggcgcctgg ctcacgaggt tggctggaag taccaggcag tgacagccac 540
cctggaggag aagaggaaag agaaagccaa gatccactac cggaagaaga aacagctcat 600
gaggctacgg aaacaggccg agaagaacgt ggagaagaaa attgacaaat acacagaggt 660
cctcaagacc cacggactcc tggtctgagc ccaataaaga ctgttaattc ctcatgcgtt 720
gcctgccctt cctccattgt tgccctggaa tgtacgggac ccaggggcag cagcagtcca 780
ggtgccacag gcagccctgg gacataggaa gctgggagca aggaaagggt cttagtcact 840
gcctcccgaa gttgcttgaa agcactcgga gaattgtgca ggtgtcattt atctatgacc 900
aataggaaga gcaaccagtt actatgagtg aaagggagcc agaagactga ttggagggcc 960
ctatcttgtg agtggggcat ctgttggact ttccacctgg tcatatactc tgcagctgtt 1020
agaatgtgca agcacttggg gacagcatga gcttgctgtt gtacacaggg tatttctaga 1080
agcagaaata gactgggaag atgcacaacc aaggggttac aggcatcgcc catgctcctc 1140
acctgtattt tgtaatcaga aataaattgc ttttaaagaa aaaaaaaaaa aaaaaa 1196

<210> SEQ ID NO 60
<211> LENGTH: 987
<212> TYPE: DNA
<213> ORGANISM: Homo sapiens

<400> SEQUENCE: 60
aatataagtg gaggcgtcgc gctggcgggc attcctgaag ctgacagcat tcgggccgag 60
atgtctcgct ccgtggcctt agctgtgctc gcgctactct ctctttctgg cctggaggct 120
atccagcgta ctccaaagat tcaggtttac tcacgtcatc cagcagagaa tggaaagtca 180
aatttcctga attgctatgt gtctgggttt catccatccg acattgaagt tgacttactg 240
aagaatggag agagaattga aaaagtggag cattcagact tgtctttcag caaggactgg 300
tctttctatc tcttgtacta cactgaattc acccccactg aaaaagatga gtatgcctgc 360
cgtgtgaacc atgtgacttt gtcacagccc aagatagtta agtgggatcg agacatgtaa 420
gcagcatcat ggaggtttga agatgccgca tttggattgg atgaattcca aattctgctt 480
gcttgctttt taatattgat atgcttatac acttacactt tatgcacaaa atgtagggtt 540
ataataatgt taacatggac atgatcttct ttataattct actttgagtg ctgtctccat 600
gtttgatgta tctgagcagg ttgctccaca ggtagctcta ggagggctgg caacttagag 660
gtggggagca gagaattctc ttatccaaca tcaacatctt ggtcagattt gaactcttca 720
atctcttgca ctcaaagctt gttaagatag ttaagcgtgc ataagttaac ttccaattta 780

```
catactctgc ttagaatttg ggggaaaatt tagaaatata attgacagga ttattggaaa    840

tttgttataa tgaatgaaac attttgtcat ataagattca tatttacttc ttatacattt    900

gataaagtaa ggcatggttg tggttaatct ggtttatttt tgttccacaa gttaaataaa    960

tcataaaact tgatgtgtta tctctta                                        987
```

<210> SEQ ID NO 61
<211> LENGTH: 3003
<212> TYPE: DNA
<213> ORGANISM: Homo sapiens

<400> SEQUENCE: 61

```
ctttctcctt ccccttcttc cgggctcccg tcccggctca tcacccggcc tgtggcccac     60

tcccaccgcc agctggaacc ctggggacta cgacgtccct caaaccttgc ttctaggaga    120

taaaaagaac atccagtcat ggataaaaat gagctggttc agaaggccaa actggccgag    180

caggctgagc gatatgatga catggcagcc tgcatgaagt ctgtaactga gcaaggagct    240

gaattatcca atgaggagag gaatcttctc tcagttgctt ataaaaatgt tgtaggagcc    300

cgtaggtcat cttggagggt cgtctcaagt attgaacaaa agacggaagg tgctgagaaa    360

aaacagcaga tggctcgaga atacagagag aaaattgaga cggagctaag agatatctgc    420

aatgatgtac tgtctctttt ggaaaagttc ttgatcccca atgcttcaca agcagagagc    480

aaagtcttct atttgaaaat gaaaggagat tactaccgtt acttggctga ggttgccgct    540

ggtgatgaca agaaagggat tgtcgatcag tcacaacaag cataccaaga agcttttgaa    600

atcagcaaaa aggaaatgca accaacacat cctatcagac tgggtctggc ccttaacttc    660

tctgtgttct attatgagat tctgaactcc ccagagaaag cctgctctct tgcaaagaca    720

gcttttgatg aagccattgc tgaacttgat acattaagtg aagagtcata caaagacagc    780

acgctaataa tgcaattact gagagacaac ttgacattgt ggacatcgga tacccaagga    840

gacgaagctg aagcaggaga aggaggggaa aattaaccgg ccttccaact tttgtctgcc    900

tcattctaaa atttacacag tagaccattt gtcatccatg ctgtcccaca aatagttttt    960

tgtttacgat ttatgacagg tttatgttac ttctatttga atttctatat ttcccatgtg   1020

gtttttatgt ttaatattag gggagtagag ccagttaaca tttagggagt tatctgtttt   1080

catcttgagg tggccaatat ggggatgtgg aatttttata caagttataa gtgtttggca   1140

tagtactttt ggtacattgt ggcttcaaaa gggccagtgt aaaactgctt ccatgtctaa   1200

gcaaagaaaa ctgcctacat actggtttgt cctggcgggg aataaaaggg atcattggtt   1260

ccagtcacag gtgtagtaat tgtgggtact ttaaggtttg gagcacttac aaggctgtgg   1320

tagaatcata ccccatggat accacatatt aaaccatgta tatctgtgga atactcaatg   1380

tgtacacctt tgactacagc tgcagaagtg ttcctttaga caaagttgtg acccatttta   1440

ctctggataa gggcagaaac ggttcacatt ccattatttg taaagttacc tgctgttagc   1500

tttcattatt tttgctacac tcattttatt tgtatttaaa tgttttaggc aacctaagaa   1560

caaatgtaaa agtaaagatg caggaaaaat gaattgcttg gtattcatta cttcatgtat   1620

atcaagcaca gcagtaaaac aaaaacccat gtatttaact ttttttagg atttttgctt    1680

ttgtgatttt ttttttttg atacttgcct aacatgcatg tgctgtaaaa atagttaaca     1740

gggaaataac ttgagatgat ggctagcttt gtttaatgtc ttatgaaatt ttcatgaaca   1800

atccaagcat aattgttaag aacacgtgta ttaaattcat gtaagtggaa taaaagtttt   1860

atgaatggac ttttcaacta ctttctctac agcttttcat gtaaattagt cttggttctg   1920
```

```
aaacttctct aaaggaaatt gtacattttt tgaaatttat tccttattcc ctcttggcag   1980

ctaatgggct cttaccaagt ttaaacacaa aatttatcat aacaaaaata ctactaatat   2040

aactactgtt tccatgtccc atgatcccct ctcttcctcc ccaccctgaa aaaaatgagt   2100

tcctattttt tctgggagag ggggggattg attagaaaaa aatgtagtgt gttccattta   2160

aaattttggc atatggcatt ttctaactta ggaagccaca atgttcttgg cccatcatga   2220

cattgggtag cattaactgt aagttttgtg cttccaaatc actttttggt ttttaagaat   2280

ttcttgatac tcttatagcc tgccttcaat tttgatcctt tattctttct atttgtcagg   2340

tgcacaagat taccttcctg ttttagcctt ctgtcttgtc accaaccatt cttacttggt   2400

ggccatgtac ttggaaaaag gccgcatgat ctttctggct ccactcagtg tctaaggcac   2460

cctgcttcct ttgcttgcat cccacagact atttccctca tcctatttac tgcagcaaat   2520

ctctccttag ttgatgagac tgtgtttatc tccctttaaa accctaccta tcctgaatgg   2580

tctgtcattg tctgccttta aaatccttcc tctttcttcc tcctctattc tctaaataat   2640

gatggggcta agttataccc aaagctcact ttacaaaata tttcctcagt actttgcaga   2700

aaacaccaaa caaaaatgcc attttaaaaa aggtgtattt tttcttttag aatgtaagct   2760

cctcaagagc agggacaatg ttttctgtat gttctattgt gcctagtaca ctgtaaatgc   2820

tcaataaata ttgatgatgg gaggcagtga gtcttgatga taagggtgag aaactgaaat   2880

cccaaacact gttttgttgc ttgttttatt atgacctcag attaaattgg gaaatattgg   2940

ccctttttgaa taattgtccc aaatattaca ttcaaataaa agtgcaatgg agaaaaaaaa   3000

aaa                                                                 3003
```

<210> SEQ ID NO 62
<211> LENGTH: 2803
<212> TYPE: DNA
<213> ORGANISM: Homo sapiens

<400> SEQUENCE: 62

```
actgcagccc cgctcgactc cggcgtggtg cgcaggcgcg gtatccccccc tcccccgcca     60

gctcgacccc ggtgtggtgc gcaggcgcag tctgcgcagg gactggcggg actgcgcggc    120

ggcaacagca gacatgtcgg gggtccgggg cctgtcgcgg ctgctgagcg ctcggcgcct    180

ggcgctggcc aaggcgtggc caacagtgtt gcaaacagga acccgaggtt ttcacttcac    240

tgttgatggg aacaagaggg catctgctaa agtttcagat tccatttctg ctcagtatcc    300

agtagtggat catgaatttg atgcagtggt ggtaggcgct ggaggggcag gcttgcgagc    360

tgcatttggc ctttctgagg cagggtttaa tacagcatgt gttaccaagc tgtttcctac    420

caggtcacac actgttgcag cacagggagg aatcaatgct gctctgggga acatggagga    480

ggacaactgg aggtggcatt tctacgacac cgtgaagggc tccgactggc tgggggacca    540

ggatgccatc cactacatga cggagcaggc ccccgccgcc gtggtcgagc tagaaaatta    600

tggcatgccg tttagcagaa ctgaagatgg gaagatttat cagcgtgcat ttggtggaca    660

gagcctcaag tttggaaagg gcgggcaggc ccatcggtgc tgctgtgtgg ctgatcggac    720

tggccactcg ctattgcaca ccttatatgg aaggtctctg cgatatgata ccagctattt    780

tgtggagtat tttgccttgg atctcctgat ggagaatggg gagtgccgtg gtgtcatcgc    840

actgtgcata gaggacgggt ccatccatcg cataagagca aagaacactg ttgttgccac    900

aggaggctac gggcgcacct acttcagctg cacgtctgcc cacaccagca ctggcgacgg    960
```

```
cacggccatg atcaccaggg caggccttcc ttgccaggac ctagagtttg ttcagttcca   1020

ccctacaggc atatatggtg ctggttgtct cattacggaa ggatgtcgtg gagagggagg   1080

cattctcatt aacagtcaag gcgaaaggtt tatggagcga tacgcccctg tcgcgaagga   1140

cctggcgtct agagatgtgg tgtctcggtc catgactctg gagatccgag aaggaagagg   1200

ctgtggccct gagaaagatc acgtctacct gcagctgcac cacctacctc cagagcagct   1260

ggccacgcgc ctgcctggca tttcagagac agccatgatc ttcgctggcg tggacgtcac   1320

gaaggagccg atccctgtcc tccccaccgt gcattataac atgggcggca ttcccaccaa   1380

ctacaagggg caggtcctga ggcacgtgaa tggccaggat cagattgtgc ccggcctgta   1440

cgcctgtggg gaggccgcct gtgcctcggt acatggtgcc aaccgcctcg ggcaaactc    1500

gctcttggac ctggttgtct ttggtcgggc atgtgccctg agcatcgaag agtcatgcag   1560

gcctggagat aaagtccctc caattaaacc aaacgctggg gaagaatctg tcatgaatct   1620

tgacaaattg agatttgctg atggaagcat aagaacatcg gaactgcgac tcagcatgca   1680

gaagtcaatg caaaatcatg ctgccgtgtt ccgtgtggga agcgtgttgc aagaaggttg   1740

tgggaaaatc agcaagctct atggagacct aaagcacctg aagacgttcg accggggaat   1800

ggtctggaac acggacctgg tggagaccct ggagctgcag aacctgatgc tgtgtgcgct   1860

gcagaccatc tacggagcag aggcacggaa ggagtcacgg ggcgcgcatg ccagggaaga   1920

ctacaaggtg cggattgatg agtacgatta ctccaagccc atccaggggc aacagaagaa   1980

gccctttgag gagcactgga ggaagcacac cctgtcctat gtggacgttg gcactgggaa   2040

ggtcactctg gaatatagac ccgtgatcga caaaactttg aacgaggctg actgtgccac   2100

cgtcccgcca gccattcgct cctactgatg agacaagatg tggtgatgac agaatcagct   2160

tttgtaatta tgtataatag ctcatgcatg tgtccatgtc ataactgtct tcatacgctt   2220

ctgcactctg gggaagaagg agtacattga agggagattg gcacctagtg gctgggagct   2280

tgccaggaac ccagtggcca gggagcgtgg cacttacctt tgtcccttgc ttcattcttg   2340

tgagatgata aaactgggca cagctcttaa ataaaatata aatgaacaaa ctttctttta   2400

tttccaaatc catttgaaat attttactgt tgtgacttta gtcatatttg ttgacctaaa   2460

aatcaaatgt aatctttgta ttgtgttaca tcaaaatcca gatattttgt atagtttctt   2520

ttttctttt ctttctttt ttttttga gacaggatcg gtgcagtagt acaatcacag   2580

ctcactgcag cctcaaactc ctgggcagct caggtgatct tcctgactca gccttctgag   2640

tagttggggc tacaggtgtg caccaccatg cccagctcat ttattttgta attgtaggga   2700

cagggtctca ctgtgttgcc taggctggtc tcaagtgatc ctccctcctt ggcctcccaa   2760

ggtgctggaa ttataggtgt gaacaaacca aaaaaaaaaa aaa                      2803
```

```
<210> SEQ ID NO 63
<211> LENGTH: 1435
<212> TYPE: DNA
<213> ORGANISM: Homo sapiens

<400> SEQUENCE: 63

ggcggggcct gcttctcctc agcttcaggc ggctgcgacg agccctcagg cgaacctctc     60

ggctttcccg cgcggcgccg cctcttgctg cgcctccgcc tcctcctctg ctccgccacc    120

ggcttcctcc tcctgagcag tcagcccgcg cgccggccgg ctccgttatg gcgacccgca    180

gccctggcgt cgtgattagt gatgatgaac caggttatga ccttgattta ttttgcatac    240

ctaatcatta tgctgaggat ttggaaaggg tgtttattcc tcatggacta attatggaca    300
```

```
ggactgaacg tcttgctcga gatgtgatga aggagatggg aggccatcac attgtagccc    360
tctgtgtgct caaggggggc tataaattct ttgctgacct gctggattac atcaaagcac    420
tgaatagaaa tagtgataga tccattccta tgactgtaga ttttatcaga ctgaagagct    480
attgtaatga ccagtcaaca ggggacataa aagtaattgg tggagatgat ctctcaactt    540
taactggaaa gaatgtcttg attgtggaag atataattga cactggcaaa acaatgcaga    600
ctttgctttc cttggtcagg cagtataatc caaagatggt caaggtcgca agcttgctgg    660
tgaaaaggac cccacgaagt gttggatata agccagactt tgttggattt gaaattccag    720
acaagtttgt tgtaggatat gcccttgact ataatgaata cttcagggat ttgaatcatg    780
tttgtgtcat tagtgaaact ggaaaagcaa aatacaaagc ctaagatgag agttcaagtt    840
gagtttggaa acatctggag tcctattgac atcgccagta aaattatcaa tgttctagtt    900
ctgtggccat ctgcttagta gagctttttg catgtatctt ctaagaattt tatctgtttt    960
gtactttaga aatgtcagtt gctgcattcc taaactgttt atttgcacta tgagcctata   1020
gactatcagt tccctttggg cggattgttg tttaacttgt aaatgaaaaa attctcttaa   1080
accacagcac tattgagtga aacattgaac tcatatctgt aagaaataaa gagaagatat   1140
attagttttt taattggtat tttaattttt atatatgcag gaaagaatag aagtgattga   1200
atattgttaa ttataccacc gtgtgttaga aaagtaagaa gcagtcaatt ttcacatcaa   1260
agacagcatc taagaagttt tgttctgtcc tggaattatt ttagtagtgt ttcagtaatg   1320
ttgactgtat tttccaactt gttcaaatta ttaccagtga atctttgtca gcagttccct   1380
tttaaatgca aatcaataaa ttcccaaaaa tttaaaaaaa aaaaaaaaaa aaaaa        1435
```

<210> SEQ ID NO 64
<211> LENGTH: 4476
<212> TYPE: DNA
<213> ORGANISM: Homo sapiens

<400> SEQUENCE: 64

```
agcagagaga acacacgtcc ttgcggaagt gacggcagtt ccgagtccag tgggggcggt     60
gggagcgatg agggtctgag acggtgggag cggttgtgtg aagatggaga cattccatac    120
accaagcttg ggtgatgagg aatttgaaat cccacctatc tccttggatt ctgatccctc    180
attggctgtc tcagatgtgg ttggccactt tgatgacctg gcagaccctt cctcttcaca    240
ggatggcagt tttcagccc agtatggggt ccagacattg gacatgcctg tgggcatgac    300
ccatggcttg atggagcagg gcggggggct cctgagtggg ggcttgacca tggacttgga    360
ccactctata ggaactcagt atagtgccaa cccacctgtt acaattgatg taccaatgac    420
agacatgaca tctggcttga tggggcatag ccagttgacc accattgatc agtcagaact    480
gagttcccag ctgggtttga gcctaggggg tggcaccatc ctgccacctg cccagtcacc    540
tgaagatcgt ctttcaacca ccccttcacc tactagttca cttcacgagg atggtgttga    600
ggatttccgg aggcaacttc ccagccagaa gacagtcgtg gtggaagcag ggaaaaagca    660
gaaggcccca aagaagagaa aaaagaaaga tcctaatgaa cctcagaaac cagtttcagc    720
atatgcttta ttctttcgtg atacacaggc tgccatcaag ggacagaatc ctaatgccac    780
ttttggtgag gtttcaaaaa ttgtggcctc catgtgggat agtcttggag aggagcaaaa    840
acaggtatat aagaggaaaa ctgaggctgc caagaaagag tatctgaagg cactggctgc    900
ttacaaagac aaccaggagt gtcaggccac tgtggaaaca gtggaattgg atccagcacc    960
```

```
accatcacaa actccttctc cacctcctat ggctactgtt gacccagcat ctccagcacc   1020
agcttcaata gagccccctg ccctgtcccc atccattgtt gttaactcca ccctttcatc   1080
ctatgtggca aaccaggcat cttctggagc tgggggtcag cccaatatca ccaagttgat   1140
tattaccaaa caaatgttgc cctcttctat tactatgtct caaggaggga tggttactgt   1200
tatcccagcc acagtggtga cctcccgggg gctccaacta ggccaaacca gtacagctac   1260
tatccagccc agtcaacaag cccagattgt cactcggtca gtgttgcagg cagcagcagc   1320
tgctgctgct gctgcttcta tgcaactgcc tccaccccga ctacagcccc ctccattaca   1380
acagatgcca cagcccccga ctcagcagca agttaccatt ctgcagcagc ctcctccact   1440
ccaggccatg caacagcctc cacctcagaa agttcgaatc aatttacagc aacagcctcc   1500
tcctctgcag atcaagagtg tgcctctacc cactttgaaa atgcagacta ccttagtccc   1560
accaactgtg gaaagtagtc ctgagcggcc tatgaacaac agccctgagg cccatacagt   1620
ggaggcacct tctcctgaga ctatctgtga gatgatcaca gatgtagttc ctgaggttga   1680
gtctccttct cagatggatg ttgaattggt gagtgggtct cctgtggcac tctcacccca   1740
gcctcgatgt gtgaggtctg gttgtgagaa ccctcccatt gtgagtaagg actgggacaa   1800
tgaatactgc agcaatgagt gtgtggtgaa gcactgcagg gatgtattct tggcctgggt   1860
agcctctaga aattcaaaca cagtggtgtt tgtgaaatag tccttcctgt tctccaagcc   1920
agtgaagagt tatctgctgg gaaagtgtcc aagagcctgt ttttgaaaca caagctgggc   1980
ttctggtagt gcctcatcac aacccatgat ggctgttcat gtttcacccc ttttcttcct   2040
tcagcagagg ccaggctatg gagcagggcc actgaatttg ctgtaatctg gagatgcttt   2100
ttactttcaa ccataagcgg taatagcaga ggaaagggtg aagggagtct gggcaagcaa   2160
agcatagaga tggtggggtg gtggtggggt tgaagaaact tgttggtata attgtcatag   2220
gacttgccta aaatattatt aaaattacgg gagtgtactc agctttgagc ctaggagaaa   2280
atgccactgt gtgcatccat tttaaagggt tccctcataa aaaaatgtta ttccccatta   2340
tcacatcagt acactgcttt gaaaacaaaa cttttcaaca tgggcatact gggctacatg   2400
gaaaatgaca tcacccagga gtgatttctc tttatatata ttatttctgc agttaccatc   2460
cttatctgag ttatcacagt tcatgaatct aagaggcgga actctacatc attagtaaga   2520
ggttccacca aagtctaaag ttgtattcac ttgtgtttga tgaactatct ttaaaagacc   2580
ataggtctat cattatttct tagacataat ctaaagaaaa acagactaga gaagccacct   2640
ggttgtaaca gaataagcag aagtttacag catgatagtc caagtggtga taactttaaa   2700
taaaactcaa atttttactg tttgtagaca ggaatgctgt cctagagaac ctcctcctca   2760
accagctacg tacatagttt tatcctatgc attcctgttt tctgtgtgtt ttttgttttt   2820
ttttttttt tttttttttg agacagagtc tcgctctgtc acccaggctg gagtgcagtg   2880
gtgcgacctc agctcactga aacctctgcc tcccgggttc aagcgattct cctgcatcag   2940
cctcccgagt agctaggatt acaggcgccc gccactacgc ccagctaatt tgtggtattt   3000
ttagtagaga cagggtttca ccatgttggc caggctggtc tcgaactcct gacctcatga   3060
tccgcccgcc ttgacctccc aaagtgctgg gattacaggc atgagccacc gcacccagcc   3120
tgcattcctg tttttttaat ggttttggag ggtagcagta gagatggggt ctcactatgt   3180
tgcccagtct agtcttgaac tcctgggcta cagttaccct cctacctcgg cttcccaaag   3240
tgctcggatt acaggtgtga gccactgtgc ctagcctata atgatcattt taatgtttcc   3300
catgcactca tttagtttga accttcacag caacccaatg aggtaatact cccatttcac   3360
```

```
atataatact gagagatgag ttgcacaaga ttatacactg ttaagtagca gagccagaat   3420

ggacttcaga atcccaacta caatacaaat gtttatttaa ataaagaaga aagctattgt   3480

acaaatatca ctcttcaggt ttagcttaca gagccatggc tatggattct tagctctgta   3540

aggaagtgct tctataaatt cttaggttta gagatgatac catctgggta cctttgcttg   3600

aaccgtgcaa ccacatctgg gtctagtagg tggatcccat ccagttggtt tccaagggtg   3660

atcctgaaac agtgtaaaag gaggggcaaa ccagaaatcc tggaattaga gggtttaata   3720

ttgttaaaaa atgcatacca aatgaagact gcctatcatc atatcaaata tgccaattct   3780

aaaaagagct taacattaga atagtatatg gtagaattac tagttcagaa ttggcataga   3840

ttctggtgtt aaaatagact ggatctgtat tatctgaggg ttagtaacta atgcttagcc   3900

aggcctgctt cacagagttg ctaccaggga gtattctttg gataagcaaa atgctagcag   3960

catgtgtttt aagctctgtt aaggggtgaa agatgtaatt attgacagat taaatagata   4020

acttcgtaac caccaggggg cagattcaat acatcacaga atggctgagg aagatccttg   4080

ggttgtgaag agagtagaaa ccctagggag cagtgctttt gggtcctaga acctgttgag   4140

tttctaatga atatttgtag aatctcataa aacagtttaa atacaagctt aagtggctta   4200

tgaatcctgt gaagctcatt tatggactag tgtaaaacaa tgtgaagctc tactaagttc   4260

tgtccttaat cataaataat agccccttga ggactagcct gttctctggt caccttacca   4320

gttgggttgc acattgtgtg gtcgtccaaa taactcaatc ttgcgagtgc caggagatag   4380

tctttcaatc atgccataga tttcatctgg tttatgactg gtggaacgaa cctaggaaat   4440

aaaaactagc tgcttttttaa gttacacaag aaaaaa                             4476
```

<210> SEQ ID NO 65
<211> LENGTH: 4814
<212> TYPE: DNA
<213> ORGANISM: Homo sapiens

<400> SEQUENCE: 65

```
cttcgtgcca cgtcaccgcc tgcgtcgctt ccggaggcgc agcgggcgat gacgtagagg     60

gacgtgccct ctatatgagg ttggggagcg gctgagtcgg ccttttccgc ccgctccccc    120

ctccccccga gcgccgctcc ggctgcaccg cgctcgctcc gagtttcagg ctcgtgctaa    180

gctagcgccg tcgtcgtctc ccttcagtcg ccatcatgat tatctaccgg gacctcatca    240

gccacgatga gatgttctcc gacatctaca agatccggga gatcgcggac gggttgtgcc    300

tggaggtgga ggggaagatg gtcagtagga cagaaggtaa cattgatgac tcgctcattg    360

gtggaaatgc ctccgctgaa ggccccgagg gcgaaggtac cgaaagcaca gtaatcactg    420

gtgtcgatat tgtcatgaac catcacctgc aggaaacaag tttcacaaaa gaagcctaca    480

agaagtacat caaagattac atgaaatcaa tcaaagggaa acttgaagaa cagagaccag    540

aaagagtaaa accttttatg acaggggctg cagaacaaat caagcacatc cttgctaatt    600

tcaaaaacta ccagttcttt attggtgaaa acatgaatcc agatggcatg gttgctctat    660

tggactaccg tgaggatggt gtgaccccat atatgatttt ctttaaggat ggtttagaaa    720

tggaaaaatg tgatgcaaaa gaaagaaatc cctgcgcttt ctgtctgtct ttgtggcggc    780

ccagattgaa ttggggaata catctttagc ctggaaatgt aggctgcatg ttaatggtaa    840

tgtaactttt gcagtgtaat gtttgaaaaa tattaatgta gtttttgctt ttacagtaac    900

aaatgtggca attattttgg atctatcacc tgtcatcata actggcttct gcttgtcatc    960
```

```
cacacaacac caggacttaa gacaaatggg actgatgtca tcttgagctc ttcatttatt   1020
ttgactgtga tttatttgga gtggaggcat tgtttttaag aaaaacatgt catgtaggtt   1080
gtctaaaaat aaaatgcatt taaactcatt tgagagaatg ccttttagtt taatgcatat   1140
ttaaactaaa ttgatcctgt agtgttcctg gagaagctag agcctgattg taggctacta   1200
ctcatcaatt aacttctaca gtggagacta cttctgggac tggaatataa aaaagaatca   1260
aaggttctga ttttgagttg caataaaggg aaagaccatg ctcatagcag tgccaacatc   1320
tgaagtgtgg agccttaccc atttcatcac ctacaacgga agtagttaac tggaagagat   1380
taccaagaga ataaaaagag actcattcag tggaagcaac tttgtctcag cttatttcac   1440
ataaagagag cgaagtcttt tgggatgaat gttaattaaa ctccctggta actagaacag   1500
ggactggcaa actagcctat ctgaccacct gttttgtaca ctttaaggtg gttggttgcc   1560
tttttaaatg gttgagggga aaagaatacc ttgtgggata tggaatttaa gttcgagtcc   1620
agttttattg gaacgtggct atgcttattc atttatggat tgactgtggc tgttgtcagt   1680
gcatgagcag agttgtgtct aacagactag agcctgcaag tttgccagcc cctgatttaa   1740
aagatgaagg tacacagaat gtgggctggc tggtgggcaa aggggtaaaa atgttctcta   1800
tattgtatct gaaaagatgg ggtgtctgaa taagaaaatg catctatttg acagacctgg   1860
agcagttgct atctgctgct atggtttcca ccacagatgc aagaagaaca tgtccttgcg   1920
ctttccgtct gtctaattgt ggcagctgag attgaataga ggaatacagg aggaaaaaaa   1980
gcgggaagag tttttgaggc aggtcggtca cccaggcttg tagtgcagtg gcacaagcaa   2040
ctcactgcat tctctgcatc ctgtgctcaa gccattttcc cacctcagtc tcactagttg   2100
ctgggactgc aggcatgcac ccctatgccc agctaatttt tgtagagacc gagtatcgct   2160
tagttgccca gggtggtctc aactcctggg ctcaaggaga tctgcccacc tcagcctccc   2220
aaagtgcagg cctagcctgg gaggggaatt ttcaaaacgt gagttttggg aaatagtcta   2280
tcagccttac ctggttgatt acacttgtaa aagaaagatt aaaagcaggc cagtgactct   2340
ggtctgcttg aacatgtgaa tgtagtggtt tgagcaatct ggagtttgcc ctagtgtcaa   2400
attccagact gtccatagtg tccaaaacct gaggcagata ctaatgttaa cccccagcac   2460
cccgtgattg gaaacaaacc taaatacgta ttgggaactt aatagcaatt ttaagcattc   2520
tgatagattt tttgtaggga tggggtcatg ccatgtggcc caggctggtc tgaaaactct   2580
ggcctcaagt gatctcaagc tttggccttc taaagtgttg ggattacagg tgtgaggcat   2640
tgcacctggc ttagcgttct gatttgacat tgtaatgaaa agtgtgagtc tcatctacag   2700
ggccttttgt cctctgaaat gatagcagga agggaatttt caggcagtgg tcaaagctgg   2760
ggaaaccagg atagtgaaga aggccttgag gtgagagatg gaagctaatt ggtgaactag   2820
ccttggaagc ctgaaacaga caagtagcaa ttcagagact ttgtgggctc cactgctcca   2880
acttgttttg aagattttca gttctgcaga agaggtattt ccccagttgt cctttcagtg   2940
ctcttagctg ttttcccaac atccagatcc aatcaaggct gggacatagc attttatcat   3000
gtctatttaa gtcagaagtg atgaacccca gctgtttacc tcatggtaaa cctttgaaga   3060
ttccaggtag aatcttctca gactttgaag actgtctcat tttatatctt tttctcgtta   3120
ttcctagggt caagacgttt tggcaagaa taaggatgtg aacatcagaa agctcataac   3180
attttgtttt tgatgctaag tttaacaaag gcatgcttta gtagcctgtg ggccctaggg   3240
tttgttaaag tgtggagaac aactgagtgg agcaagagga cttttctagg aaggtccttg   3300
taatgtgaca tttgaaaaca aatgaaggtg tggaagtagg ccatgtggat atcaggacaa   3360
```

```
accattccag gccaagacaa cagcagttag tctggagtgt gatgtgttct gggaaaaaag   3420

tggccacttt gctaacccaa gaagacagga agggttgtaa agcagtggga gtgtgcaagg   3480

aaggaagacc agacctcaag gaaaccacag gcgctctgag cagaagagtt acatgatatg   3540

actcaaattt ttaaaggatc actttggctg ccaggtggca gggtaaaagc atagaataat   3600

tgtgtataat gtgtttttaa ggcaaagata gtggcttagt ctagggtagt agactgaggt   3660

ggtaggaaat gaagatagag acaacaggat atgctggtgg gtgaggatgg atttaatgtt   3720

gatacaagta ttttggtctg agcgtttgga agaaagttgg cactgaggtg ggaagtcgag   3780

tttagttttg ttagttttgg atgtgttaag tttgagatgc tgattcttca gagaagtcta   3840

agctggagaa ctatatagag agtggaaaga taacaataga cattgaaagc catgatacag   3900

gataaggtca tttggagaga ggatagactg cattccaaca tgagattggt tgacaaagag   3960

aaaccaacaa aggtaattaa gaggtgctcc cactgcactt gtactcagaa ggctgaggta   4020

ggattgttag aggccagcct gggcaccaca gggagacccc atctctaaaa tttagccagg   4080

aaccatggct catgcctgta gccccaggaa tttgggaggc tgagtgggga ggatcgcttg   4140

aggtcaggag tttgagacca gcctgggcaa catagggaga cctaaaaaaa ttaattgggc   4200

atctgtagtc ccagctactc aggcggctga gctgagagga tggcttgagt ccgagagatt   4260

gagggtgcag tgagctgtga tcataccact gcactccagc ctgggcggca gtgagacact   4320

atctgaaaaa agtttaaaaa ttttaaaaaa gaaggaactg cccctgaggt aagaaccaag   4380

ggagggcctc ccagaggtca ggtggaaaaa gttttaggaa ggaggaagta gtcaacaggg   4440

ttacctgttg caaagtactt aagtaatatg aggcctgata gtggtaaact tgactaccgt   4500

tggatttcac tagtgggaaa ggaagtctaa ttaaaatgca ctcaagagac taacagtcgc   4560

aggcatgaaa tacaatacag gtacatggtt ttttattatg tgtgcatctg cttcagtaat   4620

aggtgtgaat tactcatttg gatcattagg agtttcaaaa tctagttaaa tgactagatt   4680

tttgttgatg taaattctgt cattctgaac tgcagggatt gtcagtaact taactgcaaa   4740

ctaaactggt gataattatg gtaaaattgc aagacgagca ataaatctca accaacttga   4800

gagaacactg ataa                                                     4814
```

METHODS FOR PROSTATE CANCER DETECTION AND TREATMENT

CROSS-REFERENCE TO RELATED APPLICATIONS

This application claims priority to, and the benefit of, U.S. Provisional Application No. 62/633,675, filed Feb. 22, 2018, the contents of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Feb. 19, 2019, is named "LBIO-005_001US_SeqList.txt" and is 299 KB in size.

FIELD OF THE INVENTION

The present invention relates to prostate cancer detection.

BACKGROUND OF THE INVENTION

Prostate cancer (PCA) is the fourth most commonly diagnosed cancer worldwide and the second most common cancer in men. Although the incidence and prevalence have been decreasing, 200,000 men will be diagnosed in the USA with PCA annually. Multiple factors including age and family history, genetic susceptibility and ethnicity all contribute to the high incidence of the disease. While 90% of PCA are diagnosed while they are localized (non-disseminated), the clinical behavior of tumors is highly variable and ranges from indolence that can be monitored through watchful waiting or active surveillance (e.g., biomarkers and 6 monthly digital rectal examination) to malignant evolution and androgen-resistant disease, metastatic dissemination and death.

Multiple risk stratification systems have been developed that combines clinical data and pathological information e.g., Gleason score. These, including the more recently developed next generation tools, are only ~70% accurate for predicting outcome.

Molecular genetic information is increasingly being used to inform pathology and better subtype cancers. This information has been used as both prognostic tools as well as to stratify patients for different therapeutic interventions. Prostate cancers have been examined and mutations, DNA copy number alterations, rearrangements and gene fusions have all been identified. These may correlate with some pathological features. For example, low-Gleason tumors have few DNA copy number alterations while high grade tumors exhibit significant genome-wide copy number alterations. Somatic point mutations in contrast are relatively uncommon with the frequency of mutations ranging from 1% (IDH 1) to 11% (SPOP). The most common abnormality is androgen-regulated fusions of ERG and other ETS family members (~50% of tumors). However, fusion-bearing tumors do not have a significantly different prognosis to fusion-negative tumors after prostatectomy. Androgen receptor variant 7 (AR-V7) in contrast is implicated in the progression to castration resistance prostate cancer (CRPC) and is considered potentially useful as a treatment selection biomarker. Overall, however, there is an incomplete understanding of the molecular mechanisms underpinning PCA pathogenesis and an absence of molecular-based biomarkers that can be used to predict sensitivity to therapeutic agents. Consequently, the development of diagnostic methods that more accurately define disease status, identify sensitivity to therapy and can ultimately be used to better monitor disease progression, is critical.

Surveillance remains a cornerstone approach to monitor PCA and detect recurrence at an early stage. After potentially curative resection, monitoring can be undertaken through measurement of blood biomarkers and/or imaging like CT to detect asymptomatic metastatic disease earlier. The current biomarker used for monitoring is prostate specific antigen (PSA) (also gamma-seminoprotein or kallikrein-3). This glycoprotein enzyme is encoded by the KLK3 gene and is secreted by epithelial cells in the prostate. It, however, is not a unique indicator of prostate cancer, but may also detect prostatitis or benign prostatic hyperplasia (BPH). Use of PSA in isolation results in either unnecessary biopsies for men without cancer or an under diagnosis of men with significant disease. This is based on the low sensitivity (20-40%) and specificity (70-90%) ranges with a consequent positive predictive value of only 25-40%. The United States Preventive Services Task Force (USPSTF) does not recommend PSA use for prostate cancer. PSA, however, is included in clinical nomograms e.g., the UCSF-CAPRA score for prostate cancer risk, which has some utility in predicting disease free survival after surgery.

There remains a need for biomarker-based tools to accurately diagnose PCA.

SUMMARY OF THE INVENTION

The present disclosure provides a method for detecting a prostate cancer in a subject in need thereof, the method comprising: determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; inputting each normalized expression level into an algorithm to generate a score; comparing the score with a first predetermined cutoff value; and identifying the presence of a prostate cancer in the subject when the score is equal to or greater than the first predetermined cutoff value or identifying the absence of a prostate cancer in the subject when the score is less than the first predetermined cutoff value.

The present disclosure provides a method for detecting a prostate cancer in a subject in need thereof, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) producing a report, wherein the report identifies the presence of a prostate cancer in the subject when the score is equal to or greater than the first predetermined cutoff value or identifies the absence of a prostate cancer in the subject when the score is less than the first predetermined cutoff value.

The present disclosure also provides a method for determining whether a prostate cancer in a subject is stable or progressive, the method comprising: determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; inputting each normalized expression level into an algorithm to generate a score; comparing the score with a first predetermined cutoff value; and identifying that the prostate cancer is progressive when the score is equal to or greater than the first predetermined cutoff value or identifying that the prostate cancer is stable when the score is less than the first predetermined cutoff value.

The present disclosure provides a method for determining whether a prostate cancer in a subject is stable or progressive, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCL1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) producing a report, wherein the report identifies that the prostate cancer is progressive when the score is equal to or greater than the first predetermined cutoff value or identifies that the prostate cancer is stable when the score is less than the first predetermined cutoff value.

The present disclosure also provides a method for determining whether a prostate cancer in a subject is low or high grade, the method comprising: determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; inputting each normalized expression level into an algorithm to generate a score; comparing the score with a first predetermined cutoff value; and identifying that the prostate cancer is high grade when the score is equal to or greater than the first predetermined cutoff value or identifying that the prostate cancer is low grade when the score is less than the first predetermined cutoff value.

The present disclosure provides a method for determining whether a prostate cancer in a subject is low or high grade, the method comprising: determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; inputting each normalized expression level into an algorithm to generate a score; comparing the score with a first predetermined cutoff value; and producing a report, wherein the report identifies that the prostate cancer is high grade when the score is equal to or greater than the first predetermined cutoff value or identifies that the prostate cancer is low grade when the score is less than the first predetermined cutoff value.

The present disclosure also provides a method for determining whether a prostate cancer in a subject is a low Gleason score (≤6) prostate cancer or a high Gleason score (≥7) prostate cancer, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) identifying that the prostate cancer is a high Gleason score prostate cancer when the score is equal to or greater than the first predetermined cutoff value or identifying that the prostate cancer is a low Gleason score prostate cancer when the score is less than the first predetermined cutoff value.

The present disclosure provides a method for determining whether a prostate cancer in a subject is a low Gleason score (≤6) prostate cancer or a high Gleason score (≥7) prostate cancer, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) producing a report, wherein the report identifies that the prostate cancer is a high Gleason score prostate cancer when the score is equal to or greater than the first predetermined cutoff value or identifies that the prostate cancer is a low Gleason score prostate cancer when the score is less than the first predetermined cutoff value.

The present disclosure also provides a method for determining the completeness of surgery in a subject having a prostate cancer, the method comprising: determining the expression level of at least 38 biomarkers from a test sample from the subject after the surgery by contacting the test sample with a plurality of agents specific to detect the expression of the at least 38 biomarkers, wherein the 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; inputting each normalized expression level into an algorithm to generate a score; comparing the score with a first predetermined cutoff value; and identifying that the prostate cancer is not completely removed when the score is equal to or greater than the first predetermined cutoff value or identifying that the prostate cancer is completely removed when the score is less than the first predetermined cutoff value.

The present disclosure provides a method for determining the completeness of surgery in a subject having a prostate cancer, the method comprising: (a) determining the expression level of at least 38 biomarkers from a test sample from the subject after the surgery by contacting the test sample with a plurality of agents specific to detect the expression of the at least 38 biomarkers, wherein the 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) producing a report, wherein the report identifies that the prostate cancer is not completely removed when the score is equal to or greater than the first predetermined cutoff value or identifies that the prostate cancer is completely removed when the score is less than the first predetermined cutoff value.

The present disclosure also provides a method for differentiating benign prostate hyperplasia from a prostate cancer in a subject having an enlarged prostate, the method comprising: determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; inputting each normalized expression level into an algorithm to generate a score; comparing the score with a first predetermined cutoff value; and identifying the presence of a prostate cancer in the subject when the score is equal to or greater than the first predetermined cutoff value or identifying the presence of benign prostate hyperplasia in the subject when the score is less than the first predetermined cutoff value.

The present disclosure provides a method for differentiating benign prostate hyperplasia from a prostate cancer in a subject having an enlarged prostate, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) producing a report, wherein the report identifies the presence of a prostate cancer in the subject when the score is equal to or greater than the first predetermined cutoff value or identifies the presence of benign prostate hyperplasia in the subject when the score is less than the first predetermined cutoff value.

The present disclosure provides a method for evaluating the response of a subject having a prostate cancer to a first therapy, the method comprising: (1) at a first time point: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf9, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a first score; (2) at a second time point, wherein the second time point is after the first time point and after the administration of the first therapy to the subject: (d) determining the expression level of the at least 38 biomarkers from a test sample from the subject by contacting the test sample with a plurality of agents specific to detect the expression of the at least 38 biomarkers; (e) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (f) inputting each normalized expression level into an algorithm to generate a second score; (3) comparing the first score with the second score; and (4) identifying the subject as responsive to the first therapy when the second score is significantly decreased as compared to the first score or identifying the subject as not responsive to the first therapy when the second score is not significantly decreased as compared to the first score.

The preceding method can further comprise continuing to administer the first therapy to the subject when the second score is significantly decreased as compared to the first score. The preceding method can further comprise discontinuing administration of the first therapy to the subject when the second score is not significantly decreased as compared to the first score. The preceding method can further comprise administering a second therapy to the subject when the second score is not significantly decreased as compared to the first score.

The present disclosure provides a method for evaluating the response of a subject having a prostate cancer to a first therapy, the method comprising: (1) at a first time point: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each ofAAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a first score; (2) at a second time point, wherein the second time point is after the first time point and after the administration of the therapy to the subject: (d) determining the expression level of the at least 38 biomarkers from a test sample from the subject by contacting the test sample with a plurality of agents specific to detect the expression of the at least 38 biomarkers; (e) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (f) inputting each normalized expression level into an algorithm to generate a second score; (3) comparing the first score with the second score; and (4) producing a report, wherein the report identifies that the subject is responsive to the first therapy when the second score is significantly decreased as compared to the first score or identifies that the subject is not responsive to the first therapy when the second score is not significantly decreased as compared to the first score.

The preceding method can further comprise continuing to administer the first therapy to the subject when the second score is significantly decreased as compared to the first score. The preceding method can further comprise discontinuing administration of the first therapy to the subject when the second score is not significantly decreased as compared to the first score. The preceding method can further comprise administering a second therapy to the subject when the second score is not significantly decreased as compared to the first score.

The present disclosure also provides a method for treating a prostate cancer in a subject in need thereof, the method comprising: determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSs2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; inputting each normalized expression level into an algorithm to generate a score; comparing the score with a first predetermined cutoff value; and administering at least a first therapy to the subject when the score is equal to or greater than the first predetermined cutoff value or identifies the absence of a prostate cancer in the subject when the score is less than the first predetermined cutoff value.

In the methods of the present disclosure, the housekeeping gene can be selected from the group consisting of ALG9, SEPN, YWHAQ, VPS37A, PRRC2B, DOPEY2, NDUFB11, ND4, MRPL19, PSMC4, SF3A1, PUM1, ACTB, GAPD, GUSB, RPLP0, TFRC, MORF4L1, 18S, PPIA, PGK1, RPL13A, B2M, YWHAZ, SDHA, HPRT1, TOX4 and TPT1. The housekeeping gene can be TOX4.

In the methods of the present disclosure, a predetermined cutoff value can be at least 33% on a scale of 0-100%, or at least 50% on a scale of 0-100%. A first predetermined cutoff value can be at least 33% on a scale of 0-100%, or at least 50% on a scale of 0-100%.

The methods of the present disclosure can further comprise administering a therapy to a subject. The methods of the present disclosure can further comprise administering a first therapy a subject. The methods of the present disclosure can further comprise administering a second therapy to a subject.

In the methods of the present disclosure, a therapy can comprise active surveillance, radiation therapy, surgery, cryotherapy, hormone therapy, chemotherapy, vaccine treatment, bone-directed treatment, or any combination thereof. A first therapy can comprise active surveillance, radiation therapy, surgery, cryotherapy, hormone therapy, chemotherapy, vaccine treatment, bone-directed treatment, or any combination thereof. A second therapy can comprise active surveillance, radiation therapy, surgery, cryotherapy, hormone therapy, chemotherapy, vaccine treatment, bone-directed treatment, or any combination thereof.

In some aspects, hormone therapy can comprise androgen suppression therapy. In some aspects, chemotherapy can comprise docetaxel, cabazitaxel, mitoxantrone, estramustine, or a combination thereof. In some aspects, a vaccine treatment can comprise Sipuleucel-T. In some aspects, a bone-directed treatment can comprise a bisphosphonate, denosumab, a corticosteroid, or a combination thereof.

In the methods of the present disclosure, an algorithm can be XGB, RF, glmnet, cforest, CART, treebag, knn, nnet, SVM-radial, SVM-linear, NB, or mlp. An algorithm can be XGB.

In the methods of the present disclosure, a first time point can be either prior to or after the administration of a therapy to the subject. A first time point can be either prior to or after the administration of a first therapy to the subject.

In the methods of the present disclosure, a second score is significantly decreased as compared to the first score when the second score is at least 25% less than the first score.

The methods of the present diclsoure can have a sensitivity of at least 92%. The methods of the present disclosure can have a specificity of at least 95%.

In the methods of the present disclosure, at least one of the at least 38 biomarkers can be RNA, cDNA, or protein.

In the methods of the present disclosure, when the biomarker is RNA, the RNA can be reverse transcribed to produce cDNA, and the produced cDNA expression level can be detected.

In the methods of the present disclosure, the expression level of a biomarker can be detected by forming a complex between the biomarker and a labeled probe or primer.

In the methods of the present disclosure, when the biomarker is protein, the protein can be detected by forming a complex between the protein and a labeled antibody. The label can be a fluorescent label.

In the methods of the present disclosure, when the biomarker is RNA or cDNA, the RNA or cDNA can be detected by forming a complex between the RNA or cDNA and a labeled nucleic acid probe or primer. For example, a label can be a fluorescent label. A complex between the RNA or cDNA and the labeled nucleic acid probe or primer can be a hybridization complex.

In the methods of the present disclosure, a predetermined cutoff value can be derived from a plurality of reference samples obtained from subjects not having or not diagnosed with a neoplastic disease. The neoplastic disease can be prostate cancer.

In the methods of the present disclosure, a test sample can be blood, serum, plasma, or neoplastic tissue. A reference sample can be blood, serum, plasma, or non-neoplastic tissue.

In the methods of the present disclosure, a subject can have at least one prostate cancer symptom. In the methods of the present disclosure, a subject can have a predisposition or familial history for developing a prostate cancer.

In the methods of the present disclosure, a subject can have been previously diagnosed with a prostate cancer and is tested for prostate cancer recurrence.

In the methods of the present disclosure, a subject can be human.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and further features will be more clearly appreciated from the following detailed description when taken in conjunction with the accompanying drawings.

(FIG. 1A) Expression in E-GEOD-46691. (FIG. 1B) Expression in E-GEOD-46602.

DETAILED DESCRIPTION OF THE INVENTION

Figure 1A:
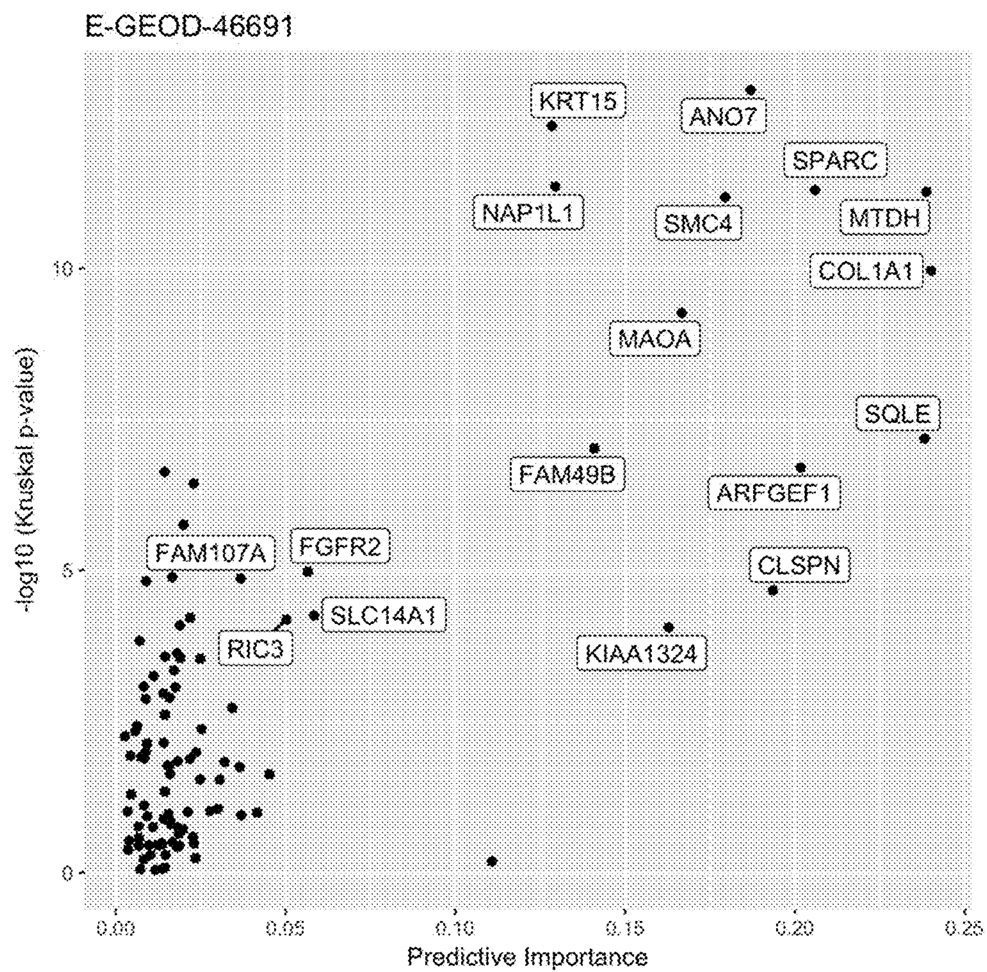
FIGS. 1A-1B are graphs showing visualisation of 30 putative marker genes identified by the Random Forest algorithm in the derivation cohort of n=595 tissue samples.

The details of the invention are set forth in the accompanying description below.

Described herein are methods to quantitate (score) the circulating prostate cancer molecular signature with high sensitivity and specificity for purposes including, but not limited to, detecting a prostate cancer, determining whether a prostate cancer is stable or progressive, differentiating benign prostate hyperplasia (BPH) from prostate cancer, determining the completeness of surgery, and evaluating the response to a prostate cancer therapy. Specifically, the present invention is based on the discovery that the expression levels of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC, normalized by the expression level of a housekeeping gene, are elevated in subjects having prostate cancers as compared to healthy subjects or subjects with BPH.

Symptoms of prostate cancers include problems urinating, blood in the urine or semen, trouble getting an erection, pain in the hips, back (spine), chest (ribs), or other areas from cancer that has spread to bones, weakness or numbness in the legs or feet, or even loss of bladder or bowel control from cancer pressing on the spinal cord.

As described in the examples, measurements of circulating prostate cancer transcripts—the ProstaTest—diagnoses prostate cancer and decreases in the ProstaTest score in blood correlates with the efficacy of therapeutic interventions such as surgery and chemotherapy. A targeted gene expression profile of prostate cancer RNA can be isolated from the peripheral blood of patients. The expression profile is evaluated in an algorithm and converted to an output (score). It can diagnose and identify active disease and provide an assessment of treatment responses in conjunction with standard clinical assessment and imaging.

Accordingly, the present disclosure provides a method for detecting a prostate cancer in a subject in need thereof, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSs2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) identifying the presence of a prostate cancer in the subject when the score is equal to or greater than the first predetermined cutoff value or identifying the absence of a prostate cancer in the subject when the score is less than the first predetermined cutoff value.

In some aspects of the preceding method, step (e) can comprise producing a report, wherein the report identifies the presence of a prostate cancer in the subject when the score is equal to or greater than the first predetermined cutoff value or identifies the absence of a prostate cancer in the subject when the score is less than the first predetermined cutoff value.

In some aspects of the preceding method, the first predetermined cutoff value can be 33% on a scale of 0-100%.

In some aspects, the preceding method can further comprise administering to the subject a first therapy. The preceding method can further comprise administering to the subject a first therapy when the score is equal to or greater than the predetermined cutoff value.

The present disclosure also provides a method for determining whether a prostate cancer in a subject is stable or progressive, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) identifying that the prostate cancer is progressive when the score is equal to or greater than the first predetermined cutoff value or identifying that the prostate cancer is stable when the score is less than the first predetermined cutoff value.

In some aspects of the preceding method, step (e) can comprise producing a report, wherein the report identifies that the prostate cancer is progressive when the score is equal to or greater than the first predetermined cutoff value or identifies that the prostate cancer is stable when the score is less than the first predetermined cutoff value.

In some aspects of the preceding method, the first predetermined cutoff value can be 50% on a scale of 0-100%.

In some aspects, the preceding method can further comprise administering to the subject a first therapy. The preceding method can further comprise administering to the subject a first therapy when the score is equal to or greater than the predetermined cutoff value.

The present disclosure also provides a method for determining whether a prostate cancer in a subject is low or high grade, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) identifying that the prostate cancer is high grade when the score is equal to or greater than the first predetermined cutoff value or identifying that the prostate cancer is low grade when the score is less than the first predetermined cutoff value.

In some aspects of the preceding method, step (e) can comprise producing a report, wherein the report identifies that the prostate cancer is high grade when the score is equal to or greater than the first predetermined cutoff value or identifies that the prostate cancer is low grade when the score is less than the first predetermined cutoff value.

In some aspects of the preceding method, the first predetermined cutoff value can be 50% on a scale of 0-100%.

In some aspects, the preceding method can further comprise administering to the subject a first therapy. The preceding method can further comprise administering to the subject a first therapy when the score is equal to or greater than the predetermined cutoff value.

In some aspects, a low grade prostate cancer is a prostate cancer with a Gleason score that is less than or equal to 6. In some aspects, a high grade prostate cancer is a prostate cancer with a Gleason score that is greater than or equal to 7.

The Gleason Grading System is commonly used in the art as a parameter of prognosis, often used in combination with other prognostic factors or tests, for prostate cancer. Prostate biopsy samples are examined, for example, by microscope, and a Gleason score is determined by a pathologist, based on the architectural pattern of the prostate tumor. The Gleason score is based upon the degree of loss of the normal glandular tissue architecture (i.e. shape, size and differentiation of the glands). The sample is assigned a grade to the most common tumor pattern, and a second grade to the next most common tumor pattern. There may be a primary or most common pattern and then a secondary or second most common pattern which can be identified; alternatively, there may be only a single grade. Gleason patterns are associated with the following features: Pattern 1—The cancerous prostate closely resembles normal prostate tissue. The glands are small, well-formed, and closely packed; Pattern 2—The tissue still has well-formed glands, but they are larger and have more tissue between them; Pattern 3—The tissue still has recognizable glands, but the cells are darker. At high magnification, some of these cells have left the glands and are beginning to invade the surrounding tissue; Pattern 4—The tissue has few recognizable glands. Many cells are invading the surrounding tissue; Pattern 5—The tissue does not have recognizable glands. There are often just sheets of cells throughout the surrounding tissue. The two grades are added together to get a Gleason Score, also known as a Gleason sum.

The present disclosure also provides a method for determining whether a prostate cancer in a subject is a low Gleason score (≤6) prostate cancer or a high Gleason score (≥7) prostate cancer, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a second predetermined cutoff value; and (e) identifying that the prostate cancer is a high Gleason score prostate cancer when the score is equal to or greater than the first predetermined cutoff value or identifying that the prostate cancer is a low Gleason score prostate when the score is less than the first predetermined cutoff value.

In some aspects of the preceding method, step (e) can comprise producing a report, wherein the report identifies that the prostate cancer is a high Gleason score prostate cancer when the score is equal to or greater than the first predetermined cutoff value or identifies that the prostate cancer is a low Gleason score prostate cancer when the score is less than the second predetermined cutoff value, In some aspects of the preceding method, the first predetermined cutoff value can be 50% on a scale of 0-100%.

In some aspects, the preceding method can further comprise administering to the subject a first therapy. The preceding method can further comprise administering to the subject a first therapy when the score is equal to or greater than the predetermined cutoff value.

The present disclosure also provides a method for determining the completeness of surgery in a subject having a prostate cancer, the method comprising: (a) determining the expression level of at least 38 biomarkers from a test sample from the subject after the surgery by contacting the test sample with a plurality of agents specific to detect the expression of the at least 38 biomarkers, wherein the 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) identifying that the prostate cancer is not completely removed when the score is equal to or greater than the first predetermined cutoff value or identifying that the prostate cancer is completely removed when the score is less than the first predetermined cutoff value.

In some aspects of the preceding method, step (e) can comprise producing a report, wherein the report identifies that the prostate cancer is not completely removed when the score is equal to or greater than the first predetermined cutoff value or identifies that the prostate cancer is completely removed when the score is less than the first predetermined cutoff value.

In some aspects of the preceding method, the first predetermined cutoff value can be 33% on a scale of 0-100%.

In some aspects, the preceding method can further comprise administering to the subject a first therapy. The preceding method can further comprise administering to the subject a first therapy when the score is equal to or greater than the predetermined cutoff value.

The present disclosure also provides a method for differentiating benign prostate hyperplasia from a prostate cancer in a subject having an enlarged prostate, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) identifying the presence of a prostate cancer in the subject when the score is equal to or greater than the first predetermined cutoff value or identifying the presence of benign prostate hyperplasia in the subject when the score is less than the first predetermined cutoff value.

In some aspects of the preceding method, step (e) can comprise producing a report, wherein the report identifies the presence of a prostate cancer in the subject when the score is equal to or greater than the first predetermined cutoff value or identifies the presence of benign prostate hyperplasia in the subject when the score is less than the first predetermined cutoff value, In some aspects of the preceding method, the first predetermined cutoff value can be 33% on a scale of 0-100%.

In some aspects, the preceding method can further comprise administering to the subject a first therapy. The preceding method can further comprise administering to the subject a first therapy when the score is equal to or greater than the predetermined cutoff value.

The present disclosure provides a method for treating a prostate cancer in a subject in need thereof, the method comprising: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a score; (d) comparing the score with a first predetermined cutoff value; and (e) administering at least a first therapy to the subject when the score is equal to or greater than the first predetermined cutoff value or identifies the absence of a prostate cancer in the subject when the score is less than the first predetermined cutoff value.

The present disclosure also provides a method for evaluating the response of a subject having a prostate cancer to a first therapy, the method comprising: (1) at a first time point: (a) determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene; (b) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each ofAAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (c) inputting each normalized expression level into an algorithm to generate a first score; (2) at a second time point, wherein the second time point is after the first time point and after the administration of the first therapy to the subject: (d) determining the expression level of the at least 38 biomarkers from a test sample from the subject by contacting the test sample with a plurality of agents specific to detect the expression of the at least 38 biomarkers; (e) normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC; (f) inputting each normalized expression level into an algorithm to generate a second score; (3) comparing the first score with the second score; and (4) identifying the subject as responsive to the first therapy when the second score is significantly decreased as compared to the first score or identifying the subject as not responsive to the first therapy when the second score is not significantly decreased as compared to the first score.

In some aspects of the preceding method, step (4) can comprise producing a report, wherein the report identifies that the subject is responsive to the first therapy when the second score is significantly decreased as compared to the first score or identifies that the subject is not responsive to the first therapy when the second score is not significantly decreased as compared to the first score.

In some aspects, the preceding method can further comprise continuing to administer the first therapy to the subject when the second score is significantly decreased as compared to the first score. The preceding method can further comprise discontinuing administration of the first therapy to the subject when the second score is not significantly decreased as compared to the first score. The preceding method can further comprise administering a second therapy to the subject when the second score is not significantly decreased as compared to the first score.

In some aspects of the preceding method, the second score is significantly decreased as compared to the first score when the second score is at least about 10% less than the first score, or at least about 20% less than the first score, or at least about 25% less than the first score, or at least about 30% less than the first score, at least about 40% less than the first score, at least about 50% less than the first score, or at least about 60% less than the first score, or at least about 70% less than the first score, or at least about 75% less than the first score, or at least about 80% less than the first score, or at least about 90% less than the first score, or at least about 95% less than the first score or at least about 99% less than the first score. In some aspects, when the second score is not significantly decreased as compared to the first score, the subject is considered to be not responsive to the therapy.

In some aspects of the preceding method, a first time point can be prior to the administration of a first therapy to the subject. A first time point can be after the administration of a first therapy to the subject.

In some aspects of the methods of the present disclosure, housekeeping genes include, but are not limited to, ALG9, SEPN, YWHAQ, VPS37A, PRRC2B, DOPEY2, NDUFB11, ND4, MRPL19, PSMC4, SF3A1, PUM1, ACTB, GAPD, GUSB, RPLP0, TFRC, MORF4L1, 18S, PPIA, PGK1, RPL13A, B2M, YWHAZ, SDHA, HPRT1, TOX4 and TPT1. In some aspects, the housekeeping gene is TOX4.

In some aspects of the methods of the present disclosure, a predetermined cutoff value can be about 33% on a scale of 0-100%. In some aspects of the methods of the present disclosure, a predetermined cutoff value can be about 50% on a scale of 0-100%. A predetermined cutoff value can be about 60% on a scale of 0-100%. A predetermine cutoff value can be about 10%, or about 20%, or about 30%, or about 40%, or about 70%, or about 80%, or about 90% on a scale of 0-100%.

The methods of the present disclosure can have a sensitivity of at least about 50%, or at least about 60%, or at least about 70%, or at least about 75%, or at least about 80%, or at least about 85%, or at least about 90%, or at least about 95%, or at least about 99%. The methods of the present disclosure can have a sensitivity of greater than about 50%, or greater than about 60%, or greater than about 70%, or greater than about 75%, or greater than about 80%, or greater than about 85%, or greater than about 90%, or greater than about 95%, or greater than about 99%.

The methods of the present disclosure can have a specificity of at least about 50%, or at least about 60%, or at least about 70%, or at least about 75%, or at least about 80%, or at least about 85%, or at least about 90%, or at least about 95%, or at least about 99%. The methods of the present disclosure can have a specificity of greater than about 50%, or greater than about 60%, or greater than about 70%, or greater than about 75%, or greater than about 80%, or greater than about 85%, or greater than about 90%, or greater than about 95%, or greater than about 99%.

The methods of the present disclosure can have an accuracy of at least about 50%, or at least about 60%, or at least about 70%, or at least about 75%, or at least about 80%, or at least about 85%, or at least about 90%, or at least about 95%, or at least about 99%. The methods of the present disclosure can have an accuracy of greater than about 50%, or greater than about 60%, or greater than about 70%, or greater than about 75%, or greater than about 80%, or greater than about 85%, or greater than about 90%, or greater than about 95%, or greater than about 99%.

In some aspects of the methods of the present disclosure, a predetermined cutoff value, for example a first predetermined cutoff value, is derived from a plurality of reference samples obtained from subjects not having or not diagnosed with a neoplastic disease. The plurality of reference samples can be about 2-500, 2-200, 10-100, or 20-80. Each reference sample produces a score using the algorithm, and the first predetermined cutoff value can be, for example, an arithmetic mean of these scores. Each reference sample can be blood, serum, plasma, or non-neoplastic tissue. In some aspects, each reference sample is blood. In some aspects, each reference sample is of the same type as the test sample.

In some aspects of the methods of the present disclosure, a test sample can comprise any biological fluid obtained from a subject. In some aspects, a test sample comprises blood, serum, plasma, neoplastic tissue or any combination thereof. In some aspects, a test sample comprises blood. In some aspects, a test sample comprises serum. In some aspects, a test sample comprises plasma.

In some aspects of the methods of the present disclosure, a reference sample can comprise any biological fluid obtained from a subject. In some aspects, a reference sample comprises blood, serum, plasma, neoplastic tissue or any combination thereof. In some aspects, a reference sample comprises blood. In some aspects, a reference sample comprises serum. In some aspects, a reference sample comprises plasma.

Each of the biomarkers disclosed herein may have one or more transcript variants. The methods disclosed herein can measure the expression level of any one of the transcript variants for each biomarker.

The expression level can be measured in a number of ways, including, but not limited to: measuring the mRNA encoded by the selected genes; measuring the amount of protein encoded by the selected genes; and measuring the activity of the protein encoded by the selected genes.

The biomarker can be RNA, cDNA, or protein. When the biomarker is RNA, the RNA can be reverse transcribed to produce cDNA (such as by RT-PCR), and the produced cDNA expression level is detected. The expression level of the biomarker can be detected by forming a complex between the biomarker and a labeled probe or primer. When the biomarker is RNA or cDNA, the RNA or cDNA is detected by forming a complex between the RNA or cDNA and a labeled nucleic acid probe or primer. The complex between the RNA or cDNA and the labeled nucleic acid probe or primer can be a hybridization complex.

Gene expression can also be detected by microarray analysis. Differential gene expression can also be identified, or confirmed using the microarray technique. Thus, the expression profile biomarkers can be measured in either fresh or fixed tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. The source of mRNA typically is total RNA isolated from a biological sample, and corresponding normal tissues or cell lines may be used to determine differential expression.

In some embodiments of the microarray technique, PCR amplified inserts of cDNA clones are applied to a substrate in a dense array. In some embodiments, at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the microarray chip is scanned by a device such as, confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pair-wise to the array. The relative abundance of the transcripts from the two sources corresponding to each specified gene is thus determined simultaneously. Microarray analysis can be performed by commercially available equipment, following manufacturer's protocols.

In some embodiments, the biomarkers can be detected in a biological sample using qRT-PCR. The first step in gene expression profiling by RT-PCR is extracting RNA from a biological sample followed by the reverse transcription of the RNA template into cDNA and amplification by a PCR reaction. The reverse transcription reaction step is generally primed using specific primers, random hexamers, or oligo-dT primers, depending on the goal of expression profiling. The two commonly used reverse transcriptases are avilo myeloblastosis virus reverse transcriptase (AMV-RT) and Moloney murine leukemia virus reverse transcriptase (MLV-RT).

When the biomarker is protein, the protein can be detected by forming a complex between the protein and a labeled antibody. The label can be any label for example a fluorescent label, chemiluminescence label, radioactive label, etc. Exemplary methods for protein detection include, but are not limited to, enzyme immunoassay (EIA), radioimmunoassay (MA), Western blot analysis and enzyme linked immunoabsorbant assay (ELISA). For example, the biomarker can be detected in an ELISA, in which the biomarker antibody is bound to a solid phase and an enzyme-antibody conjugate is employed to detect and/or quantify biomarker present in a sample. Alternatively, a western blot assay can be used in which solubilized and separated biomarker is bound to nitrocellulose paper. The combination of a highly specific, stable liquid conjugate with a sensitive chromogenic substrate allows rapid and accurate identification of samples.

In some aspects of the methods of the present disclosure, the methods described herein can have a specificity, sensitivity, and/or accuracy of at least 75%, 80%, 85%, 90%, 91%, 92%, 93%, 94%, 95%, 96%, 97%, 98%, or 99%.

In some aspects of the methods of the present disclosure, a labeled probe, a labeled primer, a labeled antibody or a labeled nucleic acid can comprise a fluorescent label.

Any algorithm that can generate a score for a sample by assessing where that sample value falls onto a prediction model generated using different techniques, e.g., decision trees, can be used in the methods disclosed herein. The algorithm analyzes the data (i.e., expression levels) and then assigns a score. In some embodiments, the algorithm can be a machine-learning algorithm. Exemplary algorithms that can be used in the methods disclosed herein can include, but are not limited to, XGBoost (XGB), Random Forest (RF), glmnet, cforest, Classification and Regression Trees for Machine Learning (CART), treebag, K-Nearest Neighbors (kNN), neural network (nnet), Support Vector Machine radial (SVM-radial), Support Vector Machine linear (SVM-linear), Naïve Bayes (NB), multilayer perceptron (mlp) or any combination thereof.

In some aspects of the methods of the present disclosure, the algorithm can be XGB (also called XGBoost). XGB is an implementation of gradient boosted decision trees designed for speed and performance.

In some aspects of the methods of the present disclosure, a therapy, for example a first therapy or a second therapy, can comprise active surveillance, surgery, radiation therapy, cryotherapy, hormone therapy, chemotherapy, vaccine treatment, bone-directed treatment, immunotherapy or any combination thereof.

In some aspects of the methods of the present disclosure, active surveillance can comprise a doctor visit with a prostate-specific antigen blood test and digital rectal exam about every 6 months. Active surveillance can also comprise prostate biopsies, which may be done every year.

In some aspects of the methods of the present disclosure, surgery can comprise a radical prostatectomy.

In some aspects of the methods of the present disclosure, radiation therapy can comprise external beam radiation and brachytherapy.

Cryotherapy, also referred to as cryosurgery or cryoablation, is the use of very cold temperatures to freeze and kill prostate cancer cells.

In some aspects of the methods of the present disclosure, hormone therapy can comprise androgen deprivation therapy or androgen suppression therapy. The goal is to reduce levels of male hormones, called androgens, in the body, or to stop them from affecting prostate cancer cells. Hormone therapy can comprise orchiectomy. Hormone therapy can also comprise administration of a compound that lowers the level of androgens, such as Luteinizing hormone-releasing hormone (LHRH) agonists, LHRH antagonists, and CYP17 inhibitors. Known LHRH agonists include, but are not limited to, leuprolide, goserelin, triptorelin, and histrelin. Known LHRH antagonists include degarelix. Known CYP17 inhibitors include abiraterone. Hormone therapy can also comprise administration of an anti-androgen, such as flutamide, bicalutamide, nilutamide, and enzalutamide. Hormone therapy can also include administration of an androgen-suppressing drug, such as estrogens and ketoconazole.

In some aspects of the methods of the present disclosure, chemotherapy can comprise docetaxel, cabazitaxel, mitoxantrone, estramustine, or a combination thereof.

In some aspects of the methods of the present disclosure, vaccine treatment can comprise Sipuleucel-T.

If the cancer has grown outside the prostate, preventing or slowing the spread of the cancer to the bones is a major goal of treatment. Bone-directed treatment can comprise bisphosphonates (e.g., zoledronic acid), denosumab, corticosteroids, external radiation therapy, radiopharmaceuticals (e.g., Strontium-89, Samarium-153, or Radium-223), and pain medicines.

The response of a subject having a prostate cancer to a therapy can also be evaluated by comparing the scores determined by the same algorithm at different time points of the therapy. For example, the first time point can be prior to or after the administration of the therapy to the subject; the second time point is after the first time point and after the administration of the therapy to the subject. A first score is generated at the first time point, and a second score is generated at the second time point. When the second score is significantly decreased as compared to the first score, the subject is considered to be responsive to the therapy. In some embodiments, the second score is significantly decreased as compared to the first score when the second score is at least 10% less than the first score, e.g., at least 20% less than the first score, at least 25% less than the first score, at least 40% less than the first score, at least 50% less than the first score, at least 75% less than the first score, or at least 90% less than the first score. When the second score is not significantly decreased as compared to the first score, the subject is considered to be not responsive to the therapy.

The sequence information of the prostate cancer biomarkers and housekeeper genes is shown in Table 1.

TABLE 1

Prostate Cancer Biomarker/Housekeeper Sequence Information

| Gene Name | RefSeq Accession | Sequence | SEQ ID NO: |
|---|---|---|---|
| AAMP | NM_001087.4 | ctgctggggagtcgcctacgcctacttcctgccgggaggaggggctcgagttccgcgtcgtc<br>gcgcagagctgactctgggaggcgtttgggcccagagaagtggatccgccgcttgcgccgc<br>atggagtccgaatcggaaagcggggctgctgctgacacccccccactggagaccctaagct<br>tccatggtgatgaagagattatcgaggtggtagaacttgatcccggtccgccggacccagatg<br>acctggcccaggagatggaagatgtggactttgaggaagaagaggaggaagagggcaac<br>gaagagggctgggttctagaaccccaggaaggggtggtcggcagcatggagggccccga<br>cgatagcgaggtcacctttgcattgcactcagcatctgtgttttgtgtgagcctggaccccaag<br>accaataccttggcagtgaccgggggtgaagatgacaaagccttcgtatggcggctcagcg<br>atggggagctgctctttgagtgtgcaggccataaagactctgtgacttgtgctggtttcagccat<br>gactccactctagtggccacaggggacatgagtggcctcttgaaagtgtggcaggtggacac<br>taaggaggaggtctggtcctttgaagcgggagacctggagtggatggagtggcatcctcgg<br>gcacctgtcctgttggcgggcacagctgacggcaacacctggatgtggaaagtcccgaatg<br>gtgactgcaagaccttccagggtcccaactgcccagccacctgtggccgagtcctccctgat<br>gggaagagagctgtggtaggctatgaagatgggaccatcaggatttgggacctgaagcagg<br>gaagccctatccatgtactgaaagggactgagggtcaccagggcccactcacctgtgttgct<br>gccaaccaggatggcagcttgatcctaactggctctgtggactgccaggccaagctggtcag<br>tgccaccaccggcaaggtggtgggtgtttttagacctgagactgtggcctcccagcccagcct<br>gggagaaggggaggagagtgagtccaactcggtggagtccttgggcttctgcagtgtgatg<br>cccctggcagctgttggctacctggatgggaccttggccatctatgacctggctacgcagact<br>cttaggcatcagtgtcagcaccagtcgggcatcgtgcagctgctgtgggaggcaggcactgc<br>cgtggtatatacctgcagcctggatggcatcgtgcgcctctgggacgcccggaccggccgc<br>ctgcttactgactaccggggccacacggctgagatcctggactttgccctcagcaaagatgcc<br>tccctggtggtgaccacgtcaggagaccacaaagcgaaagtatttgtgtccaaaggcctgac<br>cgttaatggctgcagcccctgcctgtgtgtctggtgttgaggggacgaagggacccctgccc | 1 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | ctgtctgccagcagaggcagtagggcacagagggaagaggagggtggggccctggatga ctttccagcctcttcaactgacttgctcccctctccttttcttctctttagagacccagcccagggc cctcccacccttgtccagacctggtgggcccttcagagggaggggtggacctgtttctctttca ctttcatttgctggtgtgagccatggggtgtgtatttgtatgtggggagtaggtgtttgaggttcc cgttctttcccttcccaagtctctgggggtggaaaggaggaagagatactagttaaagattttaa aaatgtaaataaaatatacttcccagaaaaaaaaaaa | |
| ANO7 | NM_001001891.3 | aaagatagatcctgctccaggagccgggaagccttgccctggccagctgtgctgggcacctc ccctgcctgcttcctggcccacttgcaggcaaggtgagggcatgcgaatggctgccactgcc tgggcggggctccaagggccacccctccccaccctctgtcccgcagtgaggacgggactct actgccgagaccaggctcacgctgagaggtgggccatgacctccgagacctcttccggaag ccactgtgccaggagcaggatgctgcggcgacgggcccaggaagaggacagcaccgtcc tgatcgatgtgagccccccctgaggcagagaagaggggctcttacgggagcacagcccacg cctcggagccaggtggacagcaagcggccgcctgcagagctgggagtcctgccaagccc cggatcgcagacttcgtcctcgtttgggaggaggacctgaagctagacaggcagcaggaca gtgccgcccgggacagaacagacatgcacaggacctggcgggagacttttctggataatctt cgtgcggctgggctgtgtgtagaccagcaggacgtccaggacgggaacaccacagtgcac tacgccctcctcagcgcctcctgggctgtgctctgctactacgccgaagacctgcgcctgaag ctgcccttgcaggagttacccaaccaggcctccaactggtcggccggcctgctggcatggct gggcatccccaacgtcctgctggaggttgtgccagacgtacccccgagtactactcctgcc ggttcagagtgaacaagctgccacgcttcctcgggagtgacaaccaggacaccttcttcacaa gcaccaagaggcaccaaattctgtttgagatcctggccaagaccccgtatggccacgagaag aaaaacctgcttgggatccaccagctgctggcagagggtgtcctcagtgccgccttcccccctg catgacggccccttcaagacgcccccagagggcccgcaggctccacgcctcaaccagcgc caagtccttttccagcactgggcgcgctggggcaagtggaacaagtaccagcccctggacc acgtgcgcaggtacttcggggagaaggtggccctctacttcgcctggctcgggttttacacag gctggctcctgccagcggcagtggtgggcacactggtgttcctggtgggctgcttcctggtgt tctcagacatacccacgcaggaactgtgtggcagcaaggacagcttcgagatgtgcccacttt gcctcgactgccctttctggctgctctccagcgcctgtgccctggcccaggccggccggctgt tcgaccacggcggcaccgtgttcttcagcttgttcatggcactgtgggccgtgctgctgctgga gtactggaagcggaagagcgccacgctggcctaccgctgggactgctctgactacgaggac actgaggagaggcctcggccccagtttgccgcctcagcccccatgacagccccgaacccca tcacgggtgaggacgagccctacttccctgagaggagccgcgcgcgccgcatgctggccg gctctgtggtgatcgtggtgatggtggccgtggtggtcatgtgcctcgtgtctatcatcctgtac cgtgccatcatggccatcgtggtgtccaggtcgggcaacacccttctcgcagcctgggcctct cgcatcgccagcctcacggggtctgtagtgaacctcgtcttcatcctcatcctctccaagatcta tgtatccctggcccacgtcctgacacgatgggaaatgcaccgcacccagaccaagttcgagg acgccttcaccctcaaggtgttcatcttccagttcgtcaacttctactcctcacccgtctacattgc cttcttcaagggcaggtttgtgggatacccaggcaactaccacaccttgtttggagtccgcaat gaggagtgcgcggctggaggctgcctgatcgagctggcacaggagctcctggtcatcatgg tgggcaagcaggtcatcaacaacatgcaggaggtcctcatcccgaagctaaagggctggtg gcagaagttccggcttcgctccaagaagaggaaggcgggagcttctgcaggggctagcca ggggccctgggaggacgactatgagcttgtgccctgtgagggtctgtttgacgagtacctgg aaatggtgctgcagttcggcttcgtcaccatcttcgtggccgcctgtccgctcgcgccgctctt cgccctgctcaacaactgggtggagatccgcttggacgcgcgcaagttcgtctgcgagtacc ggcgcccggtggccgagcgcgcccaggacatcggcatctggttccacatcctggcgggcc tcacgcacctggcggtcatcagcaacgccttcctcctggccttctcgtccgacttcctgccgcg cgcctactaccggtggacccgcgcccacgacctgcgcggcttcctcaacttcacgctggcgc gagccccgtcctccttcgccgccgcgcacaaccgcacgtgcaggtatcgggctttccgggat gacgatggacattattcccagacctactggaatcttcttgccatccgcctggccttcgtcattgtg tttgagcatgtggttttctccgttggccgcctcctggacctcctggtgcctgacatcccagagtct gtggagatcaaagtgaagcgggagtactacctggctaagcaggcactggctgagaatgagg ttctttttggaacgaacggaacaaaggatgagcagcccgagggctcagagctcagctcccac tggacacccttcacggttcccaaggccagccagctgcagcagtgacgcctggaaggacatct ggtggtccttaggggagtggcccctcctgagccctgcgagcagcgtccttttcctcttccctca ggcagcggctgtgtgaaccgctggctgctgttgtgcctcatctctgggcacattgcctgcttcc ccccagcgccggcttctctcctcagagcgcctgtcactccatccccggcagggagggaccgt cagctcacaaggccctctttgtttcctgctcccagacataagcccaaggggcccctgcaccca agggaccctgtccctcggtggcctccccaggcccctggacacgacagttctcctcaggcag gtgggctttgtggtcctcgccgcccctggccacatcgccctctcctcttacacctggtgaccttc gaatgtttcagagcgcagggccgttctccctcgtgtcctctggacccacccgccccttcctgcc ctgtttgcgcagggacatcacccacatgccccagctctcggaccctgcagctctgtgtcccag gccacagcaaaggtctgttgaacccctccctccattcccagttatctgggtcctctggattcttct gtttcttgaatcaggctctgctttcccccctagccactacaggcagcctctgacagtgccgcttta cttgcattctgcagcaattacatgtgtccttttgatccttgcccaacttccctccctctcccagctcc tggcccctggcccagggcccctcttgctgtttttacctctgttccttggggcctagtacccagca agcacccaaatgggggaggttttgggatgagaggaggaaacgtgtatacctgtaacatctgg tggctcttcccccagaagtttgtgttcatacataattgttttccacgctggatcataatgtgacgtg cagttctgccctgtgctggggagccacatgaagcttcccctggctaacttgctaccccgcagc aatcccagtgtggccgtctgcttgctaaaaaatggatctgtgctcatctgtattgatgtccttgga gttctacaagtggaacttaagtgtcaaaaagaatatgtggttttagctgagcgtggtggctcac acctgtaatcccaggactttgggaggctgaggcaggaggattacaaggtcaggagttcggg actagcctgtccaacatggtgaaaccctgtctttactaaaaatgcaaaaatt | 2 |

TABLE 1-continued

| Prostate Cancer Biomarker/Housekeeper Sequence Information | | | |
|---|---|---|---|
| Gene Name | RefSeq Accession | Sequence | SEQ ID NO: |
| AR | NM_000044.3 | cgagatcccggggagccagcttgctgggagagcgggacggtccggagcaagcccagag<br>gcagaggaggcgacagagggaaaaagggccgagctagccgctccagtgctgtacaggag<br>ccgaagggacgcaccacgccagccccagcccggctccagcgacagccaacgcctcttgca<br>gcgcggcggcttcgaagccgccgcccggagctgccctttcctcttcggtgaagtttttaaaag<br>ctgctaaagactcggaggaagcaaggaaagtgcctggtaggactgacggctgcctttgtcct<br>cctcctctccaccccgcctccccccaccctgccttccccccctcccccgtcttctctcccgcag<br>ctgcctcagtcggctactctcagccaaccccctcaccacccttctccccacccgcccccccg<br>cccccgtcggcccagcgctgccagcccgagtttgcagagaggtaactccctttggctgcgag<br>cgggcgagctagctgcacattgcaaagaaggctcttaggagccaggcgactggggagcgg<br>cttcagcactgcagccacgacccgcctggttaggctgcacgcggagagaaccctctgttttcc<br>cccactctctctccacctcctcctgccttccccaccccgagtgcggagccagagatcaaaaga<br>tgaaaaggcagtcaggtcttcagtagccaaaaaacaaaacaaacaaaaacaaaaaagccga<br>aataaaagaaaaagataataactcagttcttatttgcacctacttcagtggacactgaatttggaa<br>ggtggaggattttgtttttttcttttaagatctgggcatcttttgaatctacccttcaagtattaagag<br>acagactgtgagcctagcagggcagatcttgtccaccgtgtgtcttcttctgcacgagactttg<br>aggctgtcagagcgctttttgcgtggttgctcccgcaagtttccttctctggagcttcccgcagg<br>tgggcagctagctgcagcgactaccgcatcatcacagcctgttgaactcttctgagcaagaga<br>aggggaggcggggtaagggaagtaggtggaagattcagccaagctcaaggatggaagtg<br>cagttagggctgggaagggtctaccctcggccgccgtccaagacctaccgaggagctttcca<br>gaatctgttccagagcgtgcgcgaagtgatccagaacccgggccccaggcacccagaggc<br>cgcgagcgcagcacctcccggcgccagtttgctgctgctgcagcagcagcagcagcagca<br>gcagcagcagcagcagcagcagcagcagcagcagcagcagcagcagcaagagactagc<br>cccaggcagcagcagcagcagcagggtgaggatggttctccccaagcccatcgtagaggc<br>cccacaggctacctggtcctggatgaggaacagcaaccttcacagccgcagtcggccctgg<br>agtgccaccccgagagaggttgcgtcccagagcctggagccgccgtggccgccagcaag<br>gggctgccgcagcagctgccagcacctccggacgaggatgactcagctgccccatccacgt<br>tgtccctgctgggccccactttccccggcttaagcagctgctccgctgaccttaaagacatcct<br>gagcgaggccagcaccatgcaactccttcagcaacagcagcaggaagcagtatccgaagg<br>cagcagcagcgggagagcgagggaggcctcgggggctcccacttcctccaaggacaatta<br>cttagggggcacttcgaccatttctgacaacgccaaggagttgtgtaaggcagtgtcggtgtc<br>catgggcctgggtgtggaggcgttggagcatctgagtccaggggaacagcttcggggggat<br>tgcatgtacgccccacttttgggagttccacccgctgtgcgtcccactccttgtgccccattggc<br>cgaatgcaaaggttctctgctagacgacagcgcaggcaagagcactgaagatactgctgagt<br>attcccctttcaagggaggttacaccaaagggctagaaggcgagagcctaggctgctctggc<br>agcgctgcagcagggagctccgggacacttgaactgccgtctaccctgtctctctacaagtcc<br>ggagcactggacgaggcagctgcgtaccagagtcgcgactactacaactttccactggctct<br>ggccggaccgccgcccccctccgccgcctccccatccccacgctcgcatcaagctggagaa<br>cccgctggactacggcagcgcctgggcggctgcggcggcgcagtgccgctatggggacct<br>ggcgagcctgcatggcgcgggtgcagcgggacccggttctgggtcaccctcagccgccgc<br>ttcctcatcctggcacactctcttcacagccgaagaaggccagttgtatggaccgtgtggtggt<br>ggtgggggtggtggcggcggcggcggcggcggcggcggcggcggcggcggcggcgg<br>cggcggcgaggcgggagctgtagccccctacggctacactcggccccctcaggggctggc<br>gggccaggaaagcgacttcaccgcacctgatgtgtggtaccctggcggcatggtgagcaga<br>gtgccctatcccagtcccacttgtgtcaaaagcgaaatgggcccctggatggatagctactcc<br>ggaccttacggggacatgcgtttggagactgccagggaccatgttttgcccattgactattactt<br>tccaccccagaagacctgcctgatctgtggagatgaagcttctgggtgtcactatggagctctc<br>acatgtggaagctgcaaggtcttcttcaaaagagccgctgaagggaaacagaagtacctgtg<br>cgccagcagaaatgattgcactattgataaattccgaaggaaaaattgtccatcttgtcgtcttc<br>ggaaatgttatgaagcagggatgactctgggagcccggaagctgaagaaacttggtaatctg<br>aaactacaggaggaaggagaggcttccagcaccaccagccccactgaggagacaaccca<br>gaagctgacagtgtcacacattgaaggctatgaatgtcagcccatctttctgaatgtcctggaa<br>gccattgagccaggtgtagtgtgtgctggacacgacaacaaccagcccgactcctttgcagc<br>cttgctctctagcctcaatgaactgggagagagacagcttgtacacgtggtcaagtgggccaa<br>ggccttgcctggcttccgcaacttacacgtggacgaccagatggctgtcattcagtactcctgg<br>atggggctcatggtgtttgccatgggctggcgatccttcaccaatgtcaactccaggatgctct<br>acttcgcccctgatctggttttcaatgagtaccgcatgcacaagtcccggatgtacagccagtg<br>tgtccgaatgaggcacctctctcaagagtttggatggctccaaatcacccccaggaattcctg<br>tgcatgaaagcactgctactcttcagcattattccagtggatgggctgaaaaatcaaaaattcttt<br>gatgaacttcgaatgaactacatcaaggaactcgatcgtatcattgcatgcaaaagaaaaaatc<br>ccacatcctgctcaagacgcttctaccagctcaccaagctcctggactccgtgcagcctattgc<br>gagagagctgcatcagttcacttttgacctgctaatcaagtcacacatggtgagcgtggactttc<br>cggaaatgatggcagagatcatctctgtgcaagtgcccaagatcctttctgggaaagtcaagc<br>ccatctatttccacacccagtgaagcattggaaaccctatttccccaccccagctcatgcccct<br>ttcagatgtcttctgcctgttataactctgcactactcctctgcagtgccttggggaatttcctctat<br>tgatgtacagtctgtcatgaacatgttcctgaattctatttgctgggctttttttttctctttctctccttt<br>ctttttcttcttccctccctatctaaccctcccatggcaccttcagactttgcttcccattgtggctcc<br>tatctgtgttttgaatggtgttgtatgcctttaaatctgtgatgatcctcatatggcccagtgtcaag<br>ttgtgcttgtttacagcactactctgtgccagccacacaaacgtttacttatcttatgccacggga<br>agtttagagagctaagattatctggggaaatcaaaacaaaaacaagcaaacaaaaaaaaaaa<br>gcaaaaacaaaacaaaaaataagccaaaaaaccttgctagtgtttttcctcaaaaataaataaa<br>taaataaataaatacgtacatacatacacacatacatacaaacatatagaaatccccaaagagg<br>ccaatagtgacgagaaggtgaaaattgcaggcccatggggagttactgatttttcatctcctcc<br>ctccacgggagactttattttctgccaatggctattgccattagagggcagagtgaccccagag<br>ctgagttgggcagggggtggacagagaggagaggacaaggagggcaatggagcatca | 3 |

TABLE 1-continued

Prostate Cancer Biomarker/Housekeeper Sequence Information

| Gene Name | RefSeq Accession | Sequence | SEQ ID NO: |
|---|---|---|---|
| | | gtacctgcccacagccttggtccctgggggctagactgctcaactgtggagcaattcattatac | |
| | | tgaaaatgtgcttgttgttgaaaatttgtctgcatgttaatgcctcacccccaaaccctttctctct | |
| | | cactctctgcctccaacttcagattgactttcaatagtttttctaagacctttgaactgaatgttctct | |
| | | tcagccaaaacttggcgacttccacagaaaagtctgaccactgagaagaaggagagcagag | |
| | | atttaaccctttgtaaggccccatttggatccaggtctgctttctcatgtgtgagtcagggagga | |
| | | gctggagccagaggagaagaaaatgatagcttggctgttctcctgcttaggacactgactgaa | |
| | | tagttaaactctcactgccactaccttttccccacctttaaaagacctgaatgaagttttctgccaa | |
| | | actccgtgaagccacaagcaccttatgtcctcccttcagtgttttgtgggcctgaatttcatcaca | |
| | | ctgcatttcagccatggtcatcaagcctgtttgcttcttttgggcatgttcacagattctctgttaag | |
| | | agcccccaccaccaagaaggttagcaggccaacagctctgacatctatctgtagatgccagt | |
| | | agtcacaaagatttcttaccaactctcagatcgctggagcccttagacaaactggaaagaagg | |
| | | catcaaagggatcaggcaagctgggcgtcttgcccttgtcccccagagatgataccctccca | |
| | | gcaagtggagaagttctcacttccttctttagagcagctaaaggggctacccagatcagggttg | |
| | | aagagaaaactcaattaccagggtgggaagaatgaaggcactagaaccagaaaccctgcaa | |
| | | atgctcttcttgtcacccagcatatccacctgcagaagtcatgagaagagagaaggaacaaag | |
| | | aggagactctgactactgaattaaaatcttcagcggcaaagcctaaagccagatggacaccat | |
| | | ctggtgagtttactcatcatcctcctctgctgctgattctgggctctgacattgcccatactcactc | |
| | | agattccccacctttgttgctgcctcttagtcagagggaggccaaaccattgagactttctacag | |
| | | aaccatggcttctttcggaaaggtctggttggtgtggctccaatactttgccacccatgaactca | |
| | | gggtgtgccctgggacactggttttatatagtcttttggcacacctgtgttctgttgacttcgttctt | |
| | | caagcccaagtgcaagggaaaatgtccacctactttctcatcttggcctctgcctccttacttag | |
| | | ctcttaatctcatctgttgaactcaagaaatcaagggccagtcatcaagctgcccattttaattgat | |
| | | tcactctgtttgttgagaggatagtttctgagtgacatgatatgatccacaagggtttccttccctg | |
| | | atttctgcattgatattaatagccaaacgaacttcaaaacagctttaaataacaagggagaggg | |
| | | gaacctaagatgagtaatatgccaatccaagactgctggagaaaactaaagctgacaggttcc | |
| | | ctttttggggtgggatagacatgttctggttttctttattattacacaatctggctcatgtacaggat | |
| | | cacttttagctgttttaaacagaaaaaaatatccaccactcttttcagttacactaggttacattttaa | |
| | | taggtcctttacatctgttttggaatgatttcatcttttgtgatacacagattgaattatatcattttca | |
| | | tatctctccttgtaaatactagaagctctcctttacatttctctatcaaatttttcatctttatgggtttc | |
| | | ccaattgtgactcttgtcttcatgaatatatgtttttcatttgcaaaagccaaaaatcagtgaaaca | |
| | | gcagtgtaattaaaagcaacaactggattactccaaatttccaaatgacaaaactagggaaaaa | |
| | | tagcctacacaagcctttaggcctactctttctgtgcttgggtttgagtgaacaaaggagatttta | |
| | | gcttggctctgttctcccatggatgaaaggaggaggatttttttttcttttggccattgatgttcta | |
| | | gccaatgtaattgacagaagtctcatttgcatgcgctctgctctacaaacagagttggtatggtt | |
| | | ggtatactgtactcacctgtgagggactggccactcagacccacttagctggtgagctagaag | |
| | | atgaggatcactcactggaaaagtcacaaggaccatctccaaacaagttggcagtgctcgatg | |
| | | tggacgaagagtgaggaagagaaaaagaaggagcaccagggagaaggctccgtctgtgct | |
| | | gggcagcagacagctgccaggatcacgaactctgtagtcaaagaaaagagtcgtgtggcag | |
| | | tttcagctctcgttcattgggcagctcgcctaggcccagcctctgagctgacatgggagttgttg | |
| | | gattctttgtttcatagcttttctatgccataggcaatattgttgttcttggaaagtttattattttttaa | |
| | | ctcccttactctgagaaagggatatttgaaggactgtcatatatctttgaaaaagaaaatctgt | |
| | | aatacatatatttttatgtatgttcactggcactaaaaaatatagagagcttcattctgtcctttgggt | |
| | | agttgctgaggtaattgtccaggttgaaaaataatgtgctgatgctagagtccctctctgtccata | |
| | | ctctacttctaaatacatataggcatacatagcaagttttatttgacttgtactttaagagaaaatat | |
| | | gtccaccatccacatgatgcacaaatgagctaacattgagcttcaagtagcttctaagtgtttgtt | |
| | | tcattaggcacagcacagatgtggcctttccccccttctctcccttgatatctggcagggcataa | |
| | | aggcccaggccacttcctctgccccttcccagccctgcaccaaagctgcatttcaggagactc | |
| | | tctccagacagcccagtaactacccgagcatggcccctgcatagccctggaaaaataagagg | |
| | | ctgactgtctacgaattatcttgtgccagttgcccaggtgagagggcactgggccaagggagt | |
| | | ggttttcatgtttgacccactacaaggggtcatgggaatcaggaatgccaaagcaccagatca | |
| | | aatccaaaacttaaagtcaaaataagccattcagcatgttcagtttcttggaaaaggaagtttcta | |
| | | cccctgatgcctttgtaggcagatctgttctcaccattaatctttttgaaaatcttttaaagcagtttt | |
| | | taaaaagagagatgaaagcatcacattatataaccaaagattacattgtacctgctaagatacc | |
| | | aaaattcataagggcagggggggagcaagcattagtgcctctttgataagctgtccaaagac | |
| | | agactaaaggactctgctggtgactgacttataagagctttgtgggttttttttccctaataatata | |
| | | catgtttagaagaattgaaaataatttcgggaaaatgggattatgggtccttcactaagtgattta | |
| | | taagcagaactggctttccttttctctagtagttgctgagcaaattgttgaagctccatcattgcat | |
| | | ggttggaaatggagctgttcttagccactgtgtttgctagtgcccatgttagcttatctgaagatg | |
| | | tgaaacccttgctgataagggagcatttaaagtactagattttgcactagagggacagcaggc | |
| | | agaaatccttatttctgcccactttggatggcacaaaaagttatctgcagttgaaggcagaaagt | |
| | | tgaaatacattgtaaatgaatatttgtatccatgtttcaaaattgaaatatatatatatatatatata | |
| | | tatatatatatatatatagtgtgtgtgtgtgttctgatagctttaactttctctgcatctttatatttggtt | |
| | | ccagatcacacctgatgccatgtacttgtgagagaggatgcagttttgttttggaagctctctca | |
| | | gaacaaacaagacacctggattgatcagttaactaaaagttttctcccctattgggtttgaccca | |
| | | caggtcctgtgaaggagcagagggataaaaagagtagaggacatgatacattgtactttacta | |
| | | gttcaagacagatgaatgtggaaagcataaaaactcaatggaactgactgagatttaccacag | |
| | | ggaaggcccaaacttggggccaaaagcctacccaagtgattgaccagtggccccctaatgg | |
| | | gacctgagctgttggaagaagagaactgttccttggtcttcaccatccttgtgagagaagggc | |
| | | agtttcctgcattggaacctggagcaagcgctctatctttcacacaaattccctcacctgagattg | |
| | | aggtgctcttgttactgggtgtctgtgtgctgtaattctggttttggatatgttctgtaaagattttga | |
| | | caaatgaaaatgtgtttttctctgttaaaacttgtcagagtactagaagttgtatctctgtaggtgc | |
| | | aggtccatttctgcccacaggtagggtgtttttctttgattaagagattgacacttctgttgcctag | |
| | | gacctcccaactcaaccatttctaggtgaaggcagaaaaatccacattagttactcctcttcaga | |
| | | catttcagctgagataacaaatcttttggaatttttcacccatagaaagagtggtagatatttgaa | |

TABLE 1-continued

| Prostate Cancer Biomarker/Housekeeper Sequence Information | | | |
|---|---|---|---|
| Gene Name | RefSeq Accession | Sequence | SEQ ID NO: |
| | | tttagcaggtggagtttcatagtaaaaacagcttttgactcagctttgatttatcctcatttgatttgg<br>ccagaaagtaggtaatatgcattgattggcttctgattccaattcagtatagcaaggtgctaggtt<br>ttttcctttccccacctgtctcttagcctggggaattaaatgagaagccttagaatgggtggccct<br>tgtgacctgaaacacttcccacataagctacttaacaagattgtcatggagctgcagattccatt<br>gcccaccaaagactagaacacacacatatccatacaccaaaggaaagacaattctgaaatgc<br>tgtttctctggtggttccctctctggctgctgcctcacagtatgggaacctgtactctgcagaggt<br>gacaggccagatttgcattatctcacaaccttagcccttggtgctaactgtcctacagtgaagtg<br>cctggggggttgtcctatcccataagccacttggatgctgacagcagccaccatcagaatgac<br>ccacgcaaaaaaaagaaaaaaaaaattaaaaagtcccctcacaacccagtgacacctttctgc<br>tttcctctagactggaacattgattagggagtgcctcagacatgacattcttgtgctgtccttgga<br>attaatctggcagcaggagggagcagactatgtaaacagagataaaaattaattttcaatattg<br>aaggaaaaaagaaataagaagagagagagaaagaaagcatcacacaaagattttcttaaaa<br>gaaacaattttgcttgaaatctctttagatggggctcatttctcacggtggcacttggcctccact<br>gggcagcaggaccagctccaagcgctagtgttctgttctctttttgtaatcttggaatcttttgttg<br>ctctaaatacaattaaaaatggcagaaacttgtttgttggactacatgtgtgactttgggtctgtct<br>ctgcctctgctttcagaaatgtcatccattgtgtaaaatattggcttactggtctgccagctaaaac<br>ttggccacatcccctgttatggctgcaggatcgagttattgttaacaaagagacccaagaaaag<br>ctgctaatgtcctcttatcattgttgttaatttgttaaaacataaagaaatctaaaatttcaaaaaa | |
| AR-V7 | | gacactgaatttggaaggtggaggattttgtttttttcttttaagatctgggcatcttttgaatctacc<br>cttcaagtattaagagacagactgtgagcctagcagggcagatcttgtccaccgtgtgtcttctt<br>ctgcacgagactttgaggctgtcagagcgctttttgcgtggttgctcccgcaagtttccttctctg<br>gagcttcccgcaggtgggcagctagctgcagcgactaccgcatcatcacagcctgttgaact<br>cttctgagcaagagaaggggaggcggggtaagggaagtaggtggaagattcagccaagct<br>caaggatggaagtgcagttagggctgggaagggtctaccctcggccgccgtccaagaccta<br>ccgaggagctttccagaatctgttccagagcgtgcgcgaagtgatccagaacccgggcccc<br>aggcacccagaggccgcgagcgcagcacctcccggcgccagtttgctgctgcagcagcag<br>cagcagcagcagcagcagcagcagcagcagcagcagcagcagcagcagcagcagcagc<br>agcagcagcagcagcagcaagagactagccccaggcagcagcagcagcagcagcagggtga<br>ggatggttctccccaagcccatcgtagaggccccacaggctacctggtcctggatgaggaac<br>agcaaccttcacagccgcagtcggccctggagtgccaccccgagagaggttgcgtcccaga<br>gcctggagccgccgtggccgccagcaaggggctgccgcagcagctgccagcacctccgg<br>acgaggatgactcagctgccccatccacgttgtccctgctgggccccactttccccggcttaa<br>gcagctgctccgctgaccttaaagacatcctgagcgaggccagcaccatgcaactccttcag<br>caacagcagcaggaagcagtatccgaaggcagcagcagcgggagagcgagggaggcct<br>cgggggctcccacttcctccaaggacaattacttagggggcacttcgaccatttctgacaacg<br>ccaaggagttgtgtaaggcagtgtcggtgtccatgggcctgggtgtggaggcgttggagcat<br>ctgagtccaggggaacagcttcggggggattgcatgtacgccccacttttgggagttccaccc<br>gctgtgcgtcccactccttgtgccccattggccgaatgcaaaggttctctgctagacgacagc<br>gcaggcaagagcactgaagatactgctgagtattcccctttcaagggaggttacaccaaagg<br>gctagaaggcgagagcctaggctgctctggcagcgctgcagcagggagctccgggacact<br>tgaactgccgtctaccctgtctctctacaagtccggagcactggacgaggcagctgcgtacca<br>gagtcgcgactactacaactttccactggctctggccggaccgccgcccctccgccgcctc<br>cccatccccacgctcgcatcaagctggagaacccgctggactacggcagcgcctgggcgg<br>ctgcggcggcgcagtgccgctatggggacctggcgagcctgcatggcgcgggtgcagcg<br>ggacccggttctgggtcaccctcagccgccgcttcctcatcctggcacactctcttcacagcc<br>gaagaaggccagttgtatggaccgtgtggtggtggggggtggtggcggcggcggcggc<br>ggcggcggcggcggcggcggcgaggcgggagctgtagccccctacggctacactc<br>ggccccctcaggggctggcgggccaggaaagcgacttcaccgcacctgatgtgtggtaccc<br>tggcggcatggtgagcagagtgccctatcccagtcccacttgtgtcaaaagcgaaatgggcc<br>cctggatggatagctactccggaccttacggggacatgcgtttggagactgccagggaccat<br>gttttgcccattgactattactttccaccccagaagacctgcctgatctgtggagatgaagcttct<br>gggtgtcactatggagctctcacatgtggaagctgcaaggtcttcttcaaaagagccgctgaa<br>gggaaacagaagtacctgtgcgccagcagaaatgattgcactattgataaattccgaaggaa<br>aaattgtccatcttgtcgtcttcggaaatgttatgaagcagggatgactctgggagaaaaattcc<br>gggttggcaattgcaagcatctcaaaatgaccagaccctgaagaaaggctgacttgcctcatt<br>caaaatgagggctctagagggctctagtggatagtctggagaaacctggcgtctgaggctta<br>ggagcttaggtttttgctcctcaacacagactttgacgttggggttgggggctactctcttgattg<br>ctgactccctccagcgggaccaatagtgttttcctacctcacagggatgttgtgaggacgggct<br>gtagaagtaatagtggttaccactcatgtagttgtgagtatcatgattattgtttcctgtaatgtgg<br>cttggcattggcaaagtgcttttttgattgttcttgatcacatatgatgggggccaggcactgactc<br>aggcggatgcagtgaagctctggctcagtcgcttgcttttcgtggtgtgctgccaggaagaaa<br>ctttgctgatgggactcaaggtgtcaccttggacaagaagcaactgtgtctgtctgaggttcctg<br>tggccatctttatttgtgtattaggcaattcgtatttccccttaggttctagccttctggatcccag<br>ccagtgacctagatcttagcctcaggccctgtcactgagctgaaggtagtagctgatccacag<br>aagttcagtaaacaaggaccagatttctgcttctccaggagaagaagccagccaacccctctc<br>ttcaaacacactgagagactacagtccgactttccctcttacatctagccttactgtagccacact<br>ccttgattgctctctcacatcacatgcttctcttcatcagttgtaagcctctcattcttctcccaagc<br>cagactcaaatattgtattgatgtcaaagaagaatcacttagagtttggaatatcttgttctctctct<br>gctccatagcttccatattgacaccagtttctttctagtggagaagtggagtctgtgaagccagg<br>gaaacacacatgtgagagtcagaaggactctccctgacttgcctggggcctgtctttcccacct<br>tctccagtctgtctaaacacacacacacacacacacacacacacacacacacacacacgc<br>tctctctctctctccccccccaacacacacacactctctctctcacacacacacacatacacaca<br>cacttctttctctttcccctgactcagcaacattctggagaaaagccaaggaaggacttcagga | 4 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | ggggagtttccccttctcagggcagaattttaatctccagaccaacaagaagttccctaatgt<br>ggattgaaaggctaatgaggtttatttttaactactttctatttgtttgaatgttgcatatttctactagt<br>gaaattttcccttaataaagccattaatacacccaaaaaaaaaaaaaaaa | |
| C16orf89 | NM_001098514.2 | ctacgcccaggactggcctaacctccgctgcctaaccgtcatccccctgcagccacccttccc<br>agagtcctttgcccaggccaccccaggcttcttggcagccctgccgggccacttgtcttcatgt<br>ctgccagggggaggtgggaaggaggtgggaggagggcgtgcagaggcagtctgggcttg<br>gccagagctcagggtgctgagcgtgtgaccagcagtgagcagaggccggccatggccag<br>cctggggctgctgctcctgctcttactgacagcactgccaccgctgtggtcctcctcactgcct<br>gggctggacactgctgaaagtaaagccaccattgcagacctgatcctgtctgcgctggagag<br>agccaccgtcttcctagaacagaggctgcctgaaatcaacctggatggcatggtgggggtcc<br>gagtgctggaagagcagctaaaaagtgtccgggagaagtgggcccaggagcccctgctgc<br>agccgctgagcctgcgcgtggggatgctgggggagaagctggaggctgccatccagagat<br>ccctccactacctcaagctgagtgatcccaagtacctaagagagttccagctgaccctccagc<br>ccgggttttggaagctcccacatgcctggatccacactgatgcctccttggtgtaccccacgtt<br>cgggccccaggactcattctcagaggagagaagtgacgtgtgcctggtgcagctgctggga<br>accgggacggacagcagcgagccctgcggcctctcagacctctgcaggagcctcatgacc<br>aagcccggctgctcaggctactgcctgtcccaccaactgctcttcttcctctgggccagaatga<br>gggggtgcacacagggaccactccaacagagccaggactatatcaacctcttctgcgccaa<br>catgatggacttgaaccgcagagctgaggccatcggatacgcctaccctacccgggacatct<br>tcatggaaaacatcatgttctgtggaatgggcggcttctccgacttctacaagctccggtggct<br>ggaggccattctcagctggcagaaacagcaggaaggatgcttcggggagcctgatgctgaa<br>gatgaagaattatctaaagctattcaatatcagcagcatttttcgaggagagtgaagaggcgag<br>aaaaacaatttccagatggctgctcctcccacaacacagccacagcagtggcagccctgggt<br>ggcttcctatacatcctggcagaataccccccagcaaacagagagccacacccatccacacc<br>gccaccaccaagcagccgctgagacggacggttccatgccagctgcctggaggaggaaca<br>gacccctttagtcctcatcccttagatcctggagggcacggatcacatcctgggaagaaggca<br>tctggaggataagcaaagccaccccgacacccaatcttggaagccctgagtaggcagggcc<br>agggtaggtgggggccgggagggacccaggtgtgaacggatgaataaagttcaactgcaa<br>ctgaaaaaaaaaaaaaaaaaaaaaaaaaa | 5 |
| CHTOP | NM_001206612.1 | tttcccgccctctagtcgtgcgcggatctgacgcctgacgtaattgcgtagacgccattttagcc<br>ggtcagacaagcactggacgtggcggccattttgttttggacaccgagcaggagctggcgg<br>ccgctgcagacgaaaggcaggaaagggcaggccgggtgagcagacggatcggccgact<br>agacagccaaccagcaacaacgaactgagctcgcatactaccgcttacgcatctaaccaacc<br>gcccatctagctaacccgagcccctccaccgtcaactcaggttcggccggtccccggcccgc<br>ctgccggagccgtggtggcagccccgggaggagcactggcgtctgtttccttcgattctcgg<br>gattcgaagatggctgcacagtcagcgccgaaagttgtgctaaaaagcaccaccaagatgtc<br>tctaaatgagcgctttactaatatgctgaagaacaaacagccgacgccagtgaatattcgggct<br>tcgatgcagcaacaacagcagctagccagtgccagaaacagaagactggcccagcagatg<br>gagaatagaccctctgtccaggcagcattaaaacttaagcagaagagcttaaagcagcgcct<br>gggtaagagtaacatccaggcacggttaggccgacccataggggccctggccaggggagc<br>aatcggaggacgaggcctacccataatccagagaggcttgcccagaggaggactacgtgg<br>gggacgtgccaccagaaccctacttaggggcgggatgtcactccgaggtcaaaacctgctc<br>cgaggtggacgagccgtagctccccgaatgggcttaagaagaggtggtgttcgaggtcgtg<br>gaggtcctgggagagggggcctagggcgtggagctatgggtcgtggcggaatcggtggta<br>gaggtcggggtatgataggtcggggaagagggggctttggaggccgaggccgaggccgt<br>ggacgagggagaggtgcccttgctcgccctgtattgaccaaggagcagctggacaaccaat<br>tggatgcatatatgtcgaaaacaaaaggacacctggatgctgagttggatgcctacatggcgc<br>agacagatcccgaaaccaatgattgaagcctgcccatcctcccatgagagactcttgttagtca<br>acacatctgtaaataaccttgagataacagatgagaagaaatctgattgatgctggatggacct<br>atcacaataggctgtggacttacttgccaccagcttgtgcatttagtgtgttccttttactttttgata<br>ctgtgttgtatgaaacccttttgtcctttgatttggtttttttgtttttgtttttttttagggggggaggggg<br>gtttcccctcctttgcccagacttctctttgaacacaaatgcattagccttgtggctagaacaccct<br>cttcctacctctgtctcccctcacttgtcatatgctctgacatgctaacatttcttttgttcatccctgt<br>tgcccccacagaaacatcccagaaaaaccggtcagtgttccttcctccctgatccttaggtttct<br>gaaatagggttctgttacatcctcttcgatagcctgtttaaaatgtttagaaggtctggagctcaa<br>aaatgcgttcttccacattgataatttagtaaactgagaacattgacatcactacagggcagcat<br>aagaggttgcttacatgtggtagcagctctggtttgattcaagttgctaccatgtacattgacagc<br>acatataccataaccagcgtgttgggttgaattgcactttctacctttgtatgagatttacagacttt<br>ccttctgggtttgtatcatgaccagaggggtactatagggttggtttatactgcaatatagaggat<br>cagaagccatttgatttggtaggtgtgtcagaagggagaatgatggcagacgaactgctgga<br>agaggtcagaagatagccatgctaaaatgcaattatatcctcatgtttatcccaaactaatcttgg<br>acttttccactcattagctttgttttgcccttgtttcccttgaaggtttaagttcaaccatattctgtca<br>actgttcagtttcagtggaatcttgtatttctggttcattataacaaactgttcgcttaaatccaaaa<br>aaaaaa | 6 |
| COL1A1 | NM_000088.3 | tcgtcggagcagacgggagtttctcctcggggtcggagcaggaggcacgcggagtgtgag<br>gccacgcatgagcggacgctaacccccctccccagccacaaagagtctacatgtctagggtct<br>agacatgttcagctttgtggacctccggctcctgctcctcttagcggccaccgccctcctgacg<br>cacggccaagaggaaggccaagtcgagggccaagacgaagacatcccaccaatcacctg<br>cgtacagaacggcctcaggtaccatgaccgagacgtgtggaaacccgagccctgccggatc<br>tgcgtctgcgacaacggcaaggtgttgtgcgatgacgtgatctgtgacgagaccaagaactg<br>ccccggcgccgaagtccccgagggcgagtgctgtcccgtctgccccgacggctcagagtc | 7 |

TABLE 1-continued

Prostate Cancer Biomarker/Housekeeper Sequence Information

| Gene Name | RefSeq Accession | Sequence | SEQ ID NO: |
|---|---|---|---|
| | | acccaccgaccaagaaaccaccggcgtcgagggacccaagggagacactggcccccgag | |
| | | gcccaaggggacccgcaggccccctggccgagatggcatccctggacagcctggacttc | |
| | | ccggacccccggacccccggacctcccggacccctggcctcggaggaaactttgctcc | |
| | | ccagctgtcttatggctatgatgagaaatcaaccggaggaatttccgtgcctggccccatgggt | |
| | | ccctctggtcctcgtggtctccctggccccctggtgcacctggtccccaaggcttccaaggt | |
| | | ccccctggtgagcctggcgagcctggagcttcaggtcccatgggtccccgaggtcccccag | |
| | | gtccccctggaaagaatggagatgatggggaagctggaaaacctggtcgtcctggtgagcg | |
| | | tgggcctcctgggcctcagggtgctcgaggattgcccggaacagctggcctccctggaatga | |
| | | agggacacagaggtttcagtggtttggatggtgccaagggagatgctggtcctgctggtccta | |
| | | agggtgagcctggcagccctggtgaaaatggagctcctggtcagatgggccccgtggcct | |
| | | gcctggtgagagaggtcgccctggagcccctggccctgctggtgctcgtggaaatgatggtg | |
| | | ctactggtgctgccgggcccctggtcccaccggccccgctggtcctcctggcttccctggtg | |
| | | ctgttggtgctaagggtgaagctggtccccaagggccccgaggctctgaaggtccccaggg | |
| | | tgtgcgtggtgagcctggccccctggccctgctggtgctgctggccctgctggaaaccctg | |
| | | gtgctgatggacagcctggtgctaaaggtgccaatggtgctcctggtattgctggtgctcctgg | |
| | | cttccctggtgcccgaggcccctctggaccccagggccccggcggccctcctggtcccaag | |
| | | ggtaacagcggtgaacctggtgctcctggcagcaaaggagacactggtgctaagggagag | |
| | | cctggccctgttggtgttcaaggacccctggccctgctggagaggaaggaaagcgaggag | |
| | | ctcgaggtgaacccggacccactggcctgcccggacccctggcgagcgtggtggacctg | |
| | | gtagccgtggtttccctggcgcagatggtgttgctggtcccaagggtcccgctggtgaacgtg | |
| | | gttctcctggccctgctggccccaaaggatctcctggtgaagctggtcgtcccggtgaagctg | |
| | | gtctgcctggtgccaagggtctgactggaagccctggcagccctggtcctgatggcaaaact | |
| | | ggccccctggtcccgccggtcaagatggtcgccccggaccccaggcccacctggtgcc | |
| | | cgtggtcaggctggtgtgatgggattccctggacctaaaggtgctgctggagagcccggcaa | |
| | | ggctggagagcgaggtgttcccggacccctggcgctgtcggtcctgctggcaaagatgga | |
| | | gaggctggagctcagggacccctggccctgctggtcccgctggcgagagaggtgaacaa | |
| | | ggccctgctggctcccccggattccagggtctccctggtcctgctggtcctccaggtgaagca | |
| | | ggcaaacctggtgaacagggtgttcctggagaccttggcgcccctggcccctctggagcaa | |
| | | gaggcgagagaggtttccctggcgagcgtggtgtgcaaggtcccctggtcctgctggtccc | |
| | | cgaggggccaacggtgctcccggcaacgatggtgctaagggtgatgctggtgcccctgga | |
| | | gctcccggtagccagggcgcccctggccttcagggaatgcctggtgaacgtggtgcagctg | |
| | | gtcttccagggcctaagggtgacagaggtgatgctggtcccaaaggtgctgatggctctcctg | |
| | | gcaaagatggcgtccgtggtctgactggccccattggtcctcctggccctgctggtgcccctg | |
| | | gtgacaagggtgaaagtggtcccagcggccctgctggtcccactggagctcgtggtgcccc | |
| | | cggagaccgtggtgagcctggtcccccggccctgctggctttgctggccccctggtgctg | |
| | | acggccaacctggtgctaaaggcgaacctggtgatgctggtgctaaaggcgatgctggtccc | |
| | | cctggccctgccggacccgctggacccctggccccattggtaatgttggtgctcctggagc | |
| | | caaaggtgctcgcggcagcgctggtccccctggtgctactggtttccctggtgctgctggccg | |
| | | agtcggtcctcctggcccctctggaaatgctggacccctggccctcctggtcctgctggcaa | |
| | | agaaggcggcaaaggtccccgtggtgagactggccctgctggacgtcctggtgaagttggt | |
| | | ccccctggtccccctggccctgctggcgagaaaggatcccctggtgctgatggtcctgctggt | |
| | | gctcctggtactcccgggcctcaaggtattgctggacagcgtggtgtggtcggcctgcctggt | |
| | | cagagaggagagagaggcttccctggtcttcctggcccctctggtgaacctggcaaacaag | |
| | | gtccctctggagcaagtggtgaacgtggtccccctggtcccatgggcccccctggattggct | |
| | | ggacccctggtgaatctggacgtgaggggctcctggtgccgaaggttcccctggacgag | |
| | | acggttctcctggcgccaagggtgaccgtggtgagaccggccccgctggacccctggtgc | |
| | | tcctggtgctcctggtgcccctggccccgttggccctgctggcaagagtggtgatcgtggtga | |
| | | gactggtcctgctggtcccgccggtcctgtcggccctgttggcgcccgtggccccgccggac | |
| | | cccaaggcccccgtggtgacaagggtgagacaggcgaacagggcgacagaggcataaag | |
| | | ggtcaccgtggcttctctggcctccagggtccccctggccctcctggctctcctggtgaacaa | |
| | | ggtccctctggagcctctggtcctgctggtccccgaggtcccctggctctgctggtgctcctg | |
| | | gcaaagatggactcaacggtctccctggccccattgggcccctggtcctcgcggtcgcact | |
| | | ggtgatgctggtcctgttggtcccccggccctcctggacctcctggtcccctggtcctccca | |
| | | gcgctggtttcgacttcagcttcctgccccagccacctcaagagaaggctcacgatggtggcc | |
| | | gctactaccgggctgatgatgccaatgtggttcgtgaccgtgacctcgaggtggacaccacc | |
| | | ctcaagagcctgagccagcagatcgagaacatccggagcccagagggcagccgcaagaa | |
| | | ccccgcccgcacctgccgtgacctcaagatgtgccactctgactggaagagtggagagtact | |
| | | ggattgaccccaaccaaggctgcaacctggatgccatcaaagtcttctgcaacatggagactg | |
| | | gtgagacctgcgtgtaccccactcagcccagtgtggcccagaagaactggtacatcagcaag | |
| | | aaccccaaggacaagaggcatgtctggttcggcgagagcatgaccgatggattccagttcga | |
| | | gtatggcggccagggctccgaccctgccgatgtggccatccagctgaccttcctgcgcctga | |
| | | tgtccaccgaggcctcccagaacatcacctaccactgcaagaacagcgtggcctacatggac | |
| | | cagcagactggcaacctcaagaaggccctgctcctccagggctccaacgagatcgagatcc | |
| | | gcgccgagggcaacagccgcttcacctacagcgtcactgtcgatggctgcacgagtcacac | |
| | | cggagcctggggcaagacagtgattgaatacaaaaccaccaagacctcccgcctgcccatc | |
| | | atcgatgtggccccttggacgttggtgccccagaccaggaattcggcttcgacgttggccct | |
| | | gtctgcttcctgtaaactccctccatcccaacctggctccctcccacccaaccaactttcccccc | |
| | | aacccggaaacagacaagcaacccaaactgaacccccctcaaaagccaaaaaatgggagac | |
| | | aatttcacatggactttggaaaatatttttttcctttgcattcatctctcaaacttagtttttatctttgac | |
| | | caaccgaacatgaccaaaaaccaaaagtgcattcaaccttaccaaaaaaaaaaaaaaaaaaa | |
| | | gaataaataaataactttttaaaaaaggaagcttggtccacttgcttgaagacccatgcggggg | |
| | | taagtccctttctgcccgttgggcttatgaaaccccaatgctgccctttctgctcctttctccacac | |
| | | ccccttggggcctcccctccactccttcccaaatctgtctccccagaagacacaggaaacaa | |
| | | tgtattgtctgcccagcaatcaaaggcaatgctcaaacacccaagtggccccaccctcagcc | |

TABLE 1-continued

Prostate Cancer Biomarker/Housekeeper Sequence Information

| Gene Name | RefSeq Accession | Sequence | SEQ ID NO: |
|---|---|---|---|
| | | cgctcctgcccgcccagcacccccaggccctggggggacctggggttctcagactgccaaag<br>aagccttgccatctggcgctcccatggctcttgcaacatctccccttcgtttttgaggggtcat<br>gccgggggagccaccagcccctcactgggttcggaggagagtcaggaagggccacgaca<br>aagcagaaacatcggatttggggaacgcgtgtcaatcccttgtgccgcagggctgggcggg<br>agagactgttctgttccttgtgtaactgtgttgctgaaagactacctcgttcttgtcttgatgtgtca<br>ccggggcaactgcctgggggcggggatgggggcagggtggaagcggctccccattttata<br>ccaaaggtgctacatctatgtgatgggtggggtggggagggaatcactggtgctatagaaatt<br>gagatgcccccccaggccagcaaatgttcctttttgttcaaagtctatttttattccttgatatttttc<br>tttttttttttttttttttgtggatggggacttgtgaatttttctaaaggtgctatttaacatgggaggag<br>agcgtgtgcggctccagcccagcccgctgctcactttccaccctctctccacctgcctctggct<br>tctcaggcctctgctctccgacctctctcctctgaaaccctcctccacagctgcagcccatcctc<br>ccggctccctcctagtctgtcctgcgtcctctgtccccgggtttcagagacaacttcccaaagc<br>acaaagcagtttttccccctaggggtgggaggaagcaaaagactctgtacctattttgtatgtgt<br>ataataatttgagatgtttttaattattttgattgctggaataaagcatgtggaaatgacccaaacat<br>aa | |
| EDC4 | NM_014329.4 | tttcttctccggccctggcaggttccgggagcctcggctcgtgggtgccggaagtggaggcg<br>gttggtggggttggcggggctcagcgacgctgcgcgggtggcggtttgcgaactgcgggtg<br>gactgtgtagtgaccggcgtcccgctgtctcgccccgtggcgggtgagcgagggtgcgtgg<br>tgcgcggcggcggcggaacgaacgcggtgcgggcggggcgcccgccgcagggcccat<br>ggcctcctgcgcgagcatcgacatcgaggacgccacgcagcacctgcgggacatcctcaa<br>gctggaccggcccgcgggcggccccagtgcagagagcccacggccatccagtgcctaca<br>atggggacctcaatggacttctggtcccagacccgctctgctcaggtgatagtacctcagcaa<br>acaagactggtcttcggaccatgccacccattaacctgcaagagaagcaggtcatctgtctctc<br>aggagatgatagctccacctgcattgggattttggccaaggaggtggagattgtggctagcag<br>tgactctagcatttcaagcaaggcccggggaagcaacaaggtgaaaattcagcctgtcgcca<br>agtatgactgggaacagaagtactactatggcaacctgattgctgtgtctaactccttcttggcc<br>tatgccattcgggctgccaacaatggctctgccatggtgcgggtgatcagcgtcagcacttcg<br>gagcggaccttgctcaagggcttcacaggcagtgtggctgatctggctttcgcgcacctcaac<br>tctccacagctggcctgcctggatgaggcaggcaacctgttcgtgtggcgcttggctctggtta<br>atggcaaaattcaagaagagatcttggtccatattcggcagccagagggcacgccactgaac<br>cactttcgcaggatcatctggtgccccttcatccctgaggagagcgaagactgctgtgaggag<br>agcagcccaacagtggccctgctgcatgaagaccgggctgaggtgtgggacctggacatg<br>ctccgctccagccacagtacctggcctgtggatgttagccagatcaagcagggcttcattgtg<br>gtaaaaggtcatagcacgtgcctcagtgaaggagccctctctcctgatgggactgtgctggct<br>actgcgagccacgatggctatgtcaagttctggcagatctacattgaggggcaagatgagcc<br>aaggtgtctgcacgagtggaaacctcatgatgggcggcccctctcctgcctcctgttctgtgac<br>aaccataagaaacaagaccctgatgtccctttctggaggttccttattactggtgctgaccagaa<br>ccgagagttaaagatgtggtgtacagtatcctggacctgcctgcagactattcgcttctcccca<br>gatatcttcagctcagtgagtgtgccccctagcctcaaggtttgcttggacctctcagcagaata<br>cctgattctcagcgatgtgcaacggaaggtcctctatgtgatggagctgctgcaaaaccagga<br>ggagggccacgcctgcttcagctccatctcggagttcctgctcacccaccctgtgctgagcttt<br>ggtatccaggttgtgagtcgctgccggctacggcacactgaggtgctgcctgccgaagagg<br>aaaatgacagcctgggtgctgatggtacccatggagccggtgccatggagtctgcggccgg<br>tgtgctcatcaagctcttttgtgtgcatactaaggcactgcaagatgtgcagatccgcttccagc<br>cacagctgaaccctgatgtggtggccccactgcccacccacactgcccacgaggacttcaca<br>tttggagagtctcggcccgaactgggctctgagggcctggggtcagccgctcacggctccca<br>gcctgacctccgacgaatcgtggagctgcctgcacctgccgacttcctcagtctgagcagtga<br>gaccaagcccaagttgatgacacctgacgccttcatgacacctagcgcctccttgcagcagat<br>cactgcctctcccagcagcagcagcagcggtagcagcagcagcagcagcagtagcagcag<br>ctcccttacagctgtgtctgccatgagcagcacctcagctgtggacccctccttgaccaggcc<br>acctgaggagctgaccttgagccccaagctgcagctggatggcagcctgacaatgagcagc<br>agtggcagccttcaggcaagcccgcgtggcctcctgcctggcctgctcccagccccagctg<br>acaaactgactcccaaggggccgggccaggtgcctactgccacctctgcactgtccctggag<br>ctgcaggaagtggagcccctggggctaccccaagcctcccctagccgcactcgttcccctga<br>tgtcatctcctcagcttccactgccctgtcccaggacatccctgagattgcatctgaggccctgt<br>cccgtggttttggctcctctgcaccagagggccttgagccagacagtatggcttcagccgcct<br>cggcactgcacctgctgtccccacggccccggccagggcccgagctcggcccccagctcg<br>ggcttgatggaggccctggggatggagatcggcataatacccctccctcctggaggcagc<br>cttgacccaggaggcctcgactcctgacagtcaggtttggcccacagcacctgacattactcg<br>tgagacctgcagcaccctggcagaaagccccaggaatggccttcaggaaaagcacaagag<br>cctggccttccaccgaccaccatatcacctgctgcagcaacgtgacagccaggatgccagtg<br>ctgagcaaagtgaccatgatgatgaggtggccagccttgcctctgcttcaggaggctttggca<br>ccaaagttcctgctccacggctgcctgccaaggactggaagaccaagggatcccctcgaac<br>ctcacccaagctcaagaggaaaagcaagaaggatgatggggatgcagccatgggatcccg<br>gctcacagagcaccaggtggcagagccccctgaggactggccagcactaatttggcaacag<br>cagagagagctggcagagctgcggcacagccaggaagagctgctgcagcgtctgtgtacc<br>caactcgaaggcctgcagagcacagtcacaggccacgtagaacgtgcccttgagactcggc<br>acgagcaggaacagcggcggctggagcgagcactggctgaggggcagcagcggggag<br>ggcagctgcaggagcagctgacacaacagttgtcccaagcactgtcgtcagctgtagctgg<br>gcggctagagcgcagcatacgggatgagatcaagaagacagtccctccatgtgtctcaagg<br>agtctggagcctatggcaggccaactgagcaactcagtggctaccaagctcacagctgtgga<br>gggcagcatgaaagagaacatctccaagctgctcaagtccaagaacttgactgatgccatcg<br>cccgagcagctgcagacacattacaagggccgatgcaggctgcctaccgggaagccttcca | 8 |

TABLE 1-continued

Prostate Cancer Biomarker/Housekeeper Sequence Information

| Gene Name | RefSeq Accession | Sequence | SEQ ID NO: |
|---|---|---|---|
| | | gagtgtggtgctgccggcctttgagaagagctgccaggccatgttccagcaaatcaatgatag<br>cttccggctggggacacaggaatacttgcagcagctagaaagccacatgaagagccggaag<br>gcacgggaacaggaggccagggagcctgtgctagcccagctgcggggcctggtcagcac<br>actgcagagtgccactgagcagatggcagccaccgtggccggcagtgttcgtgctgaggtg<br>cagcaccagctgcatgtggctgtgggcagcctgcaggagtccattttagcacaggtacagcg<br>catcgttaagggtgaggtgagtgtggcgctcaaggagcagcaggccgccgtcacctccagc<br>atcatgcaggccatgcgctcagctgctggcacacctgtcccctctgcccaccttgactgccag<br>gcccagcaagcccatatcctgcagctgctgcagcagggccacctcaatcaggccttccagca<br>ggcgctgacagctgctgacctgaacctggtgctgtatgtgtgtgaaactgtggacccagccca<br>ggtttttgggcagccaccctgcccgctctcccagcctgtgctcctttccctcatccagcagctg<br>gcatctgaccttggcactcgaactgacctcaagctcagctacctggaagaggccgtgatgca<br>cctggaccacagtgaccccatcactcgggaccacatgggctccgttatggcccaggtgcgcc<br>aaaagctttttcagttcctgcaggctgagccacacaactcacttggcaaagcagctcggcgtct<br>cagcctcatgctgcatggcctcgtgacccccagcctcccttagctgctaagcctgccttgccca<br>ggggtgggatggcactgaaggccagcagacaggcctaggctggggcagggtcacggctg<br>gcctttacctgctcaggcccccatctctggggtgtttggggggtcagggagcagggagcactg<br>gccgtggtctacagcgtgtggtagtcagaaggtttagctgggcccagggcaggtattgcgcc<br>tgcttgggttctgccatgcctggagcatgaccctgagatcgtgacaccacttgagtggaattttc<br>catgttcctttttacctctaatttggatctttttgtttttgaaaaacattgagaaattcaattaaatgcttt<br>tggaataaaatggagtatgtgtgtg | |
| FGFR2 | NM_000141.4 | ggcggcggctggaggagagcgcggtggagagccgagcgggcgggcggcgggtgcgga<br>gcgggcgagggagcgcgcgcggccgccacaaagctcgggcgccgcggggctgcatgc<br>ggcgtacctggcccggcgcggcgactgctctccgggctggcgggggccggccgcgagcc<br>ccgggggccccgaggccgcagcttgcctgcgcgctctgagccttcgcaactcgcgagcaa<br>agtttggtggaggcaacgccaagcctgagtcctttcttcctctcgttccccaaatccgagggca<br>gcccgcgggcgtcatgcccgcgctcctccgcagcctggggtacgcgtgaagcccgggag<br>gcttggcgccggcgaagacccaaggaccactcttctgcgtttggagttgctccccgcaaccc<br>cgggctcgtcgctttctccatcccgacccacgcggggcgcggggacaacacaggtcgcgg<br>aggagcgttgccattcaagtgactgcagcagcagcggcagcgcctcggttcctgagcccac<br>cgcaggctgaaggcattgcgcgtagtccatgcccgtagaggaagtgtgcagatgggattaac<br>gtccacatggagatatggaagaggaccggggattggtaccgtaaccatggtcagctggggt<br>cgtttcatctgcctggtcgtggtcaccatggcaaccttgtccctggcccggccctccttcagttt<br>agttgaggataccacattagagccagaagagccaccaaccaaataccaaatctctcaaccag<br>aagtgtacgtggctgcgccaggggagtcgctagaggtgcgctgcctgttgaaagatgccgc<br>cgtgatcagttggactaaggatggggtgcacttggggcccaacaataggacagtgcttattgg<br>ggagtacttgcagataaagggcgccacgcctagagactccggcctctatgcttgtactgcca<br>gtaggactgtagacagtgaaacttggtacttcatggtgaatgtcacagatgccatctcatccgg<br>agatgatgaggatgacaccgatggtgcggaagattttgtcagtgagaacagtaacaacaaga<br>gagcaccatactggaccaacacagaaaagatggaaaagcggctccatgctgtgcctgcggc<br>caacactgtcaagtttcgctgcccagccggggggaacccaatgccaaccatgcggtggctg<br>aaaaacgggaaggagtttaagcaggagcatcgcattggaggctacaaggtacgaaaccagc<br>actggagcctcattatggaaagtgtggtcccatctgacaagggaaattatacctgtgtagtgga<br>gaatgaatacgggtccatcaatcacacgtaccacctggatgttgtggagcgatcgcctcaccg<br>gcccatcctccaagccggactgccggcaaatgcctccacagtggtcggaggagacgtagag<br>tttgtctgcaaggtttacagtgatgcccagccccacatccagtggatcaagcacgtggaaaag<br>aacggcagtaaatacgggcccgacgggctgccctacctcaaggttctcaaggccgccggtg<br>ttaacaccacggacaaagagattgaggttctctatattcggaatgtaacttttgaggacgctgg<br>ggaatatacgtgcttggcgggtaattctattgggatatcctttcactctgcatggttgacagttctg<br>ccagcgcctggaagagaaaaggagattacagcttccccagactacctggagatagccattta<br>ctgcataggggtcttcttaatcgcctgtatggtggtaacagtcatcctgtgccgaatgaagaac<br>acgaccaagaagccagacttcagcagccagccggctgtgcacaagctgaccaaacgtatcc<br>ccctgcggagacaggtaacagtttcggctgagtccagctcctccatgaactccaacaccccg<br>ctggtgaggataacaacacgcctctcttcaacggcagacacccccatgctggcaggggtctc<br>cgagtatgaacttccagaggacccaaaatgggagtttccaagagataagctgacactgggca<br>agcccctgggagaaggttgctttgggcaagtggtcatggcggaagcagtgggaattgacaa<br>agacaagcccaaggaggcggtcaccgtggccgtgaagatgttgaaagatgatgccacaga<br>gaaagacctttctgatctggtgtcagagatggagatgatgaagatgattgggaaacacaagaa<br>tatcataaatcttcttggagcctgcacacaggatgggcctctctatgtcatagttgagtatgcctc<br>taaaggcaacctccgagaatacctccgagcccggaggccacccgggatggagtactcctat<br>gacattaaccgtgttcctgaggagcagatgaccttcaaggacttggtgtcatgcacctaccag<br>ctggccagaggcatggagtacttggcttcccaaaaatgtattcatcgagatttagcagccaga<br>aatgttttggtaacagaaaacaatgtgatgaaaatagcagactttggactcgccagagatatca<br>acaatatagactattacaaaaagaccaccaatgggcggcttccagtcaagtggatggctccag<br>aagccctgtttgatagagtatacactcatcagagtgatgtctggtccttcggggtgttaatgtgg<br>gagatcttcactttaggggctcgccctacccagggattcccgtggaggaactttttaagctgc<br>tgaaggaaggacacagaatggataagccagccaactgcaccaacgaactgtacatgatgat<br>gagggactgttggcatgcagtgccctcccagagaccaacgttcaagcagttggtagaagact<br>tggatcgaattctcactctcacaaccaatgaggaatacttggacctcagccaacctctcgaaca<br>gtattcacctagttaccctgacacaagaagttcttgttcttcaggagatgattctgtttttctccag<br>accccatgccttacgaaccatgccttcctcagtatccacacataaacggcagtgttaaaacatg<br>aatgactgtgtctgcctgtccccaaacaggacagcactgggaacctagctacactgagcagg<br>gagaccatgcctcccagagcttgttgtctccacttgtatatatggatcagaggagtaaataattg<br>gaaaagtaatcagcatatgtgtaaagatttatacagttgaaaacttgtaatcttccccaggagga | 9 |

TABLE 1-continued

Prostate Cancer Biomarker/Housekeeper Sequence Information

| Gene Name | RefSeq Accession | Sequence | SEQ ID NO: |
|---|---|---|---|
| | | gaagaaggtttctggagcagtggactgccacaagccaccatgtaacccctctcacctgccgt gcgtactggctgtggaccagtaggactcaaggtggacgtgcgttctgccttccttgttaattttgt aataattggagaagatttatgtcagcacacacttacagagcacaaatgcagtatataggtgctg gatgtatgtaaatatattcaaattatgtataaatatatattatatatttacaaggagttatttttgtatt gattttaaatggatgtcccaatgcacctagaaaattggtctctcttttttaatagctatttgctaaat gctgttcttacacataatttcttaattttcaccgagcagaggtggaaaaatacttttgctttcaggg aaaatggtataacgttaatttattaataaattggtaatatacaaaacaattaatcatttatagttttttt gtaatttaagtggcatttctatgcaggcagcacagcagactagttaatctattgcttggacttaac tagttatcagatcctttgaaaagagaatatttacaatatatgactaatttggggaaaatgaagtttt gatttatttgtgtttaaatgctgctgtcagacgattgttcttagacctcctaaatgccccatattaaa agaactcattcataggaaggtgtttcattttggtgtgcaaccctgtcattacgtcaacgcaacgtc taactggacttcccaagataaatggtaccagcgtcctcttaaaagatgccttaatccattccttga ggacagaccttagttgaaatgatagcagaatgtgcttctctctggcagctggccttctgcttctg agttgcacattaatcagattagcctgtattctcttcagtgaattttgataatggcttccagactcttt ggcgttggagacgcctgttaggatcttcaagtcccatcatagaaaattgaaacacagagttgtt ctgctgatagttttggggatacgtccatctttttaagggattgctttcatctaattctggcaggacct caccaaaagatccagcctcatacctacatcagacaaaatatcgccgttgttccttctgtactaaa gtattgtgttttgctttggaaacacccactcactttgcaatagccgtgcaagatgaatgcagatta cactgatcttatgtgttacaaaattggagaaagtatttaataaaacctgttaatttttatactgacaa taaaaatgtttctacagatattaatgttaacaagacaaaataaatgtcacgcaacttattttttaata aaaaaaaaaaaaaa | |
| FXYD7 | NM_022006.1 | ccccacatcggtccgtcctgcttccagctgctgcagcgcgccttcgccgccaaagcatccag cagccccctgctccggcccagcatggcgaccccgacccagaccccccacaaaggctcctga ggaacctgacccattttactatgactacaacacggtgcagactgtgggcatgactctggcaac catcttgttcctgctgggtatcctcatcgtcatcagcaagaaggtgaagtgcaggaaggcgga ctccaggtctgagagcccaacctgcaaatcctgtaagtctgagcttccctcttcagcccctggt ggcggcggcgtgtaacaccttcccgaggaaactccgctgccgaccctgcctgagcgcggg agcctgaggaccgggtggaggcggtggggacccagccgcgcgccgggagcgctccccg gaatgagccgccccacccaccccaaggctggagccgctgcaccctgctgtccctctccagg ccttggcaatgacgatcccccaaagagcccgtctgcaccccagacccagggcctcaggcct ccagctcctgggatccgggagtccatcccggcccagcacccccagcatccccgtgtatggc ccccctgcacctccttgtctcatccccgaagatccgtccccctggcccctcagtgtccatgtctt gagcttaataaatgtgcatttggtttttcctctg | 10 |
| FYCO1 | NM_024513.3 | accctcttggtgtgcgcgtcatggccgtcagcaccgcgttcccgtcctcttccgcttggcccca gaaagtttcggttctgcccggcggtggacccacgagcgcgtgccaccatggagtctgacca ctgctgagcagacagccaccgagggccgaaattctgagccttcctctggacccaggcagga gacatacagacaagaaaggcaaactcaccatggcctccaccaatgcagagagccagctcca gagaatcatccgagacttgcaagatgctgtgacagaactaagcaaagaatttcaggaagcag gggaacccatcacggatgacagcaccagcttgcataaatttttcttataaacttgagtatctcctg caatttgatcagaaagagaaggccaccctcctgggcaacaagaaggactactgggattacttc tgtgcctgcctggccaaggtgaaaggagccaatgatgggatccgctttgtcaagtctatctca gagctccgaacatccttggggaaaggaagagcatttattcgctactccttggtgcaccagagg ttggcagacaccttacagcagtgcttcatgaacaccaaagtgaccagtgactggtactatgca agaagcccctttctgcagccaaagctgagctcggacattgtgggccaactctatgagctgact gaggttcagtttgacctggcgtcgaggggctttgacttggatgctgcctggccaacatttgcca ggaggacgctgaccactggctcttctgcttacctgtggaaacccctagccgcagctccagc atgagcagcttggtgagcagctacctgcagactcaagagatggtgtccaactttgacctgaac agccccctaaacaacgaggcattggagggctttgatgagatgcgactagagctggaccagtt ggaggtgcgggagaagcagctacgggagcgcatgcagcagctggacagagagagaaccag gagctgagggcagctgtcagccagcaaggggagcaactgcagacagagaggagggagaggg ggcgcactgcagcggaggacaacgttcgcctcacttgcttggtagctgagctccagaagca gtgggaggtcacccaggccacccagaacactgtgaaggagctgcagacatgcctgcaggg cctggagctaggagcagcagagaaggaggaggactaccacacagccctgcggcggctgg agtccatgctgcagcccttggcacaggagcttgaggccacacgggactcactggacaagaa aaaccagcatttagccagcttcccaggctggctagccatggctcagcagaaggcagatacgg catcagacacaaagggccggcaagaacctattcccagtgatgcggcccaggagatgcagg agctaggggagaagcttcaagccctagaaagggagagaaccaaggtcgaggaggtcaac agacagcagagtgcccaactggaacagctggtcaaggagcttcagctgaaagaggatgccc gggccagcctggagcgcctggtgaaggagatggccccactccaggaggagttgtctggga agggacaggaggcagaccagctctggcgacggctgcaggagttgctggcccacacgagct cctgggaggaggagctagcagagttgaggcgggagaaaaaacagcaacaggaggagaa ggagctgctggagcaggaggtcaggtctctgacccggcagctgcagttcctggagacccag ctggcacaggtgagccaacatgtgagtgacctggaggagcagaagaagcagctcattcagg acaaagaccacctcagccagcaggtgggtatgctcgagcggcttgctgggccgcctggccc agaactgccagtggcaggtgagaagaatgaggccctggtccctgtgaactccagtctgcaa gaggcctggggggaagccagaggaggagcagaggggcctgcaggaggcacagttagacg ataccaaggtgcaagagggcagccaggaggaagagctccggcaggccaacagggagct ggagaaggagctacagaatgtggtcgggcgtaaccagctcctggagggcaagctgcaagc cctgcaggccgattaccaggctttgcagcagcgggaatcagccatccagggctccttggcct ccctggaggccgagcaggccagcatccggcacttgggtgaccagatggaggcgagcttgc tggctgtaaggaaggccaaggaggccatgaaagcccagatggcagagaaggaggccattc tacagagcaaggagggcgagtgtcagcagctgcgggaggaggtggagcagtgccagcaa | 11 |

TABLE 1-continued

Prostate Cancer Biomarker/Housekeeper Sequence Information

| Gene Name | RefSeq Accession | Sequence | SEQ ID NO: |
|---|---|---|---|
| | | ctggcagaagcccggcacagagagcttagggctctcgagagccagtgccagcagcagacc | |
| | | cagctgattgaggtcctcacagcagagaaaggccaacagggagttggcccacccactgaca | |
| | | atgaagcccgtgagctggctgcccagctagccctgtctcaggcgcagctggaagtccatcag | |
| | | ggggaggtccaacggctgcaggctcaggtggtggacctccaggccaagatgcgggcagc | |
| | | cctggatgaccaggacaaggtgcagagccagctaagcatggctgaggccgtcctgaggga | |
| | | gcacaaaacccttgtgcagcagctgaaggagcagaatgaagcccttaacagagcccatgtc | |
| | | caggagctgctgcaatgctcggagcgtgaaggggcactgcaggaggagagggccgatga | |
| | | ggcccagcagagggaggaggagctgcgggccctgcaggaggagctgtcccaggccaaat | |
| | | gcagctccgaggaagcacagctggagcacgctgagctgcaagagcagctgcaccgggcc | |
| | | aacacagacacagctgagctgggcatccaggtttgcgcactgaccgtggaaaaggagcga | |
| | | gtggaggaggcactggcctgtgctgtccaggagctccaggacgccaaagaggcagcctca | |
| | | agggagcgagagggcctggagcgccaagtagctgggctgcagcaagagaaggagagctt | |
| | | gcaggagaagctgaaggcggccaaggcagcagccggctcactgcctggcctgcaggccc | |
| | | agctcgcccaggcagagcagcgggcccagagcctccaagaggctgcacaccaggagctc | |
| | | aacaccctcaagttccagctgagtgctgaaatcatggactaccagagcagacttaagaatgct | |
| | | ggtgaagagtgcaagagcctcaggggccagcttgaggagcaaggccggcagctgcaggc | |
| | | tgctgaggaagctgtggagaagctgaaggccacccaagcagacatgggagagaagctgag | |
| | | ctgcactagcaaccatcttgcagagtgccaggcggccatgctgaggaaggacaaggaggg | |
| | | ggctgccctgcgtgaagacctagaaaggacccagaaggaactcgaaaaagccacaacaaa | |
| | | aatccaagagtattacaacaaactctgccaggaggtgacaaatcgtgagaggaatgaccaga | |
| | | agatgcttgctgacctggatgacctcaacagaaccaagaagtatctcgaggagcggctgata | |
| | | gagctgctcagggacaaggatgctctctggcagaagtcagatgccctggaattccagcagaa | |
| | | gctcagtgctgaggagagatggctcggagacacagaggcaaaccactgcctcgactgtaag | |
| | | cgggagttcagctggatggtgcggcggcaccactgcaggatatgtggccgcatcttctgttac | |
| | | tactgctgcaacaactacgtcctgagcaagcacggtggcaaaaaggagcgctgctgccgag | |
| | | cctgtttccagaagctcagtgaaggccctggctcccctgatagcagtggctcaggcactagcc | |
| | | agggagagcccagccctgcactgtcaccagcctcacctgggccccaggccacaggaggcc | |
| | | aaggagcaaatacagactacaggccaccggacgacgctgtgtttgatatcatcacagatgag | |
| | | gaattgtgccagatacaggagtccggctcctctttgcctgaaacacccactgaaactgattctct | |
| | | cgacccaaatgcggctgaacaggatactacatcaacctcgctaacgcctgaggacactgaag | |
| | | acatgcccgtggggcaggattcggaaatctgcctgctgaagtctggagaactgatgatcaaa | |
| | | gtacccctcacagtggatgagatcgccagcttcggggagggtagcagggagctgtttgtgag | |
| | | gtccagcacctacagcctgatccccatcactgtggccgaggcaggcctcaccatcagctggg | |
| | | tcttctcctctgaccccaagagcatctccttcagtgtggtcttccaggaggccgaggacacacc | |
| | | gctggatcagtgtaaggtcctcattcccacgacccgatgcaactcccacaaggagaacatcc | |
| | | agggccagctcaaggttcgcacacccggcatctacatgctcatcttcgacaataccttctcaag | |
| | | gtttgtctctaaaaaggtattttatcacttgacggttgatcggcctgtgatctacgatggaagtgat | |
| | | ttcctgtagcttcagcacctcagtaacttcacttcatccacaggaaacactgctcttcctcacctg | |
| | | tcacataaagcatttttttaaaaagtcagctgctccaaaatcatcaactcagcccctgggctgcc | |
| | | cctcagaggcggtgtctggggaggactttgtgctcagcactctgcaccggccactcttagccc | |
| | | ccgaggcgttgaagggctcaggcaatgtttccattaagtagagactcagctgttgtcacaccc | |
| | | aaagggatgctctgccaaaggtttaaacacccaggagaccatcagcctctcctgggagcaca | |
| | | gttggctacaggcctcttgtggagagtttcacgggcaggggtgattccaacttctgcctgtgga | |
| | | gagattttctgccctgccccaccagggccctgcatgttggagactgagctgggtgcactggcc | |
| | | atgccctgtgaatcctcaggctgtgacgccctcaggtactcctgggaaaaggaggtacacag | |
| | | ccatcatgcgagtcggtgccaggggacccccggagatcctgaccagctcctccagtcatgc | |
| | | tcttgtccctcactgccccagtaagctggaggctgctccagaactcagcagtgttggaggggc | |
| | | ctctaagctgcactctctttctggcccttttgtctgggtgattctgtcctcaaataaagcccttcact | |
| | | cagccagacctctccacagctcaaagcattgccctaagaatcagaagtaaagataatccaag | |
| | | agcaaaacccactgtacttggggcctgcaatggctgtgtgtacactacatctaatgcccaaatg | |
| | | ccagccagtgtggatgttgtgaccacagagcaggattgtgcattggctttagagctactcctca | |
| | | gctgatggcccacttttgtttatataaataagagcttctgccccacctgcagacatgtttactaatg | |
| | | atcatagccaggattagaaccactttcaaacattggggccttcttaacaaaagtctttgataactt | |
| | | aagaaccaaagtaacagagtaaacagaggcatgatggatccctgggccccactcccctcctg | |
| | | acaggttccccaacagcccatttgcccacttcccactgctcagcccacaccagacctccagga | |
| | | gacatcccccttgaggcagagagatcctgttccctattcccagacaagaattatttaatcttcc | |
| | | ctgttctctgtggtccttttcttccccaacaacagatagctcaccttggacagctcttcgtcccttg | |
| | | ttcatggaaccagctgcctgcagtcaggccccaggttcttccatgggtgaacagagcatctga | |
| | | caaaaggtcccagtttggccaggggtgagggagagagcaccagacaggctatccgagaat | |
| | | ctgagagctgggcccggcagttcctccagctacccttgtgacctaagtccagtcacacatttcc | |
| | | caaagtttctctttgtcataaccctggtctggctggttttgagggcttgagaatgggtcagggact | |
| | | ccaggccaagtccaacagagaccccaaacccaccacacaccagcagccacaacctcacca | |
| | | ccaacaaagaggacttttgtggggccacaagtaagaggtcatttctggaatggactcagacct | |
| | | ttaaacaggagagttgagcacttccagtcagtttttaagcaaggcatggggaacagggaatag | |
| | | aacctttcaaagaggttgcccagagaaaagctgggcctcttgcattcggcttccttggagcag | |
| | | cctcttctggcagaaagccatcaggtgctcaatcatcttctcctggccaaggctctgaccatgct | |
| | | tagtactggaatagaggtggccaggcccccagcgactcttcttggcctgatgtttgtcctcaca | |
| | | ggcatgccacgtggcctgagatgattcagaacaaatcatgctaactttgaatccatccagccac | |
| | | ttgcaaatgataatcagaagtcagcttgttcactgttagaaagaaactaacaaaagagaaccca | |
| | | gagcaatctagaatctttgagtgcttggctttccaaggatactgcggagactctggccaagctg | |
| | | atgaccttctgaagtgtcactggcaccatatgcaacaagaaccaccattcactgagtagctaat | |
| | | gggtttggggcctgggacattccatctgaggtccttcctgaacatgtcactccacagcagagg | |
| | | accggttgcagcttacccagaaccactcctccaggagagctggatgttttgcgtgcaacacctt | |
| | | gagcactgactgctattgttcaaaaaaagcctttgctgcattcggaggactgccccgtgccctg | |

TABLE 1-continued

Prostate Cancer Biomarker/Housekeeper Sequence Information

| Gene Name | RefSeq Accession | Sequence | SEQ ID NO: |
|---|---|---|---|
| | | aggtgacttcctaactatgtggtttcattagcgaatttattttttgtgctgggtggacatttgtattttg<br>ttaggttgctgtttaagctcaagtttgctgtgctctctgcagctacaaaacatcttggcatatttaa<br>gagtggcttttataaatagctttattctgatattaatcagattcccaactttactgagaattaaggac<br>tggggtactttaaagaaatgcaaatagcaattgaagaaccactgctgcaggtggtagccctgg<br>ctagactgaattacactagaaatcagccagaaggaagcgtccttgggatcccagatcactcttt<br>tttttttttttaaaaggggcagccccttgatggctcatctctctgaataacagttacgtcttcatatc<br>gataccagatgccttcttcatcatgccactgaagccactcaccaccttcaagaacatgccaacc<br>tctgtcagattcacttacccacaaacaaggaggcacgtttggcacaaagtgttgtcctccaggt<br>ccaagtggactctacagagtgcttgacctcaacacactggattccaggtggactggaccaag<br>agcaggcaaagacacgggaactgaaaaactccacagggtttggagaatagaaatgaaaag<br>ccacgtcatataactcaagaataaatggtgttttggaaattttaaaattatcatcgaaggtggtga<br>aactatttcaggcccaaatgaaaggaaatcgccagttggggatgaaatcacagagcctgtgtt<br>ttatgatatggttggatgtccactgatgaaattttaaaggagtttcagttttaaaagtgcgcatgatt<br>ctacatatgagaattctttaggccaagaaactgtccttggctcagaggtgttgggaattaaagca<br>gagagaagccattcgtgatgcttagaaccaaggatggtcatgtacacaaagaccatcgagac<br>ggccattcttgtttacaaaacacttaccaagaaagcactttgtaggggaactttagtaagttcttct<br>catttcattatgtttcttccaaggaaacaggagagactgaattaataattctctctttcctcttaagc<br>acttttaaaataataaagtacatcttgaaatttggggaggcatctctgatttaaaaaaagaaaaag<br>gctgcttgatgtatgttatgcagagacactctgcctctggtggctgcagagcaatacccaagcc<br>tcatttggaaggctcaacatttggaattgcactttaattgattaatcctcaattcatgtggccttacg<br>ggatggtgggtctgggaccccaattcattcttatctgccaaagaattatctagaagcacatcaa<br>ataccagcaccccacctgctcaatggggtggaaaacttttgtatccctaagcatattattttata<br>gtgtctgccatgccatgtggaaatactttatttttaacctcaggatttaaataaagtaaacactatg<br>acatttagaca | |
| HNRNPU | NM_004501.3 | ctcgcgccaggcgagtctccgcgtctccctcgcgaactcggtgaaaggaattggcgccgttc<br>gacaccaggcggatccgctctgcagcacgaacccatctccagccgcagccgcagccgccg<br>cccgggccgaggagcagccgcagcagccgccaccagtggccgagtgagcggagccgag<br>tttgaggcagcgcctagcggtgaatcggggccctcaccatgagttcctcgcctgttaatgtaaa<br>aaagctgaaggtgtcggagctgaaagaggagctcaagaagcgacgcctttctgacaagggt<br>ctcaaggccgagctcatggagcgactccaggctgcgctggacgacgaggaggccggggg<br>ccgcccgccatggagcccgggaacggcagcctagacctgggcggggattccgctgggc<br>gctcgggagcaggcctcgagcaggaggccgcggccggcggcgatgaagaggaggagg<br>aagaggaagaggaggaggaggaaggaatctccgctctggacggcgaccagatggagctagga<br>gaggagaacggggccgcgggggcggccgactcggcccgatggaggaggaggaggcc<br>gcctcggaagacgagaacggcgacgatcagggtttccaggaaggggaagatgagctcgg<br>ggacgaagaggaaggcgcgggcgacgagaacgggcacggggagcagcagcctcaacc<br>gccggcgacgcagcagcaacagccccaacagcagcgcggggccgccaaggaggccgc<br>ggggaagagcagcggccccacctcgctgttcgcggtgacggtggcgccgcccggggcga<br>ggcagggccagcagcaggcgggaggggacggcaaaacagaacagaaaggcggagata<br>aaaagaggggtgttaaaagaccacgagaagatcatggccgtggatattttgagtacattgaag<br>agaacaagtatagcagagccaaatctcctcagccacctgttgaagaagaagatgaacacttc<br>gatgacacagtggtttgtcttgatacttataattgtgatctacattttaaaatatcaagagatcgtct<br>cagtgcttcttcccttacaatggagagttttgcttttctttgggctggaggaagagcatcctatggt<br>gtgtcaaaaggcaaagtgtgttttgagatgaaggttacagagaagatcccagtaaggcatttat<br>atacaaaagatattgacatacatgaagttcgtattggctggtcactaactacaagtggaatgtta<br>cttggtgaagaagaattttcttatgggtattctctaaaaggaataaaaacatgcaactgtgagact<br>gaagattatggagaaaagtttgatgaaaatgatgtgattacatgttttgctaactttgaaagtgat<br>gaagtagaactctcgtatgctaagaatggacaagatcttggcgttgccttcaaaatcagtaagg<br>aagttcttgctggacggccactgttcccgcatgttctctgccacaactgtgcagttgaatttaattt<br>tggtcagaaggaaaagccatattttccaatacctgaagagtatactttcatccagaacgtcccct<br>tagaggatcgagttagaggaccaaaggggcctgaagagaagaaagattgtgaagttgtgat<br>gatgattggcttgccaggagctggaaaaactacctgggttactaaacatgcagcagaaaatcc<br>agggaaatataacattcttggcacaaatactattatggataagatgatggtggcaggttttaaga<br>agcaaatggcagatactggaaaactgaacacactgttgcagagagcccccagtgtcttggg<br>aaatttattgagattgctgcccgaaagaagcgaaattttattctggatcagacaaatgtgtctgct<br>gctgcccagaggagaaaaatgtgcctgtttgcaggcttccagcgaaaagctgttgtagtttgc<br>ccaaaagatgaagactataagcaaagaacacagaagaaagcagaagtagaggggaaaga<br>cctaccagaacatgcggtcctcaaaatgaaaggaaactttaccctcccagaggtagctgagtg<br>ctttgatgaaataacctatgttgaacttcagaaggaagaagcccaaaaactcttggagcaatat<br>aaggaagaaagcaaaaaggctcttccaccagaaaagaaacagaacactggctcaaagaaa<br>agcaataaaaataagagtggcaagaaccagtttaacagaggtggtggccatagaggacgtg<br>gaggattcaatatgcgtggtggaaatttcagaggaggagcccctgggaatcgtggcggatat<br>aataggaggggcaacatgccacagagaggtggtggcggtggaggaagtggtggaatcgg<br>ctatccataccctcgtgcccctgtttttcctggccgtggtagttactcaaacagagggaactaca<br>acagaggtggaatgcccaacagagggaactacaaccagaacttcagaggacgaggaaaca<br>atcgtggctacaaaaatcaatctcagggctacaaccagtggcagcagggtcaattctggggtc<br>agaagccatggagtcagcattatcaccaaggatattattgaatacccaaataaaacgaactgat<br>acatatttctccaaaaccttcacaagaagtcgactgttttctttagtaggctaactttttaaacattc<br>cacaagaggaagtgcctgcgggttcctttttttagaagctttgtgggttgattttttttcttttctttttt<br>gtacatttttaattgcagtttaaaagtgaatcgtaagagaacctcagcattgtgcacgataagag<br>aatgtgtcagtatttcagggttctacattttatctgtaaaatgtgacttttttttttttttatcacaacag<br>aagtaaaatgttgctttgtacctggtgtcttttattaagaatttactcccccatttctcacagagaa<br>taacagtcgggagtcattgtcacaatataatagaaatgttagcaaccagattcatgtaaggacta | 12 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | agtggtcctcatgaattgcattaagactctgtactgctcatattacactccatcctctctgtagtttg<br>ctgggtagtggagggggtaagctaaatcatagtttctgacaataactgggaaggtttttttcttaa<br>aataacaatggaattggtataattgggattgaaaactaaaacttggaactaagatagagaagat<br>ggagtgtatgtagaagggctgttaaaaatgtaaaacttggttgcattatttgtggaggctcaaac<br>ttgtgaaggttaataccataattttccatttgttctgcattttgattctgaaaagaaagctggctttg<br>cccatttcttattaaaaaaacttgttgtaaatccagttgtctaatgggatctatatgaagttagccat<br>gtctgtatgcccttctcccacaaaatactgtataactagtgtgcttgtagtagttaactccaccatc<br>tttgtaagctaatgaaattgtgagtcacccatttatatcttaattttaatcatgtcagttcttgaatgg<br>gtatctccttagcctgctgatttctttttctttctaaagaaagtgggtggagaaattaatttagacgtt<br>tgtttgcaataaaaagaattcattttactcttgttttgggattctcgccatcaaggttcaaaatccctt<br>tatataactcccaagaggagaaatttattaagtgtgtgctttctggacagcttattctttactctgca<br>tagaacatttaggttttaaaaacttaaatgtatactgacaattgatacataattatgaagtaaagttg<br>aattcttcccttcccctccccccagacaacttttaacatatttaatgaggggaaaaggtactgg<br>ctgggagaagttaacactgagtttatcatctttacagaatgctaatgctgtcctcaactgattatttt<br>atatacatatatatgatacatgaaactctgggatcagatgcttttagaagccatcatgcaagcca<br>gtcattgatgtcactgctacacaacactgctaacttgactgtagctatgtaataacattagatccc<br>ctaattgtaattatattgggtttgcacagaacactttaatcttcccctcaccaatgtgaagtgagga<br>atcaggagtcaaactgtagaactaaaatttgacttcagtctagcgtttccttggtgtttttaggttg<br>ctttggtaagtttaggtttgctatatttctgattgcttagaattttgttttagccctttaaaatcagatca<br>taaatatgaattcatacttctaaggaattttcttgctataagctggagtttaggtgatgtataggttc<br>agttgagacattttggaacaggcaaatccttagttaacataagatatttaacagttgaagatagt<br>gtcatggatttttatctttttagcaagtaatgctaagaaccactggcctgagctactactcttcagt<br>atacattattaggattgcatagacttactagaggaacagtttcaggttttgatgctaatcagtgttg<br>tgtcctaaagttgtcctttgtgcctttaaaaagttttggatatatcttctagtttaaaattgcttattaa<br>ggaattcattttataattgcagtgggaaagtaatggtcaagtaacactaggtagactatcatgcc<br>tgtttagcccagagaatttgggggagagagaatagataaaaatggcacccagaaaaatgtt<br>aaaatctttagtcaagactagaattaatacaattgtctacacttgtatggcagaaataaccttataa<br>agtgtttaaggaattcagagaagggaatgtaccaaataagcaacagggagaaaattaggtaa<br>gaagtaagatacgaacgagaaacctgatttattgctcatccttcccttgcctccctaatggcaag<br>caaaactctgaacatctgaaaaggatgtagttctggacaaatcctgactacccagaggaaact<br>cactgtgagattgctgttgatttgaagggtgctttcactaaggttatattttaaagtagaataacac<br>atgctgagtgtaaactggctttggattggtcagctgcagtagtacaaaaacagcatagaatttg<br>agaaaactaaaactgctatgagatagctatgagaaaactaaaactgctatgagatagaaatgat<br>gtaaaattatgtggaaagttttccctcatatactcacatacagcctttgaagggctctggctctga<br>ccggttgatggccttgagcgagatgaaatcatgaaattgagtcaaatcaatttgacattgaaatg<br>acaagaggaaactcttaaatacataaaaacaagctctcatttgcctaggatagatactgtcttaa<br>aaataaagactgaacctagatgttctgagcactagcaacaaggtattttaacaagtttaaagga<br>attctctgaaaaagttataaaattattctaggaaacataaccataatagtgttttaagggactttca<br>cctggggattttatattcatgaacagagtgtattctgtatttaaaatgtctcatttgtgggaattgga<br>tgacatgtttttgataaatttattcacaatataaattgactttttattctaggaccatgtgaataatgg<br>gttccattgcacaaatacaaatattttaatagcttcttaggcagtggtgtagacatcttggatataa<br>ataattgtagatcttgtatatttgattttaaaaaactagaataaacagagaggcataaacatatctt<br>agagtccaagtggtagtgtttagcattggatataataaatggatgttttacaaagtgtttccataat<br>tctcttcctatacataaatgtcttgttttcaaaagtggatggaacttggctgggtgtggtggctcac<br>gcctgtaatcctagcactttgggaggccaaggcgggaggatcacttgagctcaggagtttga<br>gaccatcctgggcaacatagtgagacctggtctcttgaaaaaaaaaaagtggatggaacttgt<br>agcagagaattttatctacttctcaacctgcttcagaatacccatttgagatgttcccctggaaag<br>atgaacacaatactgcatctgaagccatttcttcccacctaacattcttaaaatgattagagtctaa<br>actttgtcattcattcctaattctggagctctgaggttgaggtgttcagagtttggtgaataattgg<br>gtttaagttttaacattttagtaataataaaagcaaacacatacatgttaaggcctgacaataggtt<br>gcaatacccatgcattgggactcatacccagcataaatggtgagggactgaacattagtgcttt<br>gagcaagaattggttaactacctgagatctctaaaacagtaatttgaattactaatacataaacca<br>caagtctcttcgaattgttaattgcctaaatttaccctaaaacttagttaacgctgcagtgcctttat<br>taaagctttttttttgggggggggtgtgggcacagctactccataactttaaattttaaagcatgaa<br>ggtgatctagctagtgttagtgcttgagttggtagttacataggctgctcttgaatcgtcctgttttc<br>tttgcctagtattagcaccacaggtacatatttgtaaaataagcattaaaagtactttgtccagc | |
| HPN | NM_002151.2 | tcgagcccgctttccagggaccctacctgagggcccacaggtgaggcagcctggcctagca<br>ggccccacgccaccgcctctgcctccaggccgcccgctgctgcggggccaccatgctcctg<br>cccaggcctggagactgacccgaccccggcactacctcgaggctccgcccccacctgctgg<br>accccagggtcccaccctggcccaggaggtcagccagggaatcattaacaagaggcagtg<br>acatggcgcagaaggagggtggccggactgtgccatgctgctccagacccaaggtggcag<br>ctctcactgcggggaccctgctacttctgacagccatcggggcggcatcctgggccattgtgg<br>ctgttctcctcaggagtgaccaggagccgctgtacccagtgcaggtcagctctgcggacgct<br>cggctcatggtctttgacaagacggaagggacgtggcggctgctgtgctcctcgcgctccaa<br>cgccagggtagccggactcagctgcgaggagatgggcttcctcagggcactgacccactcc<br>gagctggacgtgcgaacggcgggcgccaatggcacgtcgggcttcttctgtgtggacgagg<br>ggaggctgccccacacccagaggctgctggaggtcatctccgtgtgtgattgccccagagg<br>ccgtttcttggccgccatctgccaagactgtggccgcaggaagctgcccgtggaccgcatcg<br>tgggaggccgggacaccagcttgggccggtggccgtggcaagtcagccttcgctatgatgg<br>agcacacctctgtgggggatccctgctctccggggactgggtgctgacagccgcccactgct<br>tcccggagcggaaccgggtcctgtcccgatggcgagtgtttgccggtgccgtggcccaggc<br>ctctccccacggtctgcagctgggggtgcaggctgtggtctaccacgggggctatcttcccttt<br>cgggaccccaacagcgaggagaacagcaacgatattgccctggtccacctctccagtcccct | 13 |

TABLE 1-continued

| Gene Name | RefSeq Accession | Sequence | SEQ ID NO: |
|---|---|---|---|
| | | gcccctcacagaatacatccagcctgtgtgcctcccagctgccggccaggccctggtggatg gcaagatctgtaccgtgacgggctggggcaacacgcagtactatggccaacaggccgggg tactccaggaggctcgagtccccataatcagcaatgatgtctgcaatggcgctgacttctatgg aaaccagatcaagcccaagatgttctgtgctggctaccccgagggtggcattgatgcctgcca gggcgacagcggtggtccctttgtgtgtgaggacagcatctctcggacgccacgttggcggc tgtgtggcattgtgagttggggcactggctgtgccctggcccagaagccaggcgtctacacc aaagtcagtgacttccgggagtggatcttccaggccataaagactcactccgaagccagcgg catggtgacccagctctgaccggtggcttctcgctgcgcagcctccagggcccgaggtgatc ccggtggtgggatccacgctgggcctaggatgggacgtttttcttcttgggcccggtccacag gtccaaggacaccctccctccagggtcctctcttccacagtggcgggcccactcagccccga gaccacccaacctcaccctcctgacccccatgtaaatattgttctgctgtctgggactcctgtct aggtgcccctgatgacgggatgctctttaaataataaagatggttttgattaaaaaaaaaaaaaa aaaaaaaaaaaa | |
| KRT15 | NM_002275.3 | cactcaaggtgtgcaggcagctgtgtttgtcaggaaggcagaaggagttggctttgctttagg ggaggagacgaggtcccacaacaccctctgaagggtatataaggagccccagcgtgcagc ctggcctggtacctcctgccagcatctcttgggtttgctgagaactcacgggctccagctacct ggccatgaccaccacatttctgcaaacttcttcctccacctttgggggtggctcaacccgaggg ggttccctcctggctgggggaggtggctttggtgggggagtctctctgggggaggtggaa gccgaagtatctcagcttcttctgctaggtttgtctcttcagggtcaggaggaggatatggggt ggcatgagggtctgtggctttggtggaggggctggtagtgttttcggtggaggctttggaggg ggcgttggtgggggttttggtggtggctttggtggtggcgatggtggtctcctctctggcaatg agaaaattaccatgcagaacctcaatgaccgcctggcctcctacctggacaaggtacgtgcc ctggaggaggccaatgctgacctggaggtgaagatccatgactggtaccagaagcagaccc caaccagcccagaatgcgactacagccaatacttcaagaccattgaagagctccgggacaa gatcatggccaccaccatcgacaactcccgggtcatcctggagatcgacaatgccaggctgg ctgcggacgacttcaggctcaagtatgagaatgagctggccctgcgccagggcgttgaggct gacatcaacggcttgcgccgagtcctggatgagctgaccctggccaggactgacctggaga tgcagatcgagggcctgaatgaggagctagcctacctgaagaagaaccacgaagaggaga tgaaggagttcagcagccagctggccggccaggtcaatgtggagatggacgcagcaccgg gtgtggacctgacccgtgtgctggcagagatgagggagcagtacgaggccatggcggaga agaaccgccgggatgtcgaggcctggttcttcagcaagactgaggagctgaacaaagaggt ggcctccaacacagaaatgatccagaccagcaagacggagatcacagacctgagacgcac gatgcaggagctggagatcgagctgcagtcccagctcagcatgaaagctgggctggagaa ctcactggccgagacagagtgccgctatgccacgcagctgcagcagatccaggggctcatt ggtggcctggaggcccagctgagtgagctccgatgcgagatggaggctcagaaccaggag tacaagatgctgcttgacataaagacacggctggagcaggagatcgctacttaccgcagcct gctcgagggccaggatgccaagatggctggcattggcatcagggaagcctcttcaggaggt ggtggtagcagcagcaatttccacatcaatgtagaagagtcagtggatggacaggtggtttctt cccacaagagagaaatctaagtgtctattgcaggagaaacgtcccttgccactccccactctc atcaggccaagtggaggactggccagagggcctgcacatgcaaactccagtccctgccttca gagagctgaaaagggtccctcggtcttttatttcagggctttgcatgcgctctattcccctctgc ctctccccaccttctttggagcaaggagatgcagctgtattgtgtaacaagctcatttgtacagt gtctgttcatgtaataaagaattacttttccttttgcaataaaaaaaaaaaaaaaaaaaaaa | 14 |
| KRT23 | NM_001282433.1 | aactagcacgtggctcccgcccccagactgcttctttattcattcctaacctttaccttggcagat gaaatataagattcatcaaccacatttgacagcccatggcaggtttcctgttttccatcgtccctct gcaggtcacagacacacagagcccagccgtggcaggctcagccggggtccggggctgct aacaacggctacattcctcccccagggccaagggaaatcctgagcgcaggccagggttgttt ggttttgaggtgtgctgggatgaaaggcaccctggaagtggaaggttcggtcattcattaatta attacatctataattgagggtttgttcttaagagcgagtcctttgaaagtactttccttcaaacagtg actgccacaaaggcatcagatattcaccaccttctcggctgcctcagcacagcaagctttattct gggacctgagatcctgttctgagctggctttcccttctccaggctcgctcaccctccctttagag atagtggatggtaagatgaccaatgctcagattattcttctcattgacaatgccaggatggcagt ggatgacttcaacctcaagtatgaaaatgaacactcctttaagaaagacttggaaattgaagtc gagggcctccgaaggaccttagacaacctgaccattgtcacaacagacctagaacaggagg tggaaggaatgaggaaagagctcattctcatgaagaagcaccatgagcaggaaatggagaa gcatcatgtgccaagtgacttcaatgtcaatgtgaaggtggatacaggtcccagggaagatct gattaaggtcctggaggatatgagacaagaatatgagcttataataaagaagaagcatcgaga cttggacacttggtataaagaacagtctgcagccatgtcccaggaggcagccagtccagcca ctgtgcagagcagacaaggtgacatccacgaactgaagcgcacattccaggccctggagatt gacctgcagacacagtacagcacgaaatctgctttggaaaacatgttatccgagacccagtct cggtactcctgcaagctccaggacatgcaagagatcatctcccactatgaggaggaactgac gcagctacgccatgaactggagcggcagaacaatgaataccaagtgctgctgggcatcaaa acccacctggagaaggaaatcaccacgtaccgacggctcctggagggagagagtgaagg gacacgggaagaatcaaagtcgagcatgaaagtgtctgcaactccaaagatcaaggccata acccaggagaccatcaacggaagattagttctttgtcaagtgaatgaaatccaaaagcacgca tgagaccaatgaaagtttccgcctgttgtaaaatctattttcccccaaggaaagtccttgcacag acaccagtgagtgagttctaaaagatacccttggaattatcagactcagaaacttttattttttttt ctgtaacagtctcaccagacttctcataatgctcttaatatattgcacttttctaatcaaagtgcga gtttatgagggtaaagctctactttcctactgcagccttcagattctcatcattttgcatctattttgt agccaataaaactccgcactagctgcaaaaaaaaaaaaaaaaaa | 15 |

TABLE 1-continued

| Prostate Cancer Biomarker/Housekeeper Sequence Information | | | |
|---|---|---|---|
| Gene Name | RefSeq Accession | Sequence | SEQ ID NO: |
| MAN2B2 | NM_001292038.1 | ggaagtgggcctggcaccttcccggcctgccgcagggatggggcagctgtgctggctgcc<br>gctgctggcaccgctcctgttgctgcgaccgccaggggtccagtccgccggccccatccgg<br>gccttcgtggtgccccacagccacatggacgtgggctgggtctacactgtgcaggaaagcat<br>gcgggcgtacgccgccaatgtctacacctcagtggtggaagagctggcccgcggccagca<br>gcgccggttcatcgctgtggagcaggagtttttccggctgtggtgggatggcgtcgcctcgga<br>ccagcagaaataccaggtccgccagctcctggaggaaggacgcctggaatttgtcatcgga<br>ggccaggtcatgcatgacgaggctgtgacgcaccttgatgaccagatcctgcagctcacaga<br>aggacacgggtttctctatgaaacatttgggatccggccacagttctcctggcacgttgacccg<br>tttggcgcctctgccacgacgcccaccctatttgcgctggcgggcttcaatgcccacctcggc<br>tcccggatcgactacgacctgaaggcagccatgcaggaggcccgggggctgcagttcgtgt<br>ggcgagggtccccatccctctcagagcggcaggaaatcttcacgcacatcatggaccagtac<br>agctactgcaccccgtcccacatccctttctccaacaggtcaggattttactggaatggcgtgg<br>ctgtcttccccaagcctccccaagatggggtgtaccccaacatgagtgagcctgtcaccccag<br>ccaacatcaacctctatgccgagctcggtgtctcggtgcagtatgccacgctgggcgactact<br>tccgtgccctgcacgctctcaatgtcacctggcgtgtccgcgaccaccacgacttcctgccct a<br>ttccacagaaccattccaggcctggacggcttctacacgtcccgcagctcactgaaggggc<br>tggcccggcgagccagcgccttgttgtatgccggggagtccatgttcacacgctacctgtgg<br>ccggccccccgtgggcatctggaccccacctgggccctgcagcagctccagcagcttcgct<br>gggccgtctccgaggtccagcaccatgatgccatcactgggactgagtcccccaaggtgag<br>agacatgtacgcaacgcacctggcctcggggatgctgggcatgcgcaagctgatggcctcc<br>atcgtcctagatgagctccagccccaggcacccatggcggccagctccgatgcaggacctg<br>caggacattttgcctcggtctacaacccgctggcctggacggtcaccaccatcgtcaccctga<br>ctgttggtttccctggagtccgcgtcacagatgaggcgggccacccagtgccctcgcagatc<br>cagaactcaacagagaccccatctgcgtatgacctgcttattctgaccacaatcccaggcctca<br>gttaccggcactacaacatcagacccactgcaggggcccaagagggcacccaggagccgg<br>ctgccactgtggcgagcacccttcaatttggccgcaggctgaggagacgcaccagccatgc<br>gggcaggtacttggtgcctgtggcaaacgactgctacattgtgctgctcgaccaggataccaa<br>cctgatgcacagcatctgggagagacagagtaaccgaacggtgcgcgtgacccaggaattc<br>ctggagtaccacgtcaacggggatgtgaaacagggccccatttccgataactacctgttcaca<br>ccgggcaaggccgcggtgcctgcgtgggaagctgtggaaatggagattgtggcgggacag<br>cttgtgactgagatccggcagtacttctacaggaacatgacagcacagaattacacgtatgca<br>atccgctcccggctcacccatgtgccgcagggccatgacggggagctgctctgccaccgga<br>tagagcaggagtaccaagccggcccccctggagctgaaccgtgaggctgtcctgaggacca<br>gcaccaacctaaacagccagcaggtcatctactcagacaacaacggctaccagatgcagcg<br>gaggccctacgtttcctatgtgaacaacagcatcgcccggaattactaccccatggttcagtcg<br>gccttcatggaggatggcaaaagcaggcttgtgttgctgtcggagcgggcacatggcatctc<br>cagccaagggaatgggcaggtggaggtcatgctccaccggcggctgtggaacaacttcga<br>ctgggacctgggctacaacctcacgctgaacgacacctcagtcgtccacccagtgctctggct<br>tctgctgggatcctggtccctcaccactgccctgcgccagaggagcgcactggcgctgcagc<br>acaggcccgtggtgctgttcggagacctcgctgggactgcgccgaagctcccaggacccca<br>gcagcaagaggccgtgacgctgcccccgaatcttcacctgcagatcctgagcatccctggct<br>ggcgctacagctccaaccacacggagcactctcagaatctccggaaaggccatcgagggg<br>aagcccaggctgacctccgccgtgtcctgctgcggctctaccacctgtatgaagtgggcgag<br>gacccagtcctgtctcagccagtgacagtgaatctggaggctgtgctgcaggcgctggggtc<br>cgtggtggcagtggaggagcgctcgctcacagggacctgggatttgagcatgctgcaccgc<br>tggagctggaggacggggcctggccgccacagaggtgacaccacctctccctcgaggcca<br>ccaggaggccccatcatcaccgtccacccaaaggaaatccggacgttctttattcactttcaac<br>agcagtgagccctgggcagatgccccggccccagggcttcccccaggaactccatgtaaca<br>gaacagacccaggacagggaaaagcagtgcggagggatgggactggggagtcagctgct<br>catctgcaggctaatggcaggaaatggtcatatttggggtttttccctaattttttaaacaaaaatt<br>acattacaagatccaggttcttccccccacactcaatcaagccagccctctcctcttctgtcac<br>gtaaaggatatttggcacactcatgcgtcattcattcacaaaacacaaacccaggactttctgcc<br>taaggcagagcacaagactcacagcagcaccgaagcgcatctgccgtccgggccctgcca<br>ggcttgccaggctgccagtggtaactgtggacctactgcgtgccacgtgttttcatagactcat<br>cccatgctggcaacagccctgcaaggggcttggctctgccacagggcaggagaggaagtt<br>gtagcgcctagcgagagttccagccccagacgcccacctgtgcctcagggcaccgcctgcc<br>gagcagagaaggcacagcagccgtcagagtccatgagaggtgaaaccacacagcaggga<br>tgtccaatatcagaactattaatatcaataaaagtataaccttcccaggtctatgcccaagagaat<br>tgaaaacatccatccacacaatacctgtgctcccgcgttcatagcagcattactcaaaagtcaa<br>acggtagcaacaacccaaatgtccatccacagatgaattaagacatgaagtgtgttctgtccat<br>acaatggaatattatttggccataaaaaggaaggaaattctgacgcatgccacagcctgagtg<br>aatcctacaaatattacgctaagtgaaagaagccaatcacgagtttatgtgaaatgtccagaata<br>ggcaaatctgtgtatcagagacaaagcacattggtggttgccaggtactggaggaagagaga<br>agaggcatgacagctaacagggacgggctttctttggaagatgatgaaattgtggaatgatgg<br>ttgcacaactttgtgaatatactagaaaccaatgaattaaaaactttggaagatgaaaaaaaaaa<br>aaaaaaaa | 16 |
| MAX | NM_001320415.1 | tgcgtgccgccgttgatccggtgctgcagtgaggaggtggttcttgcccgtgttgtgtgtgtgt<br>gtgagtgagagagcgagtgagtgagtgagtgagtgtgtgtgtggggggggactcggcttgttg<br>ttgtcggtgacttcccccctcccccttcacccccttcccctccccgccgccgctgcagtggccgctc<br>cctgggccgtaggaaatgagcgataacgatgacatcgaggtggagagcgacgaagagcaa<br>ccgaggtttcaatctgcggctgacaaacgggctcatcataatgcactggaacgaaaacgtag<br>ggaccacatcaaagacagctttcacagtttgcgggactcagtcccatcactccaaggagaga | 17 |

TABLE 1-continued

Prostate Cancer Biomarker/Housekeeper Sequence Information

| Gene Name | RefSeq Accession | Sequence | SEQ ID NO: |
|---|---|---|---|
| | | aggcatcccgggcccaaatcctagacaaagccacagaatatatccagtatatgcgaaggaaa<br>aaccacacacaccagcaagatattgacgacctcaagcggcagaatgctcttctggagcagca<br>aggggaaagcgagagctgatcaagttctttgttcctggggaattcacttctcttcctccctcatg<br>gaagatgcaagtaaaaggaaattccgtgcactggagaaggcgaggtcaagtgcccaactgc<br>agaccaactacccctcctcagacaacagcctctacaccaacgccaagggcagcaccatctct<br>gccttcgatgggggctcggactccagctcggagtctgagcctgaagagccccaaagcagga<br>agaagctccggatggaggccagctaagccactcggggcaggccagcaataaaaactgtctg<br>tctccatcgtctcatcctcctttcagttcgttggtagagccctcagaaccatttaagagactctttat<br>ttttctctttctccctttttttttttaaatttttatttttacgtagaagctcttggacaacagctctcgttctc<br>cttccccatttccactgtatatttttttaatgtattcccttcagggattccctgtccccaacaggaattt<br>ttaaaccaaaacaccccaacttggcagctttttctgtggaggacagacggccggccggacctc<br>tgagcacatagtgtcctgcccaccctaccagctcctccagccctgccgggcacatgcccggg<br>ggacgcctgccctgcccaggtggcctcctggcccgccctcacctctgatagactttgtgaatc<br>tgaactgctctactttgagaagatgaccggtttggagtaatcagaatgaaccctcctcctttttaa<br>gggtttttttttttttccttttttctaaaaagctatgtatcgctcctattgaaagaccagatccttagaga<br>agtttgtggtataaaaaggaagtggggacagattcgcagcacagagtcgctggcatgtttcac<br>tcctgcttctctcagccagctgtttaagcctgcggcgccagcctcacggagggccgtgtgaca<br>ctctcgtggtatgtatgggagatggcagcagtgaagcagcagccaccagggagtggccattt<br>ggggttgggacagggagggtgttttgggtggcatagaggttttgtattgagggccagtgatga<br>tgttttgatatttatttcctgctacttaaatttgaatctgagtgaattgtacctatttctgatgatgtcgg<br>tcttgcaaagcgacagattcataaagtaatgatgaaatctttctttcttcccgtgtgtatttctaaga<br>aatagagccaactgattttgtatgtaaataccaagagcaatttacctggtactaaacccgcaccc<br>cagtgcggacccttcccagccctcatcccacttcctttcctactgtcctggaacctgtctccattg<br>tgtgatccagccctggttctggctgtggtcagcagatgccagtgaagggttttgtgtgtttaggc<br>ctcatttctttgtcttttttcctactccgttcctggcatttgctgatttctagtgtatactctgtagtctca<br>gttcgtgtttgattccattccatggaaataaaaagtatgttgtacatactgccgaagaattgtcttg<br>caagttaaggcttccccctttactataagactataaataaaaacttattttatccttcttaaaaaaaa<br>aaaaaaaa | |
| MRPS25 | NM_022497.4 | gaagcgtctcctgtgcgtctgcgcgggaagtggaacctggctctggggagaagccgcgtga<br>gatccgcgcgggtgctagctagtcctttctcgtcgctgctcggctcgcggcccgtggggtcg<br>gccccgccaccgttgccgccatgcccatgaagggccgcttccccatccgccgcaccctgca<br>atatctgagccaggggaacgtggtgttcaaggactccgtgaaggtcatgacagtgaattacaa<br>cacgcatggggagctgggcgagggcgccaggaagtttgtgtttttcaacatacctcagattca<br>atacaaaaacccttgggtgcagatcatgatgtttaagaacatgacgccgtcacccttcctgcga<br>ttctacttagattctggggagcaggtcctggtggatgtggagaccaagagcaataaggagatc<br>atggagcacatcagaaaaatcttggggaagaatgaggaaaccctcagggaagaggaggag<br>gagaaaaagcagctttctcacccagccaacttcggccctcgaaagtactgcctgcgggagtg<br>catctgtgaagtggaagggcaggtgccctgccccagcctggtgccattacccaaggagatg<br>agggggaagtacaaagccgctctgaaagccgatgcccaggactaaggcccacggtcactgt<br>gggctggggtgatggtgtctgaccagtggggagattggaatgggattactttggcccaggga<br>agcccctggttctgtccctggagactctggaaatccttttgcattaaaaggactttacacacctgt<br>gtaaaaggatgtgggagaggagggtctgaagctgagctgctaaatgaatatccctgctctgct<br>ggtcaataaaacgcttcctaatagcagcttggcgtgtatctggtcctagtgaagaggaaggcct<br>gtgtagcagaaaggctttgggcctgagaggttaaggccacagcctgttgacacctgttttggtc<br>ctgcgacccctttactggtctccgctggctttgaatcttcctctgggctctactctggagaacataa<br>gggctgctgtggttgagtctggctagcactgtctgtggttggcagtgtgtacacccctccgttca<br>gttccttgggggtatttttcagaaatccaaaggcaacccttcgtgcagtgctcacttttttaagtac<br>agttgattacccttgcctgctggggggcctagccatgggccagagatggaggagccccagt<br>ggctgacaggccagcctcactcaggcacgtacctgctgaccagtcagccactgccaacccat<br>ggcccagccactgtgtgcattagcagggaggtttgtaggccatggaggaaatgaggagaca<br>ccacctagtggagacattggggccctgctggggggatggtgtctatagctggctctgctggct<br>ccctcaggccctgcttaccaagctctggaggagggagtgctgcattactgagcaccttccttgt<br>tctttcctcataggacactgatgttactgtcactttagttatgctaaagtggaggtttcagcctcca<br>gaagacagcagagccttctagggtcaccttaagaataggtttagctaggctgggtgtggtggc<br>tcatgcctgtaatcccagcactttgggaggctgatgtgggcggatagttgagcccaggagttc<br>gagaccagcctgggcaacatggcaagaccttgtctctacaaaaagtacaaaaattagatgggt<br>gtggtgtttcgcgtctgtagtcccagctatttgggaagctgaggtgggaggatctcgagcctgc<br>gagatcaaggctgcagtgaatcatgatcgtgcgctactgcactccagcctgggccacagagc<br>aagactgtctcaagaaaaaaaatttttttaaataagtttaattataaagtgaaggaccagttggacc<br>acggaccccctagaaactcagccaaggagacctgactttatctgagacaggaaggcagtggtt<br>aaaagaattaaaaaaggacagtggtgcttgacagagcaggactgaagttttcattcctctacct<br>gctggggccttggtcaagtcctaaaagctttccaggtctgtaactggttttgtctgtaaaatggg<br>gaaaaggttaccttttctgccacatgaagtagctggctggtgaaatgatgtcatactacgatgtg<br>tttcattaactgttggagattatcacattaaattgagcagatttggatcttttacatttgatgctcaag<br>tttgattctgtaccagatctgggtttggggtgatggcttgtcgggggtgggaggggaaggtgg<br>gcagagactgatgtataatggacaggtgttccttgagtgacagacttacaaagggagtgtttaa<br>ttgaaatctagcatcttgtctctctgctatcagcattttggctgggtggaaaaagctctcctccac<br>agagagccctcccatgtctgctggtttcagttccccacccaactgactgaagtcttgaccttgat<br>accacctgcctgggcgttctacttggctgcaagggctcttcagaaagcacctagttccttttggc<br>tttcatctgcagtgtaggtctccatagctagtgacacacaaagccttatgagagtattccttccct<br>ctagggcccaaagaggctgctaaccagcaggaatgtcctgaaccaaaaggagtggtgacca<br>ttctctagacagaataaatgtctggtccctaatgggacagataactagggtttgagttcaggctt<br>gacacaggagcaatgggcagtgaggtggacagcccagaccctgaaaggacgtgtggaga | 18 |

TABLE 1-continued

Prostate Cancer Biomarker/Housekeeper Sequence Information

| Gene Name | RefSeq Accession | Sequence | SEQ ID NO: |
|---|---|---|---|
| | | cagcagcagtcctgtggtgcagttactgcctgtgtggccagcttcacaggcagcagataattt<br>gtggaaataaacattattttctttttttgttccctgtaggctacttgatcctggatagtttctctttaaa<br>cctttgtctttccctattttgtttagtagtgatgaaagatgggtttaaaatatacagaaatgggaga<br>aaattaattagagaaaatgtgaggattttataattgataacatgttcttaattttacttgcacaagca<br>gtgttcacagccttattctgaagtgaccacttttcttctctttgaggcactacctggcagcaccatc<br>taaacctgtatcatctgctgtggtcccagttactcaggaggctgaggcaggaggatcacttga<br>gcccaggaggttgaggctggagtgagccatgactgtaccactgcattccagcctgggtgacg<br>gagtgaggccctatctgcctgccagtgagttctgtcatgcatcagactttggacctcagaatttt<br>cacctggaacatgagaggtcagatgacataatgaatatgttctaacttctgaaacttttggagctt<br>gtttttgcccttgatagcacgtatccttagagaataagcttgccaatttaaggcctgtctgtaatgg<br>catctgaatgttccagcagcctaactgtgctctgctccagaaacatgtgtgtggcttccctacct<br>ccacaccaaggagctgccttgctgggtggatgtaaagactgtcctgccagggtttcccactaa<br>aggtattaataagtccagtggaccacagagggcccaatccctcttggccgctaaggctaaggt<br>aggagccagagagctgtagagacaggaccaccaggatgcttcatgtccataacacaagaga<br>gcgctgcattgtttgggggccaggcattactactatcatgaagaaaaatgaagagcaggatgc<br>atgttagtctttaattcacttttaatagtataaacctcatttaggtagtagtattaagccacaacaata<br>atgccacattgaaacagcatttaataaaatgcataaagctaattcatgcactgcaatactctatat<br>acaaacacaacaatgcaaattcttcttcaagactgaagacattgattagatataaaattcagttta<br>aaaagaacatgctatttttaaatgccatcacataaacaaagtgatttcacagggagaagaaag<br>ctgtataaagctgcagctttcaacaggttttaaacctggcattaaaatgtaatggcaaaaccaat<br>attttctatattgtgaagggcaaaggttacagaaacggtcccaagaaaatctaacacccaaattt<br>tcctttgatagatagatgcctttaaaagggctggtaatgcagttacattctaacagagaagtcca<br>aactacaggtaaaaactacggcttgtactgtgaaaaatgtgcagcttttcagttataaaactagtt<br>gaacactggtttacaagataatccgtagaacagagagactgtagaaaaatattccagcacttga<br>gttgtgtgtggcagcagcatttgagtccatgaatgctatggtcattaaaataattgattatactttc<br>ctaaagaaaagccatttttaatgcaaagtctactacttccaaatgttattccaaacattaaatttta<br>acagtctatcaatcaataaatgttgaacattttttttctaaaaaaaaa | |
| NDUFS2 | NM_001166159.1 | aaaagccagccaggagctgtgggaggaaacgccctcagtaaagatgaccgcggtcactgtt<br>atctaaacgcaagtgaagccgagtcacaggacccggatgttgtcagttcgacggtaaacgac<br>cctgccagcttccaagagggcggcttcactgtgcgaataggtgagaagccaagaaggaggc<br>gcgctggagttacttccgcccggttctccttcccgcagtctgcagccggagtaagatggcggc<br>gctgagggctttgtgcggcttccggggcgtcgcggcccaggtgctgcggcctggggctgga<br>gtccgattgccgattcagcccagcagaggtgttcggcagtggcagccagatgtggaatggg<br>cacagcagtttgggggagctgttatgtacccaagcaaagaaacagcccactggaagcctcca<br>ccttggaatgatgtggaccctccaaaggacacaattgtgaagaacattaccctgaactttgggc<br>cccaacacccagcagcgcatggtgtcctgcgactagtgatggaattgagtggggagatggtg<br>cggaagtgtgatcctcacatcgggctcctgcaccgaggcactgagaagctcattgaatacaa<br>gacctatcttcaggcccttccatactttgaccggctagactatgtgtccatgatgtgtaacgaac<br>aggcctattctctagctgtggagaagttgctaaacatccggcctcctcctcgggcacagtggat<br>ccgagtgctgtttggagaaatcacacgtttgttgaaccacatcatggctgtgaccacacatgcc<br>ctggaccttggggccatgacccctttcttctggctgtttgaagaaagggagaagatgtttgagtt<br>ctacgagcgagtgtctggagcccgaatgcatgctgcttatatccggccaggaggagtgcacc<br>aggacctaccccttgggcttatggatgacatttatcagttttctaagaacttctctcttcggcttgat<br>gagttggaggagttgctgaccaacaataggatctggcgaaatcggacaattgacattggggtt<br>gtaacagcagaagaagcacttaactatggttttagtggagtgatgcttcggggctcaggcatc<br>cagtgggacctgcggaagacccagccctatgatgtttacgaccaggttgagtttgatgttcctg<br>ttggttctcgaggggactgctatgataggtacctgtgccgggtggaggagatgcgccagtcc<br>ctgagaattatcgcacagtgtctaaacaagatgcctcctggggagatcaaggttgatgatgcc<br>aaagtgtctccacctaagcgagcagagatgaagacttccatggagtcactgattcatcacttta<br>agttgtatactgagggctaccaagttcctccaggagccacatatactgccattgaggctcccaa<br>gggagagtttggggtgtacctggtgtctgatggcagcagccgcccttatcgatgcaagatcaa<br>ggctcctggttttgcccatctggctggtttggacaagatgtctaagggacacatgttggcagat<br>gtcgttgccatcataggtacgaggcctattgtgtagtagaggtatcctagacaaaggagttcgg<br>gacgcccactggggacagaaggagaacacttcctgttcaccataggccatggcatggactc<br>gggtcctcaatcttttgagcacagtaatgggttctggatcttgggtaacaccactttttttgtttgttt<br>tgcctcacaacaggaagataagtaacatcactttttttcctccatcctctcacctaggtacccaag<br>atattgtatttggagaagtagatcggtgagcaggggagcagcgtttgatccccccctgcctatca<br>gcttcttctgtggagcctgttcctcactggaaattggcctctgtgtgtgtgtgtgtgtgtgtgtg<br>tgtgtatgttcatgtacacttggctgtcaggctttctgtgcatgtactaaaaaaggagaaattataa<br>taaattagccgtcttgcggcccctaggcctaaaaaaaaaaaaaaaaaa | 19 |
| PPARGC1A | NM_013261.3 | tagtaagacaggtgccttcagttcactctcagtaaggggctggttgcctgcatgagtgtgtgct<br>ctgtgtcactgtggattggagttgaaaaagcttgactggcgtcattcaggagctggatggcgtg<br>ggacatgtgcaaccaggactctgagtctgtatggagtgacatcgagtgtgctgctctggttggt<br>gaagaccagcctctttgcccagatcttcctgaacttgatctttctgaactagatgtgaacgacttg<br>gatacagacagctttctgggtggactcaagtggtgcagtgaccaatcagaaataatatccaatc<br>agtacaacaatgagccttcaaacatatttgagaagatagatgaagagaatgaggcaaacttgc<br>tagcagtcctcacagagacactagacagtctccctgtggatgaagacggattgccctcatttga<br>tgcgctgacagatggagacgtgaccactgacaatgaggctagtccttcctccatgcctgacg<br>gcacccctccaccccaggaggcagaagagccgtctctacttaagaagctcttactggcacca<br>gccaacactcagctaagttataatgaatgcagtggtctcagtacccagaaccatgcaaatcac<br>aatcacaggatcagaacaaaccctgcaattgttaagactgagaattcatggagcaataaagcg<br>aagagtatttgtcaacagcaaaagccacaaagacgtccctgctcggagcttctcaaatatctga | 20 |

TABLE 1-continued

Prostate Cancer Biomarker/Housekeeper Sequence Information

| Gene Name | RefSeq Accession | Sequence | SEQ ID NO: |
|---|---|---|---|
| | | ccacaaacgatgaccctcctcacaccaaacccacagagaacagaaacagcagcagagaca<br>aatgcacctccaaaaagaagtcccacacacagtcgcagtcacaacacttacaagccaaacca<br>acaactttatctcttcctctgaccccagagtcaccaaatgaccccaagggttccccatttgagaa<br>caagactattgaacgcaccttaagtgtggaactctctggaactgcaggcctaactccacccac<br>cactcctcctcataaagccaaccaagataacccttttagggcttctccaaagctgaagtcctctt<br>gcaagactgtggtgccaccaccatcaaagaagcccaggtacagtgagtcttctggtacacaa<br>ggcaataactccaccaagaaagggccggagcaatccgagttgtatgcacaactcagcaagt<br>cctcagtcctcactggtggacacgaggaaaggaagaccaagcggcccagtctgcggctgttt<br>ggtgaccatgactattgccagtcaattaattccaaaacagaaatactcattaatatatcacagga<br>gctccaagactctagacaactagaaaataaagatgtctcctctgattggcaggggcagatttgt<br>tcttccacagattcagaccagtgctacctgagagagactttggaggcaagcaagcaggtctct<br>ccttgcagcacaagaaaacagctccaagaccaggaaatccgagccgagctgaacaagcact<br>tcggtcatcccagtcaagctgtttttgacgacgaagcagacaagaccggtgaactgagggac<br>agtgatttcagtaatgaacaattctccaaactacctatgtttataaattcaggactagccatggat<br>ggcctgtttgatgacagcgaagatgaaagtgataaactgagctacccttgggatggcacgca<br>atcctattcattgttcaatgtgtctccttcttgttcttcttttaactctccatgtagagattctgtgtcac<br>cacccaaatccttatttctcaaagaccccaaaggatgcgctctcgttcaaggtccttttctcgac<br>acaggtcgtgttcccgatcaccatattccaggtcaagatcaaggtctccaggcagtagatcctc<br>ttcaagatcctgctattactatgagtcaagccactacagacaccgcacgcaccgaaattctccc<br>ttgtatgtgagatcacgttcaagatcgccctacagccgtcggcccaggtatgacagctacgag<br>gaatatcagcacgagaggctgaagagggaagaatatcgcagagagtatgagaagcgagag<br>tctgagagggccaagcaaagggagaggcagaggcagaaggcaattgaagagcgccgtgt<br>gatttatgtcggtaaaatcagacctgacacaacacggacagaactgagggaccgttttgaagt<br>ttttggtgaaattgaggagtgcacagtaaatctgcgggatgatggagacagctatggtttcatta<br>cctaccgttatacctgtgatgcttttgctgctcttgaaaatggatacactttgcgcaggtcaaacg<br>aaactgactttgagctgtacttttgtggacgcaagcaatttttcaagtctaactatgcagacctag<br>attcaaactcagatgactttgaccctgcttccaccaagagcaagtatgactctctggattttgata<br>gtttactgaaagaagctcagagaagcttgcgcaggtaacatgttccctagctgaggatgacag<br>agggatggcgaatacctcatgggacagcgcgtccttccctaaagactattgcaagtcatactta<br>ggaatttctcctactttacactctctgtacaaaaacaaaacaaaacaacaacaatacaacaaga<br>acaacaacaacaataacaacaatggtttacatgaacacagctgctgaagaggcaagagaca<br>gaatgatatccagtaagcacatgtttattcatgggtgtcagctttgcttttcctggagtctcttggt<br>gatggagtgtgcgtgtgtgcatgtatgtgtgtgtatgtatgtgtgtggtgtgtgtgcttggttta<br>ggggaagtatgtgtgggtacatgtgaggactgggggcacctgaccagaatgcgcaagggc<br>aaaccatttcaaatggcagcagttccatgaagacacgcttaaaacctagaacttcaaaatgttc<br>gtattctattcaaaaggaaatatatatatatatatatatatatatatatatatatataaattaaaaagg<br>aaagaaaactaacaaccaaccaaccaaccaaccaaccacaaaccaccctaaaatgacagcc<br>gctgatgtctgggcatcagcctttgtactctgtttttttaagaaagtgcagaatcaacttgaagca<br>agctttctctcataacgtaatgattatatgacaatcctgaagaaaccacaggttccatagaactaa<br>tatcctgtctctctctctctctctctctctctcttttttttttcttttttcctttttgccatggaatctgggtgg<br>gagaggatactgcgggcaccagaatgctaaagtttcctaacattttgaagtttctgtagttcatc<br>cttaatcctgacacccatgtaaatgtccaaaatgttgatcttccactgcaaatttcaaaagccttgt<br>caatggtcaagcgtgcagcttgttcagcggttctttctgaggagcggacaccgggttacattac<br>taatgagagttgggtagaactctctgagatgtgttcagatagtgtaattgctacattctctgatgta<br>gttaagtatttacagatgttaaatggagtatttttattttatgtatatactatacaacaatgttctttttttg<br>ttacagctatgcactgtaaatgcagccttcttttcaaaactgctaaatttttcttaatcaagaatattc<br>aaatgtaattatgaggtgaaacaattattgtacactaacatatttagaagctgaacttactgcttat<br>atatatttgattgtaaaaacaaaaagacagtgtgtgtgtctgttgagtgcaacaagagcaaaatg<br>atgctttccgcacatccatcccttaggtgagcttcaatctaagcatcttgtcaagaaatatcctagt<br>cccctaaaggtattaaccacttctgcgatatttttccacatttcttgtcgcttgtttttctttgaagttt<br>tatacactggatttgttaggggaatgaaattttctcatctaaaatttttctagaagatatcatgatttt<br>atgtaaagtctctcaatgggtaaccattaagaaatgtttttatttctctatcaacagtagttttgaaa<br>ctagaagtcaaaaatctttttaaaatgctgttttgttttaatttttgtgattttaatttgatacaaaatgc<br>tgaggtaataattatagtatgatttttacaataattaatgtgtgtctgaagactatctttgaagccag<br>tatttctttcccttggcagagtatgacgatggtatttatctgtatttttttacagttatgcatcctgtata<br>aatactgatatttcattcctttgtttactaaagagacatatttatcagttgcagatagcctatttattat<br>aaattatgagatgatgaaaataataaagccagtggaaattttctacctaggatgcatgacaattg<br>tcaggttggagtgtaagtgcttcatttgggaaattcagcttttgcagaagcagtgtttctacttgca<br>ctagcatggcctctgacgtgaccatggtgttgttcttgatgacattgcttctgctaaatttaataaa<br>aacttcagaaaaacctccatttttgatcatcaggatttcatctgagtgtggagtccctggaatgga<br>attcagtaacatttggagtgtgtattcaagtttctaaattgagattcgattactgtttggctgacatg<br>acttttctggaagacatgatacacctactactcaattgttcttttcctttctctcgcccaacacgatc<br>ttgtaagatggatttcacccccaggccaatgcagctaattttgatagctgcattcatttatcacca<br>gcatattgtgttctgagtgaatccactgtttgtcctgtcggatgcttgcttgatttttttggcttcttattt<br>ctaagtagatagaaagcaataaaaatactatgaaatgaaagaacttgttcacaggttctgcgtta<br>caacagtaacacatctttaatccgcctaattcttgttgttctgtaggttaaatgcaggtattttaact<br>gtgtgaacgccaaactaaagtttacagtctttctttctgaattttgagtatcttctgttgtagaataat<br>aataaaaagactattaagagcaataaattatttttaagaaatcgagatttagtaaatcctattatgt<br>gttcaaggaccacatgtgttctctatttgcctttaaatttttgtgaaccaattttaaatacattctcct<br>ttttgccctggattgttgacatgagtggaatacttggtttcttttcttacttatcaaaagacagcact<br>acagatatcatattgaggattaatttatccccccctacccccagcctgacaaatattgttaccatga<br>agatagttttcctcaatggacttcaaattgcatctagaattagtggagcttttgtatcttctgcagac<br>actgtgggtagcccatcaaaatgtaagctgtgctcctctcatttttatttttatttttttgggagagaa<br>tatttcaaatgaacacgtgcaccccatcatcactggaggcaaatttcagcatagatctgtaggat | |

TABLE 1-continued

Prostate Cancer Biomarker/Housekeeper Sequence Information

| Gene Name | RefSeq Accession | Sequence | SEQ ID NO: |
|---|---|---|---|
| | | ttttagaagaccgtgggccattgccttcatgccgtggtaagtaccacatctacaattttggtaacc<br>gaactggtgctttagtaatgtggatttttttctttttttaaaagagatgtagcagaataattcttccagt<br>gcaacaaaatcaatttttttgctaaacgactccgagaacaacagttgggctgtcaacattcaaag<br>cagcagagagggaactttgcactattggggtatgatgtttgggtcagttgataaaaggaaacct<br>tttcatgcctttagatgtgagcttccagtaggtaatgattatgtgtcctttcttgatggctgtaatga<br>gaacttcaatcactgtagtctaagacctgatctatagatgacctagaatagccatgtactataatg<br>tgatgattctaaatttgtacctatgtgacagacattttcaataatgtgaactgctgatttgatggag<br>ctactttaagatttgtaggtgaaagtgtaatactgttggttgaactatgctgaagagggaaagtg<br>agcgattagttgagcccttgccgggcctttttttccacctgccaattctacatgtattgttgtggtttt<br>attcattgtatgaaaattcctgtgatttttttttaaatgtgcagtacacatcagcctcactgagctaat<br>aaagggaaacgaatgtttcaaatcta | |
| PPRC1 | NM_001288727.1 | gtagttcctttcccacaatcggctgggcgaggcggcgccagcgatcagagcagcgctgggt<br>gttcaggggccaagatggcggcgcgccggggacggagagacggagtcgcgccgccccc<br>gagtgggggccccggtccggaccctggcgggggagcccgcggcagtggttggggaagtc<br>gaagccaagcgccgtatgggactttgggcgctgtgagcggcggcgagcaggtgctgctgc<br>atgaggaggcgggtgattctggctttgtcagtctctctcggctgggcccatctctgagggaca<br>aggacctggaaatggaggagctaatgctgcaggatgagacactgctggggaccatgcaga<br>gctacatggatgcctcccttatctccctcattgaggattttgggagccttggagagagcaggtta<br>tctctggaggaccagaatgaagtgtcgctgctcacggctctgacggagatcttggacaatgca<br>gattctgagaacctttctccatttgacagcattcctgattcggagctgcttgtgtcaccccggga<br>gggctcctctctgcacaagctgcttactctctctcggacacccccagaacgtgacctcatcacc<br>ccagttgacccactggggcccagtacaggcagcagtagagggagtggggttgaaatgtctct<br>tccagatccctcttgggacttctccccaccctctttcttagagacctcttcccccaagcttcctag<br>ctggagacccccaagatcaagaccacgctggggccaatccccacctccccagcagcgcag<br>tgatggagaagaagaggaggaggtggccagcttcagtggccagattcttgccggggagctt<br>gacaactgtgtgagcagtatcccggacttccccatgcatttggcctgccctgaggaggaagat<br>aaagcaacagcagcagagatggcagtgccagcagctggtgatgagagcatctcctccctga<br>gtgagctggtgcgggccatgcacccatactgcctgcccaacctcacccacctggcatcacttg<br>aggatgagcttcaggagcagccagatgatttgacactgcctgagggctgcgtagtgctggag<br>attgtggggcaggcagccacagctggcgatgacctggagatcccagttgtggtgcgacagg<br>tctctcctggaccccggcctgtgctcctggatgactcgctagagactagttctgccttgcagct<br>gcttatgcctacactggagtcagagacagaggctgctgtgcccaaggtaaccctctgctctga<br>gaaagaggggttgtcattgaactcagaggagaagctggactcagcctgcttattgaagccca<br>gggaggtcgtggagccggtggtgcccaaggagcctcagaacccacctgccaatgcagcac<br>caggttcccagagagctcgaaagggcaggaagaagaagagcaaggagcagccagcagc<br>ctgtgtggaaggctatgccaggaggctgaggtcatcttctcgcgggcagtctactgtaggtac<br>agaagtgacctctcaggtagacaacttgcagaaacagcctcaggaagaacttcaaaaagagt<br>ctgggcctctccagggtaaggggaagccccgggcttgggctcgggcctgggcagctgcctt<br>ggagaattctagccctaagaacttggagagaagtgctggacaaagtagtcctgctaaagaag<br>gccctctagacctctacccaaagctggctgacactatccaaaccaatcctataccaacccatct<br>ctcattggtcgactctgcccaagccagccccatgccagttgactctgttgaagctgatcccact<br>gcagttggccctgttctagctggccctgtacctgttgaccctgggttggttgaccttgcttcaac<br>cagctcagaactggttgagcctctcccggctgagccagtgctgatcaacccagtcctggctga<br>ctcagcagcagttgaccctgcagtggttcccatctcagataacttgccaccagttgatgctgtc<br>ccgtctggcccagcaccagttgatctagcactggttgaccctgttcctaatgacctgactccag<br>ttgacccagtgctagttaagtccagaccaactgatcccagacgtggtgcagtgtcatcagccct<br>gggggggttcagcaccccagctcctcgtggagtcagagtccttggacccaccaaagaccatca<br>tccctgaagtcaaagaggttgtggattctctgaaaattgaaagtggtaccagtgctacaaccca<br>tgaagccagacctcggcctctcagcttatctgagtaccggcgacgaaggcagcaacgccaa<br>gcagaaacagaagagagaagtccacagcccccaactgggaagtggcctagccttccagag<br>actcccacagggctggcagacatcccttgtcttgtcatcccaccagccccagccaagaagac<br>agctctgcagagaagccctgaaacaccccttgagatttgccttgtgcctgtaggtcccagccct<br>gcttctcctagtcctgagccacctgtaagcaaacctgtggcctcatctcccactgagcaggtgc<br>catcccaggagatgccactgttggcgagaccttcccctcctgtgcagtctgtgtcccctgctgt<br>gcccacacctccctcgatgtctgctgccctgcctttccctgcaggtgggcttggcatgcccccc<br>agtctgcccccacctcccttgcagcctcctagtcttccattgtctatggggccagtactacctgat<br>ccgtttactcactatgccccccttgccatcctggccttgttatcctcatgtgtccccttctggctatcc<br>ttgcctgcccccccccaccaacggtgcccctagtgtctggtactcctggtgcctatgccgtgcct<br>cccacttgcagtgtgccttgggcacccccctcctgccccagtctcaccttacagttccacatgtac<br>ctatgggcccttgggatggggcccagggcctcaacatgctccattctggtctactgttccccca<br>cctcctttgcctccagcctccattgggagagctgttccccaacctaaaatggagtctaggggca<br>ctccagctggccctcctgaaaatgtacttcccttgtcgatggctcctcccctcagtcttgggcta<br>cctggccatggagctcctcagacagagcctaccaaggtggaggtcaagccagtgcctgcat<br>ctccccatccgaaacacaaggtgtctgccctggtgcaaagtccccagatgaaggctctagcat<br>gtgtgtctgctgaaggtgtgactgttgaggagcctgcatcagagaggctaaagcctgagacc<br>caagagaccaggcccagggagaagcccccccttgcctgctaccaaggctgttcccacaccaa<br>ggcagagcactgtccccaagctgcctgctgtccacccagcccgtctaaggaagctgtccttcc<br>tgcctaccccacgtactcagggttctgaagatgtggtacaggctttcatcagtgagattggaatt<br>gaggcatcggacctgtccagtctgctggagcagtttgagaaatcagaagccaaaaaggagt<br>gtcctcctccggctcctgctgacagcttggctgtaggaaactcagggtccagctgtagttcctc<br>tggacgttctcgaagatgctcttcctcttcttcgtcatcatcttcctcttcgtcttcctcatcctcatc<br>atccagttctcgaagccgctcacgatccccatcccccgccggagaagtgacaggaggcgg<br>cggtacagctcttatcgttcacatgaccattaccaaaggcaaagagtgctacaaaaggagcgt | 21 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | gcaatagaagaaagaagggtggtcttcattggaaagatacctggccgcatgactcgatcaga gctgaaacagaggttctccgtttttggagagattgaggagtgcaccatccacttccgtgtccaa ggggacaactacggcttcgtcacttatcgctatgctgaggaggcatttgcagccattgagagt ggccacaagctgcggcaggcagatgagcagccctttgatctctgctttgggggccgaaggc agttctgcaagaggagctattctgatcttgactccaaccgggaagactttgacccagcacctgt aaagagcaaatttgattctcttgactttgacacattgttgaaacaggcccagaagaacctcagg aggtaaccttgggcccttccctgctatcctttttctcctttggaggtgcccaacctcctccacccc cttcccctactctaggggagagagctgctagtgagatgactgttttataaagaaatggaaaaaa gtgaaataaaaaatatgttgaatcagatttttttaaaaggggtatttgtttttttataacaggtattgaa acaagttaacttgcattcctatgtaagataggagggggctgaggggatccccagtgtttggaac ataagtcactatgcagactaataaacatcaactagagagaactcccaaaaaaaaaaaaaaaaaaa | |
| RAD23A | NM_001270362.1 | ggtggtcagcgcgcgcattgcctgccccggaagtggtcggcgcgcggcgcggcgcgcct gggcgctaagatggcggcggcgtgagttgcatgttgtgtgaggatcccggggccgccgcgt cgctcgggccccgccatggccgtcaccatcacgctcaaaacgctgcagcagcagaccttca agatccgcatggagcctgacgagacggtgaaggtgctaaaggagaagatagaagctgaga agggtcgtgatgccttccccgtggctggacagaaactcatctatgccggcaagatcttgagtg acgatgtccctatcagggactatcgcatcgatgagaagaactttgtggtcgtcatggtgaccaa gaccaaagccggccagggtacctcagcaccccccagaggcctcacccacagctgccccaga gtcctctacatccttcccgcctgcccccacctcaggcatgtcccatcccccacctgccgccag agaggacaagagcccatcagaggaatccgcccccacgacgtccccagagtctgtgtcagg ctctgttccctcttcaggtagcagcgggcgagaggaagacgcggcctccacgctagtgacg ggctctgagtatgagacgatgctgacggagatcatgtccatgggctatgagcgagagcgggt cgtggccgccctgagagccagctacaacaaccccccaccgagccgtggagtatctgctcacg ggaattcctgggagccccgagccggaacacggttctgtccaggagagccaggtatcggag cagccggccacggaagcaggagagaaccccctggagttcctgcgggaccagccccagttc cagaacatgcggcaggtgattcagcagaaccctgcgctgctgcccgccctgctccagcagct gggccaggagaaccctcagcttttacagcaaatcagccggcaccaggagcagttcatccag atgctgaacgagccccctggggagctggcggacatctcagatgtggagggggaggtgggc gccataggagaggaggccccgcagatgaactacatccaggtgacgccgcaggagaaaga agctatagagaggttgaaggccctgggcttcccagagagcctggtcatccaggcctatttcgc gtgtgaaaaaaatgagaacttggctgccaacttcctcctgagtcagaactttgatgacgagtga tgccaggaagccaggccaccgaagccccccaccctacccttattccatgaaagttttataaaag aaaaaatatatatatattcatgtttatttaagaaatggaaaaaaaaatcaaaaatcttaaaaaaaca agcaaacagtccagcttcctgtcctcctaaagtggcccctgttcccatctcccgggccagaca gctgtcccccgtcctcctccccagcccagcctgctcagagaagctggcaggactgggagg cgacagatgggcccctcttggcctctgtcccagctctctgcagccagacggaaaggcggctg cttgcctctccatcctccgaaaaacccctgaggacccccccccatcctcttctaggatgaggg gaagctggagccccaactttgatcctccattggagtggcccaaatctttccatctagggcaagt cctgaaaggcccaaggcccctccccagtctggccttggcctccagcctggagaagggcta acatcagctcattgtcaaggccaccccaccccagaacagaaccgtgtctctgataaaggtttt gaagtgaataaagttttaaaaactag | 22 |
| REPIN1 | NM_013400.3 | cccggcgggggaggttggggacgggcctggcagttgtgaactcgaacctgccgctgtcg ccgcggcggggcggggagcgagagtgggccgcggaggccggccttcgggctccatgga cgggcgccgcgtccctgcacagcccgccgcagaggtaaggctggcctctctgcagtcaga ggtctgagctctgccatggggataggggtgtctttattactgcagttttctctaacacctggggg ctaccggagtgtgggccgaagcaggcgctgcagccgcggaagtatccccaggaacatccc caagaggagctggaaaaagcctcatccccagctctgcagtctccaggggagctcagtgtctg tttgtccagcttctcagagttgctgtgcagctcggatgtggcataggaaacagcagacacagg gagagggcagcataaggcactgtagggagcagtggccacattttctgcagaggaagaacc gatgctggaacgtcgttgcaggggcccccctggccatgggcctggcccagccccgactccttt ctgggccctcccaggagtcaccccagaccctggggaaggagtcccgcgggctgaggcaa caaggcacgtcagtggcccagtctggtgcccaagccccaggcagggcccatcgctgtgccc actgtcgaaggcacttccctggctgggtggctctgtggcttcacacccgccggtgccaggcc cggctgcccttgccctgccctgagtgtggccgtcgctttcgccatgccccttcttagcactgc accgccaggtccatgctgctgccaccccagacctgggctttgcctgccacctctgtgggcag agcttccgaggctgggtggccctggttctgcatctgcgggcccattcagctgcaaagcggcc catcgcttgtcccaaatgcgagagacgcttctggcgacgaaagcagcttcgagctcatctgcg gcggtgccaccctcccgccccggaggcccggcccttcatatgcggcaactgtggccggag ctttgcccagtgggaccagctagttgcccacaagcgggtgcacgtagctgaggccctggag gaggccgcagccaaggctctggggcccccggcccaggggccgccccgcggtgaccgccc cccggcccggtggagatgccgtcgaccgccccttccagtgtgcctgttgtggcaagcgcttc cggcacaagcccaacttgatcgctcaccgccgcgtgcacacgggcgagcggccccaccag tgccccgagtgcgggaagcgctttaccaataagccctatctgacttcgcaccggcgcatccac accggcgagaagccctacccgtgcaaagagtgcggccgccgcttccggcacaaacccaac ctgctgtctcacagcaagattcacaagcgatccgaggggtcggcccaggccgcccccggcc cggggagcccccagctgccagccggccccaggagtccgcggccgagcccaccccggc ggtacctctgaaaccggcccaggagccgccgccaggggccccgccagagcacccgcagg acccgatcgaagcccccccctccctctacagctgcgacgactgcggcaggagcttccggct ggagcgcttcctgcgggcccaccagcggcagcacaccggggagcggcccttcacctgcg ccgagtgcgggaagaacttcggcaagaagacgcacctggtggcgcactcgcgcgtgcact ccggcgagcggcccttcgcctgcgaggagtgcggccgccgcttctcccagggcagccatct ggcggcgcatcggcgcgaccacgcccccgatcggcccttcgtgtgtcccgactgcggcaa | 23 |

TABLE 1-continued

Prostate Cancer Biomarker/Housekeeper Sequence Information

| Gene Name | RefSeq Accession | Sequence | SEQ ID NO: |
|---|---|---|---|
| | | ggccttccgccacaaaccctacctggcggcgcaccggcgcatccacaccggcgagaagcc<br>ctacgtctgccccgactgcggcaaagccttcagccagaagtccaacctggtgtcgcaccggc<br>gcatccacacgggcgagcggccctacgcctgtcccgactgcgaccgcagcttcagccaga<br>agtccaacctcatcacccaccgcaagagccacatccgggacggcgccttctgctgtgccatc<br>tgtggccagaccttcgacgacgaggagagactcctggcccaccagaagaagcacgatgtct<br>gagacggtgggcggggccgtgttggctgagagagggctggggtccttcgtggtgggagtc<br>gcagtgggctgggggtgcctgcctagtgctggagtaggggacaatgggaatcctagaggg<br>gatggaagacgcggggagtgagctgggtgggccctgctagcgagagaggtcaaccccgg<br>tggccagggaacccacttccaagcgcagggacgccggcctccagctggtgtgtgctaaggc<br>tccgtcctgactgccctgtgccctggaaaagcagcaatagcatccgccccttagagccctctg<br>gctagaggagccaccagtggaaaggaagaccctccatcctctggtattaacgccttaatgccc<br>ctgtcttttactgtaagttacttaagatcattttggaagcaggcgtggtagagtcctgtaaatgaa<br>tgctctgggctagatacagcttggagaacctgctggccttgttagacagcacttgggcctttgc<br>cagcagcaagaggtgaagcgaagccactcttacctctcccttcccctcccacctgcccctgc<br>gtaggcacccagacttggagagacccgtctgctgttaatacttccatcctcttccttcccaaaga<br>gcagatcccaaggcatttactccttggtctgtctcgctttatctgtcgcccctcccagcgctgag<br>agcctcccctggctgtcagcagcactgtgtccaggctcttgtctgaacaccgcagcccctcctt<br>cgctccttccagagctcagcatgtcacggcaaggactgccgcattggtgatggagggccag<br>ctgaggggaagttgctggtgagtttccttttctccatttctagcatatggacacctggcctctgctt<br>gagcacttaggtgacaggaacttccgcacctcctgaggccctggatgattctaattgttagaaa<br>ttctaattgttagaaatccttccttataatgaatgaattctgctttcctataatttctacctattgggcc<br>ttgttctgttctctggaactaaacagaacaaccatttacccctccttttcaaactagagaataaag<br>atttggttttagaactggtaaaaaaaaaaaaaaaaaa | |
| SDR39U1 | NM_020195.2 | actttacgcaggcgcgttaggtcctagtcgctatgcgtgtgcttgtgggtggcgggacaggctt<br>cattgggacagccctaacccagctgctgaatgccagaggccacgaagtgacgttggtctccc<br>gaaagcccgggcccggccggatcacgtgggatgagctcgctgcatcggggctgccgagct<br>gcgatgccgccgtcaacctggccggagagaacatcctcaaccctctccgaagatggaatga<br>aaccttccaaaaagaggtaatcggcagccgcctagagaccacccaattgctggctaaagcca<br>tcaccaaagccccacaacccccaaggcctgggtcttagtcacaggtgtagcttactaccagc<br>ccagtctgactgcggagtatgatgaagacagcccaggaggggactttgactttttctccaacct<br>cgtaaccaaatgggaagctgcagccaggcttcctggagattctacacgccaggtggtggtgc<br>gctcaggggttgtgctgggccgtgggggtggtgccatgggccacatgctgctgccctttcgc<br>ctgggcctgggggccccatcggctcaggccaccaattcttcccctggatacacatcgggga<br>cctggcaggaatcctgacccatgcccttgaagcaaaccacgtgcacggggtcctgaatgga<br>gtggctccatcctccgccactaatgctgagtttgcccagaccttgggtgctgccctgggccgc<br>cgagccttcatccctctccccagcgctgtggtgcaagctgtctttgggcgacagcgtgccatc<br>atgctgctggagggccagaaggtgatcccacagcgaacactggccactggctaccagtattc<br>cttcccagagctaggggctgccttaaaggaaattgtagcctaagtaggtcgtggcaagggcct<br>gaggcctgttcctcacaggcttccaggttaggcactgtgaataggctcagctcctctagagag<br>ctgaagccatctggttcttagattcctctcccagtcctctttcccattgttctgttgctccaccttatt<br>gtctcaaggccgtaatctcatcaggttgggacattaatcttttcaactccttgtaagatttcccagt<br>ttggtttctctacatgtcctgcagctgccccacttctcctttacgctgtgtagagaatgctctgcag<br>tttaggcaataaaaataaattgtctcactaaaaaaaaaaaaaaaaaa | 24 |
| SETBP1 | NM_001130110.1 | aagcgcggggccggccggggcgcccgccgctcgccgccgcctccgcgcgcccggggg<br>ccccggcgcccccccgagctagggcggccagctcgcggctcgccgtttgacagatgctcatc<br>gccatggagttgccgcagcagcacctttgggggctcgggcgagcgacgggagccgggatc<br>tgagcgagcgccggggccagcggagccggagccgccgggacatggttgcagatctgatct<br>cttctgaacacctcatcgtgtctccatccctgggaatctgaccctagcaactggaccactttgttc<br>ttggaattttgggtgtcctcttttctcacctttccctttttcccttttccccttccccctcctgagaactc<br>cggaagactgtagagattgtcatggagtccagggaaaccttaagcagctcccggcaaagag<br>ggggcgagtcagacttcctgccggtctcctcagccaagcccccagctgctcctggctgtgca<br>ggagaacctttgctctccactccaggacctgggaaggggatcccggtgggcggagagcgc<br>atggagccagaggaggaggatgaactaggctcagggcgggatgtggattccaactccaac<br>gcggacagtgagaaatgggtggcaggagatggtttggaagagcaggaattttctatcaagga<br>ggcaaacttcacagagggaagtctgaagctaaagattcagaccacaaagcgggctaagaaa<br>cccccaaagaatttggagaactatatatgtccacctgagatcaagatcaccatcaagcagtctg<br>gggaccagaaggtgtcccgtgctggaaaaaatagcaaagccacgaaggaggaagaaaga<br>agccactccaaaaagaagctcctcacagccagtgaccttgcagccagtgacctcaaaggattt<br>cagccacagattaaagactccagtaaggaggaagtctggaagagaagaggaggccaaggc<br>atcccattcaaaaagcaattcctgtcccaggaacgtgccatgtgcttctcatgcccccggaacc<br>cattccccgcaaaacccggttctctcactcttccttttcacagtgaacctgcagtctgggcacaa<br>gaagtataacttcgcatggattctgcaaagcccacacctgtggtcattccctgttctttccattca<br>acaatggagacttgcccaagattgtaaactagtgagtgacagcatttgggcttatgatcttctct<br>gcctgctagctagacattctctctgggtctaaaagataatccaaaaagatccagcttcacaatgc<br>tgccctgaagagataatgcattaggcggccctgatgcagcattcactgtcttccagggcaggc<br>ttgatcccatgagtttgcttgctcagacgatcacttaggaaacacatgcctttactctctaggcctt<br>ttttctagcttgccttgtatcagctatgccatggatctttgctctcttaccccatgctatacagagtat<br>gggctccaagccacagctggcctgtcaagtgtgtgtcgctggtccaccatgggatacatttag<br>aaacttttatagcaatttgacatttttgtgatatccaagcatgtgattgttttcctacggatttgtctta<br>tagtattttaccaaagtttccacacaaaaagtatggattaaggacaaagtatctggtccttcatca<br>aagatcgtttgataagctctgttctagttaaccaacactgagctttcctagttttaataaaagagta<br>ggatttggaaaaaaaaaaaaaaaaaaaa | 25 |

TABLE 1-continued

Prostate Cancer Biomarker/Housekeeper Sequence Information

| Gene Name | RefSeq Accession | Sequence | SEQ ID NO: |
|---|---|---|---|
| SLC14A1 | NM_001128588.3 | acacagagcagagtggggctctgagtatataactgttaggtgcctccctccagcaccatctcct gagaagcactctcccttgtcgtggaggtgggcaaatctttatcagccactgccttctgctgcca ggaagccagctagagtggtctttaaagaaaactgggcatctcctgctacttaaaatcaaaaact acctaaaataaagattataaaaaagtaaggatgaatggacggtctttgattggcggcgctggtg acgcccgtcatggtcctgtttggaaggacccttttggaactaaagctggtgacgcagcgcgca gaggcatcgcccggctaagcttggccctggcagatgggtcgcaggaacaggagccagag gaagagatagccatggaggacagccccactatggttagagtggacagccccactatggttag gggtgaaaaccaggtttcgccatgtcaagggagaaggtgcttccccaaagctcttggctatgt caccggtgacatgaaagaacttgccaaccagcttaaagacaaacccgtggtgctccagttcat tgactggattctccggggcatatcccaagtggtgttcgtcaacaaccccgtcagtggaatcctg attctggtaggacttcttgttcagaacccctggtgggctctcactggctggctgggaacagtgg tctccactctgatggccctcttgctcagccaggacaggtcattaatagcatctgggctctatggc tacaatgccaccctggtgggagtactcatggctgtcttttcggacaagggagactatttctggtg gctgttactccctgtatgtgctatgtccatgacttgcccaatttctcaagtgcattgaattccatgc tcagcaaatgggacctccccgtcttcaccctccctttcaacatggcgttgtcaatgtacctttcag ccacaggacattacaatccattctttccagccaaactggtcatacctataactacagctccaaat atctcctggtctgacctcagtgccctggagttgttgaaatctataccagtgggagttggtcagat ctatggctgtgataatccatggacagggggcattttcctgggagccatcctactctcctcccca ctcatgtgcctgcatgctgccataggatcattgctgggcatagcagcgggactcagtctttcag ccccatttgaggacatctactttggactctggggtttcaacagctctctggcctgcattgcaatg ggaggaatgttcatggcgctcacctggcaaacccacctcctggctcttggctgtgccctgttca cggcctatcttggagtcggcatggcaaactttatggctgaggttggattgccagcttgtacctg gcccttctgtttggccacgctattgttcctcatcatgaccacaaaaaattccaacatctacaagat gcccctcagtaaagttacttatcctgaagaaaaccgcatcttctacctgcaagccaagaaaaga atggtggaaagccctttgtgagaacaagccccatttgcagccatggtcacgagtcatttctgcc tgactgctccagctaacttccagggtctcagcaaactgctgtttttcacgagtatcaactttcata ctgacgcgtctgtaatctgttcttatgctcattttgtattttcctttcaactccaggaatatccttgag catatgagagtcacatccaggtgatgtgctctggtatggaatttgaaaccccaatggggccttg gcactaagactggaatgtatataaagtcaaagtgctccaacagaaggaggaagtgaaaacaa actattagtatttattgatattcttggtgtttagctggctcgatgatgttaacagtattaaaaattaaa ccccataaaccaactaagccttatggaattcacagtcacaaaatcgaagttaatccagaattctg tgataagcagcttggcttttttttaaatcaatgcaagttacacattatagccagaatctgtatcaca gaggtgcaagctgacagcagagctcagtccccacttcctgcaaacaatggcctgcaccctat cccttgtgtgtgtgacattctctcatgggacaatgttggggtttttcagactgacaggactgcaa gagggagaaaggaattttgtcaatcaaaattattctgtattgcaacttttctcagagattgcaaag gattttttaggtagagattatttttccttatgaaaaatgatctgttttaaatgagataaaataggaga agttcctggcttaacctgttcttacatattaaagaaaagttacttactgtatttatgaaatactcagc ttaggcatttttactttaacccctaaattgattttgtaaatgccacaaatgcatagaattgttaccaa cctccaaagggctctttaaaatcatatttttattcatttgaggatgtcttataaagactgaaggca aaggtcagattgcttacgggtgttattttataagttgttgaattccttaatttaaaaaagctcattatt ttttgcacactcacaatattctctctcagaaatcaatggcatttgaaccaccaaaaagaaataaa gggctgagtgcggtggctcacgcctgtaatcccagcactttggggagcccaggcgggcaga ttgcttgaacccaggagttcaagaccagcctgggcagcatggtgaaaccctgtatctacaaaa aatacaaaaattagccaggcatggtggtgggtgcctgtagttccagctacttgggaggctgag gtgggaaaatgacttgagcccaggaggaggaggctgcagtgagctaagattgcaccactgc actccaacctgggcgacaagagtgaaactgtgtctctcaaaaaaaaaaaaaaaacaaacaaaa acaaaaacaaaacaaaacaaaacaaaacaaaacaggtaaggattcccctgttttcctctcttta attttaaagttatcagttccgtaaagtctctgtaaccaaacatactgaagacagcaacagaagtc acgttcagggactggctcacacctgtaatcccagcactttgggagatggaggtaaaaggatct cttgagcccaggagttcaagaccagcttgggcaacatagcaagactccatctcttaaaaaata aaaatagtaacattagccaggtgtagcagcacacatctgcagcagctactcaggaggctgag gtggaaagatcgcttgtgcacagaagttcgaggctgcagtgagctatatgatcatgtcactgc actccagcctgtgtgaccgagcaagaccctatctcaaaaaaattaattaattaattaattaat ttaaaaaggaagtcatgttcatttactttccacttcagtgtgtatcgtgtagtattttggaggttgga aagtgaaacgtaggaatcctgaagatttttccacttctagtttgcagtgctcagtgcacaatata cattttgctgaatgaataaacagaaatagggaagtaaacctacaaatattttagggagaagctc acttcttccttttctcaggaaaccaagcaagcaaacatatcgttccaattttaaaacccagtgacc aaagcctttggaactatgaatttgcaactgtcataggtttatggatattgctgtggagaagctcaa ttttcagtgtttgaactgaaccctttcttgttagggaacgtgtgaaagaagaattgtggggaaaa aaaagcaagcataaccaaagatcatcagcagtgaagaatctaggctgtggctgagagaacc agaggcctctaaaatggacccgagtcgatcttcagaacagggatctaccatgcaggagcttct tgtgctcacacaaatctgtaaatgggaacattgtacattgtcgaatttaaatgatattaattttctca agctatttttgttactatttcctaaaattgaatatttgcagggagcacttatactttttcctaatgtctg tataacaaatttctatgcaagtacatgaataaattatgctcacagctca | 26 |
| SLC18A2 | NM_003054.4 | agagccggacggggtaaactgagcggcggcggcggggcgctggggcggagactgcgac ccggagccgcccggactgacggagcccactgcggtgcgggcgttggcgcgggcacgga ggacccgggcaggcatcgcaagcgaccccgagcggagccccggagccatggccctgag cgagctggcgctggtccgctggctgcaggagagccgccgctcgcggaagctcatcctgttc atcgtgttcctggcgctgctgctggacaacatgctgctcactgtcgtggtccccatcatcccaa gttatctgtacagcattaagcatgagaagaatgctacagaaatccagacggccaggccagtg cacactgcctccatctcagacagcttccagagcatcttctcctattatgataactcgactatggtc accgggaatgctaccagagacctgacacttcatcagaccgccacacagcacatggtgacca | 27 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | acgcgtccgctgttccttccgactgtcccagtgaagacaaagacctcctgaatgaaaacgtgc<br>aagttggtctgttgtttgcctcgaaagccaccgtccagctcatcaccaaccctttcataggacta<br>ctgaccaacagaattggctatccaattcccatatttgcgggattctgcatcatgtttgtctcaaca<br>attatgtttgccttctccagcagctatgccttcctgctgattgccaggtcgctgcagggcatcgg<br>ctcgtcctgctcctctgtggctgggatgggcatgcttgccagtgtctacacagatgatgaagag<br>agaggcaacgtcatgggaatcgccttgggaggcctggccatgggggtcttagtgggccccc<br>ccttcgggagtgtgctctatgagtttgtggggaagacggctccgttcctggtgctggccgccct<br>ggtactcttggatggagctattcagctctttgtgctccagccgtcccgggtgcagccagagagt<br>cagaaggggacacccctaaccacgctgctgaaggacccgtacatcctcattgctgcaggctc<br>catctgctttgcaaacatgggcatcgccatgctggagccagccctgcccatctggatgatgga<br>gaccatgtgttcccgaaagtggcagctgggcgttgccttcttgccagctagtatctcttatctcat<br>tggaaccaatatttttgggatacttgcacacaaaatggggaggtggctttgtgctcttctgggaa<br>tgataattgttggagtcagcattttatgtattccatttgcaaaaaacatttatggactcatagctccg<br>aactttggagttggttttgcaattggaatggtggattcgtcaatgatgcctatcatgggctacctc<br>gtagacctgcggcacgtgtccgtctatgggagtgtgtacgccattgcggatgtggcattttgtat<br>ggggtatgctataggtccttctgctggtggtgctattgcaaaggcaattggatttccatggctcat<br>gacaattattgggataattgatattctttttgcccctctctgctttttcttcgaagtccacctgccaa<br>agaagaaaaaatggctattctcatggatcacaactgccctattaaaacaaaaatgtacactcag<br>aataatatccagtcatatccgataggtgaagatgaagaatctgaaagtgactgagatgagatcc<br>tcaaaaatcatcaaagtgtttaattgtataaaacagtgtttccagtgacacaactcatccagaact<br>gtcttagtcataccatccatccctggtgaaagagtaaaaccaaaggttattatttcctttccatggt<br>tatggtcgattgccaacagccttataaagaaaaagaagcttttctaggggtttgtataaatagtgt<br>tgaaactttattttatgtatttaattttattaaatatcatacaatatattttgatgaaataggtattgtgta<br>aatctataaatatttgaatccaaaccaaatataatttttttaacttacattaacaaacatttgggcaaa<br>aatcatattggtaatgagtgtttaaaattaaagcacacattatctctgagactcttccaacaaaga<br>gaaactagaatgaagtctgaaaaacagaatcaagtaagacagcatgttatatagtgacactga<br>atgttatttaacttgtagttactatcaatatatttatgcgttaaacagctagttctctcaagtgtagag<br>gacaagaacttgtgtcagttatcttttgaatccataaatcttagctggcattagttttctatgtaatca<br>cctacctagagagagttgtaaattatatgttaacatgttatctggttggcagcaaacactaaagc<br>caataaaggaaaaacagtaaatgttccgaaagcagagaaaagcaaccaaacatattgttatga<br>actaaaagctttccctttaagatgcatacttgtcttactggatgaagaaaattgagggtacatgta<br>ccttatactgtcaaggttgtttaaacatgataaggttaatcgccatctacttcaagttttagaaaag<br>gaaacaagaagctgaaaacagctgctctgactttaatatctgactatatctttgatctgtttgcag<br>gtcatccaagtgttttctaggaatatatttattttaggttgtctgaaactactattttttagactcctga<br>aagttgttcacatcaatgtgaagacaaattttaaatgaaaatgaagaatgaaattatgtcttgaat<br>catatattaagaagtaaaaataatagtgatcaggcagaaaagaaaaatggaacatctaaaaat<br>gtatgtgctaactatatcatccagtgtgcagtgttgtgtatttttctaagcatgacaacattgatgtg<br>ccttttcagtgtaacagcaaatactgttagtgaacattgtcaatttatgtcattttgttaagagatat<br>gactggagtgtgcagtgtggaatgtctctaatactacttgtgaatcctgcagttctataatcataa<br>acaaaaattacttagtttcgttaagctaagattgtgtttgtgttaacttcgacatcaaggagcaaa<br>gaactttagaacagactcctcaatcttgtgactttcttattctctaggaaagtaacacttcgtttcat<br>gaagcttttctgtggggcttcgattatttcaagtctggtttctaagtgcagtgtgtttgaagcaaac<br>gaacttccaactcacttatttggcattgggcaacttggccaagtctgccactttggaagatggct<br>ctggaggaaactctcatatggctaaaaaggcaggctagtttcttacttctacaggggtagagcc<br>ttaaaaaagaacgtgctacaaattggttctctttgagggtttctggttctccctgcccccaatacc<br>atatactttattgcaattttatttttgcctttacggctctgtgtctttctgcaagaaggcctggcaaag<br>gtatgcctgctgttggtccctcgggataagataaaatataaaaccttcagaactgttttgga<br>gcaaaagatagcttgtacttggggaaaaaaattctaagttcttttatatgactaatattcttggttag<br>caagactggaaagaggtgtttttttaaaatgtacataccagaacaaagaacatacagctctctg<br>aacatttatttttgaacagaggtggtttttatgtttggacctggtaatacagatacaaaaactttaa<br>tgaggtagcaatgaatattcaactgtttgactgctaagtgtatctgtccatattttagcaagtttact<br>taataaatcttctgaaccatgaaaaaaaaaaaaa | |
| SMC4 | NM_001002800.2 | gccctcttctgaagaggcgtttctggaccactgagccccgcctcccactgtgagcggaaccct<br>accgtttttaaaaaaatctttttcaaaacttgccaggttgtctttccaaatatttttaataatagtgctg<br>ctgctgtagaccacagagaaaagaatccctcgctcttccttttcacttagtagaaacttctaccg<br>cgtaggtcccgccaggagttcgcgcatgcgcaggagcgacaataagatggcggtgataatc<br>gccgcactttttttcaaattagtggatcccagaaatcattgcgcgcatttgtaacgaatttccgttc<br>gagtttgtattttaggcgccattttcgagtgaaggacccggagccgaaacaccggtaggagc<br>ggggaggtgggtactacacaaccgtctccagccttggtctgagtggactgtcctgcagcgac<br>catgccccgtaaaggcacccagccctccactgcccggcgcagagaggaagggccgccgc<br>cgccgtcccctgacggcgccagcagcgacgcggagcctgagccgccgtccggccgcacg<br>gagagcccagccaccgccgcagagactgcaagtgaggaacttgataatagaagtttagaag<br>agattttgaacagcattcctcctcccccgcctccagcaatgaccaatgaagctggagctcctcg<br>gcttatgataactcatattgtaaaccagaacttcaaatcctatgctggggagaaaattctgggac<br>ctttccataagcgcttttcctgtattatcgggccaaatggcagtggcaaatccaatgttattgattc<br>tatgctttttgtgtttggctatcgagcacaaaaaataagatctaaaaaactctcagtattaatacat<br>aattctgatgaacacaaggacattcagagttgtacagtagaagttcattttcaaaagataattgat<br>aaggaaggggatgattatgaagtcattcctaacagtaatttctatgtatccagaacggcctgca<br>gagataatacttctgtctatcacataagtggaaagaaaaagacatttaaggatgttggaaatctt<br>cttcgaagccatggaattgacttggaccataatagatttttaattttacagggtgaagttgaacaa<br>attgctatgatgaaaccaaaaggccagactgaacacgatgagggtatgcttgaatatttagaa<br>gatataattggttgtggacggctaaatgaacctattaaagtcttgtgtcggagagttgaaatatta<br>aatgaacacagaggagagaagttaaacagggtaaagatggtggaaaaggaaaaggatgcc | 28 |

TABLE 1-continued

Prostate Cancer Biomarker/Housekeeper Sequence Information

| Gene Name | RefSeq Accession | Sequence | SEQ ID NO: |
|---|---|---|---|
| | | ttagaaggagagaaaaacatagctatcgaatttcttaccttggaaaatgaaatatttagaaaaaa<br>gaatcatgtttgtcaatattatatttatgagttgcagaaacgaattgctgaaatggaaactcaaaa<br>ggaaaaaattcatgaagataccaaagaaattaatgagaagagcaatatactatcaaatgaaat<br>gaaagctaagaataaagatgtaaaagatacagaaaagaaactgaataaaattacaaaatttatt<br>gaggagaataaagaaaaatttacacagctagatttggaagatgttcaagttagagaaaagttaa<br>aacatgccacgagtaaagccaaaaaactggagaaacaacttcaaaaagataaagaaaaggtt<br>gaagaatttaaaagtatacctgccaagagtaacaatatcattaatgaaacaacaaccagaaac<br>aatgccctcgagaaggaaaaagagaaagaagaaaaaaaattaaaggaagttatggatagcc<br>ttaaacaggaaacacaagggcttcagaaagaaaaagaaagtcgagagaaagaacttatggg<br>tttcagcaaatcggtaaatgaagcacgttcaaagatggatgtagcccagtcagaacttgatatc<br>tatctcagtcgtcataatactgcagtgtctcaattaactaaggctaaggaagctctaattgcagct<br>tctgagactctcaaagaaaggaaagctgcaatcagagatatagaaggaaaactccctcaaact<br>gaacaagaattaaaggagaaagaaaaagaacttcaaaaacttacacaagaagaaacaaactt<br>taaaagtttggttcatgatctctttcaaaaagttgaagaagcaaagagctcattagcaatgaatc<br>gaagtagggggaaagtccttgatgcaataattcaagaaaaaaaatctggcaggattccagga<br>atatatggaagattgggggacttaggagccattgatgaaaaatacgacgtggctatatcatcct<br>gttgtcatgcactggactacattgttgttgattctattgatatagcccaagaatgtgtaaacttcctt<br>aaaagacaaaatattggagttgcaacctttataggtttagataagatggctgtatgggcgaaaa<br>agatgaccgaaattcaaactcctgaaaatactcctcgtttatttgatttagtaaaagtaaaagatg<br>agaaaattcgccaagctttttattttgctttacgagataccttagtagctgacaacttggatcaagc<br>cacaagagtagcatatcaaaaagatagaagatggagagtggtaactttacagggacaaatcat<br>agaacagtcaggtacaatgactggtggtggaagcaaagtaatgaaaggaagaatgggttcct<br>cacttgttattgaaatctctgaagaagaggtaaacaaaatggaatcacagttgcaaaacgactc<br>taaaaaagcaatgcaaatccaagaacagaaagtacaacttgaagaaagagtagttaagttacg<br>gcatagtgaacgagaaatgaggaacacactagaaaaatttactgcaagcatccagcgtttaat<br>agagcaagaagaatatttgaatgtccaagttaaggaacttgaagctaatgtacttgctacagcc<br>cctgacaaaaaaaagcagaaattgctagaagaaaacgttagtgctttcaaaacagaatatgat<br>gctgtggctgagaaagctggtaaagtagaagctgaggttaaacgcttacacaataccatcgta<br>gaaatcaataatcataaactcaaggcccaacaagacaaacttgataaaataaataagcaattag<br>atgaatgtgcttctgctattactaaagcccaagtagcaatcaagactgctgacagaaaccttcaa<br>aaggcacaagactctgtcttgcgtacagagaaagaaataaaagatactgagaaagaggtgga<br>tgacctaacagcagagctgaaaagtcttgaggacaaagcagcagaggtcgtaaagaataca<br>aatgctgcagaggaatccttaccagagatccagaaagaacatcgcaatctgcttcaagaatta<br>aaagttattcaagaaaatgaacatgctcttcaaaaagatgcacttagtattaagttgaaacttgaa<br>caaatagatggtcacattgctgaacataattctaaaataaaatattggcacaaagagatttcaaa<br>aatatcactgcatcctatagaagataatcctattgaagagatttcggttctaagcccagaggatct<br>tgaagcgatcaagaatccagattctataacaaatcaaattgcacttttggaagcccggtgtcatg<br>aaatgaaaccaaacctcggtgccatcgcagagtataaaaagaaggaagaattgtatttgcaac<br>gggtagcagaattggacaaaattacttatgaaagagacagttttagacaggcatatgaagatct<br>tcggaaacaaaggcttaatgaatttatggcaggtttttatataataacaaataaattaaaggaaaa<br>ttaccaaatgcttactttgggaggggacgccgaactcgagcttgtagacagcttggatcctttct<br>ctgaaggaatcatgttcagtgttcgaccacctaagaaaagttggaaaaagatcttcaacctttcg<br>ggaggagagaaaacacttagttcattggctttagtatttgctcttcaccactacaagcccactcc<br>cctttacttcatggatgagattgatgcagcccttgattttaaaaatgtgtccattgttgcattttatat<br>atatgaacaaacaaaaaatgcacagttcataataatttctcttcgaaataatatgtttgagatttcg<br>gatagacttattggaatttacaagacatacaacataacaaaaagtgttgctgtaaatccaaaaga<br>aattgcatctaagggactttgttgaactttatgctgaagattcttcaagttgattcagtgtattactg<br>atttttttctatttgtaaaggattatgagttgtataaaatacatactccctaaactagatcatgaaact<br>ggtttctgttttatgcagttgtcatttgtaaagtctaataaaatattctctataattgcttctagattaca<br>aaaatatgacaatcttgtaagtagcagactatggagaaaaatgagttacctggagggtcaggt<br>aacttgccaaactaaaaagtatgttagttgaggcaaagtcctaagcaaggttgtgctatcaagg<br>ctcagcataccttcgtgggcctttgatttaccaacactggaaatgcctgccaactaatcttggata<br>gattctttaaggcattccacttagcttgccagttgagacaatcaccacagttattacccaaatact<br>atgaacatatttttgtaaaccagtcattctgaattatagtgatgagaatttaaatatatgcttttctag<br>aatttgatgtttgaccatttatgacttaattaccagagagccagtaaattaggacagtgtttcaaca<br>agcctaggctatctcgtaagttgaaaaatatcccactatagttgcttcatgagtatgaagtaagat<br>ggcctctgatttacactggttcaatttacaaattttcaactttatgataggtttatccgggtactaaat<br>gcatttcaacttgatagtttcaacttatgataggtttaccaggatgtagtcccactgttgaggagc<br>atctatttaggggttaattactttagtaataagtggaaagtaagataccttgagtaatgtttgcctat<br>aaaattgtcagcgtatttttacactattggctcaagaatgttataatgctaagggacataagttgg<br>caaccacttggtttttggaaggactttcggtattgtattagaagtctgccctagctgttaaatttctg<br>ggtatttatcctaaggaattaattaaagagttaattgttcctttcttcagtgggccattgttttagata<br>tttaaaaaatccaacagtttctatcataatgtaactgtaaaaatgtaaacacattattagcatggac<br>ttttaaataaagatttaaagaaagcaagatcggaaaaaaaaaaaaaaaaaa | |
| SPARC | NM_001309443.1 | gggagaaggaggaggccgggggaaggaggagacaggaggaggagggaccacggggt<br>ggaggggagatagacccagcccagagctctgagtggtttcctgttgcctgtctctaaacccct<br>ccacattcccgcggtccttcagactgcccggagagcgcgctctgcctgccgcctgcctgcct<br>gccactgagggttcccagcaccatgagggcctggatcttctttctcctttgcctggccgggag<br>ggccttggcagcccctcaagaagccctgcctgatgagacagaggtggtggaagaaactgtg<br>gcagaggtgactgaggtatctgtgggagctaatcctgtccaggtggaagtaggagaatttgat<br>gatggtgcagaggaaaccgaagaggaggtggtggcggaaaatccctgccagaaccacca<br>ctgcaaacacggcaaggtgtgcgagctggatgagaacaacacccccatgtgcgtgtgccag<br>gaccccaccagctgcccagcccccattggcgagtttgagaaggtgtgcagcaatgacaaca | 29 |

TABLE 1-continued

Prostate Cancer Biomarker/Housekeeper Sequence Information

| Gene Name | RefSeq Accession | Sequence | SEQ ID NO: |
|---|---|---|---|
| | | agaccttcgactcttcctgccacttctttgccacaaagtgcaccctggagggcaccaagaagg<br>gccacaagctccacctggactacatcgggccttgcaaatacatccccccttgcctggactctg<br>agctgaccgaattcccctgcgcatgcgggactggctcaagaacgtcctggtcaccctgtatg<br>agagggatgaggacaacaaccttctgactgagaagcagaagctgcgggtgaagaagatcc<br>atgagaatgagaagcgcctggaggcaggagaccaccccgtggagctgctggcccgggact<br>tcgagaagaactataacatgtacatcttccctgtacactggcagttcggccagctggaccagc<br>accccattgacgggtacctctcccacaccgagctggctccactgcgtgctcccctcatcccca<br>tggagcattgcaccacccgctttttcgagacctgtgacctggacaatgacaagtacatcgccct<br>ggatgagtgggccggctgcttcggcatcaagcagaaggatatcgacaaggatcttgtgatct<br>aaatccactccttccacagtaccggattctctctttaaccctcccttcgtgtttcccccaatgttta<br>aaatgtttggatggtttgttgttctgcctggagacaaggtgctaacatagatttaagtgaatacatt<br>aacggtgctaaaaatgaaaattctaacccaagacatgacattcttagctgtaacttaactattaag<br>gcctttttccacacgcattaatagtcccatttttctcttgccatttgtagctttgcccattgtcttattgg<br>cacatgggtggacacggatctgctgggctctgccttaaacacacattgcagcttcaacttttctc<br>tttagtgttctgtttgaaactaatacttaccgagtcagactttgtgttcatttcatttcagggtcttgg<br>ctgcctgtgggcttccccaggtggcctggaggtgggcaaagggaagtaacagacacacgat<br>gttgtcaaggatggttttgggactagaggctcagtggtgggagagatccctgcagaacccac<br>caaccagaacgtggtttgcctgaggctgtaactgagagaaagattctggggctgtgttatgaa<br>aatatagacattctcacataagcccagttcatcaccatttcctcctttacctttcagtgcagtttcttt<br>tcacattaggctgttggttcaaacttttgggagcacggactgtcagttctctgggaagtggtcag<br>cgcatcctgcagggcttctcctcctctgtcttttggagaaccagggctcttctcaggggctctag<br>ggactgccaggctgtttcagccaggaaggccaaaatcaagagtgagatgtagaaagttgtaa<br>aatagaaaaagtggagttggtgaatcggttgttctttcctcacatttggatgattgtcataaggttt<br>ttagcatgttcctccttttcttcaccctcccctttttttcttctattaatcaagagaaacttcaaagttaat<br>gggatggtcggatctcacaggctgagaactcgttcacctccaagcatttcatgaaaaagctgc<br>ttcttattaatcatacaaactctcaccatgatgtgaagagtttcacaaatccttcaaaataaaaagt<br>aatgacttagaaactgccttcctgggtgatttgcatgtgtcttagtcttagtcaccttattatcctga<br>cacaaaaacacatgagcatacatgtctacacatgactacacaaatgcaaacctttgcaaacac<br>attatgcttttgcacacacacacctgtacacacacaccggcatgtttatacacagggagtgtatg<br>gttcctgtaagcactaagttagctgttttcatttaatgacctgtggtttaaccttttgatcactacca<br>ccattatcagcaccagactgagcagctatatccttttattaatcatggtcattcattcattcattcatt<br>cacaaaatatttatgatgtatttactctgcaccaggtcccatgccaagcactggggacacagtta<br>tggcaaagtagacaaagcatttgttcatttggagcttagagtccaggaggaatacattagataat<br>gacacaatcaaatataaattgcaagatgtcacaggtgtgatgaagggagagtaggagagacc<br>atgagtatgtgtaacaggaggacacagcattattctagtgctgtactgttccgtacggcagcca<br>ctacccacatgtaacttttttaagatttaaatttaaattagttaacattcaaaacgcagctccccaatc<br>acactagcaacatttcaagtgcttgagagccatgcatgattagtggttaccctattgaataggtc<br>agaagtagaatcttttcatcatcacagaaagttctattggacagtgctcttctagatcatcataag<br>actacagagcacttttcaaagctcatgcatgttcatcatgttagtgtcgtattttgagctggggtttt<br>gagactccccttagagatagagaaacagacccaagaaatgtgctcaattgcaatgggccaca<br>tacctagatctccagatgtcatttcccctctcttattttaagttatgttaagattactaaaacaataaa<br>agctcctaaaaaatcaaactgtattctggtgttctcttctacacagtgggagggcgagcagtag<br>gagagattggcccatttggtgctggccatttgaggaatgcaagcccagcactagtctcataatc<br>tctaggaatctgtagagagaggaattgaagtaaatttcagcattggctcattcagtcattcggcg<br>acattcatcaggtacctgcaatgtgttaggggatcttatgagtaggcagcgtgcgtgatccttgc<br>tcccctggagctttctaacattctagcaggcagaccacacataaatttgcaatactgtttctgata<br>aaaacgtgctgtaaaggaaataaagcagagaactatcatggaaaaaaaaaaaaaaaaaa | |
| SQLE | NM_003129.3 | gtctgggccgagcccgcccagctggctgagacgcgtggagcctggcggcgagtgggggc<br>gtgcgacggttactctggttactggggccgcgccgcgctggcgagagccgccgcccgcga<br>gggatgctggtgaggaagccgtcgggagccgccgccgccatctgagggaggtaccctgga<br>aaccaccttttatcggtggggaagtgcagtcgcggtgggcggctctgggggccagcgaaac<br>gggaggcctctaaatctttaggttggggctgcattgccctggagccgcactcttgagtccgag<br>gccatcttttgttggagaaggcgtcggcgttggcgttttcccgaggttgggctgtacagtgtctc<br>cgtccgcggaaaaagaagcctctgaacccgcgccggcccgcagcccccgtgccttccggc<br>cgctgctcgccgtcgccagaggctaggccacgtttcccccagtgccgaggtgtttctgtgacc<br>ctccctccactcccattcccttctgaaagggcacctgctcttggtgagaaaagaaattatagcac<br>gaagagccagtatcagaagagtatccatcacccgcagcaaccgctcagggaacaccatcaa<br>aaaagaaaaaaagggaatatctggatttcctgggcgaggaggagcgagtctgctcgggagc<br>tgttccagcaggcgatttttaaatactgctttctacgccctatacaacttggcttcacatacttttac<br>actaactttatatgatttttaaaaactggtctgatcggacttctcgtcctgggacactgtttactgga<br>gtctggccggctctccgtgctcctcttggtacctcattttggggagaaccttaaacccactcgag<br>cagataatctccgccttgaccggtgccaccaaagaagccttggaaccatgtggacttttctgg<br>gcattgccactttcacctatttttataagaagttcggggacttcatcactttggccaacagggag<br>gtcctgttgtgcgtgctggtgttcctctcgctgggcctggtgctctcctaccgctgtcgccaccg<br>aaacgggggtctcctcgggcgccagcagagcggctcccagttcgccctcttctcggatattct<br>ctcaggcctgcctttcattggcttcttctgggccaaatccccccctgaatcagaaaataaggag<br>cagctcgaggccaggaggcgcagaaaaggaaccaatatttcagaaacaagcttaataggaa<br>cagctgcctgtacatcaacatcttctcagaatgacccagaagttatcatcgtgggagctggcgt<br>gcttggctctgctttggcagctgtgctttccagagatggaagaaaggtgacagtcattgagaga<br>gacttaaaagagcctgacagaatagttggagaattcctgcagccgggtggttatcatgttctca<br>aagaccttggtcttggagatacagtggaaggtcttgatgcccaggttgtaaatggttacatgatt<br>catgatcaggaaagcaaatcagaggttcagattccttaccctctgtcagaaaacaatcaagtgc<br>agagtggaagagctttccatcacggaagattcatcatgagtctccggaaagcagctatggca | 30 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | gagcccaatgcaaagtttattgaaggtgttgtgttacagttattagaggaagatgatgttgtgatg<br>ggagttcagtacaaggataaagagactggagatatcaaggaactccatgctccactgactgtt<br>gttgcagatgggcttttctccaagttcaggaaaagcctggtctccaataaagtttctgtatcatct<br>cattttgttggctttcttatgaagaatgcaccacagtttaaagcaaatcatgctgaacttattttagc<br>taacccgagtccagttctcatctaccagatttcatccagtgaaactcgagtacttgttgacattag<br>aggagaaatgccaaggaatttaagagaatacatggttgaaaaaatttacccacaaatacctgat<br>cacctgaaagaaccattcttagaagccactgacaattctcatctgaggtccatgccagcaagct<br>tccttcctccttcatcagtgaagaaacgaggtgttcttcttttgggagacgcatataatatgaggc<br>atccacttactggtggaggaatgactgttgcttttaaagatataaaactatggagaaaactgcta<br>aagggtatccctgacctttatgatgatgcagctatttcgaggccaaaaaatcattttactgggca<br>agaaaaacatctcattcctttgtcgtgaatatccttgctcaggctctttatgaattattttctgccac<br>agatgattccctgcatcaactaagaaaagcctgttttctttatttcaaacttggtggcgaatgtgtt<br>gcgggtcctgttgggctgctttctgtattgtctcctaaccctctagttttaattggacacttctttgct<br>gttgcaatctatgccgtgtatttttgctttaagtcagaaccttggattacaaaacctcgagcccttc<br>tcagtagtggtgctgtattgtacaaagcgtgttctgtaatatttcctctaatttactcagaaatgaa<br>gtatatggttcattaagcttaaaggggaaccatttgtgaatgaatatttggaacttaccaagtcct<br>aagagacttttggaagaggatatatatagcatagtaccataccacttataaagtggaaactcttg<br>gaccaagatttggattaatttgtttttgaagtttttttgtatataaatatgtaaatacatgctttaatttgc<br>aatttaaaatgaaggggttaaataagttagacatttaaaagaaatgattgttaccataaattagtg<br>ctaatgctgaggagaactacagtttttcttttgaatttagtatttgagatgagttgttgggacatgc<br>aaataaaatgaagaatgaa | |
| STRIP1 | NM_001270768.1 | attttacccagcccctgttcaagatggagttgctgtggttcacacatctctgacaaaaatacagg<br>gctattcggagtcaccagacctggagtttgagtatgctgacacagacaagtgggctgcagag<br>ctctcggagctttacagctacacggaagggccagaattcctgatgaatcgaaaatgctttgag<br>gaggacttccggatccatgtgacagacaagaagtggactgagctggataccaaccagcacc<br>ggacccatgccatgaggctcctggatggcttggaagtcactgccagggagaagagactcaa<br>ggtggctcgagcaattctctatgttgctcaaggcacgtttggggagtgcagctcggaggcaga<br>ggtgcagtcctggatgcgctacaacatctttctcctcctggaggtgggcacgttcaatgctttgg<br>tggagcttctgaacatggaaatagacaacagtgccgcctgcagcagtgctgtgaggaagcct<br>gccatctccctggctgacagcacagacctcagggtcctgctcaacatcatgtacctgatagtg<br>gagaccgttcatcaggagtgtgagggtgacaaggctgagtggaggaccatgcggcagacct<br>tcagagccgagctgggctccccgctgtacaacaatgagccatttgccatcatgctgtttgggat<br>ggtgaccaaattttgcagtggtcacgcccctcactttcccatgaagaaagttctcttgctgctctg<br>gaagacagtattgtgcacgctaggcggctttgaggagctgcagagcatgaaggctgagaag<br>cgcagcatcctgggcctcccccgcttcctgaggacagcatcaaagtgattcgcaacatgag<br>agcagcctctccaccagcatctgcttcagacttgattgagcagcagcagaaacggggccgcc<br>gagagcacaaggctctgataaagcaggacaacctagatgccttcaacgagcgggatcccta<br>caaggctgatgactctcgagaagaggaagaggagaatgatgatgacaacagtctggaggg<br>ggagacgtttcccctggaacgggatgaagtgatgcctcccccgctacagcacccacagactg<br>acaggctgacttgccccaaagggctcccgtgggctcccaaggtcagagagaaagacattga<br>gatgttccttgagtccagccgcagcaaatttataggttacactctaggcagtgacacgaacaca<br>gtggtggggctgcccaggccaatccacgaaagcatcaagactctgaaacagcacaagtaca<br>cgtcgattgcagaggtccaggcacagatggaggaggaatacctccgctcccctctctcaggg<br>ggagaagaagaagttgagcaagtccctgcagaaaccctctaccaaggcttgctccccagcct<br>gcctcagtatatgattgccctcctgaagatcctgttggctgcagcacccacctcaaaagccaaa<br>acagactcaatcaacatcctagcggacgtcttgcctgaggagatgcccaccacagtgttgcag<br>agcatgaagctgggggtggatgtaaaccgccacaaagaggtcattgttaaggccatttctgct<br>gtcctgctgctgctgctcaagcactttaagttgaaccatgtctaccagtttgaatacatggccca<br>gcacctggtgtttgccaactgcattcctttgatcctaaagttcttcaatcaaaacatcatgtcctac<br>atcactgccaagaacagcatttctgtcctggattaccctcactgcgtggtgcatgagctgccag<br>agctgacggcggagagtttggaagcaggtgacagtaaccaattttgctggaggaacctctttt<br>cttgtatcaatctgcttcggatcttgaacaagctgacaaagtggaagcattcaaggacaatgat<br>gctggtggtgttcaagtcagcccccatcttgaagcgggccctaaaggtgaaacaagccatga<br>tgcagctctatgtgctgaagctgctcaaggtacagaccaaatacttggggcggcagtggcga<br>aagagcaacatgaagaccatgtctgccatctaccagaaggtgcggcatcggctgaacgacg<br>actgggcatacggcaatgatcttgatgcccggccttgggacttccaggcagaggagtgtgcc<br>cttcgtgccaacattgaacgcttcaacgcccggcgctatgaccgggcccacagcaaccctga<br>cttcctgccagtggacaactgcctgcagagtgtcctgggccaacgggtggacctccctgagg<br>actttcagatgaactatgacctctggttagaaagggaggtcttctccaagcccatttcctgggaa<br>gagctgctgcagtgaggctgttggttaggggactgaaatggagagaaaagatgatctgaagg<br>tacctgtgggactgtcctagttcattgctgcagtgctcccatcccccaccaggtggcagcaca<br>gccccactgtgtcttccgcagtctgtcctgggcttgggtgagcccagcttgacctccccttggtt<br>cccagggtcctgctccgaagcagtcatctctgcctgagatccattcttcctttacttcccccacc<br>ctcctctcttggatatggttggttttggctcatttcacaatcagcccaaggctgggaaagctgga<br>atgggatgggaacccctccgccgtgcatctgaatttcaggggtcatgctgatgcctctcgaga<br>catacaaatccttgctttgtcagcttgcaaaggaggagagtttaggattagggccagggccag<br>aaagtcggtatcttggttgtgctctggggtgggggtggggtgtttctgatgttattccagcctcct<br>gctacattatatccagaagtaattgcggaggctccttcagctgcctcagcactttgattttggaca<br>gggacaaggtaggaagagaagcttcccttaaccagaggggccatttttccttttggctttcgag<br>ggcctgtaaatatctatatataattctgtgtgtattctgtgtcatgttggggtttttaatgtgattgtgt<br>attctgtttacattaaaaagaagcaaaaataaaaaaaaaaaaa | 31 |

TABLE 1-continued

Prostate Cancer Biomarker/Housekeeper Sequence Information

| Gene Name | RefSeq Accession | Sequence | SEQ ID NO: |
|---|---|---|---|
| STX12 | NM_177424.2 | gcacgcagccttagctccttccccgcccttgctcttcccagtttctccgtcagcctgcgggtccc<br>ggctggcggctgcttccggtaggagagcggtgtagagcgagcaggtctcagctcctcgtcat<br>gtcatacggtcccttagacatgtaccggaacccggggccctcggggccccagctccgggac<br>ttcagcagcatcatccagacgtgcagcggcaacatccagcggatcagccaagccactgctca<br>gataaagaatttgatgagccagctaggaactaagcaggactcaagcaagctacaggaaaatc<br>tgcaacagttacaacactccacaaatcagctcgccaaggaaacaaatgaattgctgaaagaat<br>tagggtccttgccccttcccttatctacttcagaacagcgccagcagagacttcagaaggaac<br>gcctcatgaatgacttctctgcagccttaaacaatttccaggctgtgcagagaagggtatctga<br>aaaggaaaaggagagtattgccagagcaagagctggatctcgtctttctgcagaagagagg<br>caaagagaggagcagctggtctcatttgacagccatgaggagtggaaccagatgcagagcc<br>aggaggatgaggtggccatcactgagcaggatttggaacttattaaagaaagagaaacggc<br>aattcggcagctggaggctgacattttggatgtcaatcagatatttaaagatttggccatgatgat<br>ccatgaccagggtgatctgattgatagcatagaagccaatgtggaaagctcagaggtgcacg<br>tcgaaagagccactgaacagttacagcgagctgcttactatcagaaaaaatctcgcaagaag<br>atgtgtatcctggtgcttgtcctgtcagtgattattctaatcttgggacttattatctggctagtttata<br>aaacgaagtgattgcctccgatcgttctcccgctgagctgttttcaagggcaagtgcttgttgaa<br>gtcttgccagaacaaactgatcacaagaagacagcatatatcagaacgtcctgtaatcatttagt<br>tagaaactaactactaactagtctttggaattcgtgacctatggagacagtaattatcaatttattg<br>attctattgatttctcaaattaggaattaacttatgtggattttgcttcctcttgtattctgattgccctt<br>catcccaagtgtttactgaaaattccattctagatattcttgttttgacaaatgacactacagtctcg<br>taatattgtcttttatgtatatacaaaatttaccttttttactagcatctgagatagagttactttctggta<br>cccagtatattggagtctgtcagaaactctataataggccaccagtttttattatttaacatttttattt<br>gaatttctaagaagcctattctctatctattttgaaagattttggcactatatttaattggaaggtaaa<br>atattgtacatgtgatccagagtaaatgagaagtctctatctgagctggtcagttactggagtac<br>atgttactaatctgggtttaaagtttacttcattatctgctagtgtcatccacagcagttcatcctcat<br>ccacactaagccatcctgttagcttttaaaggaagttaatttaattaacattaatatactctatggg<br>ctccctctcccacctgtctgcatagaaaggcagaattagacatagcatgctttggaaaagcaaa<br>taggaattgttgggaatgatttaatcttgttgttgttgttgttgttcacttgtggttctacattcctg<br>gtgaatgatgaatgttgctgtcaaagggctgccccctaccttataagggttgctgggcatttgaa<br>ggcaggaagattttaaagatagattgaggttggtttaaaattattcctgtaaaccaacaataaag<br>caaagaagaggttcatttttgtaaataacactggtttcaaatagtgatgttagacttaacctaattt<br>ataaacaagagattaatatctccatgcatagttttagacaaaaaagatgtttcaataaaattact<br>gtcttgtaatataaatgttgtccacttcccttttccacaggcctagaacagttaaagggaacataa<br>tttgtttaggctcccacataaatgtgaatctggccaacaactttggttcatcctttagtgaattaga<br>ggatttggctaccctgagtatatttatattcatttcttctgttctccttctgttattatacttaatcttcta<br>aactaaactaatgtgaacagtagggaagcaagggcccaaatgcataagtttctttgcactgttg<br>cacttacttaatacaaataaatgtttttaaagcttttgtagtatgtttttatgagttaacatcctaatgt<br>ggtaggtattaggtaatgtgctgtcatgagaaaaattgagacttccaagaaaactggacacca<br>ggtgagggttggtttggagacggaataggtgtagctgcctttccttgaaaaacagtgtgtagag<br>atggctgagtgcaatggctcacacttgtaatcccaacactttggaaggctgaggcgggaggat<br>cagtatatcggtacgtctgagcccaagagttcaagatcagcctgggcagtatagcaagaccc<br>catctccatttttttttaatgatttttaattaaaaaaaagaacaacaggatagagctgttggggtg<br>gcacagtggcccaaagagcagcttcagagataattccttggttctatgatccctgtttaactcca<br>aattacagtcggacttggatacatcatttgtaacattgtaggaaagaaaaaagtcttggttgtga<br>aaaacgatttgcatttgggtaaaataaagtgaccatgcttttgttctgtaatactgtgtgacctgtg<br>gttgttgtaatggtgatcatggagagcaaatatgaacttggcctggattttaaatggcctagaatt<br>tgtggtagttgccaaagaggttctcctaggtggtcttaataaacctattcacagaattctccttaa<br>aaaaaaaaaaaaaaaaaa | 32 |
| TMPRSS2_1 | DQ204772.1 | taggcgcgagctaagcaggaggcggaggcggaggcggagggcgaggggcggggagc<br>gccgcctggagcgcggcaggaagccttatcagttgtgagtgaggaccagtcgttgtttgagt<br>gtgcctacggaacgccacacctggctaagacagagatgaccgcgtcctcctccagcgactat<br>ggacagacttccaagatgagcccacgcgtccctcagcaggattggctgtctcaacccccagc<br>cagggtcaccatcaaaatggaatgtaaccctagccaggtgaatggctcaag | 33 |
| TMPRSS2_2 | OM_TMPRSS2-ERG_T2E4__COSF28.0 | gggaacaaaagctggagctccaccgcggtggcggccgctctagccctcaaggaactctcct<br>gatgaatgcagtgtggccaaaggcgggaagatggtgggcagcccagacaccgttgggatg<br>aactacggcagctacatggaggagaagcacatgccacccccaaacatgaccacgaacgag<br>cgcagagttatcgtgccagcagatcctacgctatggagtacagaccatgtgcggcagtggct<br>ggagtgggcggtgaaagaatatggccttccagacgtcaacatcttgttattccagaacatcgat<br>gggaaggaactgtgcaagatgaccaaggacgacttccagaggctcacccccagctacaac<br>gccgacatccttctctcacatctccactacctcagagagactcctcttccacatttgacttcagat<br>gatgttgataaagccttacaaaactctccacggttaatgcatgctagaaacacaggggtgca<br>gcttttattttcccaaatacttcagtatatcctgaagctacgcaaagaattacaactaggccagatt<br>taccatatgagcccccaggagatcagcctggaccggtcacggccaccccacgccccagtc<br>gaaagctgctcaaccatctccttccacagtgcccaaaactgaagaccagcgtcctcagttaga<br>accttatcagattcttggaccaacaagtagccgccttgcaaatccaggcagtggccagatcca<br>gctttggcagttcctcctggagctcctgtcggacagctccaactccagctgcatcacctggga<br>aggcaccaacggggagttcaagatgacggatcccgacgaggtggcccggcgctggggag<br>agcggaagagcaaacccaacatgaactacgataagctcagccgcgccctccgttactactat<br>gacaagaacatcatgaccaaggtccatgggaagcgctacgcctacaagttcgacttccacgg<br>gatcgcccaggccctccagccccacccccggagtcatctctgtacaagtacccctcagacc<br>tcccgtacatgggctcctatcacgcccacccacagaagatgaactttgtggcgccccaccctc | 34 |

TABLE 1-continued

Prostate Cancer Biomarker/Housekeeper Sequence Information

| Gene Name | RefSeq Accession | Sequence | SEQ ID NO: |
|---|---|---|---|
| | | cagccctccccgtgacatcttccagtttttttgctgccccaaacccatactggaattcaccaactg | |
| | | ggggtatataccccaacactaggctccccaccagccatatgccttctcatctgggcacttacta | |
| | | ctaaagacctggcggaggcttttcccatcagcgtgcattcaccagcccatcgccacaaactct | |
| | | atcggagaacatgaatcaaaagtgcctcaagaggaatgaaaaaagctttactggggctgggg | |
| | | aaggaagccggggaagagatccaaagactcttgggagggagttactgaagtcttactgaagt | |
| | | cttactacagaaatgaggaggatgctaaaaatgtcacgaatatggacatatcatctgtggactg | |
| | | accttgtaaaagacagtgtatgtagaagcatgaagtcttaaggacaaagtgccaaagaaagtg | |
| | | gtcttaagaaatgtataaactttagagtagagtttgaatcccactaatgcaaactgggatgaaac | |
| | | taaagcaatagaaacaacacagttttgacctaacataccgtttataatgccattttaaggaaaact | |
| | | acctgtatttaaaaatagaaacatatcaaaaacaagagaaaagacacgagagagactgtggc | |
| | | ccatcaacagacgttgatatgcaactgcatggcatgtgctgttttggttgaaatcaaatacattcc | |
| | | gtttgatggacagctgtcagctttctcaaactgtgaagatgacccaaagtttccaactcctttaca | |
| | | gtattaccgggactatgaactaaaaggtgggactgaggatgtgtatagagtgagcgtgtgatt | |
| | | gtagacagaggggtgaagaaggaggaggaagaggcagagaaggaggagaccagggct | |
| | | gggaaagaaacttctcaagcaatgaagactggactcaggacatttggggactgtgtacaatg | |
| | | agttatggagactcgagggttcatgcagtcagtgttataccaaacccagtgttaggagaaagg | |
| | | acacagcgtaatggagaaaggggaagtagtagaattcagaaacaaaaatgcgcatctctttct | |
| | | ttgtttgtcaaatgaaaattttaactggaattgtctgatatttaagagaaacattcaggacctcatc | |
| | | attatgtgggggctttgttctccacagggtcaggtaagagatggccttcttggctgccacaatca | |
| | | gaaatcacgcaggcattttgggtaggcggcctccagttttcctttgagtcgcgaacgctgtgcg | |
| | | tttgtcagaatgaagtatacaagtcaatgtttttcccccctttttatataataattatataacttatgcatt | |
| | | tatacactacgagttgatctcggccagccaaagacacacgacaaaagagacaatcgatataat | |
| | | gtggccttgaattttaactctgtatgcttaatgtttacaatatgaagttattagttcttagaatgcaga | |
| | | atgtatgtaataaaataagcttggcctagcatggcaaatcagatttatacaggagtctgcatttgc | |
| | | acttttttagtgactaaagttgcttaatgaaaacatgtgctgaatgttgtggattttgtgttataattt | |
| | | actttgtccaggaacttgtgcaagggagagccaaggaaataggatgtttggcacccaaatgg | |
| | | cgtcagcctctccaggtccttcttgcctcccctcctgtcttttatttctagccccttttggaacagaa | |
| | | ggaccccgggtttcacattggagcctccatatttatgcctggaatggaaagaggcctatgaag | |
| | | ctggggttgtcattgagaaattctagttcagcacctggtcacaaatcacccttaattcctgctatg | |
| | | attaaaatacatttgttgaacagtgaacaagctaccactcgtaaggcaaactgtattattactggc | |
| | | gggcggatcccccgggctgcaggaattcgatatcaagcttatcgataccgtcga | |
| TRIM29 | NM_012101.3 | ctcctcacaggtgtgtctctagtcctcgtggttgcctgccccactccctgccgagacgcctgcc | 35 |
| | | agaaaggtcacctatcctgaaccccagcaagcctgaaacagctcagccaagcaccctgcga | |
| | | tggaagctgcagatgcctccaggagcaacgggtcgagcccagaagccagggatgcccgg | |
| | | agcccgtcggccccagtggcagcctggagaatggcaccaaggctgacggcaaggatgc | |
| | | caagaccaccaacgggcacggcggggaggcagctgagggcaagagcctgggcagcgcc | |
| | | ctgaagccaggggaaggtaggagcgccctgttcgcgggcaatgagtggcggcgacccatc | |
| | | atccagtttgtcgagtccggggacgacaagaactccaactacttcagcatggactctatggaa | |
| | | ggcaagaggtcgccgtacgcagggctccagctgggggctgccaagaagccacccgttacc | |
| | | tttgccgaaaagggcgagctgcgcaagtccattttctcggagtcccggaagcccacggtgtc | |
| | | catcatggagcccggggagacccggcggaacagctaccccgggccgacacgggcctttt | |
| | | ttcacggtccaagtccggctccgaggaggtgctgtgcgactcctgcatcggcaacaagcaga | |
| | | aggcggtcaagtcctgcctggtgtgccaggcctccttctgcgagctgcatctcaagccccacc | |
| | | tggagggcgccgccttccgagaccaccagctgctcgagcccatccgggactttgaggcccg | |
| | | caagtgtcccgtgcatggcaagacgatggagctcttctgccagaccgaccagacctgcatct | |
| | | gctacctttgcatgttccaggagcacaagaatcatagcaccgtgacagtggaggaggccaag | |
| | | gccgagaaggagacggagctgtcattgcaaaaggagcagctgcagctcaagatcattgaga | |
| | | ttgaggatgaagctgagaagtggcagaaggagaaggaccgcatcaagagcttcaccaccaa | |
| | | tgagaaggccatcctggagcagaacttccgggacctggtgcgggacctggagaagcaaaa | |
| | | ggaggaagtgagggctgcgctggagcagcgggagcaggatgctgtggaccaagtgaagg | |
| | | tgatcatggatgctctggatgagagagccaaggtgctgcatgaggacaagcagacccggga | |
| | | gcagctgcatagcatcagcgactctgtgttgtttctgcaggaatttggtgcattgatgagcaatt | |
| | | actctctcccccaccccctgcccacctatcatgtcctgctggaggggggagggcctgggacag | |
| | | tcactaggcaacttcaaggacgacctgctcaatgtatgcatgcgccacgttgagaagatgtgc | |
| | | aaggcggacctgagccgtaacttcattgagaggaaccacatggagaacggtggtgaccatc | |
| | | gctatgtgaacaactacacgaacagcttcgggggtgagtggagtgcaccggacaccatgaa | |
| | | gagatactccatgtacctgacacccaaaggtggggtccggacatcataccagccctcgtctcc | |
| | | tggccgcttcaccaaggagaccacccagaagaatttcaacaatctctatggcaccaaaggtaa | |
| | | ctacacctcccgggtctgggagtactcctccagcattcagaactctgacaatgacctgcccgtc | |
| | | gtccaaggcagctcctccttctccctgaaaggctatccctccctcatgcggagccaaagcccc | |
| | | aaggcccagccccagacttggaaatctggcaagcagactatgctgtctcactaccggccattc | |
| | | tacgtcaacaaaggcaacgggattgggtccaacgaagccccatgagctcctggcggaagga | |
| | | acgaggcgccacacccctgctcttcctcctgaccctgctgctcttgccttctaagctactgtgctt | |
| | | gtctgggtgggagggagcctggtcctgcacctgccctctgcagccctctgccagcctcttgg | |
| | | gggcagttccggcctctccgacttccccactggccacactccattcagactcctttcctgccttg | |
| | | tgacctcagatggtcaccatcattcctgtgctcagaggccaacccatcacaggggtgagatag | |
| | | gttggggcctgccctaacccgccagcctcctcctctcggctggatctgggggctagcagtg | |
| | | agtacccgcatggtatcagcctgcctctcccgcccacgccctgctgtctccaggcctatagac | |
| | | gtttctctccaaggccctatcccccaatgttgtcagcagatgcctggacagcacagccacccat | |
| | | ctcccattcacatggcccacctcctgcttcccagaggactggccctacgtgctctctctcgtcct | |
| | | acctatcaatgcccagcatggcagaacctgcagcccttggccactgcagatggaaacctctc | |
| | | agtgtcttgacatcaccctacccaggcggtgggtctccaccacagccactttgagtctgtggtc | |
| | | cctggagggtggcttctcctgactggcaggatgaccttagccaagatattcctctgttccctctg | |

TABLE 1-continued

Prostate Cancer Biomarker/Housekeeper Sequence Information

| Gene Name | RefSeq Accession | Sequence | SEQ ID NO: |
|---|---|---|---|
| | | ctgagataaagaattcccttaacatgatataatccacccatgcaaatagctactggcccagcta<br>ccatttaccatttgcctacagaatttcattcagtctacactttggcattctctctggcgatggagtgt<br>ggctgggctgaccgcaaaaggtgccttacacactgcccccaccctcagccgttgccccatca<br>gaggctgcctcctccttctgattacccccatgttgcatatcagggtgctcaaggattggagag<br>gagacaaaaccaggagcagcacagtggggacatctcccgtctcaacagccccaggcctatg<br>ggggctctggaaggatgggccagcttgcaggggttggggagggagacatccagcttgggc<br>tttcccctttggaataaaccattggtctgtcaaaaaaaaaaaaaaaaaaa | |
| UNC45A | NM_001039675.1 | acttaacaaccgaagtaacccgcaatgcggaagggcgaggggattgcgagtcaccgagttt<br>cccgcgcggcttgagtcacggcctagaaagagagatgttggggttcccaggaccaggaca<br>gaggtggtagtgaactctcatgggcatccagagaaggtcaggccccttgctgacaggcctat<br>ctgtggggctactgctgctcttcagctgggtgacccttgtccagccaacctctctctcagctctg<br>gtccaccaccctcacttgtgccagaccacccgggatgtccatggccgtcactaccctggtttct<br>tttgccctcgtctgtctgattctccagaggaagcctactgctgccacctgcaggctgcagggg<br>gctcctgctgcacccgggctgaatttgaggccctgtaccaagtcaatctgtccgctcttccgcc<br>cccgcccatcctcaggggcccaggcccgctcctagtgctgggcctctacaacctactggttgt<br>gaccctgatgaccgtagacctcgtgcacttctgctgcggtcggggccggagtctgggctgga<br>gccaccgcaggcctccctctgggtcctccgccgcgagctccctgcaggtctctgcggggac<br>agcttaggtgcgcccggagcttgcctgcacctgcgatccagagccaagcgccccgcccctg<br>cccgggcgcgctccctccttagccctgcccctctctgaccccacctccgacgcaagagtggg<br>gcggggcagctgccggtggcgtcccgaacccagactcgccccgccccagagactgcgcct<br>gcgcgggcacgagacaacctctccgcgatgactgccagctcagtggagcagctgcggaag<br>gagggcaatgagctgttcaaatgtggagactacgggggcgccctggcggcctacactcagg<br>ccctgggtctggacgcgacgccccaggaccaggccgttctgcaccggaaccgggccgcct<br>gccacctcaagctggaagattacgacaaagcagaaacagaggcatccaaagccattgaaaa<br>ggatggtggggatgtcaaagcactctaccggcggagccaagccctagagaagctgggccg<br>cctggaccaggctgtccttgacctgcagagatgtgtgagcttggagcccaagaacaaagtttt<br>ccaggaggccttgcggaacatcgggggccagattcaggagaaggtgcgatacatgtcctcg<br>acggatgccaaagtggaacagatgtttcagatactgttggacccagaagagaagggcactga<br>gaaaaagcaaaaggcttctcagaacctggtggtgctggccagggaggatgctggagcgga<br>gaagatcttccggagtaatggggttcagctcttgcaacgtttactggacatgggagagactga<br>cctcatgctggcggctctgcgtacgctggttggcatttgctctgagcatcagtcacggacagtg<br>gcaaccctgagcatactgggaactcggcgagtagtctccatcctgggcgtggaaagccagg<br>ctgtgtccctggctgcctgccacctgctgcaggttatgtttgatgccctcaaggaaggtgtcaa<br>aaaaggcttccgaggcaaagaaggtgccatcattgtggatcctgcccgggagctgaaggtc<br>ctcatcagtaacctcttagatctgctgacagaggtgggggtctctggccaaggccgagacaat<br>gccctgaccctcctgattaaagcggtgccccggaagtctctcaaggaccccaacaacagcct<br>caccctctgggtcatcgaccaaggtctgaaaaagattttggaagtgggggctctctacagga<br>ccctcctggggagctcgcagtgaccgcaaacagccgcatgagcgcctctattctcctcagca<br>agctctttgatgacctcaagtgtgatgcggagagggagaatttccacagactttgtgaaaacta<br>catcaagagctggtttgagggccaagggctggccgggaagctacgggccatccagacggt<br>gtcctgcctcctgcagggcccatgtgacgctggcaaccgggccttggagctgagcggtgtca<br>tggagagtgtgattgctctgtgtgcctctgagcaggaggaggagcagctggtggccgtggag<br>gctctgatccatgcagccggcaaggctaagcgggcctcattcatcactgccaatggtgtctcg<br>ctgctgaaggacctatataagtgcagcgagaaggacagcatccgcatccgggcgctagtgg<br>gactctgtaagctcggttcggctggagggactgacttcagcatgaagcagtttgctgaaggct<br>ccactctcaaactggctaagcagtgtcgaaagtggctgtgcaatgaccagatcgacgcaggc<br>actcggcgctgggcagtggagggcctggcttacctgacctttgatgccgacgtgaaggaag<br>agtttgtggaggatgcggctgctctgaaagctctgttccagctcagcaggttggaggagaggt<br>cagtgctctttgcggtggcctcagcgctggtgaactgcaccaacagctatgactacgaggag<br>cccgaccccaagatggtggagctggccaagtatgccaagcagcatgtgcccgagcagcac<br>cccaaggacaagccaagcttcgtgcgggctcgggtgaagaagctgctggcagcgggtgtg<br>gtgtcggccatggtgtgcatggtgaagacggagagccctgtgctgaccagttcctgcagaga<br>gctgctctccagggtcttcttggctttagtggaagaggtagaggaccgaggcactgtggttgc<br>ccagggaggcggcagggcgctgatcccgctggccctggaaggcacggacgtggggcag<br>acaaaggcagcccaggcccttgccaagctcaccatcacctccaacccggagatgaccttccc<br>tggcgagcggatctatgaggtggtccggcccctcgtctccctgttgcacctcaactgctcagg<br>cctgcagaacttcgaggcgctcatggccctaacaaacctggctgggatcagcgagaggctc<br>cggcagaagatcctgaaggagaaggctgtgcccatgatagaaggctacatgtttgaggagc<br>atgagatgatccgccgggcagccacggagtgcatgtgtaacttggccatgagcaaggaggt<br>gcaggacctcttcgaagcccagggcaatgaccgactgaagctgctggtgctgtacagtgga<br>gaggatgatgagctgctacagcgggcagctgccgggggcttggccatgcttacctccatgc<br>ggcccacgctctgcagccgcattccccaagtgaccacacactggctggagatcctgcaggc<br>cctgcttctgagctccaaccaggagctgcagcaccggggtgctgtggtggtgctgaacatgg<br>tggaggcctcgagggagattgccagcaccctgatggagagtgagatgatggagatcttgtca<br>gtgctagctaagggtgaccacagccctgtcacaagggctgctgcagcctgcctggacaaag<br>cagtggaatatgggcttatccaacccaaccaagatggagagtgaggggggttgtccctgggcc<br>caaggctcatgcacacgctacctattgtggcacggagagtaaggacggaagcagctttggct<br>ggtggtggctggcatgcccaatactcttgcccatcctcgcttgctgccctaggatgtcctctgtt<br>ctgagtcagcggccacgttcagtcacacagccctgcttggccagcactgcctgcagcctcact<br>cagaggggccctttttctgtactactgtagtcagctgggaatggggaaggtgcatcccaacac<br>agcctgtggatcctggggcatctggaagggcgcacacatcagcagcctcaccagctgtgag<br>cctgctatcaggcctgcccctccaataaaagtgtgtagaactccaaaaaaaaaaaaaaaaaaa<br>aaaaaaaaaaaaaaa | 36 |

TABLE 1-continued

| Prostate Cancer Biomarker/Housekeeper Sequence Information | | | |
|---|---|---|---|
| Gene Name | RefSeq Accession | Sequence | SEQ ID NO: |
| XPC | NM_004628.4 | cgaaggggcgtggccaagcgcaccgcctcggggcggggccggcgttctagcgcatcgcg<br>gccgggtgcgtcactcgcgaagtggaatttgcccagacaagcaacatggctcggaaacgcg<br>cggccggcggggagccgcggggacgcgaactgcgcagccagaaatccaaggccaagag<br>caaggcccggcgtgaggaggaggaggaggatgcctttgaagatgagaaacccccaaaga<br>agagccttctctccaaagtttcacaaggaaagaggaaaagaggctgcagtcatcctggggt<br>tcagcagatggtccagcaaaaaagaaagtggccaaggtgactgttaaatctgaaaacctcaa<br>ggttataaaggatgaagccctcagcgatggggatgacctcagggactttccaagtgacctca<br>agaaggcacaccatctgaagagaggggctaccatgaatgaagacagcaatgaagaagagg<br>aagaaagtgaaaatgattgggaagaggttgaagaacttagtgagcctgtgctgggtgacgtg<br>agagaaagtacagccttctctcgatctcttctgcctgtgaagccagtggagatagagattgaaa<br>cgccagagcaggcgaagacaagagaaagaagtgaaaagataaaactggagtttgagacat<br>atcttcggagggcgatgaaacgtttcaataaaggggtccatgaggacacacacaaggttcac<br>cttctctgcctgctagcaaatggcttctatcgaaataacatctgcagccagccagatctgcatgc<br>tattggcctgtccatcatcccagcccgctttaccagagtgctgcctcgagatgtggacacctac<br>tacctctcaaacctggtgaagtggttcattggaacatttacagttaatgcagaactttcagccagt<br>gaacaagataacctgcagactacattggaaaggagatttgctatttactctgctcgagatgatg<br>aggaattggtccatatattcttactgattctccgggctctgcagctcttgacccggctggtattgt<br>ctctacagccaattcctctgaagtcagcaacagcaaagggaaagaaaccttccaaggaaaga<br>ttgactgcggatccaggaggctcctcagaaacttccagccaagttctagaaaaccacaccaaa<br>ccaaagaccagcaaaggaaccaaacaagaggaaacctttgctaagggcacctgcaggcca<br>agtgccaaagggaagaggaacaagggaggcagaaagaaacggagcaagccctcctccag<br>cgaggaagatgagggcccaggagacaagcaggagaaggcaacccagcgacgtccgcat<br>ggccgggagcggcgggtggcctccagggtgtcttataaagaggagagtgggagtgatgag<br>gctggcagcggctctgattttgagctctccagtggagaagcctctgatccctctgatgaggatt<br>ccgaacctggccctccaaagcagaggaaagccccgctcctcagaggacaaaggctgggt<br>ccaagagtgcctccaggacccatcgtgggagccatcgtaaggacccaagcttgccagcggc<br>atcctcaagctcttcaagcagtaaaagaggcaagaaaatgtgcagcgatggtgagaaggca<br>gaaaaaagaagcatagctggtatagaccagtggctagaggtgttctgtgagcaggaggaaa<br>agtgggtatgtgtagactgtgtgcacggtgtggtgggccagcctctgacctgttacaagtacg<br>ccaccaagcccatgacctatgtggtgggcattgacagtgacggctgggtccgagatgtcaca<br>cagaggtacgacccagtctggatgacagtgacccgcaagtgccgggttgatgctgagtggt<br>gggccgagaccttgagaccataccagagcccatttatggacagggagaagaaagaagactt<br>ggagtttcaggcaaaacacatggaccagcctttgcccactgccattggcttatataagaaccac<br>cctctgtatgccctgaagcggcatctcctgaaatatgaggccatctatcccgagacagctgcc<br>atccttgggtattgtcgtggagaagcggtctactccagggattgtgtgcacactctgcattccag<br>ggacacgtggctgaagaaagcaagagtggtgaggcttggagaagtaccctacaagatggtg<br>aaaggcttttctaaccgtgctcggaaagcccgacttgctgagccccagctgcgggaagaaaa<br>tgacctgggcctgtttggctactggcagacagaggagtatcagcccccagtggccgtggacg<br>ggaaggtgccccggaacgagtttgggaatgtgtacctcttcctgcccagcatgatgcctattg<br>gctgtgtccagctgaacctgcccaatctacaccgcgtggcccgcaagctggacatcgactgt<br>gtccaggccatcactggctttgatttccatggcggctactcccatcccgtgactgatggatacat<br>cgtctgcgaggaattcaaagacgtgctcctgactgcctgggaaaatgagcaggcagtcattg<br>aaaggaaggagaaggagaaaaaggagaagcgggctctagggaactggaagttgctggcc<br>aaaggtctgctcatcagggagaggctgaagcgtcgctacgggcccaagagtgaggcagca<br>gctccccacacagatgcaggaggtggactctcttctgatgaagaggaggggaccagctctca<br>agcagaagcggccaggatactggctgcctcctggcctcaaaaccgagaagatgaagaaaa<br>gcagaagctgaagggtgggcccaagaagaccaaaagggaaaagaaagcagcagcttccc<br>acctgttcccatttgagcagctgtgagctgagcgcccactagaggggcacccaccagttgct<br>gctgccccactacaggccccacacctgccctgggcatgcccagcccctggtggtgggggct<br>tctctgctgagaaggcaaactgaggcagcatgcacggaggcggggtcaggggagacgag<br>gccaagctgaggaggtgctgcaggtcccgtctggctccagcccttgtcagattcacccaggg<br>tgaagccttcaaagctttttgctaccaaagcccactcaccctttgagctacagaacactttgcta<br>ggagatactcttctgcctcctagacctgttctttccatctttagaaacatcagtttttgtatggaagc<br>caccgggagatttctggatggtggtgcatccgtgaatgcgctgatcgtttcttccagttagagtc<br>ttcatctgtccgacaagttcactcgcctcggttgcggacctaggaccatttctctgcaggccact<br>taccttcccctgagtcaggcttactaatgctgccctcactgcctctttgcagtaggggagagag<br>cagagaagtacaggtcatctgctgggatctagttttccaagtaacattttgtggtgacagaagc<br>ctaaaaaaagctaaaatcaggaaagaaaaggaaaaatacgaattgaaaattaaggaaatgtta<br>gtaaaatagatgagtgttaaactagattgtattcattactagataaaatgtataaagctctctgtac<br>taaggagaaatgacttttataacattttgagaaaataataaagcatttatctaaaaaaaaaaa | 37 |
| ALG9 | NM_001077690.1 | gtcttttgtccctcggcggacaccgtttgccagccaaagctatgtctgcgcgctcaccgacttc<br>atagggtgccgaattctttttttccccaggcttgccatggctagtcgaggggctcggcagcgcct<br>gaagggcagcggggccagcagtggggatacggccccggctgcggacaagctgcgggag<br>ctgctgggcagccgagaggcgggcggcgcggagcaccggaccgagttatctgggaacaa<br>agcaggacaagtctgggcacctgaaggatctactgctttcaagtgtctgctttcagcaaggtta<br>tgtgctgctctcctgagcaacatctctgactgtgatgaaacattcaactactgggagccaacac<br>actacctcatctatggggaagggtttcagacttgggaatattccccagcatatgccattcgctcc<br>tatgcttacctgttgcttcatgcctggccagctgcatttcatgcaagaattctacaaactaataag<br>attcttgtgttttactttttgcgatgtcttctggcttttgtgagctgtatttgtgaactttacttttacaag<br>gctgtgtgcaagaagtttgggttgcacgtgagtcgaatgatgctagccttcttggttctcagcac<br>tggcatgttttgctcatcatcagcattccttcctagtagcttctgtatgtacactacgttgatagcca<br>tgactggatggtatatggacaagacttccattgctgtgctgggagtagcagctggggctatctt | 38 |

TABLE 1-continued

Prostate Cancer Biomarker/Housekeeper Sequence Information

| Gene Name | RefSeq Accession | Sequence | SEQ ID NO: |
|---|---|---|---|
| | | aggctggccattcagtgcagctcttggtttacccattgcctttgatttgctggtcatgaaacacag<br>gtggaagagtttctttcattggtcgctgatggccctcatactatttctggtgcctgtggtggtcatt<br>gacagctactattatgggaagttggtgattgcaccactcaacattgttttgtataatgtctttactcc<br>tcatggacctgatctttatggtacagaaccctggtatttctatttaattaatggatttctgaatttcaa<br>tgtagcctttgctttggctctcctagtcctaccactgacttctcttatggaatacctgctgcagaga<br>tttcatgttcagaatttaggccacccgtattggcttaccttggctccaatgtatatttggtttataattt<br>tcttcatccagcctcacaaagaggagagatttcttttccctgtgtatccacttatatgtctctgtgg<br>cgctgtggctctctctgcacttcagaaatgttaccactttgtgtttcaacgatatcgcctggagca<br>ctatactgtgacatcgaattggctggcattaggaactgtcttcctgtttgggctcttgtcattttctc<br>gctctgtggcactgttcagaggatatcacgggccccttgatttgtatccagaattttaccgaattg<br>ctacagacccaaccatccacactgtcccagaaggcagacctgtgaatgtctgtgtgggaaaa<br>gagtggtatcgatttcccagcagcttccttcttcctgacaattggcagcttcagttcattccatca<br>gagttcagaggtcagttaccaaaaccttttgcagaaggacctctggccacccggattgttccta<br>ctgacatgaatgaccagaatctagaagagccatccagatatattgatatcagtaaatgccattat<br>ttagtggatttggacaccatgagagaaacaccccgggagccaaaatattcatccaataaagaa<br>gaatggatcagcttggcctatagaccattccttgatgcttctagatcttcaaagctgctgcgggc<br>attctatgtccccttcctgtcagatcagtatacagtgtacgtaaactacaccatcctcaaaccccg<br>gaaagcaaagcaaatcaggaagaaaagtggaggttagcaacacacctgtggccccaaagg<br>acaaccatcttgttaactattgattccagtgacctgactccctgcaagtcatcgcctgtaacatttg<br>taataaaggtcttctgacatgaatactggaatctgggtgctctgggctagtcaaagtctatttcaa<br>agtctaatcaaagtcacatttgctccctgtgtgtgtctctgttctgcatgtaaacttttgcagctag<br>gcagagaaaggccctaaagcacagatagatatattgctccacatctcattgtttttcctctgttca<br>attatttactagaccggagaagagcagaaccaacttacaggaagaattgaaaatcctggtact<br>ggatggctgtgataagctgttctccacactctggcctggcatctgagaactagcaagcctctctt<br>aggccatatgggcttctccaccaaagctgtttggcagctcctagcagaccttcttattgaaatcc<br>tcatgctgaaaatgaacacagcctagttgccaacccacatgtccttttcacctccagcaagact<br>aagcttctttaaagcacttcacaggactaggaccctgtcctggagctatctcaggaaaaaggtg<br>accatttgaggaactgtgacctaattttattataatgatgcctctaattttcatttcctttacaaccaa<br>ctgtaactataaggttgtattgctttttttgttcagttttagcatgctatttttttgaattctagactcctcc<br>atgtgaagatatcaacagacaaaactacaactgtataggacatatttggagaaaattctatcaat<br>tgatacatttggatgacatcacattttttaagtaatgtaatctgaggccattgctgaggaaattaag<br>aattttccttttttttttaaccacccccagtgaaaaggatcagtgtatatttatagcacctatttttttagt<br>tctgtctgttgtgaggcacatcctgcatggggcacttctagtcaaataggcaatgataaggacc<br>taattaaaatgtgataagtgtatactattactttaaaagcctttacagtcagtacttcagtttacaag<br>gcactttcacagcatctcgtttgatcctcacagtcacaacatgtggtagacaaggcaggtgattt<br>ttatccccattttacagataaggaaacaggctgcgggtggggagtgaggggaggtaaagata<br>gttagttgcctaaggtcacacagccagtaagtaatagagctgggactggaacccaggtttcctt<br>actctcatctattgctcctccatattcctcactcaaccatgaaaacattacttgaaaggactgatga<br>ggttaaccagagacctaactgatattgtaactttctattttaaggaagaattgtgtctgtatttgagt<br>tctttggagcctccagtctgcctgtgtgttagaccagcacagcagtgctgtgtgatgcagcctg<br>acctgtggcaggaaagtagtgcttctgtttggaagtcatgttcttttgcagccacacaggatcca<br>aatatcagtactattcctgtagtcaatctggggtcacattataggtgccttatttccctaagggtaa<br>ctgatctgaatatctgcaaataggatgaatctatttttcagaagttccatctttcattttttcttttttttttttt<br>gagacagagtctcattctgtcgcccatgctggagtgcagtggcgcgatctcggctcgctgcaa<br>cctctgcctcccaggttgaagcaattctcatgcctcagccacccgagtagctgggattacagg<br>catgcgccatcatgcccagctaatttatgtatttttagtagagttggagtttcaccatgttggccag<br>gctggtcttggactcctgacctcaggtcatccacccgcctcagcctcccaaagtgctggtatta<br>caggcgtgagccaccgcacccagccccatctttcattttcaaagagaagggcattctaatagg<br>aactggtgccaagagagaagaaaagaagtgataacagaagaaatggctagttacaatattaa<br>aaagctcctctttgagatctcctctgcaggaatatcagagacggagttgaagcgctggagagg<br>taataggtctagacagtacagaacaataactggggagtgtgtgaggatagactgggctcccc<br>cttgcttgaaagatctctggcatttaattctcaattcttgattactattttccagtgtaaaactagcac<br>atatgatctgactacaggacagagaattttaagtgaaacatttgccttacttgcagtaataatgtg<br>ctgttcttcacagtagctaaggccctctatgtttcccagaggtaaataagaatccaggaatgga<br>ggtccatctgtgatgaatggctttttttctaatcaaagtagtataatgctgttttatctgttttgtcatctt<br>gtttttttttttttttaaaaaaacaaaaccttaattataatatagcgcaaagaaaggccaggactgat<br>gcagggattccttggaaatatcagttcctatcacttttaaaacctgattttggatctctctgttctat<br>gtatgtctttagtgagagcacaatacatggcagaacgctgtgccaaatgttataggtaaggaat<br>atagaaatgaatgtttttttgttgtgaaggtgttttcatgtgatattttataaacacattttaaaaaatct<br>ccatcacttttttagtataggaaggatagctttgcctgggaaaaacagtttcaacacacctgctca<br>gagtagcagttctccctcaaaaaagcagtgttcagcctgcactgactgttctgcttgccaaaag<br>gaggaagcatgcaagatacttatttctccatagattgtggagtatagagggatgtgggactaca<br>gattattattttttttccccgagacagagtcttgctctgtcgcccaggttggaacacaatggcacg<br>acctcagctcactgcaacctctgtctcccgggttcaagcaattctcctgcttcagcctcctgagt<br>agctgggattacaggcacacaccaccaccgcactcagctaattttttgtatttttagtagaggtgg<br>ggttttaccatgttggccaggctggtcttaaactcctgaccttgtaatcatcccgcctcggcctcc<br>taaagtgctaggattacaggcatgagccaccgcacccggcccagataattttttaatagcctttg<br>atcatggggtgagtgagggagtaggtatacttggcaaatgcatggttctctgatttctagctcta<br>aagcagccttatctgaatccccaaatcttgtgatgctgagtaccattactgaaccagtctgcacg<br>gtaggcatctgctaccaaaatttacctcctacctggtaggtgtcatctgataagaaagaagaca<br>ggttattttaatttttttgagataatcacagaaaattgcagcccatactctttattaccgaattcaagtt<br>tggaaatagaccctttgttttaaatcatgatgggtctttatcccaatcatttatctgggtcatttttcc<br>aactttggagttctaggaaagaaccttgaaaacctgatatgattctgcagcatgaggtctacggt<br>gaccatttgggcaaagctccagtggcaatcatttattgtgttttgcatttcctgggatttattgaaat | |

TABLE 1-continued

| Prostate Cancer Biomarker/Housekeeper Sequence Information | | | |
|---|---|---|---|
| Gene Name | RefSeq Accession | Sequence | SEQ ID NO: |
| | | aagaattcactgtgattatgtagtcttctggctagtatcaggcagctctgcttttaatttggttaattt<br>tattttctctgaagagggagaagaggtacaatttaatcttggcctccacaagcatattaaagctc<br>acgtgttaatcagtgcattcttatgctcctacattaaatgccttgggtaaatggataaatggacat<br>gtgcccagctttaattttttttgcaacagaaagatcagacttccgtatggcatcgttggatttcaga<br>ggctttctggtgtatctgtaaatctgaatgttgccttctgccagtctgtataaccaggtgattcatg<br>ctgcaaatgaaatcaggaagcagtaaagtgttaaagcaagagtattgtccaattcacttgtcttc<br>ctgatccttgtactttatttcacgtgtcggtgtttacattacatacttatatttcctgtgaaagaaaga<br>gttaaataaattgtagcagtttga | |
| SEPN | NM_031475.2 | agcggagcgccaggcagcgcggagcggaggccaggcccacagccgctccgcctcccgg<br>cccgcagatccccgacggccgcaccgcgggctcctctggcccgcaagaacacgtgcatgg<br>cgtcctggggaaggcgctgagtgcggagtcgcggcgccgcacgcggcaccatggccctg<br>gagcaggcgctgcaggcggcgcggcagggcgagctggacgtgctgaggtcgctgcacgc<br>cgcaggcctcctggggccctcgctgcgcgacccgctggacgcgctgcccgtgcaccacgc<br>ggcccgcgctgggaagctgcactgtctgcgcttcctggtggaggaagccgccctccccgcc<br>gcggcccgcgcccgcaacggcgccacaccggcccacgacgcctccgccaccggccacct<br>cgcctgcctgcagtggctgctgtcgcagggcggctgcagagtgcaggacaaagacaattct<br>ggtgccacagtcttgcatctggctgcccgcttcggccaccccgaggtggtgaactggctcttg<br>catcatggcggtggggaccccaccgcggccacagacatgggcgccctgcctatccactacg<br>ctgccgccaaaggagacttcccctccctgaggcttctcgtcgagcactaccctgagggagtg<br>aatgcccaaaccaagaacggtgccacgcccctgtacctggcgtgccaggagggccacctg<br>gaggtgacccagtacctggtgcaggaatgcggcgcagacccgcacgcgcgcgcccacga<br>cggcatgaccccgctgcacgccgcggcgcagatgggccacagcccagtcatcgtgtggttg<br>gtgagctgcaccgacgtgagcctgtccgagcaggacaaagacggcgccaccgccatgcac<br>ttcgcggcgagccgcggccacaccaaggtgctcagctggctgctgctgcacggcggggag<br>atctcggctgacctgtggggcgggaccccgctgcacgacgccgccgagaacggggagcta<br>gagtgctgccagatcctggtagtgaacggcgcggagctggacgtccgcgaccgcgacggg<br>tacacggccgccgacctgtcggacttcaacggccacagccactgcacccgctacctgcgca<br>cggtggagaacctgagcgtggagcaccgcgtgctttcccgggatccatccgcagagctgga<br>ggctaagcagccggattcaggcatgtcctcacccaataccacggtgtcggtccagccgctga<br>actttgacctcagctcgcctaccagcaccctctccaactacgactcctgctcctccagccactc<br>cagcatcaagggccagcaccctccatgtgggctttccagcgctagagctgcagacatacaga<br>gctacatggacatgctgaacccggagctgggcctgcctcggggcacgattgggaagcccac<br>acccccaccaccccccacccagcttccccccgccaccccccgcccccaggcacccaactgcc<br>cccaccccccacctggctacccagctcccaagcctcctgtaggaccacaggcagctgacatct<br>acatgcagaccaagaacaaactccgccacgtggagacagaggccctcaagaaggagctga<br>gctcctgtgacggccacgacgggctgcggaggcaggactccagccgcaagccccgcgcc<br>ttcagcaagcagcccagcacgggggactactaccggcagctgggccgctgccccggcga<br>gacgctggccgcacgcccgggcatggcgcacagcgaggaggtgcgtgcccgccagccc<br>gcgcgcgccggctgcccgcgcctcggccctgccgcccgcggctcactcgaaggcccctcc<br>gctcccccgcaggcggcgctgcttcctgggaaccatgttcctaacggctgcgccgcggacc<br>ccaaggcgtccagggagctgccaccgccgcccccaccgccgccgccgcccctgccggag<br>gccgcgagttcgccaccgccggccccgcctctgcccctcgagagcgctggccctggctgc<br>gggcagcgccgctcctcctcgtccaccggcagcaccaagtctttcaacatgatgtccccgac<br>gggcgacaactcggagctactggctgagattaaggcaggcaagagcctgaagccgacgcc<br>ccagagcaaggggctgaccacagtgttctcaggcatcgggcagccggccttccagcccgat<br>tcgccgctgccttctgtgtcacctgcactgtcaccagtccggagccccacaccgccagctgcg<br>gggtttcagccgctgctcaatggaagcttggttcccgtgccgcccactactcctgcgccggga<br>gtgcagctggacgtggaggctctcatccccacgcacgatgagcagggccggcccatcccc<br>gagtggaagcgccaggtgatggtgcgcaagatgcagctgaagatgcaggaggaggagga<br>gcagaggcggaaggaggaggaggaggaggcccggctggccagcatgcccgcctggag<br>gcgggacctcctgcggaagaagctggaagaagagagggagcagaagcggaaagaggag<br>gagcgacagaagcaggaggagctgcggcgggagaaggaacagtcagagaagctgcgga<br>cgctgggctacgatgagagcaagctggcgccctggcagcgacaggtcatcctgaagaagg<br>gggacatcgctaagtactagaggccgcagactcctgtccgcagcctcgcagctccgtgggg<br>ccctccgccccagccccagccagccaggccctggtggaaaggctgggagccgcacagcc<br>ctcccctcctgcgctggaaaccctccctgacccccaccctggccccccgtatccccagccctt<br>ggcaacactggagtgcacacgccgccacggttgcccagaaaaagtgcccaagctgctgac<br>gcaaacaacaacaaatgctgcttatttgcatgccgacttacatatatttgcatgttcgttgactatc<br>aaagagtgcagagctctccccagccccgtgggtggtgactttgttttcctgcggggctcagcc<br>ccctccaggatgcagcccccctcccccgcaccccggaaccggcgtcgctggcgcatcctgg<br>gtggaggcaggccccgagctcggggaaggggttttcccttcctctctgacccagatctgcgc<br>gcggcctagcccgggcctcatttcttatccccgccaagggtttcctctcagtcatttgtttaccag<br>aaacatgaaaactgcctgtctggccgggccgcacttgtggcccccgggaccccacctctggc<br>cccacctccctcaagtctgcgccccgtccccagccagacccactcgctgccgggaccctttc<br>actgccccggtggagtgaatagaggatgaggggccctgaccctgtgtctccaactgctgcac<br>cccatcccgaccctgtctccgccacctcgcagccccattaaagcgctctcatctgggctccgg<br>ttcactca | 39 |
| YWHAQ | NM_006826.3 | ttgggcggtggaccgcccctcggccccggggtaggctgacacgggagggtcctcagctaa<br>agccaaaagcagatcaaagtggtgggactcgcgtcgcggccgcggagacgtgaagctctc<br>gaggctcctcccgctgcgggtcggcgctcgccctcgctctcctcgccctccgccccggcccc<br>ggccccgcgcccgccatggagaagactgagctgatccagaaggccaagctggccgagca<br>ggccgagcgctacgacgacatggccacctgcatgaaggcagtgaccgagcagggcgccg | 40 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | agctgtccaacgaggagcgcaacctgctctccgtggcctacaagaacgtggtcgggggccg<br>caggtccgcctggagggtcatctctagcatcgagcagaagaccgacacctccgacaagaag<br>ttgcagctgattaaggactatcgggagaaagtggagtccgagctgagatccatctgcaccac<br>ggtgctggaattgttggataaatatttaatagccaatgcaactaatccagagagtaaggtcttct<br>atctgaaaatgaagggtgattacttccggtaccttgctgaagttgcgtgtggtgatgatcgaaaa<br>caaacgatagataattcccaaggagcttaccaagaggcatttgatataagcaagaaagagatg<br>caacccacacacccaatccgcctggggcttgctcttaacttttctgtattttactatgagattctta<br>ataacccagagcttgcctgcacgctggctaaaacggcttttgatgaggccattgctgaacttga<br>tacactgaatgaagactcatacaaagacagcaccctcatcatgcagttgcttagagacaaccta<br>acactttggacatcagacagtgcaggagaagaatgtgatgcggcagaaggggctgaaaact<br>aaatccatacagggtgtcatccttctttccttcaagaaaccttttttacacatctccattccttattcca<br>cttggatttcctatagcaaagaaacccattcatgtgtatggaatcaactgtttatagtcttttcacac<br>tgcagctttgggaaaacttcattccttgatttgtgtttgtcttggccttcctggtgtgcagtactgct<br>gtagaaaagtattaatagcttcatttcatataaacataagtaactcccaaacacttatgtagagga<br>ctaaaaatgtatctggtatttaagtaatctgaaccagttctgcaagtgactgtgttttgtattactgt<br>gaaaataagaaaatgtagttaattacaatttaaagagtattccacataacttcttaatttctacattc<br>cctcccttactcttcgggggtttcctttcagtaagcaacttttccatgctcttaatgtattccttttttag<br>taggaatccggaagtattagattgaatggaaaagcacttgccatctctgtctaggggtcacaaa<br>ttgaaatggctcctgtatcacatacggaggtcttgtgtatctgtggcaacagggagtttccttatt<br>cactctttatttgctgctgtttaagttgccaacctcccctcccaataaaaattcacttacacctcctg<br>cctttgtagttctggtattcactttactatgtgatagaagtagcatgttgctgccagaatacaagca<br>ttgcttttggcaaattaaagtgcatgtcatttcttaatacactagaaaggggaaataaattaaagta<br>cacaagtccaagtctaaaactttagtacttttccatgcagatttgtgcacatgtgagagggtgtcc<br>agtttgtctagtgattgttatttagagagttggaccactattgtgtgttgctaatcattgactgtagtc<br>ccaaaaaagccttgtgaaaatgttatgccctatgtaacagcagagtaacataaaataaaagtac<br>attttataaaccatttactatggctttgtaacaattgcatacccatattttaagggacaggtgaattt<br>actactttctaaagtttattgatacttcccttttatgtaaaatgtagtagtgatacctatatttccacatt<br>gtgcattgtgacacacttgtctagggatgcctggaagtgtataaaattggactgcatttcttaga<br>gtgttttactatagatcagtctcatgggccatctcttcctcagatgtaaatgatatctggttaagtgt<br>tatatggaataaagtggacattttaaaactagcaaagttaaaaaaaaaaaaaaaaaaaa | |
| VPS37A | NM_001145152.1 | gcagagggggcggagagcgcccccgggggcggggcacgcaagtgacggcggcgcgg<br>gtggtggagcgctgggcggccaggctccctggctggccggtttgggcgtctgggccgtgaa<br>ggtgggacctcctgttccgggccgcaagtttccctctccagccgcccgccgttcgtagcatgt<br>cccccagaactcggggagcgcaggcaggacaggcttagagaagacgcggtccccagcgc<br>ttgggccacggacgtcccaccccgctcctctgtcgctggagaaccgccgggccgagccact<br>gggagaagcaggccagagccttccagggcctccggcccgtggacccgaggaggatgagc<br>tggctttttcccctgaccaagagcgcctcctcctccgcggctgggtcccccggtggcctcacc<br>agcctccagcagcagaagcagcgcctgatcgagtccctccggaactcacactccagattgct<br>tcctccacagtttcctcaggaaaaaccagtgatcagtgtttatccaccaatacgacatcacttaat<br>ggataaacaaggagtgtatgttacctctccattagtaaacaattttacaatgcactcagatcttgg<br>aaaaattattcagagtctgttggatgagttttggaagaatcctccagttttagctcctacttcaaca<br>gcatttccttatctatacagtaacccaagtgggatgtctccttatgcttctcagggttttccatttctt<br>cctccatatcctccacaagaagcaaacaggagtatcacttctttatctgttgctgacactgtttctt<br>cttcaacaacaagtcataccacagccaagcctgccgctccttcatttggtgtcctttcaaatctgc<br>cattacccattcccacagtggatgcttcaataccgacaagccaaaatggttttgggtacaagat<br>gccagatgtccctgatgcatttccagaactctcagaactaagtgtgtcacaactcacagatatg<br>aatgaacaagaggaggtattactagaacagtttctgactttgcctcaactaaaacaaattattac<br>cgacaaagatgacttagtaaaaagtattgaggaactagcaagaaaaaatctccttttggagccc<br>agcttggaagccaaaagacaaactgttttagataagtatgaattacttacacagatgaagtcca<br>ctttcgaaaagaagatgcaaaggcagcatgaacttagtgagagctgtagtgcaagtgcccttc<br>aggcaagattgaaagtagctgcacatgaagctgaggaagaatctgataatattgcagaagact<br>tcttggagggaaagatggaaatagatgattttctcagtagcttcatggaaaagagaacaatttg<br>ccactgtagaagagccaaggaagagaaacttcagcaggcgatagcaatgcacagccaattt<br>catgctccactatagattttcctggaaacatgaactgccaagagaggaatgggacacaaaacc<br>aaacactgttttatatttatggtttgcaaactggcatttcatcagtggctaaattcacagatatccta<br>tatagattgtatacagaactgagactgattttgtaccgattagaatgattgctatgatctttgagaa<br>atttttctgcactatttgcactgaaatgtttatttattgttgataaattgtatcatatttaagttccactg<br>ctgttcctcttaccttgattaaatgcctatgcatgtacttttagctagtttttaatattttataaacttc<br>atttaaatttgtatttttaacttgaagttccatttctttatcaaggatggtatttagatttttttcctcttaa<br>cctttttttcaaaaactattttcaactgtgaggaaacccttatttttctttctttgtggataaaactttcaa<br>aagcaatttaagatattcatagtgttaggaaacaccaaacctgcctatgtgccatctcacaaaag<br>aaacttttaatacctacaataaatcaaaagaataaaccagctgttcttatatattgtttcatttttaaa<br>actaaagatgcatttaagaagcaatacaagtaaatattttacctaataggaaaaaaaaaagttgc<br>ctttcatttaaaccattccaacagaaattcttatgctaatttaaaacatatatatatctggtaggtttg<br>tggttggataggttttctaaattcctaatgttaaaaacaatctttatgttaatatacactaaatctata<br>cacaaaaaaagtcagtgaacttttctgacctttactgtgagttaccttttcctaagaggaaagcta<br>tagtaataagtaaaatttaattttaggcaatcctgattttaatgaatttaattgagtgttcttgtatac<br>tacattgagcagtttgcttctataccgtgtcacaaaattcatgtatttcttgagaagccctaaaagc<br>tcataaaggaaaatgccgtgaactatgtagctcaggcttggtaaggtgccatctaaattacaaa<br>acaaactaatgcataattttgcttaaatttcatcccagtatgattgtcttcccaacaccagcatata<br>gtatagattgtctgtctttttttatatttttttagttcttcctgtacatgtttttggcaataaagttataggaa<br>gaacaaaattattttgttagaattaaaacatgcttaatatttagtctgtttgtggagggcaggtattc<br>acgtggactgagatacaatgttggatacagaaaataactttcattgtcttcctgacactgtgctaa | 41 |

TABLE 1-continued

Prostate Cancer Biomarker/Housekeeper Sequence Information

| Gene Name | RefSeq Accession | Sequence | SEQ ID NO: |
|---|---|---|---|
| | | ggacatgctgttaaagcttcaaagtgaccagatgaggaaggaataattaattattactcctgattt<br>gtagataactgaggtaagagtgtttcaaatttatgatagtcttttgggtattcagaaacctttcctta<br>tactgcactggccaccagagcttaattttcccagcagttacagcaatgggagatagaacagtct<br>caatcttttgccaaccatcaggttcctagaaaccaggtaggtgtatcccataacaagggagga<br>gcataccacagcccctcatttgattaattcatttgatctatctatgttattaagtacctactaggaat<br>aaggcattgtggaaatactatacaaagataaacattgtttagatgcttatctactttccttttcacca<br>gaaaaacagaaaaaaaagaaacatttcttacagagtaaaaatgttctacataatcacatgagta<br>gttcatctcagtgtttttttattctttaaagttgaactatcccagtttcattctataccattcattggataa<br>ccttgttacaacccagtcatgaaacagagcagtgtgatcagttatctgcatttaacaaatagaca<br>aatcagtttacataaaggttatgtatgtcacccacgatgaaaagaatctgcatttgaatatgcccg<br>tatgaatgtgggttctgtttttgcaacagagattaagtgaccatttttttctaattttatggctatatattt<br>tcttcataaaaattggtcacatcggagaagcagtgccacaggaaaaatgaaatgcatgtgaaa<br>gtttgtattctgattttacaagatgagatagaaatcagaattaaagaggaatacttaggagttact<br>aggctaatcagtgtacgaatttgtcataggtagagatttaaaggttaatatcttaaaatagaagaa<br>aattctaaatcaatcaatcagtgagatataaactaaacagacccacttcaaagttgaaagaaatt<br>tctaggcataaattgagactaggaaatttatatcagaatagagggtgcttgacacatatatatgct<br>taaattgaaggacagctcagattcatttttaggagaagaaagtaaactaatgtgctcttaaagaa<br>taaaaatttattctatggtttctgtctctgatcatcaccttccattctataaaaagctcagttactgatt<br>tgctgggtcatggtcaaaattcttacctatttatttcatatcaactttaaaaaataaattacttgcatt<br>ctatatattactaattgggaagtaatatgcctcaaatcagttttatactggattattccctatgcttta<br>aaccactgctctcaataaaacacttcctgattaatgtttgattattagatattttagtcttgttgggga<br>tattttagtcttgttgggttagccatgctctgaagaatctgtgaaagtacagtaaagttttaataag<br>caataaatgtaaccttttatataaatctcagtgctaggttaacttctaataagcagacgaacatgtt<br>acataaattataatgtctgtcttgtaaaaaagttgaggggactaaaagtttatgactctgatatgg<br>aagttgtcatattaaaaaactacattttaaaacatcaaatatttatactatttgcttttcaaataaaag<br>catagtgctgtttggcata | |
| PRRC2B | NM_013318.3 | gcagatcgggagcggtgccgagaaaaatttccttactagatgacatttcatcgcaatgtccgat<br>cgtttggggcaaattaccaagggcaaggatgggaaaagcaagtactcgactctcagcctgttt<br>gataagtataaaggaaaatcagtagacgcgattagatcctcagttattcctagacatggcttaca<br>gagtcttgggaaagttgctgcagcccggcgcatgccaccgcctgcaaacctgccaagcttga<br>agtctgaaaacaaaggaaacgaccccaacatcgtgatagtacccaaggacgggacgggat<br>gggcaaacaagcaggatcagcaagacccaaagagttccagtgcgacggcctctcagccgc<br>cggagtcgctgccgcagccgggtttgcagaaatctgtctccaatttgcagaaaccgacacagt<br>caatcagtcaggagaatacaaattcagtgccaggtggaccaaagtcatgggcacagctgaat<br>ggaaagccagtaggacacgaaggtggtttaaggggctcaagccgactgttatccttctctccc<br>gaggaatttccgacgctgaaagcagctggagggcaggacaaggctggcaaagaaaaggg<br>cgtcttagatctgtcgtatgggccaggaccaagcctccgccctcagaatgtgacaagctgga<br>gggagggcggtgggcgacacataatttctgccacgtctctgagcacctccccaactgagctg<br>ggcagcaggaactcgagtacgggagatggagcccctcctcggcatgtaccagcgattcta<br>aggacccctctctccgcccggctcagcctgtccgaaaggggcttcacagttcatgggaaat<br>gtataccacccacctacataccatgacatgcttcctgcttttatgtgttcgccgaagtcatcagaa<br>aaccagggtacagtggaacgaggctcttttccccttcctcagctccgccttgaacctcgagttc<br>cttttagacagttccagatgaatgaccaagacggaaaagaaaacaggctgggattgtctcgcc<br>cactccgcccactaaggcagctggtggagcgggcaccacggcccaccattatcaatgcgga<br>aaacctgaagggccttgacgatctggacgccgatgccgatgatggctgggcaggcctccat<br>gaagaagtggactattctgagaaactgaagttcagtgatgatgaagaggaggaagaagttgt<br>gaaggacggcaggccaaagtggaacagttgggaccctaggaggcagcggcagttgtcaat<br>gagctctgcagacagtgcggacgctaagcggactcgagaggaagggaaggactgggctg<br>aagcagtgggtgcgtcccgtgtggtccgaaaggcgccagaccctcagccaccgcccagga<br>agcttcatggctgggcaccaggccctgactaccagaagtcatcaatgggcagcatgttccgg<br>caacagtccatcgaggacaaggaggacaagcccccaccaaggcagaagttcattcagtcag<br>agatgtccgaggcggtggagcgagcccgaaagcgccgggaagaagaggagcgccgagc<br>ccgggaggagaggctggccgcctgtgctgccaaactcaagcagctggaccagaagtgtaa<br>gcaggcacgaaaggcaggtgaggcccggaagcaggcagagaaggaagtgccctggtctc<br>caagtgctgagaaggcatctccccaggaaaacggccctgctgtccacaaaggctccccaga<br>attccctgcccaagagacccccaccacattcccagaagaggcacccacagtgtccccagca<br>gtggcacagagcaacagcagtgaggaagaggccagagaggctgggtcccctgcacagga<br>gttcaagtatcagaagtcccttcctccccgattccagcgccagcagcagcaacaacagcagg<br>agcagctgtacaagatgcagcactggcagccggtgtaccccccgccgtcccacccccagcg<br>caccttttacccacaccacccccagatgttgggcttcgatcccaggtggatgatgatgccttcct<br>acatggacccacgtatcacgcccactcggaccccggtggacttctacccctccgccctgcatc<br>cctcaggactgatgaagcccatgatgccccaggagtccctcaatgggacaggctgtcgctct<br>gaggatcagaactgtgtgcccccactccaagaaagaaaagtgacccccatcgactcacccc<br>ctgtgtggagcccagagggctacatggcactgcagagcaagggctacccgctcccgcaccc<br>gaagtcgagtgacaccttggctatggacatgcgtgtcaggaatgaaagctctttctctgcctca<br>ctcggaagggcagggggcgtaagtgctcagcgcgatctctttgaggagagaggggaggag<br>tacttgagtgcttttgacaagaaggcccaagcagactttgacagctgtatctcttctcaaagaat<br>aggccaggagcttttgtttccaccccaagaaaatgttcaggatgcaggtgctcctgggggtca<br>cacccaaaacctcaggtgttccccattggagcctgactttgtcccagatgagaaaaagccaga<br>gtgtggcagttgggatgttagccaccagccagagaccgctgacacagcccatggtgttgagc<br>gggagacaccccgggaggggacggcctttaacatctcctcctgggacaagaacgggagcc<br>ccaacaaacagccatcctcggagcctgaatggactcccgagccccggagctccagcagcc<br>agcacccggagcagacgggcaggacccggaggtcgggacccatcaagaaaccagtcctg | 42 |

TABLE 1-continued

Prostate Cancer Biomarker/Housekeeper Sequence Information

| Gene Name | RefSeq Accession | Sequence | SEQ ID NO: |
|---|---|---|---|
| | | aaagccctcaaggtggaagacaaggagaaggagcttgagaagattaagcaggagctaggg<br>gaggagagtacccggctggccaaggagaaggagcagagccccacggcagaaaaggatg<br>aggacgaagagaacgatgcctctctggccaactcctccaccaccactttggaggacaaagg<br>ccctggccatgccacttttggccgcgaggccaccaaatttgaagaggaggagaaacctgaca<br>aggcctgggaagccagacccccacgagagtccagcgatgttccccccatgaagagaaataa<br>ctggatctttattgatgaggagcaagcctttggggtcagaggacaggcccggggccggggc<br>cgtggtttcagagagttcacttttcgtggtcggcctgctggcggaaatgggagcggcctctgtg<br>gtgggggggtcctgggggcccgcagcatctactgcagcagtcagcgcagcggccgtggcc<br>ggggcctgcgagagtttgcgcggccagaggactgccccagagccaagccccgacggaga<br>gttgccagtgagacccatagcgagggctcagagtatgaagaacttcccaagcgccgccggc<br>agaggggctccgagaacgggaatgaaggctcgctcctggagagggaggagagcaccttg<br>aagaagggcgactgcagagattcttggcggtccaacaaggggtgctctgaggaccacagc<br>ggtctagatgccaagagccgaggccctcgggcctttgggcgagccctccctccccggctga<br>gcaattgcgggtatggacggagaaccttcgtctccaaagagtcaccccactggcagagcaaa<br>agtccaggcagctcttggcaggaatatggcccttccgacacatgcggatcccggcgacctac<br>agacagagactatgtcccagattcctacagacaccctgacgcatttggtggccggggctttga<br>ggacagccgcgcggaggacaagagatccttcttccaagatgaacacgtggcagattctgaa<br>aatgcagagaaccggcccttcaggagaaggcgcccccccacgccaagataagccccctcga<br>ttccggcgcctccggcaagagcgggagtccctgggcctgtggggacccgaggaggagcc<br>ccacctgctggcaggtcagtggccaggcaggcccaaactgtgttctggggacaagagtggc<br>actgtgggccgcaggtcccctgagctctcctaccagaactcctccgatcacgccaatgagga<br>gtgggagacggcctccgaaagcagcgacttcagcgagcggcgggagcggcgggaaggc<br>cctgggtccgagcccgactcccaggtggatggtggcctgtcgggggctagtttgggtgaga<br>agaaggagctggccaagaggagcttctccagtcagagacccgtggttgacagacagagcc<br>gaaagctggagccgggagggtttggggagaagcccgttaggccaggtggtggtgacacct<br>cccctcgctatgagagccaacagaatgggacgcctttgaaagtgaaaagatccccagacga<br>ggccttgcctggaggtcttagtggctgcagcagtgggagtggccactcccccctatgccctgg<br>agcgggcagcccatgccagtgctgaccttcccgaagcctccagtaaaaaggcagagaagg<br>aggccaagttggctgctccgagggcaggtgaacagggagaggccatgaaacagtttgacct<br>gaactatggaagtgccatcattgaaaattgcgggtccagccccggggaggagagtgaggtg<br>ggttctatggtgggcgaaggcttcatcgaagtcctgaccaagaagcagcgccgcctgctgga<br>ggaagagagaagaaagaaggagcaggccgtgcaggtgcctgtcaaaggtcgaggcctttc<br>ctcccgtattcctcctcgatttgcaaaaaagcagaacaacttatgtctggagcaaggtgacgtg<br>accgtgcctggcagcagcctgggcactgagatctgggagagcagcagccaggctctccctg<br>tgcaggccccagccaacgactcctggaggaaagctgtcactgccttcagcagcaccgagac<br>tggctctgcggagcagggttttaagagcagccagggagatagtggcgttgacttgagtgccg<br>agtctcgggagtcgtctgcgacctcctcgcagcgcagctccccatatgggactctgaagcca<br>gaggagatgagcgggcccggcctggcggaacccaaggccgacagccacaaggagcagg<br>ctccaaagccatctgagcagaaggattcagaacaaggctctggacagagcaaggagcaca<br>gaccaggacccatcggcaacgagcgttctctgaaaaacagaaagggctcggagggggcc<br>gagcggctgcaaggggctgtcgtcccgcctgttaacggggtggagattcacgtggactccgt<br>gctgcctgtgccacccattgaatttggagtcagtccaaaagactccgatttcagcttgccacct<br>ggttctgcctctggtcctactgggagtccagttgttaaacttcaggatgccttggccagtaatgc<br>agggttaacacagagtatccccatcctgcggcgggaccatcacatccagagggccatcggtc<br>tctccccaatgtccttccccaccgccgaccttactctgaagatggagtctgcgcgcaaggcttg<br>ggaaaactcccccagtttgccggagcagagctctccaggcggcgctggctcaggcatccag<br>cctccatcctctgtgggtgcctccagcggggtcaactacagctccttcggtggagtgtccatgc<br>cacccatgcctgtggcctctgtagcaccttctgcttctatgccaggcagccacctcccgcccct<br>gtacctggatggccatgtgtttgcaagtcagccccggctggttcctcaaacgatacctcagca<br>gcagagttaccaacaggccgccgctgcccagcagatcccgatctcccttcacacatctctgca<br>ggcacaagctcagcttggactgaggggtgggcttcctgtgtcccagtcccaggagatcttca<br>gctccttgcagcccttcagatctcaggtgtacatgcaccccagcctgtcaccgcccagcacca<br>tgatcctctctgggggcacagccttgaagcctccatactcggcgttcccaggcatgcagccct<br>tggagatggtgaagccgcagtctggctcaccctaccagcccatgagcgggaaccaagccct<br>ggtctacgagggccagctcagccaggctgctggcctgggtgcctcccagatgttggactccc<br>agctcccacagctgaccatgccactgcctcggtacggctccgggcagcagccactgatcctg<br>ccccagtctattcagctgccacctgggcagagcctctccgttggggcccccgaaggattcct<br>ccgcccgggtcccagccgccagtcctgaacaccagcagagagccctctcagatggagatg<br>aaaggcttccactttgccgacagtaaacagaatgtcccttcaggaggccccgtgccatcgcca<br>cagacctacaggcctagctctgctagccccagtgggaagccctctggatcagcagttaacat<br>gggctctgtgcagggacactacgtgcaacaggcaaaacaacgagtggatgagaaacccag<br>cctgggagccgtgaagctgcaggaggccccctcggctgcctcccagatgaagcgaaccgg<br>agcgatcaagcctcgggctgtcaaagtggaggagagtaaggcctgacagtgcctggctgcc<br>acctcgcctctccctactgaggacggtgccgccatgcggcctcgacacagccgacactcgg<br>gagcctcaccagatccaccgtccaaatgcgtggcccagactgagagacctccctcctctcca<br>ctcccgaaagctccgttgtcaaccagcttgcacccgtggatatatggcattgacccgcttgcttt<br>gatacgaaacaaaaaagcagacgactccttcatcccatctgctcctaccgtgactgtggagtg<br>acgcctcctgtgcagtgcagatttgccctccctgcctcctccctgtcctgccgcgcagccagg<br>gcgccttctcagcagtgcttccggcccagccgcccatccctaggcacagtgatttggcagca<br>gggtcattttactttgaggctttttgttttaaaatgtagccaaggtttttacaaaggggaaaggaaa<br>agaaaacaaaaacgcaagctccatgtgtatagctgaacttttatatgtttcttgccagcccctcc<br>gctcccttccatctctagcctctgtcctgtttagtttgatacgtcactgcagtaccttaagaggtga<br>ctcttaagaatgcatcccctcctgattcctcagctggttcacccttgaggttatttgcaaaaagaa<br>aaggaggttcttgagggcaccgattgcgagcattctggtgcctggctccccgcctgggaagc | |

TABLE 1-continued

| Prostate Cancer Biomarker/Housekeeper Sequence Information | | | |
|---|---|---|---|
| Gene Name | RefSeq Accession | Sequence | SEQ ID NO: |
| | | gatggggtgctcagagcagcaggcaggttgggggaggggggggtcatagttgggttcca<br>gctcctggcttgatgagcccagggcgcttacaggcagcccatgaagttgatgacagttttagc<br>atgagaatcacacagggtccctgtcctgggctcctctaaagccagtggatgtgctgggcacc<br>agagacaaatcatggagatggctgctggtggctcccaggttggcccagatggggtgagctg<br>acataccacaggcccatcccaggccccgtgggctctgcttctggggctccatacccctgccctg<br>caggggtgctgtgtttttcacacatttctttccctgaagccttctgtaacctgtcattttccttccttc<br>ctcttccggagcctgctgctttctctggacctgtctccacctcccacacagctcatcgtgaacac<br>cacttggtgatggagggagtggacccgtgtgtggtccccaagtgaggccactgggagtttgt<br>ccttttcctcctttgcttcactcccagcagcagacccaggttgtcaggacaggagggcctgag<br>ctaagcagtaggcatcagtctcgtttgtcttcagacggcgggggcaggtccagggtgaggct<br>gggtggagggctgaccaaggtccaaagggcctgcgcagcctccgggagggcagcttctcc<br>agccagaggcttgtgtgagccatcgtgtgctgggcttgtttttaagtaagaaacaaggaaatca<br>ctccagattctgtcattccaaggaaagggaaggggacagttcaggtttctcagctgttcttagg<br>ggtcactgagcgtctacctcctcctccagaggaggctggctcagaacacctagaggagggg<br>gccggggatgcacccccaccagaggctgccttcagcgtctcacgggtgcaggacagcgc<br>tcaggcttgggctctaagctctgtgtctagtgtagaacatggggaaggagcatcttaggaactg<br>ctgaagtaacttcttactgctctcacaattctaaggaagcgggagaacggcctcctaccaacag<br>cgcccaccccagagctgcctgggaaagggcagttttactgaaaggtgctttactgttcacctg<br>catctttcagcagctcccctcctgccctcacctggtcttttccctctttatcccaagcctttatgctt<br>gagtcccttccccaggggctgcccacccgacagttccaggcattccctacctgagcttcttgtc<br>tgcttttccttctcccactgcaagcggctgcttgtggggcctgggatgagccctctctgtcccca<br>ccggccctccttgccaagccattcctgggtgagttcaggcctgcgggagccacacattcatct<br>ccacctggacacttgagccgcatggccagacccctcccacctgatgcggtggtgcgtgtgat<br>ttgtcaaaagaaagccttctggatgctgttaagatgtacccttcaggtgaacctggtatcagacc<br>cacagtacttgctgtttgagaaaaaataaaaacaaaaaggtcacctgttctccagcccttttctct<br>tacctggtatttccttcctttctcctcccccaccccaaataaaaaaacaaaaaacactagaatttat<br>ttatatgtattgatgttgtaggtctaggtgaaaaaaaaagaagtaaatgtttcactgctctatttata<br>tataatgtctgaattaattctgtgcaggaaaggccaggaaattgcatgtgaagttcggtgcagtc<br>accacctgtgtgtgacctgagctgcagtctcttcgctgagatgcaggttttaaatgagacttggg<br>gggctgagggcaggcctcaggcctcccagcgccccaacccctccttggtctaatgaaatgca<br>gttcttagtgcagagatgttttaaggtgcaatatatctcttcctttcccgtggttttagagccaagct<br>caaggtagtaggacgtagggtcttatttgttttcaaaccccccatcctcagagcgcagatacatg<br>cagaggcttctgccaggataccacggggccttagtgggaacaggtggagaccagcacttcc<br>ctttcctgctgctgaggtagggattgggggtcagaacccactcacttttgcctgttaaagttgc<br>cctcctgacgctggcagctctgccttggtcactggggatgcggctcgttgctcagccaccagt<br>ggccttgcggtattgtccaccatccactagagtgggatgaagtccagagtgtgggtatacatct<br>cagatgcccatctacccactggggacttcaatgccagctgcatttggtttggttttcttaactgttg<br>gcttctccccacagcgtttttttgttttttttaaacattcatattgttttcaaacttggaattcatagaca<br>ctctggctctaggttccttaaggggaaaacaaaagatgactttatttcacattcaagaaaatca<br>gttcagttccaaagctgtggtccttccagccacttctagggacactggggaaccttgttaaacgt<br>tgacatcagtgctctccagccgtgctgtcaccctcctatcttctggatctgccttcgcgatggtca<br>gtgacagcttctggaagctgagcacacacaggtgcacagccatgctgtggtctggcctgcta<br>cggcagcatggcagctctggtggagccttctcccttgccatttggttcccctgtgccaagtagc<br>tgcaggctgcccctcaaatcttcatttgtcccttttcacttcctgcagaacaagcctgggttagag<br>ggtctgctggaaatggcctttgaagaccaaggataccaggatgtgtgcactctgtcgtgttctg<br>tgatgaatgggaaacgtaggcttccagaaagccagctctcttctgaaatgtgacggacctaag<br>caggaagtcatccaggacaggagtggctcagtgttggggatggacgctgtcgcccagccat<br>gctccaccagggccaccaatgtgtagttggctggtggtcttcgggcatgtgagacctgctcttc<br>actgtttccaccccacttggtggcctccaggatggtagtggcaccctcagagccccatcttcag<br>catgttctgaagcctcagagtggaaattcctgctaaggctctgtgtggacgcctttctcccgtga<br>tctaaaggggacactgtactcaagcttttgacctcatgccttgtgtagtaaaaaaggatttgggg<br>gttttgtttggttcctgagagggttgtgttttgtttttgtttccttttgtttatgttttggcctttcctctttg<br>tctttccatgtagaccagatatttgaaagggcagacgatggctagaggtgtaatgtgcagcttgt<br>ttatacggtatttgggaaacttaccttggatgggaaatcgaatcgtggattcaccaggccggtg<br>ctggcacactcaccctcgccctttccctccggttcagtacctattgtttctcctttcaaatatgtgat<br>tgtactagctctttccatatgaaagaattctccttatttaaataaaaaaagtttaaaaa | |
| DOPEY2 | NM_005128.3 | tcccacagtgcctggcccagaagccttgctaaatatttgaacaggattgcccaatacttttctgct<br>gtgagaatgtaagatggatccagaagagcaggagctcttaaatgattacagatacagaagcta<br>ctcttcagtgattgaaaaggctttgagaaattttgagtcctcgagtgaatgggcggatctcatatc<br>ttcacttggcaaactcaacaaggctcttcagagtaacctgaggtactccttgttgccaagacgg<br>ctcctcatcagcaaaagattagctcagtgtttgcaccctgccctgcccagtggtgtccacttaaa<br>agctctggaaacctacgagattatctttaaaatcgtggggaccaaatggctggccaaggactt<br>gtttctgtacagctgcgggttatttcctctcctggcacacgcggcggtgtcggtgaggccggtg<br>ctgctcaccctgtacgagaagtacttcctcccactgcagaagctgctcctgcccagtctgcag<br>gccttcatcgtgggcctgctgcccggccttgaagagggctccgagatctccgacagaacgg<br>atgctctgctcctgagactgtcgctggtggttggcaaagaggtgttttacaccgccctctgggg<br>gagcgtcctggccagcccgtccatccgcctccctgcctcagtcttcgtggtgggccacatcaa<br>cagggatgcccccggccgggagcagaagtacatgctggggaccaatcaccaactcacggt<br>gaagtctttgcgtgcctccctgttggactcaaatgttcttgtgcaaagaaataatctggaaatcgt<br>tctgtttttcttcccatttatacctgtctggattccaatgagagagccatcccccctcctcagatctg<br>acatcgtgcgcattctctcagccgccacccagaccctactgagaagggacatgtccctgaac<br>agaagactgtatgcatggttactaggctcagacataaaaggaaataccgttgtgccagaatct<br>gaaatctcaaattcttatgaagaccagtcgtcttatttttttgaaaaatactccaaggatcttttagtt | 43 |

TABLE 1-continued

Prostate Cancer Biomarker/Housekeeper Sequence Information

| Gene Name | RefSeq Accession | Sequence | SEQ ID NO: |
|---|---|---|---|
| | | gagggtttggctgagatattgcatcagaagttcatagatgctgacgtggaggaacgccatcat | |
| | | gcatacctgaagccttttcgcgtcctcatcagtctgcttgacaagccagaaatagggcctcaag | |
| | | tggttgggaatttgtttctcgaagtcatcagggccttttattcttactgcagagatgcccttggctc | |
| | | tgatcttaaacttagctacacccagagtggaaattcgctgataagtgcaatcaaggaaaacaga | |
| | | aatgcctctgagattgtcaaaacggtaaatttgctgataacttctctaagcacagactttctctgg | |
| | | gattatatgacaaggtgttttgaggaatgctttagaccagtgaagcagcgttacagcgtgagga | |
| | | acagcgtcagccctcccccacggtctcggagctctgcgccctcctggtcttcctgctggatg | |
| | | tcattcctttggaactttactctgaggtgcaaacccagtatctccctcaggtgctcggctgcctg | |
| | | gtgcagcctcttgctgaggacatggaggccttaagtttacctgaactcacgcatgccttgaaga | |
| | | cgtgtttcaaggtgctcagcaaagtccagatgcctccttcctacctcgacacggagtccacca | |
| | | gcggaacctcgagtccagtaaaaggtgaaaacggcaaaataattttggaaacaaaggcagtg | |
| | | attcccggtgacgaagatgcttcgtttcccctctgaagtctgaggacagtgggatcgggctc | |
| | | agtgcctcgtcaccggagctctctgagcacttgagggttcctcgagtttctctggaaagggac | |
| | | gacgtttggaagaagggcgggagcatgcagaggacgtttctttgcatccaagagctaatcgc | |
| | | caactttgccagcaagaacattttggagtacagctgacagcgtcaggagaagaaagcaagt | |
| | | ccgaggagcctgcagggaagagggacagggatgggacgcagagcctggcagccaatgat | |
| | | tccagcaggaagaactcttgggagcccaagcccatcactgtgcctcagttcaagcagatgct | |
| | | gtcagacttgttcacagcacgagggtctccattcaagacaaaaagttcagagtcaccatcgtct | |
| | | tcgcccagcagccctgccaggaaaaacgggggagaatgggatgttgagaaggtggtcattg | |
| | | acctggggggttccagggaggaacgcagggaggcctttgccgccgcctgccacctgctgct | |
| | | ggattgtgccactttccctgtctacctgtccgaggaagagaccgagcagctctgtgcaacgct | |
| | | cttccagctgccaggagccggtgattccagttttccatcttggctgaagtccctcatgactatttg | |
| | | ctgctgtgtgactgactgctacctccagaacgtggccatttccactctgctggaagtgataaac | |
| | | cattcccagtccctggcgcttgtcattgaagacaagatgaaacgctataagagctctggacac | |
| | | aacccttttttggcaagctgcagatggtgacggttcctcccattgctccagggatattgaaagt | |
| | | cattgcagagaaaacagatttctatcagagggtggctcgtgtgctttggaatcagctgaacaaa | |
| | | gagacccgggagcatcacgtcacctgcgtagaattgttctaccggctgcactgcctggcccct | |
| | | acggccaacatctgcgaggacatcatctgccatgccctcctggaccctgacaagggaacaa | |
| | | ggctggaagctctgtttagattttccgtgatctggcatctgacaagagagatccaaggcagtcg | |
| | | agtaacatctcacaatcgctcctttgataggtccttgtttgtcgtgctggacagcctggcctgca | |
| | | cggatggtgccatcggtgcggcagcccagggctggctggtgcgtgcgctctccctcgggga | |
| | | cgtggctcgcatcctcgaacccgtgctcctgctgctgctgcagccaaaaacccagagaacct | |
| | | ccatccactgcctcaagcaggagaactcggccgatgacttgcaccgttggtttaacaggaag | |
| | | aaaacctctttcagagaggcatgcgcagtgcccgagcctcaggagagcggctctgaagagc | |
| | | acctgcctctgagccagttcaccacagtggaccgtgaagccatttgggccgaagtggagaag | |
| | | gagcccgagaagtacccgctgcgaggcgagctgagcgaggaagagctgccctactacgtg | |
| | | gagcttccagacaggacggcccacggcgccccggacagcagcgagcacaccgagtctgc | |
| | | agatacaagctcctgccacacggacagcgagaacacgtcctccttctcctcccttcccacga | |
| | | cctgcaggagctgagcaacgaagagaactgctgtgcacccatccccatgggggcagggc | |
| | | gtaccccaagcgctcggccctgctggcggccttccagtcagaaagcttcaaggctggggcc | |
| | | aagttaagcctggtgcgggtggactcggacaagacgcaggcttctgagtcgttctccagcga | |
| | | cgaggaggcggacttggagctccaggccctcaccacatccaggctgctaaagcagcagcg | |
| | | ggaaaggcaggaggccgtcgaggccttgttcaagcacatcctgctctacctgcagccctacg | |
| | | actctcggcgggtcctctatgccttctcggtgctggaggctgtgctcaaaaccaaccctaagg | |
| | | aattcatcgaggctgtgtccaggactagcatggataccagctccaccgcgcacctcaacctca | |
| | | tctccaacctcctcgctcgccaccaggaggccctcattggccagagtttctacggaaagctcc | |
| | | agacccaggtccccaacgtgtgcccccactctctgctcctggagctgctcacctacctctgcct | |
| | | gagcttcctgcgctcctactacccttgctatttgaaggtctcgcaccgagacattctcggcaacc | |
| | | gggacgtgcaggtcaaaagtgtcgaggttttgatcaggataatgatgcagctggtctcagtgg | |
| | | ccaagtcttcggaagggaagaacgtggagttcatccacagcttgctgcagaggtgcaaagtt | |
| | | caggagtttgtcctgctctccctgtcggcgtccatgtacacgagccagaagcgctacgggctg | |
| | | gccaccgcccaccacggcagggccctgccagaggacagcctctttgaggagagtctcatta | |
| | | acttgggtcaggaccagatctggagtgagcacccgctgcagattgagctgctgaagctgctg | |
| | | caggtgctgattgtcttggaacaccacctgggtcgggcccatgaggaggcggaaaaccagc | |
| | | ccgacctgtcccgggagtggcagagagccctgaacttccagcaggccatcagcgccctgca | |
| | | gtacgtgcagccccacccctcacctcccagggtcttctggtctctgcggtggtgaggggtct | |
| | | gcagcccgcctacggttacggcatgcatccggcctgggtgagcttggtcacgcattccttgcc | |
| | | ctacttcggaaagtccctgggctggacggtgacaccctttgttgtccagatttgcaaaaacttg | |
| | | gatgacttggtcaagcagtatgaaagcgaatctgtgaagctctctgtcagcacaacctccaag | |
| | | agggaaaacatttctccagattatccactcacccttctagaaggtctaacgaccattagtcattttt | |
| | | gtcttttggaacaagccaaccaaaacaaaaagaccatggctgcaggtgatcctgccaacttga | |
| | | ggaatgccagaaatgccattttggaagagctgcctcgaactgttaacaccatggcccttctctg | |
| | | gaatgttctcagaaaggaggagactcaaaagagacctgtcgatctcctaggggccacgaag | |
| | | ggatcctcttccgtttactttaaaaccaccaaaaccataagacaaaaaattttagacttcttaaac | |
| | | cccttgacggcccatcttggggttcagttgacagcggctgttgcggcagtgtggagcagaaa | |
| | | gaaagcccagcgtcacagtaagatgaagattatcccaacggcaagtgcatcccagctaaccc | |
| | | ttgtcgacttggtgtgtgcactcagcaccctgcagactgacacgctgctgcacctggtgaagg | |
| | | aggtggtgaagaggccaccccaagtcaaagggggtgatgagaaatcgcccctagtggacat | |
| | | tcctgtgttgcagttttgctatgcttttctccaaaggctcccagtaccagccttgcaagagaacttt | |
| | | tcttcactgttgggagtattgaaagagtctgtacagttgaatctagccccacctgggtattttctg | |
| | | cttctcagcatgctgaatgactttgtaacaagaactcccaacctggaaaacaagaaggaccaa | |
| | | aaagacctgcaggaaatcactcagaaaatcctagaagctgtggggaacattgccggctcttcc | |
| | | ttggagcaaaccagctggctaagcagaaacctggaagtgaaggcccaacctcaggcctctct | |
| | | agaagaatctgatgctgaggaggacctgtatgatgctgctgcagcttcagcaatggtgtcttca | |

TABLE 1-continued

Prostate Cancer Biomarker/Housekeeper Sequence Information

| Gene Name | RefSeq Accession | Sequence | SEQ ID NO: |
|---|---|---|---|
| | | tccgccccgtcggtgtacagcgtgcaagccctctctctcctggcagaggtactggcttccctc<br>ctggacatggtttatcgaagtgatgagaaggagaaagctgtgccgttaatctcccgtctgcttta<br>ctatgtttttccatacttacgcaaccacagtgcctacaatgctcccagcttccgggctggcgctc<br>agctgctgagctccctgagtggctatgcctacacaaagcgagcctggaggaaggaggtcct<br>ggagctgtttctcgaccccgctttctttcagatggatacttcctgtgttcattggaagtccattattg<br>accatcttttgactcatgagaaaacaatgtttaaggatttaatgaacatgcagagcagttctttga<br>aactattctcaagttttgaacagaaagccatgctgttaaagcgccaggcttttgctgtcttcagtg<br>gagaacttgatcaataccacctttaccttccactgatacaagaacgcctgacagacaatctcag<br>agttggacagacatccatagttgctgctcagatgtttcttttttcagagttttgctgctaagaatat<br>ctcctcaacatttgacttcattgtggccaataatggtctctgaattgattcagacattcacacagct<br>tgaagaagatctaaaagatgaagatgagtcattgagaagcaccaacaaagtaaacagaacga<br>aagtttcagtcccggatgcaaatggaccctcagtggggagataccccagagtgaactcatct<br>tgtatttatcagcttgcaaattcttggacacagcgctttcttttccacctgacaagatgccattattt<br>caaatttataggtgggcatttattccagaagtggacacagagggccctgccttcctgtcggatg<br>tagaggagaatcaccaagaatgcaaaccccacactgtcaggattctagaacttctaaaattaaa<br>gtttggggaaatcagtagctctgatgagatcaccatgaagagtgaattcccgcttctgcgccaa<br>cattctgtttccagcatcaggcagttgatgccattcttcatgactctaaatggtgcatttaagaccc<br>agagacagctgcctgctgatagcccaggaactccattcttggactttcctgtcacagatagccc<br>aaggatcttaaaacaactggaagaatgcatcgaatatgattttctggaacatccagaatgttaac<br>catgtgagagagaatatgtttaatccatgtattggtactttactgaaaaccaggttatattctaaag<br>aagaaagaaggcaggatagtgcttttgaacaagcctatttccattttgaaagtagatttcaggct<br>aggtgcggtggctcacacctgtaatctcagcactttgggaggccaaggcaggcagatcactt<br>gaggtcaggagttcgagaccagcctgaccaacatggtgagaccctgtctctactaaaaataca<br>aaaattagctgggtgtggtggcggcgcctgtaatcccagctacttgggaggctaaggcatga<br>gaattgcttgaacccaggaggtggaggctgcagtgagccgagatcacgacactgcactcca<br>gctgtgtgacagaatgagaccatctccaaaaaaaaaaaaaagtagatttcagataatttactgtt<br>cagcaacaggacacacctccctaaatgccttgtaatatatttgaatctgattctgcatttcttcctc<br>aatttatgtaatgaaaataaaattaatatatcatctaacagtagcacaaaatttgtaatatgaagta<br>aagtatgaagataatgaagaagttgttttctttgttgaagcagttatatgggtctttctcagtatattt<br>ctcttttctctaaaagtttaaacttattaaaagaatgttatttttaacctttcaaaaaaaaaaa | |
| NDUFB11 | NM_019056.6 | gctctggccggccccggcgattggtcaccgcccgctaggggacagccctggcctcctctga<br>ttggcaagcgctggccacctccccacaccccttgcgaacgctcccctagtggagaaaagga<br>gtagctattagccaattcggcagggcccgctttttagaagcttgatttcctttgaagatgaaaga<br>ctagcggaagctctgcctctttccccagtgggcgagggaactcggggcgattggctgggaa<br>ctgtatccacccaaatgtcaccgatttcttcctatgcaggaaatgagcagacccatcaataaga<br>aatttctcagcctggccgaaaatggttggccccacgaagccacgacaactggaggcaaaga<br>gggttgctcaacgccccgcctcattggaaaaccaaatcagatctgggacctatatagcgtggc<br>ggaggcggggcgatgattgtcgcgctcgcacccactgcagctgcgcacagtcgcatttctttc<br>cccgcccctgagaccctgcagcaccatctgtcatggcggctgggctgtttggtttgagcgctc<br>gccgtcttttggcggcagcggcgacgcgagggctcccggccgcccgcgtccgctgggaat<br>ctagcttctccaggactgtggtcgccccgtccgctgtggcgggaaagcggcccccagaacc<br>gaccacaccgtggcaagaggacccagaacccgaggacgaaaacttgtatgagaagaaccc<br>agactcccatggttatgacaaggaccccgttttggacgtctggaacatgcgacttgtcttcttctt<br>tggcgtctccatcatcctggtccttggcagcacctttgtggcctatctgcctgactacaggtgca<br>cagggtgtccaagagcgtgggatgggatgaaagagtggtcccgccgcgaagctgagaggc<br>ttgtgaaataccgagaggccaatggccttcccatcatggaatccaactgcttcgaccccagca<br>agatccagctgccagaggatgagtgaccagttgctaagtggggctcaagaagcaccgccttc<br>cccacccccctgcctgccattctgacctcttctcagagcacctaattaaaggggctgaaagtctg<br>aaaaaaaaaaaaaaa | 44 |
| ND4 | NC_012920.1 | atgctaaaactaatcgtcccaacaattatattactaccactgacatgactttccaaaaaacacata<br>atttgaatcaacacaaccacccacagcctaattattagcatcatccctctactattttttaaccaaa<br>tcaacaacaacctatttagctgttccccaaccttttcctccgacccctaacaacccccctcctaa<br>tactaactacctgactcctacccctcacaatcatggcaagccaacgccacttatccagtgaacc<br>actatcacgaaaaaaactctacctctctatactaatctccctacaaatctccttaattataacattca<br>cagccacagaactaatcatattttatatcttcttcgaaaccacacttatccccaccttggctatcat<br>cacccgatgaggcaaccagccagaacgcctgaacgcaggcacatacttcctattctacaccc<br>tagtaggctcccttcccctactcatcgcactaatttacactcacaacaccctaggctcactaaac<br>attctactactcactctcactgcccaagaactatcaaactcctgagccaacaacttaatatgacta<br>gcttacacaatagcttttatagtaaagatacctctttacggactccacttatgactccctaaagcc<br>catgtcgaagccccatcgctgggtcaatagtacttgccgcagtactcttaaaactaggcggct<br>atggtataatacgcctcacactcattctcaacccccctgacaaaacacatagcctaccccttcctt<br>gtactatccctatgaggcataattataacaagctccatctgcctacgacaaacagacctaaaatc<br>gctcattgcatactcttcaatcagccacatagccctcgtagtaacagccattctcatccaaaccc<br>cctgaagcttcaccggcgcagtcattctcataatcgcccacgggcttacatcctcattactattct<br>gcctagcaaactcaaactacgaacgcactcacagtcgcatcataatcctctctcaaggacttca<br>aacttactcccactaatagcttttttgatgacttctagcaagcctcgctaacctcgccttacccccc<br>actattaacctactgggagaactctctgtgctagtaaccacgttctcctgatcaaatatcactctc<br>ctacttacaggactcaacatactagtcacagccctatactccctctacatatttaccacaacaca<br>atggggctcactcacccaccacattaacaacataaaaccctcattcacacgagaaaacaccct<br>catgttcatacacctatcccccattctcctcctatccctcaaccccgacatcattaccgggttttcc<br>tctt | 45 |

TABLE 1-continued

Prostate Cancer Biomarker/Housekeeper Sequence Information

| Gene Name | RefSeq Accession | Sequence | SEQ ID NO: |
|---|---|---|---|
| MORF4L1 | NM_001265603.1 | cggcgtgccctggggcggcgcgggcgcaggggcgcgtgcgcggcgggctgtcgttggct<br>ggagcagcggctgcgcgggtcgcggtgctgtgaggtctgcgggcgctggcaaatccggcc<br>caggatgtagagctggcagtgcctgacggcgcgtctgacgcggagttgggtggggtagag<br>agtagggggcggtagtcgggggtggtgggagaaggaggaggcggcgaatcacttataaat<br>ggcgccgaagcaggacccgaagcctaaattccaggaggttgggatgaatgggttccggag<br>agcagagtactcaaatacgtggacaccaatttgcagaaacagcgagaacttcaaaaagccaa<br>tcaggagcagtatgcagaggggaagatgagaggggctgccccaggaaagaagacatctg<br>gtctgcaacagaaaaatgttgaagtgaaaacgaaaaagaacaaacagaaaacacctggaaa<br>tggagatggtggcagtaccagtgagacccctcagcctcctcggaagaaaagggcccgggta<br>gatcctactgttgaaaatgaggaaacattcatgaacagagttgaagttaaagtaaagattcctg<br>aagagctaaaaccgtggcttgttgatgactgggacttaattaccaggcaaaaacagctcttttat<br>cttcctgccaagaagaatgtggattccattcttgaggattatgcaaattacaagaaatctcgtgg<br>aaacacagataataaggagtatgcggttaatgaagttgtggcagggataaaagaatacttcaa<br>cgtaatgttgggtacccagctactctataaatttgagagaccacagtatgctgaaattcttgcag<br>atcatcccgatgcacccatgtcccaggtgtatggagcgccacatctcctgagattatttgtacg<br>aattggagcaatgttggcttatacacctctggatgagaagagccttgctttattactcaattatctt<br>cacgatttcctaaagtacctggcaaagaattctgcaactttgttcagtgccagcgattatgaagt<br>ggctcctcctgagtaccatcggaaagctgtgtgagaggcactctcactcacttatgtttggatct<br>ccgtaaacacatttttgttcttagtctatctcttgtacaaacgatgtgctttgaagatgttagtgtata<br>acaattgatgtttgttttctgtttgattttaaacagagaaaaaataaaagggggtaatagctcctttt<br>ttcttctttctttttttttttcatttcaaaattgctgccagtgttttcaatgatggacaacagagggatat<br>gctgtagagtgttttattgcctagttgacaaagctgcttttgaatgctggtggttctattcctttgac<br>actacgcacttttataatacatgttaatgctatatgacaaaatgctctgattcctagtgccaaaggt<br>tcaattcagtgtatataactgaacacactcatccatttgtgcttttgtttttttttatggtgcttaaagta<br>aagagcccatcctttgcaagtcatccatgttgttacttaggcattttatcttggctcaaattgttgaa<br>gaatggtggcttgtttcatggtttttgtatttgtgtctaatgcacgttttaacatgatagacgcaatg<br>cattgtgtagctagttttctggaaaagtcaatcttttaggaattgtttttcagatcttcaataaattttt<br>ctttaaatttcaaagaacaaaaaaaaaaaaaaa | 46 |
| MRPL19 | NM_014763.3 | gtagtcttgacgtgagctagctggcatggcggcctgcattgcagcggggcactgggctgcaa<br>tgggcctaggccggagtttccaagccgccaggactctgctccccccgccggcctctatcgcc<br>tgcagggtccacgcggggcctgtccggcagcagagcactgggccttccgagcccggtgcg<br>ttccaaccgccgccgaaaccggtcatcgtggacaagcaccgccccgtggaaccggaacgc<br>aggttcttgagtcctgaattcattcctcgaaggggaagaacagatcctctgaaatttcaaataga<br>aagaaaagatatgttagaaaggagaaaagtactccacattccagagttctatgttggaagtatt<br>cttcgtgttactacagctgacccatatgccagtggaaaaatcagccagtttctggggatttgcat<br>tcagagatcaggaagaggacttggagctactttcatccttaggaatgttatcgaaggacaaggt<br>gtcgagatttgctttgaactttataatcctcgggtccaggagattcaggtggtcaaattagagaa<br>acggctggatgatagcttgctatacttacgagatgcccttcctgaatatagcacttttgatgtgaa<br>tatgaagccagtagtacaagagcctaaccaaaaagttcctgttaatgagctgaaagtaaaaatg<br>aagcctaagccctggtctaaacgctgggaacgtccaaattttaatattaaaggaatcagatttga<br>tctttgtttaactgaacagcaaatgaaagaagctcagaagtggaatcagccatggcttgaatttg<br>atatgatgagggaatatgatacttcaaaaattgaagctgcaatatggaaggaaattgaagcgtc<br>gaaaaggtcttgattctgagaatgaatttggttagttgcagaagatacattggctctaagaggat<br>atattttgagaccaatttaatttcatttataagaacatagtaattaagtgaactaagcattcattgtttt<br>attaatactttttttctaaaataaaacttgtacaccagtttattactctaaaaagagaattacacatgc<br>caaatggaccaatgtccatttgcttattggaggcaaagctacaatagaagtcagagcatcacca<br>gaatggtctttaatgagcatggaacctgagcaaagggaataggtgggatgaattttttttttaatt<br>gtgaaacaattcataagcacaatatgatttacagaataataaacattcatgtacccactatcaggt<br>taagaaatagaacatttattaatatgtaggaatgttaagaaataaaacatttaataagatctcaga<br>agactccagtaaatctgcaattgtatctctctcctttttaaatgtaaatatcatcttgacttgttaatta<br>ttcccttgcatttctttagtttactgccaacacatatattcttcaacaatatatttaattttgaaaaacc<br>tgaaaaaaaaaacctgttagcaagtataaaggggcagtattactattattgcatgaaggcttcaa<br>gggaaacgttacagtctttgggtcatagtctggcttcagcttcctctgagagtttacagaggcca<br>attttgagcaaattcatggctaaggttatgagtgagttctgctaaacagaaggctcaccacaag<br>gtatctggcaggattatactgggtagctggatgttgcagaaatgtggttagaggaagtaaactg<br>tttttgatgctcacagcatgatgaatcaaactctgtatcttaggattaggttaaaacaatacctttg<br>gtatgatatgagtgttgttgctgatccatgcagcatggattggaaagctggggtataagcacac<br>atgctaaagaaaaacatgtaatttggtccatactcacctggatatactgttcctcaggttaaaaaa<br>tacagtactatcctaaatcttgaaggcaactctcagcctatccattgagttaccttcagatctgcc<br>ctctggttcctagctgtcttgggactaacttctttcctgcgctcagctgttttctggattccatgtttt<br>ccattttattgagtactaacttgttttgctgcagcacatcctttggtagcttctagaggaagtttgtg<br>tggaggtaaaatttttgagaccttgcatgtctcatgtttgattgatactttatacgtttaggtaggag<br>gtaattttccttcaggactttaaaaatattgttgctccatttttctttgtttctattgttgtattgagaaatc<br>caatgccattttgatttccccatcataaatttcatgatgatgtgtcttggtgtgggtctatatttatcc<br>attgtattgggttttaggtgaacccttccagatagtaactcatttctgtcagttctgggaaacactt<br>agcattggttgatgatttattctctgctgctttgttctcccaactattatttggatgttggatatccag<br>cactgggtatctatttcttacctccctcccttgaccccagtctctgtttttagctctttagctcaatc<br>ttccaactctttgctattgtattttaaaatcttaagaccccttcttgatttgtagaagttccttttcttac<br>aaccaaaaagcctttatctatggatttgttcacagataaggggtattcaatatagtgtattttttttc<br>atttaaaattgtttgcgcatctatttcctccaaatttcttctgtatttattttttgttgtctatatttcagac<br>ttttccaggatatctgataatctttggctgtcttcttatggttgaaagagggactaaaaagcttgga<br>aagcctttgggttgtgggaaggggctgtctttaggattatctgaatgggctttttgggagtcccc<br>tcctccacatgaatattttggttttgtcagattccctagaatagaggcttccaatctccttcctgga | 47 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | ggggtctgtccaggaaggagattgtctaggggtctgtcagacagcagctttcagctacttcctt | |
| | | gatctttttcactaatgattatatagtcatctaactactgtcaacaagtaatagatatcctatccttca | |
| | | cttgtttagattatttgctgagataacctctcaaaagaacctctcaaaataaaaggttaacaagag | |
| | | cctatatcttatatttttcttctctttatcttgttagaagatagctattaaaacctgttctttttctgtcttg | |
| | | ataaacacacttcaatcttggtagaatggtagatgggacagtatattttaggacctaaagctctg | |
| | | caaatgtatgatcagcttgtaagtacaggtgctcaaaaacatgtaaacaatcatgctttttactct | |
| | | gtaggaatatctttaaaattcttgtgaattttccccagaagtaaagcaaatcttcccccagaaata | |
| | | aaattaaatgtgcataatctaaagcttttttttttttattgtggtaggatatatatataaaacataatttg | |
| | | ccattgtaaacattttaaatttacaagtcagaggcattaattacatcacaatgttgtgaaattattac | |
| | | tactatttccaaaatttctcatcaccccaaactgaaactctgtaactgttgagcaataacctcattc | |
| | | ctgtatctctcccaaccccaggtaacctcaaatctttctttttatctttgagacaaggtctcattctat | |
| | | cactcaggtaggagtgcagtggtgtgatcatagctcattgcagcctcaaaatcctgggctcaa | |
| | | gcaatcctccttgagtagctaagactataggcacacattaactgcgcctggctgattttgtttttttg | |
| | | tagagatgtggtcttgctatgtttcccatgctggtcttgagttcctggcctcaagcagtccttaag | |
| | | attcatccatgttgtggcatgtgtcagaatttcatttgtttttatgactaaataatattccattgtatgt | |
| | | atatacattttgttcatccatcttctgatgaacactgggatatgtctaccttttggctattgtgaataa | |
| | | tgctgcagtaaacattgacataacaagtatgtatttgattgcctgtttctaagttcttttgggtatac | |
| | | atcttgagtagaattgctagataatgtcatgttttatttctcttgtgatttcttcttcgatcccctggttg | |
| | | agtgtgttaatttctacatgtttatgaatttcccactgttttttgttattgatttccaagttcattccatt | |
| | | gtgattagagaagatacttagtatgattttaatgtttttgagaattggtgtgtggcctgatagatgg | |
| | | tctgtcctggagaatgttcctcatacacttgagcaaaatatttatcatgctattgttgactgtagtttt | |
| | | ctatatgtctcttaggtcaaggtggtttacaatgtgttaaggttctctttttttaaaaaaattttgcac | |
| | | agagtatctttttctatgtgttccatgtatttgtgtctttggagctatagtctcttgtagacagcatatc | |
| | | actatcttgttttgttttgtttttctgtccattctgccaatttctgccttttgattggaaaatttaatccat | |
| | | ttgcatttaaagtaattaaggaaggactttcttctaccatttaacacttcttctatatgtcatatactttt | |
| | | ttggcccctcatttcctctttatggccttcttttctgtttttttgtagtgaactagtctgattctctttcca | |
| | | ctcccctttgtgtatatttgttagatgttttatttgtggttgctatggggattatagttaacatcctaca | |
| | | cttaaaacaatctaatttaaactgataccaatttaccttcaatagcatacaaaatctctactcctgta | |
| | | aagctctgcccctgccccccttatgttattgatggcacaaattgcctaataaataatttatagttatt | |
| | | tgtatgagtttgtcttttaaatcatttaggaaataaaaagtggagttagaaaacagtatgatagtaa | |
| | | tactgacttttatatttgtcaatatatttatcttattttggatccttatttcattatatagatttgagttact | |
| | | gtctagtgcccttccatttcggcccaaaggattcccttatgcatttcttgcagggcaagtctaatt | |
| | | gtaataaactccctcagcttttgttttatctgagaatgtcttgatttctcccttatttttgatggataatt | |
| | | ttgccagatacatgaattttggtaacagtatttttctttcagcactttaaatatgtcatcccactacc | |
| | | ttctgacttcatggtttctcatgagatattagatgttataaaatttgaggattcctcattcttgatgag | |
| | | tcagttctgtcttattgcttttcggatttgctcagcttttgtcttttgacagtttgattataacgcggct | |
| | | cagtgtgggtctctgagtttatcccacttagagtttgttgagtttcttggagtcatagatttatgtctt | |
| | | ttatcaaattttggacatatttggctattatttcttcaatttttttcactgcttctttcttttccttctgaaat | |
| | | attcttaatgtatatgttggtctgtttgatgctgtctcaccagtttcttaggctgtgttctcttttgttcct | |
| | | cagacttgattattgcagttgcccttctttttattttttttcaagtttgttgattcttctccctgttcagatc | |
| | | aactgttgaactcctctagtgaatttatttcagttactgtacttttcagctccaagatttatctttggtt | |
| | | ccttttttataacgtctgtgtctttattgatattctcattttgttcatatgtctctttcttcctttagttctttgt | |
| | | ccatgttttcctttagctctttgggcttatttaagacaattgtttaaagtctttgcatagtaagtccaat | |
| | | gtctgtgtttcttcagggatggttttcattattttgttttcaatgagccatactttcctgtgtctttgtat | |
| | | gctgtctttttgttgttgaaaactgtatgtttgaacatcataacgtggtggccctgaaaatcagata | |
| | | ttcccccttcctgagagttagttttatttttattattgaagattgtagcagtctattgctacatgtgca | |
| | | gtcatttccaaactatttttgcaaagactgtattccttctgtgtgtcatcactgaagtctctgttcctt | |
| | | agtttgtgtttaatagtttgacatagatttccttgaaaggagttaaaactagcagaaaaatctctct | |
| | | cccagtctttccagtctttgtagattggttctgtgctgggcttttccattaatacttagccaggcttg | |
| | | tactgagcctaacaatcaggcccaaaagcgtagggtctttgcagatcttgtctgagcatgcttct | |
| | | tgctgtgtatgcacgtagttttctaaatctccctgtatgtgctgttgaatattctaatttcccaaaga | |
| | | aactcctttgcagcttttttctcacagaacatagatggtttttttggatatcttgaccatagtctttcgac | |
| | | ccaggtgtttgcggttgttagttcaccttacactttttttcaagcattgcctactgcttacgatgagtg | |
| | | ctctgtcaatcctttaagtagccccagacaggctaccagagacttaaacaagaatttgtaagttc | |
| | | tgctcagcttcctctagaaatggggatcagggtccaagacagaatgcagttgctgatttcaaga | |
| | | ctgctgcaacaccagggagcttgtgggggaagggcaagcagaaatgtcacaaagctttcttg | |
| | | ccattttaaagttgcctgttcttgactcagcatttgcttcattgctataaactttttactgtttttcagag | |
| | | ttctgataaaattggctatgcctgttcctgctttaaaaaatatatatatatttttttagggattggggtc | |
| | | tcactatactgaccaggctggtcttgaacttctggcctcaagccatcctctcatttcagcttccca | |
| | | aagtgctgcaattacacgcgtgaaccaccacacccagcccctgcttgtttttcaatgtgcctact | |
| | | ccaccatgttgctcaagtatgtatatttctaaactaccttgtagtgttgtgatgggaaataaatcc | |
| | | ctgagccttttgaataactcagagagatcaaaaacttagtttatcctattcgaaggattagaaaaa | |
| | | tgatatatctttcactttttcagggataggctcctcattagaaggctcctatgtgccgatgctgtac | |
| | | aagacatttcatttctcttaatgtttacaacaagcttgttgccaaggctgatcttgaactcctggcc | |
| | | tcaaacgatcctcccagctcagtctcacaaagtgttgggatgtctggccaactaatgactatctt | |
| | | aactcttgtgtttcaatgtttatgccttcttttatcttgactgattgtatgactatgtcttctagaacaat | |
| | | gttgaacagaaatggtgagagcagacatccttgctttaatatttcaccattatatatgatgttaggt | |
| | | atagatttttctcacagatgccttttatcagattgaggaatttatattcctactttgccgaaaggttttt | |
| | | gtagtatgagggggtgctgaattttgtcaaacactttttcggtaataattgagatgattggttctgc | |
| | | agtcatcgagatgtggattttctcctttattctgttcgtgagtgattacactggttgactaatgttaa | |
| | | aacaaccttactttccaggaataaaccctattatctttttttataca | |
| PSMC4 | NM_153001.2 | tgcgggtacggacagcgcatgagcttatgttgagggcggagcccagaccagcccttcgtcct | 48 |
| | | atcctgcccttccagcacctctcagccgtaacttaaactacacttcccagaagcctcctcagcc | |

TABLE 1-continued

| Prostate Cancer Biomarker/Housekeeper Sequence Information | | | |
|---|---|---|---|
| Gene Name | RefSeq Accession | Sequence | SEQ ID NO: |
| | | agggacttccgttgtcgtcagcggaagcggtgacagatcatcccaggccacacagaggccg<br>gcttggtcactatggaggagataggcatcttggtggagaaggctcaggatgagatcccagca<br>ctgtccgtgtcccggccccagaccggcctgtccttcctgggccctgagcctgaggacctgga<br>ggacctgtacagccgctacaaggaggaggtgaagcgaatccaaagcatcccgctggtcatc<br>ggacaatttctggaggctgtggatcagaatacagccatcgtgggctctaccacaggctccaac<br>tattatgtgcgcatcctgagcaccatcgatcgggagctgctcaagcccaacgcctcagtggcc<br>ctccacaagcacagcaatgcactggtggacgtgctgccccccgaagccgacagcagcatca<br>tgatgctcacctcagaccagaagccagatgtgatgtacgcggacatcggaggcatggacatc<br>cagaagcaggaggtgcgggaggccgtggagctcccgctcacgcatttcgagctctacaagc<br>agatcggcatcgatccccccgaggcgtcctcatgtatggcccacctggctgtgggaagacc<br>atgttggcaaaggcggtggcacatcacacaacagctgcattcatccgggtcgtgggctcgga<br>gtttgtacagaagtatctgggtgagggccccgcatggtccgggatgtgttccgcctggccaa<br>ggagaatgcacctgccatcatcttcatagacgagattgatgccatcgccaccaagagattcga<br>tgctcagacaggggccgacagggaggttcagaggatcctgctggagctgctgaatcagatg<br>gatggatttgatcagaatgtcaatgtcaaggtaatcatggccacaaacagagcagacaccctg<br>gatccggccctgctacggccaggacggctggaccgtaaaattgaatttccacttcctgaccgc<br>cgccagaagagattgatttctccactatcactagcaagatgaacctctctgaggaggttgactt<br>ggaagactatgtggcccggccagataagatttcaggagctgatattaactccatctgtcagga<br>gagtggaatgttggctgtccgtgaaaaccgctacattgtcctggccaaggacttcgagaaagc<br>atacaagactgtcatcaagaaggacgagcaggagcatgagttttacaagtgacccttcccttc<br>cctccaccacaccactcaggggctggggcttctctcgcacccccagcacctctgtcccaaaa<br>cctcattccctttttttctttacccaggattggtttcttcaataaatagataagatcgaatccatttaatt<br>tcttcttagaagtttaactcctttggagaatgtgggccttgaataggatcctctgggtccctcttaa<br>tctgacagatgagcagacgaggtgcatggcctgggttgcagcttgagagaaccaaaatattc<br>aaaccagatgacttccaaaatgtggggaaagggatggaaaatgaacctgagatggagtcctt<br>aatcacgggataaagccctgtgcatctccctcatttcctacaggtaaaagacagtaaagaaatt<br>caggtcacaggccttgggagttcataggaaggagatgtccagtgctgtccagtagaacttt | |
| SF3A1 | NM_005877.5 | ggtcccggaagtgcgccagtcgtaccttcgcggccgcaactcgctcggccgccgccatcttg<br>cgagctcgtcgtactgaccgagcggggaggctgtcttgaggcggcaccgctcaccgacacc<br>gaggcggactggcagccctgagcgtcgcagtcatgccggccggacccgtgcaggcggtg<br>cccccgccgccgcccgtgcccacggagcccaaacagcccacagaagaagaagcatcttca<br>aaggaggattctgcaccttctaagccagttgtggggattatttaccctcctccagaggtcagaa<br>atattgttgacaagactgccagctttgtggccagaaacgggcctgaatttgaagctaggatccg<br>acagaacgagatcaacaaccccaagttcaactttctgaaccccaatgacccttaccatgcctac<br>taccgccacaaggtcagcgagttcaaggaagggaaggctcaggagccgtccgccgccatc<br>cccaaggtcatgcagcagcagcagcagaccacccagcagcagctgccccagaaggtccaa<br>gcccaagtaatccaagagaccatcgtgcccaaagagcctcctcctgagtttgagttcattgctg<br>atcctccctctatctcagccttcgacttggatgtggtgaagctgacggctcagtttgtggccagg<br>aatgggcgccagtttctgacccagctgatgcagaaagagcagcgcaactaccagtttgacttt<br>ctccgcccacagcacagcctcttcaactacttcacgaagctagtggaacagtacaccaagatc<br>ttgattccacccaaaggtttattttcaaagctcaagaaagaggctgaaaacccccgagaagtttt<br>ggatcaggtgtgttaccgagtggaatgggccaaattccaggaacgtgagaggaagaaggaa<br>gaagaggagaaggagaaggagcgggtggcctatgctcagatcgactggcatgattttgtggt<br>ggtggaaacagtggacttccaacccaatgagcaagggaacttccctcccccccaccacgcca<br>gaggagctgggggcccgaatcctcattcaggagcgctatgaaaagtttggggagagtgagg<br>aagttgagatggaggtcgagtctgatgaggaggatgacaaacaggagaaggcggaggagc<br>ctccttcccagctggaccaggacacccaagtacaagatatggatgagggttcagatgatgaa<br>gaagaagggcagaaagtgcccccacccccagagacacccatgcctccacctctgcccccca<br>actccagaccaagtcattgtccgcaaggattatgatcccaaagcctccaagcccttgcctcca<br>gcccctgctccagatgagtatcttgtgtcccccattactggggagaagatccccgccagcaaa<br>atgcaggaacacatgcgcattggacttcttgaccctcgctggctggagcagcgggatcgctc<br>catccgtgagaagcagagcgatgatgaggtgtacgcaccaggtctggatattgagagcagct<br>tgaagcagttggctgagcggcgtactgacatcttcggtgtagaggaaacagccattggtaag<br>aagatcggtgaggaggagatccagaagccagaggaaaaggtgacctgggatggccactca<br>ggcagcatggcccggacccagcaggctgcccaggccaacatcaccctccaggagcagatt<br>gaggccattcacaaggccaaaggcctggtgccagaggatgacactaaagagaagattggcc<br>ccagcaagcccaatgaaatccctcaacagccaccgccaccatcttcagccaccaacatcccc<br>agctcggctccacccatcacttcagtgccccgaccacccacaatgccacctccagttcgtact<br>acagttgtctccgcagtacccgtcatgccccggcccccaatggcatctgtggtccggctgccc<br>ccaggctcagtgatcgcccccatgccgcccatcatccacgcgcccagaatcaacgtggtgcc<br>catgcctccctcggcccctcctattatggcccccgcccacccccccatgattgtgccaacagc<br>ctttgtgcctgctccacctgtggcacctgtcccagctccagccccaatgccccctgtgcatccc<br>ccacctcccatggaagatgagcccacctccaaaaaactgaagacagaggacagcctcatgc<br>cagaggaggagttcctgcgcagaaacaagggtccagtgtccatcaaagtccaggtgcccaa<br>catgcaggataagacggaatggaaactgaatgggcaggtgctggtcttcaccctcccactca<br>cggaccaggtctctgtcattaaggtgaagattcatgaagccacaggcatgcctgcagggaaa<br>cagaagctacagtatgagggtatcttcatcaaagattccaactcactggcttactacaacatgg<br>ccaatggcgcagtcatccacctggccctcaaggagagaggcgggaggaagaagtagacaa<br>gaggaacctgctgtcaagtccctgccattttgcctctcctgtctcccacccccctgccccagacc<br>caggagccccccctgaggctttgccttgcctgcatatttgtttcgctcttactcagtttgggaattca<br>aattgtcctgcagaggttcattcccctgaccctttccccacattggtaagagtagctgggttttct<br>aagccactctctggaatctctttgtgttagggtctcgatttgaggacattcatttcttcagcagccc<br>attagcaactgagagcccagggatgtcctacaggatagtttcatagtgacaggtggcacttgg | 49 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | ctaatagaatatggctgatattgtcattaatcattttgtaccttgacatgggttgtctaataaaactc<br>ggacccttcttgtgaaatcagttaaataagacttgtctcggtcacctgtgccctgtccagactcg<br>aggcagtggtaacactgcacagtgctatgtggcttctctttgaggattttgggttttgtaactaaa<br>ttcttgctgccctcatactttttatgtattagaatcatattcgtattgcccttttaaaacattgggatcc<br>tccaaaggcctgccccatgtatttaacagtaatacaggaagcatggcaggcaccatgcaaac<br>caaggatggatggtgcagtccctgtgtcagtgggcggtggtttcctgctggcctggaatcact<br>catcacctgattgattggctctgtggtcctgggcaggtgcctcataggtgtgtggatatgatgac<br>gtttctttaaaatgtatgtatttaacaaatacttaattgtattaaggtcatgtaccaaggatttgataa<br>agtttaaataatttactctctacttttatccattttatccattttaactcatgtaatcctcatgtgagtatt<br>cctgtttaacacttgagtaaactgaggcacagagaacataagttgcatgccatagtcacacact<br>gtgaaagtgaaaagagaatgtgtgcaaaacacgtcacagtcctggtttctgagtaaaggcag<br>gctgttatctttagaatcaagctatcacagggagataggcaatgctgtgggtgttggaggaag<br>gtgagagcctgttgctaacaatttcctggttttaaagctaaggctgattttattgggaagatctca<br>catgtgtgtggcccctgagagttcccagtgccttttatttgcagtccttccatttggacctcctagc<br>tgccccatcaggtcatctccagggctcagaggggtgagaccatttcccaaggtcacagaacc<br>agctctctagtcaccaccctgcctctccctctcacccagagtcagtaccagttttatggctttatta<br>caaactgctgggtccctcccattttcaacttgattgatgggatgtcatcccttatcctgtctgacat<br>ttgcctctggcctggttgctagaagtttgccccaggggcaagagttgaaatttggcttcctgag<br>gtgggctttgtggtttgcgtccctaaagtgagcccactactggttgcttgtccatggccaacacc<br>agaaatcccctgagcactacctgggtctcattccaagaaggaagagggtcaggagacctgg<br>ggagtctcatattccaagttcttctttctttctgggagcagtgggcagttcatggtgttagggcac<br>tcacccccacagactggcaaaccctgcaggacttccgtggctgaggctgtgaccggaggcc<br>aggaatgccgttgggtggattgtgagtgaatgggccctttgagctgccctctagagagcaaat<br>ccagtttcctggagctcctgaatgaatatctgtactggctcgctcagatgcagaagctccattga<br>ccatgaggccttgtgaacatcagtggccacaggcccagtgtgctgcttggcactgcactagttt<br>aggacctgcagcatgtaggtagcgtcctagtgtttataatacaaagctgctctgcacagcttttc<br>tgattcttcttgcaatctcctgaggattatctgccccatttttaaaacgaggtggaatacccaagg<br>tcatgtagccagtgagtgctctggaaagccaaagcagctcatcccttcctggggaccacactg<br>ctctgctccaccagaccacactatgaaataggaataagtgctcctgttgcaggactgctggga<br>aaacaggtggtgtgggacttaagtcaccataattttgaagacttgcatgcagagggctccagg<br>aattgtagacattaaggaatttcactttcagttctacccactacttaagtacttgtcatgtactctta<br>gaggaggccagtaatgatcagaaccattttactttaaaattaataatattgtattagagaatatatt<br>aaatggttatattgggttatgttaggatatatacttgaatggaaatacatgtactattagcaatcata<br>tttcatttatccctgtaattagacaagaaagcataatatagctctactcatgggtacacataccagt<br>gtataagatttttagaagtttactttttaaaaataaaagcaaaatgtaagatcttaaaaaaaaaaaa<br>aaaaaa | |
| PUM1 | NM_001020658.1 | agtgggccgccatgttgtcggagtgaaaggtaagggggagcgagagcgccagagagaga<br>agatcggggggctgaaatccatcttcatcctaccgctccgcccgtgttggtggaatgagcgtt<br>gcatgtgtcttgaagagaaaagcagtgctttggcaggactctttcagcccccacctgaaacatc<br>accctcaagaaccagctaatcccaacatgcctgttgttttgacatctggaacagggtcgcaagc<br>gcagccacaaccagctgcaaatcaggctcttgcagctgggactcactccagccctgtcccag<br>gatctataggagttgcaggccgttcccaggacgacgctatggtggactacttctttcagaggc<br>agcatggtgagcagcttgggggaggaggaagtggaggaggcggctataataatagcaaac<br>atcgatggcctactggggataacattcatgcagaacatcaggtgcgttccatggatgaactga<br>atcatgattttcaagcacttgctctggagggaagagcgatgggagagcagctcttgccaggta<br>aaaagttttgggaaacagatgaatccagcaaagatggaccaaaaggaatattcctgggtgatc<br>aatggcgagacagtgcctggggaacatcagatcattcagtttcccagccaatcatggtgcaga<br>gaagacctggtcagagtttccatgtgaacagtgaggtcaattctgtactgtccccacgatcgga<br>gagtgggggactaggcgttagcatggtggagtatgtgttgagctcatccccgggcgattcctg<br>tctaagaaaaggaggatttggcccaagggatgcagacagtgatgaaaacgacaaaggtgaa<br>aagaagaacaagggtacgtttgatggagataagctaggagatttgaaggaggagggtgatgt<br>gatggacaagaccaatggtttaccagtgcagaatgggattgatgcagacgtcaaagattttag<br>ccgtaccccctggtaattgccagaactctgctaatgaagtggatcttctgggtccaaaccagaat<br>ggttctgagggcttagcccagctgaccagcaccaatggtgccaagcctgtggaggatttctcc<br>aacatggagtcccagagtgtccccttggaccccatggaacatgtgggcatggagcctcttca<br>gtttgattattcaggcacgcaggtacctgtggactcagcagcagcaactgtgggactttttgact<br>acaattctcaacaacagctgttccaaagacctaatgcgcttgctgtccagcagttgacagctgc<br>tcagcagcagcagtatgcactggcagctgctcatcagccgcacatcggtttagctcccgctgc<br>gtttgtccccaatccatacatcatcagcgctgctcccccagggacggacccctacacagctgg<br>attggctgcagcagcgacactaggcccagctgtggtccctcaccagtattatggagttactcc<br>ctggggagtctaccctgccagtcttttccagcagcaagctgccgctgccgctgcagcaactaa<br>ttcagctaatcaacagaccaccccacaggctcagcaaggacagcagcaggttctccgtgga<br>ggagccagccaacgtcctttgaccccaaaccagaaccagcagggacagcaaacggatccc<br>cttgtggcagctgcagcagtgaattctgcccttgcatttggacaaggtctggcagcaggcatg<br>ccaggttatccggtgttggctcctgctgcttactatgaccaaactggtgcccttgtagtgaatgc<br>aggcgcgagaaatggtcttggagctcctgttcgacttgtagctcctgccccagtcatcattagtt<br>cctcagctgcacaagcagctgttgcagcagccgcagcttcagcaaatggagcagctggtggt<br>cttgctggaacaacaaatggaccatttcgccctttaggaacacagcagcctcagccccagccc<br>cagcagcagcccaataacaacctggcatccagttctttctacggcaacaactctctgaacagc<br>aattcacagagcagctccctcttctcccagggctctgcccagcctgccaacacatccttgggat<br>tcggaagtagcagttctctcggcgccaccctgggatccgcccttggagggtttggaacagca<br>gttgcaaactccaacactggcagtggctcccgccgtgactccctgactggcagcagtgacctt<br>tataagaggacatcgagcagcttgacccccattggacacagtttttataacggccttagcttttc | 50 |

TABLE 1-continued

Prostate Cancer Biomarker/Housekeeper Sequence Information

| Gene Name | RefSeq Accession | Sequence | SEQ ID NO: |
|---|---|---|---|
| | | ctcctctcctggacccgtgggcatgcctctccctagtcagggaccaggacattcacagacacc<br>acctccttccctctcttcacatggatcctcttcaagcttaaacctgggaggactcacgaatggca<br>gtggaagatacatctctgctgctccaggcgctgaagccaagtaccgcagtgcaagcagcgc<br>ctccagcctcttcagcccgagcagcactcttttctcttcctctcgtttgcgatatggaatgtctgat<br>gtcatgccttctggcaggagcaggcttttggaagattttcgaaacaaccggtaccccaatttac<br>aactgcgggagattgctggacatataatggaattttcccaagaccagcatgggtccagattcat<br>tcagctgaaactggagcgtgccacaccagctgagcgccagcttgtcttcaatgaaatcctcca<br>ggctgcctaccaactcatggtggatgtgtttggtaattacgtcattcagaagttctttgaatttggc<br>agtcttgaacagaagctggctttggcagaacggattcgaggccacgtcctgtcattggcacta<br>cagatgtatggctgccgtgttatccagaaagctcttgagtttattccttcagaccagcaggtaatt<br>aatgagatggttcgggaactagatggccatgtcttgaagtgtgtgaaagatcagaatggcaat<br>cacgtggttcagaaatgcattgaatgtgtacagccccagtctttgcaatttatcatcgatgcgttt<br>aagggacaggtatttgccttatccacacatccttatggctgccgagtgattcagagaatcctgg<br>agcactgtctccctgaccagacactccctattttagaggagcttcaccagcacacagagcagc<br>ttgtacaggatcaatatggaaattatgtaatccaacatgtactggagcacggtcgtcctgaggat<br>aaaagcaaaattgtagcagaaatccgaggcaatgtacttgtattgagtcagcacaaatttgcaa<br>gcaatgttgtggagaagtgtgttactcacgcctcacgtacggagcgcgctgtgctcatcgatg<br>aggtgtgcaccatgaacgacggtccccacagtgccttatacaccatgatgaaggaccagtat<br>gccaactacgtggtccagaagatgattgacgtggcggagccaggccagcggaagatcgtca<br>tgcataagatccggccccacatcgcaactcttcgtaagtacacctatggcaagcacattctggc<br>caagctggagaagtactacatgaagaacggtgttgacttagggcccatctgtggccccctaa<br>tggtatcatctgaggcagtgtcacccgctgttccctcattcccgctgacctcactggcccactg<br>gcaaatccaaccagcaaccagaaatgttctagtgtagagtctgagacgggcaagtggttgctc<br>caggattactccctcctccaaaaaaggaatcaaatccacgagtggaaaagcctttgtaaattta<br>attttattacacataacatgtactatttttttaattgactaattgccctgctgttttactggtgtatagg<br>atacttgtacataggtaaccaatgtacatgggaggccacatattttgttcactgttgtatctatattt<br>cacatgtggaaactttcagggtggttggtttaacaaaaaaaaaaagctttaaaaaaaaaagaaa<br>aaaaggaaaaggtttttagctcatttgcctggccggcaagttttgcaaatagctcttccccacct<br>cctcattttagtaaaaaacaaacaaaaacaaaaaaacctgagaagtttgaattgtagttaaatga<br>ccccaaactggcatttaacactgtttataaaaaatatatatatatatatatatatatataatgaaaaa<br>ggtttcagagttgctaaagcttcagtttgtgacattaagtttatgaaattctaaaaaatgccttttttg<br>gagactatattatgctgaagaaggctgttcgtgaggaggagatgcgagcacccagaacgtctt<br>ttgaggctgggcgggtgtgattgtttactgcctactggatttttttctattaacattgaaaggtaaa<br>atctgattatttagcatgagaaaaaaaaatccaactctgcttttggtcttgcttctataaatatatag<br>tgtatacttggtgtagactttgcatatatacaaatttgtagtattttcttgttttgatgtctaatctgtat<br>ctataatgtaccctagtagtcgaacatacttttgattgtacaattgtacatttgtatacctgtaatgta<br>aatgtggagaagtttgaatcaacataaacacgtttttttggtaagaaaagagaattagccagccc<br>tgtgcattcagtgtatattctcaccttttatggtcgtagcatatagtgttgtatattgtaaattgtaattt<br>caaccagaagtaaattttttttcttttgaaggaataaatgttctttatacagcctagttaatgtttaaaa<br>agaaaaaaatagcttggttttatttgtcatctagtctcaagtatagcgagattctttctaaatgttatt<br>caagattgagttctcactagtgtttttttaatcctaaaaaagtaatgttttgattttgtgacagtcaaa<br>aggacgtgcaaaagtctagccttgcccgagctttccttacaatcagagcccctctcaccttgta<br>aagtgtgaatcgcccttccctttttgtacagaagatgaactgtattttgcattttgtctacttgtaagt<br>gaatgtaacatactgtcaattttccttgtttgaatatagaattgtaacactacacggtgtacatttcc<br>agagccttgtgtatatttccaatgaactttttttgcaagcacacttgtaaccatatgtgtataattaac<br>aaacctgtgtatgcttatgcctgggcaactattttttgtaactcttgtgtagattgtctctaaacaat<br>gtgtgatctttattttgaaaaatacagaactttggaatctgaaaaaaaaaaaaaaaaaaaaaaa<br>aaaaaaa | |
| ACTB | NM_001101.4 | gagtgagcggcgcggggccaatcagcgtgcgccgttccgaaagttgccttttatggctcgag<br>cggccgcggcggcgccctataaaacccagcggcgcgacgcgccaccaccgccgagacc<br>gcgtccgccccgcgagcacagagcctcgcctttgccgatccgccgcccgtccacacccgcc<br>gccagctcaccatggatgatgatatcgccgcgctcgtcgtcgacaacggctccggcatgtgc<br>aaggccggcttcgcgggcgacgatgccccccgggccgtcttcccctccatcgtggggcgcc<br>ccaggcaccagggcgtgatggtgggcatgggtcagaaggattcctatgtgggcgacgagg<br>cccagagcaagagaggcatcctcaccctgaagtaccccatcgagcacggcatcgtcaccaa<br>ctgggacgacatggagaaaatctggcaccacaccttctacaatgagctgcgtgtggctcccg<br>aggagcaccccgtgctgctgaccgaggcccccctgaaccccaaggccaaccgcgagaag<br>atgacccagatcatgtttgagaccttcaacaccccagccatgtacgttgctatccaggctgtgct<br>atccctgtacgcctctggccgtaccactggcatcgtgatggactccggtgacggggtcaccc<br>acactgtgcccatctacgaggggtatgccctcccccatgccatcctgcgtctggacctggctg<br>gccgggacctgactgactacctcatgaagatcctcaccgagcgcggctacagcttcaccacc<br>acggccgagcgggaaatcgtgcgtgacattaaggagaagctgtgctacgtcgccctggactt<br>cgagcaagagatggccacggctgcttccagctcctccctggagaagagctacgagctgcct<br>gacggccaggtcatcaccattggcaatgagcggttccgctgccctgaggcactcttccagcct<br>tccttcctgggcatggagtcctgtggcatccacgaaactaccttcaactccatcatgaagtgtg<br>acgtggacatccgcaaagacctgtacgccaacacagtgctgtctggcggcaccaccatgtac<br>cctggcattgccgacaggatgcagaaggagatcactgccctggcacccagcacaatgaaga<br>tcaagatcattgctcctcctgagcgcaagtactccgtgtggatcggcggctccatcctggcctc<br>gctgtccaccttccagcagatgtggatcagcaagcaggagtatgacgagtccggcccctcca<br>tcgtccaccgcaaatgcttctaggcggactatgacttagttgcgttacaccctttcttgacaaaac<br>ctaacttgcgcagaaaacaagatgagattggcatggctttatttgtttttttttgttttgttttggtttttt<br>tttttttttggcttgactcaggatttaaaaactggaacggtgaaggtgacagcagtcggttggag<br>cgagcatcccccaaagttcacaatgtggccgaggactttgattgcacattgttgtttttttaatagt | 51 |

TABLE 1-continued

Prostate Cancer Biomarker/Housekeeper Sequence Information

| Gene Name | RefSeq Accession | Sequence | SEQ ID NO: |
|---|---|---|---|
| | | cattccaaatatgagatgcgttgttacaggaagtcccttgccatcctaaaagccaccccacttct<br>ctctaaggagaatggcccagtcctctcccaagtccacacaggggaggtgatagcattgctttc<br>gtgtaaattatgtaatgcaaaatttttttaatcttcgccttaatactttttttattttgttttattttgaatgat<br>gagccttcgtgcccccccttccccctttttttgtcccccaacttgagatgtatgaaggcttttggtct<br>ccctgggagtgggtggaggcagccagggcttacctgtacactgacttgagaccagttgaata<br>aaagtgcacaccttaaaaatgaggaaaaaaaaaaaaaaaaaa | |
| GAPD | NM_002046.6 | gctctctgctcctcctgttcgacagtcagccgcatcttcttttgcgtcgccagccgagccacatc<br>gctcagacaccatggggaaggtgaaggtcggagtcaacggatttggtcgtattgggcgcctg<br>gtcaccagggctgcttttaactctggtaaagtggatattgttgccatcaatgaccccttcattgac<br>ctcaactacatggtttacatgttccaatatgattccacccatggcaaattccatggcaccgtcaa<br>ggctgagaacgggaagcttgtcatcaatggaaatcccatcaccatcttccaggagcgagatc<br>cctccaaaatcaagtggggcgatgctggcgctgagtacgtcgtggagtccactggcgtcttca<br>ccaccatggagaaggctggggctcatttgcaggggggagccaaaagggtcatcatctctgc<br>cccctctgctgatgcccccatgttcgtcatgggtgtgaaccatgagaagtatgacaacagcctc<br>aagatcatcagcaatgcctcctgcaccaccaactgcttagcacccctggccaaggtcatccat<br>gacaactttggtatcgtggaaggactcatgaccacagtccatgccatcactgccacccagaag<br>actgtggatggcccctccgggaaactgtggcgtgatggccgcggggctctccagaacatcat<br>ccctgcctctactggcgctgccaaggctgtgggcaaggtcatccctgagctgaacgggaag<br>ctcactggcatggccttccgtgtccccactgccaacgtgtcagtggtggacctgacctgccgt<br>ctagaaaaacctgccaaatatgatgacatcaagaaggtggtgaagcaggcgtcggagggcc<br>ccctcaagggcatcctgggctacactgagcaccaggtggtctcctctgacttcaacagcgaca<br>cccactcctccacctttgacgctggggctggcattgccctcaacgaccactttgtcaagctcatt<br>tcctggtatgacaacgaatttggctacagcaacagggtggtggacctcatggcccacatggc<br>ctccaaggagtaagacccctggaccaccagccccagcaagagcacaagaggaagagaga<br>gaccctcactgctggggagtccctgccacactcagtcccccaccacactgaatctcccctcct<br>cacagttgccatgtagaccccttgaagaggggaggggcctagggagccgcaccttgtcatgt<br>accatcaataaagtaccctgtgctcaaccagttaaaaaaaaaaaaaaaaaaaaa | 52 |
| GUSB | NM_000181.3 | gtcctcaaccaagatggcgcggatggcttcaggcgcatcacgacaccggcgcgtcacgcga<br>cccgccctacgggcacctcccgcgcttttcttagcgccgcagacggtggccgagcggggga<br>ccgggaagcatggcccgggggtcggcggttgcctgggcggcgctcgggccgttgttgtgg<br>ggctgcgcgctggggctgcagggcgggatgctgtacccccaggagagcccgtcgcggga<br>gtgcaaggagctggacggcctctggagcttccgcgccgacttctctgacaaccgacgccgg<br>ggcttcgaggagcagtggtaccggcggccgctgtgggagtcaggccccaccgtggacatg<br>ccagttccctccagcttcaatgacatcagccaggactggcgtctgcggcattttgtcggctggg<br>tgtggtacgaacgggaggtgatcctgccggagcgatggacccaggacctgcgcacaagag<br>tggtgctgaggattggcagtgcccattcctatgccatcgtgtgggtgaatggggtcgacacgc<br>tagagcatgagggggctacctccccttcgaggccgacatcagcaacctggtccaggtggg<br>gcccctgccctcccggctccgaatcactatcgccatcaacaacacactcacccccaccaccct<br>gccaccagggaccatccaatacctgactgacacctccaagtatcccaagggttactttgtcca<br>gaacacatattttgactttttcaactacgctggactgcagcggtctgtacttctgtacacgacacc<br>caccacctacatcgatgacatcaccgtcaccaccagcgtggagcaagacagtgggctggtg<br>aattaccagatctctgtcaagggcagtaacctgttcaagttggaagtgcgtcttttggatgcaga<br>aaacaaagtcgtggcgaatgggactgggacccagggccaacttaaggtgccaggtgtcagc<br>ctctggtggccgtacctgatgcacgaacgccctgcctatctgtattcattggaggtgcagctga<br>ctgcacagacgtcactggggcctgtgtctgacttctacacactccctgtggggatccgcactgt<br>ggctgtcaccaagagccagttcctcatcaatgggaaacctttctatttccacggtgtcaacaag<br>catgaggatgcggacatccgagggaagggcttcgactggccgctgctggtgaaggacttca<br>acctgcttcgctggcttggtgccaacgctttccgtaccagccactacccctatgcagaggaagt<br>gatgcagatgtgtgaccgctatgggattgtggtcatcgatgagtgtcccggcgtgggcctggc<br>gctgccgcagttcttcaacaacgtttctctgcatcaccacatgcaggtgatggaagaagtggtg<br>cgtagggacaagaaccaccccgcggtcgtgatgtggtctgtggccaacgagcctgcgtccc<br>acctagaatctgctggctactacttgaagatggtgatcgctcacaccaaatccttggacccctc<br>ccggcctgtgacctttgtgagcaactctaactatgcagcagacaaggggctccgtatgtgga<br>tgtgatctgtttgaacagctactactcttggtatcacgactacgggcacctggagttgattcagct<br>gcagctggccacccagtttgagaactggtataagaagtatcagaagcccattattcagagcga<br>gtatggagcagaaacgattgcagggtttcaccaggatccacctctgatgttcactgaagagta<br>ccagaaaagtctgctagagcagtaccatctgggtctggatcaaaaacgcagaaaatacgtgg<br>ttggagagctcatttggaattttgccgatttcatgactgaacagtcaccgacgagagtgctggg<br>gaataaaaaggggatcttcactcggcagagacaaccaaaaagtgcagcgttccttttgcgag<br>agagatactggaagattgccaatgaaaccaggtatccccactcagtagccaagtcacaatgttt<br>ggaaaacagcctgtttacttgagcaagactgataccacctgcgtgtcccttcctccccgagtca<br>gggcgacttccacagcagcagaacaagtgcctcctggactgttcacggcagaccagaacgtt<br>tctggcctgggttttgtggtcatctattctagcagggaacactaaaggtggaaataaaagatttc<br>tattatggaaataaagagttggcatgaaagtggctactgaaaaaaaaaaaaaaaaaaaaaaaaaa | 53 |
| RPLP0 | NM_001002.3 | gtctgacgggcgatggcgcagccaatagacaggagcgctatccgcggtttctgattggctac<br>tttgttcgcattataaaaggcacgcgcgggcgcgaggcccttctctcgccaggcgtcctcgtg<br>gaagtgacatcgtctttaaaccctgcgtggcaatccctgacgcaccgccgtgatgcccaggg<br>aagacagggcgacctggaagtccaactacttccttaagatcatccaactattggatgattatcc<br>gaaatgtttcattgtgggagcagacaatgtgggctccaagcagatgcagcagatccgcatgtc<br>ccttcgcgggaaggctgtggtgctgatgggcaagaacaccatgatgcgcaaggccatccga<br>gggcacctggaaaacaacccagctctggagaaactgctgcctcatatccgggggaatgtgg | 54 |

TABLE 1-continued

Prostate Cancer Biomarker/Housekeeper Sequence Information

| Gene Name | RefSeq Accession | Sequence | SEQ ID NO: |
|---|---|---|---|
| | | gctttgtgttcaccaaggaggacctcactgagatcagggacatgttgctggccaataaggtgc<br>cagctgctgcccgtgctggtgccattgccccatgtgaagtcactgtgccagcccagaacactg<br>gtctcgggcccgagaagacctcctttttccaggctttaggtatcaccactaaaatctccagggg<br>caccattgaaatcctgagtgatgtgcagctgatcaagactggagacaaagtgggagccagcg<br>aagccacgctgctgaacatgctcaacatctccccttctcctttgggctggtcatccagcaggt<br>gttcgacaatggcagcatctacaaccctgaagtgcttgatatcacagaggaaactctgcattct<br>cgcttcctggagggtgtccgcaatgttgccagtgtctgtctgcagattggctacccaactgttgc<br>atcagtaccccattctatcatcaacgggtacaaacgagtcctggccttgtctgtggagacggat<br>tacaccttcccacttgctgaaaaggtcaaggccttcttggctgatccatctgcctttgtggctgct<br>gcccctgtggctgctgccaccacagctgctcctgctgctgctgcagccccagctaaggttgaa<br>gccaaggaagagtcggaggagtcggacgaggatatgggatttggtctctttgactaatcacc<br>aaaaagcaaccaacttagccagttttatttgcaaaacaaggaaataaaggcttacttctttaaaa<br>agtaaaaaaaaaaaaaaaaaaaaaaaa | |
| TFRC | NM_003234.3 | agagcgtcgggatatcgggtggcggctcgggacggaggacgcgctagtgtgagtgcggg<br>cttctagaactacaccgaccctcgtgtcctcccttcatcctgcggggctggctggagcggccg<br>ctccggtgctgtccagcagccatagggagccgcacggggagcgggaaagcggtcgcggc<br>cccaggcggggcggccgggatggagcggggccgcgagcctgtggggaaggggctgtgg<br>cggcgcctcgagcggctgcaggttcttctgtgtggcagttcagaatgatggatcaagctagat<br>cagcattctctaacttgtttggtggagaaccattgtcatatacccggttcagcctggctcggcaa<br>gtagatggcgataacagtcatgtggagatgaaacttgctgtagatgaagaagaaaatgctgac<br>aataacacaaaggccaatgtcacaaaaccaaaaaggtgtagtggaagtatctgctatgggact<br>attgctgtgatcgtctttttcttgattggatttatgattggctacttgggctattgtaaaggggtaga<br>accaaaaactgagtgtgagagactggcaggaaccgagtctccagtgagggaggagccagg<br>agaggacttccctgcagcacgtcgcttatattgggatgacctgaagagaaagttgtcggagaa<br>actggacagcacagacttcaccggcaccatcaagctgctgaatgaaaattcatatgtccctcgt<br>gaggctggatctcaaaaagatgaaaatcttgcgttgtatgttgaaaatcaatttcgtgaatttaaa<br>ctcagcaaagtctggcgtgatcaacattttgttaagattcaggtcaaagacagcgctcaaaact<br>cggtgatcatagttgataagaacggtagacttgtttacctggtggagaatcctgggggttatgtg<br>gcgtatagtaaggctgcaacagttactggtaaactggtccatgctaattttggtactaaaaaaga<br>ttttgaggatttatacactcctgtgaatggatctatagtgattgtcagagcagggaaaatcaccttt<br>gcagaaaaggttgcaaatgctgaaagcttaaatgcaattggtgtgttgatatacatggaccaga<br>ctaaatttcccattgttaacgcagaactttcattctttggacatgctcatctggggacaggtgacc<br>cttacacacctggattcccttccttcaatcacactcagtttccaccatctcggtcatcaggattgc<br>ctaatatacctgtccagacaatctccagagctgctgcagaaaagctgtttgggaatatggaag<br>gagactgtccctctgactggaaaacagactctacatgtaggatggtaacctcagaaagcaaga<br>atgtgaagctcactgtgagcaatgtgctgaaagagataaaaattcttaacatctttggagttatta<br>aaggctttgtagaaccagatcactatgttgtagttggggcccagagagatgcatggggccctg<br>gagctgcaaaatccggtgtaggcacagctctcctattgaaacttgcccagatgttctcagatat<br>ggtcttaaaagatgggtttcagcccagcagaagcattatctttgccagttggagtgctggagac<br>tttggatcggttggtgccactgaatggctagagggatacctttcgtccctgcatttaaaggctttc<br>acttatattaatctggataaagcggttcttggtaccagcaacttcaaggtttctgccagcccactg<br>ttgtatacgcttattgagaaaacaatgcaaaatgtgaagcatccggttactgggcaatttctatat<br>caggacagcaactgggccagcaaagttgagaaactcactttagacaatgctgctttccctttcc<br>ttgcatattctggaatcccagcagtttctttctgtttttgcgaggacacagattatccttatttgggta<br>ccaccatggacacctataaggaactgattgagaggattcctgagttgaacaaagtggcacga<br>gcagctgcagaggtcgctggtcagttcgtgattaaactaacccatgatgttgaattgaacctgg<br>actatgagaggtacaacagccaactgctttcatttgtgagggatctgaaccaatacagagcag<br>acataaaggaaatgggcctgagtttacagtggctgtattctgctcgtggagacttcttccgtgct<br>acttccagactaacaacagatttcgggaatgctgagaaaacagacagatttgtcatgaagaaa<br>ctcaatgatcgtgtcatgagagtggagtatcacttcctctctccctacgtatctccaaaagagtct<br>cctttccgacatgtcttctggggctccggctctcacacgctgccagctttactggagaacttgaa<br>actgcgtaaacaaaataacggtgcttttaatgaaacgctgttcagaaaccagttggctctagcta<br>cttggactattcagggagctgcaaatgccctctctggtgacgtttgggacattgacaatgagttt<br>taaatgtgatacccatagcttccatgagaacagcagggtagtctggtttctagacttgtgctgat<br>cgtgctaaattttcagtagggctacaaaacctgatgttaaaattccatcccatcatcttggtactac<br>tagatgtctttaggcagcagcttttaatacagggtagataacctgtacttcaagttaaagtgaata<br>accacttaaaaaatgtccatgatggaatattcccctatctctagaattttaagtgctttgtaatggg<br>aactgcctctttcctgttgttgttaatgaaaatgtcagaaaccagttatgtgaatgatctctctgaat<br>cctaagggctggtctctgctgaaggttgtaagtggtcgcttactttgagtgatcctccaacttcat<br>ttgatgctaaataggagataccaggttgaaagaccttctccaaatgagatctaagcctttccata<br>aggaatgtagctggtttcctcattcctgaaagaaacagttaactttcagaagagatgggcttgttt<br>tcttgccaatgaggtctgaaatggaggtccttctgctggataaaatgaggttcaactgttgattg<br>caggaataaggccttaatatgttaacctcagtgtcatttatgaaaagaggggaccagaagcca<br>aagacttagtatattttcttttcctctgtcccttccccataagcctccatttagttctttgttatttttgt<br>ttcttccaaagcacattgaaagagaaccagtttcaggtgtttagttgcagactcagtttgtcagac<br>tttaaagaataatatgctgccaaattttggccaaagtgttaatcttaggggagagctttctgtcctt<br>ttggcactgagatatttattgtttatttatcagtgacagagttcactataaatggtgtttttttaataga<br>atataattatcggaagcagtgccttccataattatgacagttatactgtcggtttttttaaataaaa<br>gcagcatctgctaataaaacccaacagatactggaagttttgcatttatggtcaacacttaaggg<br>ttttagaaaacagccgtcagccaaatgtaattgaataaagttgaagctaagatttagagatgaat<br>taaatttaattaggggttgctaagaagcgagcactgaccagataagaatgctggttttcctaaat<br>gcagtgaattgtgaccaagttataaatcaatgtcacttaaaggctgtggtagtactcctgcaaaa<br>ttttatagctcagtttatccaaggtgtaactctaattcccattttgcaaaatttccagtacctttgtca | 55 |

TABLE 1-continued

Prostate Cancer Biomarker/Housekeeper Sequence Information

| Gene Name | RefSeq Accession | Sequence | SEQ ID NO: |
|---|---|---|---|
| | | caatcctaacacattatcgggagcagtgtcttccataatgtataaagaacaaggtagtttttacct<br>accacagtgtctgtatcggagacagtgatctccatatgttacactaagggtgtaagtaattatcg<br>ggaacagtgtttcccataattttcttcatgcaatgacatcttcaaagcttgaagatcgttagtatct<br>aacatgtatcccaactcctataattccctatcttttagttttagttgcagaaacattttgtggtcatta<br>agcattgggtgggtaaattcaaccactgtaaaatgaaattactacaaaatttgaaatttagcttgg<br>gtttttgttacctttatggtttctccaggtcctctacttaatgagatagtagcatacatttataatgttt<br>gctattgacaagtcattttaactttatcacattatttgcatgttacctcctataaacttagtgcggac<br>aagttttaatccagaattgaccttttgacttaaagcagagggactttgtatagaaggtttggggg<br>ctgtggggaaggagagtcccctgaaggtctgacacgtctgcctacccattcgtggtgatcaat<br>taaatgtaggtatgaataagttcgaagctccgtgagtgaaccatcattataaacgtgatgatcag<br>ctgtttgtcatagggcagttggaaacggcctcctagggaaaagttcatagggtctcttcaggttc<br>ttagtgtcacttacctagatttacagcctcacttgaatgtgtcactactcacagtctctttaatcttca<br>gttttatctttaatctcctcttttatcttggactgacatttagcgtagctaagtgaaaaggtcatagct<br>gagattcctggttcgggtgttacgcacacgtacttaaatgaaagcatgtggcatgttcatcgtat<br>aacacaatatgaatacagggcatgcatttgcagcagtgagtctcttcagaaaaccccttttctac<br>agttagggttgagttacttcctatcaagccagtacgtgctaacaggctcaatattcctgaatgaa<br>atatcagactagtgacaagctcctggtcttgagatgtcttctcgttaaggagatgggccttttgg<br>aggtaaaggataaaatgaatgagttctgtcatgattcactattctagaacttgcatgacctttact<br>gtgttagctctttgaatgttcttgaaattttagactttctttgtaaacaaatgatatgtccttatcattgt<br>ataaaagctgttatgtgcaacagtgtggagattccttgtctgatttaataaaatacttaaacactga<br>aaaaaaaaaa | |
| 18S | X03205.1 | tacctggttgatcctgccagtagcatatgcttgtctcaaagattaagccatgcatgtctaagtacg<br>cacggccggtacagtgaaactgcgaatggctcattaaatcagttatggttcctttggtcgctcg<br>ctcctctcccacttggataactgtggtaattctagagctaatacatgccgacgggcgctgaccc<br>ccttcgcggggggggatgcgtgcatttatcagatcaaaaccaacccggtcagcccctctccgg<br>ccccggccgggggggcgggcgccggcggctttggtgactctagataacctcgggccgatcg<br>cacgccccccgtggcggcgacgacccattcgaacgtctgccctatcaactttcgatggtagtc<br>gccgtgcctaccatggtgaccacgggtgacggggaatcagggttcgattccggagaggga<br>gcctgagaaacggctaccacatccaaggaaggcagcaggcgcgcaaattacccactcccg<br>acccggggaggtagtgacgaaaaataacaatacaggactctttcgaggccctgtaattggaat<br>gagtccactttaaatcctttaacgaggatccattggagggcaagtctggtgccagcagccgcg<br>gtaattccagctccaatagcgtatattaaagttgctgcagttaaaaagctcgtagttggatcttgg<br>gagcgggcgggcggtccgccgcgaggcgagccaccgcccgtccccgccccttgcctctc<br>ggcgccccctcgatgctcttagctgagtgtcccgcggggcccgaagcgtttactttgaaaaaa<br>ttagagtgttcaaagcaggcccgagccgcctggataccgcagctaggaataatggaatagga<br>ccgcggttctattttgttggttttcggaactgaggccatgattaagagggacggccgggggcat<br>tcgtattgcgccgctagaggtgaaattcttggaccggcgcaagacggaccagagcgaaagc<br>atttgccaagaatgttttcattaatcaagaacgaaagtcggaggttcgaagacgatcagatacc<br>gtcgtagttccgaccataaacgatgccgaccggcgatgcggcggcgttattcccatgacccg<br>ccgggcagcttccgggaaaccaaagtctttgggttccgggggggagtatggttgcaaagctga<br>aacttaaaggaattgacggaagggcaccaccaggagtggagcctgcggcttaatttgactca<br>acacgggaaacctcacccggcccggacacggacaggattgacagattgatagctctttctcg<br>attccgtgggtggtggtgcatggccgttcttagttggtggagcgatttgtctggttaattccgata<br>acgaacgagactctggcatgctaactagttacgcgacccccgagcggtcggcgtcccccaa<br>cttcttagagggacaagtggcgttcagccacccgagattgagcaataacaggtctgtgatgcc<br>cttagatgtccggggctgcacgcgcgctacactgactggctcagcgtgtgcctaccctacgc<br>cggcaggcgcgggtaacccgttgaaccccattcgtgatggggatcggggattgcaattattc<br>cccatgaacgaggaattcccagtaagtgcgggtcataagcttgcgttgattaagtccctgccct<br>ttgtacacaccgcccgtcgctactaccgattggatggtttagtgaggccctcggatcggcccc<br>gccggggtcggcccacggccctggcggagcgctgagaagacggtcgaacttgactatcta<br>gaggaagtaaaagtcgtaacaaggtttccgtaggtgaacctgcggaaggatcatta | 56 |
| PPIA | NM_021130.4 | ggggccgaacgtggtataaaaggggcgggaggccaggctcgtgccgttttgcagacgcca<br>ccgccgaggaaaaccgtgtactattagccatggtcaaccccaccgtgttcttcgacattgccgt<br>cgacggcgagcccttgggccgcgtctcctttgagctgtttgcagacaaggtcccaaagacag<br>cagaaaattttcgtgctctgagcactggagagaaaggatttggttataagggttcctgctttcac<br>agaattattccagggtttatgtgtcagggtggtgacttcacacgccataatggcactggtggca<br>agtccatctatggggagaaatttgaagatgagaacttcatcctaaagcatacgggtcctggcat<br>cttgtccatggcaaatgctggacccaacacaaatggttcccagtttttcatctgcactgccaaga<br>ctgagtggttggatggcaagcatgtggtgtttggcaaagtgaaagaaggcatgaatattgtgg<br>aggccatggagcgctttgggtccaggaatggcaagaccagcaagaagatcaccattgctga<br>ctgtggacaactcgaataagtttgacttgtgttttatcttaaccaccagatcattccttctgtagctc<br>aggagagcacccctccaccccatttgctcgcagtatcctagaatctttgtgctctcgctgcagtt<br>ccctttgggttccatgttttccttgttccctcccatgcctagctggattgcagagttaagtttatgatt<br>atgaaataaaaactaaataacaattgtcctcgtttgagttaagagtgttgatgtaggctttattttaa<br>gcagtaatgggttacttctgaaacatcacttgtttgcttaattctacacagtacttagattttttttact<br>ttccagtcccaggaagtgtcaatgtttgttgagtggaatattgaaaatgtaggcagcaactggg<br>catggtggctcactgtctgtaatgtattacctgaggcagaagaccacctgagggtaggagtca<br>agatcagcctgggcaacatagtgagacgctgtctctacaaaaaataattagcctggcctggtg<br>gtgcatgcctagtcctagctgatctggaggctgacgtgggaggattgcttgagcctagagtga<br>gctattatcatgccactgtacagcctgggtgttcacagatcttgtgtctcaaaggtaggcagag<br>gcaggaaaagcaaggagccagaattaagaggttgggtcagtctgcagtgagttcatgcattta<br>gaggtgttcttcaagatgactaatgtcaaaaattgagacatctgttgcggtttttttttttttttttccc | 57 |

TABLE 1-continued

Prostate Cancer Biomarker/Housekeeper Sequence Information

| Gene Name | RefSeq Accession | Sequence | SEQ ID NO: |
|---|---|---|---|
| | | ctggaatgcagtggcgtgatctcagctcactgcagcctccgcctcctgggttcaagtgattcta<br>gtgcctcagcctcctgagtagctgggataatgggcgtgtgccaccatgcccagctaatttttgt<br>atttttagtatagatggggtttcatcattttgaccaggctggtctcaaactcttgacctcagctgat<br>gcgcctgccttggcctcccaaactgctgagattacagatgtgagccaccgcaccctacctcatt<br>ttctgtaacaaagctaagcttgaacactgttgatgttcttgagggaagcatattgggctttaggct<br>gtaggtcaagtttatacatcttaattatggtggaattcctatgtagagtctaaaaagccaggtactt<br>ggtgctacagtcagtctccctgcagagggttaaggcgcagactacctgcagtgaggaggtac<br>tgcttgtagcatatagagcctctccctagctttggttatggaggctttgaggttttgcaaacctga<br>ccaatttaagccataagatctggtcaaagggatacccttcccactaaggacttggtttctcagga<br>aattatatgtacagtgcttgctggcagttagatgtcaggacaatctaagctgagaaaaccccttc<br>tctgcccaccttaacagacctctagggttcttaacccagcaatcaagtttgcctatcctagaggt<br>ggcggatttgatcatttggtgtgttgggcaattttttgttttactgtctggttccttctgcgtgaattac<br>caccaccaccacttgtgcatctcagtcttgtgtgttgtctggttacgtattccctgggtgataccat<br>tcaatgtcttaatgtacttgtggctcagacctgagtgcaaggtggaaataaacatcaaacatcttt<br>tcattatcccta | |
| PGK1 | NM_000291.3 | gagagcagcggccgggaaggggcggtgcgggaggcggggtgtggggcggtagtgtgg<br>gccctgttcctgcccgcgcggtgttccgcattctgcaagcctccggagcgcacgtcggcagt<br>cggctccctcgttgaccgaatcaccgacctctctccccagctgtatttccaaaatgtcgctttcta<br>acaagctgacgctggacaagctggacgttaaagggaagcgggtcgttatgagagtcgacttc<br>aatgttcctatgaagaacaaccagataacaaacaaccagaggattaaggctgctgtcccaagc<br>atcaaattctgcttggacaatggagccaagtcggtagtccttatgagccacctaggccggcct<br>gatggtgtgcccatgcctgacaagtactccttagagccagttgctgtagaactcaaatctctgct<br>gggcaaggatgttctgttcttgaaggactgtgtaggcccagaagtggagaaagcctgtgcca<br>acccagctgctgggtctgtcatcctgctggagaacctccgctttcatgtggaggaagaaggga<br>agggaaaagatgcttctgggaacaaggttaaagccgagccagccaaaatagaagctttccga<br>gcttcactttccaagctaggggatgtctatgtcaatgatgcttttggcactgctcacagagccca<br>cagctccatggtaggagtcaatctgccacagaaggctggtgggtttttgatgaagaaggagct<br>gaactactttgcaaaggccttggagagcccagagcgacccttcctggccatcctgggcggag<br>ctaaagttgcagacaagatccagctcatcaataatatgctggacaaagtcaatgagatgattatt<br>ggtggtggaatggcttttaccttccttaaggtgctcaacaacatggagattggcacttctctgttt<br>gatgaagagggagccaagattgtcaaagacctaatgtccaaagctgagaagaatggtgtgaa<br>gattaccttgcctgttgactttgtcactgctgacaagtttgatgagaatgccaagactggccaag<br>ccactgtggcttctggcatacctgctggctggatgggcttggactgtggtcctgaaagcagca<br>agaagtatgctgaggctgtcactcgggctaagcagattgtgtggaatggtcctgtgggggtatt<br>tgaatgggaagcttttgcccggggaaccaaagctctcatggatgaggtggtgaaagccacttc<br>taggggctgcatcaccatcataggtggtggagacactgccacttgctgtgccaaatggaaca<br>cggaggataaagtcagccatgtgagcactgggggtggtgccagtttggagctcctggaaggt<br>aaagtccttcctggggtggatgctctcagcaatatttagtactttcctgccttttagttcctgtgca<br>cagcccctaagtcaacttagcatttctgcatctccacttggcattagctaaaaccttccatgtca<br>agattcagctagtggccaagagatgcagtgccaggaacccttaaacagttgcacagcatctca<br>gctcatcttcactgcaccctggatttgcatacattcttcaagatcccatttgaatttttttagtgacta<br>aaccattgtgcattctagagtgcatatatttatatttgcctgttaaaaagaaagtgagcagtgtta<br>gcttagttctcttttgatgtaggttattatgattagctttgtcactgtttcactactcagcatggaaac<br>aagatgaaattccatttgtaggtagtgagacaaaattgatgatccattaagtaaacaataaaagt<br>gtccattgaaaccgtgatttttttttttttcctgtcatactttgttaggaagggtgagaatagaatctt<br>gaggaacggatcagatgtctatattgctgaatgcaagaagtggggcagcagcagtggagag<br>atgggacaattagataaatgtccattctttatcaagggcctactttatggcagacattgtgctagt<br>gcttttattctaacttttatttttatcagttacacatgatcataatttaaaaagtcaaggcttataacaa<br>aaaagccccagcccattcctcccattcaagattcccactccccagaggtgaccactttcaactc<br>ttgagtttttcaggtatatacctccatgtttctaagtaatatgcttatattgttcacttcttttttttttatttt<br>ttaaagaaatctatttcataccatggaggaaggctctgttccacatatatttccacttcttcattctct<br>cggtatagttttgtcacaattatagattagatcaaaagtctacataactaatacagctgagctatgt<br>agtatgctatgattaaatttacttatgtaaaaaaaaaaaaaaaaaa | 58 |
| RPL13A | NM_012423.3 | cacttctgccgcccctgtttcaagggataagaaaccctgcgacaaaacctcctccttttccaag<br>cggctgccgaagatggcggaggtgcaggtcctggtgcttgatggtcgaggccatctcctgg<br>gccgcctggcggccatcgtggctaaacaggtactgctgggccggaaggtggtggtcgtacg<br>ctgtgaaggcatcaacatttctggcaatttctacagaaacaagttgaagtacctggctttcctcc<br>gcaagcggatgaacaccaacccttcccgaggcccctaccacttccgggcccccagccgcat<br>cttctggcggaccgtgcgaggtatgctgccccacaaaaccaagcgaggccaggccgctctg<br>gaccgtctcaaggtgtttgacggcatcccaccgccctacgacaagaaaaagcggatggtggt<br>tcctgctgccctcaaggtcgtgcgtctgaagcctacaagaaagtttgcctatctggggcgcctg<br>gctcacgaggttggctggaagtaccaggcagtgacagccaccctggaggagaagaggaaa<br>gagaaagccaagatccactaccggaagaagaaacagctcatgaggctacggaaacaggcc<br>gagaagaacgtggagaagaaaattgacaaatacacagaggtcctcaagacccacggactcc<br>tggtctgagcccaataaagactgttaattcctcatgcgttgcctgcccttcctccattgttgccct<br>ggaatgtacgggacccaggggcagcagcagtccaggtgccacaggcagccctgggacat<br>aggaagctgggagcaaggaaagggtcttagtcactgcctcccgaagttgcttgaaagcactc<br>ggagaattgtgcaggtgtcatttatctatgaccaataggaagagcaaccagttactatgagtga<br>aagggagccagaagactgattggagggccctatcttgtgagtggggcatctgttggactttcc<br>acctggtcatatactctgcagctgttagaatgtgcaagcacttggggacagcatgagcttgctg | 59 |

TABLE 1-continued

| Prostate Cancer Biomarker/Housekeeper Sequence Information | | | |
|---|---|---|---|
| Gene Name | RefSeq Accession | Sequence | SEQ ID NO: |
| | | ttgtacacagggtatttctagaagcagaaatagactgggaagatgcacaaccaaggggttaca<br>ggcatcgcccatgctcctcacctgtattttgtaatcagaaataaattgcttttaaagaaaaaaaaa<br>aaaaaaaaa | |
| B2M | NM_004048.2 | aatataagtggaggcgtcgcgctggcgggcattcctgaagctgacagcattcgggccgagat<br>gtctcgctccgtggccttagctgtgctcgcgctactctctctttctggcctggaggctatccagc<br>gtactccaaagattcaggtttactcacgtcatccagcagagaatggaaagtcaaatttcctgaat<br>tgctatgtgtctgggtttcatccatccgacattgaagttgacttactgaagaatggagagagaatt<br>gaaaaagtggagcattcagacttgtctttcagcaaggactggtctttctatctcttgtactacact<br>gaattcacccccactgaaaaagatgagtatgcctgccgtgtgaaccatgtgactttgtcacagc<br>ccaagatagttaagtgggatcgagacatgtaagcagcatcatggaggtttgaagatgccgcat<br>ttggattggatgaattccaaattctgcttgcttgctttttaatattgatatgcttatacacttacacttta<br>tgcacaaaatgtagggttataataatgttaacatggacatgatcttctttataattctactttgagtg<br>ctgtctccatgtttgatgtatctgagcaggttgctccacaggtagctctaggagggctggcaact<br>tagaggtggggagcagagaattctcttatccaacatcaacatcttggtcagatttgaactcttca<br>atctcttgcactcaaagcttgttaagatagttaagcgtgcataagttaacttccaatttacatactct<br>gcttagaatttgggggaaaatttagaaatataattgacaggattattggaaatttgttataatgaat<br>gaaacattttgtcatataagattcatatttacttcttatacattgataaagtaaggcatggttgtggt<br>taatctggtttatttttgttccacaagttaaataaatcataaaacttgatgtgttatctctta | 60 |
| YWHAZ | NM_003406.3 | ctttctccttcccctcttccgggctcccgtcccggctcatcacccggcctgtggcccactccca<br>ccgccagctggaaccctggggactacgacgtccctcaaaccttgcttctaggagataaaaag<br>aacatccagtcatggataaaaatgagctggttcagaaggccaaactggccgagcaggctga<br>gcgatatgatgacatggcagcctgcatgaagtctgtaactgagcaaggagctgaattatccaa<br>tgaggagaggaatcttctctcagttgcttataaaaatgttgtaggagcccgtaggtcatcttgga<br>gggtcgtctcaagtattgaacaaaagacggaaggtgctgagaaaaaacagcagatggctcg<br>agaatacagagagaaaattgagacggagctaagagatatctgcaatgatgtactgtctcttttg<br>gaaaagttcttgatccccaatgcttcacaagcagagagcaaagtcttctatttgaaaatgaaag<br>gagattactaccgttacttggctgaggttgccgctggtgatgacaagaaagggattgtcgatca<br>gtcacaacaagcataccaagaagcttttgaaatcagcaaaaaggaaatgcaaccaacacatc<br>ctatcagactgggtctggcccttaacttctctgtgttctattatgagattctgaactccccagaga<br>aagcctgctctcttgcaaagacagcttttgatgaagccattgctgaacttgatacattaagtgaa<br>gagtcatacaaagacagcacgctaataatgcaattactgagagacaacttgacattgtggacat<br>cggatacccaaggagacgaagctgaagcaggagaaggaggggaaaattaaccggccttcc<br>aacttttgtctgcctcattctaaaatttacacagtagaccatttgtcatccatgctgtcccacaaata<br>gtttttttgtttacgatttatgacaggtttatgttacttctatttgaatttctatatttcccatgtggtttttat<br>gtttaatattaggggagtagagccagttaacatttagggagttatctgttttcatcttgaggtggc<br>caatatggggatgtggaatttttatacaagttataagtgtttggcatagtacttttggtacattgtgg<br>cttcaaaagggccagtgtaaaactgcttccatgtctaagcaaagaaaactgcctacatactggt<br>ttgtcctggcggggaataaaagggatcattggttccagtcacaggtgtagtaattgtgggtactt<br>taaggtttggagcacttacaaggctgtggtagaatcataccccatggataccacatattaaacc<br>atgtatatctgtggaatactcaatgtgtacacctttgactacagctgcagaagtgttcctttagac<br>aaagttgtgacccatttttactctggataagggcagaaacggttcacattccattatttgtaaagtt<br>acctgctgttagctttcattattttttgctacactcattttatttgtatttaaatgttttaggcaacctaag<br>aacaaatgtaaaagtaaagatgcaggaaaaatgaattgcttggtattcattacttcatgtatatca<br>agcacagcagtaaaacaaaaacccatgtatttaacttttttttaggatttttgcttttgtgattttttttt<br>ttttgatacttgcctaacatgcatgtgctgtaaaaatagttaacagggaaataacttgagatgatg<br>gctagctttgtttaatgtcttatgaaattttcatgaacaatccaagcataattgttaagaacacgtgt<br>attaaattcatgtaagtggaataaaagttttatgaatggacttttcaactactttctctacagcttttc<br>atgtaaattagtcttggttctgaaacttctctaaaggaaattgtacatttttttgaaatttattccttattc<br>cctcttggcagctaatgggctcttaccaagtttaaacacaaaatttatcataacaaaaatactact<br>aatataactactgtttccatgtcccatgatcccctctcttcctccccaccctgaaaaaaatgagttc<br>ctatttttttctgggagagggggggattgattagaaaaaaatgtagtgtgttccatttaaaattttgg<br>catatggcattttctaacttaggaagccacaatgttcttggcccatcatgacattgggtagcatta<br>actgtaagttttgtgcttccaaatcactttttggtttttaagaatttcttgatactcttatagcctgcctt<br>caattttgatcctttattctttctatttgtcaggtgcacaagattaccttcctgttttagccttctgtctt<br>gtcaccaaccattcttacttggtggccatgtacttggaaaaaggccgcatgatctttctggctcc<br>actcagtgtctaaggcaccctgcttcctttgcttgcatcccacagactatttccctcatcctatttac<br>tgcagcaaatctctccttagttgatgagactgtgtttatctccctttaaaaccctacctatcctgaat<br>ggtctgtcattgtctgcctttaaaatccttcctctttcttcctcctctattctctaaataatgatgggg<br>ctaagttatacccaaagctcactttacaaaatatttcctcagtactttgcagaaaacaccaaacaa<br>aaatgccattttaaaaaaggtgtattttttctttttagaatgtaagctcctcaagagcagggacaat<br>gttttctgtatgttctattgtgcctagtacactgtaaatgctcaataaatattgatgatgggaggca<br>gtgagtcttgatgataagggtgagaaactgaaatcccaaacactgttttgttgcttgttttattatg<br>acctcagattaaattgggaaatattggccctttttgaataattgtcccaaatattacattcaaataaa<br>agtgcaatggagaaaaaaaaaaa | 61 |
| SDHA | NM_004168.3 | actgcagccccgctcgactccggcgtggtgcgcaggcgcggtatccccccctcccccgccag<br>ctcgaccccggtgtggtgcgcaggcgcagtctgcgcagggactggcgggactgcgcggc<br>ggcaacagcagacatgtcgggggtccggggcctgtcgcggctgctgagcgctcggcgcct<br>ggcgctggccaaggcgtggccaacagtgttgcaaacaggaacccgaggttttcacttcactg<br>ttgatgggaacaagagggcatctgctaaagtttcagattccatttctgctcagtatccagtagtg<br>gatcatgaatttgatgcagtggtggtaggcgctggaggggcaggcttgcgagctgcatttggc<br>ctttctgaggcagggtttaatacagcatgtgttaccaagctgtttcctaccaggtcacacactgtt | 62 |

TABLE 1-continued

Prostate Cancer Biomarker/Housekeeper Sequence Information

| Gene Name | RefSeq Accession | Sequence | SEQ ID NO: |
| --- | --- | --- | --- |
| | | gcagcacagggaggaatcaatgctgctctggggaacatggaggaggacaactggaggtgg<br>catttctacgacaccgtgaagggctccgactggctgggggaccaggatgccatccactacat<br>gacggagcaggcccccgccgccgtggtcgagctagaaaattatggcatgccgtttagcaga<br>actgaagatgggaagatttatcagcgtgcatttggtggacagagcctcaagtttggaaagggc<br>gggcaggcccatcggtgctgctgtgtggctgatcggactggccactcgctattgcacacctta<br>tatggaaggtctctgcgatatgataccagctattttgtggagtattttgccttggatctcctgatgg<br>agaatggggagtgccgtggtgtcatcgcactgtgcatagaggacgggtccatccatcgcata<br>agagcaaagaacactgttgttgccacaggaggctacgggcgcacctacttcagctgcacgtc<br>tgcccacaccagcactggcgacggcacggccatgatcaccagggcaggccttccttgccag<br>gacctagagtttgttcagttccaccctacaggcatatatggtgctggttgtctcattacggaagg<br>atgtcgtggagagggaggcattctcattaacagtcaaggcgaaaggtttatggagcgatacg<br>cccctgtcgcgaaggacctggcgtctagagatgtggtgtctcggtccatgactctggagatcc<br>gagaaggaagaggctgtggccctgagaaagatcacgtctacctgcagctgcaccacctacct<br>ccagagcagctggccacgcgcctgcctggcatttcagagacagccatgatcttcgctggcgt<br>ggacgtcacgaaggagccgatccctgtcctccccaccgtgcattataacatgggcggcattc<br>ccaccaactacaaggggcaggtcctgaggcacgtgaatggccaggatcagattgtgcccgg<br>cctgtacgcctgtggggaggccgcctgtgcctcggtacatggtgccaaccgcctcggggca<br>aactcgctcttggacctggttgtctttggtcgggcatgtgccctgagcatcgaagagtcatgca<br>ggcctggagataaagtccctccaattaaaccaaacgctggggaagaatctgtcatgaatcttg<br>acaaattgagatttgctgatggaagcataagaacatcggaactgcgactcagcatgcagaagt<br>caatgcaaaatcatgctgccgtgttccgtgtgggaagcgtgttgcaagaaggttgtgggaaaa<br>tcagcaagctctatggagacctaaagcacctgaagacgttcgaccggggaatggtctggaac<br>acggacctggtggagaccctggagctgcagaacctgatgctgtgtgcgctgcagaccatcta<br>cggagcagaggcacggaaggagtcacggggcgcgcatgccagggaagactacaaggtg<br>cggattgatgagtacgattactccaagcccatccaggggcaacagaagaagccctttgagga<br>gcactggaggaagcacaccctgtcctatgtggacgttggcactgggaaggtcactctggaat<br>atagacccgtgatcgacaaaactttgaacgaggctgactgtgccaccgtcccgccagccattc<br>gctcctactgatgagacaagatgtggtgatgacagaatcagcttttgtaattatgtataatagctc<br>atgcatgtgtccatgtcataactgtcttcatacgcttctgcactctggggaagaaggagtacatt<br>gaagggagattggcacctagtggctgggagcttgccaggaacccagtggccagggagcgt<br>ggcacttacctttgtcccttgcttcattcttgtgagatgataaaactgggcacagctcttaaataaa<br>atataaatgaacaaactttcttttatttccaaatccatttgaaatattttactgttgtgactttagtcata<br>tttgttgacctaaaaatcaaatgtaatctttgtattgtgttacatcaaaatccagatattttgtatagtt<br>tctttttttctttttctttttctttttttttttttgagacaggatcggtgcagtagtacaatcacagctcactgc<br>agcctcaaactcctgggcagctcaggtgatcttcctgactcagccttctgagtagttggggcta<br>caggtgtgcaccaccatgcccagctcatttattttgtaattgtagggacagggtctcactgtgttg<br>cctaggctggtctcaagtgatcctccctccttggcctcccaaggtgctggaattataggtgtga<br>acaaaccaaaaaaaaaaaaaa | |
| HPRT1 | NM_000194.2 | ggcggggcctgcttctcctcagcttcaggcggctgcgacgagccctcaggcgaacctctcg<br>gctttcccgcgcggcgccgcctcttgctgcgcctccgcctcctcctctgctccgccaccggctt<br>cctcctcctgagcagtcagcccgcgcgccggccggctccgttatggcgacccgcagccctg<br>gcgtcgtgattagtgatgatgaaccaggttatgaccttgatttattttgcatacctaatcattatgct<br>gaggatttggaaagggtgtttattcctcatggactaattatggacaggactgaacgtcttgctcg<br>agatgtgatgaaggagatgggaggccatcacattgtagccctctgtgtgctcaaggggggct<br>ataaattctttgctgacctgctggattacatcaaagcactgaatagaaatagtgatagatccattc<br>ctatgactgtagattttatcagactgaagagctattgtaatgaccagtcaacaggggacataaa<br>agtaattggtggagatgatctctcaactttaactggaaagaatgtcttgattgtggaagatataat<br>tgacactggcaaaacaatgcagactttgctttccttggtcaggcagtataatccaaagatggtc<br>aaggtcgcaagcttgctggtgaaaaggaccccacgaagtgttggatataagccagactttgtt<br>ggatttgaaattccagacaagtttgttgtaggatatgcccttgactataatgaatacttcagggatt<br>tgaatcatgtttgtgtcattagtgaaactggaaaagcaaaatacaaagcctaagatgagagttc<br>aagttgagtttggaaacatctggagtcctattgacatcgccagtaaaattatcaatgttctagttct<br>gtggccatctgcttagtagagctttttgcatgtatcttctaagaattttatctgttttgtactttagaaa<br>tgtcagttgctgcattcctaaactgtttatttgcactatgagcctatagactatcagttccctttggg<br>cggattgttgtttaacttgtaaatgaaaaaattctcttaaaccacagcactattgagtgaaacattg<br>aactcatatctgtaagaaataaagagaagatatattagtttttttaattggtattttaatttttatatatg<br>caggaaagaatagaagtgattgaatattgttaattataccaccgtgtgttagaaaagtaagaag<br>cagtcaattttcacatcaaagacagcatctaagaagttttgttctgtcctggaattattttagtagtg<br>tttcagtaatgttgactgtattttccaacttgttcaaattattaccagtgaatctttgtcagcagttcc<br>cttttaaatgcaaatcaataaattcccaaaaatttaaaaaaaaaaaaaaaaaaaaaa | 63 |
| TOX4 | NM_001303523.1 | agcagagagaacacacgtccttgcggaagtgacggcagttccgagtccagtgggggcggt<br>gggagcgatgagggtctgagacggtgggagcggttgtgtgaagatggagacattccataca<br>ccaagcttgggtgatgaggaatttgaaatcccacctatctccttggattctgatccctcattggct<br>gtctcagatgtggttggccactttgatgacctggcagacccttcctcttcacaggatggcagtttt<br>tcagcccagtatggggtccagacattggacatgcctgtgggcatgacccatggcttgatgga<br>gcagggcggggggctcctgagtgggggcttgaccatggacttggaccactctataggaact<br>cagtatagtgccaacccacctgttacaattgatgtaccaatgacagacatgacatctggcttgat<br>ggggcatagccagttgaccaccattgatcagtcagaactgagttcccagctgggtttgagcct<br>agggggtggcaccatcctgccacctgcccagtcacctgaagatcgtctttcaaccacccccttc<br>acctactagttcacttcacgaggatggtgttgaggatttccggaggcaacttcccagccagaa<br>gacagtcgtggtggaagcagggaaaaagcagaaggccccaaagaagagaaaaaagaaag<br>atcctaatgaacctcagaaaccagtttcagcatatgctttattctttcgtgatacacaggctgccat | 64 |

TABLE 1-continued

Prostate Cancer Biomarker/Housekeeper Sequence Information

| Gene Name | RefSeq Accession | Sequence | SEQ ID NO: |
|---|---|---|---|
| | | caagggacagaatcctaatgccacttttggtgaggtttcaaaaattgtggcctccatgtgggat<br>agtcttggagaggagcaaaaacaggtatataagaggaaaactgaggctgccaagaaagagt<br>atctgaaggcactggctgcttacaaagacaaccaggagtgtcaggccactgtggaaacagtg<br>gaattggatccagcaccaccatcacaaactccttctccacctcctatggctactgttgacccag<br>catctccagcaccagcttcaatagagcccctgccctgtccccatccattgttgttaactccacc<br>ctttcatcctatgtggcaaaccaggcatcttctggagctgggggtcagcccaatatcaccaagt<br>tgattattaccaaacaaatgttgccctcttctattactatgtctcaaggagggatggttactgttatc<br>ccagccacagtggtgacctcccggggctccaactaggccaaaccagtacagctactatcca<br>gcccagtcaacaagcccagattgtcactcggtcagtgttgcaggcagcagcagctgctgctg<br>ctgctgcttctatgcaactgcctccacccgactacagccccctccattacaacagatgccaca<br>gcccccgactcagcagcaagttaccattctgcagcagcctcctccactccaggccatgcaac<br>agcctccacctcagaaagttcgaatcaatttacagcaacagcctcctcctctgcagatcaagag<br>tgtgcctctacccactttgaaaatgcagactaccttagtcccaccaactgtggaaagtagtcctg<br>agcggcctatgaacaacagccctgaggcccatacagtggaggcaccttctcctgagactatct<br>gtgagatgatcacagatgtagttcctgaggttgagtctccttctcagatggatgttgaattggtga<br>gtgggtctcctgtggcactctcaccccagcctcgatgtgtgaggtctggttgtgagaaccctcc<br>cattgtgagtaaggactgggacaatgaatactgcagcaatgagtgtgtggtgaagcactgca<br>gggatgtattcttggcctgggtagcctctagaaattcaaacacagtggtgtttgtgaaatagtcc<br>ttcctgttctccaagccagtgaagagttatctgctgggaaagtgtccaagagcctgtttttgaaa<br>cacaagctgggcttctggtagtgcctcatcacaacccatgatggctgttcatgtttcacccctttt<br>cttccttcagcagaggccaggctatggagcagggccactgaatttgctgtaatctggagatgc<br>tttttactttcaaccataagcggtaatagcagaggaaagggtgaagggagtctgggcaagcaa<br>agcatagagatggtggggtggtggtggggttgaagaaacttgttggtataattgtcataggact<br>tgcctaaaatattattaaaattacgggagtgtactcagctttgagcctaggagaaaatgccactg<br>tgtgcatccattttaaagggttccctcataaaaaaatgttattccccattatcacatcagtacactg<br>ctttgaaaacaaaacttttcaacatgggcatactgggctacatggaaaatgacatcacccagga<br>gtgatttctctttatatatattatttctgcagttaccatccttatctgagttatcacagttcatgaatcta<br>agaggcggaactctacatcattagtaagaggttccaccaaagtctaaagttgtattcacttgtgtt<br>tgatgaactatctttaaaagaccataggtctatcattatttcttagacataatctaaagaaaaacag<br>actagagaagccacctggttgtaacagaataagcagaagtttacagcatgatagtccaagtgg<br>tgataactttaaataaaactcaaatttttactgtttgtagacaggaatgctgtcctagagaacctcc<br>tcctcaaccagctacgtacatagttttatcctatgcattcctgttttctgtgtgtttttttgttttttttttttt<br>tttttttttttgagacagagtctcgctctgtcacccaggctggagtgcagtggtgcgacctcagct<br>cactgaaacctctgcctcccgggttcaagcgattctcctgcatcagcctcccgagtagctagg<br>attacaggcgcccgccactacgcccagctaatttgtggtatttttagtagagacagggtttcacc<br>atgttggccaggctggtctcgaactcctgacctcatgatccgcccgccttgacctcccaaagtg<br>ctgggattacaggcatgagccaccgcacccagcctgcattcctgtttttttaatggttttggagg<br>gtagcagtagagatggggtctcactatgttgcccagtctagtcttgaactcctgggctacagtta<br>ccctcctacctcggcttcccaaagtgctcggattacaggtgtgagccactgtgcctagcctata<br>atgatcattttaatgtttcccatgcactcatttagtttgaaccttcacagcaacccaatgaggtaat<br>actcccatttcacatataatactgagagatgagttgcacaagattatacactgttaagtagcaga<br>gccagaatggacttcagaatcccaactacaatacaaatgtttatttaaataaagaagaaagctat<br>tgtacaaatatcactcttcaggtttagcttacagagccatggctatggattcttagctctgtaagg<br>aagtgcttctataaattcttaggtttagagatgataccatctgggtacctttgcttgaaccgtgcaa<br>ccacatctgggtctagtaggtggatcccatccagttggtttccaagggtgatcctgaaacagtg<br>taaaaggaggggcaaaccagaaatcctggaattagagggtttaatattgttaaaaaatgcatac<br>caaatgaagactgcctatcatcatatcaaatatgccaattctaaaaagagcttaacattagaata<br>gtatatggtagaattactagttcagaattggcatagattctggtgttaaaatagactggatctgtat<br>tatctgagggttagtaactaatgcttagccaggcctgcttcacagagttgctaccagggagtatt<br>ctttggataagcaaaatgctagcagcatgtgttttaagctctgttaaggggtgaaagatgtaatta<br>ttgacagattaaatagataacttcgtaaccaccagggggcagattcaatacatcacagaatggc<br>tgaggaagatccttgggttgtgaagagagtagaaaccctagggagcagtgcttttgggtccta<br>gaacctgttgagtttctaatgaatatttgtagaatctcataaaacagtttaaatacaagcttaagtg<br>gcttatgaatcctgtgaagctcatttatggactagtgtaaaacaatgtgaagctctactaagttct<br>gtccttaatcataaataatagccccttgaggactagcctgttctctggtcaccttaccagttgggt<br>tgcacattgtgtggtcgtccaaataactcaatcttgcgagtgccaggagatagtctttcaatcat<br>gccatagatttcatctggtttatgactggtggaacgaacctaggaaataaaaactagctgctttt<br>aagttacacaagaaaaaa | |
| TPT1 | NM_001286272.1 | cttcgtgccacgtcaccgcctgcgtcgcttccggaggcgcagcgggcgatgacgtagaggg<br>acgtgccctctatatgaggttggggagcggctgagtcggcctttttccgcccgctccccctcc<br>ccccgagcgccgctccggctgcaccgcgctcgctccgagtttcaggctcgtgctaagctagc<br>gccgtcgtcgtctcccttcagtcgccatcatgattatctaccgggacctcatcagccacgatga<br>gatgttctccgacatctacaagatccgggagatcgcggacgggttgtgcctggaggtggagg<br>ggaagatggtcagtaggacagaaggtaacattgatgactcgctcattggtggaaatgcctccg<br>ctgaaggccccgagggcgaaggtaccgaaagcacagtaatcactggtgtcgatattgtcatg<br>aaccatcacctgcaggaaacaagtttcacaaaagaagcctacaagaagtacatcaaagattac<br>atgaaatcaatcaaagggaaacttgaagaacagagaccagaaagagtaaaacccttttatgaca<br>ggggctgcagaacaaatcaagcacatccttgctaatttcaaaaactaccagttctttattggtga<br>aaacatgaatccagatggcatggttgctctattggactaccgtgaggatggtgtgaccccatat<br>atgattttctttaaggatggtttagaaatggaaaaatgtgatgcaaaagaaagaaatccctgcgc<br>tttctgtctgtctttgtggcggcccagattgaattggggaatacatctttagcctggaaatgtagg<br>ctgcatgttaatggtaatgtaacttttgcagtgtaatgtttgaaaaatattaatgtagtttttgcttta<br>cagtaacaaatgtggcaattattttggatctatcacctgtcatcataactggcttctgcttgtcatc | 65 |

TABLE 1-continued

Prostate Cancer Biomarker/Housekeeper Sequence Information

| Gene Name | RefSeq Accession | Sequence | SEQ ID NO: |
|---|---|---|---|
| | | cacacaacaccaggacttaagacaaatgggactgatgtcatcttgagctcttcatttattttgact | |
| | | gtgatttatttggagtggaggcattgtttttaagaaaaacatgtcatgtaggttgtctaaaaataaa | |
| | | atgcatttaaactcatttgagagaatgccttttagtttaatgcatatttaaactaaattgatcctgtag | |
| | | tgttcctggagaagctagagcctgattgtaggctactactcatcaattaacttctacagtggaga | |
| | | ctacttctgggactggaatataaaaaagaatcaaaggttctgattttgagttgcaataaagggaa | |
| | | agaccatgctcatagcagtgccaacatctgaagtgtggagccttacccatttcatcacctacaa | |
| | | cggaagtagttaactggaagagattaccaagagaataaaaagagactcattcagtggaagca | |
| | | actttgtctcagcttatttcacataaagagagcgaagtcttttgggatgaatgttaattaaactccc | |
| | | tggtaactagaacagggactggcaaactagcctatctgaccacctgttttgtacactttaaggtg | |
| | | gttggttgcctttttaaatggttgaggggaaaagaataccttgtgggatatggaatttaagttcga | |
| | | gtccagttttattggaacgtggctatgcttattcatttatggattgactgtggctgttgtcagtgcat | |
| | | gagcagagttgtgtctaacagactagagcctgcaagtttgccagcccctgatttaaaagatga | |
| | | aggtacacagaatgtgggctggctggtgggcaaaggggtaaaaatgttctctatattgtatctg | |
| | | aaaagatggggtgtctgaataagaaaatgcatctatttgacagacctggagcagttgctatctg | |
| | | ctgctatggtttccaccacagatgcaagaagaacatgtccttgcgctttccgtctgtctaattgtg | |
| | | gcagctgagattgaatagaggaatacaggaggaaaaaaagcgggaagagtttttgaggcag | |
| | | gtcggtcacccaggcttgtagtgcagtggcacaagcaactcactgcattctctgcatcctgtgc | |
| | | tcaagccattttcccacctcagtctcactagttgctgggactgcaggcatgcacccctatgccc | |
| | | agctaattttgtagagaccgagtatcgcttagttgcccagggtggtctcaactcctgggctcaa | |
| | | ggagatctgcccacctcagcctcccaaagtgcaggcctagcctgggaggggaattttcaaaa | |
| | | cgtgagttttgggaaatagtctatcagccttacctggttgattacacttgtaaaagaaagattaaa | |
| | | agcaggccagtgactctggtctgcttgaacatgtgaatgtagtggtttgagcaatctggagtttg | |
| | | ccctagtgtcaaattccagactgtccatagtgtccaaaacctgaggcagatactaatgttaaccc | |
| | | ccagcaccccgtgattggaaacaaacctaaatacgtattgggaacttaatagcaattttaagcat | |
| | | tctgatagatttttttgtagggatggggtcatgccatgtggcccaggctggtctgaaaactctggc | |
| | | ctcaagtgatctcaagctttggccttctaaagtgttgggattacaggtgtgaggcattgcacctg | |
| | | gcttagcgttctgatttgacattgtaatgaaaagtgtgagtctcatctacagggcctttttgtcctct | |
| | | gaaatgatagcaggaagggaattttcaggcagtggtcaaagctggggaaaccaggatagtg | |
| | | aagaaggccttgaggtgagagatggaagctaattggtgaactagccttggaagcctgaaaca | |
| | | gacaagtagcaattcagagactttgtgggctccactgctccaacttgttttgaagattttcagttct | |
| | | gcagaagaggtatttccccagttgtcctttcagtgctcttagctgttttcccaacatccagatcca | |
| | | atcaaggctgggacatagcattttatcatgtctatttaagtcagaagtgatgaaccccagctgttt | |
| | | acctcatggtaaacctttgaagattccaggtagaatcttctcagactttgaagactgtctcatttta | |
| | | tatctttttctcgttattcctagggtcaagacgttttgggcaagaataaggatgtgaacatcagaa | |
| | | agctcataacattttgtttttgatgctaagtttaacaaaggcatgctttagtagcctgtgggcccta | |
| | | gggtttgttaaagtgtggagaacaactgagtggagcaagaggacttttctaggaaggtccttgt | |
| | | aatgtgacatttgaaaacaaatgaaggtgtggaagtaggccatgtggatatcaggacaaacca | |
| | | ttccaggccaagacaacagcagttagtctggagtgtgatgtgttctgggaaaaaagtggccac | |
| | | tttgctaacccaagaagacaggaagggttgtaaagcagtgggagtgtgcaaggaaggaaga | |
| | | ccagacctcaaggaaaccacaggcgctctgagcagaagagttacatgatatgactcaaatttt | |
| | | aaaggatcactttggctgccaggtggcagggtaaaagcatagaataattgtgtataatgtgtttt | |
| | | taaggcaaagatagtggcttagtctagggtagtagactgaggtggtaggaaatgaagataga | |
| | | gacaacaggatatgctggtgggtgaggatggatttaatgttgatacaagtattttggtctgagcg | |
| | | tttggaagaaagttggcactgaggtgggaagtcgagtttagttttgttagttttggatgtgttaagt | |
| | | ttgagatgctgattcttcagagaagtctaagctggagaactatatagagagtggaaagataaca | |
| | | atagacattgaaagccatgatacaggataaggtcatttggagagaggatagactgcattccaa | |
| | | catgagattggttgacaaagagaaaccaacaaaggtaattaagaggtgctcccactgcacttg | |
| | | tactcagaaggctgaggtaggattgttagaggccagcctgggcaccacagggagaccccat | |
| | | ctctaaaatttagccaggaaccatggctcatgcctgtagccccaggaatttgggaggctgagt | |
| | | ggggaggatcgcttgaggtcaggagtttgagaccagcctgggcaacatagggagacctaaa | |
| | | aaaattaattgggcatctgtagtcccagctactcaggcggctgagctgagaggatggcttgag | |
| | | tccgagagattgagggtgcagtgagctgtgatcataccactgcactccagcctgggcggcag | |
| | | tgagacactatctgaaaaaagtttaaaaattttaaaaaagaaggaactgcccctgaggtaagaa | |
| | | ccaagggagggcctcccagaggtcaggtggaaaaagttttaggaaggaggaagtagtcaa | |
| | | cagggttacctgttgcaaagtacttaagtaatatgaggcctgatagtggtaaacttgactaccgt | |
| | | tggatttcactagtgggaaaggaagtctaattaaaatgcactcaagagactaacagtcgcagg | |
| | | catgaaatacaatacaggtacatggtttttattatgtgtgcatctgcttcagtaataggtgtgaatt | |
| | | actcatttggatcattaggagtttcaaaatctagttaaatgactagattttgttgatgtaaattctgt | |
| | | cattctgaactgcagggattgtcagtaacttaactgcaaactaaactggtgataattatggtaaa | |
| | | attgcaagacgagcaataaatctcaaccaacttgagagaacactgataa | |

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the terms "polynucleotide" and "nucleic acid molecule" are used interchangeably to mean a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence that serves as a probe in a microarray analysis preferably comprises a chain of nucleotides, more preferably DNA and/or RNA. In other embodiments, a nucleic acid molecule or nucleic acid sequence comprises other kinds of nucleic acid structures such a for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the terms "hybridize," "hybridizing", "hybridizes," and the like, used in the context of polynucleotides, are meant to refer to conventional hybridization conditions, such as hybridization in 50% formamide/6×SSC/0.1% SDS/100 μg/ml ssDNA, in which temperatures for hybridization are above 37 degrees centigrade and temperatures for washing in 0.1×SSC/0.1% SDS are above 55 degrees C., and preferably to stringent hybridization conditions.

As used herein, the term "normalization" or "normalizer" refers to the expression of a differential value in terms of a standard value to adjust for effects which arise from technical variation due to sample handling, sample preparation, and measurement methods rather than biological variation of biomarker concentration in a sample. For example, when measuring the expression of a differentially expressed protein, the absolute value for the expression of the protein can be expressed in terms of an absolute value for the expression of a standard protein that is substantially constant in expression.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore, the term diagnosis includes: a. prediction (determining if a patient will likely develop aggressive disease (hyperproliferative/invasive)), b. prognosis (predicting whether a patient will likely have a better or worse outcome at a pre-selected time in the future), c. therapy selection, d. therapeutic drug monitoring, and e. relapse monitoring.

"Accuracy" refers to the degree of conformity of a measured or calculated quantity (a test reported value) to its actual (or true) value. Clinical accuracy relates to the proportion of true outcomes (true positives (TP) or true negatives (TN)) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarkers. Examples of biological samples include tissue, organs, or bodily fluids such as whole blood, plasma, serum, tissue, lavage or any other specimen used for detection of disease.

The term "subject" as used herein refers to a mammal, preferably a human. In some embodiments, the subject has at least one prostate cancer symptom. In some embodiments, the subject has a predisposition or familial history for developing a prostate cancer. The subject could also be previously diagnosed with a prostate cancer and is tested for cancer recurrence. In some embodiments, the subject has benign prostate hyperplasia.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present disclosure. Changes in biomarker levels may be used to monitor the progression of disease or therapy.

"Altered", "changed" or "significantly different" refer to a detectable change or difference from a reasonably comparable state, profile, measurement, or the like. Such changes may be all or none. They may be incremental and need not be linear. They may be by orders of magnitude. A change may be an increase or decrease by 5%, 10%, 20%, 30%, 40%, 50%, 60%, 70%, 80%, 90%, 95%, 99%, 100%, or more, or any value in between 0% and 100%. Alternatively, the change may be 1-fold, 1.5-fold, 2-fold, 3-fold, 4-fold, 5-fold or more, or any values in between 1-fold and 5-fold. The change may be statistically significant with a p value of 0.1, 0.05, 0.001, or 0.0001.

The term "stable disease" refers to a diagnosis for the presence of a prostate cancer, however the prostate cancer has been treated and remains in a stable condition, i.e. one that that is not progressive, as determined by imaging data and/or best clinical judgment.

The term "progressive disease" refers to a diagnosis for the presence of a highly active state of a prostate cancer, i.e. one has not been treated and is not stable or has been treated and has not responded to therapy, or has been treated and active disease remains, as determined by imaging data and/or best clinical judgment.

The term "neoplastic disease" refers to any abnormal growth of cells or tissues being either benign (non-cancerous) or malignant (cancerous). For example, the neoplastic disease can be a prostate cancer.

The term "neoplastic tissue" refers to a mass of cells that grow abnormally.

The term "non-neoplastic tissue" refers to a mass of cells that grow normally.

The term "immunotherapy" can refer to activating immunotherapy or suppressing immunotherapy. As will be appreciated by those in the art, activating immunotherapy refers to the use of a therapeutic agent that induces, enhances, or promotes an immune response, including, e.g., a T cell response while suppressing immunotherapy refers to the use of a therapeutic agent that interferes with, suppresses, or inhibits an immune response, including, e.g., a T cell response. Activating immunotherapy may comprise the use of checkpoint inhibitors. Activating immunotherapy may comprise administering to a subject a therapeutic agent that activates a stimulatory checkpoint molecule. Stimulatory checkpoint molecules include, but are not limited to, CD27, CD28, CD40, CD122, CD137, OX40, GITR and ICOS. Therapeutic agents that activate a stimulatory checkpoint molecule include, but are not limited to, MEDI0562, TGN1412, CDX-1127, lipocalin.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (RIA) or biacore assay. In certain embodiments, an antibody that binds to a target has a dissociation constant (Kd) of <1 μM, <100 nM, <10 nM, <1 nM, <0.1 nM, <0.01 nM, or <0.001 nM (e.g. 108 M or less, e.g. from 108 M to 1013 M, e.g., from 109 M to 1013 M). In certain embodiments, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some embodiments, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Administering chemotherapy to a subject can comprise administering a therapeutically effective dose of at least one chemotherapeutic agent. Chemotherapeutic agents include, but are not limited to, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abemaciclib, Abiraterone acetate, Abraxane, Accutane, Actinomycin-D, Adcetris, Ado-Trastuzumab Emtansine, Adriamycin, Adrucil, Afatinib, Afinitor, Agrylin, Ala-Cort, Aldesleukin, Alemtuzumab, Alecensa, Alectinib, Alimta, Alitretinoin, Alkaban-AQ, Alkeran, All-transretinoic Acid, Alpha Interferon, Altretamine, Alunbrig, Amethopterin, Amifostine, Aminoglutethimide, Anagrelide, Anandron, Anastrozole, Apalutamide, Arabinosylcytosine, Ara-C, Aranesp, Aredia, Arimidex, Aromasin, Arranon, Arsenic Trioxide, Arzerra, Asparaginase, Atezolizumab, Atra, Avastin, Avelumab, Axicabtagene Ciloleucel, Axitinib, Azacitidine, Bavencio, Bcg, Beleodaq, Belinostat, Bendamustine, Bendeka, Besponsa, Bevacizumab, Bexarotene, Bexxar, Bicalutamide, Bicnu, Blenoxane, Bleomycin, Blinatumomab, Blincyto, Bortezomib, Bosulif, Bosutinib, Brentuximab Vedotin, Brigatinib, Busulfan, Busulfex, C225, Cabazitaxel, Cabozantinib, Calcium Leucovorin, Campath, Camptosar, Camptothecin-11, Capecitabine, Caprelsa, Carac, Carboplatin, Carfilzomib, Carmustine, Carmustine Wafer, Casodex, CCI-779, Ccnu, Cddp, Ceenu, Ceritinib, Cerubidine, Cetuximab, Chlorambucil, Cisplatin, Citrovorum Factor, Cladribine, Clofarabine, Clolar, Cobimetinib, Cometriq, Cortisone, Cosmegen, Cotellic, Cpt-11, Crizotinib, Cyclophosphamide, Cyramza, Cytadren, Cytarabine, Cytarabine Liposomal, Cytosar-U, Cytoxan, Dabrafenib, Dacarbazine, Dacogen, Dactinomycin, Daratumumab, Darbepoetin Alfa, Darzalex, Dasatinib, Daunomycin, Daunorubicin, Daunorubicin Cytarabine (Liposomal), daunorubicin-hydrochloride, Daunorubicin Liposomal, DaunoXome, Decadron, Decitabine, Degarelix, Delta-Cortef, Deltasone, Denileukin Diftitox, Denosumab, DepoCyt, Dexamethasone, Dexamethasone Acetate, Dexamethasone Sodium Phosphate, Dexasone, Dexrazoxane, Dhad, Dic, Diodex, Docetaxel, Doxil, Doxorubicin, Doxorubicin Liposomal, Droxia, DTIC, Dtic-Dome, Duralone, Durvalumab, Eculizumab, Efudex, Ellence, Elotuzumab, Eloxatin, Elspar, Eltrombopag, Emcyt, Empliciti, Enasidenib, Enzalutamide, Epirubicin, Epoetin Alfa, Erbitux, Eribulin, Erivedge, Erleada, Erlotinib, Erwinia L-asparaginase, Estramustine, Ethyol, Etopophos, Etoposide, Etoposide Phosphate, Eulexin, Everolimus, Evista, Exemestane, Fareston, Farydak, Faslodex, Femara, Filgrastim, Firmagon, Floxuridine, Fludara, Fludarabine, Fluoroplex, Fluorouracil, Fluorouracil (cream), Fluoxymesterone, Flutamide, Folinic Acid, Folotyn, Fudr, Fulvestrant, G-Csf, Gazyva, Gefitinib, Gemcitabine, Gemtuzumab ozogamicin, Gemzar, Gilotrif, Gleevec, Gleostine, Gliadel Wafer, Gm-Csf, Goserelin, Granix, Granulocyte-Colony Stimulating Factor, Granulocyte Macrophage Colony Stimulating Factor, Halaven, Halotestin, Herceptin, Hexadrol, Hexalen, Hexamethylmelamine, Hmm, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibrance, Ibritumomab, Ibritumomab Tiuxetan, Ibrutinib, Iclusig, Idamycin, Idarubicin, Idelalisib, Idhifa, Ifex, IFN-alpha, Ifosfamide, IL-11, IL-2, Imbruvica, Imatinib Mesylate, Imfinzi, Imidazole Carboxamide, Imlygic, Inlyta, Inotuzumab Ozogamicin, Interferon-Alfa, Interferon Alfa-2b (PEG Conjugate), Interleukin-2, Interleukin-11, Intron A (interferon alfa-2b), Ipilimumab, Iressa, Irinotecan, Irinotecan (Liposomal), Isotretinoin, Istodax, Ixabepilone, Ixazomib, Ixempra, Jakafi, Jevtana, Kadcyla, Keytruda, Kidrolase, Kisqali, Kymriah, Kyprolis, Lanacort, Lanreotide, Lapatinib, Lartruvo, L-Asparaginase, Lbrance, Lcr, Lenalidomide, Lenvatinib, Lenvima, Letrozole, Leucovorin, Leukeran, Leukine, Leuprolide, Leurocristine, Leustatin, Liposomal Ara-C, Liquid Pred, Lomustine, Lonsurf, L-PAM, L-Sarcolysin, Lupron, Lupron Depot, Lynparza, Marqibo, Matulane, Maxidex, Mechlorethamine, Mechlorethamine Hydrochloride, Medralone, Medrol, Megace, Megestrol, Megestrol Acetate, Mekinist-Mercaptopurine, Mesna, Mesnex, Methotrexate, Methotrexate Sodium, Methylprednisolone, Meticorten, Midostaurin, Mitomycin, Mitomycin-C, Mitoxantrone, M-Prednisol, MTC, MTX, Mustargen, Mustine, Mutamycin, Myleran, Mylocel, Mylotarg, Navelbine, Necitumumab, Nelarabine, Neosar, Neratinib, Nerlynx, Neulasta, Neumega, Neupogen, Nexavar, Nilandron, Nilotinib, Nilutamide, Ninlaro, Nipent, Niraparib, Nitrogen Mustard, Nivolumab, Nolvadex, Novantrone, Nplate, Obinutuzumab, Octreotide, Octreotide Acetate, Odomzo, Ofatumumab, Olaparib, Olaratumab, Omacetaxine, Oncospar, Oncovin, Onivyde, Ontak, Onxal, Opdivo, Oprelvekin, Orapred, Orasone, Osimertinib, Otrexup, Oxaliplatin, Paclitaxel, Paclitaxel Protein-bound, Palbociclib, Pamidronate, Panitumumab, Panobinostat, Panretin, Paraplatin, Pazopanib, Pediapred, Peg Interferon, Pegaspargase, Pegfilgrastim, Peg-Intron, PEG-L-asparaginase, Pembrolizumab, Pemetrexed, Pentostatin, Perj eta, Pertuzumab, Phenylalanine Mustard, Platinol, Platinol-AQ, Pomalidomide, Pomalyst, Ponatinib, Portrazza, Pralatrexate, Prednisolone, Prednisone, Prelone, Procarbazine, Procrit, Proleukin, Prolia, Prolifeprospan 20 with Carmustine Implant, Promacta, Provenge, Purinethol, Radium 223 Dichloride, Raloxifene, Ramucirumab, Rasuvo, Regorafenib, Revlimid, Rheumatrex, Ribociclib, Rituxan, Rituxan Hycela, Rituximab, Rituximab Hyalurodinase, Roferon-A (Interferon Alfa-2a), Romidepsin, Romiplostim, Rubex, Rubidomycin Hydrochloride, Rubraca, Rucaparib, Ruxolitinib, Rydapt, Sandostatin, Sandostatin LAR, Sargramostim, Siltuximab, Sipuleucel-T, Soliris, Solu-Cortef, Solu-Medrol, Somatuline, Sonidegib, Sorafenib, Sprycel, Sti-571, Stivarga, Streptozocin, SU11248, Sunitinib, Sutent, Sylvant, Synribo, Tafinlar, Tagrisso, Talimogene Laherparepvec, Tamoxifen, Tarceva, Targretin, Tasigna, Taxol, Taxotere, Tecentriq, Temodar, Temozolomide, Temsirolimus, Teniposide, Tespa, Thalidomide, Thalomid, TheraCys, Thioguanine, Thioguanine Tabloid, Thiophosphoamide, Thioplex, Thiotepa, Tice, Tisagenlecleucel, Toposar, Topotecan, Toremifene, Torisel, Tositumomab, Trabectedin, Trametinib, Trastuzumab, Treanda, Trelstar, Tretinoin, Trexall, Trifluridine/Tipiricil, Triptorelin pamoate, Trisenox, Tspa, T-VEC, Tykerb, Valrubicin, Valstar, Vandetanib, VCR, Vectibix, Velban, Velcade, Vemurafenib, Venclexta, Venetoclax, VePesid, Verzenio, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, Vlb, VM-26, Vorinostat, Votrient, VP-16, Vumon, Vyxeos, Xalkori Capsules, Xeloda, Xgeva, Xofigo, Xtandi, Yervoy, Yescarta, Yondelis, Zaltrap, Zanosar, Zarxio, Zejula, Zelboraf, Zevalin, Zinecard, Ziv-aflibercept, Zoladex, Zoledronic Acid, Zolinza, Zometa, Zydelig, Zykadia, Zytiga, or any combination thereof.

The terms "effective amount" and "therapeutically effective amount" of an agent or compound are used in the broadest sense to refer to a nontoxic but sufficient amount of an active agent or compound to provide the desired effect or benefit.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer or cervical cancer.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

As used herein, the term "about" when used in conjunction with numerical values and/or ranges generally refers to those numerical values and/or ranges near to a recited numerical value and/or range. In some instances, the term "about" can mean within ±10% of the recited value. For example, in some instances, "about 100 [units]" can mean within ±10% of 100 (e.g., from 90 to 110).

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Derivation of a 38-Marker Gene Panel

Figure 1B:
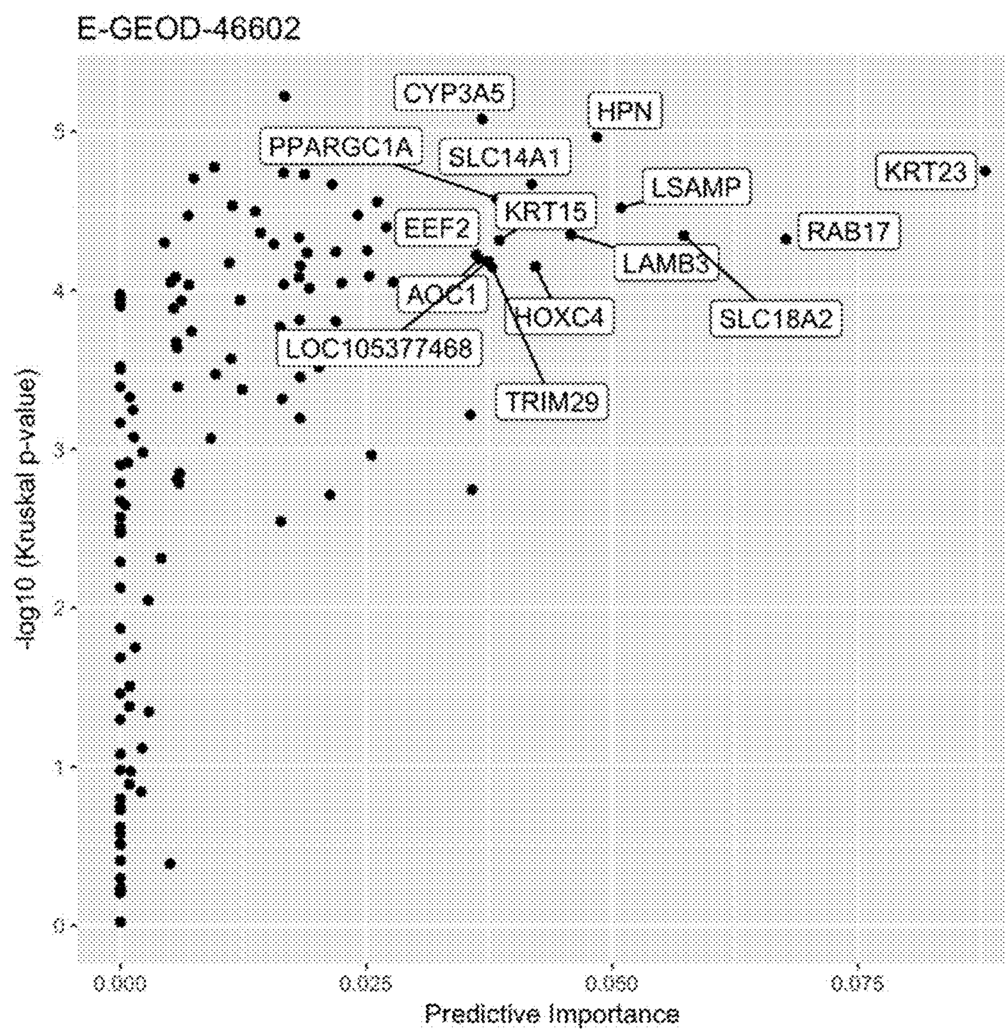
Figure 2:
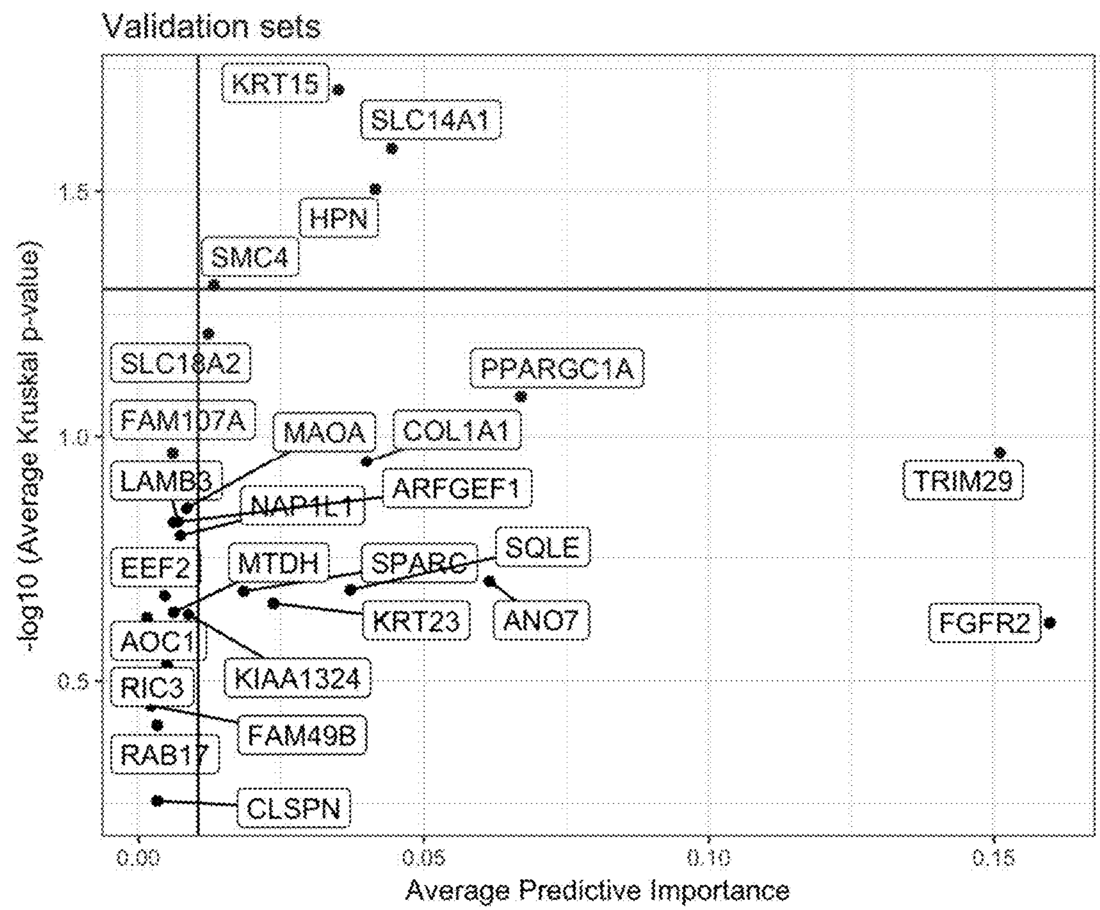
FIG. 2 is a scatter plot of average predictive importance vs. Kruskal Wallis p-values. Vertical and horizontal lines represent p-value of 0.05 and median Predictive Importance value respectively.

Two microarray datasets (E-GEOD-46691 and E-GEOD-46602, Table 2) were used as derivation cohorts (n=595 samples). Random Forest algorithm was applied to each dataset to identify the most important sets of transcripts that are predictive of phenotypic diversity within each set. Each microarray dataset comprised 22,011 and 54,675 probe sets, respectively. The Random Forest-drive marker selection algorithm identified n=129 transcripts as predictive of disease progression across the two datasets. Of these n=30 exhibited high Predictive Importance scores in both datasets (FIGS. 1A-1B). Three microarray datasets (E-GEOD-62116, E-GEOD-62667, E-GEOD-72220, Table 2) were then used to validate the putative Prostate Cancer signature. For each transcript across the validation cohort (n=564 samples) Predictive Importance and Kruskal-Wallis p-values were obtained and averaged across the three datasets (FIG. 2). Examination of the literature identified the ARv7 variant, the ERG-TRMS22 fusion gene and AR1/AR2 signaling as additional gene sets to include and evaluate.

Figure 3:
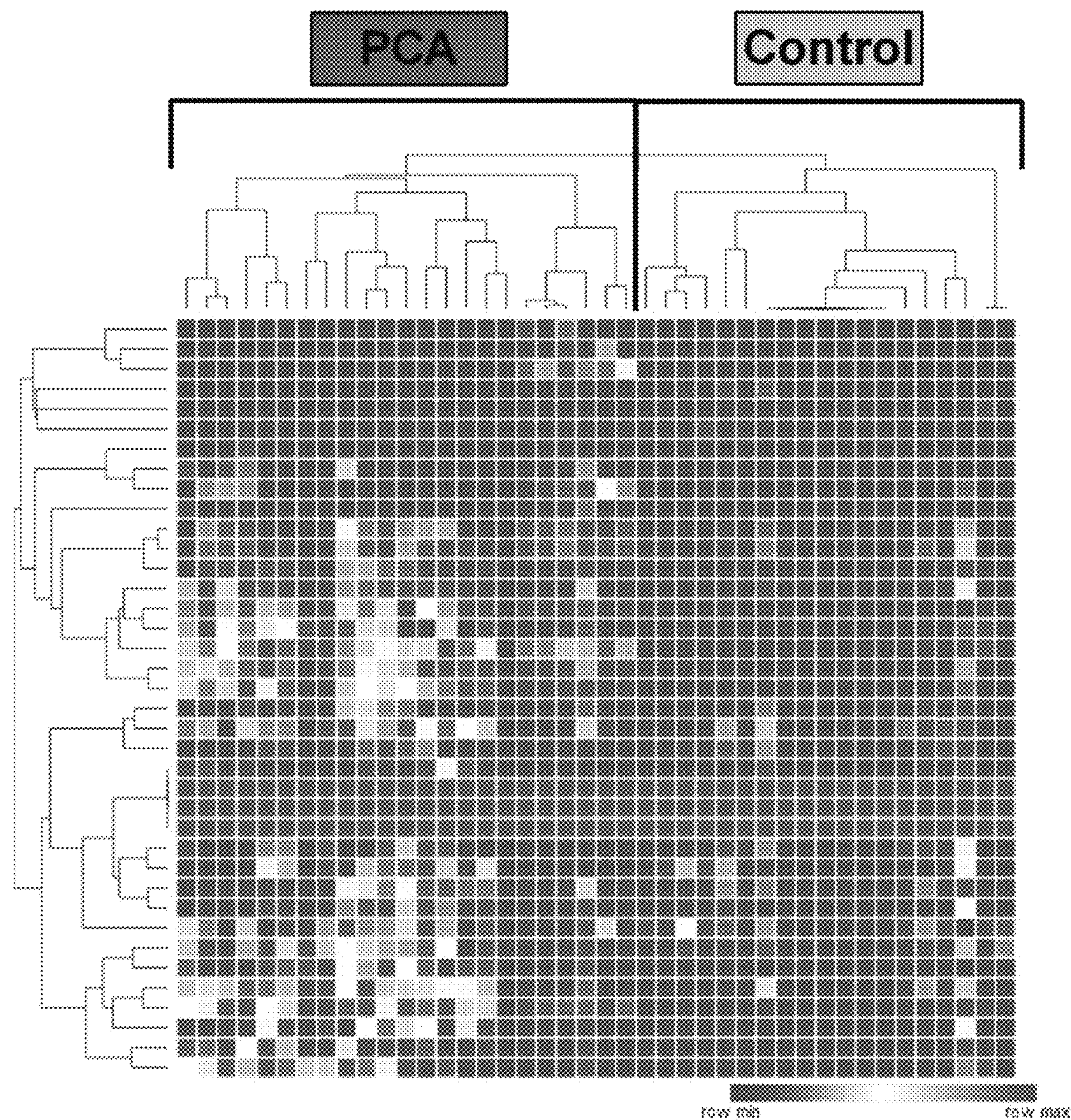
FIG. 3 is a graph showing hierarchical clustering of gene expression identified that PCA tumor tissue and control tissue were separately clustered. Gene expression was significantly higher in the PCA tissue.
Figure 4:
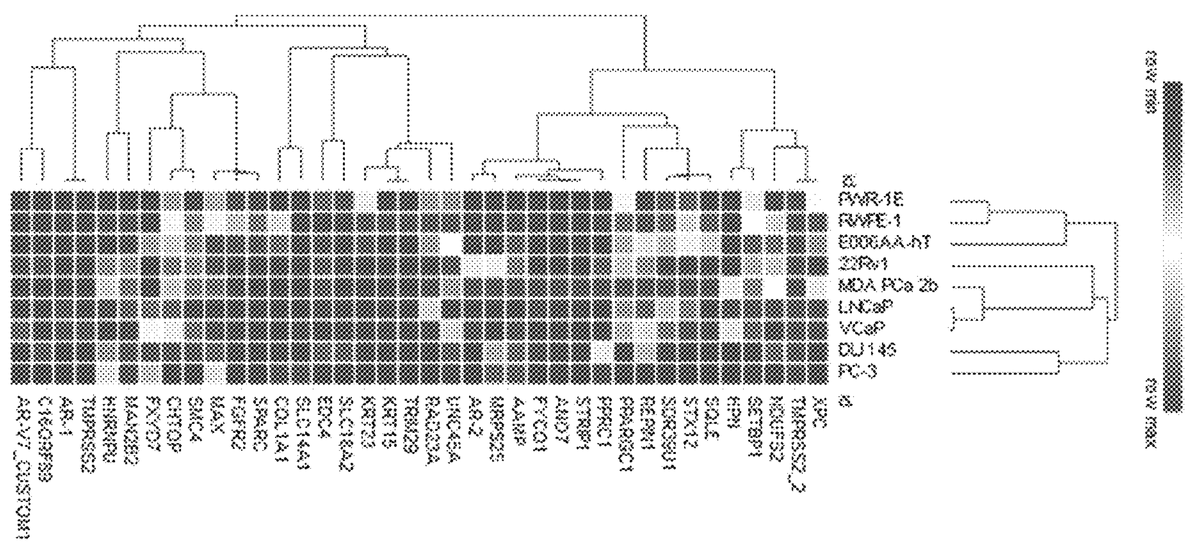
FIG. 4 is a graph showing clustering of normalized gene expression separates prostate-derived cell lines into their tissue of origin (i.e., normal, localized, metastatic).

Evaluation of transcripts in a preliminary dataset of blood samples from prostate cancer (n=20) and matched normal blood (n=20) confirmed expression of the 37 genes as markers of PCA (Table 3). These genes were demonstrated to be highly expressed in PCA tumor tissue compared to normal prostate and this could be used to effectively differentiate tumor from control (FIG. 3). They also differentiated seven different PCA cell lines, 22Rv1 and E006AA-hT (localized); VCaP; PC-3; LNCaP; DU145 and MDA PCa2b (all metastatic) from two normal prostate epithelial lines: PWR-1E and RWPE-1 (FIG. 4). These data demonstrate the candidate target transcripts are produced by neoplastic transformed prostate epithelial cell and are detectable in blood.

An artificial intelligence model of prostate cancer disease was built using normalized gene expression of these 37 markers in whole blood from Controls (n=100), and PCA (n=21) samples. The dataset was randomly split into training and testing partitions for model creation and validation respectively. Twelve algorithms were evaluated (XGB, RF, glmnet, cforest, CART, treebag, knn, nnet, SVM-radial, SVM-linear, NB and mlp). The top performing algorithm (XGB—"gradient boosting") best predicted the training data. In the test set, XGB produced probability scores that predicted the sample. Each probability score reflects the "certainty" of an algorithm that an unknown sample belongs to either "Control" or "PCA" class. For example, an unknown sample S1 can have the following probability vector [Control=20%, PCA=80%]. This sample would be considered a PCA sample.

TABLE 2

Summary of all public microarray datasets that were used to derived Prostate Cancer specific gene signature.

| Accession Number | Sample Count | Dataset Description |
|---|---|---|
| E-GEOD-46691 | 545 | Gleason Score 5-10<br>Score 5 (n = 3)<br>Score 6 (n = 60)<br>Score 7 (n = 271)<br>Score 8 (n = 68)<br>Score 9 (n = 134)<br>Score 10 (n = 9) |
| E-GEOD-46602 | 50 | Benign Prostate Glands (n = 14)<br>Prostate Tumor (n = 36) |
| E-GEOD-62116 | 235 | Gleason Score 5-10<br>Score 5 (n = 1)<br>Score 6 (n = 17)<br>Score 7 (n = 119)<br>Score 8 (n = 39)<br>Score 9 (n = 58)<br>Score 10 (n = 1) |
| E-GEOD-62667 | 182 | Gleason Score 6-9<br>Score 6 (n = 25)<br>Score 7 (n = 112)<br>Score 8 (n = 23)<br>Score 9 (n = 22) |
| E-GEOD-72220 | 147 | Normal Tissue (n = 90)<br>Tumor Tissue (n = 57 |

TABLE 3

37 PCA marker gene panel (not including the housekeeping gene)

| Prostate Cancer Biomarker Gene | | NCBI Chromosome | UniGene | | Exon | Assay | Amplicon |
|---|---|---|---|---|---|---|---|
| Symbol | Name | Location | ID | RefSeq | Boundary | Location | Length |
| AAMP | Angio-associated migratory cell protein | Chr.2: 218264129-218270209 | Hs.83347 | NM_001087.4 | 2-3 | 395 | 58 |
| ANO7 | Anoctamin 7 | Chr.2: 241188509-241239602 | Hs.163909 | NM_001001891.3 | 5-6 | 686 | 60 |
| AR | androgen receptor | Chr.X: 67544032-67730619 | Hs.76704 | NM_000044.3 | 2-3 | 2882 | 144 |
| AR-V7 | androgen receptor transcript variant 7 | AR truncation | | | | | 73 |
| C16orf89 | chromosome 16 open reading frame 89 | Chr.16: 5042772-5066145 | Hs.11782 | NM_001098514.2 | 5-6 | 995 | 75 |
| CHTOP | chromatin target of PRMT1 | Chr.1: 153633982-153646306 | Hs.611057 | NM_001206612.1 | 2-3 | 445 | 66 |
| COL1A1 | collagen type I alpha 1 | Chr.17: 50184096-50201648 | Hs.172928 | NM_000088.3 | 1-2 | 230 | 66 |
| EDC4 | enhancer of mRNA decapping 4 | Chr.16: 67873023-67884514 | Hs.75682 | NM_014329.4 | 27-28 | 4089 | 72 |
| FGFR2 | fibroblast growth factor receptor 2 | Chr.10: 121478330-121598656 | Hs.533683 | NM_000141.4 | 13-14 | 2516 | 74 |
| FXYD7 | FXYD domain containing ion transport regulator 7 | Chr.19: 35143250-35154302 | Hs.134729 | NM_022006.1 | 5-6 | 300 | 89 |
| FYCO1 | FYVE and coiled-coil domain containing 1 | Chr.3: 45917899-45995824 | Hs.200227 | NM_024513.3 | 11-12 | 3651 | 59 |
| HNRNPU | heterogeneous nuclear ribonucleoprotein U | Chr.1: 244842123-244864720 | Hs.106212 | NM_004501.3 | 8-9 | 1773 | 79 |
| HPN | hepsin | Chr.19: 35040506-35066573 | Hs.182385 | NM_002151.2 | 10-11 | 1052 | 89 |

TABLE 3-continued

| 37 PCA marker gene panel (not including the housekeeping gene) | | | | | | | |
|---|---|---|---|---|---|---|---|
| Prostate Cancer Biomarker Gene | | NCBI Chromosome | UniGene | | Exon | Assay | Amplicon |
| Symbol | Name | Location | ID | RefSeq | Boundary | Location | Length |
| KRT15 | keratin 15 | Chr.17: 41513745-41522413 | Hs.654570 | NM_002275.3 | 7-8 | 1461 | 81 |
| KRT23 | keratin 23 | Chr.17: 40922696-40937643 | Hs.9029 | NM_001282433.1 | 5-6 | 1045 | 90 |
| MAN2B2 | mannosidase alpha class 2B member 2 | Chr.4: 6575174-6622403 | Hs.188464 | NM_001292038.1 | 5-6 | 716 | 55 |
| MAX | MYC associated factor X | Chr.14: 65006101-65102695 | Hs.285354 | NM_001320415.1 | 3-4 | 377 | 61 |
| MRPS25 | mitochondrial ribosomal protein S25 | Chr.3: 15042251-15065337 | Hs.657764 | NM_022497.4 | 2-3 | 380 | 80 |
| NDUFS2 | NADH: ubiquinone oxidoreductase core subunit S2 | Chr.1 161197377-161214395 | Hs.173611 | NM_001166159.1 | 3-4 | 632 | 80 |
| PPARGC1A | PPARG coactivator 1 alpha | Chr.4: 23792021-24472975 | Hs.527078 | NM_013261.3 | 7-8 | 998 | 83 |
| PPRC1 | peroxisome proliferator-activated receptor gamma, coactivator-related 1 | Chr.10: 102132994-102150333 | Hs.533551 | NM_001288727.1 | 1-2 | 224 | 55 |
| RAD23A | RAD23 homolog A, nucleotide excision repair protein | Chr.19: 12945814-12953643 | Hs.643267 | NM_001270362.1 | 1-2 | 203 | 74 |
| REPIN1 | replication initiator 1 | Chr.7: 150368228-150374044 | Hs.647086 | NM_013400.3 | 3-4 | 474 | 70 |
| SDR39U1 | short chain dehydrogenase/ reductase family 39U member 1 | Chr.14: 24439766-24442905 | Hs.643552 | NM_020195.2 | 4-5 | 358 | 91 |
| SETBP1 | SET binding protein 1 | Chr.18: 44680173-45068510 | Hs.435458 | NM_001130110.1 | 2-3 | 882 | 70 |
| SLC14A1 | solute carrier family 14 member 1 (Kidd blood group) | Chr.18: 45724123-45752520 | Hs.101307 | NM_001128588.3 | 7-8 | 1057 | 80 |
| SLC18A2 | solute carrier family 18 member A2 | Chr.10: 117241073-117279430 | Hs.596992 | NM_003054.4 | 15-16 | 1605 | 145 |
| SMC4 | structural maintenance of chromosomes 4 | Chr.3: 160399304-160434962 | Hs.58992 | NM_001002800.2 | 5-6 | 1134 | 91 |
| SPARC | secreted protein acidic and cysteine rich | Chr.5: 151661096-151687054 | Hs.111779 | NM_001309443.1 | 6-7 | 650 | 76 |
| SQLE | squalene epoxidase | Chr.8: 124998478-125022283 | Hs.71465 | NM_003129.3 | 9-10 | 2368 | 109 |
| STRIP1 | striatin interacting protein 1 | Chr.1: 110031577-110054641 | Hs.584996 | NM_001270768.1 | 12-13 | 1303 | 64 |
| STX12 | syntaxin 12 | Chr.1: 27773183-27824452 | Hs.523855 | NM_177424.2 | 1-2 | 248 | 70 |
| TMPRSS2_1 | TMPRSS2-ERG fusion | TMPRSS2 exon 1 and | | DQ204772.1 | | 49 | 106 |
| TMPRSS2_2 | TMPRSS2-ERG fusion | ERG exon 4 fusion | | OM_TMPRSS2-ERG_T2E4_COSF28.0 | | 58 | 88 |
| TRIM29 | tripartite motif containing 29 | Chr.11: 120111286-120138179 | Hs.504115 | NM_012101.3 | 2-3 | 1025 | 62 |
| UNC45A | unc-45 myosin chaperone A | Chr.15: 90929980-90954093 | Hs.389461 | NM_001039675.1 | 20-21 | 3095 | 62 |

TABLE 3-continued

| 37 PCA marker gene panel (not including the housekeeping gene) | | | | | | | |
|---|---|---|---|---|---|---|---|
| Prostate Cancer Biomarker Gene | | NCBI Chromosome | UniGene | | Exon | Assay | Amplicon |
| Symbol | Name | Location | ID | RefSeq | Boundary | Location | Length |
| XPC | XPC complex subunit, DNA damage recognition and repair factor | Chr.3: 14145147-14178672 | Hs.475538 | NM_004628.4 | 2-3 | 403 | 104 |

Example 2

Clinical Utility

Figure 5:
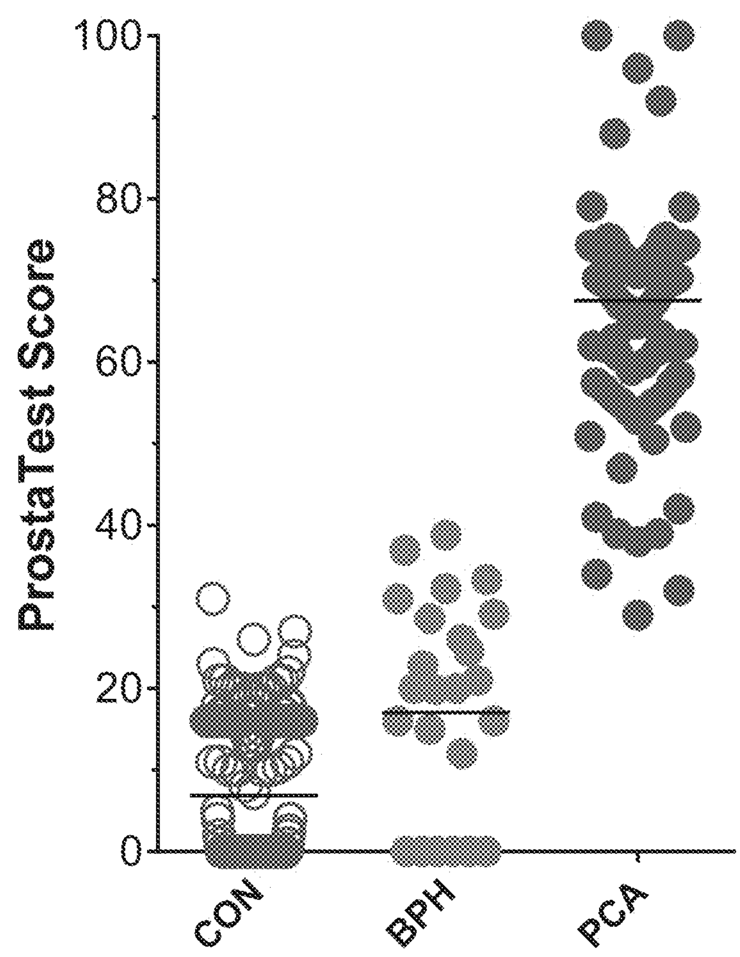
FIG. 5 is a graph showing gene expression in the control (n=201), BPH (prostate hyperplasia, n=26) and prostate cancer cases (n=125). Identified expression levels were significantly ($p<0.0001$) elevated in cases (63±19%) versus benign prostatic hyperplasia (BPH: 17±13%) and controls (8±9%).
Figure 6:
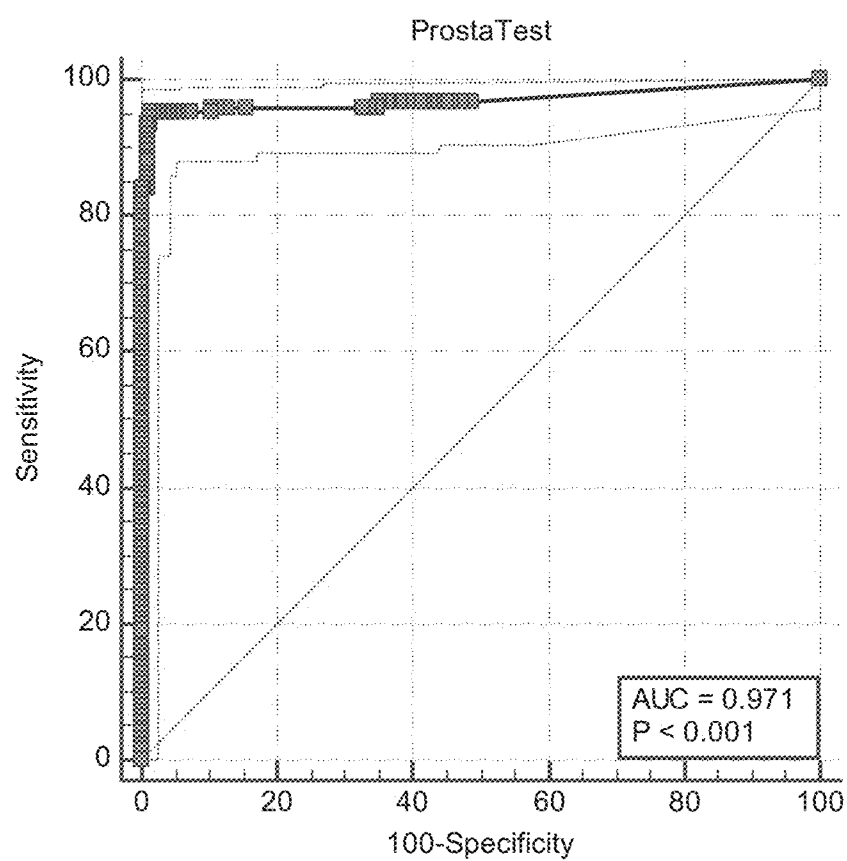
FIG. 6 is a graph showing receiver operator curve analysis. The AUROC was 0.97 and the Youden J index was 0.94. The Z-statistic was highly significant (38.9; $p<0.0001$).
Figure 7:
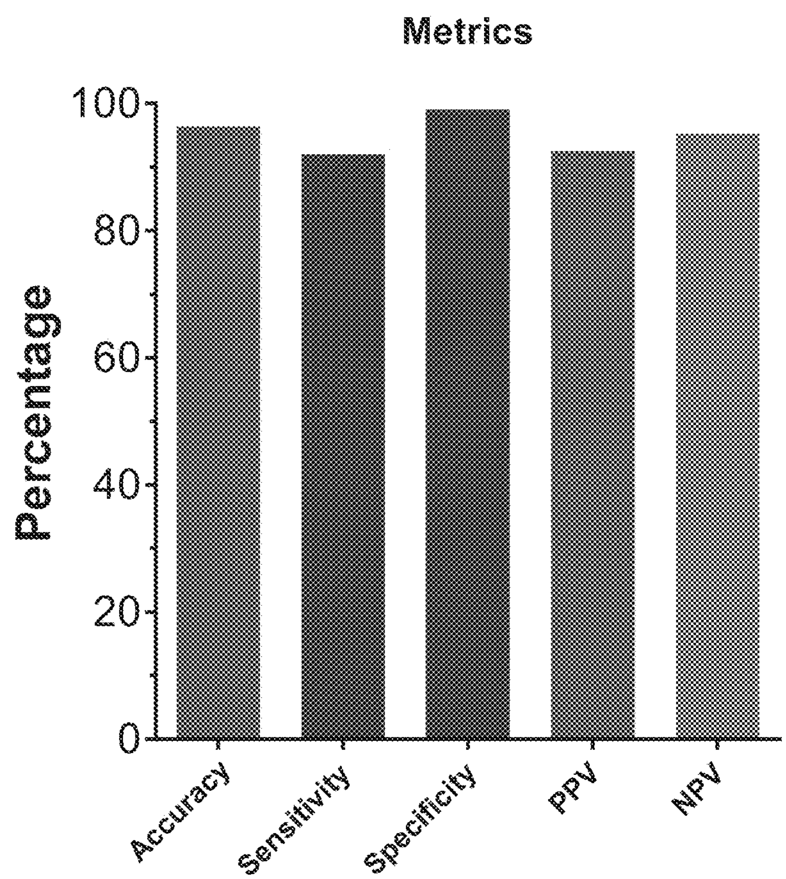
FIG. 7 is a graph showing the metrics of the ProstaTest for determining PCA ranged 92-99%.

The ProstaTest scores were significantly ($p<0.001$) elevated in PCA (63±19%) compared to men with benign prostate hyperplasia (17±13%) and controls (8±9%) (FIG. 5). There was no difference in levels between controls and hyperplasia. The data (receiver operator cuve analysis and metrics) for the utility of the test to differentiate patients with prostate cancer (n=125) from controls (n=201) in the validation is included in FIG. 6. The score exhibited an area under the curve (AUROC) of 0.97. The metrics are: sensitivity: 92% and specificity: 99% (FIG. 7). The Youden index J is 0.94 and the Z-statistic for differentiating controls was 38.9.

Figure 8:
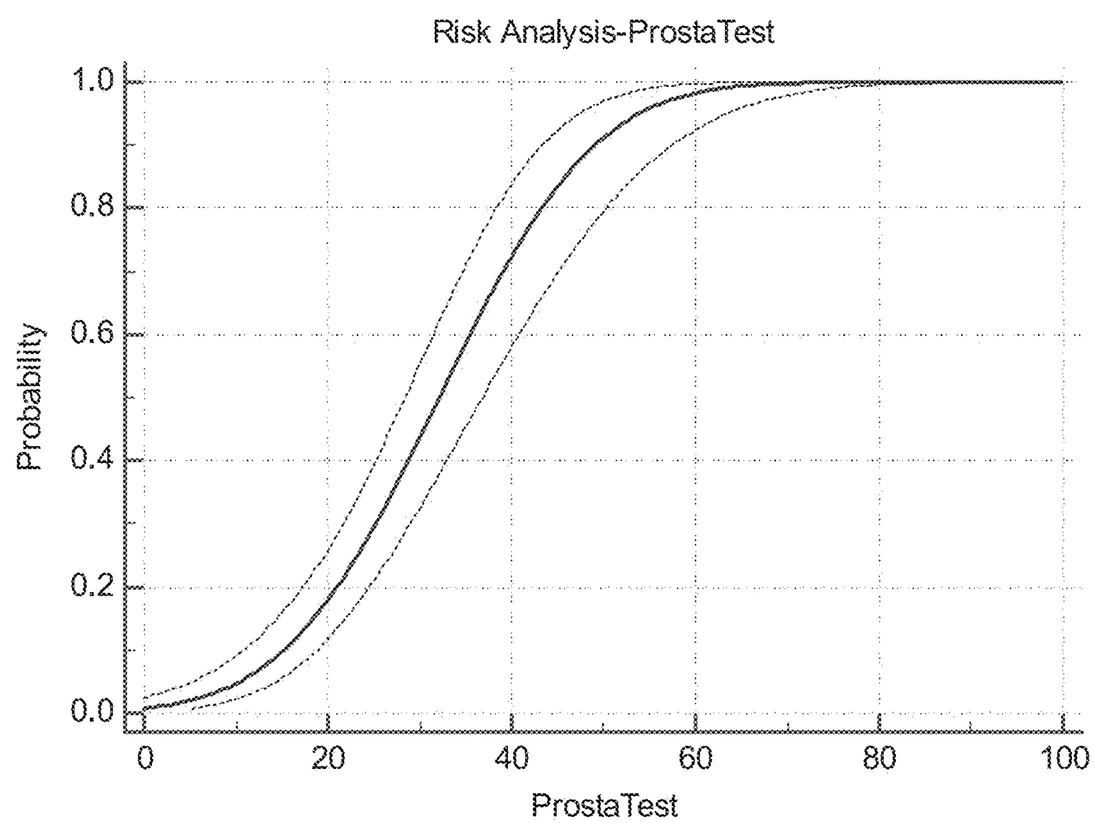
FIG. 8 is a Probit risk assessment plot that identifies a ProstaTest score >30 was 60% accurate for predicting prostate cancer in a blood sample. This was increased to >80% at a test scores ≥34. Dotted lines represent the 95% confidence interval.

A Probit-risk assessment plot identified a ProstaTest score >30 was 50% accurate for predicting PCA in a blood sample (FIG. 8). This was increased to 60% at a ProstaTest score ≥32 and was >80% at a score >34. The tool can therefore accurately differentiate between controls and prostate cancer disease.

Figure 9:
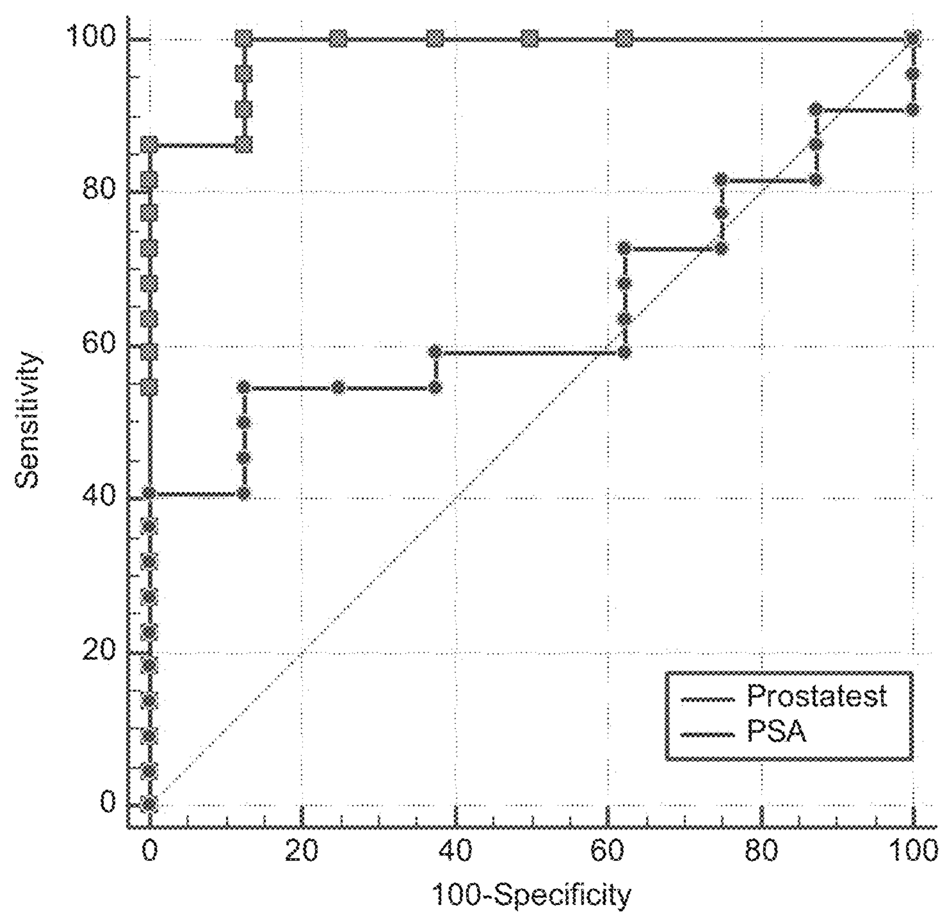
FIG. 9 is a graph showing receiver operator curve analysis comparing the ProstaTest with measurements of PSA for predicting high grade (≥Gleason 7) compared to low grade (Gleason 5+6) tumors. The AUROC was 0.98 and the Youden J index was 0.87 for the ProstaTest. For PSA, the AUROC was 0.64 and the Youden J index was 0.42. The ProstaTest was significantly better than PSA for predicting grade (Z-statistic: 3.05, $p=0.002$).

The ProstaTest scores were significantly ($p<0.001$) elevated in high grade (Gleason score ≥7: 70±19%) compared to low grade (Gleason 5+6) PCA (41±7%). The data (receiver operator cuve analysis and metrics) for the utility of the test to differentiate high from low grade scores is included in FIG. 9. The score exhibited an area under the curve (AUROC) of 0.98. The metrics are: sensitivity: 100% and specificity: 88%. The Youden index J is 0.87. PSA levels, in comparison, exhibited an AUROC of 64%. The sensitivity and specificity were 54% and 87% respectively. The Z-statistic for differentiating the ProstaTest from PSA was 3.05 ($p=0.002$).

Figure 10:
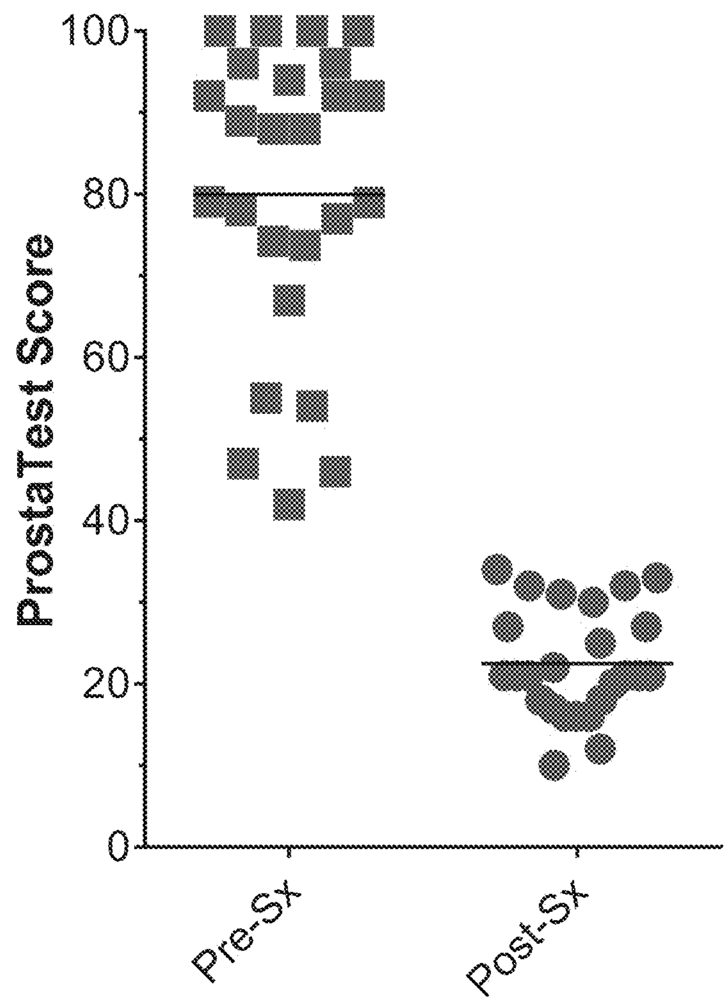
FIG. 10 is a graph showing the effect of surgery on the ProstaTest. Levels prior to surgery are elevated (80±18%). Surgery reduced levels to 22±7% ($p<0.0001$), not different to control levels.
Figure 11:
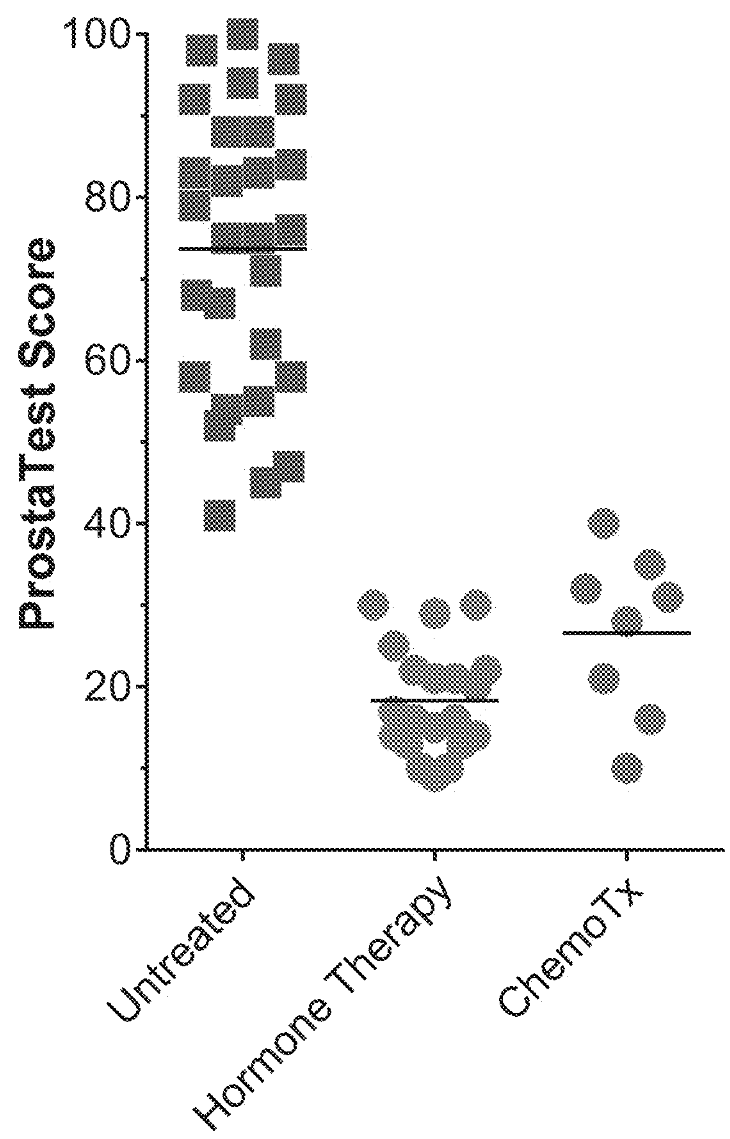
FIG. 11 is a graph showing the effect of treatment on the ProstaTest. Levels prior to treatment are elevated (74±18%). In those who responded to hormone therapy, levels were reduced to 18±7% ($p<0.0001$). In those requiring chemotherapy, levels were reduced to 27±10% ($p<0.001$).

Specific evaluation of a PCA cohort before and after surgery identified that complete removal of a tumor and no evidence of disease was associated with a significant decrease ($p<0.0001$) in the ProstaTest (FIG. 10). Levels were not significantly different to controls or those with prostate hyperplasia. Evaluation of separate cohort identified that patients who underwent and responded to therapy exhibited a significant lower score ($p<0.001$) that those diagnosed with disease (FIG. 11). Therapies included hormone and chemotherapy. The tool can therefore accurately identify treatment response in prostate cancer disease.

REFERENCES

Ferlay J, Steliarova-Foucher E, Lortet-Tieulent J, Rosso S, Coebergh J W, Comber H, Forman D, Bray F. Cancer incidence and mortality patterns in Europe: estimates for 40 countries in 2012. Eur J Cancer. 2013; 49: 1374-403. doi: 10.016/j.ejca.2012.12.027. Epub 3 Feb. 26.

Jemal A, Fedewa S A, Ma J, Siegel R, Lin C C, Brawley O, Ward E M. Prostate Cancer Incidence and PSA Testing Patterns in Relation to USPSTF Screening Recommendations. JAMA. 2015; 314:2054-61. doi: 10.1001/jama.2015.14905.

Nam R K, Satkunavisam R, Chin J L, Izawa J, Trachtenberg J, Rendon R, Bell D, Singal R, Sherman C, Sugar L, Chagin K, Kattan W M. Next-generation prostate cancer risk calculator for primary care physicians. Can Urol Assoc J. 2017; 1.

The Molecular Taxonomy of Primary Prostate Cancer. Cell. 2015; 163:1011-25. doi: 10.6/j.cell.2015.10.025.

Lalonde E, Ishkanian A S, Sykes J, Fraser M, Ross-Adams H, Erho N, Dunning M J, Halim S, Lamb A D, Moon N C, Zafarana G, Warren A Y, Meng X, et al. Tumour genomic and microenvironmental heterogeneity for integrated prediction of 5-year biochemical recurrence of prostate cancer: a retrospective cohort study. Lancet Oncol. 2014; 15: 1521-32. doi: 10.016/S470-2045(14) 71021-6. Epub 2014 Nov. 13.

Barbieri C E, Baca S C, Lawrence M S, Demichelis F, Blattner M, Theurillat J P, White T A, Stojanov P, Van Allen E, Stransky N, Nickerson E, Chae S S, Boysen G, et al. Exome sequencing identifies recurrent SPOP, FOXA1 and MED12 mutations in prostate cancer. Nat Genet. 2012; 44: 685-9. doi: 10.1038/ng.2279.

Tomlins S A, Rhodes D R, Perner S, Dhanasekaran S M, Mehra R, Sun W, Varambally S, Cao X, Tchinda J, Kuefer R, Lee C, Montie J E, Shah R B, et al. Recurrent fusion of TMPRSS2 and ETS transcription factor genes in prostate cancer. Science. 2005; 310: 644-8. doi: 10.1126/science.1117679.

Pettersson A, Graff R E, Bauer S R, Pitt M J, Lis R T, Stack E C, Martin N E, Kunz L, Penney K L, Ligon A H, Suppan C, Flavin R, Sesso H D, et al. The TMPRSS2:ERG rearrangement, ERG expression, and prostate cancer outcomes: a cohort study and meta-analysis. Cancer Epidemiol Biomarkers Prev. 2012; 21: 1497-509. doi: 10.158/055-9965.EPI-12-0042. Epub 2012 Jun. 26.

Antonarakis E S, Lu C, Luber B, Wang H, Chen Y, Nakazawa M, Nadal R, Paller C J, Denmeade S R, Carducci M A, Eisenberger M A, Luo J. Androgen Receptor Splice Variant 7 and Efficacy of Taxane Chemotherapy in Patients With Metastatic Castration-Resistant Prostate Cancer. JAMA Oncol. 2015; 1: 582-91. doi: 10.1001/jamaonco1.2015.1341.

Velonas V M, Woo H H, dos Remedios C G, Assinder S J. Current status of biomarkers for prostate cancer. Int J Mol Sci. 2013; 14: 11034-60. doi: 10.3390/ijms140611034.

Schroder F H, Hugosson J, Roobol M J, Tammela T L, Zappa M, Nelen V, Kwiatkowski M, Lujan M, Maattanen L, Lilja H, Denis L J, Recker F, Paez A, et al. Screening and prostate cancer mortality: results of the European Randomised Study of Screening for Prostate Cancer (ER- SPC) at 13 years of follow-up. Lancet. 2014; 384: 2027-35. doi: 10.1016/S0140-6736(14)60525-0. Epub 2014 Aug. 6.

Schroder F H, Carter H B, Wolters T, van den Bergh R C, Gosselaar C, Bangma C H, Roobol M J. Early detection of prostate cancer in 2007. Part 1: PSA and PSA kinetics. Eur Urol. 2008; 53: 468-77. doi: 10.1016/j.eururo.2007.10.047. Epub November 5.

Cooperberg M R, Pasta D J, Elkin E P, Litwin M S, Latini D M, Du Chane J, Carroll P R. The University of California, San Francisco Cancer of the Prostate Risk Assessment score: a straightforward and reliable preoperative predictor of disease recurrence after radical prostatectomy. J Urol. 2005; 173: 1938-42. doi: 10.097/01.ju.0000158155.33890.e7.

Troyer D A, Lucia M S, de Bruine A P, Mendez-Meza R, Baldewijns M M, Dunscomb N, Van Engeland M, McAskill T, Bierau K, Louwagie J, Bigley J W. Prostate cancer detected by methylated gene markers in histopathologically cancer-negative tissues from men with subsequent positive biopsies. Cancer Epidemiol Biomarkers Prev. 2009; 18: 2717-22. doi: 10.1158/055-9965.EPI-09-0068. Epub 2009 Sep. 15.

Van Neste L, Partin A W, Stewart G D, Epstein J I, Harrison D J, Van Criekinge W. Risk score predicts high-grade prostate cancer in DNA-methylation positive, histopathologically negative biopsies. Prostate. 2016; 76: 1078-87. doi: 10.02/pros.23191. Epub 2016 Apr. 28.

Stewart G D, Van Neste L, Delvenne P, Delree P, Delga A, McNeill S A, O'Donnell M, Clark J, Van Criekinge W, Bigley J, Harrison D J. Clinical utility of an epigenetic assay to detect occult prostate cancer in histopathologically negative biopsies: results of the MATLOC study. J Urol. 2013; 189: 1110-6. doi: 10.016/j.juro.2012.08.219. Epub October 8.

Day J R, Jost M, Reynolds M A, Groskopf J, Rittenhouse H. PCA3: from basic molecular science to the clinical lab. Cancer Lett. 2011; 301: 1-6. doi: 10.1016/j.canlet.2010.10.019. Epub November 18.

Cuzick J, Swanson G P, Fisher G, Brothman A R, Berney D M, Reid J E, Mesher D, Speights V O, Stankiewicz E, Foster C S, Moller H, Scardino P, Warren J D, et al. Prognostic value of an RNA expression signature derived from cell cycle proliferation genes in patients with prostate cancer: a retrospective study. Lancet Oncol. 2011; 12: 245-55. doi: 10.1016/S470-2045(10)70295-3.

Erho N, Crisan A, Vergara I A, Mitra A P, Ghadessi M, Buerki C, Bergstralh E J, Kollmeyer T, Fink S, Haddad Z, Zimmermann B, Sierocinski T, Ballman K V, et al. Discovery and validation of a prostate cancer genomic classifier that predicts early metastasis following radical prostatectomy. PLoS One. 2013; 8: e66855. doi: 10.1371/journal.pone.0066855. Print 2013.

Karnes R J, Bergstralh E J, Davicioni E, Ghadessi M, Buerki C, Mitra A P, Crisan A, Erho N, Vergara I A, Lam L L, Carlson R, Thompson D J, Haddad Z, et al. Validation of a genomic classifier that predicts metastasis following radical prostatectomy in an at risk patient population. J Urol. 2013; 190: 2047-53. doi: 10.1016/j.juro.2013.06.017. Epub June 11.

Knezevic D, Goddard A D, Natraj N, Cherbavaz D B, Clark-Langone K M, Snable J, Watson D, Falzarano S M, Magi-Galluzzi C, Klein E A, Quale C. Analytical validation of the Oncotype D X prostate cancer assay—a clinical RT-PCR assay optimized for prostate needle biopsies. BMC Genomics. 2013; 14:690: 10.1186/471-2164-14-690.

Klein E A, Cooperberg M R, Magi-Galluzzi C, Simko J P, Falzarano S M, Maddala T, Chan J M, Li J, Cowan J E, Tsiatis A C, Cherbavaz D B, Pelham R J, Tenggara-Hunter I, et al. A 17-gene assay to predict prostate cancer aggressiveness in the context of Gleason grade heterogeneity, tumor multifocality, and biopsy undersampling. Eur Urol. 2014; 66: 550-60. doi: 10.1016/j.eururo.2014.05.004. Epub May 16.

Zhao S G, Evans J R, Kothari V, Sun G, Larm A, Mondine V, Schaeffer E M, Ross A E, Klein E A, Den R B, Dicker A P, Karnes R J, Erho N, et al. The Landscape of Prognostic Outlier Genes in High-Risk Prostate Cancer. Clin Cancer Res. 2016; 22: 1777-86. doi: 10.158/078-0432.CCR-15-1250. Epub 2015 Dec. 2.

Zhao S G, Chang S L, Spratt D E, Erho N, Yu M, Ashab H A, Alshalalfa M, Speers C, Tomlins S A, Davicioni E, Dicker A P, Carroll P R, Cooperberg M R, et al. Development and validation of a 24-gene predictor of response to postoperative radiotherapy in prostate cancer: a matched, retrospective analysis. Lancet Oncol. 2016; 17: 1612-20. doi: 10.016/S470-2045(16)30491-0. Epub 2016 Oct. 12.

Ross R W, Galsky M D, Scher H I, Magidson J, Wassmann K, Lee G S, Katz L, Subudhi S K, Anand A, Fleisher M, Kantoff P W, Oh W K. A whole-blood RNA transcript-based prognostic model in men with castration-resistant prostate cancer: a prospective study. Lancet Oncol. 2012; 13: 1105-13. doi: 10.016/S470-2045(12)70263-2. Epub 2012 Oct. 9.

Olmos D, Brewer D, Clark J, Danila D C, Parker C, Attard G, Fleisher M, Reid A H, Castro E, Sandhu S K, Barwell L, Oommen N B, Carreira S, et al. Prognostic value of blood mRNA expression signatures in castration-resistant prostate cancer: a prospective, two-stage study. Lancet Oncol. 2012; 13: 1114-24. doi: 10.016/S470-2045(12)70372-8. Epub 2012 Oct. 9.

Danila D C, Anand A, Schultz N, Heller G, Wan M, Sung C C, Dai C, Khanin R, Fleisher M, Lilja H, Scher H I. Analytic and clinical validation of a prostate cancer-enhanced messenger RNA detection assay in whole blood as a prognostic biomarker for survival. Eur Urol. 2014; 65: 1191-7. doi: 10.016/j.eururo.2013.07.006. Epub July 26.

Wang L, Gong Y, Chippada-Venkata U, Heck M M, Retz M, Nawroth R, Galsky M, Tsao C K, Schadt E, de Bono J, Olmos D, Zhu J, Oh W K. A robust blood gene expression-based prognostic model for castration-resistant prostate cancer. BMC Med. 2015; 13:201: 10.1186/s12916-015-0442-0.

Kohli M, Young C Y, Tindall D J, Nandy D, McKenzie K M, Bevan G H, Donkena K V. Whole blood defensin mRNA expression is a predictive biomarker of docetaxel response in castration-resistant prostate cancer. Onco Targets Ther. 2015; 8:1915-22: 10.2147/OTT. S86637. eCollection 2015.

Diaz-Uriarte R, Alvarez de Andres S. Gene selection and classification of microarray data using random forest. BMC Bioinformatics. 2006; 7: 3. doi: 10.1186/1471-2105-7-3.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A method of treating prostate cancer in a subject comprising:

determining the expression level of at least 38 biomarkers from a test sample from the subject by contacting the test sample with a plurality of agents specific to detect the expression of the at least 38 biomarkers, wherein the at least 38 biomarkers comprise AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, XPC, and a housekeeping gene, wherein the housekeeping gene is TOX4;

normalizing the expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC to the expression level of the housekeeping gene, thereby obtaining a normalized expression level of each of AAMP, ANO7, AR, AR-V7, C16orf89, CHTOP, COL1A1, EDC4, FGFR2, FXYD7, FYCO1, HNRNPU, HPN, KRT15, KRT23, MAN2B2, MAX, MRPS25, NDUFS2, PPARGC1A, PPRC1, RAD23A, REPIN1, SDR39U1, SETBP1, SLC14A1, SLC18A2, SMC4, SPARC, SQLE, STRIP1, STX12, TMPRSS2_1, TMPRSS2_2, TRIM29, UNC45A, and XPC;

inputting each normalized expression level into an algorithm to generate a score, wherein the algorithm is a product of a model of prostate cancer derived using the XGB algorithm;

comparing the score with a first predetermined cutoff value;

determining that the score is equal to or greater than the predetermined cutoff value, thereby identifying the subject as having prostate cancer; and administering to the subject identified as having prostate cancer a therapy, wherein the therapy comprises surgery.

2. The method of claim 1, wherein the first predetermined cutoff value is at least 33% on a scale of 0-100%.

3. The method of claim 1, wherein the predetermined cutoff value has a sensitivity of identifying the subject as having prostate cancer that is at least 92%.

4. The method of claim 1, wherein the predetermined cutoff value has a specificity of identifying the subject as having prostate cancer that is at least 95%.

5. The method of claim 1, wherein at least one of the at least 38 biomarkers is RNA, cDNA, or protein.

6. The method of claim 5, wherein when the biomarker is RNA, the RNA is reverse transcribed to produce cDNA, and the produced cDNA expression level is detected.

7. The method of claim 1, wherein the first predetermined cutoff value is derived from a plurality of reference samples obtained from subjects not having or not diagnosed with a prostate cancer.

8. The method of claim 1, wherein the test sample comprises blood, serum, plasma, or neoplastic tissue.

9. The method of claim 7, wherein reference sample comprises blood, serum, plasma, or non-neoplastic tissue.

* * * * *